US010823733B2

(12) United States Patent
Anderberg et al.

(10) Patent No.: US 10,823,733 B2
(45) Date of Patent: Nov. 3, 2020

(54) METHODS AND COMPOSITIONS FOR DIAGNOSIS AND PROGNOSIS OF RENAL INJURY AND RENAL FAILURE

(71) Applicant: ASTUTE MEDICAL, INC., San Diego, CA (US)

(72) Inventors: Joseph Anderberg, Encinitas, CA (US); Jeff Gray, Solana Beach, CA (US); Paul McPherson, Encinitas, CA (US); Kevin Nakamura, Cardiff by the Sea, CA (US)

(73) Assignee: Astute Medical, Inc., San Diego, CA (US)

( * ) Notice: Subject to any disclaimer, the term of this patent is extended or adjusted under 35 U.S.C. 154(b) by 0 days.

(21) Appl. No.: 14/327,513

(22) Filed: Jul. 9, 2014

(65) Prior Publication Data

US 2014/0323594 A1    Oct. 30, 2014

Related U.S. Application Data

(62) Division of application No. 13/125,360, filed as application No. PCT/US2009/061561 on Oct. 21, 2009, now Pat. No. 8,778,615.

(60) Provisional application No. 61/107,281, filed on Oct. 21, 2008, provisional application No. 61/107,301, filed on Oct. 21, 2008, provisional application No. 61/107,297, filed on Oct. 21, 2008, provisional application No. 61/107,290, filed on Oct. 21, 2008, provisional application No. 61/107,304, filed on Oct. 21, 2008, provisional application No. 61/113,096, filed on Nov. 10, 2008, provisional application No. 61/113,045, filed on Nov. 10, 2008, provisional application No. 61/113,083, filed on Nov. 10, 2008, provisional application No. 61/113,021, filed on Nov. 10, 2008, provisional application No. 61/115,019, filed on Nov. 14, 2008, provisional application No. 61/113,102, filed on Nov. 10, 2008, provisional application No. 61/113,050, filed on Nov. 10, 2008, provisional application No. 61/113,056, filed on Nov. 10, 2008, provisional application No. 61/115,022, filed on Nov. 14, 2008, provisional application No. 61/115,017, filed on Nov. 14, 2008, provisional application No. 61/115,044, filed on Nov. 15, 2008, provisional application No. 61/115,047, filed on Nov. 15, 2008, provisional application No. 61/115,051, filed on Nov. 15, 2008, provisional application No. 61/115,057, filed on Nov. 15, 2008, provisional application No. 61/115,048, filed on Nov. 15, 2008, (Continued)

(51) Int. Cl.
*G01N 33/573*   (2006.01)
*G01N 33/68*    (2006.01)
*G01N 33/50*    (2006.01)

(52) U.S. Cl.
CPC ....... *G01N 33/573* (2013.01); *G01N 33/5088* (2013.01); *G01N 33/5091* (2013.01); *G01N 33/6893* (2013.01); *G01N 2800/347* (2013.01); *G01N 2800/50* (2013.01); *G01N 2800/56* (2013.01); *G01N 2800/60* (2013.01)

(58) Field of Classification Search
None
See application file for complete search history.

(56) References Cited

U.S. PATENT DOCUMENTS 5,480,792 A    1/1996    Buechler et al.
5,525,524 A    6/1996    Buechler et al.
(Continued)

FOREIGN PATENT DOCUMENTS

CN    1791797 A      6/2006
CN    101010001 A    8/2007
(Continued)

OTHER PUBLICATIONS

Coca et al. Biomarkers for the diagnosis and risk stratification of acute kidney injury: A systematic review. Kidney International. 2008; 73: 1008-1016.*

(Continued)

*Primary Examiner* — Vanessa L. Ford
*Assistant Examiner* — Sandra E Dillahunt
(74) *Attorney, Agent, or Firm* — Womble Bond Dickinson (US) LLP

(57) ABSTRACT

The present invention relates to methods and compositions for monitoring, diagnosis, prognosis, and determination of treatment regimens in subjects suffering from or suspected of having a renal injury. In particular, the invention relates to using assays that detect one or more markers selected from the group consisting of Cytoplasmic aspartate aminotransferase, soluble Tumor necrosis factor receptor superfamily member 5, soluble CD40 Ligand, soluble C-X-C Motif chemokine 16, S100-A12, Eotaxin, soluble E-selectin, Fibronectin, Granulocyte colony-stimulating factor, Granulocyte-macrophage colony-stimulating factor, Heparin-binding growth factor 2, soluble Hepatocyte growth factor receptor, Interleukin-1 receptor antagonist, Interleukin-1 beta, Interleukin-10, Interleukin-15, Interleukin-3, Myeloperoxidase, Nidogen-1, soluble Oxidized low-density lipoprotein receptor 1, Pappalysin-1, soluble P-selectin glycoprotein ligand 1, Antileukoproteinase, soluble Kit ligand, Tissue inhibitor of metalloproteinase 1, Tissue inhibitor of metalloproteinase 2, soluble Tumor necrosis factor, soluble Vascular cell adhesion molecule 1, and Vascular endothelial growth factor A as diagnostic and prognostic biomarkers in renal injuries.

19 Claims, 363 Drawing Sheets
Specification includes a Sequence Listing.

Related U.S. Application Data provisional application No. 61/117,172, filed on Nov. 22, 2008, provisional application No. 61/117,146, filed on Nov. 22, 2008, provisional application No. 61/117,140, filed on Nov. 22, 2008, provisional application No. 61/117,141, filed on Nov. 22, 2008, provisional application No. 61/117,154, filed on Nov. 22, 2008, provisional application No. 61/117,152, filed on Nov. 22, 2008, provisional application No. 61/117,157, filed on Nov. 22, 2008, provisional application No. 61/117,167, filed on Nov. 22, 2008, provisional application No. 61/115,045, filed on Nov. 15, 2008.

(56) References Cited

U.S. PATENT DOCUMENTS

| | | |
|---|---|---|
| 5,571,698 A | 11/1996 | Ladner et al. |
| 5,631,171 A | 5/1997 | Sandstrom et al. |
| 5,679,526 A | 10/1997 | Buechler et al. |
| 5,824,799 A | 10/1998 | Buechler et al. |
| 5,851,776 A | 12/1998 | Valkirs |
| 5,885,527 A | 3/1999 | Buechler |
| 5,922,615 A | 7/1999 | Nowakowski et al. |
| 5,939,272 A | 8/1999 | Buechler et al. |
| 5,947,124 A | 9/1999 | Buechler et al. |
| 5,955,377 A | 9/1999 | Maul et al. |
| 5,985,579 A | 11/1999 | Buechler et al. |
| 6,019,944 A | 2/2000 | Buechler |
| 6,057,098 A | 5/2000 | Buechler et al. |
| 6,113,855 A | 9/2000 | Buechler |
| 6,143,576 A | 11/2000 | Buechler |
| 6,218,122 B1 | 4/2001 | Friend et al. |
| 6,664,385 B1 | 12/2003 | Sanicola-Nadel et al. |
| 6,784,154 B2 | 8/2004 | Westenfelder |
| 6,861,404 B1 | 3/2005 | Cohen et al. |
| 6,941,172 B2 | 9/2005 | Nachum |
| 7,138,230 B2 | 11/2006 | Hu et al. |
| 7,141,382 B1 | 11/2006 | Parikh et al. |
| 7,235,358 B2 | 6/2007 | Wohlgemuth et al. |
| 7,608,413 B1 | 10/2009 | Joseloff et al. |
| 7,623,910 B2 | 11/2009 | Couderc et al. |
| 7,662,578 B2 | 2/2010 | Devarajan |
| 7,833,699 B2 | 11/2010 | Locht et al. |
| 7,981,684 B2 | 7/2011 | Levin et al. |
| 7,998,744 B2 | 8/2011 | Stevenson et al. |
| 8,008,008 B2 | 8/2011 | Parr et al. |
| 8,071,293 B2 | 12/2011 | High et al. |
| 8,080,394 B2 | 12/2011 | Levy et al. |
| 8,241,861 B1 | 8/2012 | Heinecke et al. |
| 8,252,905 B2 * | 8/2012 | Furusako ......... A61K 39/39541 530/387.3 |
| 8,778,615 B2 | 7/2014 | Anderberg et al. |
| 9,029,093 B2 | 5/2015 | Anderberg et al. |
| 9,360,488 B2 | 6/2016 | Anderberg et al. |
| 9,459,261 B2 | 10/2016 | Anderberg et al. |
| 9,784,750 B2 | 10/2017 | Anderberg et al. |
| 9,822,172 B2 | 11/2017 | Vijayendran et al. |
| 9,879,091 B2 | 1/2018 | Vijayendran et al. |
| 10,300,108 B2 | 5/2019 | Mcpherson et al. |
| 2003/0003588 A1 | 1/2003 | Comper |
| 2004/0029200 A1 | 2/2004 | Weimbs |
| 2004/0053309 A1 | 3/2004 | Holt et al. |
| 2004/0106155 A1 | 6/2004 | Comper |
| 2005/0002934 A1 | 1/2005 | Reed |
| 2005/0048033 A1 | 3/2005 | Fraser et al. |
| 2005/0112688 A1 | 5/2005 | Hu et al. |
| 2005/0137481 A1 | 6/2005 | Sheard et al. |
| 2005/0148029 A1 | 7/2005 | Buechler et al. |
| 2005/0158801 A1 | 7/2005 | Hu et al. |
| 2005/0256075 A1 | 11/2005 | Alitalo et al. |
| 2005/0272101 A1 | 12/2005 | Devarajan et al. |
| 2006/0003327 A1 | 1/2006 | Achiron et al. |
| 2006/0057066 A1 | 3/2006 | Natsoulis et al. |
| 2006/0088823 A1 | 4/2006 | Haab et al. |
| 2006/0204951 A1 | 9/2006 | Folkman et al. |
| 2006/0223077 A1 | 10/2006 | Ni et al. |
| 2006/0240437 A1 | 10/2006 | Krolewski et al. |
| 2006/0246485 A1 | 11/2006 | Sarwal et al. |
| 2007/0031905 A1 | 2/2007 | Shariat |
| 2007/0087387 A1 | 4/2007 | Devarajan |
| 2007/0093969 A1 | 4/2007 | Mendrick et al. |
| 2007/0105142 A1 | 5/2007 | Wilhelm |
| 2007/0112327 A1 | 5/2007 | Yun et al. |
| 2007/0154897 A1 | 7/2007 | Yen et al. |
| 2007/0248989 A1 | 10/2007 | Devarajan |
| 2007/0249002 A1 | 10/2007 | Hu et al. |
| 2008/0014644 A1 | 1/2008 | Barasch et al. |
| 2008/0038192 A1 | 2/2008 | Gervais |
| 2008/0038269 A1 | 2/2008 | Susan |
| 2008/0090304 A1 | 4/2008 | Barasch et al. |
| 2008/0116867 A1 | 5/2008 | Koegel et al. |
| 2008/0133141 A1 | 6/2008 | Frost |
| 2008/0153092 A1 | 6/2008 | Kienle et al. |
| 2008/0206794 A1 | 8/2008 | Hu et al. |
| 2008/0254483 A1 | 10/2008 | Darbouret et al. |
| 2008/0254485 A1 | 10/2008 | Valkirs et al. |
| 2009/0022730 A1 | 1/2009 | Raulf et al. |
| 2009/0047689 A1 | 2/2009 | Kolman et al. |
| 2009/0081713 A1 | 3/2009 | Klein et al. |
| 2009/0088409 A1 | 4/2009 | Charlton |
| 2009/0090856 A1 | 4/2009 | Grant et al. |
| 2009/0148539 A1 | 6/2009 | Elias et al. |
| 2009/0176656 A1 | 7/2009 | Halloran |
| 2009/0178145 A1 | 7/2009 | Carr et al. |
| 2009/0197287 A1 | 8/2009 | Hu et al. |
| 2009/0203588 A1 | 8/2009 | Willman et al. |
| 2009/0220526 A1 | 9/2009 | Hamid |
| 2009/0258002 A1 | 10/2009 | Barrett et al. |
| 2009/0298073 A1 | 12/2009 | Gerhold et al. |
| 2009/0298106 A1 | 12/2009 | Hooper |
| 2010/0022627 A1 | 1/2010 | Scherer |
| 2010/0081148 A1 | 4/2010 | Singbartl et al. |
| 2010/0190164 A1 | 7/2010 | Tammen et al. |
| 2010/0240078 A1 | 9/2010 | Lee et al. |
| 2010/0267041 A1 | 10/2010 | Shuber et al. |
| 2011/0065608 A1 | 3/2011 | Labrie et al. |
| 2011/0104726 A1 | 5/2011 | Valkirs et al. |
| 2011/0174062 A1 | 7/2011 | Anderberg et al. |
| 2011/0190156 A1 | 8/2011 | Whitfield et al. |
| 2011/0195429 A1 | 8/2011 | Anderberg et al. |
| 2011/0201038 A1 | 8/2011 | Anderberg et al. |
| 2011/0207161 A1 | 8/2011 | Anderberg et al. |
| 2012/0190044 A1 | 7/2012 | Anderberg et al. |
| 2012/0190051 A1 | 7/2012 | Anderberg et al. |
| 2012/0283128 A1 | 11/2012 | Anderberg et al. |
| 2013/0035290 A1 | 2/2013 | Elias et al. |
| 2013/0157881 A1 | 6/2013 | Anderberg et al. |
| 2013/0210043 A1 | 8/2013 | Anderberg et al. |
| 2014/0323594 A1 | 10/2014 | Anderberg et al. |
| 2014/0377777 A1 | 12/2014 | Anderberg et al. |
| 2016/0146832 A1 | 5/2016 | Chawla et al. |
| 2017/0248613 A1 | 8/2017 | Anderberg et al. |
| 2018/0074054 A1 | 3/2018 | Mcpherson et al. |
| 2019/0263926 A1 | 8/2019 | Mcpherson et al. |

FOREIGN PATENT DOCUMENTS

| | | |
|---|---|---|
| CN | 101027556 A | 8/2007 |
| CN | 101268102 A | 9/2008 |
| EP | 0828159 | 3/1998 |
| EP | 1905846 | 4/2008 |
| EP | 2261660 | 12/2010 |
| EP | 2480882 | 8/2012 |
| EP | 2513649 | 10/2012 |
| JP | H09-072906 A | 3/1997 |
| JP | H09-274036 | 10/1997 |
| JP | 2004504813 A | 2/2004 |
| JP | 2005120070 A | 5/2005 |
| JP | 2008224526 A | 9/2008 |
| JP | 2008241705 A | 10/2008 |
| KR | 101760314 B1 | 7/2017 |
| RU | 2180965 | 3/2002 |

(56) References Cited

FOREIGN PATENT DOCUMENTS

| | | |
|---|---|---|
| SU | 1429031 | 10/1988 |
| WO | WO 1998/055508 | 12/1998 |
| WO | 0128500 A2 | 4/2001 |
| WO | 0190421 A2 | 11/2001 |
| WO | WO 2001/088544 | 11/2001 |
| WO | 03006989 A1 | 1/2003 |
| WO | WO 2003/054004 | 7/2003 |
| WO | WO 2003/075016 | 9/2003 |
| WO | WO 2004/005934 | 1/2004 |
| WO | 2005002416 A2 | 1/2005 |
| WO | WO 2005/087264 | 9/2005 |
| WO | WO 2006/083986 | 8/2006 |
| WO | WO 2007/013919 | 2/2007 |
| WO | WO 2007/041623 | 4/2007 |
| WO | 2007084397 A2 | 7/2007 |
| WO | 2007093183 A2 | 8/2007 |
| WO | 2007121922 A2 | 11/2007 |
| WO | WO 2008/060607 | 5/2008 |
| WO | WO 2008/061149 | 5/2008 |
| WO | 2008084331 A2 | 7/2008 |
| WO | WO 2008/104804 | 9/2008 |
| WO | 2008116867 A1 | 10/2008 |
| WO | WO 2008/122670 | 10/2008 |
| WO | WO 2008/154238 | 12/2008 |
| WO | WO 2009/038742 | 3/2009 |
| WO | WO 2010/025424 | 3/2010 |
| WO | WO 2010/025434 | 3/2010 |
| WO | 2010048346 A1 | 4/2010 |
| WO | WO 2010/048347 | 4/2010 |
| WO | WO 2010/054389 | 5/2010 |
| WO | WO 2010/091236 | 8/2010 |
| WO | WO 2010/111746 | 10/2010 |
| WO | WO 2010/128158 | 11/2010 |
| WO | 2011035323 A1 | 3/2011 |
| WO | WO 2011/075744 | 6/2011 |
| WO | WO 2011/097539 | 8/2011 |
| WO | WO 2011/106746 | 9/2011 |
| WO | WO 2011/162821 | 12/2011 |
| WO | WO 2013/043310 | 3/2013 |
| WO | WO 2013/086359 | 6/2013 |
| WO | WO 2014/113558 | 7/2014 |
| WO | WO 2014/197729 | 12/2014 |
| WO | WO 2015/021308 | 2/2015 |
| WO | WO 2015/069880 | 5/2015 |
| WO | WO 2015/084939 | 6/2015 |
| WO | WO 2016/164854 | 10/2016 |
| WO | WO 2017/214203 | 12/2017 |
| WO | WO 2018/081578 | 5/2018 |
| WO | WO 2018/145117 | 8/2018 |
| WO | WO 2018/187453 | 10/2018 |
| WO | WO 2018/208684 | 11/2018 |

OTHER PUBLICATIONS

Devarajan et al. Update on Mechanisms of Ischemic Acute Kidney Injury. Journal of American Society Nephrology, 2006; 17:1503-1520.*
Constantin et al. Plasma neutrophil gelatinase-associated lipocalin is an early marker of acute kidney injury in adult critically ill patients: A prospective study. Journal of Critical Care. 2010; 25:176.*
Grobmeyer et al. Secretory leukocyte protease inhibitor, an inhibitor of neutrophil activation, is elevated in serum in human sepsis and experimental endotoxemia. Critical Care Medicine. 2000; 28(5): 1276-1282.*
Williamson et al.Comparison of Biomarkers in Blood and Saliva in Healthy Adults. Nursing Research and Practice vol. 2012, Article ID 246178, pp. 1-4 (Year: 2012).*
Hollander et al. Serum and bronchial lavage fluid concentrations of IL-8, SLPI, sCD14 and sICAM-1 in patients with COPD and asthma. Respiratory medicine, 2007; 101: 1947-1953 (Year: 2007).*
Grobmeyer et al. (Critical Care Medicine. 2000; 28(5): 1276-1282 (Year: 2000).*

Sykes et al., "Analytical Relationships Among Biosite, Bayer, and Roche Methods for BNP and NT-proBNP A Preliminary Study", Am J Clin Pathol, 2005, 123:584-590.
Christenson et al., "Standardization of Cardiac Troponin I Assays: Round Robin of Ten Candidate Reference Materials", Clinical Chemistry, 2001, 47(3):431-437.
Giasson et al., "Neutrophil Gelatinase-Associated Lipocalin (NGAL) as a New Biomarker for Non—Acute Kidney Injury (AKI) Diseases", Inflammation & Allergy—Drug Targets, 2011, 10:272-282.
Obuchowski et al., "ROC Curves in Clinical Chemistry: Uses, Misuses, and Possible Solutions", Clinical Chemistry, 2004, 50(7):1118-1125.
Alere Triage BNP Test Product Insert, Rapid Quantitative Test for B-type Natriuretic Peptide, 2011, 28 pages.
Office Action and Search Report issued by SIPO in Chinese patent application No. 201310576168.2 dated Mar. 25, 2015—incl Engl lang transl.
Final Rejection issued by the JPO in Japanese application No. 2011-532354 dated Jul. 28, 2015—incl Engl lang transl.
Final Rejection issued by the JPO in Japanese application No. 2014-023208 dated Jul. 28, 2015—incl Engl lang transl.
Caron et al., Ischemia injury alters endothelial cell properties of kidney cortex: stimulation of MMP-9. Exp Cell Res. Oct. 15, 2005;310(1):105-116.
Fu and Tao, Study on the expression of VEGF, MMP-2 and TIMP-2 in the progression of IgA nephropathy. J Clin Exp Pathol 2008;24(5);573-576—incl Engl lang tansl abstract only.
Gakkaish I, MMP-2, MMP-9, TIMP-1, TIMP-2. 2005;47(3):274 P-214.
Han et al., An imbalance between matrix metalloproteinase-2 and tissue inhibitor of matrix metalloproteinase-2 contributes to the development of early diabetic nephropathy. Nephrol Dial Transplant. Sep. 2006;21(9):2406-2416.
Naika, Q & A. EBM 2002;89(6):1003-1021.
Wasilewska and Zoch-Zwierz, Urinary levels of matrix metalloproteinases and their tissue inhibitors in nephrotic children. Pediatr Nephrol. Oct. 2008;23(10):1795-1802.
Zasshi, Japanese J Nursing 2000;64(11):1066-1070.
Asanuma et al., Selective modulation of the secretion of proteinases and their inhibitors by growth factors in cultured differentiated podocytes. Kidney Int. Sep. 2002;62(3):822-831.
Bagshaw et al., A multi-centre evaluation of the RIFLE criteria for early acute kidney injury in critically ill patients. Nephrol Dial Transplant. Apr. 2008;23(4):1203-1210.
Bellomo et al., Acute renal failure—definition, outcome measures, animal models, fluid therapy and information technology needs: the Second International Consensus Conference of the Acute Dialysis Quality Initiative (ADQI) Group. Crit Care. Aug. 2004;8(4):R204-R212.
Berthier and Marti, Metzincins, including matrix metalloproteinases and meprin, in kidney transplantation. Swiss Med Wkly. Dec. 23, 2006;136(49-50):789-794.
Brook et al., Fibrosis-associated gene expression in renal transplant glomeruli after acute renal allograft rejection. Br J Surg. Aug. 2003;90(8):1009-1014.
Caron et al., Ischemia—reperfusion injury stimulates gelatinase expression and activity in kidney glomeruli. Can J Physiol Pharmacol. Mar. 2005;83(3):287-300.
Catania et al., Role of matrix metalloproteinases in renal pathophysiologies. Am J Physiol Renal Physiol. Mar. 2007;292(3):F905-F911.
Chang et al., Levels in the Serum of Tissue Inhibitors of Metalloproteinaise-1 (TIMP-1) from Patients with Primary Nephrotic Syndrome. Chin J Integr Trad Western Nephrol.Oct. 2007;8(10): 600-601—Engl lang transl abstract only.
Chertow et al, Acute Kidney Injury, Mortality, Length of Stay, and Costs in Hospitalized Patients. J Am Soc Nephrol. Nov. 2005:16(11)3365-3370.
Office Action and Search Report issued by KIPO in Korean patent application No. 10-2011-7011445 dated Jun. 15, 2016—incl Engl lang transl.
Office Action and Search Report issued by SIPO in Chinese patent application No. 201410485595.4 dated Oct. 29, 2015—incl Engl lang transl.

(56) References Cited

OTHER PUBLICATIONS

Office Action and Search Report issued by SIPO in Chinese patent application No. 201410485610.5 dated Nov. 3, 2015—incl Engl lang transl.
Office Action and Search Report issued by SIPO in Chinese patent application No. 201410485543.7 dated Aug. 2, 2016—incl Engl lang transl.
Office Action issued by SIPO in PRC application No. 201310576168.2 dated Dec. 2, 2015—incl Engl lang transl.
Office Action issued by the JPO in Japanese patent application No. 2014-023208 dated Jan. 13, 2015—incl Engl lang transl.
Office Action issued by the JPO in Japanese patent application No. 2014-023208 dated Jun. 7, 2016—incl Engl lang transl.
Cwirla et al., Peptides on phage: a vast library of peptides for identifying ligands. Proc Natl Acad Sci U S A. Aug. 1990;87(16):6378-6382.
Devlin et al., Random peptide libraries: a source of specific protein binding molecules. Science. Jul. 27, 1990;249(4967):404-406.
Engers et al., Rac Affects Invasion of Human Renal Cell Carcinomas by Up-regulating Tissue Inhibitor of Metalloproteinases (TIMP)-1 and TIMP-2 Expression. J Biol Chem. Nov. 9, 2001;276(45):41889-41897.
Fischer et al., A readers' guide to the interpretation of diagnostic test properties: clinical example of sepsis. Intensive Care Med. Jul. 2003;29(7):1043-1051.
Gaggar et al., Matrix metalloprotease-9 dysregulation in lower airway secretions of cystic fibrosis patients. Am J Physiol Lung Cell Mol Physiol. Jul. 2007;293(1):L96-L104.
Gharagozlian et al., Matrix metalloproteinases in subjects with type 1 diabetes. BMC Clin Pathol. Sep. 16, 2009;9:7.
Hanley and Mcneil, The meaning and use of the area under a receiver operating characteristic (ROC) curve. Radiology. Apr. 1982;143(1):29-36.
Hayashi et al., Enhanced Expression of Membrane Type-1 Matrix Metalloproteinase in Mesangial Proliferative Glomerulonephritis. J Am Soc Nephrol. Dec. 1998;9(12):2262-2271.
J Kanazawa University Juzen Medical Society, 1995;104:36-45.
Kamata et al., Up-regulation of glomerular extracellular matrix and transforming growth factor-beta expression in RF/J mice. Kidney Int. Mar. 1999;55(3):864-876.
Kellum, Acute kidney injury. Crit Care Med. Apr. 2008;36(4 Suppl):S141-S145.
Khanna et al., Expression of TGF-beta and fibrogenic genes in transplant recipients with tacrolimus and cyclosporine nephrotoxicity. Kidney Int. Dec. 2002;62(6):2257-2263.
Laplante et al., Modulation of matrix gelatinases and metalloproteinase-activating process in acute kidney rejection. Transpl Int. Apr. 2003;16(4):262-269.
Lassnigg et al., Minimal Changes of Serum Creatinine Predict Prognosis in Patients after Cardiothoracic Surgery: A Prospective Cohort Study. J Am Soc Nephrol. Jun. 2004;15(6):1597-1605.
Mccullough et al, Contrast-Induced Nephropathy (CIN) Consensus Working Panel: executive summary. Rev Cardiovasc Med. 2006 Fall;7(4):177-197.
Mehta et al., Acute Kidney Injury Network: report of an initiative to improve outcomes in acute kidney injury. Crit Care. 2007;11(2):R31.
Nelson and Griswold, A computer program for calculating antibody affinity constants. Comput Methods Programs Biomed. Jul.-Aug. 1988;27(1):65-68.
Praught and Shlipak, Are small changes in serum creatinine an important risk factor? Curr Opin Nephrol Hypertens. May 2005;14(3):265-270.
Ricci et al., The RIFLE criteria and mortality in acute kidney injury: A systematic review. Kidney Int. Mar. 2008;73(5):538-546.
Rysz et al., Serum matrix metalloproteinases MMP-2 and MMP-9 and metalloproteinase tissue inhibitors TIMP-1 and TIMP-2 in diabetic nephropathy. J Nephrol. Jul.-Aug. 2007;20(4):444-452.
Schaefer et al., Tubular gelatinase A (MMP-2) and its tissue inhibitors in polycystic kidney disease in the Han: SPRD rat. Kidney Int. Jan. 1996;49(1):75-81.
Scott and Smith, Searching for Peptide Ligands with an Epitope Library. Science. Jul. 27, 1990;249(4967):386-390.
Thrailkill et al., Matrix Metalloproteinase-2 Dysregulation in Type 1 Diabetes. Diabetes Care. Sep. 2007;30(9):2321-2326.
Uchio-Yamada et al., Decreased Expression of Matrix Metalloproteinases and Tissue Inhibitors of Metalloproteinase in the Kidneys of Hereditary Nephrotic (ICGN) Mice. J Vet Med Sci. Jan. 2005;67(1):35-41.
Van Erp et al., Application of a sol particle immunoassay to the determination of affinity constants of monoclonal antibodies. J Immunoassay. 1991;12(3):425-43.
Wagrowska-Danilewicz and Danilewicz, Aberrant Tubulointerstitial Immunoexpression of Matrix Metalloproteinases MMP-2, MMP-9 and Tissue Inhibitor of Matrix Proteinase-2 (TIMP-2) in Acute Cellular Rejection of Human Renal Allograft. Pol J Pathol. 2008;59(4):189-194.
Ward et al., Binding activities of a repertoire of single immunoglobulin variable domains secreted from *Escherichia coli*. Nature. Oct. 12, 1989;341(6242):544-546.
When et al., The expression and significance of Serum TGF-beta1, MMP-9 and TIMP-1 in Patients with Chronic renal failure. Wanfang Data Konwledge Service Platform Sep. 21, 2007: (incl Engl lang transl abstract only).
Wijeysundera et al., Derivation and Validation of a Simplified Predictive Index for Renal Replacement Therapy After Cardiac Surgery. JAMA. Apr. 25, 2007;297(16):1801-1809.
Wilson et al., Simplified conjugation chemistry for coupling peptides to F(ab') fragments: autologous red cell agglutination assay for HIV-1 antibodies. J Immunol Methods. Oct. 14, 1994;175(2):267-273.
Yarmush et al., Coupling of antibody-binding fragments to solid-phase supports: site-directed binding of F(ab') 2 fragments. J Biochem Biophys Methods. Dec. 1992;25(4):285-297.
Zhang et al., Significance of MMP=2 and TIMP-2 mRNA Expressions on Glomerular Cells in the Development of Glomerulosclerosis. Chin Med Sci J. Jun. 2004;19(2):84-88.
Ridker, Paul M., "Clinical Application of C-Reactive Protein for Cardiovascular Disease Detection and Prevention", Circulation, 2003;107:363-369.
Ridker, Paul M., "C-Reactive Protein A Simple Test to Help Predict Risk of Heart Attack and Stroke", Circulation, 2003;108:e81-e85.).
Office Action issued by SIPO in Chinese Patent Application No. 2016106797577 dated Aug. 28, 2017—incl Engl lang transl.
Jin et al., Correlation between Pathological Classification and Levels of TNF and sTNF-R in Sera from Patients with Lupus Nephritis. Clin Med J China 2002;9(1):7-8—incl Engl lang transl abstract only.
Extended European Search Report issued in EP 17174892 dated Oct. 5, 2017.
Kallakury et al., Increased Expression of Matrix Metalloproteinases 2 and 9 and Tissue Inhibitors of Metalloproteinases 1 and 2 Correlate with Poor Prognostic Variables in Renal Cell Carcinoma. Clin Cancer Res. Oct. 2001;7(10):3113-3119.
Kawata et al., Significant Relationship of Matrix Metalloproteinase 9 with Nuclear Grade and Prognostic Impact of Tissue Inhibitor of Metalloproteinase 2 for Incidental Clear Cell Renal Cell Carcinoma. Urology. Jun. 2007;69(6):1049-1053.
The First Exam Report issued issued by IPI (Intellectual Property India) in Indian patent application No. 968/MUMN/2011 dated Jul. 14, 2017.
Office Action issued by the JPO in Japanese Patent Application No. 2016-197891 dated Sep. 12, 2017—incl Engl lang transl.
Decision to Grant issued by the Korean Intellectual Property Office in Korean Patent Application No. 10-2011-7011445 dated Apr. 25, 2017—incl Engl lang transl.
Chatterjee et al., Tempol, a membrane-permeable radical scavenger, reduces oxidant stress-mediated renal dysfunction and injury in the rat. Kidney Int. Aug. 2000;58(2):658-673.
Basile et al., Angiostatin and matrix metalloprotease expression following ischemic acute renal failure. Am J Physiol Renal Physiol. May 2004;286(5):F893-902.
Nguyen and Devarajan, Biomarkers for the early detection of acute kidney injury. Pediatr Nephrol. Dec. 2008;23(12):2151-5157.

(56) References Cited

OTHER PUBLICATIONS

Office Action issued by the Brazilian PTO in Brazilian Patent Application No. PI 0919640-4 dated Jun. 19, 2018—Incl Engl lang transl.
Office Action issued by the Brazilian PTO in Brazilian Patent Application No. PI 0919640-4 dated Oct. 16, 2018—Incl Engl lang transl.
Abd El Latif et al., "Urinary epidermal growth factor excretion: A useful prognostic marker for progression of renal damage in children," J Med Sci, Oct. 2007, 7(7):1171-1176.
Abou-Shousha et al., "Interleukin-2 Regulatory Effect on P-Selectin and Interleukin-8 Production in Patients with Chronic Renal Failure," Egypt J Immunol, 2006,13(1):11-18.
Akcay et al., "Mediators of Inflammation in Acute Kidney Injury," Mediators Inflamm, 2009, 2009:137072 (12 pp).
Alatas et al., "Beneficial Effects of Allopurinol on Glutathione Levels and Glutathione Peroxidase Activity in Rat Ischaemic Acute Renal Failure," The Journal of International Medical Research, 1996, 24:33-39.
Albright, "Acute Renal Failure: A Practical Update," Mayo Clin Proc, Jan. 2001, 76(1):67-74.
Anders et al., "Chemokines and chemokine receptors are involved in the resolution or progression of renal disease," Kidney Int, Feb. 2003, 63(2):401-415.
Anilkumar et al., "Trimeric assembly of the C-terminal region of Thrombospondin-1 or Thrombospondin-2 is necessary for cell spreading and fascin spike organisation," J Cell Sci, Jun. 1, 2002, 115(Pt 11):2357-2366.
Arribas et al., "ADAM17 as a Therapeutic Target in Multiple Diseases," Curr Pharm Des., 2009, 15 (20):2319-2335.
Arrizabalaga et al., "Tubular and Interstitial Expression of ICAM-1 as a Marker of Renal Injury in IgA Nephropathy," Am J Nephro, May-Jun. 2003, 23(3):121-128.
Bagshaw et al., "Urinary biomarkers in septic acute kidney injury," Intensive Care Med, Jul. 2007, 33(7):1285-1296.
Bajwa et al., "Immune Mechanisms and Novel Pharmacological Therapies of Acute Kidney Injury," Curr Drug Targets, Dec. 2009, 10(12):1196-1204.
Barrera-Chimal et al., "Hsp72 is an early and sensitive biomarker to detect acute kidney injury," EMBO Mol Med, Jan. 2011, 3(1):5-20.
Berahovich et al., "Proteolytic activation of alternative CCR1 ligands in inflammation," J Immunol, Jun. 1, 2005, 174(11):7341-7351.
Beushausen, "NWG Biomarker Objectives," ILSI Health and Environmental Sciences Institute, ILSI-HESI Annual Meeting 2006:17 pp.
Bicik et al., "Role of Transforming Growth Factor-.beta.2 in, and a Possible Transforming Growth Factor-beta2 Gene Polymorphism as a Marker of, Renal Dysfunction in Essential Hypertension: A Study in Turkish Patients," Current Therapeutic Research, 2005, 44(4):266-278.
Biotrin International, "Biotrin Biomarkers: How late do you want to detect preclinical kidney damage? Biotrin's acute kidney injury test (AKI Test)," Biotrin's Preclinical Kidney Biomarkers: 8 pp.
Bonomini et al., "Serum Levels of Soluble Adhesion Molecules in Chronic Renal Failure and Dialysis Patients," Nephron, Aug. 1998, 79(4):399-407.
Bonventre, "Dedifferentiation and Proliferation of Surviving Epithelial Cells in Acute Renal Failure," J Am Soc Nephrol, 14 Jun. 14, 2003, 14 Suppl 1:S55-S61.
Bonventre, "Pathophysiology of Acute Kidney Injury: Roles of Potential Inhibitors of Inflammation," Contrib Nephrol, 2007, 156:39-46.
Bonventre et al., "Ischemic acute renal failure: An inflammatory disease?," Kidney Int, Aug. 2004, 66(2):480-485.
Burne et al., "IL-1 and TNF independent pathways mediate ICAM-1NCAM-1 up-regulation in ischemia repertusion injury," J Leukoc Biol, Aug. 2001, 70(2):192-198.
Burne-Taney et al., "The role of adhesion molecules and T cells in ischemic renal injury," Curr Opin Nephrol Hypertens, Jan. 2003, 12(1):85-90.
Cai, "Detection and Application for the biomarker of Rental Injury in Early Stage," Laboratory Med Clinic, Jun. 2005, 2(3):124-127—includes English translation, abstract only.
Calabrese et al., "Oxidative stress and cellular stress response in diabetic nephropathy," Database Biosis [Online]. Biosciences Information Service, Jan. 2007, XP002705326. Database Accession No. PREV200800097004 (abstract):3 pages & Cell Stress Chaperones. 2007 Winter;12(4):299-306.
Canani et al., "The Fatty Acid-Binding Protein-2 A54T Polymorphism Is Associated With Renal Disease in Patients With Type 2 Diabetes," Diabetes, Nov. 2005, 54(11):3326-3330.
Choi et al., "Expression of Vascular Endothelial Growth Factor-C and Its Receptor mRNA in the Rat Kidney With lschemia-Reperfusion Injury," Clinical Kidney J, Jun. 2011, 4(Suppl 2):2 pages.
Coca et al., "Biomarkers for the diagnosis and risk stratification of acute kidney injury: A systematic review," Kidney Int, May 2008, 73(9):1008-1016.
Constantin et al., "Plasma neutrophil gelatinase-associated lipocalin is an early marker of acute kidney injury in adult critically ill patients: A prospective study," Journal of Cirical Care, 2010, 25:176.
Cooper, "Effect of Tobacco Smoking on Renal Function," Indian J Med Res, Sep. 2006, 124(3):261-268.
Cottone et al., "Endothelin-1 and F2-isoprostane relate to and predict renal dysfunction in hypertensive patients," Nephrol Dial Transpl, Feb. 2009, 24(2):497-503.
Cruz et al., "North East Italian Prospective Hospital Renal Outcome Survey on Acute Kidney Injury (NEiPHROS-AKI): Targeting the Problem with the RIFLE Criteria," Clin J Amer Soc Nephrol, May 2007, 2(3):418-425.
Daha et al., "Is the proximal tubular cell a proinflammatory cell?," Nephrol Dial Transplant, 2000, 15(Suppl 6):41-43.
De Sa et al., "Leukocyte, platelet and endothelial activation in patients with acute renal failure treated by intermittent hemodialysis," Am J Nephrol, Jul.-Aug. 2001, 21(4):264-273.
Devarajan, "Cellular and molecular derangements in acute tubular necrosis," Curr Opin Pediatr, Apr. 2005, 17(2):193-199.
Devarajan, "Novel biomarkers for the early prediction of acute kidney injury," Cancer Therapy, Sep. 2005, 3:477-488.
Devarajan, "Update on Mechanisms of Ischemic Acute Kidney Injury," J Am Soc Nephrol, Jun. 2006, 17(6):1503-1520.
Devarajan et al., "Proteomics for Biomarker Discovery in Acute Kidney Injury," Semin Nephrol, Nov. 2007, 27(6):637-651.
Domanski et al., "Purine and Cytokine Concentrations in the Renal Vein of the Allograft During Reperfusion," Transplant Proc, Jun. 2007, 39(5):1319-1322.
Doumas et al., "Anti-Inflammatory and Antimicrobial Roles of Secretory Leukocyte Protease Inhibitor," Infection and Immunity, Mar. 2005:1271-1274.
Drannik et al., "Production of cytokines and the levels of secretory inhibitors of leukocyte proteases in patients with chronic infections of urinary system," Zhurnal Akademii Med Nauk Ukraini, 2007, 13(4):761-771, Abstract only.
Edelstein, "Biomarkers of Acute Kidney Injury. Adv Chronic Kidney Dis," Jul. 2008, 15(3)222-234.
Eissa et al., "Noninvasive Diagnosis of Bladder Cancer by Detection of Matrix Metalloproteinases (MMP-2 and MMP-9) and Their Inhibitor (TIMP-2) in Urine," European Urology, 2007, 52(5):1388-1396—Abstract only.
Eremina et al., "Glomerular-specific alterations of VEGF-A expression lead to distinct congenital and acquired renal diseases," Mar. 31, 2003, The Journal of Clinical Investigation, 111[5]:707-716.
FDA, "European Medicines Agency to Consider Additional Test Results When Assessing New Drug Safety-Collaborative effort by FDA and EMEA expected to yield additional safety data," http://www.natap.org/2008/newsUpdates/071608_01.htm dated Jun. 12, 2008.
Ferguson et al., "Biomarkers of nephrotoxic acute kidney injury," Toxicology, Mar. 20, 2008, 245(3):182-193.

(56) References Cited

OTHER PUBLICATIONS

Flynn et al., "Urinary excretion of beta2-glycoprotein-1 (apolipoprotein H) and other markers of tubular malfunction in "non-tubular" renal disease," J Clin Pathol, Jul. 1992, 45(7):561-567.
Frangogiannis, "Chemokines in ischemia and reperfusion," Thromb Haemost, May 2007, 97(5):738-747.
Fried et al., "Inflammatory and Prothrombotic Markers and the Progression of Renal Disease in Elderly Individuals," J Am Soc Nephrol, Dec. 2004, 15(12):3184-3191.
Fujisaki et al., "Infusion of radiocontrast agents induces exaggerated release of urinary endothelin in patients with impaired renal function," Clin Exp Nephrol, Dec. 2003, 7(4):279-283.
Furuichi et al., "Chemokine/chemokine receptor-mediated inflammation regulates pathologic changes from acute kidney injury to chronic kidney disease," Clin Exp Nephrol, Feb. 2009, 13(1):9-14.
Furuichi et al., "Roles of chemokines in renal ischemia/reperfusion injury," Front Biosci, May 1, 2008, 13:4021-4028.
Galkina et al., "Leukocyte Recruitment and Vascular Injury in Diabetic Nephropathy," J Am Soc Nephrol, Feb. 2006, 17(2):368-377.
Garcia et al., "Adenosine A2A receptor activation and macrophagemediated experimental glomerulonephritis," FASEB J, Feb. 2008, 22(2):445-454.
Gbadegesin et al., "Plasma and urinary soluble adhesion molecule expression is increased during first documented acute pyelonephritis," Arch Dis Child, Mar. 2002, 86(3):218-221.
Goes et al., "Effect of Recombinant Human Insulin-Like Growth Factor-1 on the Inflammatory Response to Acute Renal Injury," J Am Soc Nephrol, May 1996, 7(5):710-720.
Grigoryev et al., "The Local and Systemic Inflammatory Transcriptome after Acute Kidney Injury," J Am Soc Nephrol, Mar. 2008, 19(3):547-558.
Grobmeyer et al., "Secretory leukocyte protease inhibitor, an inhibitor of neutrophil activiation, is elevated in serum in human sepsis and experimental endotoxema," Critical Care Medicine, 2000, 28(5):1276-1282.
Gumus et al., "Serum Levels of Total Acid Phosphatase, Prostatic Acid Phosphatase, Total and Free Prostate-Specific Antigen in Patients Within Chronic Hemodialysis Program," Braz J Urol, Mar.-Apr. 2001, 27(2):133-135.
Gupta et al., "Role of Protein C in Renal Dysfunction after Polymicrobial Sepsis," J Am Soc Nephrol, Mar. 2007, 18(3):860-867.
Haase et al., "A comparison of the RIFLE and Acute Kidney Injury Network classifications for cardiac surgery-associated acute kidney injury: A prospective cohort study," J Thorac Cardiovasc Surg, Dec. 2009, 138(6):1370-1376.
Han, "Biomarkers for Early Detection of Acute Kidney Injury," Nephrology Rounds, Apr. 2008, 6(4):6 pp.
Han et al., "Upregulation of hyaluronan and its binding receptors in an experimental model of chronic cyclosporine nephropathy," Nephrology (Carlton), Mar. 2010, 15(2):216-224.
Han et al, "Urinary biomarkers in the early diagnosis of acute kidney injury," Kidney Int, Apr. 2008, 73(7):863-869.
Harpur et al., "Biological Qualification of Biomarkers of Chemical-Induced Renal Toxicity in Two Strains of Male Rat," Toxicol Sci., Aug. 2011, 122(2):235-252.
Harris et al., "Growth Factors and Cytokines in Acute Renal Failure," Adv Ren Replace Ther., Apr. 1997, 4(2 Suppl):43-53.
Hatta et al., "Cytokine Array Comparisons of Plasma from Cycling Fertile Women on Cycle Day 5 and Ovulation," Am J Reprod Immunol, Sep. 2009, 62(3):158-164.
He et al., "Interleukin-18 binding protein transgenic mice are protected against ischemic acute kidney injury," Am J Physiol Renal Physiol, Nov. 2008, 295(5):F1414-F1421.
Herget-Rosenthal et al., "Early detection of acute renal failure by serum cystatin C," Kidney Int., Sep. 2004, 66(3):1115-1122.
Hidaka et al., "Urinary clusterin levels in the rat correlate with the severity of tubular damage and may help to differentiate between glomerular and tubular injuries," Cell Tissue Res, Dec. 2002, 310(3):289-296.
Hiemstra, "Novel roles of protease inhibitors in infection and inflammation," Biochem Soc Trans, Apr. 2002, 30(2):116-20—Abstract Only.
Hirai et al., "Plasma endothelin-1(ET-1) is a useful marker for renal dysfunction," Atheroscler Suppl, Jun. 19, 2006, 7(3):60[Mo-P1:65].
Hirschberg et al., "Factors Predicting Poor Outcome in Patients with Acute Renal Failure (ARF)," J Am Soc Nephrol, Sep. 1, 1996, 7(9):1374.
Hoste et al., "RIFLE criteria for acute kidney injury are associated with hospital mortality in critically ill patients: a cohort analysis," Crit Care, 2006, 10(3):R73 (10 pp).
Hugo et al. ,"Thrombospondin 1 precedes and predicts the development of tubulointerstitial fibrosis in glomerular disease in the rat," Kidney Int, Feb. 1998, 53(2):302-311.
Hugo et al., "Thrombospondin in Renal Disease," Nephron Exp Nephrol, 2009, 111(3):e61-e66.
Iglesias et al., "Thyroid Dysfunction and Kidney Disease," Revised version, Eur J Endocrinol, Dec. 18, 2008, 32 pp retrieved from URL:///www.eje.org/content!early/2008/12/18/EJE-08-0837.full.pdf.
Ishii et al., "Establishment of enzyme immunoassay of human thrombomodulin in plasma and urine monoclonal antibodies," Thromb Haemost, Journal, 1990, 63(2):157-162—Abstract Only.
Jang et al., "The innate immune response in ischemic acute kidney injury, Clin Immunol," Jan. 2009, 130(1):41-50.
Jonsson, "The role of fibroblast growth factor 23 in renal disease," Nephrol Dial Transplant, Mar. 2005, 20(3):479-482.
Julian et al., "Sources of Urinary Proteins and their Analysis by Urinary Proteomics for the Detection of Biomarkers of Disease," Proteomics Clin Appl, 2009, 3(9):1029-1043.
Jung et al., Diagnostic significance of urinary enzymes in detecting acute rejection crises in renal transplant recipients depending on expression of results illustrated through the example of alanine aminopeptidase, Clin Biochem, Aug. 1985, 18(4):257-260.
Kadiroglu et al., "The Evaluation of Effects of Demographic Features, Biochemical Parameters, and Cytokines on Clinical Outcomes in Patients with Acute Renal Failure," Ren Fail, 2007, 29(4):503-508.
Kalousova et al., "Soluble Receptor for Advanced Glycation End Products in Patients With Decreased Renal Function," Am J Kidney Dis, Mar. 2006, 47(3): 406-411.
Kasahara et al., "Clinical Significance of Serum Oxidized Low-Density Lipoprotein/beta2-Giycoprotein I Complexes in Patients with Chronic Renal Diseases," Nephron Clin Pract, 2004, 98(1):15-24.
Kehoe et al., "Elevated Plasma Renin Activity Associated with Renal Dysfunction," Nephron, 1986, 44:51-57—Abstract Only.
Kellum et al., "Definition and Classification of Acute Kidney Injury," Nephron Clin Pract, 2008, 109(4):c182-c187.
Keyes et al., "Early diagnosis of acute kidney injury in critically ill patients," Expert Rev Mol Diagn, Jul. 2008, 8(4):455-464.
Kharasch et al., "Gene Expression Profiling of Nephrotoxicity from the Sevoflurane Degradation Product Fluoromethy1-2,2-difluoro-1-(trifluoromethyl)vinyl Ether ("Compound A") in Rats," Toxicol Sci, Apr. 2006, 90(2):419-431.
Kiley et al., "Urinary biomarkers: The future looks promising," Kidney Int, Jul. 2009, 76(2):133-134.
Kilis-Pstrusinska et al., "Levels of selected soluble adhesion molecules in blood serum of children with chronic glomerulonephritis, Pol Merkur Lekarski, Apr. 2001, 10(58):247-249.
Kilis-Pstrusinska et al., "Serum levels of soluble adhesion molecules in children with glomerulonephritis (GN)," Nephrol Dialysis Transplant, Jun. 2001, 16(6):A62.
Kimmel et al., "Immunologic function and survival in hemodialysis patients," Kidney Int, Jul. 1998, 54(1):236-244.
Kinsey et al., "Inflammation in Acute Kidney Injury," Nephron Exp Nephrol, 2008, 109(4):e102-e107.
Koo et al., "Cadaver versus living donor kidneys: Impact of donor factors on antigen induction before transplantation," Kidney Int, Oct. 1999, 56(4):1551-1559.
Kos et al., "Cathepsins B,H and L and Their Inhibitors Stefin A and Cystatin C in Sera of Melanoma Patients," Clin Cancer Res, Oct. 1997, 3(10):1815-1822.

(56) References Cited

OTHER PUBLICATIONS

Landray et al., "Inflammation, Endothelial Dysfunction, and Platelet Activation in Patients With Chronic Kidney Disease: The Chronic Renal Impairment in Birmingham (CRIB) Study," Am J Kidney Dis, Feb. 2004, 43(2):244-253.
Lang et al., "Heat Shock Protein 60 Is Released in Immune-Mediated Glomerulonephritis and Aggravates Disease: In Vivo Evidence for an Immunologic Danger Signal," J Am Soc Nephrol, Feb. 2005, 16(2):383-391.
Lapsley et al., "Beta2-glycoprotein-1 (apolipoprotein H) excretion in chronic renal tubular disorders: Comparison with other protein markers of tubular malfunction," J Clin Pathol, Oct. 1991, 44(10):812-816.
Larsson et al., "Circulating concentration of FGF-23 increases as renal function declines in patients with chronic kidney disease, but does not change in response to variation in Phosphate intake in healthy volunteers," Kidney Int, Dec. 2003, 64(6):2272-2279.
Lemancewicz et al., "Matrix metalloproteinase-2 and tissue inhibitor of metalloproteinase-2 urine levels in preterm laboring patients," Archives of Perinatal Medicine, 2007, 13(2):50-52.
Li et al., "Predictive value of RIFLE classification on prognosis of critically ill patients with acute kidney injury treated with continuous renal replacement therapy," Chin Med J (Engl), May 5, 2009, 122(9):1020-1025.
Liu et al., "Predictive and pathogenetic value of plasma biomarkers for acute kidney injury in patients with acute lung injury," Crit Care Med, Dec. 2007, 35(12):2755-2761.
Liu et al., "Serum Interleukin-6 and interleukin-8 are early biomarkers of acute kidney injury and predict prolonged mechanical ventilation in children undergoing cardiac surgery: a case-control study," Critical Care, 2009, 13(4):R104 (9 pp).
Lopes-Virella et al., "Urinary high density lipoprotein in minimal change glomerular disease and chronic glomerulopathies," Clin Chim Acta, May 16, 1979, 94(1):73-81.
Lu et al., "Increased Macrophage Infiltration and Fractalkine Expression in Cisplatin-Induced Acute Renal Failure in Mice," J Pharmacol Exp Ther, Jan. 2008, 324(1):111-117.
Maddens et al., "Chitinase-like Proteins are Candidate Biomarkers for Sepsis-induced Acute Kidney Injury," Mol Cell Proteomics, Jan. 10, 2012, 11(6):1-13.
Malm et al., "Changes in the plasma levels of vitamin K-dependent proteins C and S and of C4b-binding protein during pregnancy and oral contraception," Br J Haematol, Apr. 1988, 68(4):437-443.
Malyszko et al., "Visfatin and apelin, new adipocytokines, and their relation to endothelial function in patients with chronic renal failure," Adv Med Sci, 2008, 53(1):32-36.
Mast et al., "Clinical utility of the soluble transferrin receptor and comparison with serum ferritin in several populations," Clin Chem, Jan. 1998, 44(1):45-51.
Matousovic et al., "IgA-containing immune complexes in the urine of IgA nephropathy patients," Nephrol Dial Transplant, Sep. 2006, 21(9):2478-2484.
Matsuda et al., "Beta 2-Glycoprotein I-Dependent and -Independent Anticardiolipin Antibody in Patients with End-Stage Renal Disease," Thromb Res, Oct. 15, 1993, 72(2):109-117.
Matsuzaka et al., "Relationship between vitamin K dependent coagulation factors and anticoagulants (protein C and protein S) in neonatal vitamin K deficiency," Arch Dis Child, Mar. 1993, 68(3 Spec No):297-302.
Mattes, "Experience With a Biomarker Consortium," CPath Predictive Safety Training Consortium, Critical Path Institute:48 pp.
Melnikov et al., "Impaired IL-18 processing protects caspase-1-deficient mice from ischemic acute renal failure," J Clin Invest, May 2001, 107(9):1145-1152.
Mezzano et al., "Endothelial Cell Markers in Chronic Uremia: Relationship with Hemostatic Defects and Severity of Renal Failure," Thromb Res, Dec. 15, 1997, 88(6):465-472.
Milford et al., "Prognostic Markers in Diarrhoea-Associated Haemolytic-Uraemic Syndrome: Initial Neutrophil Count, Human Neutrophil Elastase and Von Willebrand Factor Antigen," Nephrol Dial Transplant, 1991, 6(4):232-237.
Mishra et al., "Neutrophil gelatinase-associated lipocalin (NGAL) as a biomarker for acute renal injury after cardiac surgery," Lancet, Apr. 2-8, 2005, 365(9466):1231-1238.
Montagna et al., "Impairment of cellular redox status and membrane protein activities in kidneys from rats with ischemic acute renal failure," Biochim Biophys Acta, Aug. 14, 1998, 1407(2):99-108.
Moreau et al., "Multifaceted roles of human elafin and secretory leukocyte proteinase inhibitor (SLPI), two serine protease inhibitors of the chelonianin family," Biochimie, 2008, 90:284-295.
Musial et al., "The Heat Shock Protein Profile in Children with Chronic Kidney Disease," Pent Dial Int, Mar.-Apr. 2010, 30(2):227-232.
Musial et al., "Soluble adhesion molecules in chronic renal failure (CRF) children treated conservatively," Nephrol Dialysis Transplant, 2002, 17(Abstracts Suppl 1):232.
Nambi et al., "Down regulation of kidney neutral endopeptidase mRNA, protein and activity during acute renal failure: possible mechanism for ischemia-induced acute renal failure in rats?," Mol Cell Biochem, Jul. 1999, 197(1-2):53-59.
Neziri et al., "Cloning and molecular characterization of Dashurin encoded by C20orf116, a PCI-domain containing protein," Biochim Biophys Acta, Apr. 2010, 1800(4):430-438.
Nguyen et al., "Heparin-Binding EGF-Like Growth Factor Is Up-Regulated in the Obstructed Kidney in a Cell- and Region-Specific Manner and Acts to Inhibit Apoptosis," Am J Pathol, Mar. 2000, 156(3):889-898.
Nishiyama et al., "Up-Regulation of Galectin-3 in Acute Renal Failure of the Rat," Am J Pathol, Sep. 2000, 157(3):815-823.
Norman et al., "Progressive Renal Disease: Fibroblasts, Extracellular Matrix, and Integrins," Exp Nephrol, Mar.-Apr. 1999, 7(2):167-177.
Ohlsson et al., "Novel distribution of the secretory leucocyte proteinase inhibitor in kidney," Mediators of inflammation, 2001, 10:347-350.
Ohno et al., "Prognostic significance of tenascin-C expression in clear cell renal cell carcinoma," Oncol Rep, 2008, 20(3):511-516.
Ozer et al., "A panel of urinary biomarkers to monitor reversibility of renal injury and a serum marker with improved potential to assess renal function," Nat Biotechnol, May 2010, 28(5):486-494.
Parikh et al., "New biomarkers of acute kidney injury," Crit Care Med, 2008, 36(4 Suppl):S159-S165.
Parikh et al., "Urinary IL-18 is an early predictive biomarker of acute kidney injury after cardiac surgery," Kidney Int, 2006, 70(1):199-203.
Perco et al., "Protein biomarkers associated with acute renal failure and chronic kidney disease," Eur J Clin Invest, Nov. 2006, 36(11):753-763.
Picard et al., "Origin of renal myofibroblasts in the model of unilateral ureter obstruction in the rat," Histochem Cell Biol, Jul. 2008, 130(1):141-155.
Price, "Abrupt Changes in Prostate-Specific Antigen Concentration in Acute Renal Failure," Clin Chem, Jan. 1993, 39(1):161-162.
Prozialeck et al., "Cell Adhesion Molecules in Chemically-Induced Renal Injury," Pharmacol Ther, Apr. 2007, 114(1):74-93.
Radford et al., "Predicting renal outcome in IgA nephropathy," J Am Soc Nephrol, Feb. 1997, 8(2):199-207.
Rajashekar et al., "Systemic diseases with renal manifestations," Prim Care, Jun. 2008, 35(2):297-328—abstract retrieved from URL:www.ncbi.nlm.nih.gov/pubmed/18486717.
Ramesh et al., "Endotoxin and cisplatin synergistically induce renal dysfunction and cytokine production in mice," Am J Physiol Renal Physiol, Jul. 2007, 293(1):F325-F332.
Ramesh et al., "INF—a mediates chemokine and cytokine expression and renal injury in cisplatin nephrotoxicity," J Clin Invest, Sep. 2002, 110(6):835-842.
Ramirez et al., "Prospective Study on Autoantibodies Against Apolipoprotein H ( B2GPI) in Several Clinical Parameters From Patients With Terminal Renal Failure and Functioning Renal Transplants," Transplantation Proceedings, Jul. 2009, 41(6):2370-2372.

(56) References Cited

OTHER PUBLICATIONS

Rini et al., "Renal cell carcinoma," Lancet, Mar. 28, 2009, 373(9669):1119-1132.
Rosenkranz et al., "P-selectin deficiency exacerbates experimental glomerulonephritis: a protective role for endothelial P-selectin in inflammation," J Clin Invest, Mar. 1999, 103(5):649-659.
Rouschop et al., "Pre-transplant plasma and cellular levels of CD44 correlate with acute renal allograft rejection," Nephrol Dial Transplant, Oct. 2005, 20(10):2248-2254.
Rouschop et al., "Renal expression of CD44 correlates with acute renal allograft rejection," Kidney Int, Sep. 2006, 70(6):1127-1134.
Schaefer et al., "Urinary excretion of cathepsin B and cystatins as parameters of tubular damage," Kidney Int Suppl, Nov. 1994, 47:S64-567.
Schena et al., "EGF and MCP-1 Urinary Excretion Is a Suitable Prognostic Marker in Iga Nephropathy. J Am Soc of Nephrology; Meeting of The American Society of Nephrology," Sep. 1, 2002, 13(Program and Abstracts Issue):458A.
Schiffer et al., "Activated Renal Macrophages Are Markers of Disease Onset and Disease Remission in Lupus Nephritis," J Immunol, Feb. 1, 2008, 180(3):1938-1947.
Schmaldienst et al., Angiogenin: a novel inhibitor of neutrophil-lactoferrin release during extracorporeal circulation, Kidney Blood Press Res, 2003, 26(2):107-112.
Schmidt et al., "Sexual hormone abnormalities in male patients with renal failure," Nephrol Dial Transplant, Mar. 2002, 17(3):368-371.
Schrijvers et al., "The role of vascular endothelial factor (VEGF) in renal pathophysiology," Kidney International, 2004, 65:2003-2017.
Schulz et al., "Endothelin-1 as an early prognostic marker in acute renal failure (ARF) and sepsis. Kidney Blood Press Res," 2000, 23(3-5):341-342.
Segawa et al., "In situ expression and soluble form of P-selectin in human glomerulonephritis," Kidney Int, Oct. 1997, 52(4):1054-1063.
Segerer et al., "Chemokines, Chemokine Receptors, and Renal Disease: From Basic Science to Pathophysiologic and Therapeutic Studies," J Am Soc Nephrol, Jan. 2000, 11(1):152-176.
Senatorski et al., "Urine activity of cathepsin B, collagenase and urine excretion of TGF-beta1 and fibronectin in membranous glomerulonephritis," Res Exp Med (Berl), Dec. 1998, 198(4):199-206.
Severini et al., "Diagnostic significance of urinary enzymes: Development of a high performance liquid chromatographic method for the measurement of urinary lysozyme," Clin Chim Acta, Feb. 27, 1987, 163(1):97-103.
Sharma et al., "Two-dimensional fluorescence difference gel electrophoresis analysis of the urine proteome in human diabetic nephropathy," Proteomics, Jul. 2005, 5(10):2648-2655.
Shimano et al., "Elevated serum and urinary thrombomodulin levels in patients with non-insulin-dependent diabetes mellitus," Clinica Chimica Acta, 1994, 225:89-96.
Shlipak et al., "Elevations of Inflammatory and Procoagulant Biomarkers in Elderly Persons With Renal Insufficiency," Circulation, Jan. 2003, 107(1):87-92.
Shoji et al., "Plasma angiopoietin-like protein 3 (ANGPTL3) concentration is associated with uremic dyslipidemia," Atherosclerosis, Dec. 2009, 207(2):579-584.
Simmons et al., "Plasma cytokine levels predict mortality in patients with acute renal failure," Kidney Int, Apr. 2004, 65(4):1357-1365.
Song et al., "Expression of TRAIL, DR4, and DR5 in kidney and serum from patients receiving renal transplantation," Transplant Proc, Jun. 2004, 36(5):1340-1343.
Stafford-Smith et al., "Acute Kidney Injury and Chronic Kidney Disease After Cardiac Surgery," Adv Chronic Kidney Dis, Jul. 2008, 15(3):257-277.
Stasko et al., "Soluble P-Selectin During a Single Hemodialysis Session in Patients With Chronic Renal Failure and Erythropoietin Treatment," Clin Appl Thromb Hemost, Oct. 2007, 13(4):410-415.
Stenvinkel et al., "High Serum Hyaluronan Indicates Poor Survival in Renal Replacement Therapy," Am J Kidney Dis, Dec. 1999, 34(6):1083-1088.
Stuard et al., "Soluble adhesion molecules in chronic renal failure patients," Nephrol Dialysis Transplant, 1997, 12(9):A100.
Sun et al., "A Survey on the Relationship between the Epidermal Growth Factor and Renal Function," Int J Transpl Hemopurific, Dec. 31, 2006, 4(1):41-44—abstract English translation.
Supavekin et al., "Differential gene expression following early renal ischemia/repertusion," Kidney Int, May 2003, 63(5):1714-1724.
Sutton, "Alteration of microvascular permeability in acute kidney injury," Microvasc Res, Jan. 2009, 77(1):4-7.
Sutton et al., "Injury of the renal microvascular endothelium alters barrier function after ischemia," Am J Physiol Renal Physiol, Aug. 2003, 285(2):F191-F198.
Sutton et al., "Microvascular endothelial injury and dysfunction during ischemic acute renal failure," Kidney Int, Nov. 2002, 62(5):1539-1549.
Symon et al., "The endogenous insulin-like growth factor system in radiocontrast nephropathy," Am J Physiol Renal Physiol, Mar. 1998, 274(3 Pt 2):F490-497.
Takada et al., "The Cytokine-adhesion Molecule Cascade in Ischemia/Reperfusion Injury of the Rat Kidney. Inhibition by a Soluble P-selectin Ligand," J Clin Invest, Jun. 1997, 99(11):2682-2690.
Tan et al., "The level of urinary secretory immunoglobulin a (sIgA) of patients with IgA nephropathy is elevated and associated with pathological phenotypes," Clin Exp Immunol, Apr. 2009, 156(1):111-116.
Tao et al., "Expression of 60-kDa and Inducible 70-kDa Stress Proteins in Gentamicin-Induced Acute Renal Failure," Clin Exp Nephrol, Jul. 1997, 1:254-260.
Tary-Lehmann et al., "Enzyme-Linked Immunosorbent Assay Spot Detection of Interferon-Gamma and Interleukin 5-Producing Cells as a Predictive Marker for Renal Allograft Failure," Transplantation, Jul. 27, 1998, 66(2):219-224.
Taulan et al., "Comprehensive analysis of the renal transcriptional response to acute uranyl nitrate exposure," BMC Genomics, Jan. 11, 2006, 7(2):14 pp.
Teppo et al., "Soluble Intercellular Adhesion Molecule-1 (Sicam-1) after Kidney Transplantation: The Origin and Role of Urinary Sicam-1?," Transplantation, Apr. 27, 2001, 71(8):1113-1119.
Thaker et al., "Identification of thrombospondin 1 (TSP-1) as a novel mediator of cell injury in kidney ischemia," J Clin Invest, Dec. 2005, 115(12):3451-3458.
Thiemermann et al., "High Density Lipoprotein (HDL) Reduces Renal Ischemia/Reperfusion Injury," J Am Soc Nephrol, 2003, 14:1833-1843.
Thorburn et al., "CXC and CC chemokines induced in human renal epithelial cells by inflammatory cytokines," APMIS, Jul. 2009, 117(7):477-487.
Timoshanko et al., "Interleukin-12 from Intrinsic Cells Is an Effector of Renal Injury in Crescentic Glomerulonephritis," J Am Soc Nephrol, Mar. 2001, 12(3):464-471.
Torres et al., "The ratio of epidermal growth factor to monocyte chemotactic peptide-1 in the urine predicts renal prognosis in IgA nephropathy," Kidney Int, Feb. 2008, 73(3):327-333.
Vaidya et al., "Biomarkers of Acute Kidney Injury," Annu Rev Pharmacol Toxicol, Feb. 2008, 48:463-493.
Vaidya et al., "Mechanistic biomarkers for cytotoxic acute kidney injury," Expert Opin Drug Metab Toxicol, Oct. 2006, 2(5):697-713.
Vanhoutte et al., "Biomarker discovery with SELDI-TOF MS in human urine associated with early renal injury: evaluation with computational analytical tools," Nephrol Dial Transplant, Oct. 2007, 22(10):2932-2943.
Villanueva et al., "Ischemic acute renal failure induces the expression of a wide range of nephrogenic proteins," Am J Physiol Regul Integr Comp Physiol, Apr. 2006, 290(4):R861-R870.
Vonderscher, "Biomarker of Drug Induced Kidney Injury Qualification for Regulatory Decision Making (CRADA)," IOM/FDA, Silver Spring, MD, Apr. 23, 2007, 31 pp.
Voshol et al., "Evaluation of Biomarker Discovery Approaches to Detect Protein Biomarkers of Acute Renal Allograft Rejection," J Proteome Res, Jul.-Aug. 2005, 4(4):1192-1199.

(56) References Cited

OTHER PUBLICATIONS

Waikar et al., "Diagnosis, Epidemiology and Outcomes of Acute Kidney Injury," Clin J Am Soc Nephrol, May 2008, 3(3):844-861.
Waku et al., "Serum Level of Human Tissue Inhibitor Metalloproteinase-1 in Various Glomerulonephritides," J Kyorin Med Soc, 1997, 28:441-447—Abstract only.
Wan et al., "The pathogenesis of septic acute renal failure," Curr Opin Crit Care, Dec. 2003, 9(6):496-502.
Wang et al., "Netrin-1 and kidney injury. I. Netrin-1 protects against ischemia-repertusion injury of the kidney," Am J Physiol Renal Physiol, Apr. 2008, 294(4):F739-F747.
Wang et al., "Validation of putative genomic biomarkers of nephrotoxicity in rats," Toxicology, Apr. 18, 2008, 246(2-3):91-100.
Wasileska et al., "Urinary levels of matrix metalloproteinases and their tissue inhibitors in nephrotic children," Pediatr Nephrol, Jul. 2, 2008, 23(10):1795-1802.
Wilson et al., "Urinary lysozyme," J Pediatr, Feb. 1950, 36(2):199-211.
Winchester et al., "Sorbents in Acute Renal Failure and End-Stage Renal Disease: Middle Molecule and Cytokine Removal," Blood Purif, 2004, 22(1):73-77.
Yang et al., "Frequency of anti-bactericidal/permeability-increasing protein (BPI) and anti-azurocidin in patients with renal disease," Clin Exp Immunol, Jul. 1996, 105(1):125-131.
Yu et al., "Urinary biomarkers trefoil factor 3 and albumin enable early detection of kidney tubular injury," Nat Biotechnol, May 2010, 128(5):470-477.
Yuen et al., "Ischemic and Nephrotoxic Acute Renal Failure are Distinguished by their Broad Transcriptomic Responses," Physiol Genomics, May 16, 2006, 25(3):375-386.
Zaffanello et al., "Early diagnosis of acute kidney injury with urinary biomarkers in the newborn," J Matern Fetal Neonatal Med, 2009, 22(Suppl 3):62-66.
Zager et al., "Proximal tubular cytochrome c efflux: Determinant, and potential marker, of mitochondrial injury," Kidney Int, Jun. 2004, 65(6):2123-2134.
Zhang et al., "The level of serum secretory IgA of patients with IgA nephropathy is elevated and associated with pathological phenotypes," Nephrol Dial Transplant, Jan. 2008, 23(1):207-212.
Zheng et al., "Antiphospholipid antibody profiles in lupus nephritis with glomerular microthrombosis: a prospective study of 124 cases," Arthritis Res Ther, 2009, 11(3):1-9.
Zhu et al., "Expression of Urinary Epidermal Growth Factor and Renal Function," J Clin Urol, Dec. 31, 1998, 13(8):374-379—English translation abstract.
Extended European Search Report and Written Opinion dated Feb. 23, 2012 in PCT/US2009/065419.
Extended European Search Report and Written Opinion dated Dec. 3, 2012 in PCT/US2010/044772.
Extended European Search Report and Written Opinion dated Apr. 15, 2013 in EP 10817878.
Extended European Search Report and Written Opinion dated May 21, 2013 in EP 10829198.
Extended European Search Report and Written Opinion dated May 24, 2013 in EP 10829191.
Extended European Search Report and Written Opinion dated Jun. 3, 2013 in EP 10838357.
Extended European Search Report and Written Opinion dated Jun. 6, 2013 in EP 10818036.
Extended European Search Report and Written Opinion dated Jun. 13, 2013 in EP 11740468.
Extended European Search Report and Written Opinion dated Jun. 13, 2013 in EP 11740469.
Extended European Search Report and Written Opinion dated Jun. 18, 2013 in EP 11740470.
Extended European Search Report and Written Opinion dated Jul. 9, 2012 in PCT/US2010/023292.
Extended European Search Report and Written Opinion dated Jul. 16, 2013 in EP 10812639.
Extended European Search Report and Written Opinion dated Jul. 27, 2012 in PCT/US2010/023294.
Extended European Search Report and Written Opinion dated Aug. 13, 2013 in EP 11751238.
Extended European Search Report and Written Opinion dated Aug. 16, 2013 in EP 11748210.
Extended European Search Report and Written Opinion dated Aug. 23, 2012 in PCT/US2009/061562.
Extended European Search Report and Written Opinion dated Aug. 23, 2012 in PCT/US2010/023297.
Extended European Search Report and Written Opinion dated Oct. 24, 2011 in PCT/US2009/055449.
Extended European Search Report and Written Opinion dated Dec. 3, 2012 in PCT/US2010/044708.
Extended European Search Report and Written Opinion dated Feb. 22, 2012 in PCT/US2009/055460.
Extended European Search Report and Written Opinion dated Jun. 8, 2012 in PCT/US2009/063906.
Extended European Search Report and Written Opinion dated Jul. 9, 2012 in European Application No. 09822669.9.
Final Office Action dated Jun. 7, 2013 by the USPTO in U.S. Appl. No. 13/061,446.
Final Office Action dated Aug. 23, 2013 by the USPTO in U.S. Appl. No. 13/061,413.
International Preliminary Report on Patentability dated Mar. 10, 2011 in PCT/US2009/055449.
International Preliminary Report on Patentability dated Mar. 10, 2011 in PCT/US2009/055460.
International Preliminary Report on Patentability dated Mar. 29, 2011 in PCT/US2010/049234.
International Preliminary Report on Patentability dated Apr. 5, 2012 in PCT/US2010/049695.
International Preliminary Report on Patentability dated May 5, 2011 in PCT/US2009/061561.
Copy of International Preliminary Report on Patentability dated May 5, 2011 in PCT/US2009/061562.
International Preliminary Report on Patentability dated May 10, 2011 in PCT/US2009/063906.
International Preliminary Report on Patentability dated May 18, 2012 in PCT/US2010/055730.
International Preliminary Report on Patentability dated May 24, 2013 in PCT/US2011/055055.
International Preliminary Report on Patentability dated Jun. 3, 2011 in PCT/US2009/065419.
International Preliminary Report on Patentability dated Jul. 5, 2012 in PCT/US2010/061377.
International Preliminary Report on Patentability dated Aug. 16, 2012 in PCT/US2011/023830.
International Preliminary Report on Patentability dated Aug. 16, 2012 in PCT/US2011/023831.
International Preliminary Report on Patentability dated Aug. 16, 2012 in PCT/US2011/023832.
International Preliminary Report on Patentability dated Aug. 18, 2011 in PCT/US2010/023292.
International Preliminary Report on Patentability dated Aug. 18, 2011 in PCT/US2010/023294.
International Preliminary Report on Patentability dated Sep. 7, 2012 in PCT/US2011/026384.
International Preliminary Report on Patentability dated Oct. 21, 2011 in PCT/US2010/023297.
International Search Report and Written Opinion dated Jan. 15, 2010 in PCT/US2009/063906.
International Search Report and Written Opinion dated Jan. 18, 2012 in PCT/US2011/053015.
International Search Report and Written Opinion dated Jan. 19, 2011 in PCT/US2010/055721.
International Search Report and Written Opinion dated Jan. 20, 2010 in PCT/US2009/061561.
International Search Report and Written Opinion dated Feb. 8, 2011 in PCT/US2010/055730.
International Search Report and Written Opinion dated Feb. 24, 2012 in PCT/US2011/055055.

(56) References Cited

OTHER PUBLICATIONS

International Search Report and Written Opinion dated Mar. 8, 2011 in PCT/US2010/061377.
International Search Report and Written Opinion dated Mar. 15, 2013 in PCT/US2012/066152.
International Search Report and Written Opinion dated Mar. 30, 2010 in PCT/US2009/065419.
International Search Report and Written Opinion dated Apr. 13, 2010 in PCT/US2009/061562.
International Search Report and Written Opinion dated Apr. 22, 2010 in PCT/US2010/023294.
International Search Report and Written Opinion dated Apr. 27, 2011 in PCT/US2011/023830.
International Search Report and Written Opinion dated Apr. 27, 2011 in PCT/US2011/023831.
International Search Report and Written Opinion dated Apr. 29, 2011 in PCT/US2011/023832.
International Search Report and Written Opinion dated Apr. 30, 2010 in PCT/US2010/023292.
International Search Report and Written Opinion dated May 2, 2012 in PCT/US2012/022926.
International Search Report and Written Opinion dated May 10, 2012 in PCT/US2012/020571.
International Search Report and Written Opinion dated Jun. 3, 2010 in PCT/US2010/023297.
International Search Report and Written Opinion dated Jun. 3, 2011 in PCT/US2011/026759.
International Search Report and Written Opinion dated Jun. 18, 2013 in PCT/US2013/028005.
International Search Report and Written Opinion dated Jun. 20, 2012 in PCT/US2012/020572.
International Search Report and Written Opinion dated Jun. 30, 2011 in PCT/US2011/026384.
International Search Report and Written Opinion dated Sep. 7, 2012 in PCT/US2012/043279.
International Search Report and Written Opinion dated Sep. 21, 2012 in PCT/US2012/045583.
International Search Report and Written Opinion dated Oct. 8, 2010 in PCT/US2010/044708.
International Search Report and Written Opinion dated Oct. 28, 2010 in PCT/US2010/044772.
International Search Report and Written Opinion dated Nov. 18, 2010 in PCT/US2010/046910.
International Search Report and Written Opinion dated Nov. 23, 2013 in 200980154224.5.
International Search Report and Written Opinion dated Nov. 25, 2011 in PCT/US2011/001125.
International Search Report and Written Opinion dated Nov. 25, 2011 in PCT/US2011/001127.
International Search Report and Written Opinion dated Nov. 25, 2011 in PCT/US2011/001128.
International Search Report and Written Opinion dated Dec. 3, 2010 in PCT/US2010/049234.
International Search Report and Written Opinion dated Dec. 3, 2010 in PCT/US2010/049695.
International Search Report and Written Opinion dated Dec. 10, 2009 in PCT/US2009/055449.
International Search Report and Written Opinion dated Dec. 15, 2011 in PCT/US2011/001126.
International Search Report and Written Opinion dated Dec. 31, 2009 in PCT/US2009/055460.
Non-Final Office Action dated Jan. 2, 2013 by the USPTO in U.S. Appl. No. 13/061,413.
Non-Final Office Action dated Jun. 20, 2013 by the USPTO in U.S. Appl. No. 13/577,242.
Non-Final Office Action dated Jan. 24, 2013 by the USPTO in U.S. Appl. No. 13/125,360.
Non-Final Office Action dated Feb. 1, 2013 by the USPTO in U.S. Appl. No. 13/508,363.
Non-Final Office Action dated Feb. 5, 2013 in Japanese Patent Application No. 2011-525262.
Non-Final Office Action dated Feb. 5, 2013 in Japanese Patent Application No. 2011-525262—includes English translation.
Non-Final Office Action dated Feb. 14, 2013 by the USPTO in U.S. Appl. No. 13/577,243.
Non-Final Office Action dated Mar. 5, 2013 by the USPTO in U.S. Appl. No. 13/125,454.
Non-Final Office Action dated Apr. 18, 2013 by the USPTO in U.S. Appl. No. 13/389,363.
Non-Final Office Action dated May 1, 2013 by the USPTO in U.S. Appl. No. 13/148,030.
Non-Final Office Action dated Aug. 27, 2013 by the USPTO in U.S. Appl. No. 13/125,360.
Non-Final Office Action dated Oct. 12, 2012 by the USPTO in U.S. Appl. No. 13/061,446.
Non-Final Office Action dated Nov. 16, 2012 by the USPTO in U.S. Appl. No. 13/389,351.
Non-Final Office Action dated Nov. 27, 2012 by the USPTO U.S. Appl. No. 13/130,474.
Non-Final Office Action dated Dec. 17, 2012 in 2009801542245.
Non-Final Office Action dated Dec. 18, 2012 by the USPTO in U.S. Appl. No. 13/164,768.
Office Action and Search Report dated Apr. 23, 2013 by SIPO in Chinese Application No. 200980140805.3—includes English Translation rec'd May 16, 2013.
Office Action dated Jan. 6, 2014 by SIPO in Chinese Application No. 200980149555.X—includes English translation.
Office Action dated Mar. 7, 2013 in Mexican Application No. MX/a/2011/004174.
Office Action dated May 29, 2013 by SIPO in 2009801406946—includes English translation.
Office Action dated Jun. 25, 2013 by SIPO in Application No. 201080014932.1—includes English translation.
Office Action dated Jul. 1, 2013 by SIPO in Application No. 200980149555.X—includes English translation.
Office Action dated Jul. 1, 2013 by SIPO in Application No. 200980149636.X—includes English translation.
Office Action dated Jul. 18, 2013 by SIPO in Application No. 201080057014.7—includes English translation.
Office Action dated Sep. 12, 2018 in European Application No. 17174892.4.
Office Action dated Oct. 8, 2013 in Japanese Application No. 2011-532354.
Office Action dated Sep. 16, 2014 in Japanese Application No. 2011-532354.
Response dated May 16, 2012 to Extended European Search Report and Written Opinion in PCT/US2009/055449.
Response to Non-Final Office Action dated Jul. 2, 2013 issued in U.S. Appl. No. 13/061,413.
Response to Restriction Requirement dated Oct. 16, 2012 in U.S. Appl. No. 13/061,413.
Restriction Requirement dated Mar. 20, 2013 by the USPTO in U.S. Appl. No. 13/148,031.
Restriction Requirement dated Jul. 1, 2013 by the USPTO in U.S. Appl. No. 13/517,244.
Restriction Requirement dated Sep. 5, 2012 by the USPTO in U.S. Appl. No. 13/061,413.
Search Report and Written Opinion dated Apr. 15, 2013 by SIPO in 2009801406946—includes English translation.
Search Report and Written Opinion dated May 15, 2013 in PCT/US2013/023479.
Search Report dated May 23, 2013 by SIPO in Application No. 200980149555.X—includes English translation.
Search Report dated Jun. 9, 2013 by SIPO in Application No. 201080014932.1—includes English translation.
Search Report dated Jun. 17, 2013 by SIPO in Application No. 200980149636.X—includes English translation.
Search Report dated Jul. 8, 2013 by SIPO in Application No. 201080057014.7—includes English translation.
English Translation of International Search Report and Written Opinion dated Nov. 23, 2012 in 200980154224.5.

(56) References Cited

OTHER PUBLICATIONS

Official action dated Aug. 30, 2013 issued in Australian application (No. 2009308497).
Official action dated Feb. 28, 2014 issued in Australian application (No. 2009308497).
Official action dated Oct. 16, 2013 issued in Australian application (No. 2011220413).
Official action dated Aug. 30, 2013 issued in Australian application (No. 2013202655).
Official action dated Apr. 1, 2016 issued in Canadian application (No. 2,740,788).
Official action dated Jan. 22, 2018 issued in Canadian application (No. 2,740,788).
Official action dated Jan. 8, 2019 issued in Canadian application (No. 2,740,788).
Official action dated Sep. 20, 2019 issued in Canadian application (No. 2,740,788).
Official action dated Nov. 29, 2016 issued in European application (No. 09822669.9).
Official action dated Jul. 26, 2019 issued in European application (No. 17174892.4).
Official action dated Jun. 20, 2019 issued in Indian application (No. 968/MUMNP/2011).
Official action dated Oct. 21, 2011 issued in New Zealand application (No. 592358).
Official action dated Mar. 4, 2013 issued in New Zealand application (No. 607703).
Official action dated Sep. 3, 2014 issued in New Zealand application (No. 628843).

* cited by examiner

Aspartate aminotransferase, cytoplasmic sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 8.010 | 7.310 | 8.010 | 7.750 | 8.010 | 8.670 |
| average | 9.193 | 8.274 | 9.193 | 9.452 | 9.193 | 10.558 |
| stdev | 8.833 | 7.266 | 8.833 | 7.741 | 8.833 | 7.928 |
| p (t-test) |  | 0.479 |  | 0.833 |  | 0.442 |
| min | 0.527 | 0.584 | 0.527 | 0.865 | 0.527 | 0.931 |
| max | 104.000 | 36.100 | 104.000 | 41.200 | 104.000 | 31.500 |
| n (Samp) | 249 | 53 | 249 | 62 | 249 | 27 |
| n (Pat) | 104 | 53 | 104 | 62 | 104 | 27 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 7.540 | 7.060 | 7.540 | 8.110 | 7.540 | 8.365 |
| average | 9.546 | 8.161 | 9.546 | 8.973 | 9.546 | 10.567 |
| stdev | 10.769 | 6.576 | 10.769 | 5.925 | 10.769 | 10.517 |
| p (t-test) |  | 0.569 |  | 0.788 |  | 0.727 |
| min | 0.527 | 0.476 | 0.527 | 1.160 | 0.527 | 0.931 |
| max | 142.000 | 22.600 | 142.000 | 28.700 | 142.000 | 41.400 |
| n (Samp) | 441 | 20 | 441 | 26 | 441 | 14 |
| n (Pat) | 170 | 20 | 170 | 26 | 170 | 14 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 7.385 | 6.780 | 7.385 | 8.265 | 7.385 | 10.100 |
| average | 8.321 | 7.766 | 8.321 | 10.448 | 8.321 | 10.974 |
| stdev | 5.763 | 7.103 | 5.763 | 8.252 | 5.763 | 7.326 |
| p (t-test) |  | 0.568 |  | 0.031 |  | 0.036 |
| min | 0.527 | 0.834 | 0.527 | 0.865 | 0.527 | 0.974 |
| max | 39.200 | 36.100 | 39.200 | 41.200 | 39.200 | 31.500 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
|---|---|---|---|---|---|
| 0 hours | 0.46 | 0.043 | 249 | 53 | 0.381 |
| 24 hours | 0.51 | 0.041 | 249 | 62 | 0.756 |
| 48 hours | 0.57 | 0.060 | 249 | 27 | 0.251 | sCr only

| Time prior AKI stage | AUC | SE | nCohort 1 | nCohort 2 | p |
|---|---|---|---|---|---|
| 0 hours | 0.47 | 0.065 | 441 | 20 | 0.619 |
| 24 hours | 0.53 | 0.059 | 441 | 26 | 0.574 |
| 48 hours | 0.53 | 0.080 | 441 | 14 | 0.697 |

UO only

| Time prior AKI stage | AUC | SE | nCohort 1 | nCohort 2 | p |
|---|---|---|---|---|---|
| 0 hours | 0.45 | 0.045 | 212 | 47 | 0.316 |
| 24 hours | 0.57 | 0.045 | 212 | 52 | 0.134 |
| 48 hours | 0.63 | 0.063 | 212 | 25 | 0.034 | sCr or UO

| Time prior AKI stage | Cutoff value | sens | spec | Quartile | OR | 95% CI of OR | |
|---|---|---|---|---|---|---|---|
| 0 hours | 2.24 | 72% | 14% | 1 |  |  |  |
|  | 1.06 | 83% | 8% | 2 | 0.5 | 0.3 | 0.8 |
|  | 0.845 | 91% | 5% | 3 | 0.8 | 0.6 | 1.2 |
|  | 9.89 | 32% | 70% | 4 | 1.2 | 0.9 | 1.6 |

Fig. 1

|  |  | 12 | 23% | 80% |  |  |  |  |
|  |  | 15.7 | 11% | 90% |  |  |  |  |
|  | 24 hours | 5.92 | 71% | 31% | 1 |  |  |  |
|  |  | 3.95 | 81% | 15% | 2 | 1.4 | 1.0 | 1.8 |
|  |  | 1.18 | 90% | 10% | 3 | 0.8 | 0.6 | 1.2 |
|  |  | 9.89 | 34% | 70% | 4 | 1.4 | 1.0 | 1.8 |
|  |  | 12 | 26% | 80% |  |  |  |  |
|  |  | 15.7 | 13% | 90% |  |  |  |  |
|  | 48 hours | 6.64 | 70% | 42% | 1 |  |  |  |
|  |  | 5.07 | 81% | 23% | 2 | 0.8 | 0.4 | 1.8 |
|  |  | 0.984 | 93% | 8% | 3 | 1.0 | 0.5 | 2.0 |
|  |  | 9.89 | 44% | 70% | 4 | 1.8 | 1.0 | 3.2 |
|  |  | 12 | 33% | 80% |  |  |  |  |
|  |  | 15.7 | 15% | 90% |  |  |  |  | sCr only

| Time prior AKI stage | Cutoff value | sens | spec | Quartile | OR | 95% CI of OR | |
|---|---|---|---|---|---|---|---|
| 0 hours | 5.58 | 70% | 27% | 1 |  |  |  |
|  | 0.773 | 80% | 2% | 2 | 0.3 | 0.1 | 1.0 |
|  | 0.527 | 90% | 0% | 3 | 0.7 | 0.3 | 1.4 |
|  | 9.87 | 40% | 70% | 4 | 0.9 | 0.5 | 1.6 |
|  | 12.2 | 25% | 80% |  |  |  |  |
|  | 17.8 | 10% | 90% |  |  |  |  |
| 24 hours | 5.92 | 73% | 33% | 1 |  |  |  |
|  | 4.53 | 81% | 20% | 2 | 1.0 | 0.5 | 2.0 |
|  | 1.18 | 92% | 11% | 3 | 0.8 | 0.4 | 1.7 |
|  | 9.87 | 42% | 70% | 4 | 1.5 | 0.9 | 2.7 |
|  | 12.2 | 27% | 80% |  |  |  |  |
|  | 17.8 | 4% | 90% |  |  |  |  |
| 48 hours | 5.67 | 71% | 29% | 1 |  |  |  |
|  | 1.54 | 86% | 14% | 2 | 0.2 | 0.0 | 2.9 |
|  | 1.24 | 93% | 11% | 3 | 1.0 | 0.4 | 2.7 |
|  | 9.87 | 36% | 70% | 4 | 1.3 | 0.5 | 3.1 |
|  | 12.2 | 29% | 80% |  |  |  |  |
|  | 17.8 | 14% | 90% |  |  |  |  |

UO only

| Time prior AKI stage | Cutoff value | sens | spec | Quartile | OR | 95% CI of OR | |
|---|---|---|---|---|---|---|---|
| 0 hours | 2.24 | 70% | 15% | 1 |  |  |  |
|  | 1.08 | 83% | 9% | 2 | 0.8 | 0.5 | 1.2 |
|  | 0.923 | 91% | 7% | 3 | 0.8 | 0.5 | 1.2 |
|  | 9.53 | 26% | 70% | 4 | 1.4 | 0.9 | 2.0 |
|  | 11.6 | 19% | 81% |  |  |  |  |
|  | 14.6 | 13% | 90% |  |  |  |  |
| 24 hours | 6.37 | 73% | 41% | 1 |  |  |  |
|  | 5.58 | 81% | 29% | 2 | 1.7 | 1.1 | 2.6 |
|  | 1.41 | 90% | 12% | 3 | 1.4 | 0.9 | 2.2 |
|  | 9.53 | 37% | 70% | 4 | 2.2 | 1.5 | 3.3 |
|  | 11.6 | 27% | 81% |  |  |  |  |
|  | 14.6 | 21% | 90% |  |  |  |  |
| 48 hours | 7.23 | 72% | 50% | 1 |  |  |  |
|  | 6.24 | 80% | 38% | 2 | 1.7 | 0.6 | 5.3 |
|  | 3.91 | 92% | 17% | 3 | 1.7 | 0.6 | 5.3 |
|  | 9.53 | 52% | 70% | 4 | 4.7 | 1.9 | 11.4 |
|  | 11.6 | 32% | 81% |  |  |  |  |
|  | 14.6 | 16% | 90% |  |  |  |  |

Fig. 1 Continued

CD40 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 26.600 | 44.600 | 26.600 | 42.750 | 26.600 | 52.400 |
| average | 42.723 | 58.310 | 42.723 | 57.895 | 42.723 | 59.405 |
| stdev | 50.158 | 50.250 | 50.158 | 60.332 | 50.158 | 46.258 |
| p (t-test) |  | 0.041 |  | 0.042 |  | 0.099 |
| min | 0.994 | 0.000 | 0.994 | 2.740 | 0.994 | 1.770 |
| max | 326.000 | 254.000 | 326.000 | 286.000 | 326.000 | 164.000 |
| n (Samp) | 249 | 53 | 249 | 62 | 249 | 27 |
| n (Pat) | 104 | 53 | 104 | 62 | 104 | 27 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 32.900 | 33.450 | 32.900 | 30.950 | 32.900 | 42.450 |
| average | 47.128 | 37.576 | 47.128 | 56.576 | 47.128 | 55.461 |
| stdev | 49.778 | 28.827 | 49.778 | 65.082 | 49.778 | 49.641 |
| p (t-test) |  | 0.395 |  | 0.356 |  | 0.538 |
| min | 0.000 | 3.170 | 0.000 | 2.740 | 0.000 | 6.800 |
| max | 326.000 | 95.300 | 326.000 | 243.000 | 326.000 | 150.000 |
| n (Samp) | 441 | 20 | 441 | 26 | 441 | 14 |
| n (Pat) | 170 | 20 | 170 | 26 | 170 | 14 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 26.350 | 60.100 | 26.350 | 43.300 | 26.350 | 42.500 |
| average | 35.568 | 67.068 | 35.568 | 59.223 | 35.568 | 53.852 |
| stdev | 31.675 | 49.319 | 31.675 | 55.567 | 31.675 | 41.704 |
| p (t-test) |  | 0.000 |  | 0.000 |  | 0.009 |
| min | 0.994 | 0.000 | 0.994 | 3.240 | 0.994 | 1.770 |
| max | 174.000 | 254.000 | 174.000 | 286.000 | 174.000 | 164.000 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
| --- | --- | --- | --- | --- | --- |
| 0 hours | 0.63 | 0.044 | 249 | 53 | 0.004 |
| 24 hours | 0.60 | 0.042 | 249 | 62 | 0.016 |
| 48 hours | 0.63 | 0.060 | 249 | 27 | 0.033 | sCr only

| Time prior AKI stage | AUC | SE | nCohort 1 | nCohort 2 | p |
| --- | --- | --- | --- | --- | --- |
| 0 hours | 0.47 | 0.065 | 441 | 20 | 0.655 |
| 24 hours | 0.51 | 0.059 | 441 | 26 | 0.895 |
| 48 hours | 0.55 | 0.080 | 441 | 14 | 0.504 |

UO only

| Time prior AKI stage | AUC | SE | nCohort 1 | nCohort 2 | p |
| --- | --- | --- | --- | --- | --- |
| 0 hours | 0.73 | 0.044 | 212 | 47 | 0.000 |
| 24 hours | 0.67 | 0.045 | 212 | 52 | 0.000 |
| 48 hours | 0.64 | 0.062 | 212 | 25 | 0.025 |

Fig. 1 Continued sCr or UO

| Time prior AKI stage | Cutoff value | sens | spec | Quartile | OR | 95% CI of OR | |
|---|---|---|---|---|---|---|---|
| 0 hours | 27.4 | 72% | 52% | 1 | | | |
| | 16 | 81% | 34% | 2 | 1.5 | 0.9 | 2.5 |
| | 6.93 | 91% | 12% | 3 | 2.2 | 1.4 | 3.6 |
| | 48.2 | 45% | 70% | 4 | 4.0 | 2.6 | 6.1 |
| | 61.6 | 40% | 80% | | | | |
| | 92.6 | 19% | 90% | | | | |
| 24 hours | 22.3 | 71% | 44% | 1 | | | |
| | 17.6 | 81% | 36% | 2 | 1.8 | 1.2 | 2.7 |
| | 8.41 | 90% | 16% | 3 | 2.3 | 1.5 | 3.3 |
| | 48.2 | 35% | 70% | 4 | 2.6 | 1.8 | 3.8 |
| | 61.6 | 29% | 80% | | | | |
| | 92.6 | 15% | 90% | | | | |
| 48 hours | 24 | 70% | 46% | 1 | | | |
| | 13.6 | 81% | 29% | 2 | 0.8 | 0.3 | 2.0 |
| | 6.54 | 93% | 11% | 3 | 1.4 | 0.7 | 3.0 |
| | 48.2 | 56% | 70% | 4 | 2.4 | 1.3 | 4.6 |
| | 61.6 | 37% | 80% | | | | |
| | 92.6 | 30% | 90% | | | | | sCr only

| Time prior AKI stage | Cutoff value | sens | spec | Quartile | OR | 95% CI of OR | |
|---|---|---|---|---|---|---|---|
| 0 hours | 16 | 70% | 27% | 1 | | | |
| | 10.3 | 80% | 18% | 2 | 1.0 | 0.4 | 2.3 |
| | 6.09 | 90% | 8% | 3 | 0.8 | 0.3 | 2.0 |
| | 51.8 | 30% | 70% | 4 | 1.2 | 0.6 | 2.6 |
| | 70.1 | 20% | 80% | | | | |
| | 99.9 | 0% | 90% | | | | |
| 24 hours | 17.8 | 73% | 30% | 1 | | | |
| | 12.6 | 81% | 22% | 2 | 0.8 | 0.4 | 1.6 |
| | 5.49 | 92% | 6% | 3 | 0.8 | 0.4 | 1.6 |
| | 51.8 | 31% | 70% | 4 | 1.0 | 0.5 | 1.8 |
| | 70.1 | 23% | 80% | | | | |
| | 99.9 | 15% | 90% | | | | |
| 48 hours | 21.9 | 71% | 36% | 1 | | | |
| | 11.6 | 86% | 20% | 2 | 1.0 | 0.3 | 3.8 |
| | 6.93 | 93% | 11% | 3 | 1.3 | 0.4 | 4.3 |
| | 51.8 | 43% | 70% | 4 | 1.3 | 0.4 | 4.3 |
| | 70.1 | 29% | 80% | | | | |
| | 99.9 | 21% | 90% | | | | |

UO only

| Time prior AKI stage | Cutoff value | sens | spec | Quartile | OR | 95% CI of OR | |
|---|---|---|---|---|---|---|---|
| 0 hours | 37.6 | 70% | 65% | 1 | | | |
| | 28.2 | 81% | 55% | 2 | 1.5 | 0.6 | 3.7 |
| | 15 | 91% | 29% | 3 | 3.8 | 1.8 | 7.6 |
| | 44.2 | 64% | 70% | 4 | 8.8 | 4.6 | 16.9 |
| | 56.1 | 51% | 80% | | | | |
| | 76.9 | 36% | 90% | | | | |
| 24 hours | 27.3 | 71% | 53% | 1 | | | |
| | 22.3 | 81% | 44% | 2 | 1.8 | 1.0 | 3.2 |
| | 14.4 | 90% | 27% | 3 | 3.5 | 2.1 | 5.8 |
| | 44.2 | 46% | 70% | 4 | 4.0 | 2.4 | 6.7 |
| | 56.1 | 37% | 80% | | | | |
| | 76.9 | 19% | 90% | | | | |

Fig. 1 Continued

| 48 hours | 23.6 | 72% | 46% | 1 | | | |
| | 21.6 | 80% | 43% | 2 | 2.1 | 0.7 | 6.1 |
| | 12.2 | 92% | 25% | 3 | 1.7 | 0.6 | 5.3 |
| | 44.2 | 48% | 70% | 4 | 4.2 | 1.7 | 10.4 |
| | 56.1 | 36% | 80% | | | | |
| | 76.9 | 24% | 90% | | | | |

CD40 Ligand sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 0.198 | 0.191 | 0.198 | 0.294 | 0.198 | 0.295 |
| average | 0.243 | 0.269 | 0.243 | 0.302 | 0.243 | 0.332 |
| stdev | 0.172 | 0.189 | 0.172 | 0.191 | 0.172 | 0.208 |
| p (t-test) | | 0.319 | | 0.018 | | 0.013 |
| min | 0.011 | 0.017 | 0.011 | 0.017 | 0.011 | 0.019 |
| max | 0.869 | 0.712 | 0.869 | 0.891 | 0.869 | 0.778 |
| n (Samp) | 249 | 53 | 249 | 62 | 249 | 27 |
| n (Pat) | 104 | 53 | 104 | 62 | 104 | 27 | sCr only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 0.221 | 0.175 | 0.221 | 0.311 | 0.221 | 0.294 |
| average | 0.256 | 0.215 | 0.256 | 0.293 | 0.256 | 0.304 |
| stdev | 0.176 | 0.161 | 0.176 | 0.208 | 0.176 | 0.196 |
| p (t-test) | | 0.314 | | 0.293 | | 0.313 |
| min | 0.010 | 0.017 | 0.010 | 0.017 | 0.010 | 0.019 |
| max | 0.891 | 0.529 | 0.891 | 0.640 | 0.891 | 0.623 |
| n (Samp) | 441 | 20 | 441 | 26 | 441 | 14 |
| n (Pat) | 170 | 20 | 170 | 26 | 170 | 14 |

UO only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 0.203 | 0.264 | 0.203 | 0.308 | 0.203 | 0.282 |
| average | 0.231 | 0.300 | 0.231 | 0.320 | 0.231 | 0.323 |
| stdev | 0.155 | 0.192 | 0.155 | 0.167 | 0.155 | 0.181 |
| p (t-test) | | 0.009 | | 0.000 | | 0.006 |
| min | 0.011 | 0.057 | 0.011 | 0.047 | 0.011 | 0.019 |
| max | 0.659 | 0.712 | 0.659 | 0.891 | 0.659 | 0.778 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
| --- | --- | --- | --- | --- | --- |
| 0 hours | 0.54 | 0.044 | 249 | 53 | 0.410 |
| 24 hours | 0.59 | 0.042 | 249 | 62 | 0.029 |
| 48 hours | 0.63 | 0.060 | 249 | 27 | 0.032 | sCr only

| Time prior AKI stage | AUC | SE | nCohort 1 | nCohort 2 | p |
| --- | --- | --- | --- | --- | --- |
| 0 hours | 0.43 | 0.063 | 441 | 20 | 0.285 |
| 24 hours | 0.54 | 0.059 | 441 | 26 | 0.516 |
| 48 hours | 0.58 | 0.081 | 441 | 14 | 0.347 |

Fig. 1 Continued

UO only

| Time prior AKI stage | AUC | SE | nCohort 1 | nCohort 2 | p |
|---|---|---|---|---|---|
| 0 hours | 0.60 | 0.047 | 212 | 47 | 0.033 |
| 24 hours | 0.66 | 0.045 | 212 | 52 | 0.000 |
| 48 hours | 0.66 | 0.062 | 212 | 25 | 0.012 | sCr or UO

| Time prior AKI stage | Cutoff value | sens | spec | Quartile | OR | 95% CI of OR | |
|---|---|---|---|---|---|---|---|
| 0 hours | 0.117 | 72% | 32% | 1 | | | |
| | 0.0926 | 81% | 23% | 2 | 1.3 | 0.9 | 1.8 |
| | 0.0707 | 91% | 11% | 3 | 0.5 | 0.3 | 0.9 |
| | 0.316 | 40% | 71% | 4 | 1.8 | 1.3 | 2.4 |
| | 0.393 | 30% | 80% | | | | |
| | 0.504 | 13% | 90% | | | | |
| 24 hours | 0.164 | 71% | 45% | 1 | | | |
| | 0.11 | 81% | 30% | 2 | 0.7 | 0.5 | 1.1 |
| | 0.0497 | 90% | 6% | 3 | 1.9 | 1.3 | 2.6 |
| | 0.316 | 47% | 71% | 4 | 2.0 | 1.4 | 2.8 |
| | 0.393 | 31% | 80% | | | | |
| | 0.504 | 15% | 90% | | | | |
| 48 hours | 0.216 | 74% | 54% | 1 | | | |
| | 0.15 | 81% | 41% | 2 | 0.7 | 0.2 | 2.5 |
| | 0.0193 | 93% | 1% | 3 | 2.1 | 1.0 | 4.7 |
| | 0.316 | 44% | 71% | 4 | 3.4 | 1.7 | 7.0 |
| | 0.393 | 41% | 80% | | | | |
| | 0.504 | 26% | 90% | | | | | sCr only

| Time prior AKI stage | Cutoff value | sens | spec | Quartile | OR | 95% CI of OR | |
|---|---|---|---|---|---|---|---|
| 0 hours | 0.0916 | 70% | 22% | 1 | | | |
| | 0.075 | 80% | 14% | 2 | 1.3 | 0.5 | 3.2 |
| | 0.0401 | 90% | 5% | 3 | 1.0 | 0.4 | 2.8 |
| | 0.35 | 25% | 70% | 4 | 1.8 | 0.8 | 4.1 |
| | 0.419 | 15% | 80% | | | | |
| | 0.507 | 5% | 90% | | | | |
| 24 hours | 0.0889 | 73% | 21% | 1 | | | |
| | 0.0606 | 81% | 10% | 2 | 0.0 | 0.0 | na |
| | 0.0302 | 92% | 3% | 3 | 1.0 | 0.6 | 1.6 |
| | 0.35 | 42% | 70% | 4 | 0.9 | 0.5 | 1.4 |
| | 0.419 | 27% | 80% | | | | |
| | 0.507 | 19% | 90% | | | | |
| 48 hours | 0.178 | 71% | 43% | 1 | | | |
| | 0.102 | 86% | 25% | 2 | 2.0 | 0.4 | 9.1 |
| | 0.0193 | 93% | 1% | 3 | 1.0 | 0.1 | 7.3 |
| | 0.35 | 43% | 70% | 4 | 3.1 | 0.8 | 11.8 |
| | 0.419 | 36% | 80% | | | | |
| | 0.507 | 14% | 90% | | | | |

UO only

| Time prior AKI stage | Cutoff value | sens | spec | Quartile | OR | 95% CI of OR | |
|---|---|---|---|---|---|---|---|
| 0 hours | 0.131 | 70% | 39% | 1 | | | |
| | 0.103 | 81% | 29% | 2 | 1.9 | 1.2 | 3.0 |
| | 0.0748 | 91% | 13% | 3 | 0.5 | 0.2 | 1.0 |
| | 0.312 | 49% | 70% | 4 | 3.3 | 2.2 | 5.1 |
| | 0.373 | 45% | 80% | | | | |
| | 0.459 | 23% | 90% | | | | |

Fig. 1 Continued

| 24 hours | 0.232 | 71% | 56% | 1 | | | |
| --- | --- | --- | --- | --- | --- | --- | --- |
| | 0.158 | 81% | 43% | 2 | 2.8 | 1.3 | 5.9 |
| | 0.128 | 90% | 38% | 3 | 6.3 | 3.2 | 12.2 |
| | 0.312 | 48% | 70% | 4 | 6.3 | 3.2 | 12.2 |
| | 0.373 | 35% | 80% | | | | |
| | 0.459 | 17% | 90% | | | | |
| 48 hours | 0.221 | 72% | 54% | 1 | | | |
| | 0.216 | 80% | 53% | 2 | 1.5 | 0.3 | 8.4 |
| | 0.115 | 92% | 32% | 3 | 6.5 | 1.9 | 22.4 |
| | 0.312 | 40% | 70% | 4 | 5.0 | 1.4 | 17.9 |
| | 0.373 | 36% | 80% | | | | |
| | 0.459 | 28% | 90% | | | | |

CXCL16 (C-X-C Motif chemokine 16)

sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 0.091 | 0.311 | 0.091 | 0.226 | 0.091 | 0.189 |
| average | 0.699 | 1.025 | 0.699 | 1.305 | 0.699 | 0.853 |
| stdev | 1.674 | 1.876 | 1.674 | 2.421 | 1.674 | 1.987 |
| p (t-test) | | 0.238 | | 0.037 | | 0.673 |
| min | 0.000 | 0.000 | 0.000 | 0.000 | 0.000 | 0.011 |
| max | 10.210 | 8.620 | 10.210 | 9.522 | 10.210 | 9.506 |
| n (Samp) | 162 | 52 | 162 | 59 | 162 | 26 |
| n (Pat) | 103 | 52 | 103 | 59 | 103 | 26 | sCr only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 0.124 | 0.219 | 0.124 | 0.177 | 0.124 | 0.194 |
| average | 0.841 | 1.410 | 0.841 | 1.756 | 0.841 | 1.084 |
| stdev | 1.822 | 2.686 | 1.822 | 2.962 | 1.822 | 2.335 |
| p (t-test) | | 0.201 | | 0.025 | | 0.630 |
| min | 0.000 | 0.000 | 0.000 | 0.000 | 0.000 | 0.018 |
| max | 10.210 | 10.538 | 10.210 | 9.861 | 10.210 | 8.669 |
| n (Samp) | 320 | 19 | 320 | 24 | 320 | 14 |
| n (Pat) | 167 | 19 | 167 | 24 | 167 | 14 |

UO only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 0.091 | 0.432 | 0.091 | 0.268 | 0.091 | 0.193 |
| average | 0.573 | 1.214 | 0.573 | 1.406 | 0.573 | 1.042 |
| stdev | 1.323 | 2.019 | 1.323 | 2.459 | 1.323 | 2.117 |
| p (t-test) | | 0.014 | | 0.003 | | 0.156 |
| min | 0.000 | 0.001 | 0.000 | 0.011 | 0.000 | 0.011 |
| max | 9.383 | 8.620 | 9.383 | 9.522 | 9.383 | 9.506 |
| n (Samp) | 138 | 46 | 138 | 50 | 138 | 23 |
| n (Pat) | 84 | 46 | 84 | 50 | 84 | 23 | sCr or UO

| Time prior AKI stage | AUC | SE | nCohort 1 | nCohort 2 | p |
| --- | --- | --- | --- | --- | --- |
| 0 hours | 0.61 | 0.046 | 162 | 52 | 0.016 |
| 24 hours | 0.60 | 0.044 | 162 | 59 | 0.030 |
| 48 hours | 0.58 | 0.062 | 162 | 26 | 0.187 |

Fig. 1 Continued sCr only

| Time prior AKI stage | AUC | SE | nCohort 1 | nCohort 2 | p |
|---|---|---|---|---|---|
| 0 hours | 0.53 | 0.069 | 320 | 19 | 0.701 |
| 24 hours | 0.53 | 0.062 | 320 | 24 | 0.630 |
| 48 hours | 0.52 | 0.080 | 320 | 14 | 0.809 |

UO only

| Time prior AKI stage | AUC | SE | nCohort 1 | nCohort 2 | p |
|---|---|---|---|---|---|
| 0 hours | 0.67 | 0.048 | 138 | 46 | 0.000 |
| 24 hours | 0.66 | 0.047 | 138 | 50 | 0.001 |
| 48 hours | 0.63 | 0.066 | 138 | 23 | 0.048 | sCr or UO

| Time prior AKI stage | Cutoff value | sens | spec | Quartile | OR | 95% CI of OR | |
|---|---|---|---|---|---|---|---|
| 0 hours | 0.08716 | 71% | 49% | 1 | | | |
| | 0.03878 | 81% | 31% | 2 | 0.7 | 0.4 | 1.3 |
| | 0.01455 | 90% | 14% | 3 | 1.7 | 1.1 | 2.6 |
| | 0.30585 | 50% | 70% | 4 | 2.3 | 1.6 | 3.5 |
| | 0.70105 | 25% | 80% | | | | |
| | 1.66287 | 17% | 90% | | | | |
| 24 hours | 0.06755 | 71% | 42% | 1 | | | |
| | 0.03606 | 81% | 29% | 2 | 1.6 | 1.0 | 2.5 |
| | 0.01331 | 92% | 12% | 3 | 2.7 | 1.8 | 4.1 |
| | 0.30585 | 39% | 70% | 4 | 2.4 | 1.6 | 3.7 |
| | 0.70105 | 29% | 80% | | | | |
| | 1.66287 | 22% | 90% | | | | |
| 48 hours | 0.08349 | 73% | 48% | 1 | | | |
| | 0.03289 | 81% | 28% | 2 | 1.0 | 0.3 | 2.9 |
| | 0.0178 | 92% | 19% | 3 | 3.7 | 1.7 | 7.8 |
| | 0.30585 | 31% | 70% | 4 | 1.6 | 0.6 | 3.9 |
| | 0.70105 | 23% | 80% | | | | |
| | 1.66287 | 12% | 90% | | | | | sCr only

| Time prior AKI stage | Cutoff value | sens | spec | Quartile | OR | 95% CI of OR | |
|---|---|---|---|---|---|---|---|
| 0 hours | 0.0211 | 74% | 15% | 1 | | | |
| | 0.01723 | 84% | 13% | 2 | 0.3 | 0.1 | 1.2 |
| | 0.00761 | 95% | 5% | 3 | 0.5 | 0.2 | 1.3 |
| | 0.36491 | 42% | 70% | 4 | 1.4 | 0.7 | 2.5 |
| | 0.88165 | 37% | 80% | | | | |
| | 2.59834 | 11% | 90% | | | | |
| 24 hours | 0.0337 | 71% | 21% | 1 | | | |
| | 0.01072 | 83% | 6% | 2 | 0.4 | 0.1 | 0.9 |
| | 0.00548 | 92% | 3% | 3 | 0.5 | 0.2 | 1.0 |
| | 0.36491 | 42% | 70% | 4 | 1.1 | 0.7 | 1.9 |
| | 0.88165 | 33% | 80% | | | | |
| | 2.59834 | 25% | 90% | | | | |
| 48 hours | 0.04217 | 71% | 26% | 1 | | | |
| | 0.01984 | 86% | 15% | 2 | 0.7 | 0.2 | 2.4 |
| | 0.0178 | 93% | 13% | 3 | 0.5 | 0.1 | 2.2 |
| | 0.36491 | 36% | 70% | 4 | 1.3 | 0.5 | 3.2 |
| | 0.88165 | 21% | 80% | | | | |
| | 2.59834 | 14% | 90% | | | | |

UO only

Fig. 1 Continued

| Time prior AKI stage | Cutoff value | sens | spec | Quartile | OR | 95% CI of OR | |
|---|---|---|---|---|---|---|---|
| 0 hours | 0.19282 | 72% | 63% | 1 | | | |
| | 0.0838 | 80% | 48% | 2 | 1.7 | 0.8 | 3.6 |
| | 0.03033 | 91% | 24% | 3 | 4.0 | 2.1 | 7.5 |
| | 0.30918 | 57% | 70% | 4 | 5.3 | 2.8 | 9.8 |
| | 0.59488 | 35% | 80% | | | | |
| | 1.62097 | 20% | 91% | | | | |
| 24 hours | 0.11619 | 70% | 55% | 1 | | | |
| | 0.06755 | 80% | 41% | 2 | 2.1 | 1.1 | 3.8 |
| | 0.03681 | 90% | 29% | 3 | 3.2 | 1.8 | 5.6 |
| | 0.30918 | 46% | 70% | 4 | 4.2 | 2.4 | 7.4 |
| | 0.59488 | 34% | 80% | | | | |
| | 1.62097 | 24% | 91% | | | | |
| 48 hours | 0.13327 | 78% | 58% | 1 | | | |
| | 0.08349 | 83% | 47% | 2 | 0.6 | 0.1 | 3.7 |
| | 0.03099 | 91% | 26% | 3 | 5.3 | 2.1 | 13.5 |
| | 0.30918 | 35% | 70% | 4 | 2.1 | 0.7 | 6.3 |
| | 0.59488 | 26% | 80% | | | | |
| | 1.62097 | 17% | 91% | | | | |

EN-RAGE sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1.137 | 1.743 | 1.137 | 1.867 | 1.137 | 1.288 |
| average | 6.764 | 14.804 | 6.764 | 17.986 | 6.764 | 25.315 |
| stdev | 22.106 | 56.369 | 22.106 | 89.318 | 22.106 | 115.837 |
| p (t-test) | | 0.185 | | 0.200 | | 0.107 |
| min | 0.002 | 0.142 | 0.002 | 0.065 | 0.002 | 0.166 |
| max | 197.971 | 391.452 | 197.971 | 675.017 | 197.971 | 592.998 |
| n (Samp) | 117 | 51 | 117 | 59 | 117 | 26 |
| n (Pat) | 99 | 51 | 99 | 59 | 99 | 26 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1.460 | 1.743 | 1.460 | 1.170 | 1.460 | 2.336 |
| average | 11.640 | 3.163 | 11.640 | 4.691 | 11.640 | 49.370 |
| stdev | 53.231 | 3.808 | 53.231 | 7.908 | 53.231 | 156.852 |
| p (t-test) | | 0.513 | | 0.533 | | 0.028 |
| min | 0.002 | 0.206 | 0.002 | 0.065 | 0.002 | 0.279 |
| max | 675.017 | 12.947 | 675.017 | 31.593 | 675.017 | 592.998 |
| n (Samp) | 260 | 17 | 260 | 23 | 260 | 14 |
| n (Pat) | 160 | 17 | 160 | 23 | 160 | 14 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1.194 | 1.962 | 1.194 | 1.904 | 1.194 | 1.447 |
| average | 7.724 | 18.233 | 7.724 | 21.529 | 7.724 | 3.360 |
| stdev | 23.278 | 60.910 | 23.278 | 97.965 | 23.278 | 4.430 |
| p (t-test) | | 0.128 | | 0.173 | | 0.374 |
| min | 0.002 | 0.142 | 0.002 | 0.090 | 0.002 | 0.166 |
| max | 197.971 | 391.452 | 197.971 | 675.017 | 197.971 | 13.936 |
| n (Samp) | 105 | 45 | 105 | 49 | 105 | 23 |
| n (Pat) | 84 | 45 | 84 | 49 | 84 | 23 |

Fig. 1 Continued sCr or UO

| Time prior AKI stage | AUC | SE | nCohort 1 | nCohort 2 | p |
|---|---|---|---|---|---|
| 0 hours | 0.61 | 0.049 | 117 | 51 | 0.028 |
| 24 hours | 0.55 | 0.046 | 117 | 59 | 0.287 |
| 48 hours | 0.51 | 0.063 | 117 | 26 | 0.859 | sCr only

| Time prior AKI stage | AUC | SE | nCohort 1 | nCohort 2 | p |
|---|---|---|---|---|---|
| 0 hours | 0.51 | 0.073 | 260 | 17 | 0.874 |
| 24 hours | 0.46 | 0.061 | 260 | 23 | 0.555 |
| 48 hours | 0.59 | 0.082 | 260 | 14 | 0.253 |

UO only

| Time prior AKI stage | AUC | SE | nCohort 1 | nCohort 2 | p |
|---|---|---|---|---|---|
| 0 hours | 0.60 | 0.052 | 105 | 45 | 0.050 |
| 24 hours | 0.57 | 0.050 | 105 | 49 | 0.159 |
| 48 hours | 0.49 | 0.066 | 105 | 23 | 0.893 | sCr or UO

| Time prior AKI stage | Cutoff value | sens | spec | Quartile | OR | 95% CI of OR | |
|---|---|---|---|---|---|---|---|
| 0 hours | 0.79595 | 71% | 41% | 1 | | | |
| | 0.59513 | 80% | 31% | 2 | 1.3 | 0.8 | 2.2 |
| | 0.46286 | 90% | 24% | 3 | 1.6 | 1.0 | 2.7 |
| | 2.17016 | 43% | 70% | 4 | 2.8 | 1.7 | 4.4 |
| | 3.67125 | 33% | 80% | | | | |
| | 10.5861 | 16% | 91% | | | | |
| 24 hours | 0.66093 | 71% | 33% | 1 | | | |
| | 0.31013 | 81% | 14% | 2 | 0.5 | 0.3 | 0.8 |
| | 0.142 | 92% | 5% | 3 | 0.7 | 0.5 | 1.1 |
| | 2.17016 | 44% | 70% | 4 | 1.5 | 1.0 | 2.1 |
| | 3.67125 | 34% | 80% | | | | |
| | 10.5861 | 14% | 91% | | | | |
| 48 hours | 0.48804 | 73% | 27% | 1 | | | |
| | 0.43767 | 81% | 23% | 2 | 0.8 | 0.4 | 1.7 |
| | 0.20012 | 92% | 7% | 3 | 1.0 | 0.5 | 1.9 |
| | 2.17016 | 35% | 70% | 4 | 0.8 | 0.4 | 1.7 |
| | 3.67125 | 23% | 80% | | | | |
| | 10.5861 | 8% | 91% | | | | | sCr only

| Time prior AKI stage | Cutoff value | sens | spec | Quartile | OR | 95% CI of OR | |
|---|---|---|---|---|---|---|---|
| 0 hours | 0.96736 | 71% | 41% | 1 | | | |
| | 0.53845 | 82% | 24% | 2 | 0.7 | 0.2 | 2.5 |
| | 0.23754 | 94% | 9% | 3 | 1.5 | 0.6 | 3.7 |
| | 2.96095 | 29% | 70% | 4 | 1.0 | 0.3 | 2.8 |
| | 5.67373 | 18% | 80% | | | | |
| | 14.7646 | 0% | 90% | | | | |
| 24 hours | 0.33607 | 74% | 13% | 1 | | | |
| | 0.28358 | 83% | 11% | 2 | 1.2 | 0.6 | 2.7 |
| | 0.16594 | 91% | 5% | 3 | 1.0 | 0.4 | 2.3 |
| | 2.96095 | 30% | 70% | 4 | 1.5 | 0.7 | 3.1 |
| | 5.67373 | 22% | 80% | | | | |
| | 14.7646 | 13% | 90% | | | | |

Fig. 1 Continued

| 48 hours | 1.07186 | 71% | 43% | 1 | | | |
| | 0.43767 | 86% | 19% | 2 | 0.2 | 0.0 | 2.9 |
| | 0.3635 | 93% | 15% | 3 | 0.7 | 0.2 | 2.5 |
| | 2.96095 | 43% | 70% | 4 | 1.5 | 0.6 | 3.7 |
| | 5.67373 | 36% | 80% | | | | |
| | 14.7646 | 29% | 90% | | | | |

UO only

| Time prior AKI stage | Cutoff value | sens | spec | Quartile | OR | 95% CI of OR | |
|---|---|---|---|---|---|---|---|
| 0 hours | 0.87598 | 71% | 39% | 1 | | | |
| | 0.72955 | 80% | 34% | 2 | 1.7 | 1.0 | 3.2 |
| | 0.46286 | 91% | 23% | 3 | 1.8 | 1.0 | 3.3 |
| | 2.3998 | 42% | 71% | 4 | 3.1 | 1.8 | 5.4 |
| | 3.89368 | 36% | 80% | | | | |
| | 18.6601 | 13% | 90% | | | | |
| 24 hours | 0.90879 | 71% | 41% | 1 | | | |
| | 0.37339 | 82% | 20% | 2 | 0.8 | 0.5 | 1.5 |
| | 0.22259 | 92% | 6% | 3 | 1.6 | 1.0 | 2.7 |
| | 2.3998 | 41% | 71% | 4 | 1.9 | 1.2 | 3.1 |
| | 3.89368 | 31% | 80% | | | | |
| | 18.6601 | 10% | 90% | | | | |
| 48 hours | 0.48804 | 74% | 26% | 1 | | | |
| | 0.42945 | 83% | 22% | 2 | 1.0 | 0.4 | 2.2 |
| | 0.20012 | 91% | 5% | 3 | 1.0 | 0.4 | 2.2 |
| | 2.3998 | 35% | 71% | 4 | 0.8 | 0.3 | 1.9 |
| | 3.89368 | 26% | 80% | | | | |
| | 18.6601 | 0% | 90% | | | | |

Eotaxin sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 31.000 | 36.500 | 31.000 | 41.700 | 31.000 | 33.600 |
| average | 39.628 | 48.435 | 39.628 | 58.697 | 39.628 | 41.302 |
| stdev | 27.303 | 35.271 | 27.303 | 47.701 | 27.303 | 24.051 |
| p (t-test) | | 0.044 | | 0.000 | | 0.760 |
| min | 5.080 | 6.660 | 5.080 | 6.660 | 5.080 | 0.164 |
| max | 185.000 | 229.000 | 185.000 | 193.000 | 185.000 | 98.600 |
| n (Samp) | 249 | 53 | 249 | 62 | 249 | 27 |
| n (Pat) | 104 | 53 | 104 | 62 | 104 | 27 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 33.600 | 30.400 | 33.600 | 44.850 | 33.600 | 38.750 |
| average | 45.000 | 54.205 | 45.000 | 78.357 | 45.000 | 47.057 |
| stdev | 36.268 | 40.820 | 36.268 | 79.532 | 36.268 | 23.212 |
| p (t-test) | | 0.270 | | 0.000 | | 0.833 |
| min | 0.164 | 12.300 | 0.164 | 8.680 | 0.164 | 19.000 |
| max | 270.000 | 131.000 | 270.000 | 333.000 | 270.000 | 98.000 |
| n (Samp) | 441 | 20 | 441 | 26 | 441 | 14 |
| n (Pat) | 170 | 20 | 170 | 26 | 170 | 14 |

Fig. 1 Continued

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 32.150 | 41.200 | 32.150 | 45.550 | 32.150 | 37.500 |
| average | 40.460 | 50.486 | 40.460 | 71.253 | 40.460 | 56.791 |
| stdev | 27.391 | 35.838 | 27.391 | 82.646 | 27.391 | 79.412 |
| p (t-test) |  | 0.033 |  | 0.000 |  | 0.034 |
| min | 7.220 | 6.660 | 7.220 | 6.660 | 7.220 | 0.164 |
| max | 185.000 | 229.000 | 185.000 | 535.000 | 185.000 | 420.000 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
|---|---|---|---|---|---|
| 0 hours | 0.58 | 0.045 | 249 | 53 | 0.057 |
| 24 hours | 0.62 | 0.041 | 249 | 62 | 0.003 |
| 48 hours | 0.55 | 0.060 | 249 | 27 | 0.433 | sCr only

| Time prior AKI stage | AUC | SE | nCohort 1 | nCohort 2 | p |
|---|---|---|---|---|---|
| 0 hours | 0.53 | 0.067 | 441 | 20 | 0.674 |
| 24 hours | 0.60 | 0.060 | 441 | 26 | 0.082 |
| 48 hours | 0.58 | 0.081 | 441 | 14 | 0.318 |

UO only

| Time prior AKI stage | AUC | SE | nCohort 1 | nCohort 2 | p |
|---|---|---|---|---|---|
| 0 hours | 0.61 | 0.047 | 212 | 47 | 0.021 |
| 24 hours | 0.65 | 0.045 | 212 | 52 | 0.001 |
| 48 hours | 0.56 | 0.063 | 212 | 25 | 0.324 | sCr or UO

| Time prior AKI stage | Cutoff value | sens | spec | Quartile | OR | 95% CI of OR | |
|---|---|---|---|---|---|---|---|
| 0 hours | 27.1 | 72% | 37% | 1 |  |  |  |
|  | 24.5 | 81% | 29% | 2 | 1.3 | 0.9 | 2.0 |
|  | 18.6 | 91% | 14% | 3 | 1.1 | 0.7 | 1.7 |
|  | 43.3 | 43% | 71% | 4 | 2.2 | 1.5 | 3.1 |
|  | 53.3 | 34% | 80% |  |  |  |  |
|  | 70.4 | 25% | 90% |  |  |  |  |
| 24 hours | 28.3 | 71% | 41% | 1 |  |  |  |
|  | 25.4 | 81% | 34% | 2 | 1.1 | 0.7 | 1.7 |
|  | 18.6 | 90% | 14% | 3 | 1.9 | 1.3 | 2.7 |
|  | 43.3 | 50% | 71% | 4 | 3.0 | 2.1 | 4.2 |
|  | 53.3 | 34% | 80% |  |  |  |  |
|  | 70.4 | 24% | 90% |  |  |  |  |
| 48 hours | 28.2 | 70% | 41% | 1 |  |  |  |
|  | 21.5 | 81% | 21% | 2 | 0.5 | 0.2 | 1.3 |
|  | 18.7 | 93% | 16% | 3 | 1.2 | 0.6 | 2.1 |
|  | 43.3 | 33% | 71% | 4 | 1.2 | 0.6 | 2.1 |
|  | 53.3 | 26% | 80% |  |  |  |  |
|  | 70.4 | 15% | 90% |  |  |  |  |

Fig. 1 Continued sCr only

| Time prior AKI stage | Cutoff value | sens | spec | Quartile | OR | 95% CI of OR | |
|---|---|---|---|---|---|---|---|
| 0 hours | 24.5 | 70% | 25% | 1 | | | |
| | 20.2 | 85% | 17% | 2 | 0.8 | 0.4 | 1.8 |
| | 18.6 | 90% | 13% | 3 | 0.2 | 0.0 | 1.6 |
| | 49.4 | 40% | 70% | 4 | 1.3 | 0.7 | 2.5 |
| | 62 | 40% | 80% | | | | |
| | 81.8 | 25% | 90% | | | | |
| 24 hours | 27.1 | 77% | 32% | 1 | | | |
| | 26.7 | 81% | 31% | 2 | 1.3 | 0.5 | 3.1 |
| | 17.6 | 92% | 11% | 3 | 1.8 | 0.8 | 4.0 |
| | 49.4 | 42% | 70% | 4 | 2.6 | 1.3 | 5.4 |
| | 62 | 35% | 80% | | | | |
| | 81.8 | 31% | 90% | | | | |
| 48 hours | 30.7 | 71% | 44% | 1 | | | |
| | 27.1 | 86% | 32% | 2 | 2.0 | 0.4 | 9.1 |
| | 21.5 | 93% | 19% | 3 | 1.0 | 0.1 | 7.3 |
| | 49.4 | 43% | 70% | 4 | 3.1 | 0.8 | 11.8 |
| | 62 | 29% | 80% | | | | |
| | 81.8 | 7% | 90% | | | | |

UO only

| Time prior AKI stage | Cutoff value | sens | spec | Quartile | OR | 95% CI of OR | |
|---|---|---|---|---|---|---|---|
| 0 hours | 30.1 | 70% | 46% | 1 | | | |
| | 26.7 | 81% | 34% | 2 | 1.7 | 1.0 | 2.8 |
| | 23.1 | 91% | 24% | 3 | 2.0 | 1.2 | 3.4 |
| | 45.1 | 43% | 71% | 4 | 2.7 | 1.7 | 4.3 |
| | 54 | 34% | 80% | | | | |
| | 70.2 | 23% | 90% | | | | |
| 24 hours | 33.1 | 71% | 54% | 1 | | | |
| | 27.3 | 83% | 37% | 2 | 1.0 | 0.6 | 1.7 |
| | 20.7 | 90% | 18% | 3 | 2.1 | 1.4 | 3.3 |
| | 45.1 | 52% | 71% | 4 | 3.4 | 2.2 | 5.1 |
| | 54 | 40% | 80% | | | | |
| | 70.2 | 27% | 90% | | | | |
| 48 hours | 28.7 | 72% | 42% | 1 | | | |
| | 23.1 | 80% | 24% | 2 | 0.6 | 0.3 | 1.6 |
| | 18.6 | 92% | 13% | 3 | 1.2 | 0.6 | 2.4 |
| | 45.1 | 32% | 71% | 4 | 1.4 | 0.7 | 2.6 |
| | 54 | 28% | 80% | | | | |
| | 70.2 | 24% | 90% | | | | |

E-selectin sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.144 | 0.272 | 0.144 | 0.238 | 0.144 | 0.188 |
| average | 0.255 | 0.484 | 0.255 | 0.423 | 0.255 | 0.447 |
| stdev | 0.297 | 0.642 | 0.297 | 0.774 | 0.297 | 0.690 |
| p (t-test) | | 0.002 | | 0.040 | | 0.027 |
| min | 0.000 | 0.000 | 0.000 | 0.000 | 0.000 | 0.000 |
| max | 1.605 | 2.825 | 1.605 | 5.381 | 1.605 | 2.918 |
| n (Samp) | 117 | 51 | 117 | 60 | 117 | 26 |
| n (Pat) | 99 | 51 | 99 | 60 | 99 | 26 |

Fig. 1 Continued sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.178 | 0.116 | 0.178 | 0.212 | 0.178 | 0.196 |
| average | 0.358 | 0.330 | 0.358 | 0.491 | 0.358 | 0.509 |
| stdev | 0.590 | 0.426 | 0.590 | 0.675 | 0.590 | 0.689 |
| p (t-test) | | 0.848 | | 0.306 | | 0.354 |
| min | 0.000 | 0.000 | 0.000 | 0.000 | 0.000 | 0.019 |
| max | 5.381 | 1.553 | 5.381 | 2.759 | 5.381 | 2.158 |
| n (Samp) | 261 | 17 | 261 | 23 | 261 | 14 |
| n (Pat) | 160 | 17 | 160 | 23 | 160 | 14 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.144 | 0.241 | 0.144 | 0.247 | 0.144 | 0.176 |
| average | 0.277 | 0.558 | 0.277 | 0.447 | 0.277 | 0.362 |
| stdev | 0.352 | 0.886 | 0.352 | 0.823 | 0.352 | 0.616 |
| p (t-test) | | 0.006 | | 0.073 | | 0.366 |
| min | 0.000 | 0.000 | 0.000 | 0.000 | 0.000 | 0.000 |
| max | 2.158 | 4.435 | 2.158 | 5.381 | 2.158 | 2.918 |
| n (Samp) | 105 | 45 | 105 | 50 | 105 | 23 |
| n (Pat) | 84 | 45 | 84 | 50 | 84 | 23 | sCr or UO

| Time prior AKI stage | AUC | SE | nCohort 1 | nCohort 2 | p |
|---|---|---|---|---|---|
| 0 hours | 0.62 | 0.048 | 117 | 51 | 0.014 |
| 24 hours | 0.55 | 0.046 | 117 | 60 | 0.244 |
| 48 hours | 0.54 | 0.064 | 117 | 26 | 0.513 | sCr only

| Time prior AKI stage | AUC | SE | nCohort 1 | nCohort 2 | p |
|---|---|---|---|---|---|
| 0 hours | 0.48 | 0.072 | 261 | 17 | 0.801 |
| 24 hours | 0.52 | 0.064 | 261 | 23 | 0.724 |
| 48 hours | 0.57 | 0.082 | 261 | 14 | 0.409 |

UO only

| Time prior AKI stage | AUC | SE | nCohort 1 | nCohort 2 | p |
|---|---|---|---|---|---|
| 0 hours | 0.60 | 0.052 | 105 | 45 | 0.053 |
| 24 hours | 0.57 | 0.050 | 105 | 50 | 0.143 |
| 48 hours | 0.51 | 0.067 | 105 | 23 | 0.887 | sCr or UO

| Time prior AKI stage | Cutoff value | sens | spec | Quartile | OR | 95% CI of OR | |
|---|---|---|---|---|---|---|---|
| 0 hours | 0.10943 | 71% | 35% | 1 | | | |
| | 0.07115 | 82% | 29% | 2 | 0.9 | 0.5 | 1.5 |
| | 0.05672 | 90% | 26% | 3 | 2.5 | 1.6 | 4.0 |
| | 0.26549 | 51% | 70% | 4 | 2.5 | 1.6 | 4.0 |
| | 0.38703 | 33% | 80% | | | | |
| | 0.68139 | 16% | 91% | | | | |
| 24 hours | 0.0957 | 70% | 32% | 1 | | | |
| | 0.04386 | 80% | 18% | 2 | 0.5 | 0.3 | 0.8 |
| | 0.01302 | 90% | 10% | 3 | 1.3 | 0.9 | 2.0 |
| | 0.26549 | 43% | 70% | 4 | 1.3 | 0.9 | 1.9 |
| | 0.38703 | 25% | 80% | | | | |
| | 0.68139 | 15% | 91% | | | | |

Fig. 1 Continued

|  | 48 hours | 0.07846 | 73% | 30% | 1 |  |  |  |
|---|---|---|---|---|---|---|---|---|
|  |  | 0.01715 | 81% | 11% | 2 | 0.4 | 0.1 | 1.1 |
|  |  | 0 | 100% | 0% | 3 | 1.0 | 0.5 | 1.9 |
|  |  | 0.26549 | 42% | 70% | 4 | 1.3 | 0.7 | 2.5 |
|  |  | 0.38703 | 31% | 80% |  |  |  |  |
|  |  | 0.68139 | 19% | 91% |  |  |  |  | sCr only

| Time prior AKI stage | Cutoff value | sens | spec | Quartile | OR | 95% CI of OR | |
|---|---|---|---|---|---|---|---|
| 0 hours | 0.07115 | 71% | 26% | 1 |  |  |  |
|  | 0.06099 | 82% | 23% | 2 | 0.4 | 0.1 | 1.6 |
|  | 1E-09 | 94% | 7% | 3 | 1.2 | 0.6 | 2.7 |
|  | 0.33104 | 29% | 70% | 4 | 0.8 | 0.3 | 2.1 |
|  | 0.45478 | 24% | 80% |  |  |  |  |
|  | 0.7252 | 18% | 90% |  |  |  |  |
| 24 hours | 0.04386 | 74% | 17% | 1 |  |  |  |
|  | 0.02758 | 83% | 12% | 2 | 0.3 | 0.1 | 0.9 |
|  | 0 | 100% | 0% | 3 | 0.5 | 0.2 | 1.0 |
|  | 0.33104 | 35% | 70% | 4 | 1.0 | 0.6 | 1.7 |
|  | 0.45478 | 35% | 80% |  |  |  |  |
|  | 0.7252 | 26% | 90% |  |  |  |  |
| 48 hours | 0.14642 | 71% | 44% | 1 |  |  |  |
|  | 0.0719 | 86% | 27% | 2 | 2.6 | 0.6 | 10.8 |
|  | 0.06099 | 93% | 23% | 3 | 1.5 | 0.3 | 8.2 |
|  | 0.33104 | 43% | 70% | 4 | 2.0 | 0.4 | 9.4 |
|  | 0.45478 | 29% | 80% |  |  |  |  |
|  | 0.7252 | 21% | 90% |  |  |  |  |

UO only

| Time prior AKI stage | Cutoff value | sens | spec | Quartile | OR | 95% CI of OR | |
|---|---|---|---|---|---|---|---|
| 0 hours | 0.12656 | 71% | 44% | 1 |  |  |  |
|  | 0.07115 | 80% | 28% | 2 | 0.7 | 0.4 | 1.3 |
|  | 0.02884 | 91% | 13% | 3 | 1.9 | 1.1 | 3.2 |
|  | 0.2518 | 49% | 70% | 4 | 2.0 | 1.2 | 3.4 |
|  | 0.46344 | 24% | 80% |  |  |  |  |
|  | 0.73598 | 16% | 90% |  |  |  |  |
| 24 hours | 0.12261 | 70% | 40% | 1 |  |  |  |
|  | 0.06609 | 80% | 26% | 2 | 0.6 | 0.4 | 1.1 |
|  | 0.02884 | 90% | 13% | 3 | 1.9 | 1.2 | 3.0 |
|  | 0.2518 | 48% | 70% | 4 | 1.4 | 0.9 | 2.2 |
|  | 0.46344 | 22% | 80% |  |  |  |  |
|  | 0.73598 | 12% | 90% |  |  |  |  |
| 48 hours | 0.06609 | 74% | 26% | 1 |  |  |  |
|  | 0.00673 | 83% | 6% | 2 | 0.4 | 0.1 | 1.4 |
|  | 0 | 100% | 0% | 3 | 1.2 | 0.6 | 2.6 |
|  | 0.2518 | 39% | 70% | 4 | 1.2 | 0.6 | 2.6 |
|  | 0.46344 | 17% | 80% |  |  |  |  |
|  | 0.73598 | 9% | 90% |  |  |  |  |

Fig. 1 Continued

Fibronectin sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 15.023 | 21.926 | 15.023 | 23.468 | 15.023 | 23.743 |
| average | 83.203 | 67.441 | 83.203 | 91.230 | 83.203 | 76.715 |
| stdev | 169.416 | 169.348 | 169.416 | 145.050 | 169.416 | 123.637 |
| p (t-test) |  | 0.580 |  | 0.756 |  | 0.854 |
| min | 0.276 | 1.400 | 0.276 | 0.040 | 0.276 | 1.041 |
| max | 1020.452 | 1190.527 | 1020.452 | 810.740 | 1020.452 | 500.000 |
| n (Samp) | 117 | 51 | 117 | 59 | 117 | 26 |
| n (Pat) | 99 | 51 | 99 | 59 | 99 | 26 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 22.968 | 19.785 | 22.968 | 51.942 | 22.968 | 49.032 |
| average | 86.563 | 52.912 | 86.563 | 95.433 | 86.563 | 69.933 |
| stdev | 202.982 | 55.136 | 202.982 | 110.102 | 202.982 | 71.115 |
| p (t-test) |  | 0.497 |  | 0.836 |  | 0.761 |
| min | 0.276 | 2.742 | 0.276 | 0.040 | 0.276 | 1.041 |
| max | 2177.715 | 163.819 | 2177.715 | 451.558 | 2177.715 | 250.000 |
| n (Samp) | 260 | 17 | 260 | 23 | 260 | 14 |
| n (Pat) | 160 | 17 | 160 | 23 | 160 | 14 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 20.492 | 25.025 | 20.492 | 27.794 | 20.492 | 23.313 |
| average | 96.690 | 80.407 | 96.690 | 96.517 | 96.690 | 85.278 |
| stdev | 177.408 | 182.555 | 177.408 | 152.854 | 177.408 | 138.995 |
| p (t-test) |  | 0.610 |  | 0.995 |  | 0.773 |
| min | 0.000 | 1.400 | 0.000 | 0.088 | 0.000 | 2.742 |
| max | 1020.452 | 1190.527 | 1020.452 | 810.740 | 1020.452 | 500.000 |
| n (Samp) | 105 | 45 | 105 | 49 | 105 | 23 |
| n (Pat) | 84 | 45 | 84 | 49 | 84 | 23 | sCr or UO

| Time prior AKI stage | AUC | SE | nCohort 1 | nCohort 2 | p |
|---|---|---|---|---|---|
| 0 hours | 0.53 | 0.049 | 117 | 51 | 0.490 |
| 24 hours | 0.55 | 0.046 | 117 | 59 | 0.249 |
| 48 hours | 0.54 | 0.064 | 117 | 26 | 0.522 | sCr only

| Time prior AKI stage | AUC | SE | nCohort 1 | nCohort 2 | p |
|---|---|---|---|---|---|
| 0 hours | 0.55 | 0.074 | 260 | 17 | 0.513 |
| 24 hours | 0.60 | 0.065 | 260 | 23 | 0.132 |
| 48 hours | 0.62 | 0.082 | 260 | 14 | 0.157 |

UO only

| Time prior AKI stage | AUC | SE | nCohort 1 | nCohort 2 | p |
|---|---|---|---|---|---|
| 0 hours | 0.52 | 0.052 | 105 | 45 | 0.679 |
| 24 hours | 0.54 | 0.050 | 105 | 49 | 0.374 |
| 48 hours | 0.51 | 0.067 | 105 | 23 | 0.919 |

Fig. 1 Continued sCr or UO

| Time prior AKI stage | Cutoff value | sens | spec | Quartile | OR | 95% CI of OR | |
|---|---|---|---|---|---|---|---|
| 0 hours | 11.03 | 71% | 43% | 1 | | | |
| | 6.90238 | 80% | 28% | 2 | 1.6 | 1.0 | 2.6 |
| | 2.79427 | 90% | 12% | 3 | 1.8 | 1.1 | 2.8 |
| | 44.8301 | 33% | 70% | 4 | 1.3 | 0.8 | 2.1 |
| | 94.7705 | 20% | 80% | | | | |
| | 250 | 4% | 91% | | | | |
| 24 hours | 10.1116 | 71% | 41% | 1 | | | |
| | 5.63678 | 81% | 20% | 2 | 0.8 | 0.5 | 1.2 |
| | 3.75543 | 92% | 14% | 3 | 1.0 | 0.7 | 1.5 |
| | 44.8301 | 39% | 70% | 4 | 1.6 | 1.1 | 2.4 |
| | 94.7705 | 32% | 80% | | | | |
| | 250 | 8% | 91% | | | | |
| 48 hours | 9.34959 | 73% | 38% | 1 | | | |
| | 5.33977 | 81% | 19% | 2 | 0.8 | 0.3 | 1.8 |
| | 3.75543 | 92% | 14% | 3 | 1.4 | 0.7 | 2.8 |
| | 44.8301 | 31% | 70% | 4 | 1.2 | 0.6 | 2.4 |
| | 94.7705 | 23% | 80% | | | | |
| | 250 | 8% | 91% | | | | | sCr only

| Time prior AKI stage | Cutoff value | sens | spec | Quartile | OR | 95% CI of OR | |
|---|---|---|---|---|---|---|---|
| 0 hours | 16.0979 | 71% | 44% | 1 | | | |
| | 10.1116 | 82% | 33% | 2 | 8.9 | 0.9 | 86.0 |
| | 9.8178 | 94% | 32% | 3 | 3.1 | 0.2 | 44.7 |
| | 53.7478 | 35% | 70% | 4 | 5.2 | 0.5 | 58.3 |
| | 103.153 | 24% | 80% | | | | |
| | 236.01 | 0% | 90% | | | | |
| 24 hours | 12.9831 | 74% | 40% | 1 | | | |
| | 5.83554 | 83% | 20% | 2 | 0.6 | 0.2 | 1.7 |
| | 4.46347 | 91% | 15% | 3 | 1.2 | 0.6 | 2.6 |
| | 53.7478 | 43% | 70% | 4 | 1.9 | 1.0 | 3.7 |
| | 103.153 | 39% | 80% | | | | |
| | 236.01 | 9% | 90% | | | | |
| 48 hours | 27.5257 | 71% | 56% | 1 | | | |
| | 12.471 | 86% | 39% | 2 | 2.0 | 0.1 | 40.1 |
| | 9.50604 | 93% | 31% | 3 | 6.5 | 0.6 | 67.8 |
| | 53.7478 | 50% | 70% | 4 | 5.2 | 0.5 | 58.4 |
| | 103.153 | 21% | 80% | | | | |
| | 236.01 | 7% | 90% | | | | |

UO only

| Time prior AKI stage | Cutoff value | sens | spec | Quartile | OR | 95% CI of OR | |
|---|---|---|---|---|---|---|---|
| 0 hours | 13.0416 | 71% | 46% | 1 | | | |
| | 6.90238 | 80% | 28% | 2 | 1.4 | 0.8 | 2.4 |
| | 2.78263 | 91% | 11% | 3 | 1.9 | 1.1 | 3.2 |
| | 67.9352 | 27% | 70% | 4 | 1.1 | 0.6 | 1.9 |
| | 136.906 | 11% | 80% | | | | |
| | 254.822 | 4% | 90% | | | | |
| 24 hours | 12.8442 | 71% | 44% | 1 | | | |
| | 6.90238 | 82% | 28% | 2 | 1.8 | 1.1 | 3.0 |
| | 3.75543 | 92% | 13% | 3 | 1.5 | 0.9 | 2.5 |
| | 67.9352 | 35% | 70% | 4 | 1.8 | 1.1 | 3.0 |
| | 136.906 | 24% | 80% | | | | |
| | 254.822 | 12% | 90% | | | | |

Fig. 1 Continued

| 48 hours | 6.8426 | 74% | 27% | 1 | | | |
|---|---|---|---|---|---|---|---|
| | 4.98139 | 83% | 16% | 2 | 0.8 | 0.3 | 1.9 |
| | 3.75543 | 91% | 13% | 3 | 1.0 | 0.4 | 2.2 |
| | 67.9352 | 26% | 70% | 4 | 1.0 | 0.4 | 2.2 |
| | 136.906 | 13% | 80% | | | | |
| | 254.822 | 13% | 90% | | | | |

Granulocyte colony-stimulating factor sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 22.000 | 34.200 | 22.000 | 41.200 | 22.000 | 39.800 |
| average | 44.116 | 60.908 | 44.116 | 441.460 | 44.116 | 2127.522 |
| stdev | 70.379 | 156.044 | 70.379 | 2467.967 | 70.379 | 10471.145 |
| p (t-test) | | 0.224 | | 0.011 | | 0.002 |
| min | 1.020 | 0.907 | 1.020 | 0.020 | 1.020 | 0.020 |
| max | 521.000 | 1150.000 | 521.000 | 19300.000 | 521.000 | 54500.000 |
| n (Samp) | 249 | 53 | 249 | 62 | 249 | 27 |
| n (Pat) | 104 | 53 | 104 | 62 | 104 | 27 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 25.700 | 35.250 | 25.700 | 41.500 | 25.700 | 36.850 |
| average | 604.248 | 35.443 | 604.248 | 268.246 | 604.248 | 155.355 |
| stdev | 6495.892 | 31.160 | 6495.892 | 634.851 | 6495.892 | 420.205 |
| p (t-test) | | 0.696 | | 0.792 | | 0.796 |
| min | 0.020 | 0.907 | 0.020 | 0.020 | 0.020 | 1.750 |
| max | 103844.000 | 109.000 | 103844.000 | 3010.000 | 103844.000 | 1610.000 |
| n (Samp) | 441 | 20 | 441 | 26 | 441 | 14 |
| n (Pat) | 170 | 20 | 170 | 26 | 170 | 14 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 22.800 | 43.500 | 22.800 | 42.450 | 22.800 | 39.800 |
| average | 55.574 | 67.482 | 55.574 | 536.945 | 55.574 | 2235.649 |
| stdev | 150.602 | 164.957 | 150.602 | 2707.258 | 150.602 | 10888.539 |
| p (t-test) | | 0.630 | | 0.010 | | 0.003 |
| min | 1.020 | 3.290 | 1.020 | 6.000 | 1.020 | 0.020 |
| max | 1610.000 | 1150.000 | 1610.000 | 19300.000 | 1610.000 | 54500.000 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
|---|---|---|---|---|---|
| 0 hours | 0.55 | 0.044 | 249 | 53 | 0.246 |
| 24 hours | 0.62 | 0.041 | 249 | 62 | 0.003 |
| 48 hours | 0.63 | 0.060 | 249 | 27 | 0.027 | sCr only

| Time prior AKI stage | AUC | SE | nCohort 1 | nCohort 2 | p |
|---|---|---|---|---|---|
| 0 hours | 0.47 | 0.065 | 441 | 20 | 0.659 |
| 24 hours | 0.59 | 0.060 | 441 | 26 | 0.149 |
| 48 hours | 0.57 | 0.081 | 441 | 14 | 0.357 |

Fig. 1 Continued

UO only

| Time prior AKI stage | AUC | SE | nCohort 1 | nCohort 2 | p |
|---|---|---|---|---|---|
| 0 hours | 0.59 | 0.047 | 212 | 47 | 0.054 |
| 24 hours | 0.67 | 0.044 | 212 | 52 | 0.000 |
| 48 hours | 0.66 | 0.062 | 212 | 25 | 0.008 |

Cr or UO

| Time prior AKI stage | Cutoff value | sens | spec | Quartile | OR | 95% CI of OR | |
|---|---|---|---|---|---|---|---|
| 0 hours | 13.1 | 72% | 29% | 1 | | | |
| | 11.4 | 81% | 22% | 2 | 0.7 | 0.5 | 1.1 |
| | 4.83 | 91% | 5% | 3 | 1.2 | 0.8 | 1.7 |
| | 40.8 | 43% | 70% | 4 | 1.6 | 1.2 | 2.3 |
| | 55 | 26% | 80% | | | | |
| | 88.1 | 11% | 90% | | | | |
| 24 hours | 23.1 | 71% | 53% | 1 | | | |
| | 13.4 | 81% | 29% | 2 | 0.7 | 0.4 | 1.1 |
| | 7.73 | 90% | 12% | 3 | 2.1 | 1.5 | 2.9 |
| | 40.8 | 50% | 70% | 4 | 2.5 | 1.8 | 3.5 |
| | 55 | 35% | 80% | | | | |
| | 88.1 | 21% | 90% | | | | |
| 48 hours | 25.5 | 70% | 55% | 1 | | | |
| | 18.1 | 81% | 42% | 2 | 0.6 | 0.2 | 1.8 |
| | 3.85 | 93% | 3% | 3 | 1.2 | 0.6 | 2.7 |
| | 40.8 | 48% | 70% | 4 | 3.0 | 1.6 | 5.5 |
| | 55 | 41% | 80% | | | | |
| | 88.1 | 26% | 90% | | | | | sCr only

| Time prior AKI stage | Cutoff value | sens | spec | Quartile | OR | 95% CI of OR | |
|---|---|---|---|---|---|---|---|
| 0 hours | 11.5 | 70% | 22% | 1 | | | |
| | 5.74 | 80% | 7% | 2 | 0.8 | 0.4 | 1.8 |
| | 3.29 | 90% | 3% | 3 | 0.3 | 0.1 | 1.2 |
| | 45.3 | 30% | 70% | 4 | 1.2 | 0.6 | 2.3 |
| | 59.2 | 25% | 80% | | | | |
| | 98.2 | 5% | 90% | | | | |
| 24 hours | 11.5 | 73% | 22% | 1 | | | |
| | 10.4 | 81% | 19% | 2 | 0.2 | 0.1 | 0.8 |
| | 4.43 | 92% | 5% | 3 | 0.6 | 0.3 | 1.2 |
| | 45.3 | 46% | 70% | 4 | 1.4 | 0.9 | 2.2 |
| | 59.2 | 42% | 80% | | | | |
| | 98.2 | 31% | 90% | | | | |
| 48 hours | 21.8 | 71% | 43% | 1 | | | |
| | 9.92 | 86% | 17% | 2 | 0.7 | 0.1 | 3.5 |
| | 8.91 | 93% | 15% | 3 | 1.3 | 0.4 | 4.3 |
| | 45.3 | 36% | 70% | 4 | 1.7 | 0.6 | 5.0 |
| | 59.2 | 36% | 80% | | | | |
| | 98.2 | 21% | 90% | | | | |

UO only

| Time prior AKI stage | Cutoff value | sens | spec | Quartile | OR | 95% CI of OR | |
|---|---|---|---|---|---|---|---|
| 0 hours | 18.5 | 70% | 42% | 1 | | | |
| | 12.2 | 81% | 26% | 2 | 1.0 | 0.6 | 1.6 |
| | 4.83 | 91% | 6% | 3 | 1.1 | 0.7 | 1.8 |
| | 37.7 | 53% | 70% | 4 | 2.5 | 1.7 | 3.8 |
| | 50.7 | 38% | 80% | | | | |
| | 81.6 | 17% | 90% | | | | |

Fig. 1 Continued

| 24 hours | 27.3 | 71% | 56% | 1 |     |     |     |
|          | 22.5 | 81% | 50% | 2 | 1.6 | 0.9 | 2.9 |
|          | 13.4 | 90% | 28% | 3 | 3.2 | 1.9 | 5.4 |
|          | 37.7 | 54% | 70% | 4 | 4.7 | 2.8 | 7.7 |
|          | 50.7 | 40% | 80% |   |     |     |     |
|          | 81.6 | 21% | 90% |   |     |     |     |
| 48 hours | 28.8 | 72% | 58% | 1 |     |     |     |
|          | 21.8 | 80% | 48% | 2 | 1.0 | 0.3 | 4.0 |
|          | 12.2 | 92% | 26% | 3 | 2.9 | 1.1 | 7.7 |
|          | 37.7 | 52% | 70% | 4 | 4.2 | 1.7 | 10.4 |
|          | 50.7 | 44% | 80% |   |     |     |     |
|          | 81.6 | 24% | 90% |   |     |     |     |

Granulocyte-macrophage colony-stimulating factor sCr or UO

|          | 0 hr prior to AKI stage | | 24 hr prior to AKI stage | | 48 hr prior to AKI stage | |
|          | Cohort 1 | Cohort 2 | Cohort 1 | Cohort 2 | Cohort 1 | Cohort 2 |
|----------|----------|----------|----------|----------|----------|----------|
| median   | 7.610 | 9.720 | 7.610 | 8.365 | 7.610 | 7.500 |
| average  | 8.035 | 10.174 | 8.035 | 11.264 | 8.035 | 10.320 |
| stdev    | 4.907 | 5.888 | 4.907 | 12.417 | 4.907 | 7.843 |
| p (t-test) |     | 0.006 |       | 0.001 |       | 0.033 |
| min      | 0.230 | 0.230 | 0.230 | 0.230 | 0.230 | 0.230 |
| max      | 29.400 | 27.000 | 29.400 | 88.600 | 29.400 | 26.200 |
| n (Samp) | 249 | 53 | 249 | 62 | 249 | 27 |
| n (Pat)  | 104 | 53 | 104 | 62 | 104 | 27 | sCr only

|          | 0 hr prior to AKI stage | | 24 hr prior to AKI stage | | 48 hr prior to AKI stage | |
|          | Cohort 1 | Cohort 2 | Cohort 1 | Cohort 2 | Cohort 1 | Cohort 2 |
|----------|----------|----------|----------|----------|----------|----------|
| median   | 7.800 | 5.280 | 7.800 | 7.860 | 7.800 | 9.525 |
| average  | 9.732 | 8.228 | 9.732 | 9.430 | 9.732 | 8.926 |
| stdev    | 22.230 | 8.582 | 22.230 | 7.299 | 22.230 | 7.332 |
| p (t-test) |     | 0.763 |       | 0.945 |       | 0.892 |
| min      | 0.230 | 0.230 | 0.230 | 0.230 | 0.230 | 0.230 |
| max      | 453.000 | 37.500 | 453.000 | 34.400 | 453.000 | 24.300 |
| n (Samp) | 441 | 20 | 441 | 26 | 441 | 14 |
| n (Pat)  | 170 | 20 | 170 | 26 | 170 | 14 |

UO only

|          | 0 hr prior to AKI stage | | 24 hr prior to AKI stage | | 48 hr prior to AKI stage | |
|          | Cohort 1 | Cohort 2 | Cohort 1 | Cohort 2 | Cohort 1 | Cohort 2 |
|----------|----------|----------|----------|----------|----------|----------|
| median   | 7.775 | 10.300 | 7.775 | 9.510 | 7.775 | 7.500 |
| average  | 8.142 | 10.865 | 8.142 | 12.268 | 8.142 | 10.400 |
| stdev    | 4.785 | 5.691 | 4.785 | 13.272 | 4.785 | 7.134 |
| p (t-test) |     | 0.001 |       | 0.000 |       | 0.036 |
| min      | 0.230 | 0.230 | 0.230 | 0.230 | 0.230 | 0.230 |
| max      | 29.400 | 27.000 | 29.400 | 88.600 | 29.400 | 26.200 |
| n (Samp) | 212 | 47 | 212 | 52 | 212 | 25 |
| n (Pat)  | 85 | 47 | 85 | 52 | 85 | 25 | sCr or UO

| Time prior AKI stage | AUC | SE | nCohort 1 | nCohort 2 | p |
|----------------------|-----|-----|-----------|-----------|-----|
| 0 hours  | 0.61 | 0.044 | 249 | 53 | 0.017 |
| 24 hours | 0.59 | 0.042 | 249 | 62 | 0.039 |
| 48 hours | 0.56 | 0.060 | 249 | 27 | 0.287 |

Fig. 1 Continued sCr only

| Time prior AKI stage | AUC | SE | nCohort 1 | nCohort 2 | p |
|---|---|---|---|---|---|
| 0 hours | 0.44 | 0.063 | 441 | 20 | 0.309 |
| 24 hours | 0.53 | 0.059 | 441 | 26 | 0.671 |
| 48 hours | 0.51 | 0.079 | 441 | 14 | 0.877 |

UO only

| Time prior AKI stage | AUC | SE | nCohort 1 | nCohort 2 | p |
|---|---|---|---|---|---|
| 0 hours | 0.64 | 0.047 | 212 | 47 | 0.002 |
| 24 hours | 0.61 | 0.045 | 212 | 52 | 0.014 |
| 48 hours | 0.57 | 0.063 | 212 | 25 | 0.273 | sCr or UO

| Time prior AKI stage | Cutoff value | sens | spec | Quartile | OR | 95% CI of OR | |
|---|---|---|---|---|---|---|---|
| 0 hours | 6.17 | 74% | 37% | 1 | | | |
| | 4.94 | 81% | 26% | 2 | 0.7 | 0.4 | 1.1 |
| | 3.5 | 92% | 16% | 3 | 1.3 | 0.9 | 2.0 |
| | 9.94 | 47% | 70% | 4 | 2.1 | 1.5 | 2.9 |
| | 11.5 | 38% | 80% | | | | |
| | 14.5 | 23% | 90% | | | | |
| 24 hours | 6.17 | 73% | 37% | 1 | | | |
| | 5.04 | 81% | 27% | 2 | 1.0 | 0.7 | 1.4 |
| | 0.2296 | 90% | 9% | 3 | 1.4 | 1.0 | 2.0 |
| | 9.94 | 40% | 70% | 4 | 2.1 | 1.5 | 2.9 |
| | 11.5 | 35% | 80% | | | | |
| | 14.5 | 21% | 90% | | | | |
| 48 hours | 6.17 | 70% | 37% | 1 | | | |
| | 3.47 | 81% | 16% | 2 | 1.4 | 0.7 | 2.6 |
| | 0 | 100% | 0% | 3 | 0.5 | 0.2 | 1.4 |
| | 9.94 | 44% | 70% | 4 | 1.8 | 1.0 | 3.2 |
| | 11.5 | 30% | 80% | | | | |
| | 14.5 | 26% | 90% | | | | | sCr only

| Time prior AKI stage | Cutoff value | sens | spec | Quartile | OR | 95% CI of OR | |
|---|---|---|---|---|---|---|---|
| 0 hours | 4.85 | 70% | 25% | 1 | | | |
| | 0.2296 | 80% | 9% | 2 | 1.3 | 0.5 | 3.2 |
| | 0 | 100% | 0% | 3 | 1.3 | 0.5 | 3.2 |
| | 10.5 | 30% | 71% | 4 | 1.5 | 0.7 | 3.6 |
| | 12.5 | 15% | 80% | | | | |
| | 16 | 10% | 90% | | | | |
| 24 hours | 5.08 | 77% | 28% | 1 | | | |
| | 4.85 | 81% | 25% | 2 | 1.0 | 0.4 | 2.2 |
| | 0 | 100% | 0% | 3 | 1.4 | 0.7 | 2.9 |
| | 10.5 | 35% | 71% | 4 | 1.9 | 1.0 | 3.5 |
| | 12.5 | 23% | 80% | | | | |
| | 16 | 15% | 90% | | | | |
| 48 hours | 3.17 | 71% | 13% | 1 | | | |
| | 0 | 100% | 0% | 2 | 0.2 | 0.0 | 2.1 |
| | 0 | 100% | 0% | 3 | 0.8 | 0.3 | 2.0 |
| | 10.5 | 43% | 71% | 4 | 0.8 | 0.3 | 2.0 |
| | 12.5 | 29% | 80% | | | | |
| | 16 | 14% | 90% | | | | |

Fig. 1 Continued

UO only

| Time prior AKI stage | Cutoff value | sens | spec | Quartile | OR | 95% CI of OR | |
|---|---|---|---|---|---|---|---|
| 0 hours | 7.83 | 70% | 51% | 1 | | | |
| | 6.1 | 83% | 35% | 2 | 1.0 | 0.6 | 1.7 |
| | 4.33 | 91% | 18% | 3 | 1.8 | 1.1 | 2.8 |
| | 10.3 | 49% | 70% | 4 | 2.7 | 1.7 | 4.1 |
| | 11.8 | 34% | 80% | | | | |
| | 14.1 | 28% | 90% | | | | |
| 24 hours | 6.89 | 71% | 45% | 1 | | | |
| | 5.91 | 81% | 33% | 2 | 0.9 | 0.5 | 1.4 |
| | 3.47 | 90% | 14% | 3 | 1.4 | 0.9 | 2.1 |
| | 10.3 | 44% | 70% | 4 | 2.4 | 1.7 | 3.5 |
| | 11.8 | 35% | 80% | | | | |
| | 14.1 | 23% | 90% | | | | |
| 48 hours | 6.1 | 72% | 35% | 1 | | | |
| | 5.91 | 80% | 33% | 2 | 1.7 | 0.8 | 3.5 |
| | 3.07 | 92% | 12% | 3 | 0.8 | 0.3 | 2.0 |
| | 10.3 | 40% | 70% | 4 | 1.7 | 0.8 | 3.4 |
| | 11.8 | 32% | 80% | | | | |
| | 14.1 | 28% | 90% | | | | |

Heparin-binding growth factor 2 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 165.000 | 233.000 | 165.000 | 225.000 | 165.000 | 203.000 |
| average | 216.177 | 318.408 | 216.177 | 412.169 | 216.177 | 335.052 |
| stdev | 211.472 | 303.837 | 211.472 | 543.119 | 211.472 | 395.062 |
| p (t-test) | | 0.004 | | 0.000 | | 0.013 |
| min | 0.392 | 28.800 | 0.392 | 37.000 | 0.392 | 0.392 |
| max | 1320.000 | 1540.000 | 1320.000 | 3610.000 | 1320.000 | 2010.000 |
| n (Samp) | 249 | 53 | 249 | 62 | 249 | 27 |
| n (Pat) | 104 | 53 | 104 | 62 | 104 | 27 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 165.000 | 240.500 | 165.000 | 223.500 | 165.000 | 310.500 |
| average | 247.374 | 302.775 | 247.374 | 421.315 | 247.374 | 365.407 |
| stdev | 308.558 | 257.342 | 308.558 | 359.414 | 308.558 | 272.077 |
| p (t-test) | | 0.430 | | 0.006 | | 0.158 |
| min | 0.392 | 39.200 | 0.392 | 37.000 | 0.392 | 39.200 |
| max | 3610.000 | 997.000 | 3610.000 | 1140.000 | 3610.000 | 915.000 |
| n (Samp) | 441 | 20 | 441 | 26 | 441 | 14 |
| n (Pat) | 170 | 20 | 170 | 26 | 170 | 14 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 164.000 | 246.000 | 164.000 | 226.500 | 164.000 | 225.000 |
| average | 197.921 | 335.889 | 197.921 | 425.929 | 197.921 | 359.412 |
| stdev | 183.526 | 317.975 | 183.526 | 570.343 | 183.526 | 405.115 |
| p (t-test) | | 0.000 | | 0.000 | | 0.001 |
| min | 0.392 | 28.800 | 0.392 | 42.100 | 0.392 | 0.392 |
| max | 1320.000 | 1540.000 | 1320.000 | 3610.000 | 1320.000 | 2010.000 |
| n (Samp) | 212 | 47 | 212 | 52 | 212 | 25 |
| n (Pat) | 85 | 47 | 85 | 52 | 85 | 25 |

Fig. 1 Continued sCr or UO

| Time prior AKI stage | AUC | SE | nCohort 1 | nCohort 2 | p |
|---|---|---|---|---|---|
| 0 hours | 0.64 | 0.044 | 249 | 53 | 0.002 |
| 24 hours | 0.65 | 0.041 | 249 | 62 | 0.000 |
| 48 hours | 0.62 | 0.060 | 249 | 27 | 0.053 | sCr only

| Time prior AKI stage | AUC | SE | nCohort 1 | nCohort 2 | p |
|---|---|---|---|---|---|
| 0 hours | 0.59 | 0.068 | 441 | 20 | 0.187 |
| 24 hours | 0.64 | 0.060 | 441 | 26 | 0.017 |
| 48 hours | 0.69 | 0.080 | 441 | 14 | 0.020 |

UO only

| Time prior AKI stage | AUC | SE | nCohort 1 | nCohort 2 | p |
|---|---|---|---|---|---|
| 0 hours | 0.68 | 0.046 | 212 | 47 | 0.000 |
| 24 hours | 0.71 | 0.043 | 212 | 52 | 0.000 |
| 48 hours | 0.66 | 0.062 | 212 | 25 | 0.009 | sCr or UO

| Time prior AKI stage | Cutoff value | sens | spec | Quartile | OR | 95% CI of OR | |
|---|---|---|---|---|---|---|---|
| 0 hours | 145 | 74% | 44% | 1 | | | |
| | 124 | 81% | 35% | 2 | 1.0 | 0.6 | 1.6 |
| | 94.9 | 91% | 25% | 3 | 1.7 | 1.1 | 2.6 |
| | 229 | 51% | 70% | 4 | 2.8 | 1.9 | 4.1 |
| | 271 | 40% | 80% | | | | |
| | 392 | 25% | 90% | | | | |
| 24 hours | 161 | 71% | 49% | 1 | | | |
| | 133 | 81% | 40% | 2 | 2.4 | 1.5 | 3.8 |
| | 101 | 90% | 27% | 3 | 2.6 | 1.6 | 4.1 |
| | 229 | 45% | 70% | 4 | 4.4 | 2.9 | 6.8 |
| | 271 | 39% | 80% | | | | |
| | 392 | 29% | 90% | | | | |
| 48 hours | 165 | 70% | 52% | 1 | | | |
| | 112 | 81% | 30% | 2 | 0.8 | 0.3 | 2.0 |
| | 69.8 | 93% | 16% | 3 | 1.7 | 0.8 | 3.4 |
| | 229 | 41% | 70% | 4 | 2.2 | 1.1 | 4.2 |
| | 271 | 33% | 80% | | | | |
| | 392 | 26% | 90% | | | | | sCr only

| Time prior AKI stage | Cutoff value | sens | spec | Quartile | OR | 95% CI of OR | |
|---|---|---|---|---|---|---|---|
| 0 hours | 139 | 70% | 42% | 1 | | | |
| | 102 | 80% | 25% | 2 | 1.3 | 0.5 | 3.2 |
| | 96.7 | 90% | 24% | 3 | 0.7 | 0.2 | 2.4 |
| | 246 | 50% | 71% | 4 | 2.1 | 1.0 | 4.4 |
| | 300 | 35% | 80% | | | | |
| | 482 | 20% | 90% | | | | |
| 24 hours | 151 | 73% | 46% | 1 | | | |
| | 119 | 81% | 33% | 2 | 2.0 | 0.7 | 5.6 |
| | 82.4 | 92% | 19% | 3 | 1.7 | 0.6 | 5.0 |
| | 246 | 46% | 71% | 4 | 4.3 | 1.8 | 10.1 |
| | 300 | 46% | 80% | | | | |
| | 482 | 38% | 90% | | | | |

Fig. 1 Continued

| | | | | | | | |
|---|---|---|---|---|---|---|---|
| 48 hours | 201 | 71% | 61% | 1 | | | |
| | 154 | 86% | 47% | 2 | 0.5 | 0.0 | 9.6 |
| | 96.7 | 93% | 24% | 3 | 1.5 | 0.3 | 8.0 |
| | 246 | 57% | 71% | 4 | 4.2 | 1.2 | 14.8 |
| | 300 | 57% | 80% | | | | |
| | 482 | 21% | 90% | | | | |

UO only

| Time prior AKI stage | Cutoff value | sens | spec | Quartile | OR | 95% CI of OR | |
|---|---|---|---|---|---|---|---|
| 0 hours | 177 | 70% | 57% | 1 | | | |
| | 133 | 81% | 39% | 2 | 1.2 | 0.6 | 2.3 |
| | 94.9 | 91% | 24% | 3 | 2.2 | 1.2 | 3.8 |
| | 208 | 57% | 71% | 4 | 4.9 | 3.0 | 8.1 |
| | 257 | 45% | 80% | | | | |
| | 312 | 30% | 90% | | | | |
| 24 hours | 178 | 71% | 58% | 1 | | | |
| | 145 | 83% | 43% | 2 | 4.2 | 1.7 | 10.3 |
| | 118 | 92% | 31% | 3 | 6.2 | 2.6 | 14.5 |
| | 208 | 62% | 71% | 4 | 11.2 | 5.0 | 25.4 |
| | 257 | 44% | 80% | | | | |
| | 312 | 38% | 90% | | | | |
| 48 hours | 165 | 72% | 54% | 1 | | | |
| | 124 | 80% | 34% | 2 | 0.7 | 0.2 | 2.5 |
| | 70.4 | 92% | 14% | 3 | 1.6 | 0.6 | 3.8 |
| | 208 | 52% | 71% | 4 | 3.4 | 1.7 | 7.1 |
| | 257 | 44% | 80% | | | | |
| | 312 | 36% | 90% | | | | |

Interleukin-1 receptor antagonist sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 3100.000 | 5560.000 | 3100.000 | 5295.000 | 3100.000 | 4800.000 |
| average | 17527.197 | 11883.717 | 17527.197 | 18126.029 | 17527.197 | 32638.222 |
| stdev | 61871.460 | 16010.162 | 61871.460 | 39080.222 | 61871.460 | 84643.011 |
| p (t-test) | | 0.511 | | 0.942 | | 0.248 |
| min | 116.000 | 246.000 | 116.000 | 77.800 | 116.000 | 392.000 |
| max | 520726.000 | 90800.000 | 520726.000 | 261000.000 | 520726.000 | 439392.000 |
| n (Samp) | 249 | 53 | 249 | 62 | 249 | 27 |
| n (Pat) | 104 | 53 | 104 | 62 | 104 | 27 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 4060.000 | 2910.000 | 4060.000 | 2625.000 | 4060.000 | 4920.000 |
| average | 17960.275 | 11151.350 | 17960.275 | 24542.954 | 17960.275 | 40930.286 |
| stdev | 60125.582 | 15644.197 | 60125.582 | 44481.623 | 60125.582 | 115464.548 |
| p (t-test) | | 0.614 | | 0.583 | | 0.176 |
| min | 48.100 | 246.000 | 48.100 | 77.800 | 48.100 | 458.000 |
| max | 598080.000 | 48400.000 | 598080.000 | 187000.000 | 598080.000 | 439392.000 |
| n (Samp) | 441 | 20 | 441 | 26 | 441 | 14 |
| n (Pat) | 170 | 20 | 170 | 26 | 170 | 14 |

Fig. 1 Continued

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 3070.000 | 6210.000 | 3070.000 | 6065.000 | 3070.000 | 3090.000 |
| average | 16427.632 | 12214.681 | 16427.632 | 27716.327 | 16427.632 | 17104.920 |
| stdev | 59734.366 | 15873.688 | 59734.366 | 71777.681 | 59734.366 | 24421.592 |
| p (t-test) | | 0.632 | | 0.242 | | 0.955 |
| min | 116.000 | 776.000 | 116.000 | 937.000 | 116.000 | 392.000 |
| max | 520726.000 | 90800.000 | 520726.000 | 439392.000 | 520726.000 | 91800.000 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
|---|---|---|---|---|---|
| 0 hours | 0.59 | 0.045 | 249 | 53 | 0.039 |
| 24 hours | 0.61 | 0.042 | 249 | 62 | 0.011 |
| 48 hours | 0.58 | 0.060 | 249 | 27 | 0.180 | sCr only

| Time prior AKI stage | AUC | SE | nCohort 1 | nCohort 2 | p |
|---|---|---|---|---|---|
| 0 hours | 0.46 | 0.064 | 441 | 20 | 0.507 |
| 24 hours | 0.51 | 0.058 | 441 | 26 | 0.930 |
| 48 hours | 0.55 | 0.080 | 441 | 14 | 0.530 |

UO only

| Time prior AKI stage | AUC | SE | nCohort 1 | nCohort 2 | p |
|---|---|---|---|---|---|
| 0 hours | 0.65 | 0.047 | 212 | 47 | 0.001 |
| 24 hours | 0.65 | 0.045 | 212 | 52 | 0.001 |
| 48 hours | 0.56 | 0.063 | 212 | 25 | 0.300 | sCr or UO

| Time prior AKI stage | Cutoff value | sens | spec | Quartile | OR | 95% CI of OR | |
|---|---|---|---|---|---|---|---|
| 0 hours | 1880 | 72% | 39% | 1 | | | |
| | 1520 | 81% | 31% | 2 | 1.0 | 0.6 | 1.5 |
| | 837 | 91% | 15% | 3 | 1.6 | 1.1 | 2.4 |
| | 6920 | 43% | 70% | 4 | 2.0 | 1.4 | 2.9 |
| | 11900 | 34% | 80% | | | | |
| | 21700 | 19% | 90% | | | | |
| 24 hours | 2570 | 71% | 46% | 1 | | | |
| | 1340 | 81% | 27% | 2 | 0.7 | 0.5 | 1.1 |
| | 961 | 90% | 19% | 3 | 1.7 | 1.3 | 2.4 |
| | 6920 | 44% | 70% | 4 | 2.1 | 1.5 | 2.9 |
| | 11900 | 32% | 80% | | | | |
| | 21700 | 18% | 90% | | | | |
| 48 hours | 2130 | 70% | 41% | 1 | | | |
| | 1120 | 81% | 22% | 2 | 1.2 | 0.6 | 2.3 |
| | 501 | 93% | 6% | 3 | 0.5 | 0.2 | 1.4 |
| | 6920 | 48% | 70% | 4 | 2.0 | 1.1 | 3.5 |
| | 11900 | 41% | 80% | | | | |
| | 21700 | 33% | 90% | | | | |

Fig. 1 Continued sCr only

| Time prior AKI stage | Cutoff value | sens | spec | Quartile | OR | 95% CI of OR | |
|---|---|---|---|---|---|---|---|
| 0 hours | 1520 | 70% | 26% | 1 | | | |
| | 866 | 80% | 14% | 2 | 0.3 | 0.1 | 1.2 |
| | 665 | 90% | 10% | 3 | 1.0 | 0.5 | 2.0 |
| | 8260 | 30% | 70% | 4 | 1.0 | 0.5 | 2.0 |
| | 14200 | 30% | 80% | | | | |
| | 29700 | 15% | 90% | | | | |
| 24 hours | 1340 | 73% | 23% | 1 | | | |
| | 961 | 81% | 16% | 2 | 0.4 | 0.2 | 0.8 |
| | 557 | 92% | 8% | 3 | 0.3 | 0.1 | 0.7 |
| | 8260 | 42% | 70% | 4 | 0.9 | 0.6 | 1.4 |
| | 14200 | 35% | 80% | | | | |
| | 29700 | 27% | 90% | | | | |
| 48 hours | 2450 | 71% | 38% | 1 | | | |
| | 1120 | 86% | 19% | 2 | 1.3 | 0.4 | 4.3 |
| | 522 | 93% | 7% | 3 | 0.7 | 0.1 | 3.5 |
| | 8260 | 43% | 70% | 4 | 1.7 | 0.6 | 5.0 |
| | 14200 | 29% | 80% | | | | |
| | 29700 | 14% | 90% | | | | |

UO only

| Time prior AKI stage | Cutoff value | sens | spec | Quartile | OR | 95% CI of OR | |
|---|---|---|---|---|---|---|---|
| 0 hours | 3570 | 70% | 54% | 1 | | | |
| | 2280 | 81% | 44% | 2 | 1.9 | 1.0 | 3.7 |
| | 1440 | 91% | 28% | 3 | 4.2 | 2.3 | 7.5 |
| | 6880 | 45% | 70% | 4 | 3.9 | 2.1 | 6.9 |
| | 11900 | 34% | 81% | | | | |
| | 17500 | 28% | 90% | | | | |
| 24 hours | 3290 | 71% | 54% | 1 | | | |
| | 2070 | 81% | 41% | 2 | 1.5 | 0.9 | 2.6 |
| | 1330 | 90% | 26% | 3 | 2.7 | 1.7 | 4.3 |
| | 6880 | 48% | 70% | 4 | 3.4 | 2.2 | 5.4 |
| | 11900 | 35% | 81% | | | | |
| | 17500 | 27% | 90% | | | | |
| 48 hours | 2070 | 72% | 41% | 1 | | | |
| | 1120 | 80% | 21% | 2 | 1.0 | 0.5 | 2.1 |
| | 697 | 92% | 9% | 3 | 0.6 | 0.3 | 1.6 |
| | 6880 | 44% | 70% | 4 | 1.6 | 0.8 | 2.9 |
| | 11900 | 36% | 81% | | | | |
| | 17500 | 32% | 90% | | | | |

Interleukin-1 beta sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.890 | 1.570 | 0.890 | 1.765 | 0.890 | 1.680 |
| average | 2.773 | 3.259 | 2.773 | 5.836 | 2.773 | 7.829 |
| stdev | 8.328 | 5.092 | 8.328 | 9.783 | 8.328 | 16.132 |
| p (t-test) | | 0.683 | | 0.013 | | 0.008 |
| min | 0.006 | 0.006 | 0.006 | 0.006 | 0.006 | 0.006 |
| max | 109.000 | 23.800 | 109.000 | 40.100 | 109.000 | 76.500 |
| n (Samp) | 249 | 53 | 249 | 62 | 249 | 27 |
| n (Pat) | 104 | 53 | 104 | 62 | 104 | 27 |

Fig. 1 Continued sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1.080 | 1.790 | 1.080 | 2.405 | 1.080 | 3.810 |
| average | 5.688 | 2.780 | 5.688 | 4.732 | 5.688 | 9.668 |
| stdev | 34.459 | 3.322 | 34.459 | 5.647 | 34.459 | 19.718 |
| p (t-test) |  | 0.706 |  | 0.888 |  | 0.668 |
| min | 0.006 | 0.006 | 0.006 | 0.006 | 0.006 | 0.006 |
| max | 670.000 | 12.500 | 670.000 | 22.400 | 670.000 | 76.500 |
| n (Samp) | 441 | 20 | 441 | 26 | 441 | 14 |
| n (Pat) | 170 | 20 | 170 | 26 | 170 | 14 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.971 | 1.570 | 0.971 | 1.960 | 0.971 | 2.170 |
| average | 2.495 | 3.886 | 2.495 | 7.005 | 2.495 | 4.820 |
| stdev | 8.002 | 5.760 | 8.002 | 11.316 | 8.002 | 8.380 |
| p (t-test) |  | 0.260 |  | 0.001 |  | 0.173 |
| min | 0.006 | 0.006 | 0.006 | 0.006 | 0.006 | 0.006 |
| max | 109.000 | 23.800 | 109.000 | 40.100 | 109.000 | 38.200 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
|---|---|---|---|---|---|
| 0 hours | 0.60 | 0.044 | 249 | 53 | 0.025 |
| 24 hours | 0.62 | 0.041 | 249 | 62 | 0.003 |
| 48 hours | 0.61 | 0.060 | 249 | 27 | 0.066 | sCr only

| Time prior AKI stage | AUC | SE | nCohort 1 | nCohort 2 | p |
|---|---|---|---|---|---|
| 0 hours | 0.56 | 0.068 | 441 | 20 | 0.372 |
| 24 hours | 0.60 | 0.060 | 441 | 26 | 0.085 |
| 48 hours | 0.68 | 0.080 | 441 | 14 | 0.021 |

UO only

| Time prior AKI stage | AUC | SE | nCohort 1 | nCohort 2 | p |
|---|---|---|---|---|---|
| 0 hours | 0.61 | 0.047 | 212 | 47 | 0.019 |
| 24 hours | 0.64 | 0.045 | 212 | 52 | 0.001 |
| 48 hours | 0.62 | 0.063 | 212 | 25 | 0.058 | sCr or UO

| Time prior AKI stage | Cutoff value | sens | spec | Quartile | OR | 95% CI of OR | |
|---|---|---|---|---|---|---|---|
| 0 hours | 0.714 | 72% | 45% | 1 |  |  |  |
|  | 0.579 | 81% | 37% | 2 | 1.6 | 1.0 | 2.5 |
|  | 0.264 | 91% | 16% | 3 | 2.3 | 1.5 | 3.5 |
|  | 1.84 | 42% | 70% | 4 | 2.4 | 1.6 | 3.7 |
|  | 2.9 | 28% | 80% |  |  |  |  |
|  | 5.32 | 17% | 90% |  |  |  |  |
| 24 hours | 0.697 | 71% | 44% | 1 |  |  |  |
|  | 0.603 | 81% | 39% | 2 | 1.3 | 0.9 | 2.0 |
|  | 0.242 | 90% | 14% | 3 | 1.3 | 0.9 | 2.0 |
|  | 1.84 | 48% | 70% | 4 | 3.4 | 2.4 | 4.7 |
|  | 2.9 | 32% | 80% |  |  |  |  |
|  | 5.32 | 26% | 90% |  |  |  |  |

Fig. 1 Continued

| | 48 hours | 0.695 | 70% | 44% | 1 | | | |
|---|---|---|---|---|---|---|---|---|
| | | 0.557 | 81% | 35% | 2 | 2.1 | 1.0 | 4.7 |
| | | 0.242 | 93% | 14% | 3 | 1.0 | 0.4 | 2.8 |
| | | 1.84 | 48% | 70% | 4 | 3.1 | 1.5 | 6.4 |
| | | 2.9 | 37% | 80% | | | | |
| | | 5.32 | 30% | 90% | | | | | sCr only

| Time prior AKI stage | Cutoff value | sens | spec | Quartile | OR | 95% CI of OR | |
|---|---|---|---|---|---|---|---|
| 0 hours | 0.96 | 70% | 46% | 1 | | | |
| | 0.634 | 80% | 34% | 2 | 1.0 | 0.4 | 2.8 |
| | 0.264 | 90% | 14% | 3 | 1.5 | 0.7 | 3.6 |
| | 2.27 | 45% | 70% | 4 | 1.5 | 0.6 | 3.5 |
| | 3.33 | 25% | 80% | | | | |
| | 9.87 | 10% | 90% | | | | |
| 24 hours | 0.783 | 73% | 41% | 1 | | | |
| | 0.508 | 81% | 27% | 2 | 0.8 | 0.3 | 2.0 |
| | 0 | 100% | 0% | 3 | 1.0 | 0.4 | 2.2 |
| | 2.27 | 50% | 70% | 4 | 2.5 | 1.4 | 4.6 |
| | 3.33 | 46% | 80% | | | | |
| | 9.87 | 12% | 90% | | | | |
| 48 hours | 1.99 | 71% | 67% | 1 | | | |
| | 0.695 | 86% | 37% | 2 | 3.0 | 0.2 | 42.8 |
| | 0.557 | 93% | 30% | 3 | 1.0 | 0.0 | 51.7 |
| | 2.27 | 64% | 70% | 4 | 9.6 | 1.0 | 87.9 |
| | 3.33 | 64% | 80% | | | | |
| | 9.87 | 14% | 90% | | | | |

UO only

| Time prior AKI stage | Cutoff value | sens | spec | Quartile | OR | 95% CI of OR | |
|---|---|---|---|---|---|---|---|
| 0 hours | 0.783 | 70% | 42% | 1 | | | |
| | 0.642 | 81% | 37% | 2 | 2.0 | 1.1 | 3.5 |
| | 0.267 | 91% | 14% | 3 | 2.9 | 1.7 | 4.9 |
| | 1.84 | 40% | 70% | 4 | 2.9 | 1.7 | 4.9 |
| | 2.92 | 30% | 80% | | | | |
| | 4.63 | 23% | 90% | | | | |
| 24 hours | 0.887 | 71% | 46% | 1 | | | |
| | 0.668 | 81% | 39% | 2 | 2.1 | 1.3 | 3.4 |
| | 0.365 | 90% | 20% | 3 | 1.9 | 1.1 | 3.1 |
| | 1.84 | 50% | 70% | 4 | 3.7 | 2.3 | 5.8 |
| | 2.92 | 31% | 80% | | | | |
| | 4.63 | 27% | 90% | | | | |
| 48 hours | 0.697 | 72% | 40% | 1 | | | |
| | 0.642 | 80% | 37% | 2 | 1.6 | 0.6 | 3.8 |
| | 0.242 | 96% | 12% | 3 | 1.0 | 0.3 | 2.9 |
| | 1.84 | 52% | 70% | 4 | 3.1 | 1.5 | 6.5 |
| | 2.92 | 36% | 80% | | | | |
| | 4.63 | 28% | 90% | | | | |

Fig. 1 Continued

Interleukin-10 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1.310 | 1.430 | 1.310 | 1.750 | 1.310 | 1.750 |
| average | 2.100 | 1.403 | 2.100 | 3.429 | 2.100 | 10.327 |
| stdev | 12.138 | 1.151 | 12.138 | 13.808 | 12.138 | 43.929 |
| p (t-test) |  | 0.677 |  | 0.454 |  | 0.023 |
| min | 0.062 | 0.062 | 0.062 | 0.062 | 0.062 | 0.062 |
| max | 192.000 | 4.000 | 192.000 | 110.000 | 192.000 | 230.000 |
| n (Samp) | 249 | 53 | 249 | 62 | 249 | 27 |
| n (Pat) | 104 | 53 | 104 | 62 | 104 | 27 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1.370 | 1.121 | 1.370 | 1.870 | 1.370 | 1.925 |
| average | 2.694 | 1.120 | 2.694 | 1.833 | 2.694 | 1.737 |
| stdev | 15.177 | 1.139 | 15.177 | 1.159 | 15.177 | 1.314 |
| p (t-test) |  | 0.643 |  | 0.773 |  | 0.814 |
| min | 0.062 | 0.062 | 0.062 | 0.062 | 0.062 | 0.062 |
| max | 230.000 | 4.410 | 230.000 | 4.130 | 230.000 | 4.130 |
| n (Samp) | 441 | 20 | 441 | 26 | 441 | 14 |
| n (Pat) | 170 | 20 | 170 | 26 | 170 | 14 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1.425 | 1.430 | 1.425 | 1.590 | 1.425 | 1.570 |
| average | 2.318 | 1.411 | 2.318 | 3.709 | 2.318 | 10.985 |
| stdev | 13.140 | 1.194 | 13.140 | 15.072 | 13.140 | 45.651 |
| p (t-test) |  | 0.638 |  | 0.507 |  | 0.034 |
| min | 0.062 | 0.062 | 0.062 | 0.062 | 0.062 | 0.062 |
| max | 192.000 | 4.000 | 192.000 | 110.000 | 192.000 | 230.000 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
|---|---|---|---|---|---|
| 0 hours | 0.52 | 0.044 | 249 | 53 | 0.723 |
| 24 hours | 0.60 | 0.042 | 249 | 62 | 0.019 |
| 48 hours | 0.62 | 0.060 | 249 | 27 | 0.054 | sCr only

| Time prior AKI stage | AUC | SE | nCohort 1 | nCohort 2 | p |
|---|---|---|---|---|---|
| 0 hours | 0.42 | 0.062 | 441 | 20 | 0.180 |
| 24 hours | 0.62 | 0.060 | 441 | 26 | 0.044 |
| 48 hours | 0.59 | 0.081 | 441 | 14 | 0.254 |

UO only

| Time prior AKI stage | AUC | SE | nCohort 1 | nCohort 2 | p |
|---|---|---|---|---|---|
| 0 hours | 0.49 | 0.046 | 212 | 47 | 0.803 |
| 24 hours | 0.56 | 0.045 | 212 | 52 | 0.178 |
| 48 hours | 0.59 | 0.063 | 212 | 25 | 0.160 |

Fig. 1 Continued sCr or UO

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.9 | 0.6 | 1.3 |
| | 0 | 100% | 0% | 3 | 1.0 | 0.7 | 1.4 |
| | 1.81 | 34% | 70% | 4 | 1.2 | 0.8 | 1.7 |
| | 2.14 | 21% | 82% | | | | |
| | 2.78 | 11% | 91% | | | | |
| 24 hours | 0.992 | 71% | 38% | 1 | | | |
| | 0 | 100% | 0% | 2 | 0.8 | 0.5 | 1.2 |
| | 0 | 100% | 0% | 3 | 1.5 | 1.1 | 2.1 |
| | 1.81 | 45% | 70% | 4 | 2.3 | 1.7 | 3.1 |
| | 2.14 | 35% | 82% | | | | |
| | 2.78 | 18% | 91% | | | | |
| 48 hours | 1.09 | 70% | 41% | 1 | | | |
| | 0 | 100% | 0% | 2 | 1.3 | 0.5 | 3.3 |
| | 0 | 100% | 0% | 3 | 1.3 | 0.5 | 3.3 |
| | 1.81 | 48% | 70% | 4 | 3.8 | 1.9 | 7.6 |
| | 2.14 | 44% | 82% | | | | |
| | 2.78 | 26% | 91% | | | | | sCr only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 1.3 | 0.5 | 3.2 |
| | 0 | 100% | 0% | 3 | 1.5 | 0.7 | 3.6 |
| | 1.91 | 20% | 70% | 4 | 1.3 | 0.5 | 3.2 |
| | 2.24 | 10% | 80% | | | | |
| | 2.88 | 5% | 90% | | | | |
| 24 hours | 1.42 | 73% | 52% | 1 | | | |
| | 1.33 | 81% | 49% | 2 | 0.4 | 0.1 | 1.6 |
| | 0 | 100% | 0% | 3 | 1.9 | 1.0 | 3.5 |
| | 1.91 | 46% | 70% | 4 | 2.1 | 1.1 | 3.9 |
| | 2.24 | 35% | 80% | | | | |
| | 2.88 | 15% | 90% | | | | |
| 48 hours | 1.33 | 71% | 49% | 1 | | | |
| | 0 | 100% | 0% | 2 | 0.7 | 0.1 | 3.5 |
| | 0 | 100% | 0% | 3 | 1.0 | 0.3 | 3.8 |
| | 1.91 | 50% | 70% | 4 | 2.0 | 0.7 | 5.6 |
| | 2.24 | 29% | 80% | | | | |
| | 2.88 | 14% | 90% | | | | |

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 1.0 | 0.7 | 1.5 |
| | 0 | 100% | 0% | 3 | 0.6 | 0.4 | 1.0 |
| | 1.91 | 28% | 70% | 4 | 1.4 | 0.9 | 2.0 |
| | 2.18 | 21% | 80% | | | | |
| | 2.78 | 13% | 90% | | | | |
| 24 hours | 0.992 | 71% | 33% | 1 | | | |
| | 0 | 100% | 0% | 2 | 1.0 | 0.7 | 1.5 |
| | 0 | 100% | 0% | 3 | 1.1 | 0.7 | 1.7 |
| | 1.91 | 40% | 70% | 4 | 1.9 | 1.3 | 2.7 |
| | 2.18 | 33% | 80% | | | | |
| | 2.78 | 15% | 90% | | | | |

Fig. 1 Continued

| | | 1.09 | 72% | 37% | 1 | | | |
|---|---|---|---|---|---|---|---|---|
| 48 hours | | 0.913 | 80% | 29% | 2 | 1.2 | 0.6 | 2.7 |
| | | 0 | 100% | 0% | 3 | 0.8 | 0.3 | 2.0 |
| | | 1.91 | 44% | 70% | 4 | 2.2 | 1.1 | 4.2 |
| | | 2.18 | 36% | 80% | | | | |
| | | 2.78 | 24% | 90% | | | | |

Interleukin-15 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.124 | 0.124 | 0.124 | 0.150 | 0.124 | 0.166 |
| average | 0.129 | 0.125 | 0.129 | 0.152 | 0.129 | 0.159 |
| stdev | 0.086 | 0.090 | 0.086 | 0.094 | 0.086 | 0.125 |
| p (t-test) | | 0.757 | | 0.069 | | 0.107 |
| min | 0.005 | 0.005 | 0.005 | 0.005 | 0.005 | 0.005 |
| max | 0.451 | 0.339 | 0.451 | 0.348 | 0.451 | 0.509 |
| n (Samp) | 249 | 53 | 249 | 62 | 249 | 27 |
| n (Pat) | 104 | 53 | 104 | 62 | 104 | 27 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.130 | 0.125 | 0.130 | 0.169 | 0.130 | 0.191 |
| average | 0.130 | 0.132 | 0.130 | 0.166 | 0.130 | 0.165 |
| stdev | 0.087 | 0.080 | 0.087 | 0.080 | 0.087 | 0.141 |
| p (t-test) | | 0.921 | | 0.041 | | 0.144 |
| min | 0.005 | 0.005 | 0.005 | 0.005 | 0.005 | 0.005 |
| max | 0.451 | 0.310 | 0.451 | 0.291 | 0.451 | 0.509 |
| n (Samp) | 441 | 20 | 441 | 26 | 441 | 14 |
| n (Pat) | 170 | 20 | 170 | 26 | 170 | 14 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.124 | 0.114 | 0.124 | 0.151 | 0.124 | 0.174 |
| average | 0.132 | 0.122 | 0.132 | 0.154 | 0.132 | 0.161 |
| stdev | 0.090 | 0.095 | 0.090 | 0.094 | 0.090 | 0.095 |
| p (t-test) | | 0.501 | | 0.106 | | 0.119 |
| min | 0.005 | 0.005 | 0.005 | 0.005 | 0.005 | 0.005 |
| max | 0.451 | 0.339 | 0.451 | 0.348 | 0.451 | 0.373 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
|---|---|---|---|---|---|
| 0 hours | 0.49 | 0.043 | 249 | 53 | 0.781 |
| 24 hours | 0.58 | 0.042 | 249 | 62 | 0.065 |
| 48 hours | 0.58 | 0.060 | 249 | 27 | 0.206 | sCr only

| Time prior AKI stage | AUC | SE | nCohort 1 | nCohort 2 | p |
|---|---|---|---|---|---|
| 0 hours | 0.51 | 0.066 | 441 | 20 | 0.879 |
| 24 hours | 0.63 | 0.060 | 441 | 26 | 0.025 |
| 48 hours | 0.59 | 0.081 | 441 | 14 | 0.290 |

Fig. 1 Continued

UO only

| Time prior AKI stage | AUC | SE | nCohort 1 | nCohort 2 | p |
|---|---|---|---|---|---|
| 0 hours | 0.47 | 0.046 | 212 | 47 | 0.485 |
| 24 hours | 0.58 | 0.045 | 212 | 52 | 0.093 |
| 48 hours | 0.61 | 0.063 | 212 | 25 | 0.092 | sCr or UO

| Time prior AKI stage | Cutoff value | sens | spec | Quartile | OR | 95% CI of OR | |
|---|---|---|---|---|---|---|---|
| 0 hours | 0.0638 | 72% | 23% | 1 | | | |
| | 0.0176 | 81% | 14% | 2 | 1.0 | 0.7 | 1.5 |
| | 0.00512 | 92% | 12% | 3 | 0.7 | 0.4 | 1.0 |
| | 0.166 | 26% | 70% | 4 | 1.5 | 1.1 | 2.1 |
| | 0.191 | 19% | 80% | | | | |
| | 0.241 | 13% | 90% | | | | |
| 24 hours | 0.0951 | 71% | 37% | 1 | | | |
| | 0.0634 | 81% | 23% | 2 | 0.6 | 0.4 | 0.9 |
| | 0.00512 | 90% | 12% | 3 | 0.9 | 0.6 | 1.3 |
| | 0.166 | 42% | 70% | 4 | 1.7 | 1.3 | 2.3 |
| | 0.191 | 37% | 80% | | | | |
| | 0.241 | 19% | 90% | | | | |
| 48 hours | 0.0722 | 70% | 25% | 1 | | | |
| | 0.0161 | 81% | 14% | 2 | 0.1 | 0.0 | 1.1 |
| | 0 | 100% | 0% | 3 | 0.7 | 0.4 | 1.4 |
| | 0.166 | 48% | 70% | 4 | 1.6 | 1.0 | 2.6 |
| | 0.191 | 37% | 80% | | | | |
| | 0.241 | 19% | 90% | | | | | sCr only

| Time prior AKI stage | Cutoff value | sens | spec | Quartile | OR | 95% CI of OR | |
|---|---|---|---|---|---|---|---|
| 0 hours | 0.0872 | 70% | 34% | 1 | | | |
| | 0.0688 | 80% | 25% | 2 | 1.5 | 0.7 | 3.6 |
| | 0.0209 | 90% | 16% | 3 | 1.3 | 0.5 | 3.2 |
| | 0.174 | 30% | 70% | 4 | 1.3 | 0.5 | 3.1 |
| | 0.199 | 20% | 81% | | | | |
| | 0.247 | 10% | 90% | | | | |
| 24 hours | 0.117 | 73% | 45% | 1 | | | |
| | 0.113 | 81% | 41% | 2 | 1.0 | 0.4 | 2.7 |
| | 0.0437 | 92% | 21% | 3 | 1.8 | 0.8 | 4.0 |
| | 0.174 | 46% | 70% | 4 | 2.9 | 1.4 | 5.9 |
| | 0.199 | 38% | 81% | | | | |
| | 0.247 | 27% | 90% | | | | |
| 48 hours | 0.023 | 71% | 18% | 1 | | | |
| | 0.0161 | 86% | 15% | 2 | 0.0 | 0.0 | na |
| | 0.0109 | 93% | 15% | 3 | 0.4 | 0.1 | 1.6 |
| | 0.174 | 50% | 70% | 4 | 1.4 | 0.7 | 2.9 |
| | 0.199 | 50% | 81% | | | | |
| | 0.247 | 14% | 90% | | | | |

UO only

| Time prior AKI stage | Cutoff value | sens | spec | Quartile | OR | 95% CI of OR | |
|---|---|---|---|---|---|---|---|
| 0 hours | 0.0485 | 70% | 20% | 1 | | | |
| | 0.0161 | 85% | 13% | 2 | 0.8 | 0.5 | 1.2 |
| | 0.00512 | 91% | 11% | 3 | 0.8 | 0.5 | 1.2 |
| | 0.176 | 26% | 71% | 4 | 1.4 | 0.9 | 2.0 |
| | 0.199 | 19% | 81% | | | | |
| | 0.248 | 15% | 90% | | | | |

Fig. 1 Continued

| 24 hours | 0.0951 | 71% | 38% | 1 | | | |
| | 0.0634 | 81% | 24% | 2 | 0.5 | 0.3 | 0.8 |
| | 0.0176 | 90% | 14% | 3 | 1.0 | 0.7 | 1.5 |
| | 0.176 | 42% | 71% | 4 | 1.6 | 1.2 | 2.3 |
| | 0.199 | 35% | 81% | | | | |
| | 0.248 | 19% | 90% | | | | |
| 48 hours | 0.131 | 72% | 52% | 1 | | | |
| | 0.0776 | 80% | 33% | 2 | 0.7 | 0.2 | 2.5 |
| | 0 | 100% | 0% | 3 | 2.5 | 1.1 | 5.4 |
| | 0.176 | 44% | 71% | 4 | 2.4 | 1.1 | 5.3 |
| | 0.199 | 36% | 81% | | | | |
| | 0.248 | 12% | 90% | | | | |

Interleukin-3 sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 0.025 | 0.027 | 0.025 | 0.039 | 0.025 | 0.037 |
| average | 0.026 | 0.030 | 0.026 | 0.046 | 0.026 | 0.038 |
| stdev | 0.021 | 0.026 | 0.021 | 0.042 | 0.021 | 0.031 |
| p (t-test) | | 0.271 | | 0.000 | | 0.012 |
| min | 0.001 | 0.001 | 0.001 | 0.001 | 0.001 | 0.005 |
| max | 0.128 | 0.098 | 0.128 | 0.227 | 0.128 | 0.134 |
| n (Samp) | 249 | 53 | 249 | 62 | 249 | 27 |
| n (Pat) | 104 | 53 | 104 | 62 | 104 | 27 | sCr only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 0.027 | 0.021 | 0.027 | 0.046 | 0.027 | 0.035 |
| average | 0.030 | 0.029 | 0.030 | 0.047 | 0.030 | 0.040 |
| stdev | 0.026 | 0.034 | 0.026 | 0.031 | 0.026 | 0.034 |
| p (t-test) | | 0.879 | | 0.002 | | 0.149 |
| min | 0.001 | 0.001 | 0.001 | 0.001 | 0.001 | 0.001 |
| max | 0.227 | 0.147 | 0.227 | 0.109 | 0.227 | 0.134 |
| n (Samp) | 441 | 20 | 441 | 26 | 441 | 14 |
| n (Pat) | 170 | 20 | 170 | 26 | 170 | 14 |

UO only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 0.025 | 0.027 | 0.025 | 0.041 | 0.025 | 0.037 |
| average | 0.026 | 0.031 | 0.026 | 0.046 | 0.026 | 0.037 |
| stdev | 0.020 | 0.026 | 0.020 | 0.042 | 0.020 | 0.024 |
| p (t-test) | | 0.165 | | 0.000 | | 0.019 |
| min | 0.001 | 0.001 | 0.001 | 0.001 | 0.001 | 0.006 |
| max | 0.128 | 0.098 | 0.128 | 0.227 | 0.128 | 0.095 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
| --- | --- | --- | --- | --- | --- |
| 0 hours | 0.53 | 0.044 | 249 | 53 | 0.514 |
| 24 hours | 0.65 | 0.041 | 249 | 62 | 0.000 |
| 48 hours | 0.62 | 0.060 | 249 | 27 | 0.056 |

Fig. 1 Continued sCr only

| Time prior AKI stage | AUC | SE | nCohort 1 | nCohort 2 | p |
|---|---|---|---|---|---|
| 0 hours | 0.45 | 0.064 | 441 | 20 | 0.478 |
| 24 hours | 0.67 | 0.059 | 441 | 26 | 0.003 |
| 48 hours | 0.59 | 0.081 | 441 | 14 | 0.244 |

UO only

| Time prior AKI stage | AUC | SE | nCohort 1 | nCohort 2 | p |
|---|---|---|---|---|---|
| 0 hours | 0.54 | 0.047 | 212 | 47 | 0.454 |
| 24 hours | 0.66 | 0.045 | 212 | 52 | 0.000 |
| 48 hours | 0.63 | 0.063 | 212 | 25 | 0.032 | sCr or UO

| Time prior AKI stage | Cutoff value | sens | spec | Quartile | OR | 95% CI of OR | |
|---|---|---|---|---|---|---|---|
| 0 hours | 0.00745 | 74% | 25% | 1 | | | |
| | 0.00477 | 81% | 18% | 2 | 0.7 | 0.4 | 1.0 |
| | 0.00275 | 91% | 13% | 3 | 0.8 | 0.6 | 1.2 |
| | 0.0353 | 32% | 70% | 4 | 1.3 | 0.9 | 1.7 |
| | 0.0432 | 30% | 81% | | | | |
| | 0.0501 | 25% | 90% | | | | |
| 24 hours | 0.019 | 71% | 41% | 1 | | | |
| | 0.00681 | 81% | 23% | 2 | 0.4 | 0.2 | 0.6 |
| | 0.00275 | 90% | 13% | 3 | 0.9 | 0.6 | 1.3 |
| | 0.0353 | 52% | 70% | 4 | 2.7 | 2.0 | 3.5 |
| | 0.0432 | 47% | 81% | | | | |
| | 0.0501 | 40% | 90% | | | | |
| 48 hours | 0.0147 | 70% | 33% | 1 | | | |
| | 0.00994 | 81% | 27% | 2 | 1.2 | 0.6 | 2.7 |
| | 0.00616 | 96% | 21% | 3 | 1.0 | 0.4 | 2.3 |
| | 0.0353 | 52% | 70% | 4 | 2.4 | 1.3 | 4.6 |
| | 0.0432 | 33% | 81% | | | | |
| | 0.0501 | 30% | 90% | | | | | sCr only

| Time prior AKI stage | Cutoff value | sens | spec | Quartile | OR | 95% CI of OR | |
|---|---|---|---|---|---|---|---|
| 0 hours | 0.00745 | 70% | 23% | 1 | | | |
| | 0.00464 | 80% | 15% | 2 | 0.6 | 0.2 | 1.8 |
| | 0.00451 | 90% | 14% | 3 | 1.0 | 0.4 | 2.3 |
| | 0.039 | 25% | 70% | 4 | 1.4 | 0.7 | 2.9 |
| | 0.0466 | 25% | 80% | | | | |
| | 0.0618 | 5% | 90% | | | | |
| 24 hours | 0.028 | 73% | 52% | 1 | | | |
| | 0.019 | 81% | 38% | 2 | 0.4 | 0.1 | 1.6 |
| | 0.00464 | 92% | 15% | 3 | 1.0 | 0.4 | 2.2 |
| | 0.039 | 58% | 70% | 4 | 3.0 | 1.7 | 5.3 |
| | 0.0466 | 46% | 80% | | | | |
| | 0.0618 | 27% | 90% | | | | |
| 48 hours | 0.0188 | 71% | 38% | 1 | | | |
| | 0.00616 | 86% | 20% | 2 | 0.7 | 0.1 | 3.5 |
| | 0.00477 | 93% | 16% | 3 | 1.0 | 0.3 | 3.8 |
| | 0.039 | 50% | 70% | 4 | 2.0 | 0.7 | 5.6 |
| | 0.0466 | 43% | 80% | | | | |
| | 0.0618 | 7% | 90% | | | | |

Fig. 1 Continued

UO only

| Time prior AKI stage | Cutoff value | sens | spec | Quartile | OR | 95% CI of OR | |
|---|---|---|---|---|---|---|---|
| 0 hours | 0.00745 | 72% | 23% | 1 | | | |
| | 0.00477 | 81% | 16% | 2 | 0.5 | 0.3 | 0.8 |
| | 0.00069 | 91% | 9% | 3 | 0.5 | 0.3 | 0.8 |
| | 0.0345 | 38% | 70% | 4 | 1.3 | 0.9 | 1.8 |
| | 0.0411 | 34% | 80% | | | | |
| | 0.0495 | 26% | 90% | | | | |
| 24 hours | 0.0246 | 71% | 49% | 1 | | | |
| | 0.014 | 81% | 31% | 2 | 0.8 | 0.5 | 1.3 |
| | 0.00451 | 90% | 15% | 3 | 0.8 | 0.5 | 1.3 |
| | 0.0345 | 58% | 70% | 4 | 3.6 | 2.6 | 5.2 |
| | 0.0411 | 50% | 80% | | | | |
| | 0.0495 | 40% | 90% | | | | |
| 48 hours | 0.0174 | 72% | 36% | 1 | | | |
| | 0.0132 | 80% | 29% | 2 | 1.6 | 0.6 | 3.8 |
| | 0.00747 | 92% | 24% | 3 | 1.0 | 0.3 | 2.9 |
| | 0.0345 | 56% | 70% | 4 | 3.1 | 1.5 | 6.5 |
| | 0.0411 | 32% | 80% | | | | |
| | 0.0495 | 32% | 90% | | | | |

Myeloperoxidase sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 982.205 | 1210.274 | 982.205 | 1278.718 | 982.205 | 1290.883 |
| average | 1396.981 | 2199.242 | 1396.981 | 2731.890 | 1396.981 | 1887.672 |
| stdev | 1511.071 | 3410.876 | 1511.071 | 5439.708 | 1511.071 | 1876.519 |
| p (t-test) | | 0.036 | | 0.014 | | 0.155 |
| min | 0.000 | 0.000 | 0.000 | 0.000 | 0.000 | 710.711 |
| max | 9348.967 | 18305.965 | 9348.967 | 30781.054 | 9348.967 | 9298.715 |
| n (Samp) | 117 | 51 | 117 | 59 | 117 | 26 |
| n (Pat) | 99 | 51 | 99 | 59 | 99 | 26 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1172.517 | 1039.955 | 1172.517 | 1165.962 | 1172.517 | 1676.691 |
| average | 2094.795 | 1433.178 | 2094.795 | 1863.012 | 2094.795 | 2383.595 |
| stdev | 4019.281 | 963.062 | 4019.281 | 2282.695 | 4019.281 | 1745.167 |
| p (t-test) | | 0.499 | | 0.786 | | 0.790 |
| min | 0.000 | 367.696 | 0.000 | 463.506 | 0.000 | 1039.955 |
| max | 40151.357 | 3922.692 | 40151.357 | 10821.990 | 40151.357 | 6415.283 |
| n (Samp) | 260 | 17 | 260 | 23 | 260 | 14 |
| n (Pat) | 160 | 17 | 160 | 23 | 160 | 14 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1039.955 | 1215.779 | 1039.955 | 1314.947 | 1039.955 | 1290.883 |
| average | 1643.865 | 2330.170 | 1643.865 | 3097.984 | 1643.865 | 1710.364 |
| stdev | 1806.119 | 3612.146 | 1806.119 | 6012.209 | 1806.119 | 1745.870 |
| p (t-test) | | 0.123 | | 0.024 | | 0.872 |
| min | 0.000 | 0.000 | 0.000 | 0.000 | 0.000 | 367.696 |
| max | 10821.990 | 18305.965 | 10821.990 | 30781.054 | 10821.990 | 9298.715 |
| n (Samp) | 105 | 45 | 105 | 49 | 105 | 23 |
| n (Pat) | 84 | 45 | 84 | 49 | 84 | 23 |

Fig. 1 Continued sCr or UO

| Time prior AKI stage | AUC | SE | nCohort 1 | nCohort 2 | p |
|---|---|---|---|---|---|
| 0 hours | 0.61 | 0.049 | 117 | 51 | 0.028 |
| 24 hours | 0.60 | 0.046 | 117 | 59 | 0.038 |
| 48 hours | 0.66 | 0.063 | 117 | 26 | 0.012 | sCr only

| Time prior AKI stage | AUC | SE | nCohort 1 | nCohort 2 | p |
|---|---|---|---|---|---|
| 0 hours | 0.49 | 0.072 | 260 | 17 | 0.900 |
| 24 hours | 0.50 | 0.063 | 260 | 23 | 0.953 |
| 48 hours | 0.70 | 0.080 | 260 | 14 | 0.014 |

UO only

| Time prior AKI stage | AUC | SE | nCohort 1 | nCohort 2 | p |
|---|---|---|---|---|---|
| 0 hours | 0.59 | 0.052 | 105 | 45 | 0.101 |
| 24 hours | 0.56 | 0.050 | 105 | 49 | 0.248 |
| 48 hours | 0.58 | 0.068 | 105 | 23 | 0.212 | sCr or UO

| Time prior AKI stage | Cutoff value | sens | spec | Quartile | OR | 95% CI of OR | |
|---|---|---|---|---|---|---|---|
| 0 hours | 923.333 | 73% | 46% | 1 | | | |
| | 803.653 | 84% | 38% | 2 | 3.7 | 2.1 | 6.6 |
| | 571.515 | 90% | 22% | 3 | 2.7 | 1.5 | 4.9 |
| | 1382.48 | 41% | 70% | 4 | 3.7 | 2.1 | 6.6 |
| | 1896.43 | 31% | 80% | | | | |
| | 2886.5 | 20% | 91% | | | | |
| 24 hours | 835.148 | 71% | 38% | 1 | | | |
| | 709.902 | 81% | 32% | 2 | 1.8 | 1.1 | 2.9 |
| | 421.311 | 92% | 17% | 3 | 3.2 | 2.1 | 5.1 |
| | 1382.48 | 44% | 70% | 4 | 2.2 | 1.4 | 3.5 |
| | 1896.43 | 27% | 80% | | | | |
| | 2886.5 | 12% | 91% | | | | |
| 48 hours | 1035.79 | 81% | 52% | 1 | | | |
| | 1035.79 | 81% | 52% | 2 | na | na | na |
| | 872.465 | 92% | 42% | 3 | na | na | na |
| | 1382.48 | 42% | 70% | 4 | na | na | na |
| | 1896.43 | 19% | 80% | | | | |
| | 2886.5 | 12% | 91% | | | | | sCr only

| Time prior AKI stage | Cutoff value | sens | spec | Quartile | OR | 95% CI of OR | |
|---|---|---|---|---|---|---|---|
| 0 hours | 922.638 | 71% | 34% | 1 | | | |
| | 709.902 | 82% | 20% | 2 | 1.0 | 0.4 | 2.9 |
| | 571.515 | 94% | 13% | 3 | 1.0 | 0.4 | 2.9 |
| | 1710.25 | 29% | 70% | 4 | 1.3 | 0.5 | 3.3 |
| | 2320.83 | 12% | 80% | | | | |
| | 3113.5 | 12% | 90% | | | | |
| 24 hours | 803.653 | 74% | 25% | 1 | | | |
| | 744.986 | 83% | 22% | 2 | 1.0 | 0.5 | 2.0 |
| | 673.783 | 91% | 17% | 3 | 1.0 | 0.5 | 2.0 |
| | 1710.25 | 22% | 70% | 4 | 0.8 | 0.4 | 1.8 |
| | 2320.83 | 13% | 80% | | | | |
| | 3113.5 | 9% | 90% | | | | |

Fig. 1 Continued

| | 48 hours | 1341.77 | 71% | 60% | 1 | | | |
|---|---|---|---|---|---|---|---|---|
| | | 1225.94 | 86% | 53% | 2 | na | na | na |
| | | 1035.79 | 100% | 42% | 3 | na | na | na |
| | | 1710.25 | 50% | 70% | 4 | na | na | na |
| | | 2320.83 | 29% | 80% | | | | |
| | | 3113.5 | 21% | 90% | | | | |

UO only

| Time prior AKI stage | Cutoff value | sens | spec | Quartile | OR | 95% CI of OR | |
|---|---|---|---|---|---|---|---|
| 0 hours | 923.795 | 71% | 47% | 1 | | | |
| | 835.148 | 80% | 35% | 2 | 2.4 | 1.3 | 4.5 |
| | 709.902 | 91% | 27% | 3 | 2.8 | 1.5 | 5.2 |
| | 1681.71 | 38% | 70% | 4 | 3.0 | 1.6 | 5.6 |
| | 2352.65 | 24% | 80% | | | | |
| | 3113.5 | 18% | 90% | | | | |
| 24 hours | 835.148 | 71% | 35% | 1 | | | |
| | 709.902 | 82% | 27% | 2 | 1.2 | 0.8 | 2.1 |
| | 311.61 | 92% | 10% | 3 | 1.6 | 1.0 | 2.7 |
| | 1681.71 | 35% | 70% | 4 | 1.4 | 0.9 | 2.3 |
| | 2352.65 | 22% | 80% | | | | |
| | 3113.5 | 12% | 90% | | | | |
| 48 hours | 993.651 | 74% | 50% | 1 | | | |
| | 922.638 | 83% | 43% | 2 | 2.8 | 0.6 | 12.6 |
| | 775.366 | 91% | 31% | 3 | 9.0 | 2.4 | 33.2 |
| | 1681.71 | 26% | 70% | 4 | 2.1 | 0.4 | 10.7 |
| | 2352.65 | 9% | 80% | | | | |
| | 3113.5 | 4% | 90% | | | | |

Nidogen-1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1444.335 | 2337.209 | 1444.335 | 2034.188 | 1444.335 | 14.333 |
| average | 1866.654 | 2403.076 | 1866.654 | 2310.016 | 1866.654 | 2848.837 |
| stdev | 1401.407 | 1521.040 | 1401.407 | 1532.518 | 1401.407 | na |
| p (t-test) | | 0.083 | | 0.170 | | na |
| min | 14.333 | 259.783 | 14.333 | 97.321 | 14.333 | 2848.837 |
| max | 4906.977 | 4988.372 | 4906.977 | 4953.488 | 4906.977 | 2848.837 |
| n (Samp) | 96 | 28 | 96 | 25 | 96 | 1 |
| n (Pat) | 48 | 28 | 48 | 25 | 48 | 1 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1588.419 | 3762.127 | 1588.419 | 3251.613 | 1588.419 | 1574.335 |
| average | 1988.911 | 2729.928 | 1988.911 | 2696.128 | 1988.911 | 2126.209 |
| stdev | 1424.725 | 1715.319 | 1424.725 | 1732.452 | 1424.725 | 1185.632 |
| p (t-test) | | 0.117 | | 0.118 | | 0.869 |
| min | 0.280 | 210.366 | 0.280 | 97.321 | 0.280 | 1317.111 |
| max | 4988.372 | 4273.504 | 4988.372 | 4523.256 | 4988.372 | 3487.179 |
| n (Samp) | 158 | 10 | 158 | 11 | 158 | 3 |
| n (Pat) | 90 | 10 | 90 | 11 | 90 | 3 |

Fig. 1 Continued

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 1213.944 | 2325.581 | 1213.944 | 2034.188 | 1213.944 | 3910.256 |
| average | 1560.384 | 2401.972 | 1560.384 | 2447.934 | 1560.384 | 3735.714 |
| stdev | 1221.538 | 1474.617 | 1221.538 | 1494.185 | 1221.538 | 630.411 |
| p (t-test) |  | 0.007 |  | 0.005 |  | 0.001 |
| min | 76.493 | 259.783 | 76.493 | 501.337 | 76.493 | 2848.837 |
| max | 4906.977 | 4988.372 | 4906.977 | 4953.488 | 4906.977 | 4273.504 |
| n (Samp) | 74 | 23 | 74 | 23 | 74 | 4 |
| n (Pat) | 37 | 23 | 37 | 23 | 37 | 4 | sCr or UO

| Time prior AKI stage | AUC | SE | nCohort 1 | nCohort 2 | p |
| --- | --- | --- | --- | --- | --- |
| 0 hours | 0.60 | 0.063 | 96 | 28 | 0.109 |
| 24 hours | 0.59 | 0.066 | 96 | 25 | 0.161 |
| 48 hours | 0.73 | 0.291 | 96 | 1 | 0.430 | sCr only

| Time prior AKI stage | AUC | SE | nCohort 1 | nCohort 2 | p |
| --- | --- | --- | --- | --- | --- |
| 0 hours | 0.62 | 0.097 | 158 | 10 | 0.233 |
| 24 hours | 0.61 | 0.093 | 158 | 11 | 0.240 |
| 48 hours | 0.57 | 0.174 | 158 | 3 | 0.707 |

UO only

| Time prior AKI stage | AUC | SE | nCohort 1 | nCohort 2 | p |
| --- | --- | --- | --- | --- | --- |
| 0 hours | 0.67 | 0.068 | 74 | 23 | 0.015 |
| 24 hours | 0.69 | 0.068 | 74 | 23 | 0.006 |
| 48 hours | 0.92 | 0.095 | 74 | 4 | 0.000 | sCr or UO

| Time prior AKI stage | Cutoff value | sens | spec | Quartile | OR | 95% CI of OR | |
| --- | --- | --- | --- | --- | --- | --- | --- |
| 0 hours | 1467.82 | 71% | 52% | 1 |  |  |  |
|  | 590.062 | 82% | 24% | 2 | 0.6 | 0.2 | 1.6 |
|  | 332.474 | 93% | 9% | 3 | 1.4 | 0.7 | 3.0 |
|  | 2778.49 | 46% | 71% | 4 | 2.0 | 1.0 | 4.0 |
|  | 3466.67 | 32% | 80% |  |  |  |  |
|  | 4023.09 | 18% | 91% |  |  |  |  |
| 24 hours | 985.507 | 72% | 36% | 1 |  |  |  |
|  | 856.436 | 80% | 33% | 2 | 1.0 | 0.4 | 2.6 |
|  | 492.391 | 92% | 22% | 3 | 1.5 | 0.7 | 3.5 |
|  | 2778.49 | 40% | 71% | 4 | 1.7 | 0.8 | 3.9 |
|  | 3466.67 | 28% | 80% |  |  |  |  |
|  | 4023.09 | 20% | 91% |  |  |  |  |
| 48 hours | 2813.95 | 100% | 73% | 1 |  |  |  |
|  | 2813.95 | 100% | 73% | 2 | na | na | na |
|  | 2813.95 | 100% | 73% | 3 | na | na | na |
|  | 2778.49 | 100% | 71% | 4 | na | na | na |
|  | 3466.67 | 0% | 80% |  |  |  |  |
|  | 4023.09 | 0% | 91% |  |  |  |  |

Fig. 1 Continued sCr only

| Time prior AKI stage | Cutoff value | sens | spec | Quartile | OR | 95% CI of OR | |
|---|---|---|---|---|---|---|---|
| 0 hours | 2325.58 | 70% | 63% | 1 | | | |
| | 501.337 | 80% | 18% | 2 | 0.0 | 0.0 | na |
| | 332.474 | 90% | 9% | 3 | 0.3 | 0.0 | 4.8 |
| | 2848.84 | 60% | 70% | 4 | 2.2 | 0.7 | 6.4 |
| | 3593.02 | 60% | 80% | | | | |
| | 4174.42 | 20% | 91% | | | | |
| 24 hours | 2034.19 | 73% | 61% | 1 | | | |
| | 288.462 | 82% | 8% | 2 | 0.0 | 0.0 | na |
| | 204.762 | 91% | 4% | 3 | 1.0 | 0.2 | 4.1 |
| | 2848.84 | 64% | 70% | 4 | 1.7 | 0.5 | 5.4 |
| | 3593.02 | 45% | 80% | | | | |
| | 4174.42 | 9% | 91% | | | | |
| 48 hours | 1235.48 | 100% | 41% | 1 | | | |
| | 1235.48 | 100% | 41% | 2 | na | na | na |
| | 1235.48 | 100% | 41% | 3 | na | na | na |
| | 2848.84 | 33% | 70% | 4 | na | na | na |
| | 3593.02 | 0% | 80% | | | | |
| | 4174.42 | 0% | 91% | | | | |

UO only

| Time prior AKI stage | Cutoff value | sens | spec | Quartile | OR | 95% CI of OR | |
|---|---|---|---|---|---|---|---|
| 0 hours | 1467.82 | 74% | 58% | 1 | | | |
| | 811.594 | 83% | 36% | 2 | 0.5 | 0.1 | 2.4 |
| | 380 | 91% | 14% | 3 | 1.7 | 0.6 | 4.6 |
| | 1838.3 | 61% | 70% | 4 | 3.9 | 1.6 | 9.7 |
| | 2812.9 | 48% | 81% | | | | |
| | 3569.89 | 22% | 91% | | | | |
| 24 hours | 985.507 | 74% | 42% | 1 | | | |
| | 937.166 | 83% | 41% | 2 | 1.4 | 0.4 | 5.3 |
| | 691.176 | 91% | 28% | 3 | 2.3 | 0.7 | 7.6 |
| | 1838.3 | 57% | 70% | 4 | 4.7 | 1.6 | 13.7 |
| | 2812.9 | 43% | 81% | | | | |
| | 3569.89 | 30% | 91% | | | | |
| 48 hours | 3655.91 | 75% | 92% | 1 | | | |
| | 2813.95 | 100% | 82% | 2 | na | na | na |
| | 2813.95 | 100% | 82% | 3 | na | na | na |
| | 1838.3 | 100% | 70% | 4 | na | na | na |
| | 2812.9 | 100% | 81% | | | | |
| | 3569.89 | 75% | 91% | | | | |

Oxidized low-density lipoprotein receptor 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 20.555 | 28.176 | 20.555 | 27.762 | 20.555 | 21.624 |
| average | 27.729 | 38.940 | 27.729 | 36.498 | 27.729 | 33.064 |
| stdev | 26.915 | 39.191 | 26.915 | 35.185 | 26.915 | 30.214 |
| p (t-test) | | 0.033 | | 0.068 | | 0.373 |
| min | 0.150 | 1.212 | 0.150 | 0.480 | 0.150 | 1.292 |
| max | 148.195 | 214.368 | 148.195 | 195.814 | 148.195 | 112.070 |
| n (Samp) | 117 | 51 | 117 | 59 | 117 | 26 |
| n (Pat) | 99 | 51 | 99 | 59 | 99 | 26 |

Fig. 1 Continued sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 25.590 | 14.851 | 25.590 | 24.309 | 25.590 | 25.625 |
| average | 35.930 | 31.238 | 35.930 | 36.489 | 35.930 | 29.473 |
| stdev | 34.181 | 40.192 | 34.181 | 37.184 | 34.181 | 18.922 |
| p (t-test) | | 0.588 | | 0.941 | | 0.484 |
| min | 0.150 | 1.212 | 0.150 | 0.480 | 0.150 | 4.003 |
| max | 214.368 | 139.836 | 214.368 | 131.141 | 214.368 | 67.913 |
| n (Samp) | 260 | 17 | 260 | 23 | 260 | 14 |
| n (Pat) | 160 | 17 | 160 | 23 | 160 | 14 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 20.198 | 28.970 | 20.198 | 29.327 | 20.198 | 18.027 |
| average | 26.307 | 38.199 | 26.307 | 39.919 | 26.307 | 33.654 |
| stdev | 24.795 | 35.278 | 24.795 | 40.139 | 24.795 | 32.761 |
| p (t-test) | | 0.020 | | 0.011 | | 0.228 |
| min | 0.150 | 5.168 | 0.150 | 0.621 | 0.150 | 1.292 |
| max | 134.298 | 214.368 | 134.298 | 195.814 | 134.298 | 112.070 |
| n (Samp) | 105 | 45 | 105 | 49 | 105 | 23 |
| n (Pat) | 84 | 45 | 84 | 49 | 84 | 23 | sCr or UO

| Time prior AKI stage | AUC | SE | nCohort 1 | nCohort 2 | p |
|---|---|---|---|---|---|
| 0 hours | 0.60 | 0.049 | 117 | 51 | 0.031 |
| 24 hours | 0.60 | 0.046 | 117 | 59 | 0.037 |
| 48 hours | 0.54 | 0.064 | 117 | 26 | 0.483 | sCr only

| Time prior AKI stage | AUC | SE | nCohort 1 | nCohort 2 | p |
|---|---|---|---|---|---|
| 0 hours | 0.40 | 0.067 | 260 | 17 | 0.153 |
| 24 hours | 0.48 | 0.062 | 260 | 23 | 0.763 |
| 48 hours | 0.49 | 0.079 | 260 | 14 | 0.927 |

UO only

| Time prior AKI stage | AUC | SE | nCohort 1 | nCohort 2 | p |
|---|---|---|---|---|---|
| 0 hours | 0.65 | 0.051 | 105 | 45 | 0.003 |
| 24 hours | 0.64 | 0.049 | 105 | 49 | 0.006 |
| 48 hours | 0.53 | 0.067 | 105 | 23 | 0.652 | sCr or UO

| Time prior AKI stage | Cutoff value | sens | spec | Quartile | OR | 95% CI of OR | |
|---|---|---|---|---|---|---|---|
| 0 hours | 20.1977 | 71% | 50% | 1 | | | |
| | 11.7131 | 80% | 35% | 2 | 1.1 | 0.7 | 2.0 |
| | 6.43176 | 90% | 15% | 3 | 2.0 | 1.3 | 3.3 |
| | 29.8385 | 45% | 70% | 4 | 2.5 | 1.6 | 4.0 |
| | 42.4951 | 25% | 80% | | | | |
| | 61.9361 | 16% | 91% | | | | |
| 24 hours | 19.4441 | 71% | 47% | 1 | | | |
| | 13.3487 | 81% | 38% | 2 | 2.0 | 1.3 | 3.2 |
| | 5.73842 | 92% | 12% | 3 | 2.2 | 1.4 | 3.5 |
| | 29.8385 | 46% | 70% | 4 | 3.0 | 1.9 | 4.7 |
| | 42.4951 | 27% | 80% | | | | |
| | 61.9361 | 12% | 91% | | | | |

Fig. 1 Continued

| | 48 hours | 11.7131 | 73% | 35% | 1 | | | |
| | | 9.89067 | 81% | 26% | 2 | 1.4 | 0.6 | 3.2 |
| | | 4.14164 | 92% | 10% | 3 | 1.0 | 0.4 | 2.4 |
| | | 29.8385 | 38% | 70% | 4 | 2.0 | 0.9 | 4.2 |
| | | 42.4951 | 27% | 80% | | | | |
| | | 61.9361 | 15% | 91% | | | | | sCr only

| Time prior AKI stage | Cutoff value | sens | spec | Quartile | OR | 95% CI of OR | |
|---|---|---|---|---|---|---|---|
| 0 hours | 11.211 | 71% | 26% | 1 | | | |
| | 4.74854 | 82% | 8% | 2 | 1.0 | 0.3 | 4.0 |
| | 3.03381 | 94% | 5% | 3 | 2.1 | 0.8 | 6.0 |
| | 42.2595 | 18% | 70% | 4 | 1.7 | 0.6 | 5.3 |
| | 57.9206 | 18% | 80% | | | | |
| | 79.2451 | 12% | 90% | | | | |
| 24 hours | 15.7737 | 74% | 33% | 1 | | | |
| | 5.73842 | 83% | 9% | 2 | 1.0 | 0.4 | 2.3 |
| | 2.63939 | 91% | 5% | 3 | 1.7 | 0.8 | 3.4 |
| | 42.2595 | 26% | 70% | 4 | 1.0 | 0.4 | 2.4 |
| | 57.9206 | 22% | 80% | | | | |
| | 79.2451 | 17% | 90% | | | | |
| 48 hours | 22.2933 | 71% | 44% | 1 | | | |
| | 9.52627 | 86% | 20% | 2 | 1.4 | 0.4 | 4.6 |
| | 9.03746 | 93% | 18% | 3 | 1.4 | 0.4 | 4.5 |
| | 42.2595 | 21% | 70% | 4 | 1.0 | 0.3 | 4.0 |
| | 57.9206 | 7% | 80% | | | | |
| | 79.2451 | 0% | 90% | | | | |

UO only

| Time prior AKI stage | Cutoff value | sens | spec | Quartile | OR | 95% CI of OR | |
|---|---|---|---|---|---|---|---|
| 0 hours | 20.242 | 71% | 50% | 1 | | | |
| | 16.9088 | 80% | 42% | 2 | 2.3 | 1.1 | 4.7 |
| | 8.56994 | 91% | 23% | 3 | 3.5 | 1.7 | 6.9 |
| | 28.4908 | 51% | 70% | 4 | 5.2 | 2.7 | 10.0 |
| | 36.3886 | 38% | 80% | | | | |
| | 59.0847 | 18% | 90% | | | | |
| 24 hours | 20.1977 | 71% | 50% | 1 | | | |
| | 13.5964 | 82% | 37% | 2 | 2.7 | 1.4 | 4.9 |
| | 7.94687 | 92% | 21% | 3 | 2.5 | 1.3 | 4.6 |
| | 28.4908 | 51% | 70% | 4 | 4.6 | 2.5 | 8.2 |
| | 36.3886 | 39% | 80% | | | | |
| | 59.0847 | 14% | 90% | | | | |
| 48 hours | 10.6408 | 74% | 30% | 1 | | | |
| | 9.50588 | 83% | 26% | 2 | 1.8 | 0.8 | 4.0 |
| | 4.56964 | 91% | 10% | 3 | 0.4 | 0.1 | 1.6 |
| | 28.4908 | 39% | 70% | 4 | 1.8 | 0.8 | 4.0 |
| | 36.3886 | 35% | 80% | | | | |
| | 59.0847 | 26% | 90% | | | | |

Fig. 1 Continued

Pappalysin-1 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.027 | 0.032 | 0.027 | 0.043 | 0.027 | 0.041 |
| average | 0.037 | 0.040 | 0.037 | 0.158 | 0.037 | 0.055 |
| stdev | 0.030 | 0.029 | 0.030 | 0.854 | 0.030 | 0.052 |
| p (t-test) |  | 0.420 |  | 0.025 |  | 0.006 |
| min | 0.002 | 0.003 | 0.002 | 0.003 | 0.002 | 0.003 |
| max | 0.193 | 0.141 | 0.193 | 6.770 | 0.193 | 0.235 |
| n (Samp) | 249 | 53 | 249 | 62 | 249 | 27 |
| n (Pat) | 104 | 53 | 104 | 62 | 104 | 27 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.030 | 0.022 | 0.030 | 0.046 | 0.030 | 0.039 |
| average | 0.054 | 0.031 | 0.054 | 0.048 | 0.054 | 0.040 |
| stdev | 0.322 | 0.024 | 0.322 | 0.035 | 0.322 | 0.024 |
| p (t-test) |  | 0.750 |  | 0.919 |  | 0.870 |
| min | 0.000 | 0.003 | 0.000 | 0.003 | 0.000 | 0.003 |
| max | 6.770 | 0.092 | 6.770 | 0.124 | 6.770 | 0.082 |
| n (Samp) | 441 | 20 | 441 | 26 | 441 | 14 |
| n (Pat) | 170 | 20 | 170 | 26 | 170 | 14 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.027 | 0.040 | 0.027 | 0.045 | 0.027 | 0.037 |
| average | 0.034 | 0.046 | 0.034 | 0.182 | 0.034 | 0.055 |
| stdev | 0.025 | 0.031 | 0.025 | 0.932 | 0.025 | 0.052 |
| p (t-test) |  | 0.003 |  | 0.021 |  | 0.001 |
| min | 0.002 | 0.008 | 0.002 | 0.005 | 0.002 | 0.003 |
| max | 0.142 | 0.141 | 0.142 | 6.770 | 0.142 | 0.235 |
| n (Samp) | 212 | 47 | 212 | 52 | 212 | 25 |
| n (Pat) | 85 | 47 | 85 | 52 | 85 | 25 |

Cr or UO

| Time prior AKI stage | AUC | SE | nCohort 1 | nCohort 2 | p |
| --- | --- | --- | --- | --- | --- |
| 0 hours | 0.55 | 0.044 | 249 | 53 | 0.242 |
| 24 hours | 0.61 | 0.042 | 249 | 62 | 0.009 |
| 48 hours | 0.62 | 0.060 | 249 | 27 | 0.046 | sCr only

| Time prior AKI stage | AUC | SE | nCohort 1 | nCohort 2 | p |
| --- | --- | --- | --- | --- | --- |
| 0 hours | 0.43 | 0.063 | 441 | 20 | 0.295 |
| 24 hours | 0.58 | 0.060 | 441 | 26 | 0.209 |
| 48 hours | 0.56 | 0.081 | 441 | 14 | 0.485 |

UO only

| Time prior AKI stage | AUC | SE | nCohort 1 | nCohort 2 | p |
| --- | --- | --- | --- | --- | --- |
| 0 hours | 0.63 | 0.047 | 212 | 47 | 0.008 |
| 24 hours | 0.67 | 0.044 | 212 | 52 | 0.000 |
| 48 hours | 0.65 | 0.062 | 212 | 25 | 0.018 |

Fig. 1 Continued sCr or UO

| Time prior AKI stage | Cutoff value | sens | spec | Quartile | OR | 95% CI of OR | |
|---|---|---|---|---|---|---|---|
| 0 hours | 0.0217 | 72% | 40% | 1 | | | |
| | 0.017 | 81% | 31% | 2 | 1.8 | 1.2 | 2.7 |
| | 0.013 | 91% | 19% | 3 | 1.4 | 0.9 | 2.2 |
| | 0.0451 | 36% | 70% | 4 | 2.1 | 1.4 | 3.1 |
| | 0.0577 | 19% | 80% | | | | |
| | 0.0728 | 13% | 90% | | | | |
| 24 hours | 0.0259 | 71% | 46% | 1 | | | |
| | 0.021 | 81% | 38% | 2 | 1.2 | 0.8 | 1.9 |
| | 0.00974 | 90% | 11% | 3 | 2.0 | 1.4 | 2.9 |
| | 0.0451 | 47% | 70% | 4 | 2.6 | 1.9 | 3.7 |
| | 0.0577 | 31% | 80% | | | | |
| | 0.0728 | 19% | 90% | | | | |
| 48 hours | 0.0319 | 70% | 57% | 1 | | | |
| | 0.0187 | 81% | 33% | 2 | 0.5 | 0.1 | 2.2 |
| | 0.00343 | 93% | 2% | 3 | 2.8 | 1.3 | 5.8 |
| | 0.0451 | 48% | 70% | 4 | 3.1 | 1.5 | 6.4 |
| | 0.0577 | 30% | 80% | | | | |
| | 0.0728 | 22% | 90% | | | | | sCr only

| Time prior AKI stage | Cutoff value | sens | spec | Quartile | OR | 95% CI of OR | |
|---|---|---|---|---|---|---|---|
| 0 hours | 0.017 | 70% | 27% | 1 | | | |
| | 0.0139 | 80% | 21% | 2 | 1.3 | 0.5 | 3.2 |
| | 0.00639 | 90% | 5% | 3 | 1.3 | 0.5 | 3.2 |
| | 0.0472 | 30% | 70% | 4 | 1.5 | 0.7 | 3.6 |
| | 0.0587 | 15% | 80% | | | | |
| | 0.0763 | 5% | 90% | | | | |
| 24 hours | 0.0199 | 73% | 31% | 1 | | | |
| | 0.013 | 81% | 18% | 2 | 0.6 | 0.3 | 1.5 |
| | 0.00733 | 92% | 6% | 3 | 0.8 | 0.4 | 1.7 |
| | 0.0472 | 46% | 70% | 4 | 1.9 | 1.1 | 3.3 |
| | 0.0587 | 35% | 80% | | | | |
| | 0.0763 | 15% | 90% | | | | |
| 48 hours | 0.0312 | 71% | 51% | 1 | | | |
| | 0.0187 | 86% | 29% | 2 | 1.0 | 0.1 | 7.3 |
| | 0.00473 | 93% | 4% | 3 | 3.1 | 0.8 | 11.8 |
| | 0.0472 | 29% | 70% | 4 | 2.0 | 0.4 | 9.1 |
| | 0.0587 | 21% | 80% | | | | |
| | 0.0763 | 14% | 90% | | | | |

UO only

| Time prior AKI stage | Cutoff value | sens | spec | Quartile | OR | 95% CI of OR | |
|---|---|---|---|---|---|---|---|
| 0 hours | 0.0231 | 72% | 43% | 1 | | | |
| | 0.0217 | 81% | 41% | 2 | 2.7 | 1.4 | 5.0 |
| | 0.0149 | 91% | 24% | 3 | 2.7 | 1.4 | 5.0 |
| | 0.0451 | 43% | 71% | 4 | 4.5 | 2.5 | 8.0 |
| | 0.053 | 38% | 80% | | | | |
| | 0.0667 | 17% | 90% | | | | |
| 24 hours | 0.0303 | 71% | 56% | 1 | | | |
| | 0.0243 | 81% | 45% | 2 | 3.1 | 1.5 | 6.5 |
| | 0.0197 | 90% | 37% | 3 | 5.4 | 2.7 | 10.6 |
| | 0.0451 | 50% | 71% | 4 | 6.7 | 3.5 | 13.1 |
| | 0.053 | 35% | 80% | | | | |
| | 0.0667 | 23% | 90% | | | | |

Fig. 1 Continued

| 48 hours | | 0.0319 | 72% | 58% | 1 | | | |
|---|---|---|---|---|---|---|---|---|
| | | 0.0311 | 80% | 57% | 2 | 1.0 | 0.1 | 7.6 |
| | | 0.017 | 92% | 31% | 3 | 6.5 | 1.9 | 22.4 |
| | | 0.0451 | 40% | 71% | 4 | 5.7 | 1.6 | 19.9 |
| | | 0.053 | 32% | 80% | | | | |
| | | 0.0667 | 20% | 90% | | | | |

P-selectin glycoprotein ligand 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1.794 | 1.119 | 1.794 | 1.137 | 1.794 | 0.966 |
| average | 4.219 | 4.361 | 4.219 | 2.640 | 4.219 | 4.098 |
| stdev | 7.564 | 8.239 | 7.564 | 3.968 | 7.564 | 6.633 |
| p (t-test) | | 0.908 | | 0.128 | | 0.938 |
| min | 0.001 | 0.001 | 0.001 | 0.018 | 0.001 | 0.006 |
| max | 67.069 | 47.674 | 67.069 | 20.498 | 67.069 | 22.918 |
| n (Samp) | 164 | 52 | 164 | 59 | 164 | 26 |
| n (Pat) | 104 | 52 | 104 | 59 | 104 | 26 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1.412 | 1.000 | 1.412 | 0.977 | 1.412 | 3.100 |
| average | 3.847 | 3.565 | 3.847 | 2.259 | 3.847 | 4.196 |
| stdev | 6.885 | 5.752 | 6.885 | 2.677 | 6.885 | 5.482 |
| p (t-test) | | 0.861 | | 0.263 | | 0.852 |
| min | 0.001 | 0.016 | 0.001 | 0.016 | 0.001 | 0.018 |
| max | 67.069 | 19.906 | 67.069 | 9.204 | 67.069 | 20.907 |
| n (Samp) | 322 | 19 | 322 | 24 | 322 | 14 |
| n (Pat) | 168 | 19 | 168 | 24 | 168 | 14 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1.842 | 1.020 | 1.842 | 1.083 | 1.842 | 0.849 |
| average | 4.569 | 3.864 | 4.569 | 2.459 | 4.569 | 3.266 |
| stdev | 8.132 | 8.176 | 8.132 | 4.099 | 8.132 | 6.013 |
| p (t-test) | | 0.612 | | 0.081 | | 0.463 |
| min | 0.001 | 0.001 | 0.001 | 0.018 | 0.001 | 0.006 |
| max | 67.069 | 47.674 | 67.069 | 20.498 | 67.069 | 22.918 |
| n (Samp) | 139 | 46 | 139 | 50 | 139 | 23 |
| n (Pat) | 85 | 46 | 85 | 50 | 85 | 23 | sCr or UO

| Time prior AKI stage | AUC | SE | nCohort 1 | nCohort 2 | p |
|---|---|---|---|---|---|
| 0 hours | 0.45 | 0.045 | 164 | 52 | 0.309 |
| 24 hours | 0.43 | 0.042 | 164 | 59 | 0.080 |
| 48 hours | 0.44 | 0.059 | 164 | 26 | 0.292 | sCr only

| Time prior AKI stage | AUC | SE | nCohort 1 | nCohort 2 | p |
|---|---|---|---|---|---|
| 0 hours | 0.47 | 0.067 | 322 | 19 | 0.673 |
| 24 hours | 0.44 | 0.059 | 322 | 24 | 0.306 |
| 48 hours | 0.54 | 0.081 | 322 | 14 | 0.598 |

Fig. 1 Continued

UO only

| Time prior AKI stage | AUC | SE | nCohort 1 | nCohort 2 | p |
|---|---|---|---|---|---|
| 0 hours | 0.42 | 0.047 | 139 | 46 | 0.089 |
| 24 hours | 0.39 | 0.045 | 139 | 50 | 0.017 |
| 48 hours | 0.38 | 0.059 | 139 | 23 | 0.044 | sCr or UO

| Time prior AKI stage | Cutoff value | sens | spec | Quartile | OR | 95% CI of OR | |
|---|---|---|---|---|---|---|---|
| 0 hours | 0.46735 | 73% | 24% | 1 | | | |
| | 0.3318 | 81% | 20% | 2 | 1.0 | 0.6 | 1.6 |
| | 0.01619 | 96% | 1% | 3 | 1.6 | 1.1 | 2.5 |
| | 3.99894 | 21% | 70% | 4 | 1.4 | 0.9 | 2.1 |
| | 6.28391 | 19% | 80% | | | | |
| | 10.0248 | 13% | 90% | | | | |
| 24 hours | 0.30536 | 71% | 18% | 1 | | | |
| | 0.00132 | 100% | 1% | 2 | 1.0 | 0.7 | 1.5 |
| | 0.00132 | 100% | 1% | 3 | 1.6 | 1.1 | 2.3 |
| | 3.99894 | 22% | 70% | 4 | 1.8 | 1.2 | 2.6 |
| | 6.28391 | 10% | 80% | | | | |
| | 10.0248 | 3% | 90% | | | | |
| 48 hours | 0.1182 | 73% | 14% | 1 | | | |
| | 0.01822 | 81% | 13% | 2 | 0.5 | 0.2 | 1.3 |
| | 0.00132 | 100% | 1% | 3 | 0.8 | 0.4 | 1.7 |
| | 3.99894 | 31% | 70% | 4 | 1.4 | 0.8 | 2.5 |
| | 6.28391 | 19% | 80% | | | | |
| | 10.0248 | 12% | 90% | | | | | sCr only

| Time prior AKI stage | Cutoff value | sens | spec | Quartile | OR | 95% CI of OR | |
|---|---|---|---|---|---|---|---|
| 0 hours | 0.75253 | 74% | 34% | 1 | | | |
| | 0.01822 | 84% | 17% | 2 | 1.0 | 0.4 | 2.8 |
| | 0.01619 | 95% | 2% | 3 | 1.6 | 0.7 | 3.7 |
| | 3.27452 | 32% | 70% | 4 | 1.3 | 0.5 | 3.2 |
| | 5.39435 | 21% | 80% | | | | |
| | 10.0248 | 11% | 90% | | | | |
| 24 hours | 0.34502 | 71% | 24% | 1 | | | |
| | 0.01619 | 96% | 2% | 2 | 0.7 | 0.3 | 1.6 |
| | 0.01619 | 96% | 2% | 3 | 1.2 | 0.6 | 2.3 |
| | 3.27452 | 29% | 70% | 4 | 1.2 | 0.6 | 2.3 |
| | 5.39435 | 17% | 80% | | | | |
| | 10.0248 | 0% | 90% | | | | |
| 48 hours | 0.66465 | 71% | 33% | 1 | | | |
| | 0.00574 | 100% | 2% | 2 | 0.2 | 0.0 | 2.9 |
| | 0.00574 | 100% | 2% | 3 | 0.7 | 0.2 | 2.4 |
| | 3.27452 | 43% | 70% | 4 | 1.5 | 0.6 | 3.7 |
| | 5.39435 | 29% | 80% | | | | |
| | 10.0248 | 7% | 90% | | | | |

UO only

| Time prior AKI stage | Cutoff value | sens | spec | Quartile | OR | 95% CI of OR | |
|---|---|---|---|---|---|---|---|
| 0 hours | 0.45337 | 72% | 24% | 1 | | | |
| | 0.23619 | 80% | 17% | 2 | 1.5 | 0.9 | 2.6 |
| | 0.00132 | 98% | 1% | 3 | 2.1 | 1.3 | 3.5 |
| | 4.29127 | 17% | 71% | 4 | 1.9 | 1.2 | 3.2 |
| | 7.08102 | 17% | 81% | | | | |
| | 11.9954 | 11% | 91% | | | | |

Fig. 1 Continued

| 24 hours | 0.1182 | 72% | 14% | 1 | | | |
| --- | --- | --- | --- | --- | --- | --- | --- |
| | 0.00132 | 100% | 1% | 2 | 1.2 | 0.7 | 2.0 |
| | 0.00132 | 100% | 1% | 3 | 1.8 | 1.2 | 2.9 |
| | 4.29127 | 18% | 71% | 4 | 2.5 | 1.6 | 3.8 |
| | 7.08102 | 8% | 81% | | | | |
| | 11.9954 | 4% | 91% | | | | |
| 48 hours | 0.04883 | 74% | 14% | 1 | | | |
| | 0.02776 | 83% | 14% | 2 | 1.0 | 0.3 | 3.0 |
| | 0.00132 | 100% | 1% | 3 | 1.6 | 0.6 | 4.0 |
| | 4.29127 | 17% | 71% | 4 | 2.7 | 1.2 | 6.1 |
| | 7.08102 | 17% | 81% | | | | |
| | 11.9954 | 9% | 91% | | | | |

Secretory leukocyte peptidase inhibitor sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 8111.639 | 14624.374 | 8111.639 | 16549.815 | 8111.639 | 525.489 |
| average | 11492.522 | 15110.501 | 11492.522 | 16645.536 | 11492.522 | 25158.598 |
| stdev | 9589.114 | 9290.532 | 9589.114 | 9691.915 | 9589.114 | na |
| p (t-test) | | 0.079 | | 0.019 | | na |
| min | 525.489 | 701.419 | 525.489 | 531.250 | 525.489 | 25158.598 |
| max | 33763.353 | 29870.849 | 33763.353 | 32087.099 | 33763.353 | 25158.598 |
| n (Samp) | 96 | 28 | 96 | 25 | 96 | 1 |
| n (Pat) | 48 | 28 | 48 | 25 | 48 | 1 | sCr only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 8566.688 | 20516.605 | 8566.688 | 20780.608 | 8566.688 | 7684.086 |
| average | 12290.616 | 18287.991 | 12290.616 | 18816.183 | 12290.616 | 12905.540 |
| stdev | 9591.348 | 8941.337 | 9591.348 | 10469.281 | 9591.348 | 15296.537 |
| p (t-test) | | 0.056 | | 0.031 | | 0.913 |
| min | 525.489 | 892.467 | 525.489 | 531.250 | 525.489 | 903.384 |
| max | 33763.353 | 28363.940 | 33763.353 | 32087.099 | 33763.353 | 30129.151 |
| n (Samp) | 158 | 10 | 158 | 11 | 158 | 3 |
| n (Pat) | 90 | 10 | 90 | 11 | 90 | 3 |

UO only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 8528.761 | 10793.358 | 8528.761 | 16549.815 | 8528.761 | 22883.727 |
| average | 11512.549 | 13878.923 | 11512.549 | 16616.725 | 11512.549 | 23628.210 |
| stdev | 9508.856 | 9366.886 | 9508.856 | 8917.495 | 9508.856 | 3818.633 |
| p (t-test) | | 0.298 | | 0.025 | | 0.014 |
| min | 525.489 | 701.419 | 525.489 | 2160.494 | 525.489 | 20424.354 |
| max | 30367.279 | 29870.849 | 30367.279 | 30018.450 | 30367.279 | 28321.033 |
| n (Samp) | 74 | 23 | 74 | 23 | 74 | 4 |
| n (Pat) | 37 | 23 | 37 | 23 | 37 | 4 | sCr or UO

| Time prior AKI stage | AUC | SE | nCohort 1 | nCohort 2 | p |
| --- | --- | --- | --- | --- | --- |
| 0 hours | 0.63 | 0.063 | 96 | 28 | 0.039 |
| 24 hours | 0.65 | 0.065 | 96 | 25 | 0.018 |
| 48 hours | 0.86 | 0.234 | 96 | 1 | 0.120 |

Fig. 1 Continued sCr only

| Time prior AKI stage | AUC | SE | nCohort 1 | nCohort 2 | p |
|---|---|---|---|---|---|
| 0 hours | 0.67 | 0.096 | 158 | 10 | 0.078 |
| 24 hours | 0.68 | 0.092 | 158 | 11 | 0.050 |
| 48 hours | 0.50 | 0.169 | 158 | 3 | 1.000 |

UO only

| Time prior AKI stage | AUC | SE | nCohort 1 | nCohort 2 | p |
|---|---|---|---|---|---|
| 0 hours | 0.60 | 0.070 | 74 | 23 | 0.156 |
| 24 hours | 0.67 | 0.068 | 74 | 23 | 0.015 |
| 48 hours | 0.83 | 0.128 | 74 | 4 | 0.010 | sCr or UO

| Time prior AKI stage | Cutoff value | sens | spec | Quartile | OR | 95% CI of OR | |
|---|---|---|---|---|---|---|---|
| 0 hours | 7256.53 | 71% | 48% | 1 | | | |
| | 6306.41 | 82% | 44% | 2 | 3.2 | 1.1 | 9.3 |
| | 3620.22 | 93% | 27% | 3 | 3.8 | 1.4 | 10.7 |
| | 16611 | 43% | 71% | 4 | 3.2 | 1.1 | 9.3 |
| | 22167.9 | 25% | 80% | | | | |
| | 26549.8 | 18% | 91% | | | | |
| 24 hours | 8495.58 | 72% | 52% | 1 | | | |
| | 7450.98 | 80% | 49% | 2 | 1.8 | 0.5 | 6.0 |
| | 3415.09 | 92% | 27% | 3 | 3.3 | 1.1 | 9.4 |
| | 16611 | 48% | 71% | 4 | 3.7 | 1.3 | 10.3 |
| | 22167.9 | 36% | 80% | | | | |
| | 26549.8 | 16% | 91% | | | | |
| 48 hours | 25000 | 100% | 86% | 1 | | | |
| | 25000 | 100% | 86% | 2 | na | na | na |
| | 25000 | 100% | 86% | 3 | na | na | na |
| | 16611 | 100% | 71% | 4 | na | na | na |
| | 22167.9 | 100% | 80% | | | | |
| | 26549.8 | 0% | 91% | | | | | sCr only

| Time prior AKI stage | Cutoff value | sens | spec | Quartile | OR | 95% CI of OR | |
|---|---|---|---|---|---|---|---|
| 0 hours | 16778.6 | 70% | 68% | 1 | | | |
| | 15442.8 | 80% | 64% | 2 | 1.0 | 0.0 | 55.5 |
| | 5569.82 | 90% | 34% | 3 | 4.3 | 0.3 | 55.2 |
| | 18013.4 | 60% | 70% | 4 | 4.3 | 0.3 | 55.2 |
| | 23222 | 40% | 80% | | | | |
| | 27287.8 | 10% | 91% | | | | |
| 24 hours | 14407.3 | 73% | 62% | 1 | | | |
| | 9606.74 | 82% | 54% | 2 | 1.0 | 0.0 | 55.5 |
| | 4877.05 | 91% | 30% | 3 | 4.3 | 0.3 | 55.2 |
| | 18013.4 | 64% | 70% | 4 | 5.4 | 0.5 | 62.6 |
| | 23222 | 36% | 80% | | | | |
| | 27287.8 | 27% | 91% | | | | |
| 48 hours | 817.819 | 100% | 6% | 1 | | | |
| | 817.819 | 100% | 6% | 2 | 1.0 | 0.0 | 55.7 |
| | 817.819 | 100% | 6% | 3 | 0.0 | 0.0 | na |
| | 18013.4 | 33% | 70% | 4 | 1.0 | 0.0 | 54.3 |
| | 23222 | 33% | 80% | | | | |
| | 27287.8 | 33% | 91% | | | | |

Fig. 1 Continued

UO only

| Time prior AKI stage | Cutoff value | sens | spec | Quartile | OR | 95% CI of OR | |
|---|---|---|---|---|---|---|---|
| 0 hours | 6725.66 | 74% | 46% | 1 | | | |
| | 6306.41 | 83% | 45% | 2 | 2.9 | 0.9 | 9.0 |
| | 3620.22 | 91% | 27% | 3 | 2.9 | 0.9 | 9.0 |
| | 16611 | 35% | 70% | 4 | 2.2 | 0.7 | 7.2 |
| | 23022.9 | 22% | 81% | | | | |
| | 26549.8 | 17% | 91% | | | | |
| 24 hours | 8495.58 | 74% | 50% | 1 | | | |
| | 7110.75 | 83% | 47% | 2 | 3.7 | 0.8 | 16.5 |
| | 6452.65 | 91% | 46% | 3 | 3.7 | 0.8 | 16.5 |
| | 16611 | 48% | 70% | 4 | 6.2 | 1.5 | 25.3 |
| | 23022.9 | 35% | 81% | | | | |
| | 26549.8 | 13% | 91% | | | | |
| 48 hours | 20424.4 | 75% | 76% | 1 | | | |
| | 18848.1 | 100% | 76% | 2 | na | na | na |
| | 18848.1 | 100% | 76% | 3 | na | na | na |
| | 16611 | 100% | 70% | 4 | na | na | na |
| | 23022.9 | 50% | 81% | | | | |
| | 26549.8 | 25% | 91% | | | | |

Stem cell factor sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 162.000 | 287.000 | 162.000 | 234.500 | 162.000 | 227.000 |
| average | 301.667 | 390.823 | 301.667 | 391.260 | 301.667 | 393.689 |
| stdev | 391.044 | 374.352 | 391.044 | 455.071 | 391.044 | 506.142 |
| p (t-test) | | 0.130 | | 0.120 | | 0.261 |
| min | 9.140 | 14.300 | 9.140 | 14.300 | 9.140 | 14.300 |
| max | 2900.000 | 1610.000 | 2900.000 | 2350.000 | 2900.000 | 2420.000 |
| n (Samp) | 249 | 53 | 249 | 62 | 249 | 27 |
| n (Pat) | 104 | 53 | 104 | 62 | 104 | 27 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 182.000 | 136.500 | 182.000 | 167.000 | 182.000 | 147.500 |
| average | 315.116 | 249.810 | 315.116 | 375.338 | 315.116 | 429.400 |
| stdev | 392.514 | 334.839 | 392.514 | 443.429 | 392.514 | 503.928 |
| p (t-test) | | 0.465 | | 0.451 | | 0.288 |
| min | 9.140 | 14.300 | 9.140 | 14.300 | 9.140 | 14.300 |
| max | 2900.000 | 1440.000 | 2900.000 | 1720.000 | 2900.000 | 1560.000 |
| n (Samp) | 441 | 20 | 441 | 26 | 441 | 14 |
| n (Pat) | 170 | 20 | 170 | 26 | 170 | 14 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 180.000 | 317.000 | 180.000 | 243.000 | 180.000 | 227.000 |
| average | 287.934 | 453.455 | 287.934 | 421.458 | 287.934 | 404.608 |
| stdev | 341.616 | 392.229 | 341.616 | 469.353 | 341.616 | 515.271 |
| p (t-test) | | 0.004 | | 0.020 | | 0.130 |
| min | 9.140 | 51.000 | 9.140 | 34.000 | 9.140 | 32.800 |
| max | 1890.000 | 1610.000 | 1890.000 | 2350.000 | 1890.000 | 2420.000 |
| n (Samp) | 212 | 47 | 212 | 52 | 212 | 25 |
| n (Pat) | 85 | 47 | 85 | 52 | 85 | 25 |

Fig. 1 Continued sCr or UO

| Time prior AKI stage | AUC | SE | nCohort 1 | nCohort 2 | p |
|---|---|---|---|---|---|
| 0 hours | 0.62 | 0.044 | 249 | 53 | 0.008 |
| 24 hours | 0.58 | 0.042 | 249 | 62 | 0.063 |
| 48 hours | 0.57 | 0.060 | 249 | 27 | 0.243 | sCr only

| Time prior AKI stage | AUC | SE | nCohort 1 | nCohort 2 | p |
|---|---|---|---|---|---|
| 0 hours | 0.43 | 0.062 | 441 | 20 | 0.260 |
| 24 hours | 0.52 | 0.059 | 441 | 26 | 0.707 |
| 48 hours | 0.53 | 0.080 | 441 | 14 | 0.745 |

UO only

| Time prior AKI stage | AUC | SE | nCohort 1 | nCohort 2 | p |
|---|---|---|---|---|---|
| 0 hours | 0.67 | 0.046 | 212 | 47 | 0.000 |
| 24 hours | 0.61 | 0.045 | 212 | 52 | 0.015 |
| 48 hours | 0.59 | 0.063 | 212 | 25 | 0.136 | sCr or UO

| Time prior AKI stage | Cutoff value | sens | spec | Quartile | OR | 95% CI of OR | |
|---|---|---|---|---|---|---|---|
| 0 hours | 136 | 72% | 47% | 1 | | | |
| | 92.5 | 81% | 30% | 2 | 1.5 | 0.9 | 2.5 |
| | 82.9 | 91% | 26% | 3 | 2.8 | 1.8 | 4.5 |
| | 293 | 49% | 70% | 4 | 3.2 | 2.1 | 5.1 |
| | 416 | 32% | 80% | | | | |
| | 729 | 15% | 90% | | | | |
| 24 hours | 120 | 71% | 42% | 1 | | | |
| | 77.9 | 81% | 24% | 2 | 0.8 | 0.5 | 1.2 |
| | 54.6 | 92% | 13% | 3 | 1.5 | 1.1 | 2.0 |
| | 293 | 37% | 70% | 4 | 1.7 | 1.2 | 2.3 |
| | 416 | 27% | 80% | | | | |
| | 729 | 16% | 90% | | | | |
| 48 hours | 165 | 70% | 51% | 1 | | | |
| | 60.5 | 81% | 15% | 2 | 0.5 | 0.2 | 1.4 |
| | 34 | 93% | 5% | 3 | 1.4 | 0.7 | 2.6 |
| | 293 | 41% | 70% | 4 | 1.8 | 1.0 | 3.2 |
| | 416 | 37% | 80% | | | | |
| | 729 | 15% | 90% | | | | | sCr only

| Time prior AKI stage | Cutoff value | sens | spec | Quartile | OR | 95% CI of OR | |
|---|---|---|---|---|---|---|---|
| 0 hours | 82.9 | 70% | 23% | 1 | | | |
| | 64.3 | 80% | 16% | 2 | 2.1 | 0.8 | 5.7 |
| | 47.9 | 90% | 9% | 3 | 1.4 | 0.4 | 4.4 |
| | 310 | 25% | 70% | 4 | 2.4 | 0.9 | 6.4 |
| | 452 | 10% | 80% | | | | |
| | 753 | 10% | 90% | | | | |
| 24 hours | 95.2 | 73% | 28% | 1 | | | |
| | 80 | 81% | 22% | 2 | 1.3 | 0.7 | 2.5 |
| | 55.3 | 92% | 12% | 3 | 0.8 | 0.4 | 1.7 |
| | 310 | 27% | 70% | 4 | 1.2 | 0.6 | 2.2 |
| | 452 | 27% | 80% | | | | |
| | 753 | 15% | 90% | | | | |

Fig. 1 Continued

| | 48 hours | 121 | 71% | 39% | 1 | | | |
|---|---|---|---|---|---|---|---|---|
| | | 53 | 86% | 11% | 2 | 1.0 | 0.4 | 2.7 |
| | | 34 | 93% | 5% | 3 | 0.0 | 0.0 | na |
| | | 310 | 43% | 70% | 4 | 1.5 | 0.6 | 3.6 |
| | | 452 | 36% | 80% | | | | |
| | | 753 | 21% | 90% | | | | |
| UO only | | | | | | | | | |
| | Time prior AKI stage | Cutoff value | sens | spec | Quartile | OR | 95% CI of OR | |
| | 0 hours | 209 | 72% | 60% | 1 | | | |
| | | 128 | 81% | 40% | 2 | 1.7 | 0.8 | 3.4 |
| | | 89.6 | 91% | 25% | 3 | 3.5 | 2.0 | 6.4 |
| | | 297 | 53% | 70% | 4 | 4.9 | 2.8 | 8.6 |
| | | 383 | 40% | 80% | | | | |
| | | 682 | 23% | 90% | | | | |
| | 24 hours | 165 | 71% | 48% | 1 | | | |
| | | 102 | 81% | 31% | 2 | 1.5 | 0.9 | 2.4 |
| | | 71.1 | 90% | 17% | 3 | 2.0 | 1.2 | 3.1 |
| | | 297 | 40% | 70% | 4 | 2.9 | 1.9 | 4.5 |
| | | 383 | 35% | 80% | | | | |
| | | 682 | 19% | 90% | | | | |
| | 48 hours | 166 | 72% | 49% | 1 | | | |
| | | 123 | 80% | 38% | 2 | 1.0 | 0.3 | 2.9 |
| | | 51 | 92% | 10% | 3 | 2.5 | 1.1 | 5.4 |
| | | 297 | 40% | 70% | 4 | 2.1 | 0.9 | 4.7 |
| | | 383 | 32% | 80% | | | | |
| | | 682 | 16% | 90% | | | | |

Tissue inhibitor of metalloproteinase 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 2.220 | 3.840 | 2.220 | 3.830 | 2.220 | 3.890 |
| average | 10.227 | 10.335 | 10.227 | 20.849 | 10.227 | 19.813 |
| stdev | 28.712 | 13.788 | 28.712 | 47.669 | 28.712 | 57.815 |
| p (t-test) | | 0.979 | | 0.025 | | 0.148 |
| min | 0.034 | 0.168 | 0.034 | 0.081 | 0.034 | 0.211 |
| max | 302.000 | 62.200 | 302.000 | 302.000 | 302.000 | 302.000 |
| n (Samp) | 249 | 53 | 249 | 62 | 249 | 27 |
| n (Pat) | 104 | 53 | 104 | 62 | 104 | 27 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 2.630 | 4.200 | 2.630 | 8.890 | 2.630 | 4.655 |
| average | 12.016 | 15.626 | 12.016 | 21.562 | 12.016 | 7.505 |
| stdev | 34.277 | 33.066 | 34.277 | 37.431 | 34.277 | 8.656 |
| p (t-test) | | 0.645 | | 0.170 | | 0.623 |
| min | 0.034 | 0.168 | 0.034 | 0.081 | 0.034 | 0.326 |
| max | 302.000 | 150.000 | 302.000 | 159.000 | 302.000 | 33.100 |
| n (Samp) | 441 | 20 | 441 | 26 | 441 | 14 |
| n (Pat) | 170 | 20 | 170 | 26 | 170 | 14 |

Fig. 1 Continued

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 2.200 | 7.590 | 2.200 | 5.725 | 2.200 | 3.770 |
| average | 10.906 | 15.388 | 10.906 | 19.745 | 10.906 | 21.199 |
| stdev | 30.808 | 26.209 | 30.808 | 46.974 | 30.808 | 59.952 |
| p (t-test) | | 0.356 | | 0.099 | | 0.165 |
| min | 0.034 | 0.276 | 0.034 | 0.139 | 0.034 | 0.211 |
| max | 302.000 | 152.000 | 302.000 | 302.000 | 302.000 | 302.000 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
|---|---|---|---|---|---|
| 0 hours | 0.61 | 0.044 | 249 | 53 | 0.012 |
| 24 hours | 0.59 | 0.042 | 249 | 62 | 0.024 |
| 48 hours | 0.56 | 0.060 | 249 | 27 | 0.308 | sCr only

| Time prior AKI stage | AUC | SE | nCohort 1 | nCohort 2 | p |
|---|---|---|---|---|---|
| 0 hours | 0.56 | 0.068 | 441 | 20 | 0.411 |
| 24 hours | 0.60 | 0.060 | 441 | 26 | 0.110 |
| 48 hours | 0.55 | 0.080 | 441 | 14 | 0.503 |

UO only

| Time prior AKI stage | AUC | SE | nCohort 1 | nCohort 2 | p |
|---|---|---|---|---|---|
| 0 hours | 0.66 | 0.047 | 212 | 47 | 0.000 |
| 24 hours | 0.62 | 0.045 | 212 | 52 | 0.007 |
| 48 hours | 0.57 | 0.063 | 212 | 25 | 0.275 | sCr or UO

| Time prior AKI stage | Cutoff value | sens | spec | Quartile | OR | 95% CI of OR | |
|---|---|---|---|---|---|---|---|
| 0 hours | 2.07 | 72% | 48% | 1 | | | |
| | 1.54 | 81% | 37% | 2 | 3.4 | 1.9 | 6.2 |
| | 1.21 | 91% | 31% | 3 | 3.5 | 2.0 | 6.3 |
| | 5.59 | 47% | 70% | 4 | 4.3 | 2.5 | 7.6 |
| | 10.3 | 28% | 80% | | | | |
| | 24.6 | 15% | 90% | | | | |
| 24 hours | 1.72 | 71% | 41% | 1 | | | |
| | 1.21 | 81% | 31% | 2 | 2.2 | 1.5 | 3.1 |
| | 0.736 | 90% | 21% | 3 | 0.8 | 0.5 | 1.3 |
| | 5.59 | 48% | 70% | 4 | 3.2 | 2.2 | 4.4 |
| | 10.3 | 39% | 80% | | | | |
| | 24.6 | 16% | 90% | | | | |
| 48 hours | 1.49 | 70% | 35% | 1 | | | |
| | 1.13 | 81% | 29% | 2 | 1.7 | 0.8 | 3.4 |
| | 0.325 | 93% | 6% | 3 | 0.6 | 0.2 | 1.8 |
| | 5.59 | 41% | 70% | 4 | 2.4 | 1.3 | 4.6 |
| | 10.3 | 22% | 80% | | | | |
| | 24.6 | 19% | 90% | | | | |

Fig. 1 Continued sCr only

| Time prior AKI stage | Cutoff value | sens | spec | Quartile | OR | 95% CI of OR | |
|---|---|---|---|---|---|---|---|
| 0 hours | 1.94 | 70% | 40% | 1 | | | |
| | 1.29 | 80% | 27% | 2 | 1.0 | 0.4 | 2.8 |
| | 0.256 | 90% | 5% | 3 | 1.3 | 0.5 | 3.2 |
| | 7.88 | 35% | 70% | 4 | 1.8 | 0.8 | 4.0 |
| | 11.8 | 30% | 80% | | | | |
| | 25.1 | 10% | 90% | | | | |
| 24 hours | 1.44 | 73% | 29% | 1 | | | |
| | 0.932 | 81% | 19% | 2 | 0.4 | 0.2 | 1.1 |
| | 0.412 | 92% | 8% | 3 | 0.6 | 0.2 | 1.2 |
| | 7.88 | 58% | 70% | 4 | 1.8 | 1.1 | 2.9 |
| | 11.8 | 42% | 80% | | | | |
| | 25.1 | 19% | 90% | | | | |
| 48 hours | 1.89 | 71% | 39% | 1 | | | |
| | 1.27 | 86% | 27% | 2 | 2.0 | 0.4 | 9.1 |
| | 1.01 | 93% | 22% | 3 | 1.5 | 0.3 | 8.0 |
| | 7.88 | 43% | 70% | 4 | 2.5 | 0.6 | 10.4 |
| | 11.8 | 21% | 80% | | | | |
| | 25.1 | 7% | 90% | | | | |

UO only

| Time prior AKI stage | Cutoff value | sens | spec | Quartile | OR | 95% CI of OR | |
|---|---|---|---|---|---|---|---|
| 0 hours | 2.24 | 70% | 51% | 1 | | | |
| | 1.99 | 81% | 45% | 2 | 8.5 | 2.6 | 28.0 |
| | 1.34 | 91% | 33% | 3 | 8.5 | 2.6 | 28.0 |
| | 5.51 | 57% | 70% | 4 | 11.0 | 3.4 | 35.3 |
| | 11.2 | 30% | 80% | | | | |
| | 24.9 | 19% | 90% | | | | |
| 24 hours | 1.8 | 71% | 41% | 1 | | | |
| | 1.45 | 83% | 34% | 2 | 3.5 | 2.1 | 5.8 |
| | 1.01 | 92% | 26% | 3 | 1.2 | 0.6 | 2.3 |
| | 5.51 | 50% | 70% | 4 | 5.0 | 3.1 | 8.2 |
| | 11.2 | 38% | 80% | | | | |
| | 24.9 | 15% | 90% | | | | |
| 48 hours | 1.49 | 72% | 35% | 1 | | | |
| | 1.16 | 80% | 29% | 2 | 1.9 | 0.8 | 4.3 |
| | 0.815 | 92% | 21% | 3 | 1.3 | 0.5 | 3.3 |
| | 5.51 | 40% | 70% | 4 | 2.4 | 1.1 | 5.3 |
| | 11.2 | 24% | 80% | | | | |
| | 24.9 | 20% | 90% | | | | |

Tissue inhibitor of metalloproteinase 2 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 8619.363 | 14310.878 | 8619.363 | 12505.747 | 8619.363 | 10582.597 |
| average | 12919.212 | 14508.472 | 12919.212 | 20872.292 | 12919.212 | 14248.990 |
| stdev | 22146.588 | 9391.645 | 22146.588 | 33046.482 | 22146.588 | 18292.819 |
| p (t-test) | | 0.623 | | 0.059 | | 0.776 |
| min | 759.402 | 1026.894 | 759.402 | 52.566 | 759.402 | 746.215 |
| max | 210000.000 | 42030.967 | 210000.000 | 210000.000 | 210000.000 | 89331.344 |
| n (Samp) | 117 | 51 | 117 | 60 | 117 | 26 |
| n (Pat) | 99 | 51 | 99 | 60 | 99 | 26 |

Fig. 1 Continued sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 10640.038 | 11416.887 | 10640.038 | 9763.787 | 10640.038 | 11626.661 |
| average | 14957.752 | 13825.554 | 14957.752 | 26213.840 | 14957.752 | 12289.343 |
| stdev | 19692.771 | 11848.841 | 19692.771 | 43807.207 | 19692.771 | 7367.599 |
| p (t-test) | | 0.815 | | 0.022 | | 0.614 |
| min | 213.712 | 1026.894 | 213.712 | 52.566 | 213.712 | 1311.328 |
| max | 210000.000 | 42030.967 | 210000.000 | 210000.000 | 210000.000 | 26183.550 |
| n (Samp) | 261 | 17 | 261 | 23 | 261 | 14 |
| n (Pat) | 160 | 17 | 160 | 23 | 160 | 14 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 8532.402 | 16465.292 | 8532.402 | 13185.035 | 8532.402 | 10640.038 |
| average | 13295.674 | 15424.444 | 13295.674 | 23093.948 | 13295.674 | 15382.046 |
| stdev | 23450.084 | 8371.038 | 23450.084 | 35709.945 | 23450.084 | 19600.493 |
| p (t-test) | | 0.555 | | 0.043 | | 0.692 |
| min | 759.402 | 2687.654 | 759.402 | 1103.366 | 759.402 | 746.215 |
| max | 210000.000 | 33679.652 | 210000.000 | 210000.000 | 210000.000 | 89331.344 |
| n (Samp) | 105 | 45 | 105 | 50 | 105 | 23 |
| n (Pat) | 84 | 45 | 84 | 50 | 84 | 23 | sCr or UO

| Time prior AKI stage | AUC | SE | nCohort 1 | nCohort 2 | p |
|---|---|---|---|---|---|
| 0 hours | 0.62 | 0.048 | 117 | 51 | 0.011 |
| 24 hours | 0.63 | 0.045 | 117 | 60 | 0.005 |
| 48 hours | 0.51 | 0.063 | 117 | 26 | 0.823 | sCr only

| Time prior AKI stage | AUC | SE | nCohort 1 | nCohort 2 | p |
|---|---|---|---|---|---|
| 0 hours | 0.49 | 0.072 | 261 | 17 | 0.933 |
| 24 hours | 0.56 | 0.064 | 261 | 23 | 0.386 |
| 48 hours | 0.50 | 0.080 | 261 | 14 | 0.957 |

UO only

| Time prior AKI stage | AUC | SE | nCohort 1 | nCohort 2 | p |
|---|---|---|---|---|---|
| 0 hours | 0.68 | 0.050 | 105 | 45 | 0.000 |
| 24 hours | 0.66 | 0.048 | 105 | 50 | 0.001 |
| 48 hours | 0.53 | 0.067 | 105 | 23 | 0.643 |

Fig. 1 Continued sCr or UO

| Time prior AKI stage | Cutoff value | sens | spec | Quartile | OR | 95% CI of OR | |
|---|---|---|---|---|---|---|---|
| 0 hours | 7727.52 | 71% | 44% | 1 | | | |
| | 6693.2 | 80% | 40% | 2 | 1.7 | 1.0 | 2.9 |
| | 2825.65 | 90% | 14% | 3 | 1.9 | 1.1 | 3.2 |
| | 13779.5 | 51% | 70% | 4 | 3.2 | 1.9 | 5.2 |
| | 17295.1 | 31% | 80% | | | | |
| | 20456.1 | 24% | 91% | | | | |
| 24 hours | 8897.32 | 70% | 54% | 1 | | | |
| | 6213.75 | 80% | 38% | 2 | 2.6 | 1.6 | 4.2 |
| | 3735.29 | 90% | 23% | 3 | 2.3 | 1.4 | 3.8 |
| | 13779.5 | 43% | 70% | 4 | 3.9 | 2.5 | 6.3 |
| | 17295.1 | 35% | 80% | | | | |
| | 20456.1 | 30% | 91% | | | | |
| 48 hours | 5722.8 | 73% | 36% | 1 | | | |
| | 3623.96 | 81% | 21% | 2 | 0.8 | 0.3 | 1.8 |
| | 2281.85 | 92% | 9% | 3 | 1.9 | 1.0 | 3.6 |
| | 13779.5 | 27% | 70% | 4 | 0.8 | 0.3 | 1.8 |
| | 17295.1 | 15% | 80% | | | | |
| | 20456.1 | 15% | 91% | | | | | sCr only

| Time prior AKI stage | Cutoff value | sens | spec | Quartile | OR | 95% CI of OR | |
|---|---|---|---|---|---|---|---|
| 0 hours | 5408.72 | 71% | 23% | 1 | | | |
| | 2808.64 | 82% | 10% | 2 | 1.3 | 0.5 | 3.3 |
| | 1670.96 | 94% | 5% | 3 | 0.5 | 0.1 | 2.2 |
| | 16325.1 | 35% | 70% | 4 | 1.6 | 0.7 | 3.8 |
| | 19793.8 | 24% | 80% | | | | |
| | 26953.7 | 18% | 90% | | | | |
| 24 hours | 6042.22 | 74% | 25% | 1 | | | |
| | 4165.28 | 83% | 20% | 2 | 0.7 | 0.3 | 1.4 |
| | 3623.96 | 91% | 15% | 3 | 0.1 | 0.0 | 1.3 |
| | 16325.1 | 43% | 70% | 4 | 1.5 | 0.9 | 2.6 |
| | 19793.8 | 43% | 80% | | | | |
| | 26953.7 | 22% | 90% | | | | |
| 48 hours | 6213.75 | 71% | 25% | 1 | | | |
| | 5408.72 | 86% | 23% | 2 | 0.7 | 0.2 | 2.4 |
| | 3847.82 | 93% | 17% | 3 | 0.7 | 0.2 | 2.4 |
| | 16325.1 | 36% | 70% | 4 | 1.0 | 0.3 | 2.8 |
| | 19793.8 | 14% | 80% | | | | |
| | 26953.7 | 0% | 90% | | | | |

UO only

| Time prior AKI stage | Cutoff value | sens | spec | Quartile | OR | 95% CI of OR | |
|---|---|---|---|---|---|---|---|
| 0 hours | 8192.37 | 71% | 48% | 1 | | | |
| | 7016.45 | 80% | 43% | 2 | 3.4 | 1.5 | 7.5 |
| | 6394.01 | 91% | 42% | 3 | 4.5 | 2.0 | 9.8 |
| | 13779.5 | 58% | 70% | 4 | 6.7 | 3.1 | 14.3 |
| | 16912.3 | 44% | 80% | | | | |
| | 21664.6 | 24% | 90% | | | | |
| 24 hours | 9044.74 | 70% | 55% | 1 | | | |
| | 7056.32 | 80% | 43% | 2 | 4.8 | 2.2 | 10.2 |
| | 5722.8 | 90% | 38% | 3 | 4.8 | 2.2 | 10.2 |
| | 13779.5 | 46% | 70% | 4 | 7.3 | 3.4 | 15.4 |
| | 16912.3 | 36% | 80% | | | | |
| | 21664.6 | 26% | 90% | | | | |

Fig. 1 Continued

| 48 hours | 6183.82 | 74% | 41% | 1 | | | |
| | 2825.65 | 83% | 13% | 2 | 0.3 | 0.1 | 1.2 |
| | 2281.85 | 91% | 10% | 3 | 2.3 | 1.2 | 4.5 |
| | 13779.5 | 26% | 70% | 4 | 0.6 | 0.2 | 1.6 |
| | 16912.3 | 17% | 80% | | | | |
| | 21664.6 | 17% | 90% | | | | |

Tumor necrosis factor-alpha sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 2.650 | 5.370 | 2.650 | 5.785 | 2.650 | 2.900 |
| average | 6.664 | 10.233 | 6.664 | 11.075 | 6.664 | 16.604 |
| stdev | 10.908 | 9.597 | 10.908 | 13.478 | 10.908 | 44.935 |
| p (t-test) | | 0.028 | | 0.007 | | 0.005 |
| min | 0.016 | 0.016 | 0.016 | 0.016 | 0.016 | 0.016 |
| max | 86.200 | 34.200 | 86.200 | 66.800 | 86.200 | 234.000 |
| n (Samp) | 249 | 53 | 249 | 62 | 249 | 27 |
| n (Pat) | 104 | 53 | 104 | 62 | 104 | 27 | sCr only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 3.190 | 2.715 | 3.190 | 4.900 | 3.190 | 4.115 |
| average | 9.421 | 7.586 | 9.421 | 9.793 | 9.421 | 10.510 |
| stdev | 22.272 | 9.948 | 22.272 | 12.854 | 22.272 | 15.044 |
| p (t-test) | | 0.714 | | 0.933 | | 0.856 |
| min | 0.016 | 0.016 | 0.016 | 0.016 | 0.016 | 0.016 |
| max | 300.000 | 34.200 | 300.000 | 61.200 | 300.000 | 54.500 |
| n (Samp) | 441 | 20 | 441 | 26 | 441 | 14 |
| n (Pat) | 170 | 20 | 170 | 26 | 170 | 14 |

UO only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 2.675 | 6.510 | 2.675 | 5.785 | 2.675 | 3.310 |
| average | 5.942 | 10.353 | 5.942 | 10.984 | 5.942 | 18.963 |
| stdev | 8.786 | 8.955 | 8.786 | 12.737 | 8.786 | 46.476 |
| p (t-test) | | 0.002 | | 0.001 | | 0.000 |
| min | 0.016 | 0.016 | 0.016 | 0.016 | 0.016 | 0.016 |
| max | 72.000 | 30.600 | 72.000 | 66.800 | 72.000 | 234.000 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
| --- | --- | --- | --- | --- | --- |
| 0 hours | 0.63 | 0.044 | 249 | 53 | 0.004 |
| 24 hours | 0.62 | 0.041 | 249 | 62 | 0.003 |
| 48 hours | 0.57 | 0.060 | 249 | 27 | 0.270 |

Fig. 1 Continued sCr only

| Time prior AKI stage | AUC | SE | nCohort 1 | nCohort 2 | p |
|---|---|---|---|---|---|
| 0 hours | 0.48 | 0.065 | 441 | 20 | 0.729 |
| 24 hours | 0.56 | 0.060 | 441 | 26 | 0.338 |
| 48 hours | 0.55 | 0.080 | 441 | 14 | 0.514 |

UO only

| Time prior AKI stage | AUC | SE | nCohort 1 | nCohort 2 | p |
|---|---|---|---|---|---|
| 0 hours | 0.65 | 0.047 | 212 | 47 | 0.001 |
| 24 hours | 0.64 | 0.045 | 212 | 52 | 0.002 |
| 48 hours | 0.61 | 0.063 | 212 | 25 | 0.068 | sCr or UO

| Time prior AKI stage | Cutoff value | sens | spec | Quartile | OR | 95% CI of OR | |
|---|---|---|---|---|---|---|---|
| 0 hours | 2.41 | 72% | 47% | 1 | | | |
| | 1.02 | 81% | 21% | 2 | 0.7 | 0.4 | 1.1 |
| | 0.372 | 91% | 10% | 3 | 0.9 | 0.6 | 1.4 |
| | 6.72 | 45% | 70% | 4 | 2.7 | 1.9 | 3.7 |
| | 11.1 | 45% | 80% | | | | |
| | 17.3 | 25% | 91% | | | | |
| 24 hours | 2.48 | 71% | 49% | 1 | | | |
| | 1.46 | 81% | 32% | 2 | 1.7 | 1.1 | 2.5 |
| | 0.739 | 90% | 14% | 3 | 1.9 | 1.3 | 2.9 |
| | 6.72 | 47% | 70% | 4 | 3.2 | 2.2 | 4.6 |
| | 11.1 | 35% | 80% | | | | |
| | 17.3 | 24% | 91% | | | | |
| 48 hours | 2.17 | 70% | 45% | 1 | | | |
| | 1.68 | 81% | 35% | 2 | 1.4 | 0.7 | 3.0 |
| | 0.739 | 93% | 14% | 3 | 1.2 | 0.6 | 2.7 |
| | 6.72 | 37% | 70% | 4 | 1.9 | 1.0 | 3.8 |
| | 11.1 | 22% | 80% | | | | |
| | 17.3 | 19% | 91% | | | | | sCr only

| Time prior AKI stage | Cutoff value | sens | spec | Quartile | OR | 95% CI of OR | |
|---|---|---|---|---|---|---|---|
| 0 hours | 1.64 | 70% | 29% | 1 | | | |
| | 1.02 | 80% | 18% | 2 | 0.8 | 0.3 | 2.0 |
| | 0 | 100% | 0% | 3 | 1.2 | 0.6 | 2.6 |
| | 9.26 | 25% | 70% | 4 | 1.0 | 0.4 | 2.3 |
| | 14.7 | 25% | 80% | | | | |
| | 20.2 | 15% | 90% | | | | |
| 24 hours | 2.5 | 73% | 43% | 1 | | | |
| | 1.42 | 81% | 26% | 2 | 1.0 | 0.4 | 2.2 |
| | 0 | 100% | 0% | 3 | 1.6 | 0.8 | 3.2 |
| | 9.26 | 35% | 70% | 4 | 1.6 | 0.8 | 3.2 |
| | 14.7 | 27% | 80% | | | | |
| | 20.2 | 12% | 90% | | | | |
| 48 hours | 2.89 | 71% | 47% | 1 | | | |
| | 1.68 | 86% | 29% | 2 | 2.0 | 0.4 | 9.1 |
| | 0.77 | 93% | 13% | 3 | 2.5 | 0.6 | 10.4 |
| | 9.26 | 36% | 70% | 4 | 1.5 | 0.3 | 8.0 |
| | 14.7 | 21% | 80% | | | | |
| | 20.2 | 14% | 90% | | | | |

Fig. 1 Continued

UO only

| Time prior AKI stage | Cutoff value | sens | spec | Quartile | OR | 95% CI of OR | |
|---|---|---|---|---|---|---|---|
| 0 hours | 2.78 | 70% | 51% | 1 | | | |
| | 1.24 | 81% | 27% | 2 | 0.6 | 0.3 | 1.1 |
| | 0.435 | 91% | 11% | 3 | 1.1 | 0.7 | 1.8 |
| | 5.17 | 57% | 70% | 4 | 3.1 | 2.1 | 4.6 |
| | 9.61 | 47% | 80% | | | | |
| | 16.2 | 30% | 90% | | | | |
| 24 hours | 2.48 | 71% | 48% | 1 | | | |
| | 1.68 | 81% | 33% | 2 | 2.3 | 1.4 | 3.7 |
| | 1.09 | 90% | 23% | 3 | 1.5 | 0.9 | 2.6 |
| | 5.17 | 54% | 70% | 4 | 3.9 | 2.5 | 6.2 |
| | 9.61 | 40% | 80% | | | | |
| | 16.2 | 29% | 90% | | | | |
| 48 hours | 2.17 | 76% | 44% | 1 | | | |
| | 2.16 | 80% | 43% | 2 | 1.6 | 0.6 | 3.8 |
| | 0.944 | 92% | 19% | 3 | 1.3 | 0.5 | 3.3 |
| | 5.17 | 44% | 70% | 4 | 2.8 | 1.3 | 5.9 |
| | 9.61 | 40% | 80% | | | | |
| | 16.2 | 24% | 90% | | | | |

Vascular cell adhesion molecule 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 50.024 | 62.461 | 50.024 | 61.887 | 50.024 | 60.483 |
| average | 60.209 | 69.355 | 60.209 | 78.438 | 60.209 | 68.162 |
| stdev | 46.313 | 39.752 | 46.313 | 57.060 | 46.313 | 41.709 |
| p (t-test) | | 0.222 | | 0.024 | | 0.422 |
| min | 0.475 | 2.441 | 0.475 | 1.903 | 0.475 | 6.248 |
| max | 322.684 | 194.946 | 322.684 | 299.907 | 322.684 | 160.496 |
| n (Samp) | 117 | 51 | 117 | 59 | 117 | 26 |
| n (Pat) | 99 | 51 | 99 | 59 | 99 | 26 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 56.989 | 46.445 | 56.989 | 58.030 | 56.989 | 45.094 |
| average | 66.507 | 51.536 | 66.507 | 59.235 | 66.507 | 56.593 |
| stdev | 44.397 | 35.456 | 44.397 | 35.582 | 44.397 | 41.657 |
| p (t-test) | | 0.175 | | 0.446 | | 0.415 |
| min | 0.475 | 2.441 | 0.475 | 1.903 | 0.475 | 6.248 |
| max | 322.684 | 137.003 | 322.684 | 125.606 | 322.684 | 163.018 |
| n (Samp) | 260 | 17 | 260 | 23 | 260 | 14 |
| n (Pat) | 160 | 17 | 160 | 23 | 160 | 14 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 51.949 | 70.757 | 51.949 | 73.583 | 51.949 | 69.560 |
| average | 63.784 | 79.503 | 63.784 | 83.967 | 63.784 | 74.837 |
| stdev | 47.334 | 44.955 | 47.334 | 60.431 | 47.334 | 42.245 |
| p (t-test) | | 0.060 | | 0.026 | | 0.304 |
| min | 0.475 | 13.737 | 0.475 | 7.074 | 0.475 | 14.743 |
| max | 322.684 | 239.116 | 322.684 | 299.907 | 322.684 | 160.496 |
| n (Samp) | 105 | 45 | 105 | 49 | 105 | 23 |
| n (Pat) | 84 | 45 | 84 | 49 | 84 | 23 |

Fig. 1 Continued sCr or UO

| Time prior AKI stage | AUC | SE | nCohort 1 | nCohort 2 | p |
|---|---|---|---|---|---|
| 0 hours | 0.59 | 0.049 | 117 | 51 | 0.059 |
| 24 hours | 0.61 | 0.046 | 117 | 59 | 0.016 |
| 48 hours | 0.57 | 0.064 | 117 | 26 | 0.243 | sCr only

| Time prior AKI stage | AUC | SE | nCohort 1 | nCohort 2 | p |
|---|---|---|---|---|---|
| 0 hours | 0.39 | 0.066 | 260 | 17 | 0.096 |
| 24 hours | 0.47 | 0.062 | 260 | 23 | 0.681 |
| 48 hours | 0.42 | 0.074 | 260 | 14 | 0.266 |

UO only

| Time prior AKI stage | AUC | SE | nCohort 1 | nCohort 2 | p |
|---|---|---|---|---|---|
| 0 hours | 0.62 | 0.051 | 105 | 45 | 0.017 |
| 24 hours | 0.61 | 0.050 | 105 | 49 | 0.033 |
| 48 hours | 0.59 | 0.068 | 105 | 23 | 0.165 | sCr or UO

| Time prior AKI stage | Cutoff value | sens | spec | Quartile | OR | 95% CI of OR | |
|---|---|---|---|---|---|---|---|
| 0 hours | 47.3631 | 71% | 45% | 1 | | | |
| | 44.1723 | 80% | 43% | 2 | 1.7 | 1.0 | 2.9 |
| | 27.807 | 90% | 26% | 3 | 2.6 | 1.6 | 4.3 |
| | 72.078 | 41% | 70% | 4 | 2.4 | 1.4 | 3.9 |
| | 89.6943 | 24% | 80% | | | | |
| | 118.475 | 10% | 91% | | | | |
| 24 hours | 45.6672 | 71% | 44% | 1 | | | |
| | 36.986 | 81% | 34% | 2 | 1.5 | 0.9 | 2.4 |
| | 24.0582 | 92% | 22% | 3 | 3.2 | 2.1 | 5.1 |
| | 72.078 | 49% | 70% | 4 | 2.7 | 1.7 | 4.3 |
| | 89.6943 | 31% | 80% | | | | |
| | 118.475 | 15% | 91% | | | | |
| 48 hours | 40.7214 | 73% | 39% | 1 | | | |
| | 28.0363 | 81% | 26% | 2 | 1.0 | 0.4 | 2.4 |
| | 17.0284 | 92% | 13% | 3 | 1.2 | 0.5 | 2.8 |
| | 72.078 | 38% | 70% | 4 | 2.3 | 1.1 | 4.8 |
| | 89.6943 | 31% | 80% | | | | |
| | 118.475 | 12% | 91% | | | | | sCr only

| Time prior AKI stage | Cutoff value | sens | spec | Quartile | OR | 95% CI of OR | |
|---|---|---|---|---|---|---|---|
| 0 hours | 31.445 | 71% | 22% | 1 | | | |
| | 27.807 | 82% | 19% | 2 | 0.7 | 0.1 | 3.6 |
| | 13.1521 | 94% | 7% | 3 | 1.7 | 0.6 | 5.3 |
| | 81.7261 | 18% | 70% | 4 | 2.5 | 0.9 | 6.8 |
| | 95.1633 | 18% | 80% | | | | |
| | 119.894 | 6% | 90% | | | | |
| 24 hours | 40.1968 | 74% | 30% | 1 | | | |
| | 24.0582 | 83% | 16% | 2 | 2.1 | 1.0 | 4.7 |
| | 10.5618 | 91% | 5% | 3 | 1.5 | 0.6 | 3.7 |
| | 81.7261 | 30% | 70% | 4 | 1.3 | 0.5 | 3.3 |
| | 95.1633 | 17% | 80% | | | | |
| | 119.894 | 4% | 90% | | | | |

Fig. 1 Continued

| 48 hours | 33.6142 | 71% | 23% | 1 | | | |
| | 20.4689 | 86% | 12% | 2 | 0.7 | 0.1 | 3.6 |
| | 20.0671 | 93% | 12% | 3 | 1.4 | 0.4 | 4.5 |
| | 81.7261 | 21% | 70% | 4 | 1.7 | 0.6 | 5.3 |
| | 95.1633 | 14% | 80% | | | | |
| | 119.894 | 7% | 90% | | | | |

UO only

| Time prior AKI stage | Cutoff value | sens | spec | Quartile | OR | 95% CI of OR | |
|---|---|---|---|---|---|---|---|
| 0 hours | 52.4835 | 71% | 50% | 1 | | | |
| | 47.3631 | 80% | 42% | 2 | 4.3 | 2.0 | 9.3 |
| | 37.3466 | 91% | 33% | 3 | 5.6 | 2.6 | 12.1 |
| | 77.4613 | 40% | 70% | 4 | 4.3 | 2.0 | 9.3 |
| | 96.646 | 22% | 80% | | | | |
| | 121.836 | 13% | 90% | | | | |
| 24 hours | 46.4448 | 71% | 41% | 1 | | | |
| | 35.9153 | 82% | 31% | 2 | 1.9 | 1.1 | 3.2 |
| | 27.807 | 92% | 23% | 3 | 1.5 | 0.9 | 2.7 |
| | 77.4613 | 45% | 70% | 4 | 2.9 | 1.7 | 4.8 |
| | 96.646 | 27% | 80% | | | | |
| | 121.836 | 16% | 90% | | | | |
| 48 hours | 49.3582 | 74% | 47% | 1 | | | |
| | 27.9607 | 83% | 24% | 2 | 0.6 | 0.2 | 1.8 |
| | 18.4814 | 91% | 11% | 3 | 1.2 | 0.5 | 3.0 |
| | 77.4613 | 48% | 70% | 4 | 2.1 | 1.0 | 4.6 |
| | 96.646 | 30% | 80% | | | | |
| | 121.836 | 13% | 90% | | | | |

Vascular endothelial growth factor sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 600.000 | 925.000 | 600.000 | 762.000 | 600.000 | 669.000 |
| average | 1891.477 | 2473.508 | 1891.477 | 5984.526 | 1891.477 | 3383.500 |
| stdev | 4088.272 | 5446.685 | 4088.272 | 19167.959 | 4088.272 | 10743.443 |
| p (t-test) | | 0.378 | | 0.002 | | 0.150 |
| min | 33.400 | 80.900 | 33.400 | 49.500 | 33.400 | 64.500 |
| max | 32200.000 | 34800.000 | 32200.000 | 139000.000 | 32200.000 | 56400.000 |
| n (Samp) | 249 | 53 | 249 | 62 | 249 | 27 |
| n (Pat) | 104 | 53 | 104 | 62 | 104 | 27 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 660.000 | 811.500 | 660.000 | 1080.000 | 660.000 | 683.500 |
| average | 2601.196 | 2388.195 | 2601.196 | 3638.854 | 2601.196 | 2463.714 |
| stdev | 9010.854 | 3221.517 | 9010.854 | 4660.409 | 9010.854 | 4569.211 |
| p (t-test) | | 0.916 | | 0.561 | | 0.955 |
| min | 33.400 | 80.900 | 33.400 | 49.500 | 33.400 | 213.000 |
| max | 139000.000 | 11600.000 | 139000.000 | 18100.000 | 139000.000 | 17600.000 |
| n (Samp) | 441 | 20 | 441 | 26 | 441 | 14 |
| n (Pat) | 170 | 20 | 170 | 26 | 170 | 14 |

Fig. 1 Continued

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 569.500 | 1100.000 | 569.500 | 828.500 | 569.500 | 992.000 |
| average | 1424.303 | 2877.681 | 1424.303 | 6420.635 | 1424.303 | 3706.460 |
| stdev | 2898.589 | 5790.883 | 2898.589 | 20775.833 | 2898.589 | 11131.476 |
| p (t-test) |  | 0.013 |  | 0.001 |  | 0.017 |
| min | 33.400 | 169.000 | 33.400 | 57.000 | 33.400 | 64.500 |
| max | 25700.000 | 34800.000 | 25700.000 | 139000.000 | 25700.000 | 56400.000 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
|---|---|---|---|---|---|
| 0 hours | 0.59 | 0.045 | 249 | 53 | 0.044 |
| 24 hours | 0.59 | 0.042 | 249 | 62 | 0.037 |
| 48 hours | 0.53 | 0.059 | 249 | 27 | 0.603 | sCr only

| Time prior AKI stage | AUC | SE | nCohort 1 | nCohort 2 | p |
|---|---|---|---|---|---|
| 0 hours | 0.53 | 0.067 | 441 | 20 | 0.610 |
| 24 hours | 0.59 | 0.060 | 441 | 26 | 0.141 |
| 48 hours | 0.54 | 0.080 | 441 | 14 | 0.591 |

UO only

| Time prior AKI stage | AUC | SE | nCohort 1 | nCohort 2 | p |
|---|---|---|---|---|---|
| 0 hours | 0.67 | 0.046 | 212 | 47 | 0.000 |
| 24 hours | 0.64 | 0.045 | 212 | 52 | 0.001 |
| 48 hours | 0.58 | 0.063 | 212 | 25 | 0.205 | sCr or UO

| Time prior AKI stage | Cutoff value | sens | spec | Quartile | OR | 95% CI of OR | |
|---|---|---|---|---|---|---|---|
| 0 hours | 583 | 72% | 49% | 1 |  |  |  |
|  | 353 | 81% | 31% | 2 | 0.7 | 0.4 | 1.3 |
|  | 198 | 91% | 12% | 3 | 2.3 | 1.6 | 3.4 |
|  | 1190 | 43% | 70% | 4 | 2.4 | 1.7 | 3.6 |
|  | 2130 | 26% | 80% |  |  |  |  |
|  | 4280 | 11% | 90% |  |  |  |  |
| 24 hours | 488 | 71% | 41% | 1 |  |  |  |
|  | 373 | 81% | 32% | 2 | 1.5 | 1.0 | 2.3 |
|  | 220 | 90% | 12% | 3 | 3.2 | 2.2 | 4.6 |
|  | 1190 | 35% | 70% | 4 | 2.1 | 1.4 | 3.1 |
|  | 2130 | 27% | 80% |  |  |  |  |
|  | 4280 | 21% | 90% |  |  |  |  |
| 48 hours | 402 | 70% | 34% | 1 |  |  |  |
|  | 309 | 81% | 27% | 2 | 1.4 | 0.7 | 3.0 |
|  | 198 | 93% | 12% | 3 | 1.7 | 0.8 | 3.4 |
|  | 1190 | 37% | 70% | 4 | 1.4 | 0.7 | 3.0 |
|  | 2130 | 15% | 80% |  |  |  |  |
|  | 4280 | 11% | 90% |  |  |  |  |

Fig. 1 Continued sCr only

| Time prior AKI stage | Cutoff value | sens | spec | Quartile | OR | 95% CI of OR | |
|---|---|---|---|---|---|---|---|
| 0 hours | 373 | 70% | 29% | 1 | | | |
| | 250 | 80% | 17% | 2 | 0.8 | 0.3 | 2.0 |
| | 179 | 90% | 8% | 3 | 0.6 | 0.2 | 1.7 |
| | 1220 | 40% | 70% | 4 | 1.6 | 0.8 | 3.2 |
| | 2010 | 35% | 80% | | | | |
| | 4500 | 20% | 90% | | | | |
| 24 hours | 389 | 73% | 30% | 1 | | | |
| | 359 | 81% | 29% | 2 | 1.0 | 0.4 | 2.2 |
| | 96.9 | 92% | 3% | 3 | 0.8 | 0.3 | 2.0 |
| | 1220 | 46% | 70% | 4 | 2.5 | 1.4 | 4.6 |
| | 2010 | 46% | 80% | | | | |
| | 4500 | 31% | 90% | | | | |
| 48 hours | 432 | 71% | 34% | 1 | | | |
| | 322 | 86% | 26% | 2 | 2.5 | 0.6 | 10.4 |
| | 288 | 93% | 23% | 3 | 1.0 | 0.1 | 7.3 |
| | 1220 | 36% | 70% | 4 | 2.5 | 0.6 | 10.4 |
| | 2010 | 29% | 80% | | | | |
| | 4500 | 14% | 90% | | | | |

UO only

| Time prior AKI stage | Cutoff value | sens | spec | Quartile | OR | 95% CI of OR | |
|---|---|---|---|---|---|---|---|
| 0 hours | 714 | 70% | 60% | 1 | | | |
| | 589 | 81% | 53% | 2 | 1.0 | 0.4 | 2.3 |
| | 236 | 91% | 16% | 3 | 4.9 | 2.8 | 8.6 |
| | 1070 | 51% | 70% | 4 | 4.5 | 2.5 | 8.0 |
| | 1840 | 36% | 80% | | | | |
| | 2870 | 19% | 90% | | | | |
| 24 hours | 633 | 71% | 56% | 1 | | | |
| | 486 | 81% | 43% | 2 | 2.2 | 1.1 | 4.2 |
| | 359 | 90% | 32% | 3 | 6.1 | 3.5 | 10.7 |
| | 1070 | 40% | 70% | 4 | 3.6 | 2.0 | 6.5 |
| | 1840 | 25% | 80% | | | | |
| | 2870 | 23% | 90% | | | | |
| 48 hours | 402 | 72% | 35% | 1 | | | |
| | 322 | 80% | 27% | 2 | 1.6 | 0.6 | 3.8 |
| | 217 | 92% | 12% | 3 | 1.6 | 0.6 | 3.8 |
| | 1070 | 44% | 70% | 4 | 2.4 | 1.1 | 5.3 |
| | 1840 | 28% | 80% | | | | |
| | 2870 | 16% | 90% | | | | |

Fig. 1 Continued

Aspartate aminotransferase, cytoplasmic sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 7.520 | 6.690 | 7.520 | 7.860 | 7.520 | 7.170 |
| average | 9.111 | 13.333 | 9.111 | 8.163 | 9.111 | 9.037 |
| stdev | 8.751 | 26.570 | 8.751 | 6.318 | 8.751 | 8.832 |
| p (t-test) | | 0.046 | | 0.525 | | 0.972 |
| min | 0.451 | 0.853 | 0.451 | 0.877 | 0.451 | 0.974 |
| max | 104.000 | 142.000 | 104.000 | 23.300 | 104.000 | 30.800 |
| n (Samp) | 419 | 27 | 419 | 36 | 419 | 18 |
| n (Pat) | 164 | 27 | 164 | 36 | 164 | 18 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 7.485 | 8.990 | 7.485 | 8.200 | 7.485 | 6.000 |
| average | 9.232 | 8.506 | 9.232 | 7.708 | 9.232 | 9.439 |
| stdev | 10.199 | 2.427 | 10.199 | 5.471 | 10.199 | 9.690 |
| p (t-test) | | 0.874 | | 0.655 | | 0.958 |
| min | 0.451 | 5.620 | 0.451 | 1.160 | 0.451 | 1.040 |
| max | 142.000 | 11.800 | 142.000 | 15.400 | 142.000 | 28.700 |
| n (Samp) | 518 | 5 | 518 | 9 | 518 | 7 |
| n (Pat) | 199 | 5 | 199 | 9 | 199 | 7 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 7.310 | 6.955 | 7.310 | 8.180 | 7.310 | 7.170 |
| average | 8.700 | 14.068 | 8.700 | 8.770 | 8.700 | 8.831 |
| stdev | 7.311 | 27.060 | 7.311 | 6.488 | 7.311 | 7.478 |
| p (t-test) | | 0.008 | | 0.959 | | 0.944 |
| min | 0.476 | 0.853 | 0.476 | 0.877 | 0.476 | 0.974 |
| max | 58.800 | 142.000 | 58.800 | 23.300 | 58.800 | 30.800 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
|---|---|---|---|---|---|
| 0 hours | 0.49 | 0.057 | 419 | 27 | 0.881 |
| 24 hours | 0.49 | 0.050 | 419 | 36 | 0.781 |
| 48 hours | 0.47 | 0.068 | 419 | 18 | 0.617 | sCr only

| Time prior AKI stage | AUC | SE | nCohort 1 | nCohort 2 | p |
|---|---|---|---|---|---|
| 0 hours | 0.57 | 0.134 | 518 | 5 | 0.623 |
| 24 hours | 0.50 | 0.097 | 518 | 9 | 0.999 |
| 48 hours | 0.47 | 0.108 | 518 | 7 | 0.793 |

UO only

| Time prior AKI stage | AUC | SE | nCohort 1 | nCohort 2 | p |
|---|---|---|---|---|---|
| 0 hours | 0.52 | 0.059 | 352 | 26 | 0.688 |
| 24 hours | 0.53 | 0.056 | 352 | 30 | 0.652 |
| 48 hours | 0.49 | 0.074 | 352 | 16 | 0.929 |

Fig. 2 sCr or UO

| Time prior AKI stage | Cutoff value | sens | spec | Quartile | OR | 95% CI of OR | |
|---|---|---|---|---|---|---|---|
| 0 hours | 5.83 | 70% | 31% | 1 | | | |
| | 2.55 | 81% | 17% | 2 | 0.6 | 0.3 | 1.3 |
| | 1.02 | 93% | 9% | 3 | 1.5 | 0.9 | 2.5 |
| | 9.89 | 26% | 70% | 4 | 0.9 | 0.5 | 1.6 |
| | 12.1 | 19% | 80% | | | | |
| | 15.8 | 15% | 90% | | | | |
| 24 hours | 2.96 | 72% | 17% | 1 | | | |
| | 1.45 | 81% | 14% | 2 | 0.9 | 0.6 | 1.4 |
| | 1.08 | 92% | 11% | 3 | 0.5 | 0.3 | 0.9 |
| | 9.89 | 31% | 70% | 4 | 1.2 | 0.8 | 1.8 |
| | 12.1 | 25% | 80% | | | | |
| | 15.8 | 14% | 90% | | | | |
| 48 hours | 5.58 | 72% | 28% | 1 | | | |
| | 1.32 | 83% | 13% | 2 | 1.0 | 0.4 | 2.8 |
| | 1.02 | 94% | 9% | 3 | 1.3 | 0.5 | 3.2 |
| | 9.89 | 22% | 70% | 4 | 1.3 | 0.5 | 3.2 |
| | 12.1 | 22% | 80% | | | | |
| | 15.8 | 17% | 90% | | | | | sCr only

| Time prior AKI stage | Cutoff value | sens | spec | Quartile | OR | 95% CI of OR | |
|---|---|---|---|---|---|---|---|
| 0 hours | 6.67 | 80% | 43% | 1 | | | |
| | 6.67 | 80% | 43% | 2 | na | na | na |
| | 5.58 | 100% | 29% | 3 | na | na | na |
| | 9.84 | 20% | 70% | 4 | na | na | na |
| | 12.1 | 0% | 80% | | | | |
| | 17.1 | 0% | 90% | | | | |
| 24 hours | 1.91 | 78% | 17% | 1 | | | |
| | 1.54 | 89% | 16% | 2 | 0.7 | 0.1 | 3.5 |
| | 1.12 | 100% | 12% | 3 | 0.3 | 0.0 | 4.6 |
| | 9.84 | 33% | 70% | 4 | 1.0 | 0.3 | 3.8 |
| | 12.1 | 33% | 80% | | | | |
| | 17.1 | 0% | 90% | | | | |
| 48 hours | 5.67 | 71% | 30% | 1 | | | |
| | 1.24 | 86% | 13% | 2 | 0.5 | 0.0 | 9.7 |
| | 1.03 | 100% | 9% | 3 | 1.0 | 0.1 | 7.4 |
| | 9.84 | 29% | 70% | 4 | 1.0 | 0.1 | 7.4 |
| | 12.1 | 29% | 80% | | | | |
| | 17.1 | 14% | 90% | | | | |

UO only

| Time prior AKI stage | Cutoff value | sens | spec | Quartile | OR | 95% CI of OR | |
|---|---|---|---|---|---|---|---|
| 0 hours | 5.83 | 73% | 33% | 1 | | | |
| | 2.55 | 81% | 18% | 2 | 1.3 | 0.7 | 2.5 |
| | 1.02 | 92% | 9% | 3 | 0.8 | 0.4 | 1.8 |
| | 9.84 | 31% | 70% | 4 | 1.2 | 0.6 | 2.2 |
| | 11.8 | 23% | 80% | | | | |
| | 15.3 | 23% | 90% | | | | |
| 24 hours | 5.44 | 70% | 30% | 1 | | | |
| | 1.45 | 80% | 14% | 2 | 0.4 | 0.2 | 0.9 |
| | 1.08 | 90% | 11% | 3 | 0.8 | 0.4 | 1.3 |
| | 9.84 | 37% | 70% | 4 | 1.1 | 0.7 | 1.8 |
| | 11.8 | 23% | 80% | | | | |
| | 15.3 | 17% | 90% | | | | |

Fig. 2 Continued

| | | | | | | | |
|---|---|---|---|---|---|---|---|
| 48 hours | 5.6 | 75% | 30% | 1 | | | |
| | 5.58 | 81% | 30% | 2 | 0.7 | 0.2 | 2.4 |
| | 1.32 | 94% | 13% | 3 | 1.5 | 0.6 | 3.6 |
| | 9.84 | 25% | 70% | 4 | 0.7 | 0.2 | 2.4 |
| | 11.8 | 25% | 80% | | | | |
| | 15.3 | 13% | 90% | | | | |

CD40 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 28.300 | 42.600 | 28.300 | 44.150 | 28.300 | 44.600 |
| average | 44.460 | 52.154 | 44.460 | 54.616 | 44.460 | 44.463 |
| stdev | 49.863 | 40.666 | 49.863 | 51.895 | 49.863 | 32.270 |
| p (t-test) | | 0.433 | | 0.243 | | 1.000 |
| min | 0.000 | 2.050 | 0.000 | 3.080 | 0.000 | 3.190 |
| max | 326.000 | 180.000 | 326.000 | 243.000 | 326.000 | 134.000 |
| n (Samp) | 419 | 27 | 419 | 36 | 419 | 18 |
| n (Pat) | 164 | 27 | 164 | 36 | 164 | 18 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 32.700 | 39.000 | 32.700 | 42.700 | 32.700 | 46.800 |
| average | 47.039 | 47.890 | 47.039 | 77.103 | 47.039 | 43.714 |
| stdev | 49.339 | 36.503 | 49.339 | 88.919 | 49.339 | 22.088 |
| p (t-test) | | 0.969 | | 0.075 | | 0.859 |
| min | 0.000 | 8.250 | 0.000 | 4.430 | 0.000 | 6.800 |
| max | 326.000 | 95.300 | 326.000 | 243.000 | 326.000 | 67.900 |
| n (Samp) | 518 | 5 | 518 | 9 | 518 | 7 |
| n (Pat) | 199 | 5 | 199 | 9 | 199 | 7 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 30.900 | 48.550 | 30.900 | 45.100 | 30.900 | 43.250 |
| average | 42.818 | 60.292 | 42.818 | 55.965 | 42.818 | 45.427 |
| stdev | 42.718 | 44.622 | 42.718 | 47.862 | 42.718 | 33.439 |
| p (t-test) | | 0.045 | | 0.110 | | 0.810 |
| min | 0.000 | 2.050 | 0.000 | 3.080 | 0.000 | 3.190 |
| max | 286.000 | 180.000 | 286.000 | 171.000 | 286.000 | 134.000 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
|---|---|---|---|---|---|
| 0 hours | 0.60 | 0.059 | 419 | 27 | 0.079 |
| 24 hours | 0.58 | 0.052 | 419 | 36 | 0.120 |
| 48 hours | 0.56 | 0.071 | 419 | 18 | 0.407 | sCr only

| Time prior AKI stage | AUC | SE | nCohort 1 | nCohort 2 | p |
|---|---|---|---|---|---|
| 0 hours | 0.55 | 0.133 | 518 | 5 | 0.682 |
| 24 hours | 0.57 | 0.100 | 518 | 9 | 0.483 |
| 48 hours | 0.57 | 0.113 | 518 | 7 | 0.533 |

Fig. 2 Continued

UO only

| Time prior AKI stage | AUC | SE | nCohort 1 | nCohort 2 | p |
|---|---|---|---|---|---|
| 0 hours | 0.65 | 0.060 | 352 | 26 | 0.014 |
| 24 hours | 0.59 | 0.057 | 352 | 30 | 0.121 |
| 48 hours | 0.56 | 0.076 | 352 | 16 | 0.443 | sCr or UO

| Time prior AKI stage | Cutoff value | sens | spec | Quartile | OR | 95% CI of OR | |
|---|---|---|---|---|---|---|---|
| 0 hours | 28.3 | 70% | 50% | 1 | | | |
| | 21.6 | 81% | 40% | 2 | 2.0 | 0.7 | 5.6 |
| | 8.06 | 93% | 14% | 3 | 3.6 | 1.5 | 8.7 |
| | 50.1 | 37% | 70% | 4 | 2.8 | 1.1 | 7.1 |
| | 64.5 | 26% | 80% | | | | |
| | 96.6 | 19% | 90% | | | | |
| 24 hours | 19.8 | 72% | 37% | 1 | | | |
| | 16.4 | 81% | 32% | 2 | 2.9 | 1.4 | 5.9 |
| | 8.41 | 92% | 14% | 3 | 2.6 | 1.3 | 5.4 |
| | 50.1 | 39% | 70% | 4 | 2.9 | 1.4 | 5.9 |
| | 64.5 | 31% | 80% | | | | |
| | 96.6 | 14% | 90% | | | | |
| 48 hours | 19.8 | 72% | 37% | 1 | | | |
| | 15.6 | 83% | 30% | 2 | 1.0 | 0.3 | 3.8 |
| | 5.42 | 94% | 6% | 3 | 2.4 | 0.9 | 6.4 |
| | 50.1 | 33% | 70% | 4 | 1.7 | 0.6 | 5.0 |
| | 64.5 | 22% | 80% | | | | |
| | 96.6 | 6% | 90% | | | | | sCr only

| Time prior AKI stage | Cutoff value | sens | spec | Quartile | OR | 95% CI of OR | |
|---|---|---|---|---|---|---|---|
| 0 hours | 21.6 | 80% | 37% | 1 | | | |
| | 21.6 | 80% | 37% | 2 | 1.0 | 0.0 | 51.5 |
| | 8.06 | 100% | 13% | 3 | 1.0 | 0.0 | 51.5 |
| | 52.4 | 40% | 70% | 4 | 2.0 | 0.1 | 39.0 |
| | 71.3 | 40% | 80% | | | | |
| | 101 | 0% | 90% | | | | |
| 24 hours | 21 | 78% | 35% | 1 | | | |
| | 13.7 | 89% | 24% | 2 | 1.0 | 0.1 | 7.3 |
| | 4.4 | 100% | 5% | 3 | 1.0 | 0.1 | 7.3 |
| | 52.4 | 33% | 70% | 4 | 1.5 | 0.3 | 7.9 |
| | 71.3 | 33% | 80% | | | | |
| | 101 | 22% | 90% | | | | |
| 48 hours | 42.3 | 71% | 61% | 1 | | | |
| | 21.9 | 86% | 37% | 2 | 1.0 | 0.0 | 51.9 |
| | 6.68 | 100% | 10% | 3 | 3.0 | 0.2 | 42.9 |
| | 52.4 | 43% | 70% | 4 | 2.0 | 0.1 | 39.0 |
| | 71.3 | 0% | 80% | | | | |
| | 101 | 0% | 90% | | | | |

UO only

| Time prior AKI stage | Cutoff value | sens | spec | Quartile | OR | 95% CI of OR | |
|---|---|---|---|---|---|---|---|
| 0 hours | 37.2 | 73% | 59% | 1 | | | |
| | 22.4 | 81% | 39% | 2 | 2.6 | 0.6 | 10.5 |
| | 17.2 | 92% | 29% | 3 | 4.9 | 1.4 | 16.9 |
| | 51 | 46% | 70% | 4 | 5.4 | 1.6 | 18.3 |
| | 64 | 35% | 80% | | | | |
| | 90.3 | 23% | 90% | | | | |

Fig. 2 Continued

| 24 hours | 21.6 | 70% | 37% | 1 | | | |
|---|---|---|---|---|---|---|---|
| | 17.7 | 80% | 30% | 2 | 1.4 | 0.7 | 2.9 |
| | 15 | 90% | 24% | 3 | 1.7 | 0.8 | 3.3 |
| | 51 | 40% | 70% | 4 | 2.1 | 1.1 | 3.9 |
| | 64 | 33% | 80% | | | | |
| | 90.3 | 17% | 90% | | | | |
| 48 hours | 19.8 | 75% | 33% | 1 | | | |
| | 17.6 | 81% | 30% | 2 | 2.0 | 0.5 | 9.3 |
| | 5.42 | 94% | 6% | 3 | 3.1 | 0.8 | 12.1 |
| | 51 | 31% | 70% | 4 | 2.0 | 0.5 | 9.3 |
| | 64 | 25% | 80% | | | | |
| | 90.3 | 6% | 90% | | | | |

CD40 Ligand sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.207 | 0.230 | 0.207 | 0.216 | 0.207 | 0.258 |
| average | 0.250 | 0.265 | 0.250 | 0.250 | 0.250 | 0.232 |
| stdev | 0.180 | 0.172 | 0.180 | 0.169 | 0.180 | 0.141 |
| p (t-test) | | 0.689 | | 0.981 | | 0.662 |
| min | 0.010 | 0.024 | 0.010 | 0.033 | 0.010 | 0.019 |
| max | 0.891 | 0.641 | 0.891 | 0.631 | 0.891 | 0.419 |
| n (Samp) | 419 | 27 | 419 | 36 | 419 | 18 |
| n (Pat) | 164 | 27 | 164 | 36 | 164 | 18 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.217 | 0.407 | 0.217 | 0.297 | 0.217 | 0.376 |
| average | 0.250 | 0.343 | 0.250 | 0.287 | 0.250 | 0.287 |
| stdev | 0.176 | 0.171 | 0.176 | 0.238 | 0.176 | 0.175 |
| p (t-test) | | 0.241 | | 0.531 | | 0.583 |
| min | 0.010 | 0.088 | 0.010 | 0.033 | 0.010 | 0.019 |
| max | 0.891 | 0.529 | 0.891 | 0.640 | 0.891 | 0.440 |
| n (Samp) | 518 | 5 | 518 | 9 | 518 | 7 |
| n (Pat) | 199 | 5 | 199 | 9 | 199 | 7 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.219 | 0.241 | 0.219 | 0.244 | 0.219 | 0.280 |
| average | 0.251 | 0.286 | 0.251 | 0.267 | 0.251 | 0.255 |
| stdev | 0.173 | 0.189 | 0.173 | 0.174 | 0.173 | 0.138 |
| p (t-test) | | 0.323 | | 0.637 | | 0.935 |
| min | 0.010 | 0.024 | 0.010 | 0.039 | 0.010 | 0.047 |
| max | 0.891 | 0.674 | 0.891 | 0.694 | 0.891 | 0.529 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
|---|---|---|---|---|---|
| 0 hours | 0.53 | 0.058 | 419 | 27 | 0.556 |
| 24 hours | 0.51 | 0.050 | 419 | 36 | 0.881 |
| 48 hours | 0.48 | 0.069 | 419 | 18 | 0.823 |

Fig. 2 Continued sCr only

| Time prior AKI stage | AUC | SE | nCohort 1 | nCohort 2 | p |
|---|---|---|---|---|---|
| 0 hours | 0.66 | 0.134 | 518 | 5 | 0.219 |
| 24 hours | 0.52 | 0.098 | 518 | 9 | 0.832 |
| 48 hours | 0.56 | 0.113 | 518 | 7 | 0.567 |

UO only

| Time prior AKI stage | AUC | SE | nCohort 1 | nCohort 2 | p |
|---|---|---|---|---|---|
| 0 hours | 0.56 | 0.060 | 352 | 26 | 0.360 |
| 24 hours | 0.53 | 0.056 | 352 | 30 | 0.585 |
| 48 hours | 0.53 | 0.075 | 352 | 16 | 0.730 | sCr or UO

| Time prior AKI stage | Cutoff value | sens | spec | Quartile | OR | 95% CI of OR | |
|---|---|---|---|---|---|---|---|
| 0 hours | 0.135 | 70% | 37% | 1 | | | |
| | 0.0889 | 81% | 22% | 2 | 1.0 | 0.5 | 2.0 |
| | 0.0804 | 93% | 18% | 3 | 1.2 | 0.6 | 2.2 |
| | 0.339 | 37% | 70% | 4 | 1.3 | 0.7 | 2.5 |
| | 0.421 | 22% | 80% | | | | |
| | 0.509 | 11% | 90% | | | | |
| 24 hours | 0.134 | 72% | 37% | 1 | | | |
| | 0.0907 | 81% | 23% | 2 | 1.3 | 0.8 | 2.0 |
| | 0.0525 | 92% | 10% | 3 | 1.1 | 0.7 | 1.9 |
| | 0.339 | 31% | 70% | 4 | 1.1 | 0.7 | 1.9 |
| | 0.421 | 14% | 80% | | | | |
| | 0.509 | 11% | 90% | | | | |
| 48 hours | 0.12 | 72% | 32% | 1 | | | |
| | 0.0665 | 83% | 13% | 2 | 1.8 | 0.8 | 4.1 |
| | 0.0454 | 94% | 8% | 3 | 0.5 | 0.1 | 2.2 |
| | 0.339 | 28% | 70% | 4 | 1.3 | 0.5 | 3.2 |
| | 0.421 | 0% | 80% | | | | |
| | 0.509 | 0% | 90% | | | | | sCr only

| Time prior AKI stage | Cutoff value | sens | spec | Quartile | OR | 95% CI of OR | |
|---|---|---|---|---|---|---|---|
| 0 hours | 0.262 | 80% | 58% | 1 | | | |
| | 0.262 | 80% | 58% | 2 | 0.0 | 0.0 | na |
| | 0.088 | 100% | 21% | 3 | 1.0 | 0.0 | 51.5 |
| | 0.34 | 60% | 70% | 4 | 3.0 | 0.2 | 42.5 |
| | 0.414 | 40% | 80% | | | | |
| | 0.504 | 20% | 90% | | | | |
| 24 hours | 0.0625 | 78% | 12% | 1 | | | |
| | 0.0606 | 89% | 12% | 2 | 0.3 | 0.0 | 4.6 |
| | 0.0329 | 100% | 5% | 3 | 0.7 | 0.1 | 3.5 |
| | 0.34 | 33% | 70% | 4 | 1.0 | 0.3 | 3.8 |
| | 0.414 | 33% | 80% | | | | |
| | 0.504 | 33% | 90% | | | | |
| 48 hours | 0.262 | 71% | 58% | 1 | | | |
| | 0.0745 | 86% | 16% | 2 | 0.0 | 0.0 | na |
| | 0.0175 | 100% | 1% | 3 | 0.5 | 0.0 | 9.7 |
| | 0.34 | 57% | 70% | 4 | 2.0 | 0.4 | 9.0 |
| | 0.414 | 43% | 80% | | | | |
| | 0.504 | 0% | 90% | | | | |

Fig. 2 Continued

UO only

| Time prior AKI stage | Cutoff value | sens | spec | Quartile | OR | 95% CI of OR | |
|---|---|---|---|---|---|---|---|
| 0 hours | 0.135 | 73% | 36% | 1 | | | |
| | 0.119 | 81% | 31% | 2 | 1.4 | 0.7 | 2.9 |
| | 0.0804 | 92% | 16% | 3 | 1.0 | 0.4 | 2.3 |
| | 0.34 | 38% | 70% | 4 | 1.9 | 1.0 | 3.6 |
| | 0.419 | 23% | 80% | | | | |
| | 0.494 | 15% | 90% | | | | |
| 24 hours | 0.145 | 70% | 37% | 1 | | | |
| | 0.131 | 80% | 35% | 2 | 1.9 | 1.0 | 3.6 |
| | 0.057 | 90% | 9% | 3 | 1.7 | 0.8 | 3.3 |
| | 0.34 | 33% | 70% | 4 | 1.6 | 0.8 | 3.2 |
| | 0.419 | 13% | 80% | | | | |
| | 0.494 | 10% | 90% | | | | |
| 48 hours | 0.166 | 75% | 40% | 1 | | | |
| | 0.12 | 81% | 31% | 2 | 0.7 | 0.1 | 3.5 |
| | 0.0538 | 94% | 9% | 3 | 2.8 | 1.1 | 7.3 |
| | 0.34 | 25% | 70% | 4 | 1.0 | 0.3 | 3.9 |
| | 0.419 | 6% | 80% | | | | |
| | 0.494 | 6% | 90% | | | | |

CXCL16 (C-X-C Motif chemokine 16)

sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.121 | 0.204 | 0.121 | 0.208 | 0.121 | 0.106 |
| average | 0.832 | 0.743 | 0.832 | 1.294 | 0.832 | 0.668 |
| stdev | 1.760 | 1.756 | 1.760 | 2.438 | 1.760 | 1.458 |
| p (t-test) | | 0.813 | | 0.155 | | 0.699 |
| min | 0.000 | 0.001 | 0.000 | 0.005 | 0.000 | 0.004 |
| max | 10.210 | 8.420 | 10.210 | 9.406 | 10.210 | 5.234 |
| n (Samp) | 302 | 24 | 302 | 36 | 302 | 18 |
| n (Pat) | 163 | 24 | 163 | 36 | 163 | 18 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.126 | 1.154 | 0.126 | 0.263 | 0.126 | 0.404 |
| average | 0.880 | 3.993 | 0.880 | 3.639 | 0.880 | 1.116 |
| stdev | 1.904 | 5.685 | 1.904 | 4.309 | 1.904 | 1.434 |
| p (t-test) | | 0.006 | | 0.000 | | 0.745 |
| min | 0.000 | 0.286 | 0.000 | 0.005 | 0.000 | 0.021 |
| max | 10.210 | 10.538 | 10.210 | 9.861 | 10.210 | 3.921 |
| n (Samp) | 382 | 3 | 382 | 9 | 382 | 7 |
| n (Pat) | 196 | 3 | 196 | 9 | 196 | 7 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.150 | 0.204 | 0.150 | 0.237 | 0.150 | 0.128 |
| average | 0.827 | 0.767 | 0.827 | 0.843 | 0.827 | 1.076 |
| stdev | 1.613 | 1.762 | 1.613 | 1.642 | 1.613 | 2.564 |
| p (t-test) | | 0.863 | | 0.960 | | 0.565 |
| min | 0.000 | 0.001 | 0.000 | 0.011 | 0.000 | 0.004 |
| max | 9.506 | 8.420 | 9.506 | 6.964 | 9.506 | 9.406 |
| n (Samp) | 256 | 24 | 256 | 30 | 256 | 16 |
| n (Pat) | 132 | 24 | 132 | 30 | 132 | 16 |

Fig. 2 Continued sCr or UO

| Time prior AKI stage | AUC | SE | nCohort 1 | nCohort 2 | p |
|---|---|---|---|---|---|
| 0 hours | 0.55 | 0.063 | 302 | 24 | 0.421 |
| 24 hours | 0.57 | 0.052 | 302 | 36 | 0.197 |
| 48 hours | 0.49 | 0.070 | 302 | 18 | 0.931 | sCr only

| Time prior AKI stage | AUC | SE | nCohort 1 | nCohort 2 | p |
|---|---|---|---|---|---|
| 0 hours | 0.82 | 0.148 | 382 | 3 | 0.029 |
| 24 hours | 0.67 | 0.100 | 382 | 9 | 0.083 |
| 48 hours | 0.61 | 0.114 | 382 | 7 | 0.319 |

UO only

| Time prior AKI stage | AUC | SE | nCohort 1 | nCohort 2 | p |
|---|---|---|---|---|---|
| 0 hours | 0.53 | 0.063 | 256 | 24 | 0.621 |
| 24 hours | 0.54 | 0.057 | 256 | 30 | 0.503 |
| 48 hours | 0.48 | 0.074 | 256 | 16 | 0.786 | sCr or UO

| Time prior AKI stage | Cutoff value | sens | spec | Quartile | OR | 95% CI of OR | |
|---|---|---|---|---|---|---|---|
| 0 hours | 0.10021 | 71% | 46% | 1 | | | |
| | 0.05247 | 83% | 33% | 2 | 1.7 | 0.6 | 5.1 |
| | 0.01072 | 92% | 7% | 3 | 4.1 | 1.7 | 9.9 |
| | 0.39881 | 33% | 70% | 4 | 1.7 | 0.6 | 5.1 |
| | 1.02412 | 13% | 80% | | | | |
| | 2.59834 | 8% | 90% | | | | |
| 24 hours | 0.0838 | 72% | 42% | 1 | | | |
| | 0.06755 | 81% | 38% | 2 | 3.3 | 1.6 | 6.7 |
| | 0.01455 | 92% | 11% | 3 | 2.4 | 1.1 | 5.1 |
| | 0.39881 | 33% | 70% | 4 | 3.0 | 1.4 | 6.1 |
| | 1.02412 | 22% | 80% | | | | |
| | 2.59834 | 17% | 90% | | | | |
| 48 hours | 0.05895 | 72% | 35% | 1 | | | |
| | 0.05247 | 83% | 33% | 2 | 1.7 | 0.6 | 5.1 |
| | 0.01331 | 94% | 10% | 3 | 2.5 | 0.9 | 6.6 |
| | 0.39881 | 22% | 70% | 4 | 1.0 | 0.3 | 3.9 |
| | 1.02412 | 11% | 80% | | | | |
| | 2.59834 | 11% | 90% | | | | | sCr only

| Time prior AKI stage | Cutoff value | sens | spec | Quartile | OR | 95% CI of OR | |
|---|---|---|---|---|---|---|---|
| 0 hours | 0.28258 | 100% | 65% | 1 | | | |
| | 0.28258 | 100% | 65% | 2 | na | na | na |
| | 0.28258 | 100% | 65% | 3 | na | na | na |
| | 0.39773 | 67% | 70% | 4 | na | na | na |
| | 0.98904 | 67% | 80% | | | | |
| | 2.70424 | 33% | 90% | | | | |
| 24 hours | 0.14588 | 78% | 53% | 1 | | | |
| | 0.0907 | 89% | 42% | 2 | 1.0 | 0.0 | 51.9 |
| | 0.00415 | 100% | 3% | 3 | 3.0 | 0.2 | 43.1 |
| | 0.39773 | 44% | 70% | 4 | 4.1 | 0.3 | 49.3 |
| | 0.98904 | 44% | 80% | | | | |
| | 2.70424 | 44% | 90% | | | | |

Fig. 2 Continued

| 48 hours | 0.11619 | 71% | 49% | 1 | | | |
| | 0.05254 | 86% | 30% | 2 | 2.0 | 0.1 | 39.8 |
| | 0.01984 | 100% | 15% | 3 | 1.0 | 0.0 | 52.5 |
| | 0.39773 | 57% | 70% | 4 | 3.0 | 0.2 | 43.1 |
| | 0.98904 | 43% | 80% | | | | |
| | 2.70424 | 14% | 90% | | | | |

UO only

| Time prior AKI stage | Cutoff value | sens | spec | Quartile | OR | 95% CI of OR | |
|---|---|---|---|---|---|---|---|
| 0 hours | 0.10021 | 71% | 43% | 1 | | | |
| | 0.05247 | 83% | 29% | 2 | 1.8 | 0.8 | 4.2 |
| | 0.01072 | 92% | 5% | 3 | 2.1 | 1.0 | 4.7 |
| | 0.48913 | 29% | 70% | 4 | 1.3 | 0.5 | 3.3 |
| | 1.1193 | 13% | 80% | | | | |
| | 2.70424 | 8% | 90% | | | | |
| 24 hours | 0.0838 | 70% | 39% | 1 | | | |
| | 0.06755 | 80% | 35% | 2 | 2.7 | 1.3 | 5.7 |
| | 0.03684 | 90% | 23% | 3 | 2.4 | 1.1 | 5.2 |
| | 0.48913 | 33% | 70% | 4 | 1.8 | 0.8 | 4.1 |
| | 1.1193 | 20% | 80% | | | | |
| | 2.70424 | 10% | 90% | | | | |
| 48 hours | 0.06051 | 75% | 32% | 1 | | | |
| | 0.05406 | 81% | 30% | 2 | 1.7 | 0.6 | 5.2 |
| | 0.01331 | 94% | 7% | 3 | 1.7 | 0.6 | 5.2 |
| | 0.48913 | 19% | 70% | 4 | 1.0 | 0.3 | 3.9 |
| | 1.1193 | 13% | 80% | | | | |
| | 2.70424 | 13% | 90% | | | | |

EN-RAGE sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1.240 | 2.595 | 1.240 | 3.782 | 1.240 | 2.366 |
| average | 12.233 | 16.695 | 12.233 | 20.210 | 12.233 | 242.259 |
| stdev | 63.964 | 35.707 | 63.964 | 45.115 | 63.964 | 1007.825 |
| p (t-test) | | 0.742 | | 0.477 | | 0.000 |
| min | 0.002 | 0.196 | 0.002 | 0.065 | 0.002 | 0.225 |
| max | 675.017 | 152.128 | 675.017 | 227.285 | 675.017 | 4280.487 |
| n (Samp) | 246 | 23 | 246 | 35 | 246 | 18 |
| n (Pat) | 159 | 23 | 159 | 35 | 159 | 18 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1.474 | 0.944 | 1.474 | 1.507 | 1.474 | 1.962 |
| average | 12.758 | 0.944 | 12.758 | 2.250 | 12.758 | 615.175 |
| stdev | 58.556 | 0.937 | 58.556 | 2.282 | 58.556 | 1616.263 |
| p (t-test) | | 0.776 | | 0.613 | | 0.000 |
| min | 0.002 | 0.281 | 0.002 | 0.065 | 0.002 | 0.279 |
| max | 675.017 | 1.606 | 675.017 | 5.799 | 675.017 | 4280.487 |
| n (Samp) | 318 | 2 | 318 | 8 | 318 | 7 |
| n (Pat) | 188 | 2 | 188 | 8 | 188 | 7 |

Fig. 2 Continued

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1.362 | 2.595 | 1.362 | 3.186 | 1.362 | 2.177 |
| average | 32.417 | 16.701 | 32.417 | 23.090 | 32.417 | 4.864 |
| stdev | 299.111 | 35.704 | 299.111 | 48.221 | 299.111 | 6.065 |
| p (t-test) | | 0.802 | | 0.865 | | 0.713 |
| min | 0.002 | 0.166 | 0.002 | 0.116 | 0.002 | 0.225 |
| max | 4280.487 | 152.128 | 4280.487 | 227.285 | 4280.487 | 21.060 |
| n (Samp) | 212 | 23 | 212 | 30 | 212 | 16 |
| n (Pat) | 132 | 23 | 132 | 30 | 132 | 16 | sCr or UO

| Time prior AKI stage | AUC | SE | nCohort 1 | nCohort 2 | p |
|---|---|---|---|---|---|
| 0 hours | 0.64 | 0.065 | 246 | 23 | 0.027 |
| 24 hours | 0.67 | 0.053 | 246 | 35 | 0.002 |
| 48 hours | 0.58 | 0.073 | 246 | 18 | 0.275 | sCr only

| Time prior AKI stage | AUC | SE | nCohort 1 | nCohort 2 | p |
|---|---|---|---|---|---|
| 0 hours | 0.32 | 0.163 | 318 | 2 | 0.260 |
| 24 hours | 0.42 | 0.097 | 318 | 8 | 0.425 |
| 48 hours | 0.57 | 0.114 | 318 | 7 | 0.557 |

UO only

| Time prior AKI stage | AUC | SE | nCohort 1 | nCohort 2 | p |
|---|---|---|---|---|---|
| 0 hours | 0.62 | 0.065 | 212 | 23 | 0.057 |
| 24 hours | 0.68 | 0.057 | 212 | 30 | 0.002 |
| 48 hours | 0.55 | 0.077 | 212 | 16 | 0.518 | sCr or UO

| Time prior AKI stage | Cutoff value | sens | spec | Quartile | OR | 95% CI of OR | |
|---|---|---|---|---|---|---|---|
| 0 hours | 0.88947 | 74% | 41% | 1 | | | |
| | 0.77827 | 83% | 36% | 2 | 1.4 | 0.4 | 4.5 |
| | 0.33592 | 91% | 15% | 3 | 2.5 | 0.9 | 6.7 |
| | 2.55991 | 52% | 70% | 4 | 3.3 | 1.3 | 8.3 |
| | 4.79853 | 39% | 80% | | | | |
| | 11.8327 | 26% | 90% | | | | |
| 24 hours | 1.74804 | 71% | 61% | 1 | | | |
| | 0.92777 | 80% | 43% | 2 | 1.3 | 0.5 | 3.3 |
| | 0.29244 | 91% | 13% | 3 | 2.4 | 1.1 | 5.3 |
| | 2.55991 | 51% | 70% | 4 | 5.2 | 2.7 | 10.2 |
| | 4.79853 | 46% | 80% | | | | |
| | 11.8327 | 34% | 90% | | | | |
| 48 hours | 0.59513 | 72% | 29% | 1 | | | |
| | 0.3635 | 83% | 17% | 2 | 0.4 | 0.1 | 1.6 |
| | 0.25054 | 94% | 11% | 3 | 0.8 | 0.3 | 2.0 |
| | 2.55991 | 44% | 70% | 4 | 1.4 | 0.7 | 3.0 |
| | 4.79853 | 39% | 80% | | | | |
| | 11.8327 | 17% | 90% | | | | |

Fig. 2 Continued sCr only

| Time prior AKI stage | Cutoff value | sens | spec | Quartile | OR | 95% CI of OR | |
|---|---|---|---|---|---|---|---|
| 0 hours | 0.26201 | 100% | 11% | 1 | | | |
| | 0.26201 | 100% | 11% | 2 | na | na | na |
| | 0.26201 | 100% | 11% | 3 | na | na | na |
| | 3.30333 | 0% | 70% | 4 | na | na | na |
| | 6.7486 | 0% | 80% | | | | |
| | 16.0678 | 0% | 90% | | | | |
| 24 hours | 0.29244 | 75% | 12% | 1 | | | |
| | 0.16594 | 88% | 5% | 2 | 1.0 | 0.1 | 7.6 |
| | 0.00184 | 100% | 0% | 3 | 0.5 | 0.0 | 9.8 |
| | 3.30333 | 38% | 70% | 4 | 1.5 | 0.3 | 8.3 |
| | 6.7486 | 0% | 80% | | | | |
| | 16.0678 | 0% | 90% | | | | |
| 48 hours | 1.52936 | 71% | 52% | 1 | | | |
| | 0.3635 | 86% | 16% | 2 | 0.0 | 0.0 | na |
| | 0.26201 | 100% | 11% | 3 | 1.5 | 0.3 | 8.2 |
| | 3.30333 | 43% | 70% | 4 | 1.0 | 0.1 | 7.4 |
| | 6.7486 | 29% | 80% | | | | |
| | 16.0678 | 29% | 90% | | | | |

UO only

| Time prior AKI stage | Cutoff value | sens | spec | Quartile | OR | 95% CI of OR | |
|---|---|---|---|---|---|---|---|
| 0 hours | 0.87873 | 74% | 38% | 1 | | | |
| | 0.77827 | 83% | 32% | 2 | 1.3 | 0.4 | 4.5 |
| | 0.33592 | 91% | 13% | 3 | 2.5 | 0.9 | 6.8 |
| | 2.70443 | 48% | 70% | 4 | 3.3 | 1.3 | 8.5 |
| | 5.03011 | 39% | 80% | | | | |
| | 12.9468 | 26% | 90% | | | | |
| 24 hours | 1.86574 | 70% | 59% | 1 | | | |
| | 0.97462 | 80% | 40% | 2 | 0.7 | 0.2 | 2.4 |
| | 0.63129 | 90% | 26% | 3 | 2.5 | 1.1 | 5.4 |
| | 2.70443 | 50% | 70% | 4 | 4.2 | 2.1 | 8.5 |
| | 5.03011 | 47% | 80% | | | | |
| | 12.9468 | 37% | 90% | | | | |
| 48 hours | 0.59513 | 75% | 26% | 1 | | | |
| | 0.37339 | 81% | 16% | 2 | 0.5 | 0.1 | 2.3 |
| | 0.25054 | 94% | 9% | 3 | 1.0 | 0.3 | 2.9 |
| | 2.70443 | 38% | 70% | 4 | 1.6 | 0.6 | 3.8 |
| | 5.03011 | 38% | 80% | | | | |
| | 12.9468 | 13% | 90% | | | | |

Fig. 2 Continued

Eotaxin sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 32.600 | 39.900 | 32.600 | 49.950 | 32.600 | 42.400 |
| average | 44.675 | 49.776 | 44.675 | 79.292 | 44.675 | 88.128 |
| stdev | 36.453 | 45.492 | 36.453 | 95.015 | 36.453 | 112.509 |
| p (t-test) |  | 0.488 |  | 0.000 |  | 0.000 |
| min | 0.164 | 6.660 | 0.164 | 12.700 | 0.164 | 12.400 |
| max | 270.000 | 232.000 | 270.000 | 535.000 | 270.000 | 420.000 |
| n (Samp) | 419 | 27 | 419 | 36 | 419 | 18 |
| n (Pat) | 164 | 27 | 164 | 36 | 164 | 18 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 34.400 | 45.300 | 34.400 | 46.100 | 34.400 | 103.000 |
| average | 47.582 | 95.920 | 47.582 | 81.189 | 47.582 | 119.957 |
| stdev | 45.581 | 85.473 | 45.581 | 72.494 | 45.581 | 112.138 |
| p (t-test) |  | 0.020 |  | 0.031 |  | 0.000 |
| min | 0.164 | 33.300 | 0.164 | 17.900 | 0.164 | 19.000 |
| max | 535.000 | 232.000 | 535.000 | 221.000 | 535.000 | 333.000 |
| n (Samp) | 518 | 5 | 518 | 9 | 518 | 7 |
| n (Pat) | 199 | 5 | 199 | 9 | 199 | 7 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 33.500 | 36.150 | 33.500 | 49.950 | 33.500 | 42.400 |
| average | 46.069 | 41.960 | 46.069 | 75.330 | 46.069 | 84.800 |
| stdev | 38.727 | 27.989 | 38.727 | 97.826 | 38.727 | 105.575 |
| p (t-test) |  | 0.596 |  | 0.001 |  | 0.001 |
| min | 0.164 | 6.660 | 0.164 | 12.700 | 0.164 | 12.400 |
| max | 270.000 | 114.000 | 270.000 | 535.000 | 270.000 | 420.000 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
|---|---|---|---|---|---|
| 0 hours | 0.53 | 0.058 | 419 | 27 | 0.616 |
| 24 hours | 0.62 | 0.052 | 419 | 36 | 0.022 |
| 48 hours | 0.59 | 0.072 | 419 | 18 | 0.191 | sCr only

| Time prior AKI stage | AUC | SE | nCohort 1 | nCohort 2 | p |
|---|---|---|---|---|---|
| 0 hours | 0.73 | 0.129 | 518 | 5 | 0.069 |
| 24 hours | 0.65 | 0.100 | 518 | 9 | 0.137 |
| 48 hours | 0.72 | 0.110 | 518 | 7 | 0.048 |

UO only

| Time prior AKI stage | AUC | SE | nCohort 1 | nCohort 2 | p |
|---|---|---|---|---|---|
| 0 hours | 0.49 | 0.058 | 352 | 26 | 0.851 |
| 24 hours | 0.60 | 0.057 | 352 | 30 | 0.086 |
| 48 hours | 0.60 | 0.076 | 352 | 16 | 0.198 |

Fig. 2 Continued sCr or UO

| Time prior AKI stage | Cutoff value | sens | spec | Quartile | OR | 95% CI of OR | |
|---|---|---|---|---|---|---|---|
| 0 hours | 27.5 | 70% | 37% | 1 | | | |
| | 23.1 | 81% | 23% | 2 | 0.4 | 0.2 | 1.1 |
| | 15.4 | 93% | 7% | 3 | 1.6 | 1.0 | 2.7 |
| | 48.4 | 26% | 70% | 4 | 0.8 | 0.4 | 1.6 |
| | 62.4 | 22% | 80% | | | | |
| | 81.8 | 22% | 90% | | | | |
| 24 hours | 28.3 | 72% | 38% | 1 | | | |
| | 21.5 | 81% | 19% | 2 | 0.3 | 0.1 | 0.8 |
| | 17.6 | 92% | 10% | 3 | 0.8 | 0.4 | 1.3 |
| | 48.4 | 50% | 70% | 4 | 2.0 | 1.4 | 2.9 |
| | 62.4 | 42% | 80% | | | | |
| | 81.8 | 31% | 90% | | | | |
| 48 hours | 28.2 | 72% | 38% | 1 | | | |
| | 20.9 | 83% | 17% | 2 | 1.0 | 0.4 | 2.8 |
| | 18.7 | 94% | 15% | 3 | 0.5 | 0.1 | 2.2 |
| | 48.4 | 44% | 70% | 4 | 2.1 | 1.0 | 4.5 |
| | 62.4 | 44% | 80% | | | | |
| | 81.8 | 28% | 90% | | | | | sCr only

| Time prior AKI stage | Cutoff value | sens | spec | Quartile | OR | 95% CI of OR | |
|---|---|---|---|---|---|---|---|
| 0 hours | 39.9 | 80% | 59% | 1 | | | |
| | 39.9 | 80% | 59% | 2 | na | na | na |
| | 33.1 | 100% | 48% | 3 | na | na | na |
| | 51.3 | 40% | 70% | 4 | na | na | na |
| | 64.2 | 40% | 80% | | | | |
| | 85.3 | 40% | 90% | | | | |
| 24 hours | 36.4 | 78% | 53% | 1 | | | |
| | 27.1 | 89% | 31% | 2 | 1.0 | 0.0 | 51.5 |
| | 17.6 | 100% | 10% | 3 | 3.0 | 0.2 | 42.5 |
| | 51.3 | 44% | 70% | 4 | 4.1 | 0.3 | 48.5 |
| | 64.2 | 33% | 80% | | | | |
| | 85.3 | 33% | 90% | | | | |
| 48 hours | 42.7 | 71% | 62% | 1 | | | |
| | 28.7 | 86% | 37% | 2 | 1.0 | 0.0 | 51.9 |
| | 18.7 | 100% | 15% | 3 | 1.0 | 0.0 | 51.9 |
| | 51.3 | 57% | 70% | 4 | 4.1 | 0.3 | 48.5 |
| | 64.2 | 57% | 80% | | | | |
| | 85.3 | 57% | 90% | | | | |

UO only

| Time prior AKI stage | Cutoff value | sens | spec | Quartile | OR | 95% CI of OR | |
|---|---|---|---|---|---|---|---|
| 0 hours | 26 | 73% | 28% | 1 | | | |
| | 23.1 | 81% | 22% | 2 | 1.9 | 1.0 | 3.7 |
| | 15.4 | 92% | 7% | 3 | 1.0 | 0.4 | 2.3 |
| | 50.2 | 23% | 70% | 4 | 1.4 | 0.7 | 3.0 |
| | 63 | 19% | 80% | | | | |
| | 84.7 | 15% | 90% | | | | |
| 24 hours | 28.3 | 70% | 36% | 1 | | | |
| | 21.5 | 80% | 19% | 2 | 0.4 | 0.1 | 0.9 |
| | 17.6 | 90% | 10% | 3 | 0.6 | 0.3 | 1.2 |
| | 50.2 | 50% | 70% | 4 | 1.9 | 1.2 | 2.9 |
| | 63 | 40% | 80% | | | | |
| | 84.7 | 23% | 90% | | | | |

Fig. 2 Continued

| 48 hours | 28.2 | 75% | 36% | 1 | | | |
|---|---|---|---|---|---|---|---|
| | 25.1 | 81% | 27% | 2 | 1.3 | 0.4 | 4.4 |
| | 19 | 94% | 15% | 3 | 0.7 | 0.1 | 3.5 |
| | 50.2 | 44% | 70% | 4 | 2.4 | 0.9 | 6.5 |
| | 63 | 44% | 80% | | | | |
| | 84.7 | 25% | 90% | | | | |

E-selectin sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.166 | 0.198 | 0.166 | 0.233 | 0.166 | 0.221 |
| average | 0.320 | 0.696 | 0.320 | 0.488 | 0.320 | 0.366 |
| stdev | 0.451 | 1.111 | 0.451 | 0.968 | 0.451 | 0.530 |
| p (t-test) | | 0.001 | | 0.087 | | 0.677 |
| min | 0.000 | 0.000 | 0.000 | 0.000 | 0.000 | 0.000 |
| max | 2.918 | 4.435 | 2.918 | 5.381 | 2.918 | 2.257 |
| n (Samp) | 247 | 23 | 247 | 35 | 247 | 18 |
| n (Pat) | 159 | 23 | 159 | 35 | 159 | 18 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 0.177 | 0.087 | 0.177 | 0.218 | 0.177 | 0.775 |
| average | 0.369 | 0.087 | 0.369 | 0.299 | 0.369 | 0.743 |
| stdev | 0.621 | 0.123 | 0.621 | 0.304 | 0.621 | 0.623 |
| p (t-test) | | 0.522 | | 0.753 | | 0.116 |
| min | 0.000 | 0.000 | 0.000 | 0.000 | 0.000 | 0.019 |
| max | 5.381 | 0.174 | 5.381 | 0.735 | 5.381 | 1.891 |
| n (Samp) | 319 | 2 | 319 | 8 | 319 | 7 |
| n (Pat) | 188 | 2 | 188 | 8 | 188 | 7 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 0.161 | 0.198 | 0.161 | 0.225 | 0.161 | 0.221 |
| average | 0.331 | 0.690 | 0.331 | 0.514 | 0.331 | 0.379 |
| stdev | 0.495 | 1.115 | 0.495 | 1.038 | 0.495 | 0.555 |
| p (t-test) | | 0.005 | | 0.111 | | 0.708 |
| min | 0.000 | 0.000 | 0.000 | 0.000 | 0.000 | 0.000 |
| max | 3.078 | 4.435 | 3.078 | 5.381 | 3.078 | 2.257 |
| n (Samp) | 213 | 23 | 213 | 30 | 213 | 16 |
| n (Pat) | 132 | 23 | 132 | 30 | 132 | 16 | sCr or UO

| Time prior AKI stage | AUC | SE | nCohort 1 | nCohort 2 | p |
|---|---|---|---|---|---|
| 0 hours | 0.59 | 0.065 | 247 | 23 | 0.162 |
| 24 hours | 0.54 | 0.053 | 247 | 35 | 0.495 |
| 48 hours | 0.51 | 0.071 | 247 | 18 | 0.898 | sCr only

| Time prior AKI stage | AUC | SE | nCohort 1 | nCohort 2 | p |
|---|---|---|---|---|---|
| 0 hours | 0.26 | 0.142 | 319 | 2 | 0.090 |
| 24 hours | 0.48 | 0.102 | 319 | 8 | 0.880 |
| 48 hours | 0.73 | 0.110 | 319 | 7 | 0.038 |

Fig. 2 Continued

UO only

| Time prior AKI stage | AUC | SE | nCohort 1 | nCohort 2 | p |
|---|---|---|---|---|---|
| 0 hours | 0.57 | 0.065 | 213 | 23 | 0.283 |
| 24 hours | 0.54 | 0.057 | 213 | 30 | 0.440 |
| 48 hours | 0.51 | 0.075 | 213 | 16 | 0.870 | sCr or UO

| Time prior AKI stage | Cutoff value | sens | spec | Quartile | OR | 95% CI of OR | |
|---|---|---|---|---|---|---|---|
| 0 hours | 0.12065 | 74% | 39% | 1 | | | |
| | 0.07846 | 83% | 29% | 2 | 1.5 | 0.6 | 3.7 |
| | 0.06035 | 91% | 24% | 3 | 1.3 | 0.5 | 3.3 |
| | 0.32093 | 39% | 70% | 4 | 2.1 | 0.9 | 4.7 |
| | 0.45478 | 22% | 80% | | | | |
| | 0.74303 | 22% | 91% | | | | |
| 24 hours | 0.11194 | 71% | 37% | 1 | | | |
| | 0.04424 | 80% | 18% | 2 | 0.3 | 0.1 | 0.8 |
| | 1.1E-05 | 91% | 6% | 3 | 1.5 | 1.0 | 2.4 |
| | 0.32093 | 29% | 70% | 4 | 1.1 | 0.7 | 1.8 |
| | 0.45478 | 23% | 80% | | | | |
| | 0.74303 | 11% | 91% | | | | |
| 48 hours | 0.05672 | 72% | 22% | 1 | | | |
| | 0.01715 | 83% | 10% | 2 | 0.3 | 0.1 | 1.2 |
| | 0 | 100% | 0% | 3 | 0.6 | 0.3 | 1.6 |
| | 0.32093 | 39% | 70% | 4 | 1.0 | 0.5 | 2.0 |
| | 0.45478 | 28% | 80% | | | | |
| | 0.74303 | 11% | 91% | | | | | sCr only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | na | na | na |
| | 0 | 100% | 0% | 3 | na | na | na |
| | 0.33048 | 0% | 70% | 4 | na | na | na |
| | 0.45478 | 0% | 80% | | | | |
| | 0.74303 | 0% | 90% | | | | |
| 24 hours | 0.03167 | 75% | 14% | 1 | | | |
| | 0 | 100% | 0% | 2 | 0.3 | 0.0 | 4.7 |
| | 0 | 100% | 0% | 3 | 0.3 | 0.0 | 4.7 |
| | 0.33048 | 38% | 70% | 4 | 1.0 | 0.3 | 3.9 |
| | 0.45478 | 38% | 80% | | | | |
| | 0.74303 | 0% | 90% | | | | |
| 48 hours | 0.45478 | 71% | 80% | 1 | | | |
| | 0.16975 | 86% | 48% | 2 | 1.0 | 0.0 | 52.3 |
| | 0.01715 | 100% | 11% | 3 | 0.0 | 0.0 | na |
| | 0.33048 | 71% | 70% | 4 | 5.2 | 0.5 | 57.4 |
| | 0.45478 | 71% | 80% | | | | |
| | 0.74303 | 57% | 90% | | | | |

UO only

| Time prior AKI stage | Cutoff value | sens | spec | Quartile | OR | 95% CI of OR | |
|---|---|---|---|---|---|---|---|
| 0 hours | 0.10943 | 74% | 35% | 1 | | | |
| | 0.06531 | 83% | 24% | 2 | 0.8 | 0.3 | 2.0 |
| | 0.02884 | 91% | 11% | 3 | 1.2 | 0.6 | 2.7 |
| | 0.32093 | 39% | 70% | 4 | 1.7 | 0.8 | 3.5 |
| | 0.46344 | 22% | 80% | | | | |
| | 0.73598 | 22% | 90% | | | | |

Fig. 2 Continued

| 24 hours | 0.17758 | 70% | 53% | 1 | | | |
| | 0.05937 | 80% | 22% | 2 | 0.1 | 0.0 | 1.1 |
| | 0.00714 | 90% | 7% | 3 | 1.8 | 1.1 | 2.8 |
| | 0.32093 | 27% | 70% | 4 | 1.0 | 0.6 | 1.7 |
| | 0.46344 | 20% | 80% | | | | |
| | 0.73598 | 13% | 90% | | | | |
| 48 hours | 0.05672 | 75% | 21% | 1 | | | |
| | 0.01882 | 81% | 9% | 2 | 0.4 | 0.1 | 1.6 |
| | 0 | 100% | 0% | 3 | 0.8 | 0.3 | 2.0 |
| | 0.32093 | 38% | 70% | 4 | 1.0 | 0.4 | 2.3 |
| | 0.46344 | 19% | 80% | | | | |
| | 0.73598 | 6% | 90% | | | | |

Granulocyte colony-stimulating factor sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 23.300 | 31.800 | 23.300 | 34.300 | 23.300 | 37.050 |
| average | 638.652 | 42.797 | 638.652 | 209.348 | 638.652 | 52.017 |
| stdev | 6663.552 | 38.127 | 6663.552 | 645.465 | 6663.552 | 48.351 |
| p (t-test) | | 0.643 | | 0.700 | | 0.709 |
| min | 0.020 | 1.690 | 0.020 | 4.280 | 0.020 | 1.750 |
| max | 103844.000 | 152.000 | 103844.000 | 3010.000 | 103844.000 | 165.000 |
| n (Samp) | 419 | 27 | 419 | 36 | 419 | 18 |
| n (Pat) | 164 | 27 | 164 | 36 | 164 | 18 | sCr only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 25.600 | 46.100 | 25.600 | 55.200 | 25.600 | 61.300 |
| average | 527.583 | 54.220 | 527.583 | 342.013 | 527.583 | 480.336 |
| stdev | 5996.271 | 35.220 | 5996.271 | 849.425 | 5996.271 | 1116.476 |
| p (t-test) | | 0.860 | | 0.926 | | 0.983 |
| min | 0.020 | 12.400 | 0.020 | 4.280 | 0.020 | 1.750 |
| max | 103844.000 | 109.000 | 103844.000 | 2600.000 | 103844.000 | 3010.000 |
| n (Samp) | 518 | 5 | 518 | 9 | 518 | 7 |
| n (Pat) | 199 | 5 | 199 | 9 | 199 | 7 |

UO only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 24.250 | 32.200 | 24.250 | 36.250 | 24.250 | 37.600 |
| average | 752.529 | 46.281 | 752.529 | 160.577 | 752.529 | 208.498 |
| stdev | 7266.128 | 39.565 | 7266.128 | 545.216 | 7266.128 | 639.122 |
| p (t-test) | | 0.621 | | 0.656 | | 0.765 |
| min | 0.020 | 1.690 | 0.020 | 4.460 | 0.020 | 5.740 |
| max | 103844.000 | 152.000 | 103844.000 | 3010.000 | 103844.000 | 2600.000 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
| --- | --- | --- | --- | --- | --- |
| 0 hours | 0.55 | 0.059 | 419 | 27 | 0.366 |
| 24 hours | 0.58 | 0.052 | 419 | 36 | 0.112 |
| 48 hours | 0.59 | 0.072 | 419 | 18 | 0.206 |

Fig. 2 Continued sCr only

| Time prior AKI stage | AUC | SE | nCohort 1 | nCohort 2 | p |
|---|---|---|---|---|---|
| 0 hours | 0.68 | 0.133 | 518 | 5 | 0.186 |
| 24 hours | 0.59 | 0.101 | 518 | 9 | 0.346 |
| 48 hours | 0.69 | 0.112 | 518 | 7 | 0.096 |

UO only

| Time prior AKI stage | AUC | SE | nCohort 1 | nCohort 2 | p |
|---|---|---|---|---|---|
| 0 hours | 0.56 | 0.060 | 352 | 26 | 0.282 |
| 24 hours | 0.59 | 0.057 | 352 | 30 | 0.098 |
| 48 hours | 0.61 | 0.076 | 352 | 16 | 0.136 | sCr or UO

| Time prior AKI stage | Cutoff value | sens | spec | Quartile | OR | 95% CI of OR | |
|---|---|---|---|---|---|---|---|
| 0 hours | 19.4 | 70% | 42% | 1 | | | |
| | 11.3 | 81% | 23% | 2 | 0.3 | 0.1 | 1.0 |
| | 7.28 | 93% | 14% | 3 | 1.6 | 1.0 | 2.7 |
| | 43.7 | 41% | 70% | 4 | 1.0 | 0.5 | 1.8 |
| | 58.9 | 22% | 80% | | | | |
| | 98.2 | 11% | 90% | | | | |
| 24 hours | 21.4 | 72% | 46% | 1 | | | |
| | 13.4 | 81% | 29% | 2 | 1.5 | 0.9 | 2.7 |
| | 7.82 | 92% | 15% | 3 | 1.3 | 0.7 | 2.5 |
| | 43.7 | 36% | 70% | 4 | 2.3 | 1.4 | 3.8 |
| | 58.9 | 28% | 80% | | | | |
| | 98.2 | 14% | 90% | | | | |
| 48 hours | 25.5 | 72% | 53% | 1 | | | |
| | 13.4 | 83% | 29% | 2 | 0.7 | 0.1 | 3.5 |
| | 5.5 | 94% | 9% | 3 | 2.4 | 0.9 | 6.4 |
| | 43.7 | 44% | 70% | 4 | 2.0 | 0.7 | 5.6 |
| | 58.9 | 28% | 80% | | | | |
| | 98.2 | 17% | 90% | | | | | sCr only

| Time prior AKI stage | Cutoff value | sens | spec | Quartile | OR | 95% CI of OR | |
|---|---|---|---|---|---|---|---|
| 0 hours | 43.5 | 80% | 69% | 1 | | | |
| | 43.5 | 80% | 69% | 2 | na | na | na |
| | 12.3 | 100% | 26% | 3 | na | na | na |
| | 44.6 | 60% | 70% | 4 | na | na | na |
| | 59 | 40% | 80% | | | | |
| | 99.9 | 20% | 90% | | | | |
| 24 hours | 11.5 | 78% | 23% | 1 | | | |
| | 7.95 | 89% | 15% | 2 | 0.3 | 0.0 | 4.6 |
| | 4.23 | 100% | 6% | 3 | 0.0 | 0.0 | na |
| | 44.6 | 56% | 70% | 4 | 1.7 | 0.6 | 4.9 |
| | 59 | 44% | 80% | | | | |
| | 99.9 | 22% | 90% | | | | |
| 48 hours | 43.1 | 71% | 69% | 1 | | | |
| | 30.2 | 86% | 56% | 2 | 0.0 | 0.0 | na |
| | 1.69 | 100% | 2% | 3 | 2.0 | 0.1 | 39.3 |
| | 44.6 | 57% | 70% | 4 | 4.1 | 0.3 | 48.5 |
| | 59 | 57% | 80% | | | | |
| | 99.9 | 29% | 90% | | | | |

Fig. 2 Continued

UO only

| Time prior AKI stage | Cutoff value | sens | spec | Quartile | OR | 95% CI of OR | |
|---|---|---|---|---|---|---|---|
| 0 hours | 19.2 | 73% | 39% | 1 | | | |
| | 11.3 | 81% | 21% | 2 | 0.1 | 0.0 | 1.3 |
| | 7.28 | 92% | 14% | 3 | 1.5 | 0.9 | 2.5 |
| | 43.4 | 46% | 70% | 4 | 1.1 | 0.6 | 2.0 |
| | 59.2 | 27% | 80% | | | | |
| | 99.9 | 12% | 90% | | | | |
| 24 hours | 22.7 | 70% | 46% | 1 | | | |
| | 17.5 | 80% | 36% | 2 | 1.8 | 0.8 | 4.0 |
| | 11.8 | 90% | 22% | 3 | 2.4 | 1.1 | 5.1 |
| | 43.4 | 37% | 70% | 4 | 2.6 | 1.3 | 5.5 |
| | 59.2 | 27% | 80% | | | | |
| | 99.9 | 13% | 90% | | | | |
| 48 hours | 25.5 | 75% | 51% | 1 | | | |
| | 17.9 | 81% | 36% | 2 | 1.0 | 0.1 | 7.4 |
| | 8.18 | 94% | 15% | 3 | 3.1 | 0.8 | 12.1 |
| | 43.4 | 50% | 70% | 4 | 3.1 | 0.8 | 12.1 |
| | 59.2 | 31% | 80% | | | | |
| | 99.9 | 19% | 90% | | | | |

Heparin-binding growth factor 2 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 169.000 | 209.000 | 169.000 | 222.000 | 169.000 | 193.000 |
| average | 240.036 | 257.266 | 240.036 | 422.378 | 240.036 | 290.411 |
| stdev | 258.852 | 268.013 | 258.852 | 627.456 | 258.852 | 227.227 |
| p (t-test) | | 0.738 | | 0.001 | | 0.417 |
| min | 0.392 | 0.392 | 0.392 | 42.100 | 0.392 | 39.200 |
| max | 2010.000 | 1470.000 | 2010.000 | 3610.000 | 2010.000 | 903.000 |
| n (Samp) | 419 | 27 | 419 | 36 | 419 | 18 |
| n (Pat) | 164 | 27 | 164 | 36 | 164 | 18 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 170.000 | 269.000 | 170.000 | 225.000 | 170.000 | 314.000 |
| average | 248.956 | 294.860 | 248.956 | 437.800 | 248.956 | 532.743 |
| stdev | 298.161 | 191.046 | 298.161 | 364.885 | 298.161 | 461.717 |
| p (t-test) | | 0.731 | | 0.061 | | 0.013 |
| min | 0.392 | 81.300 | 0.392 | 84.700 | 0.392 | 39.200 |
| max | 3610.000 | 522.000 | 3610.000 | 1060.000 | 3610.000 | 1140.000 |
| n (Samp) | 518 | 5 | 518 | 9 | 518 | 7 |
| n (Pat) | 199 | 5 | 199 | 9 | 199 | 7 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 167.000 | 203.500 | 167.000 | 211.500 | 167.000 | 269.000 |
| average | 237.956 | 254.304 | 237.956 | 424.080 | 237.956 | 307.513 |
| stdev | 260.435 | 268.210 | 260.435 | 675.291 | 260.435 | 195.685 |
| p (t-test) | | 0.758 | | 0.002 | | 0.292 |
| min | 0.392 | 0.392 | 0.392 | 42.100 | 0.392 | 72.900 |
| max | 2010.000 | 1470.000 | 2010.000 | 3610.000 | 2010.000 | 702.000 |
| n (Samp) | 352 | 26 | 352 | 30 | 352 | 16 |
| n (Pat) | 133 | 26 | 133 | 30 | 133 | 16 |

Fig. 2 Continued sCr or UO

| Time prior AKI stage | AUC | SE | nCohort 1 | nCohort 2 | p |
|---|---|---|---|---|---|
| 0 hours | 0.57 | 0.059 | 419 | 27 | 0.223 |
| 24 hours | 0.62 | 0.052 | 419 | 36 | 0.016 |
| 48 hours | 0.59 | 0.072 | 419 | 18 | 0.191 | sCr only

| Time prior AKI stage | AUC | SE | nCohort 1 | nCohort 2 | p |
|---|---|---|---|---|---|
| 0 hours | 0.63 | 0.135 | 518 | 5 | 0.332 |
| 24 hours | 0.64 | 0.101 | 518 | 9 | 0.165 |
| 48 hours | 0.68 | 0.113 | 518 | 7 | 0.110 |

UO only

| Time prior AKI stage | AUC | SE | nCohort 1 | nCohort 2 | p |
|---|---|---|---|---|---|
| 0 hours | 0.58 | 0.060 | 352 | 26 | 0.189 |
| 24 hours | 0.63 | 0.056 | 352 | 30 | 0.022 |
| 48 hours | 0.65 | 0.076 | 352 | 16 | 0.045 | sCr or UO

| Time prior AKI stage | Cutoff value | sens | spec | Quartile | OR | 95% CI of OR | |
|---|---|---|---|---|---|---|---|
| 0 hours | 154 | 70% | 46% | 1 | | | |
| | 133 | 81% | 38% | 2 | 1.2 | 0.6 | 2.6 |
| | 55.2 | 93% | 9% | 3 | 1.6 | 0.8 | 3.2 |
| | 235 | 44% | 70% | 4 | 1.6 | 0.8 | 3.2 |
| | 300 | 19% | 80% | | | | |
| | 488 | 4% | 90% | | | | |
| 24 hours | 145 | 72% | 42% | 1 | | | |
| | 124 | 81% | 34% | 2 | 1.6 | 0.8 | 3.2 |
| | 94.9 | 92% | 22% | 3 | 1.4 | 0.7 | 2.9 |
| | 235 | 44% | 70% | 4 | 3.5 | 2.0 | 6.1 |
| | 300 | 39% | 80% | | | | |
| | 488 | 22% | 90% | | | | |
| 48 hours | 154 | 72% | 46% | 1 | | | |
| | 118 | 83% | 31% | 2 | 1.0 | 0.3 | 3.8 |
| | 70.4 | 94% | 14% | 3 | 1.3 | 0.4 | 4.4 |
| | 235 | 44% | 70% | 4 | 2.8 | 1.1 | 7.1 |
| | 300 | 33% | 80% | | | | |
| | 488 | 17% | 90% | | | | | sCr only

| Time prior AKI stage | Cutoff value | sens | spec | Quartile | OR | 95% CI of OR | |
|---|---|---|---|---|---|---|---|
| 0 hours | 145 | 80% | 42% | 1 | | | |
| | 145 | 80% | 42% | 2 | 1.0 | 0.0 | 51.5 |
| | 81 | 100% | 18% | 3 | 1.0 | 0.0 | 51.5 |
| | 246 | 60% | 71% | 4 | 2.0 | 0.1 | 39.0 |
| | 309 | 40% | 80% | | | | |
| | 492 | 20% | 90% | | | | |
| 24 hours | 102 | 78% | 25% | 1 | | | |
| | 96.7 | 89% | 22% | 2 | 0.5 | 0.0 | 9.6 |
| | 82.4 | 100% | 18% | 3 | 1.0 | 0.1 | 7.3 |
| | 246 | 44% | 71% | 4 | 2.0 | 0.4 | 9.0 |
| | 309 | 44% | 80% | | | | |
| | 492 | 44% | 90% | | | | |

Fig. 2 Continued

| 48 hours | 177 | 71% | 53% | 1 | | | |
| | 154 | 86% | 46% | 2 | 1.0 | 0.0 | 51.9 |
| | 37 | 100% | 5% | 3 | 1.0 | 0.0 | 51.9 |
| | 246 | 57% | 71% | 4 | 4.1 | 0.3 | 48.5 |
| | 309 | 57% | 80% | | | | |
| | 492 | 43% | 90% | | | | |

UO only

| Time prior AKI stage | Cutoff value | sens | spec | Quartile | OR | 95% CI of OR | |
|---|---|---|---|---|---|---|---|
| 0 hours | 163 | 73% | 47% | 1 | | | |
| | 148 | 81% | 44% | 2 | 1.5 | 0.6 | 3.6 |
| | 55.2 | 92% | 9% | 3 | 2.1 | 1.0 | 4.6 |
| | 228 | 42% | 70% | 4 | 2.1 | 0.9 | 4.5 |
| | 285 | 19% | 80% | | | | |
| | 475 | 4% | 90% | | | | |
| 24 hours | 148 | 70% | 44% | 1 | | | |
| | 133 | 83% | 38% | 2 | 2.8 | 1.1 | 7.2 |
| | 118 | 90% | 30% | 3 | 2.1 | 0.7 | 5.8 |
| | 228 | 47% | 70% | 4 | 4.8 | 2.1 | 11.2 |
| | 285 | 40% | 80% | | | | |
| | 475 | 17% | 90% | | | | |
| 48 hours | 178 | 75% | 55% | 1 | | | |
| | 118 | 88% | 30% | 2 | 1.0 | 0.1 | 7.4 |
| | 93.1 | 94% | 20% | 3 | 1.5 | 0.3 | 8.1 |
| | 228 | 56% | 70% | 4 | 4.9 | 1.4 | 16.9 |
| | 285 | 38% | 80% | | | | |
| | 475 | 19% | 90% | | | | |

Hepatocyte growth factor receptor sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 569.522 | 5.678 | 569.522 | 387.168 | 569.522 | 5.678 |
| average | 941.836 | 226.352 | 941.836 | 826.274 | 941.836 | 423.628 |
| stdev | 1079.422 | 447.741 | 1079.422 | 1142.611 | 1079.422 | 723.911 |
| p (t-test) | | 0.050 | | 0.676 | | 0.409 |
| min | 5.678 | 5.678 | 5.678 | 5.678 | 5.678 | 5.678 |
| max | 5086.124 | 1268.489 | 5086.124 | 4181.818 | 5086.124 | 1259.528 |
| n (Samp) | 168 | 9 | 168 | 17 | 168 | 3 |
| n (Pat) | 90 | 9 | 90 | 17 | 90 | 3 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 517.924 | 5.678 | 517.924 | 491.150 | 517.924 | 5.678 |
| average | 882.334 | 7.241 | 882.334 | 825.460 | 882.334 | 5.678 |
| stdev | 1054.530 | na | 1054.530 | 959.936 | 1054.530 | 0.000 |
| p (t-test) | | na | | 0.926 | | 0.242 |
| min | 5.678 | 7.241 | 5.678 | 77.381 | 5.678 | 5.678 |
| max | 5086.124 | 7.241 | 5086.124 | 1907.850 | 5086.124 | 5.678 |
| n (Samp) | 200 | 1 | 200 | 3 | 200 | 2 |
| n (Pat) | 110 | 1 | 110 | 3 | 110 | 2 |

Fig. 2 Continued

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 598.682 | 5.678 | 598.682 | 343.223 | 598.682 | 1259.528 |
| average | 969.054 | 226.352 | 969.054 | 754.194 | 969.054 | 1057.685 |
| stdev | 1091.838 | 447.741 | 1091.838 | 1147.419 | 1091.838 | 967.016 |
| p (t-test) | | 0.045 | | 0.460 | | 0.889 |
| min | 5.678 | 5.678 | 5.678 | 5.678 | 5.678 | 5.678 |
| max | 5086.124 | 1268.489 | 5086.124 | 4181.818 | 5086.124 | 1907.850 |
| n (Samp) | 134 | 9 | 134 | 16 | 134 | 3 |
| n (Pat) | 71 | 9 | 71 | 16 | 71 | 3 | sCr or UO

| Time prior AKI stage | AUC | SE | nCohort 1 | nCohort 2 | p |
|---|---|---|---|---|---|
| 0 hours | 0.19 | 0.055 | 168 | 9 | 0.000 |
| 24 hours | 0.43 | 0.070 | 168 | 17 | 0.330 |
| 48 hours | 0.27 | 0.122 | 168 | 3 | 0.064 | sCr only

| Time prior AKI stage | AUC | SE | nCohort 1 | nCohort 2 | p |
|---|---|---|---|---|---|
| 0 hours | 0.13 | 0.116 | 200 | 1 | 0.001 |
| 24 hours | 0.53 | 0.171 | 200 | 3 | 0.884 |
| 48 hours | 0.07 | 0.046 | 200 | 2 | 0.000 |

UO only

| Time prior AKI stage | AUC | SE | nCohort 1 | nCohort 2 | p |
|---|---|---|---|---|---|
| 0 hours | 0.18 | 0.055 | 134 | 9 | 0.000 |
| 24 hours | 0.38 | 0.069 | 134 | 16 | 0.094 |
| 48 hours | 0.55 | 0.173 | 134 | 3 | 0.785 | sCr or UO

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | na | na | na |
| | 0 | 100% | 0% | 3 | na | na | na |
| | 1187.71 | 11% | 70% | 4 | na | na | na |
| | 1499.09 | 0% | 80% | | | | |
| | 2406.53 | 0% | 90% | | | | |
| 24 hours | 110.119 | 71% | 22% | 1 | | | |
| | 57.0557 | 82% | 14% | 2 | 0.8 | 0.2 | 2.6 |
| | 0 | 100% | 0% | 3 | 0.8 | 0.2 | 2.6 |
| | 1187.71 | 24% | 70% | 4 | 1.9 | 0.8 | 4.6 |
| | 1499.09 | 24% | 80% | | | | |
| | 2406.53 | 6% | 90% | | | | |
| 48 hours | 0 | 100% | 0% | 1 | | | |
| | 0 | 100% | 0% | 2 | na | na | na |
| | 0 | 100% | 0% | 3 | na | na | na |
| | 1187.71 | 33% | 70% | 4 | na | na | na |
| | 1499.09 | 0% | 80% | | | | |
| | 2406.53 | 0% | 90% | | | | |

Fig. 2 Continued sCr only

| Time prior AKI stage | Cutoff value | sens | spec | Quartile | OR | 95% CI of OR | |
|---|---|---|---|---|---|---|---|
| 0 hours | 5.67831 | 100% | 13% | 1 | | | |
| | 5.67831 | 100% | 13% | 2 | na | na | na |
| | 5.67831 | 100% | 13% | 3 | na | na | na |
| | 1072.35 | 0% | 70% | 4 | na | na | na |
| | 1387.64 | 0% | 80% | | | | |
| | 2054.16 | 0% | 90% | | | | |
| 24 hours | 74.4048 | 100% | 21% | 1 | | | |
| | 74.4048 | 100% | 21% | 2 | 1.0 | 0.0 | 53.5 |
| | 74.4048 | 100% | 21% | 3 | 0.0 | 0.0 | na |
| | 1072.35 | 33% | 70% | 4 | 1.0 | 0.0 | 53.5 |
| | 1387.64 | 33% | 80% | | | | |
| | 2054.16 | 0% | 90% | | | | |
| 48 hours | 0 | 100% | 0% | 1 | | | |
| | 0 | 100% | 0% | 2 | na | na | na |
| | 0 | 100% | 0% | 3 | na | na | na |
| | 1072.35 | 0% | 70% | 4 | na | na | na |
| | 1387.64 | 0% | 80% | | | | |
| | 2054.16 | 0% | 90% | | | | |

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | na | na | na |
| | 0 | 100% | 0% | 3 | na | na | na |
| | 1196.63 | 11% | 70% | 4 | na | na | na |
| | 1520.87 | 0% | 81% | | | | |
| | 2196.01 | 0% | 90% | | | | |
| 24 hours | 37.4088 | 75% | 13% | 1 | | | |
| | 0 | 100% | 0% | 2 | 0.7 | 0.1 | 3.8 |
| | 0 | 100% | 0% | 3 | 1.4 | 0.4 | 4.8 |
| | 1196.63 | 19% | 70% | 4 | 2.7 | 0.9 | 7.8 |
| | 1520.87 | 19% | 81% | | | | |
| | 2196.01 | 13% | 90% | | | | |
| 48 hours | 0 | 100% | 0% | 1 | | | |
| | 0 | 100% | 0% | 2 | 0.0 | 0.0 | na |
| | 0 | 100% | 0% | 3 | 1.0 | 0.0 | 56.8 |
| | 1196.63 | 67% | 70% | 4 | 1.0 | 0.0 | 55.0 |
| | 1520.87 | 33% | 81% | | | | |
| | 2196.01 | 0% | 90% | | | | |

Interleukin-1 receptor antagonist sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 3380.000 | 6570.000 | 3380.000 | 10535.000 | 3380.000 | 5395.000 |
| average | 18473.174 | 13573.633 | 18473.174 | 29502.139 | 18473.174 | 19108.222 |
| stdev | 64699.888 | 18565.823 | 64699.888 | 75698.695 | 64699.888 | 29314.553 |
| p (t-test) | | 0.695 | | 0.334 | | 0.967 |
| min | 77.800 | 48.100 | 77.800 | 174.000 | 77.800 | 170.000 |
| max | 598080.000 | 90800.000 | 598080.000 | 439392.000 | 598080.000 | 110000.000 |
| n (Samp) | 419 | 27 | 419 | 36 | 419 | 18 |
| n (Pat) | 164 | 27 | 164 | 36 | 164 | 18 |

Fig. 2 Continued sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 3975.000 | 18900.000 | 3975.000 | 17500.000 | 3975.000 | 9930.000 |
| average | 17981.210 | 17744.000 | 17981.210 | 76661.444 | 17981.210 | 39967.143 |
| stdev | 59014.585 | 15169.966 | 59014.585 | 148431.654 | 59014.585 | 51636.218 |
| p (t-test) |  | 0.993 |  | 0.005 |  | 0.327 |
| min | 48.100 | 1560.000 | 48.100 | 801.000 | 48.100 | 1950.000 |
| max | 598080.000 | 34300.000 | 598080.000 | 439392.000 | 598080.000 | 117000.000 |
| n (Samp) | 518 | 5 | 518 | 9 | 518 | 7 |
| n (Pat) | 199 | 5 | 199 | 9 | 199 | 7 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 3710.000 | 6570.000 | 3710.000 | 11200.000 | 3710.000 | 5395.000 |
| average | 17979.068 | 12852.235 | 17979.068 | 20017.467 | 17979.068 | 39774.375 |
| stdev | 62581.890 | 18455.320 | 62581.890 | 30373.747 | 62581.890 | 108185.034 |
| p (t-test) |  | 0.678 |  | 0.860 |  | 0.191 |
| min | 77.800 | 48.100 | 77.800 | 174.000 | 77.800 | 170.000 |
| max | 598080.000 | 90800.000 | 598080.000 | 127000.000 | 598080.000 | 439392.000 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
| --- | --- | --- | --- | --- | --- |
| 0 hours | 0.63 | 0.059 | 419 | 27 | 0.024 |
| 24 hours | 0.65 | 0.051 | 419 | 36 | 0.003 |
| 48 hours | 0.58 | 0.072 | 419 | 18 | 0.263 | sCr only

| Time prior AKI stage | AUC | SE | nCohort 1 | nCohort 2 | p |
| --- | --- | --- | --- | --- | --- |
| 0 hours | 0.67 | 0.134 | 518 | 5 | 0.198 |
| 24 hours | 0.62 | 0.101 | 518 | 9 | 0.251 |
| 48 hours | 0.67 | 0.113 | 518 | 7 | 0.123 |

UO only

| Time prior AKI stage | AUC | SE | nCohort 1 | nCohort 2 | p |
| --- | --- | --- | --- | --- | --- |
| 0 hours | 0.63 | 0.060 | 352 | 26 | 0.034 |
| 24 hours | 0.67 | 0.056 | 352 | 30 | 0.002 |
| 48 hours | 0.57 | 0.076 | 352 | 16 | 0.378 | sCr or UO

| Time prior AKI stage | Cutoff value | sens | spec | Quartile | OR | 95% CI of OR | |
| --- | --- | --- | --- | --- | --- | --- | --- |
| 0 hours | 4240 | 70% | 56% | 1 |  |  |  |
|  | 3130 | 81% | 48% | 2 | 2.0 | 0.4 | 9.1 |
|  | 1540 | 93% | 29% | 3 | 6.6 | 2.0 | 21.5 |
|  | 7730 | 41% | 70% | 4 | 4.8 | 1.4 | 16.4 |
|  | 13400 | 33% | 80% |  |  |  |  |
|  | 28700 | 15% | 90% |  |  |  |  |
| 24 hours | 3280 | 72% | 49% | 1 |  |  |  |
|  | 2130 | 81% | 39% | 2 | 2.1 | 1.0 | 4.4 |
|  | 1360 | 92% | 26% | 3 | 1.5 | 0.6 | 3.6 |
|  | 7730 | 53% | 70% | 4 | 5.1 | 2.7 | 9.7 |
|  | 13400 | 42% | 80% |  |  |  |  |
|  | 28700 | 14% | 90% |  |  |  |  |

Fig. 2 Continued

| | | | | | | | |
|---|---|---|---|---|---|---|---|
| 48 hours | 2440 | 72% | 42% | 1 | | | |
| | 1920 | 83% | 37% | 2 | 1.7 | 0.6 | 5.0 |
| | 567 | 94% | 8% | 3 | 1.3 | 0.4 | 4.4 |
| | 7730 | 39% | 70% | 4 | 2.0 | 0.7 | 5.6 |
| | 13400 | 28% | 80% | | | | |
| | 28700 | 28% | 90% | | | | | sCr only

| Time prior AKI stage | Cutoff value | sens | spec | Quartile | OR | 95% CI of OR | |
|---|---|---|---|---|---|---|---|
| 0 hours | 3130 | 80% | 44% | 1 | | | |
| | 3130 | 80% | 44% | 2 | na | na | na |
| | 1540 | 100% | 27% | 3 | na | na | na |
| | 8790 | 60% | 70% | 4 | na | na | na |
| | 15000 | 60% | 80% | | | | |
| | 31600 | 20% | 90% | | | | |
| 24 hours | 1630 | 78% | 29% | 1 | | | |
| | 1360 | 89% | 24% | 2 | 1.0 | 0.1 | 7.3 |
| | 794 | 100% | 14% | 3 | 0.0 | 0.0 | na |
| | 8790 | 56% | 70% | 4 | 2.5 | 0.6 | 10.3 |
| | 15000 | 56% | 80% | | | | |
| | 31600 | 22% | 90% | | | | |
| 48 hours | 2680 | 71% | 41% | 1 | | | |
| | 2450 | 86% | 39% | 2 | na | na | na |
| | 1920 | 100% | 34% | 3 | na | na | na |
| | 8790 | 57% | 70% | 4 | na | na | na |
| | 15000 | 43% | 80% | | | | |
| | 31600 | 43% | 90% | | | | |

UO only

| Time prior AKI stage | Cutoff value | sens | spec | Quartile | OR | 95% CI of OR | |
|---|---|---|---|---|---|---|---|
| 0 hours | 4240 | 73% | 54% | 1 | | | |
| | 3650 | 81% | 49% | 2 | 2.6 | 0.6 | 10.5 |
| | 1650 | 92% | 30% | 3 | 6.1 | 1.8 | 20.3 |
| | 7760 | 42% | 70% | 4 | 4.2 | 1.2 | 15.0 |
| | 14000 | 27% | 80% | | | | |
| | 27400 | 12% | 90% | | | | |
| 24 hours | 5340 | 70% | 60% | 1 | | | |
| | 3280 | 80% | 47% | 2 | 3.1 | 0.8 | 12.0 |
| | 2090 | 90% | 37% | 3 | 4.3 | 1.2 | 15.2 |
| | 7760 | 57% | 70% | 4 | 7.9 | 2.5 | 25.5 |
| | 14000 | 37% | 80% | | | | |
| | 27400 | 17% | 90% | | | | |
| 48 hours | 2440 | 75% | 40% | 1 | | | |
| | 2170 | 81% | 37% | 2 | 1.3 | 0.4 | 4.4 |
| | 557 | 94% | 7% | 3 | 1.3 | 0.4 | 4.4 |
| | 7760 | 38% | 70% | 4 | 1.7 | 0.6 | 5.1 |
| | 14000 | 25% | 80% | | | | |
| | 27400 | 25% | 90% | | | | |

Fig. 2 Continued

Interleukin-1 beta sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.991 | 1.510 | 0.991 | 3.160 | 0.991 | 1.895 |
| average | 4.746 | 5.247 | 4.746 | 14.456 | 4.746 | 8.765 |
| stdev | 33.607 | 11.335 | 33.607 | 37.808 | 33.607 | 16.054 |
| p (t-test) |  | 0.939 |  | 0.100 |  | 0.614 |
| min | 0.006 | 0.006 | 0.006 | 0.006 | 0.006 | 0.006 |
| max | 670.000 | 54.300 | 670.000 | 224.000 | 670.000 | 62.000 |
| n (Samp) | 419 | 27 | 419 | 36 | 419 | 18 |
| n (Pat) | 164 | 27 | 164 | 36 | 164 | 18 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1.125 | 1.510 | 1.125 | 3.810 | 1.125 | 5.820 |
| average | 5.521 | 3.384 | 5.521 | 6.703 | 5.521 | 12.682 |
| stdev | 32.018 | 4.191 | 32.018 | 10.166 | 32.018 | 22.053 |
| p (t-test) |  | 0.882 |  | 0.912 |  | 0.556 |
| min | 0.006 | 0.218 | 0.006 | 0.006 | 0.006 | 0.006 |
| max | 670.000 | 10.600 | 670.000 | 32.800 | 670.000 | 62.000 |
| n (Samp) | 518 | 5 | 518 | 9 | 518 | 7 |
| n (Pat) | 199 | 5 | 199 | 9 | 199 | 7 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1.060 | 1.605 | 1.060 | 2.855 | 1.060 | 1.900 |
| average | 5.135 | 5.410 | 5.135 | 15.752 | 5.135 | 7.626 |
| stdev | 36.463 | 11.522 | 36.463 | 41.083 | 36.463 | 11.585 |
| p (t-test) |  | 0.970 |  | 0.130 |  | 0.785 |
| min | 0.006 | 0.006 | 0.006 | 0.006 | 0.006 | 0.006 |
| max | 670.000 | 54.300 | 670.000 | 224.000 | 670.000 | 38.200 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
|---|---|---|---|---|---|
| 0 hours | 0.58 | 0.059 | 419 | 27 | 0.155 |
| 24 hours | 0.70 | 0.050 | 419 | 36 | 0.000 |
| 48 hours | 0.61 | 0.072 | 419 | 18 | 0.129 | sCr only

| Time prior AKI stage | AUC | SE | nCohort 1 | nCohort 2 | p |
|---|---|---|---|---|---|
| 0 hours | 0.58 | 0.134 | 518 | 5 | 0.552 |
| 24 hours | 0.65 | 0.101 | 518 | 9 | 0.145 |
| 48 hours | 0.68 | 0.113 | 518 | 7 | 0.112 |

UO only

| Time prior AKI stage | AUC | SE | nCohort 1 | nCohort 2 | p |
|---|---|---|---|---|---|
| 0 hours | 0.58 | 0.060 | 352 | 26 | 0.190 |
| 24 hours | 0.70 | 0.055 | 352 | 30 | 0.000 |
| 48 hours | 0.63 | 0.076 | 352 | 16 | 0.098 |

Fig. 2 Continued sCr or UO

| Time prior AKI stage | Cutoff value | sens | spec | Quartile | OR | 95% CI of OR | |
|---|---|---|---|---|---|---|---|
| 0 hours | 1.04 | 70% | 52% | 1 | | | |
| | 0.592 | 81% | 34% | 2 | 1.0 | 0.4 | 2.7 |
| | 0.204 | 93% | 11% | 3 | 2.9 | 1.5 | 6.0 |
| | 2 | 33% | 70% | 4 | 2.1 | 1.0 | 4.5 |
| | 3.11 | 22% | 81% | | | | |
| | 6.59 | 15% | 90% | | | | |
| 24 hours | 1.2 | 72% | 57% | 1 | | | |
| | 0.783 | 81% | 43% | 2 | 2.0 | 0.7 | 5.6 |
| | 0.501 | 92% | 29% | 3 | 2.4 | 0.9 | 6.3 |
| | 2 | 64% | 70% | 4 | 7.8 | 3.5 | 17.2 |
| | 3.11 | 50% | 81% | | | | |
| | 6.59 | 31% | 90% | | | | |
| 48 hours | 0.733 | 72% | 42% | 1 | | | |
| | 0.315 | 83% | 17% | 2 | 0.7 | 0.2 | 2.4 |
| | 0 | 100% | 0% | 3 | 0.7 | 0.2 | 2.4 |
| | 2 | 50% | 70% | 4 | 2.1 | 1.0 | 4.5 |
| | 3.11 | 44% | 81% | | | | |
| | 6.59 | 33% | 90% | | | | | sCr only

| Time prior AKI stage | Cutoff value | sens | spec | Quartile | OR | 95% CI of OR | |
|---|---|---|---|---|---|---|---|
| 0 hours | 1.22 | 80% | 52% | 1 | | | |
| | 1.22 | 80% | 52% | 2 | 0.0 | 0.0 | na |
| | 0.204 | 100% | 10% | 3 | 2.0 | 0.1 | 39.0 |
| | 2.39 | 40% | 70% | 4 | 2.0 | 0.1 | 39.0 |
| | 3.91 | 20% | 80% | | | | |
| | 9.92 | 20% | 90% | | | | |
| 24 hours | 0.783 | 78% | 39% | 1 | | | |
| | 0.508 | 89% | 26% | 2 | 2.0 | 0.1 | 39.0 |
| | 0 | 100% | 0% | 3 | 0.0 | 0.0 | na |
| | 2.39 | 67% | 70% | 4 | 6.2 | 0.6 | 62.8 |
| | 3.91 | 44% | 80% | | | | |
| | 9.92 | 11% | 90% | | | | |
| 48 hours | 2.68 | 71% | 74% | 1 | | | |
| | 0.695 | 86% | 36% | 2 | 1.0 | 0.0 | 51.9 |
| | 0 | 100% | 0% | 3 | 1.0 | 0.0 | 51.9 |
| | 2.39 | 71% | 70% | 4 | 4.1 | 0.3 | 48.5 |
| | 3.91 | 57% | 80% | | | | |
| | 9.92 | 29% | 90% | | | | |

UO only

| Time prior AKI stage | Cutoff value | sens | spec | Quartile | OR | 95% CI of OR | |
|---|---|---|---|---|---|---|---|
| 0 hours | 0.719 | 73% | 39% | 1 | | | |
| | 0.653 | 81% | 36% | 2 | 2.0 | 0.7 | 5.7 |
| | 0.355 | 92% | 17% | 3 | 3.6 | 1.5 | 8.8 |
| | 2.14 | 35% | 70% | 4 | 2.4 | 0.9 | 6.4 |
| | 3.24 | 19% | 80% | | | | |
| | 6.97 | 15% | 90% | | | | |
| 24 hours | 1.22 | 73% | 55% | 1 | | | |
| | 1.04 | 80% | 50% | 2 | 2.6 | 0.6 | 10.5 |
| | 0.668 | 90% | 36% | 3 | 4.9 | 1.4 | 16.8 |
| | 2.14 | 60% | 70% | 4 | 7.9 | 2.5 | 25.5 |
| | 3.24 | 47% | 80% | | | | |
| | 6.97 | 30% | 90% | | | | |

Fig. 2 Continued

| 48 hours | 0.951 | 75% | 46% | 1 | | | |
| --- | --- | --- | --- | --- | --- | --- | --- |
| | 0.733 | 81% | 39% | 2 | 1.0 | 0.3 | 3.9 |
| | 0.00584 | 94% | 7% | 3 | 1.0 | 0.3 | 3.9 |
| | 2.14 | 50% | 70% | 4 | 2.4 | 0.9 | 6.5 |
| | 3.24 | 44% | 80% | | | | |
| | 6.97 | 31% | 90% | | | | |

Interleukin-10 sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 1.460 | 1.610 | 1.460 | 1.270 | 1.460 | 1.755 |
| average | 2.513 | 1.580 | 2.513 | 4.307 | 2.513 | 2.820 |
| stdev | 14.653 | 1.217 | 14.653 | 18.158 | 14.653 | 5.676 |
| p (t-test) | | 0.741 | | 0.490 | | 0.930 |
| min | 0.062 | 0.062 | 0.062 | 0.062 | 0.062 | 0.062 |
| max | 230.000 | 4.410 | 230.000 | 110.000 | 230.000 | 25.000 |
| n (Samp) | 419 | 27 | 419 | 36 | 419 | 18 |
| n (Pat) | 164 | 27 | 164 | 36 | 164 | 18 | sCr only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 1.380 | 2.020 | 1.380 | 1.460 | 1.380 | 2.540 |
| average | 2.485 | 2.044 | 2.485 | 1.223 | 2.485 | 5.313 |
| stdev | 14.016 | 1.571 | 14.016 | 1.314 | 14.016 | 8.753 |
| p (t-test) | | 0.944 | | 0.787 | | 0.595 |
| min | 0.062 | 0.062 | 0.062 | 0.062 | 0.062 | 0.062 |
| max | 230.000 | 4.410 | 230.000 | 3.930 | 230.000 | 25.000 |
| n (Samp) | 518 | 5 | 518 | 9 | 518 | 7 |
| n (Pat) | 199 | 5 | 199 | 9 | 199 | 7 |

UO only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 1.470 | 1.430 | 1.470 | 1.350 | 1.470 | 1.580 |
| average | 2.843 | 1.543 | 2.843 | 5.072 | 2.843 | 1.691 |
| stdev | 16.014 | 1.405 | 16.014 | 19.858 | 16.014 | 1.439 |
| p (t-test) | | 0.680 | | 0.474 | | 0.774 |
| min | 0.062 | 0.062 | 0.062 | 0.062 | 0.062 | 0.062 |
| max | 230.000 | 5.720 | 230.000 | 110.000 | 230.000 | 4.410 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
| --- | --- | --- | --- | --- | --- |
| 0 hours | 0.54 | 0.059 | 419 | 27 | 0.480 |
| 24 hours | 0.47 | 0.049 | 419 | 36 | 0.573 |
| 48 hours | 0.56 | 0.071 | 419 | 18 | 0.419 | sCr only

| Time prior AKI stage | AUC | SE | nCohort 1 | nCohort 2 | p |
| --- | --- | --- | --- | --- | --- |
| 0 hours | 0.65 | 0.135 | 518 | 5 | 0.279 |
| 24 hours | 0.45 | 0.094 | 518 | 9 | 0.610 |
| 48 hours | 0.72 | 0.110 | 518 | 7 | 0.046 |

Fig. 2 Continued

UO only

| Time prior AKI stage | AUC | SE | nCohort 1 | nCohort 2 | p |
|---|---|---|---|---|---|
| 0 hours | 0.50 | 0.059 | 352 | 26 | 0.952 |
| 24 hours | 0.49 | 0.055 | 352 | 30 | 0.908 |
| 48 hours | 0.54 | 0.075 | 352 | 16 | 0.598 | sCr or UO

| Time prior AKI stage | Cutoff value | sens | spec | Quartile | OR | 95% CI of OR | |
|---|---|---|---|---|---|---|---|
| 0 hours | 0.992 | 70% | 35% | 1 | | | |
| | 0 | 100% | 0% | 2 | 2.1 | 1.0 | 4.5 |
| | 0 | 100% | 0% | 3 | 1.5 | 0.7 | 3.6 |
| | 1.92 | 41% | 71% | 4 | 2.3 | 1.1 | 4.9 |
| | 2.22 | 30% | 80% | | | | |
| | 2.84 | 11% | 90% | | | | |
| 24 hours | 0 | 100% | 0% | 1 | | | |
| | 0 | 100% | 0% | 2 | 0.8 | 0.4 | 1.3 |
| | 0 | 100% | 0% | 3 | 0.8 | 0.4 | 1.3 |
| | 1.92 | 28% | 71% | 4 | 1.5 | 1.0 | 2.3 |
| | 2.22 | 22% | 80% | | | | |
| | 2.84 | 17% | 90% | | | | |
| 48 hours | 0 | 100% | 0% | 1 | | | |
| | 0 | 100% | 0% | 2 | 0.3 | 0.1 | 1.2 |
| | 0 | 100% | 0% | 3 | 0.3 | 0.1 | 1.2 |
| | 1.92 | 50% | 71% | 4 | 1.3 | 0.7 | 2.5 |
| | 2.22 | 44% | 80% | | | | |
| | 2.84 | 17% | 90% | | | | | sCr only

| Time prior AKI stage | Cutoff value | sens | spec | Quartile | OR | 95% CI of OR | |
|---|---|---|---|---|---|---|---|
| 0 hours | 1.48 | 80% | 54% | 1 | | | |
| | 1.48 | 80% | 54% | 2 | 0.0 | 0.0 | na |
| | 0 | 100% | 0% | 3 | 1.0 | 0.0 | 51.5 |
| | 1.91 | 60% | 70% | 4 | 3.0 | 0.2 | 42.5 |
| | 2.22 | 40% | 80% | | | | |
| | 2.82 | 20% | 90% | | | | |
| 24 hours | 0 | 100% | 0% | 1 | | | |
| | 0 | 100% | 0% | 2 | 4.1 | 0.3 | 48.9 |
| | 0 | 100% | 0% | 3 | 0.0 | 0.0 | na |
| | 1.91 | 22% | 70% | 4 | 4.1 | 0.3 | 49.3 |
| | 2.22 | 11% | 80% | | | | |
| | 2.82 | 11% | 90% | | | | |
| 48 hours | 1.93 | 71% | 72% | 1 | | | |
| | 1.33 | 86% | 48% | 2 | 1.0 | 0.0 | 51.9 |
| | 0 | 100% | 0% | 3 | 1.0 | 0.0 | 51.9 |
| | 1.91 | 71% | 70% | 4 | 4.1 | 0.3 | 48.5 |
| | 2.22 | 57% | 80% | | | | |
| | 2.82 | 29% | 90% | | | | |

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.6 | 0.3 | 1.2 |
| | 0 | 100% | 0% | 3 | 0.6 | 0.3 | 1.2 |
| | 1.95 | 31% | 71% | 4 | 1.0 | 0.6 | 1.7 |
| | 2.34 | 27% | 80% | | | | |
| | 2.9 | 12% | 90% | | | | |

Fig. 2 Continued

| 24 hours | 0.913 | 70% | 29% | 1 | | | |
| | 0 | 100% | 0% | 2 | 0.7 | 0.4 | 1.4 |
| | 0 | 100% | 0% | 3 | 0.9 | 0.5 | 1.5 |
| | 1.95 | 30% | 71% | 4 | 1.2 | 0.7 | 1.9 |
| | 2.34 | 27% | 80% | | | | |
| | 2.9 | 20% | 90% | | | | |
| 48 hours | 0 | 100% | 0% | 1 | | | |
| | 0 | 100% | 0% | 2 | 0.4 | 0.1 | 1.6 |
| | 0 | 100% | 0% | 3 | 0.4 | 0.1 | 1.6 |
| | 1.95 | 44% | 71% | 4 | 1.4 | 0.7 | 2.9 |
| | 2.34 | 38% | 80% | | | | |
| | 2.9 | 19% | 90% | | | | |

Interleukin-15 sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 0.127 | 0.111 | 0.127 | 0.147 | 0.127 | 0.177 |
| average | 0.130 | 0.130 | 0.130 | 0.128 | 0.130 | 0.165 |
| stdev | 0.086 | 0.115 | 0.086 | 0.085 | 0.086 | 0.108 |
| p (t-test) | | 0.973 | | 0.886 | | 0.101 |
| min | 0.005 | 0.005 | 0.005 | 0.005 | 0.005 | 0.005 |
| max | 0.451 | 0.364 | 0.451 | 0.283 | 0.451 | 0.348 |
| n (Samp) | 419 | 27 | 419 | 36 | 419 | 18 |
| n (Pat) | 164 | 27 | 164 | 36 | 164 | 18 | sCr only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 0.130 | 0.217 | 0.130 | 0.147 | 0.130 | 0.249 |
| average | 0.129 | 0.227 | 0.129 | 0.153 | 0.129 | 0.192 |
| stdev | 0.087 | 0.110 | 0.087 | 0.065 | 0.087 | 0.101 |
| p (t-test) | | 0.013 | | 0.419 | | 0.061 |
| min | 0.005 | 0.100 | 0.005 | 0.071 | 0.005 | 0.023 |
| max | 0.451 | 0.364 | 0.451 | 0.255 | 0.451 | 0.269 |
| n (Samp) | 518 | 5 | 518 | 9 | 518 | 7 |
| n (Pat) | 199 | 5 | 199 | 9 | 199 | 7 |

UO only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 0.124 | 0.097 | 0.124 | 0.148 | 0.124 | 0.177 |
| average | 0.132 | 0.117 | 0.132 | 0.124 | 0.132 | 0.175 |
| stdev | 0.090 | 0.112 | 0.090 | 0.088 | 0.090 | 0.106 |
| p (t-test) | | 0.433 | | 0.650 | | 0.067 |
| min | 0.005 | 0.005 | 0.005 | 0.005 | 0.005 | 0.005 |
| max | 0.509 | 0.348 | 0.509 | 0.283 | 0.509 | 0.348 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
| --- | --- | --- | --- | --- | --- |
| 0 hours | 0.47 | 0.056 | 419 | 27 | 0.615 |
| 24 hours | 0.50 | 0.050 | 419 | 36 | 0.951 |
| 48 hours | 0.61 | 0.072 | 419 | 18 | 0.143 |

Fig. 2 Continued sCr only

| Time prior AKI stage | AUC | SE | nCohort 1 | nCohort 2 | p |
|---|---|---|---|---|---|
| 0 hours | 0.75 | 0.128 | 518 | 5 | 0.053 |
| 24 hours | 0.59 | 0.101 | 518 | 9 | 0.364 |
| 48 hours | 0.71 | 0.111 | 518 | 7 | 0.056 |

UO only

| Time prior AKI stage | AUC | SE | nCohort 1 | nCohort 2 | p |
|---|---|---|---|---|---|
| 0 hours | 0.43 | 0.056 | 352 | 26 | 0.226 |
| 24 hours | 0.49 | 0.055 | 352 | 30 | 0.817 |
| 48 hours | 0.63 | 0.076 | 352 | 16 | 0.097 | sCr or UO

| Time prior AKI stage | Cutoff value | sens | spec | Quartile | OR | 95% CI of OR | |
|---|---|---|---|---|---|---|---|
| 0 hours | 0.0209 | 70% | 15% | 1 | | | |
| | 0.00512 | 81% | 11% | 2 | 0.9 | 0.5 | 1.6 |
| | 0 | 100% | 0% | 3 | 0.4 | 0.2 | 1.1 |
| | 0.176 | 26% | 71% | 4 | 1.7 | 1.0 | 2.7 |
| | 0.199 | 26% | 80% | | | | |
| | 0.247 | 19% | 90% | | | | |
| 24 hours | 0.0722 | 72% | 27% | 1 | | | |
| | 0.0176 | 81% | 15% | 2 | 0.6 | 0.3 | 1.0 |
| | 0 | 100% | 0% | 3 | 1.1 | 0.7 | 1.7 |
| | 0.176 | 25% | 71% | 4 | 0.9 | 0.6 | 1.4 |
| | 0.199 | 19% | 80% | | | | |
| | 0.247 | 14% | 90% | | | | |
| 48 hours | 0.133 | 72% | 53% | 1 | | | |
| | 0.0176 | 83% | 15% | 2 | 0.2 | 0.0 | 2.9 |
| | 0 | 100% | 0% | 3 | 1.3 | 0.5 | 3.2 |
| | 0.176 | 50% | 71% | 4 | 2.1 | 1.0 | 4.5 |
| | 0.199 | 39% | 80% | | | | |
| | 0.247 | 22% | 90% | | | | | sCr only

| Time prior AKI stage | Cutoff value | sens | spec | Quartile | OR | 95% CI of OR | |
|---|---|---|---|---|---|---|---|
| 0 hours | 0.144 | 80% | 54% | 1 | | | |
| | 0.144 | 80% | 54% | 2 | na | na | na |
| | 0.0979 | 100% | 38% | 3 | na | na | na |
| | 0.174 | 60% | 70% | 4 | na | na | na |
| | 0.199 | 60% | 81% | | | | |
| | 0.248 | 40% | 90% | | | | |
| 24 hours | 0.116 | 78% | 46% | 1 | | | |
| | 0.0722 | 89% | 28% | 2 | na | na | na |
| | 0.0688 | 100% | 26% | 3 | na | na | na |
| | 0.174 | 33% | 70% | 4 | na | na | na |
| | 0.199 | 33% | 81% | | | | |
| | 0.248 | 11% | 90% | | | | |
| 48 hours | 0.217 | 71% | 85% | 1 | | | |
| | 0.0688 | 86% | 26% | 2 | 1.0 | 0.0 | 51.9 |
| | 0.0209 | 100% | 17% | 3 | 0.0 | 0.0 | na |
| | 0.174 | 71% | 70% | 4 | 5.1 | 0.5 | 55.4 |
| | 0.199 | 71% | 81% | | | | |
| | 0.248 | 57% | 90% | | | | |

Fig. 2 Continued

UO only

| Time prior AKI stage | Cutoff value | sens | spec | Quartile | OR | 95% CI of OR | |
|---|---|---|---|---|---|---|---|
| 0 hours | 0.0161 | 73% | 13% | 1 | | | |
| | 0 | 100% | 0% | 2 | 0.8 | 0.4 | 1.8 |
| | 0 | 100% | 0% | 3 | 0.8 | 0.4 | 1.8 |
| | 0.179 | 23% | 70% | 4 | 1.8 | 1.0 | 3.1 |
| | 0.202 | 23% | 80% | | | | |
| | 0.249 | 15% | 90% | | | | |
| 24 hours | 0.0729 | 70% | 31% | 1 | | | |
| | 0.0161 | 80% | 13% | 2 | 1.5 | 0.9 | 2.5 |
| | 0 | 100% | 0% | 3 | 0.6 | 0.2 | 1.2 |
| | 0.179 | 23% | 70% | 4 | 1.3 | 0.8 | 2.3 |
| | 0.202 | 17% | 80% | | | | |
| | 0.249 | 7% | 90% | | | | |
| 48 hours | 0.133 | 81% | 53% | 1 | | | |
| | 0.133 | 81% | 53% | 2 | 0.0 | 0.0 | na |
| | 0 | 100% | 0% | 3 | 2.4 | 0.9 | 6.5 |
| | 0.179 | 50% | 70% | 4 | 2.1 | 0.7 | 5.8 |
| | 0.202 | 38% | 80% | | | | |
| | 0.249 | 19% | 90% | | | | |

Interleukin-3 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.027 | 0.035 | 0.027 | 0.029 | 0.027 | 0.032 |
| average | 0.029 | 0.033 | 0.029 | 0.037 | 0.029 | 0.030 |
| stdev | 0.024 | 0.023 | 0.024 | 0.042 | 0.024 | 0.025 |
| p (t-test) | | 0.411 | | 0.101 | | 0.847 |
| min | 0.001 | 0.003 | 0.001 | 0.001 | 0.001 | 0.001 |
| max | 0.192 | 0.098 | 0.192 | 0.227 | 0.192 | 0.081 |
| n (Samp) | 419 | 27 | 419 | 36 | 419 | 18 |
| n (Pat) | 164 | 27 | 164 | 36 | 164 | 18 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.027 | 0.051 | 0.027 | 0.039 | 0.027 | 0.051 |
| average | 0.030 | 0.062 | 0.030 | 0.039 | 0.030 | 0.043 |
| stdev | 0.025 | 0.049 | 0.025 | 0.031 | 0.025 | 0.026 |
| p (t-test) | | 0.006 | | 0.263 | | 0.166 |
| min | 0.001 | 0.024 | 0.001 | 0.001 | 0.001 | 0.006 |
| max | 0.227 | 0.147 | 0.227 | 0.091 | 0.227 | 0.072 |
| n (Samp) | 518 | 5 | 518 | 9 | 518 | 7 |
| n (Pat) | 199 | 5 | 199 | 9 | 199 | 7 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.027 | 0.036 | 0.027 | 0.028 | 0.027 | 0.033 |
| average | 0.030 | 0.035 | 0.030 | 0.039 | 0.030 | 0.031 |
| stdev | 0.025 | 0.025 | 0.025 | 0.045 | 0.025 | 0.023 |
| p (t-test) | | 0.374 | | 0.090 | | 0.896 |
| min | 0.001 | 0.003 | 0.001 | 0.005 | 0.001 | 0.001 |
| max | 0.192 | 0.098 | 0.192 | 0.227 | 0.192 | 0.081 |
| n (Samp) | 352 | 26 | 352 | 30 | 352 | 16 |
| n (Pat) | 133 | 26 | 133 | 30 | 133 | 16 |

Fig. 2 Continued sCr or UO

| Time prior AKI stage | AUC | SE | nCohort 1 | nCohort 2 | p |
|---|---|---|---|---|---|
| 0 hours | 0.57 | 0.059 | 419 | 27 | 0.247 |
| 24 hours | 0.53 | 0.051 | 419 | 36 | 0.519 |
| 48 hours | 0.52 | 0.070 | 419 | 18 | 0.785 | sCr only

| Time prior AKI stage | AUC | SE | nCohort 1 | nCohort 2 | p |
|---|---|---|---|---|---|
| 0 hours | 0.76 | 0.126 | 518 | 5 | 0.041 |
| 24 hours | 0.60 | 0.101 | 518 | 9 | 0.300 |
| 48 hours | 0.69 | 0.112 | 518 | 7 | 0.087 |

UO only

| Time prior AKI stage | AUC | SE | nCohort 1 | nCohort 2 | p |
|---|---|---|---|---|---|
| 0 hours | 0.57 | 0.060 | 352 | 26 | 0.230 |
| 24 hours | 0.53 | 0.056 | 352 | 30 | 0.567 |
| 48 hours | 0.53 | 0.075 | 352 | 16 | 0.671 | sCr or UO

| Time prior AKI stage | Cutoff value | sens | spec | Quartile | OR | 95% CI of OR | |
|---|---|---|---|---|---|---|---|
| 0 hours | 0.0235 | 70% | 45% | 1 | | | |
| | 0.00814 | 81% | 25% | 2 | 1.0 | 0.4 | 2.3 |
| | 0.00275 | 96% | 11% | 3 | 1.9 | 1.0 | 3.6 |
| | 0.0388 | 41% | 70% | 4 | 1.6 | 0.8 | 3.2 |
| | 0.0465 | 22% | 80% | | | | |
| | 0.0579 | 7% | 90% | | | | |
| 24 hours | 0.00819 | 72% | 26% | 1 | | | |
| | 0.00585 | 83% | 20% | 2 | 0.7 | 0.4 | 1.1 |
| | 0.00464 | 94% | 16% | 3 | 0.8 | 0.5 | 1.3 |
| | 0.0388 | 36% | 70% | 4 | 1.1 | 0.7 | 1.7 |
| | 0.0465 | 25% | 80% | | | | |
| | 0.0579 | 17% | 90% | | | | |
| 48 hours | 0.00745 | 72% | 23% | 1 | | | |
| | 0.00616 | 83% | 20% | 2 | 0.2 | 0.0 | 1.6 |
| | 0 | 100% | 0% | 3 | 0.8 | 0.4 | 1.8 |
| | 0.0388 | 33% | 70% | 4 | 1.0 | 0.5 | 2.0 |
| | 0.0465 | 28% | 80% | | | | |
| | 0.0579 | 11% | 90% | | | | | sCr only

| Time prior AKI stage | Cutoff value | sens | spec | Quartile | OR | 95% CI of OR | |
|---|---|---|---|---|---|---|---|
| 0 hours | 0.0346 | 80% | 64% | 1 | | | |
| | 0.0346 | 80% | 64% | 2 | na | na | na |
| | 0.0235 | 100% | 44% | 3 | na | na | na |
| | 0.039 | 60% | 70% | 4 | na | na | na |
| | 0.0466 | 60% | 80% | | | | |
| | 0.0605 | 20% | 90% | | | | |
| 24 hours | 0.00647 | 78% | 21% | 1 | | | |
| | 0.00585 | 89% | 19% | 2 | 0.0 | 0.0 | na |
| | 0.00069 | 100% | 9% | 3 | 0.7 | 0.1 | 3.5 |
| | 0.039 | 44% | 70% | 4 | 1.3 | 0.4 | 4.3 |
| | 0.0466 | 33% | 80% | | | | |
| | 0.0605 | 22% | 90% | | | | |

Fig. 2 Continued

| 48 hours | 0.0491 | 71% | 83% | 1 | | | |
| | 0.00745 | 86% | 23% | 2 | 0.0 | 0.0 | na |
| | 0.00616 | 100% | 20% | 3 | 0.0 | 0.0 | na |
| | 0.039 | 71% | 70% | 4 | 2.5 | 0.6 | 10.3 |
| | 0.0466 | 71% | 80% | | | | |
| | 0.0605 | 14% | 90% | | | | |

UO only

| Time prior AKI stage | Cutoff value | sens | spec | Quartile | OR | 95% CI of OR | |
|---|---|---|---|---|---|---|---|
| 0 hours | 0.014 | 73% | 30% | 1 | | | |
| | 0.00814 | 81% | 24% | 2 | 0.5 | 0.2 | 1.3 |
| | 0.00275 | 96% | 11% | 3 | 1.6 | 0.9 | 2.8 |
| | 0.0391 | 46% | 70% | 4 | 1.3 | 0.7 | 2.5 |
| | 0.0467 | 19% | 80% | | | | |
| | 0.0618 | 12% | 90% | | | | |
| 24 hours | 0.0155 | 70% | 33% | 1 | | | |
| | 0.00647 | 80% | 19% | 2 | 0.9 | 0.5 | 1.5 |
| | 0.00464 | 97% | 14% | 3 | 0.7 | 0.4 | 1.4 |
| | 0.0391 | 33% | 70% | 4 | 1.1 | 0.7 | 1.9 |
| | 0.0467 | 27% | 80% | | | | |
| | 0.0618 | 17% | 90% | | | | |
| 48 hours | 0.00747 | 75% | 23% | 1 | | | |
| | 0.00616 | 81% | 18% | 2 | 0.0 | 0.0 | na |
| | 0 | 100% | 0% | 3 | 1.2 | 0.6 | 2.6 |
| | 0.0391 | 31% | 70% | 4 | 1.0 | 0.4 | 2.3 |
| | 0.0467 | 25% | 80% | | | | |
| | 0.0618 | 6% | 90% | | | | |

Myeloperoxidase sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1092.221 | 1642.464 | 1092.221 | 1172.517 | 1092.221 | 1521.247 |
| average | 1708.898 | 2748.279 | 1708.898 | 4407.701 | 1708.898 | 1790.668 |
| stdev | 2649.816 | 3531.553 | 2649.816 | 8175.246 | 2649.816 | 1322.724 |
| p (t-test) | | 0.082 | | 0.000 | | 0.897 |
| min | 0.000 | 531.882 | 0.000 | 0.000 | 0.000 | 835.148 |
| max | 30781.054 | 17848.765 | 30781.054 | 40151.357 | 30781.054 | 6702.334 |
| n (Samp) | 246 | 23 | 246 | 35 | 246 | 18 |
| n (Pat) | 159 | 23 | 159 | 35 | 159 | 18 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1169.240 | 1325.817 | 1169.240 | 935.531 | 1169.240 | 1720.303 |
| average | 2066.041 | 1325.817 | 2066.041 | 1060.921 | 2066.041 | 2932.435 |
| stdev | 3767.829 | 155.618 | 3767.829 | 448.270 | 3767.829 | 2316.395 |
| p (t-test) | | 0.782 | | 0.452 | | 0.545 |
| min | 0.000 | 1215.779 | 0.000 | 710.553 | 0.000 | 1238.108 |
| max | 40151.357 | 1435.855 | 40151.357 | 2099.103 | 40151.357 | 6702.334 |
| n (Samp) | 318 | 2 | 318 | 8 | 318 | 7 |
| n (Pat) | 188 | 2 | 188 | 8 | 188 | 7 |

Fig. 2 Continued

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1138.659 | 1642.464 | 1138.659 | 1535.295 | 1138.659 | 1470.951 |
| average | 1875.224 | 2762.433 | 1875.224 | 4972.712 | 1875.224 | 1451.551 |
| stdev | 2889.891 | 3525.747 | 2889.891 | 8718.181 | 2889.891 | 537.393 |
| p (t-test) | | 0.173 | | 0.000 | | 0.559 |
| min | 0.000 | 531.882 | 0.000 | 0.000 | 0.000 | 819.820 |
| max | 30781.054 | 17848.765 | 30781.054 | 40151.357 | 30781.054 | 2822.742 |
| n (Samp) | 212 | 23 | 212 | 30 | 212 | 16 |
| n (Pat) | 132 | 23 | 132 | 30 | 132 | 16 | sCr or UO

| Time prior AKI stage | AUC | SE | nCohort 1 | nCohort 2 | p |
|---|---|---|---|---|---|
| 0 hours | 0.69 | 0.063 | 246 | 23 | 0.003 |
| 24 hours | 0.60 | 0.053 | 246 | 35 | 0.063 |
| 48 hours | 0.65 | 0.072 | 246 | 18 | 0.036 | sCr only

| Time prior AKI stage | AUC | SE | nCohort 1 | nCohort 2 | p |
|---|---|---|---|---|---|
| 0 hours | 0.57 | 0.212 | 318 | 2 | 0.736 |
| 24 hours | 0.39 | 0.093 | 318 | 8 | 0.252 |
| 48 hours | 0.74 | 0.109 | 318 | 7 | 0.027 |

UO only

| Time prior AKI stage | AUC | SE | nCohort 1 | nCohort 2 | p |
|---|---|---|---|---|---|
| 0 hours | 0.67 | 0.064 | 212 | 23 | 0.008 |
| 24 hours | 0.61 | 0.058 | 212 | 30 | 0.047 |
| 48 hours | 0.58 | 0.077 | 212 | 16 | 0.293 | sCr or UO

| Time prior AKI stage | Cutoff value | sens | spec | Quartile | OR | 95% CI of OR | |
|---|---|---|---|---|---|---|---|
| 0 hours | 1210.27 | 78% | 57% | 1 | | | |
| | 1087.76 | 83% | 50% | 2 | 1.5 | 0.3 | 8.3 |
| | 803.653 | 91% | 29% | 3 | 5.0 | 1.4 | 17.8 |
| | 1540.62 | 57% | 70% | 4 | 5.0 | 1.4 | 17.5 |
| | 1964.73 | 39% | 80% | | | | |
| | 2999.49 | 30% | 90% | | | | |
| 24 hours | 893.745 | 71% | 37% | 1 | | | |
| | 835.148 | 83% | 33% | 2 | 3.4 | 1.7 | 7.0 |
| | 709.902 | 91% | 23% | 3 | 1.5 | 0.6 | 3.7 |
| | 1540.62 | 46% | 70% | 4 | 3.7 | 1.8 | 7.5 |
| | 1964.73 | 34% | 80% | | | | |
| | 2999.49 | 29% | 90% | | | | |
| 48 hours | 1225.94 | 72% | 57% | 1 | | | |
| | 1039.96 | 83% | 48% | 2 | na | na | na |
| | 922.638 | 94% | 38% | 3 | na | na | na |
| | 1540.62 | 44% | 70% | 4 | na | na | na |
| | 1964.73 | 17% | 80% | | | | |
| | 2999.49 | 6% | 90% | | | | |

Fig. 2 Continued sCr only

| Time prior AKI stage | Cutoff value | sens | spec | Quartile | OR | 95% CI of OR | |
|---|---|---|---|---|---|---|---|
| 0 hours | 1210.27 | 100% | 52% | 1 | | | |
| | 1210.27 | 100% | 52% | 2 | na | na | na |
| | 1210.27 | 100% | 52% | 3 | na | na | na |
| | 1710.25 | 0% | 70% | 4 | na | na | na |
| | 2296.75 | 0% | 80% | | | | |
| | 3386.09 | 0% | 90% | | | | |
| 24 hours | 803.653 | 75% | 25% | 1 | | | |
| | 744.986 | 88% | 22% | 2 | 1.0 | 0.0 | 53.6 |
| | 709.902 | 100% | 19% | 3 | 4.2 | 0.3 | 50.6 |
| | 1710.25 | 13% | 70% | 4 | 2.1 | 0.1 | 40.7 |
| | 2296.75 | 0% | 80% | | | | |
| | 3386.09 | 0% | 90% | | | | |
| 48 hours | 1642.46 | 71% | 69% | 1 | | | |
| | 1341.77 | 86% | 58% | 2 | na | na | na |
| | 1225.94 | 100% | 53% | 3 | na | na | na |
| | 1710.25 | 57% | 70% | 4 | na | na | na |
| | 2296.75 | 29% | 80% | | | | |
| | 3386.09 | 29% | 90% | | | | |

UO only

| Time prior AKI stage | Cutoff value | sens | spec | Quartile | OR | 95% CI of OR | |
|---|---|---|---|---|---|---|---|
| 0 hours | 1253.57 | 74% | 57% | 1 | | | |
| | 1087.76 | 83% | 48% | 2 | 0.6 | 0.1 | 3.5 |
| | 803.653 | 91% | 26% | 3 | 3.3 | 1.3 | 8.5 |
| | 1681.71 | 48% | 70% | 4 | 3.3 | 1.3 | 8.5 |
| | 2252.46 | 39% | 80% | | | | |
| | 3402.16 | 17% | 90% | | | | |
| 24 hours | 925.931 | 70% | 41% | 1 | | | |
| | 872.465 | 80% | 32% | 2 | 2.1 | 0.9 | 4.7 |
| | 755.054 | 90% | 24% | 3 | 1.8 | 0.8 | 4.3 |
| | 1681.71 | 43% | 70% | 4 | 3.1 | 1.5 | 6.5 |
| | 2252.46 | 37% | 80% | | | | |
| | 3402.16 | 27% | 90% | | | | |
| 48 hours | 1039.96 | 75% | 47% | 1 | | | |
| | 925.931 | 81% | 41% | 2 | na | na | na |
| | 819.82 | 94% | 30% | 3 | na | na | na |
| | 1681.71 | 25% | 70% | 4 | na | na | na |
| | 2252.46 | 6% | 80% | | | | |
| | 3402.16 | 0% | 90% | | | | |

Fig. 2 Continued

Nidogen-1 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1619.718 | 1811.881 | 1619.718 | 1544.601 | 1619.718 | 3251.613 |
| average | 2056.796 | 1833.390 | 2056.796 | 1955.591 | 2056.796 | 2507.388 |
| stdev | 1501.778 | 1229.701 | 1501.778 | 1235.708 | 1501.778 | 2045.825 |
| p (t-test) |  | 0.662 |  | 0.784 |  | 0.609 |
| min | 14.333 | 0.280 | 14.333 | 204.762 | 14.333 | 193.627 |
| max | 4988.372 | 3440.860 | 4988.372 | 4569.767 | 4988.372 | 4076.923 |
| n (Samp) | 154 | 9 | 154 | 18 | 154 | 3 |
| n (Pat) | 87 | 9 | 87 | 18 | 87 | 3 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1649.452 | 0.280 | 1649.452 | 4132.479 | 1649.452 | 2284.362 |
| average | 2030.985 | 3991.398 | 2030.985 | 3974.915 | 2030.985 | 2284.362 |
| stdev | 1449.358 | na | 1449.358 | 643.460 | 1449.358 | 1367.899 |
| p (t-test) |  | na |  | 0.008 |  | 0.806 |
| min | 0.280 | 3991.398 | 0.280 | 3064.935 | 0.280 | 1317.111 |
| max | 4988.372 | 3991.398 | 4988.372 | 4569.767 | 4988.372 | 3251.613 |
| n (Samp) | 185 | 1 | 185 | 4 | 185 | 2 |
| n (Pat) | 106 | 1 | 106 | 4 | 106 | 2 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1562.009 | 1811.881 | 1562.009 | 1513.302 | 1562.009 | 4076.923 |
| average | 1927.815 | 1833.390 | 1927.815 | 1560.633 | 1927.815 | 2946.773 |
| stdev | 1452.031 | 1229.701 | 1452.031 | 834.970 | 1452.031 | 2396.994 |
| p (t-test) |  | 0.850 |  | 0.325 |  | 0.238 |
| min | 76.493 | 0.280 | 76.493 | 204.762 | 76.493 | 193.627 |
| max | 4988.372 | 3440.860 | 4988.372 | 3957.265 | 4988.372 | 4569.767 |
| n (Samp) | 123 | 9 | 123 | 16 | 123 | 3 |
| n (Pat) | 70 | 9 | 70 | 16 | 70 | 3 | sCr or UO

| Time prior AKI stage | AUC | SE | nCohort 1 | nCohort 2 | p |
|---|---|---|---|---|---|
| 0 hours | 0.46 | 0.096 | 154 | 9 | 0.670 |
| 24 hours | 0.52 | 0.073 | 154 | 18 | 0.819 |
| 48 hours | 0.54 | 0.172 | 154 | 3 | 0.821 | sCr only

| Time prior AKI stage | AUC | SE | nCohort 1 | nCohort 2 | p |
|---|---|---|---|---|---|
| 0 hours | 0.86 | 0.235 | 185 | 1 | 0.124 |
| 24 hours | 0.86 | 0.117 | 185 | 4 | 0.002 |
| 48 hours | 0.57 | 0.213 | 185 | 2 | 0.731 |

UO only

| Time prior AKI stage | AUC | SE | nCohort 1 | nCohort 2 | p |
|---|---|---|---|---|---|
| 0 hours | 0.49 | 0.099 | 123 | 9 | 0.888 |
| 24 hours | 0.48 | 0.076 | 123 | 16 | 0.774 |
| 48 hours | 0.62 | 0.175 | 123 | 3 | 0.492 |

Fig. 2 Continued sCr or UO

| Time prior AKI stage | Cutoff value | sens | spec | Quartile | OR | 95% CI of OR | |
|---|---|---|---|---|---|---|---|
| 0 hours | 992.611 | 78% | 36% | 1 | | | |
| | 200.806 | 89% | 5% | 2 | 5.6 | 0.5 | 64.7 |
| | 0 | 100% | 0% | 3 | 1.0 | 0.0 | 55.6 |
| | 3131.18 | 11% | 70% | 4 | 2.1 | 0.1 | 44.0 |
| | 3844.16 | 0% | 81% | | | | |
| | 4186.05 | 0% | 90% | | | | |
| 24 hours | 1467.82 | 72% | 47% | 1 | | | |
| | 977.723 | 83% | 34% | 2 | 4.7 | 1.2 | 17.7 |
| | 590.062 | 94% | 22% | 3 | 2.7 | 0.6 | 11.7 |
| | 3131.18 | 17% | 70% | 4 | 1.5 | 0.3 | 8.7 |
| | 3844.16 | 17% | 81% | | | | |
| | 4186.05 | 11% | 90% | | | | |
| 48 hours | 187.903 | 100% | 4% | 1 | | | |
| | 187.903 | 100% | 4% | 2 | 0.0 | 0.0 | na |
| | 187.903 | 100% | 4% | 3 | 1.0 | 0.0 | 55.9 |
| | 3131.18 | 67% | 70% | 4 | 1.0 | 0.0 | 54.4 |
| | 3844.16 | 33% | 81% | | | | |
| | 4186.05 | 0% | 90% | | | | |

UO only

| Time prior AKI stage | Cutoff value | sens | spec | Quartile | OR | 95% CI of OR | |
|---|---|---|---|---|---|---|---|
| 0 hours | 992.611 | 78% | 37% | 1 | | | |
| | 200.806 | 89% | 4% | 2 | 5.7 | 0.5 | 68.5 |
| | 0 | 100% | 0% | 3 | 1.0 | 0.0 | 57.0 |
| | 2860.47 | 22% | 71% | 4 | 2.1 | 0.1 | 44.2 |
| | 3569.89 | 0% | 80% | | | | |
| | 4139.53 | 0% | 90% | | | | |
| 24 hours | 992.611 | 75% | 37% | 1 | | | |
| | 977.723 | 81% | 36% | 2 | 7.0 | 0.6 | 78.5 |
| | 590.062 | 94% | 23% | 3 | 8.5 | 0.8 | 90.7 |
| | 2860.47 | 6% | 71% | 4 | 2.1 | 0.1 | 45.3 |
| | 3569.89 | 6% | 80% | | | | |
| | 4139.53 | 0% | 90% | | | | |
| 48 hours | 181.452 | 100% | 3% | 1 | | | |
| | 181.452 | 100% | 3% | 2 | 0.0 | 0.0 | na |
| | 181.452 | 100% | 3% | 3 | 0.0 | 0.0 | na |
| | 2860.47 | 67% | 71% | 4 | 2.0 | 0.1 | 43.1 |
| | 3569.89 | 67% | 80% | | | | |
| | 4139.53 | 33% | 90% | | | | |

Fig. 2 Continued

Oxidized low-density lipoprotein receptor 1 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 23.413 | 28.970 | 23.413 | 31.563 | 23.413 | 20.299 |
| average | 31.706 | 39.566 | 31.706 | 47.152 | 31.706 | 33.203 |
| stdev | 29.485 | 33.219 | 29.485 | 44.696 | 29.485 | 34.042 |
| p (t-test) |  | 0.228 |  | 0.007 |  | 0.837 |
| min | 0.150 | 1.495 | 0.150 | 0.621 | 0.150 | 2.090 |
| max | 148.195 | 109.060 | 148.195 | 187.691 | 148.195 | 121.257 |
| n (Samp) | 246 | 23 | 246 | 35 | 246 | 18 |
| n (Pat) | 159 | 23 | 159 | 35 | 159 | 18 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 24.309 | 16.852 | 24.309 | 31.828 | 24.309 | 26.557 |
| average | 35.059 | 16.852 | 35.059 | 33.037 | 35.059 | 47.585 |
| stdev | 34.672 | 11.213 | 34.672 | 19.732 | 34.672 | 42.883 |
| p (t-test) |  | 0.459 |  | 0.870 |  | 0.347 |
| min | 0.150 | 8.923 | 0.150 | 4.511 | 0.150 | 4.003 |
| max | 214.368 | 24.782 | 214.368 | 64.291 | 214.368 | 121.257 |
| n (Samp) | 318 | 2 | 318 | 8 | 318 | 7 |
| n (Pat) | 188 | 2 | 188 | 8 | 188 | 7 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 24.145 | 36.438 | 24.145 | 32.098 | 24.145 | 20.299 |
| average | 30.960 | 41.584 | 30.960 | 51.204 | 30.960 | 27.386 |
| stdev | 27.075 | 32.736 | 27.075 | 48.648 | 27.075 | 24.875 |
| p (t-test) |  | 0.081 |  | 0.001 |  | 0.609 |
| min | 0.150 | 1.495 | 0.150 | 0.621 | 0.150 | 2.090 |
| max | 137.113 | 109.060 | 137.113 | 187.691 | 137.113 | 89.538 |
| n (Samp) | 212 | 23 | 212 | 30 | 212 | 16 |
| n (Pat) | 132 | 23 | 132 | 30 | 132 | 16 | sCr or UO

| Time prior AKI stage | AUC | SE | nCohort 1 | nCohort 2 | p |
|---|---|---|---|---|---|
| 0 hours | 0.57 | 0.065 | 246 | 23 | 0.309 |
| 24 hours | 0.61 | 0.053 | 246 | 35 | 0.033 |
| 48 hours | 0.48 | 0.070 | 246 | 18 | 0.777 | sCr only

| Time prior AKI stage | AUC | SE | nCohort 1 | nCohort 2 | p |
|---|---|---|---|---|---|
| 0 hours | 0.35 | 0.174 | 318 | 2 | 0.394 |
| 24 hours | 0.55 | 0.106 | 318 | 8 | 0.622 |
| 48 hours | 0.59 | 0.114 | 318 | 7 | 0.455 |

UO only

| Time prior AKI stage | AUC | SE | nCohort 1 | nCohort 2 | p |
|---|---|---|---|---|---|
| 0 hours | 0.59 | 0.065 | 212 | 23 | 0.162 |
| 24 hours | 0.62 | 0.058 | 212 | 30 | 0.035 |
| 48 hours | 0.46 | 0.073 | 212 | 16 | 0.554 |

Fig. 2 Continued sCr or UO

| Time prior AKI stage | Cutoff value | sens | spec | Quartile | OR | 95% CI of OR | |
|---|---|---|---|---|---|---|---|
| 0 hours | 13.3487 | 74% | 32% | 1 | | | |
| | 8.72551 | 83% | 19% | 2 | 0.6 | 0.3 | 1.6 |
| | 8.46383 | 91% | 19% | 3 | 0.6 | 0.3 | 1.6 |
| | 35.666 | 48% | 70% | 4 | 1.6 | 0.8 | 2.9 |
| | 51.222 | 30% | 80% | | | | |
| | 69.8126 | 22% | 90% | | | | |
| 24 hours | 20.2476 | 71% | 44% | 1 | | | |
| | 17.623 | 80% | 39% | 2 | 1.7 | 0.8 | 3.4 |
| | 6.45486 | 91% | 13% | 3 | 1.7 | 0.8 | 3.4 |
| | 35.666 | 46% | 70% | 4 | 3.2 | 1.8 | 5.8 |
| | 51.222 | 37% | 80% | | | | |
| | 69.8126 | 20% | 90% | | | | |
| 48 hours | 7.43375 | 72% | 16% | 1 | | | |
| | 3.89135 | 83% | 7% | 2 | 0.1 | 0.0 | 1.3 |
| | 2.56368 | 94% | 5% | 3 | 0.5 | 0.2 | 1.3 |
| | 35.666 | 39% | 70% | 4 | 0.8 | 0.4 | 1.7 |
| | 51.222 | 22% | 80% | | | | |
| | 69.8126 | 11% | 90% | | | | | sCr only

| Time prior AKI stage | Cutoff value | sens | spec | Quartile | OR | 95% CI of OR | |
|---|---|---|---|---|---|---|---|
| 0 hours | 8.8314 | 100% | 19% | 1 | | | |
| | 8.8314 | 100% | 19% | 2 | na | na | na |
| | 8.8314 | 100% | 19% | 3 | na | na | na |
| | 39.1009 | 0% | 70% | 4 | na | na | na |
| | 55.9706 | 0% | 80% | | | | |
| | 79.2451 | 0% | 90% | | | | |
| 24 hours | 18.4966 | 75% | 39% | 1 | | | |
| | 17.623 | 88% | 37% | 2 | 2.0 | 0.1 | 39.7 |
| | 4.28258 | 100% | 8% | 3 | 3.1 | 0.2 | 44.1 |
| | 39.1009 | 38% | 70% | 4 | 2.0 | 0.1 | 39.7 |
| | 55.9706 | 13% | 80% | | | | |
| | 79.2451 | 0% | 90% | | | | |
| 48 hours | 22.6941 | 71% | 48% | 1 | | | |
| | 11.9175 | 86% | 28% | 2 | 2.0 | 0.1 | 40.2 |
| | 3.89135 | 100% | 7% | 3 | 1.0 | 0.0 | 52.9 |
| | 39.1009 | 43% | 70% | 4 | 3.0 | 0.2 | 43.5 |
| | 55.9706 | 43% | 80% | | | | |
| | 79.2451 | 29% | 90% | | | | |

UO only

| Time prior AKI stage | Cutoff value | sens | spec | Quartile | OR | 95% CI of OR | |
|---|---|---|---|---|---|---|---|
| 0 hours | 15.6329 | 74% | 35% | 1 | | | |
| | 8.72551 | 83% | 18% | 2 | 1.0 | 0.4 | 2.3 |
| | 8.46383 | 91% | 18% | 3 | 0.6 | 0.2 | 1.7 |
| | 35.652 | 52% | 70% | 4 | 2.2 | 1.1 | 4.2 |
| | 50.5691 | 35% | 80% | | | | |
| | 67.657 | 22% | 90% | | | | |
| 24 hours | 22.3697 | 70% | 48% | 1 | | | |
| | 15.6329 | 80% | 35% | 2 | 1.2 | 0.5 | 2.6 |
| | 6.7825 | 90% | 12% | 3 | 1.5 | 0.7 | 3.1 |
| | 35.652 | 47% | 70% | 4 | 2.7 | 1.4 | 5.1 |
| | 50.5691 | 40% | 80% | | | | |
| | 67.657 | 27% | 90% | | | | |

Fig. 2 Continued

| 48 hours | 7.43375 | 75% | 15% | 1 | | | |
|---|---|---|---|---|---|---|---|
| | 6.85756 | 81% | 12% | 2 | 0.4 | 0.1 | 1.6 |
| | 2.56368 | 94% | 5% | 3 | 0.8 | 0.3 | 2.0 |
| | 35.652 | 31% | 70% | 4 | 1.0 | 0.4 | 2.4 |
| | 50.5691 | 13% | 80% | | | | |
| | 67.657 | 6% | 90% | | | | |

P-selectin glycoprotein ligand 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1.633 | 1.987 | 1.633 | 0.830 | 1.633 | 1.079 |
| average | 3.913 | 3.619 | 3.913 | 3.771 | 3.913 | 3.162 |
| stdev | 6.490 | 5.252 | 6.490 | 8.817 | 6.490 | 5.188 |
| p (t-test) | | 0.829 | | 0.905 | | 0.631 |
| min | 0.001 | 0.018 | 0.001 | 0.018 | 0.001 | 0.018 |
| max | 67.069 | 20.872 | 67.069 | 47.674 | 67.069 | 20.498 |
| n (Samp) | 304 | 24 | 304 | 36 | 304 | 18 |
| n (Pat) | 164 | 24 | 164 | 36 | 164 | 18 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 1.509 | 0.799 | 1.509 | 0.270 | 1.509 | 1.042 |
| average | 3.840 | 0.580 | 3.840 | 4.561 | 3.840 | 2.169 |
| stdev | 6.562 | 0.491 | 6.562 | 8.660 | 6.562 | 3.195 |
| p (t-test) | | 0.391 | | 0.760 | | 0.502 |
| min | 0.001 | 0.018 | 0.001 | 0.016 | 0.001 | 0.018 |
| max | 67.069 | 0.923 | 67.069 | 24.531 | 67.069 | 8.975 |
| n (Samp) | 385 | 3 | 385 | 8 | 385 | 7 |
| n (Pat) | 197 | 3 | 197 | 8 | 197 | 7 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 1.501 | 1.987 | 1.501 | 0.411 | 1.501 | 0.913 |
| average | 3.952 | 3.588 | 3.952 | 3.204 | 3.952 | 2.925 |
| stdev | 6.888 | 5.272 | 6.888 | 8.608 | 6.888 | 5.282 |
| p (t-test) | | 0.801 | | 0.579 | | 0.559 |
| min | 0.001 | 0.018 | 0.001 | 0.018 | 0.001 | 0.018 |
| max | 67.069 | 20.872 | 67.069 | 47.674 | 67.069 | 20.498 |
| n (Samp) | 256 | 24 | 256 | 31 | 256 | 16 |
| n (Pat) | 133 | 24 | 133 | 31 | 133 | 16 | sCr or UO

| Time prior AKI stage | AUC | SE | nCohort 1 | nCohort 2 | p |
|---|---|---|---|---|---|
| 0 hours | 0.48 | 0.061 | 304 | 24 | 0.751 |
| 24 hours | 0.40 | 0.047 | 304 | 36 | 0.030 |
| 48 hours | 0.44 | 0.067 | 304 | 18 | 0.414 | sCr only

| Time prior AKI stage | AUC | SE | nCohort 1 | nCohort 2 | p |
|---|---|---|---|---|---|
| 0 hours | 0.27 | 0.120 | 385 | 3 | 0.057 |
| 24 hours | 0.38 | 0.091 | 385 | 8 | 0.188 |
| 48 hours | 0.42 | 0.103 | 385 | 7 | 0.425 |

Fig. 2 Continued

UO only

| Time prior AKI stage | AUC | SE | nCohort 1 | nCohort 2 | p |
|---|---|---|---|---|---|
| 0 hours | 0.48 | 0.061 | 256 | 24 | 0.780 |
| 24 hours | 0.38 | 0.050 | 256 | 31 | 0.017 |
| 48 hours | 0.43 | 0.071 | 256 | 16 | 0.330 | sCr or UO

| Time prior AKI stage | Cutoff value | sens | spec | Quartile | OR | 95% CI of OR | |
|---|---|---|---|---|---|---|---|
| 0 hours | 0.45337 | 71% | 25% | 1 | | | |
| | 0.00574 | 100% | 2% | 2 | 1.7 | 0.8 | 3.3 |
| | 0.00574 | 100% | 2% | 3 | 0.8 | 0.3 | 2.0 |
| | 3.56045 | 25% | 70% | 4 | 1.4 | 0.7 | 3.0 |
| | 6.10119 | 17% | 80% | | | | |
| | 10.0248 | 13% | 90% | | | | |
| 24 hours | 0.00574 | 100% | 2% | 1 | | | |
| | 0.00574 | 100% | 2% | 2 | 1.2 | 0.7 | 2.1 |
| | 0.00574 | 100% | 2% | 3 | 0.6 | 0.2 | 1.2 |
| | 3.56045 | 22% | 70% | 4 | 2.8 | 1.8 | 4.4 |
| | 6.10119 | 19% | 80% | | | | |
| | 10.0248 | 6% | 90% | | | | |
| 48 hours | 0.1182 | 78% | 16% | 1 | | | |
| | 0.09386 | 83% | 16% | 2 | 0.5 | 0.1 | 2.3 |
| | 0.02776 | 94% | 15% | 3 | 1.5 | 0.6 | 3.7 |
| | 3.56045 | 22% | 70% | 4 | 1.6 | 0.7 | 3.7 |
| | 6.10119 | 22% | 80% | | | | |
| | 10.0248 | 6% | 90% | | | | | sCr only

| Time prior AKI stage | Cutoff value | sens | spec | Quartile | OR | 95% CI of OR | |
|---|---|---|---|---|---|---|---|
| 0 hours | 0.00574 | 100% | 2% | 1 | | | |
| | 0.00574 | 100% | 2% | 2 | na | na | na |
| | 0.00574 | 100% | 2% | 3 | na | na | na |
| | 3.42404 | 0% | 70% | 4 | na | na | na |
| | 5.90572 | 0% | 80% | | | | |
| | 9.69321 | 0% | 90% | | | | |
| 24 hours | 0.01619 | 88% | 2% | 1 | | | |
| | 0.01619 | 88% | 2% | 2 | 0.5 | 0.0 | 9.8 |
| | 0.00574 | 100% | 2% | 3 | 0.5 | 0.0 | 9.8 |
| | 3.42404 | 25% | 70% | 4 | 2.1 | 0.5 | 9.4 |
| | 5.90572 | 25% | 80% | | | | |
| | 9.69321 | 13% | 90% | | | | |
| 48 hours | 0.45337 | 71% | 28% | 1 | | | |
| | 0.00574 | 100% | 2% | 2 | 1.0 | 0.0 | 52.5 |
| | 0.00574 | 100% | 2% | 3 | 3.1 | 0.2 | 43.5 |
| | 3.42404 | 14% | 70% | 4 | 2.0 | 0.1 | 39.8 |
| | 5.90572 | 14% | 80% | | | | |
| | 9.69321 | 0% | 90% | | | | |

UO only

| Time prior AKI stage | Cutoff value | sens | spec | Quartile | OR | 95% CI of OR | |
|---|---|---|---|---|---|---|---|
| 0 hours | 0.23619 | 71% | 20% | 1 | | | |
| | 0.01619 | 100% | 3% | 2 | 1.7 | 0.8 | 3.4 |
| | 0.01619 | 100% | 3% | 3 | 0.6 | 0.2 | 1.8 |
| | 3.40676 | 25% | 70% | 4 | 1.7 | 0.8 | 3.4 |
| | 5.90572 | 17% | 80% | | | | |
| | 10.0248 | 13% | 90% | | | | |

Fig. 2 Continued

| 24 hours | 0.01619 | 100% | 3% | 1 | | | |
| | 0.01619 | 100% | 3% | 2 | 1.4 | 0.7 | 3.0 |
| | 0.01619 | 100% | 3% | 3 | 0.8 | 0.3 | 2.0 |
| | 3.40676 | 19% | 70% | 4 | 3.6 | 2.0 | 6.5 |
| | 5.90572 | 16% | 80% | | | | |
| | 10.0248 | 3% | 90% | | | | |
| 48 hours | 0.1182 | 75% | 17% | 1 | | | |
| | 0.09386 | 81% | 17% | 2 | 0.7 | 0.1 | 3.6 |
| | 0.02776 | 94% | 16% | 3 | 1.7 | 0.6 | 5.2 |
| | 3.40676 | 19% | 70% | 4 | 2.1 | 0.7 | 5.9 |
| | 5.90572 | 19% | 80% | | | | |
| | 10.0248 | 6% | 90% | | | | |

Secretory leukocyte peptidase inhibitor sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 9403.188 | 4952.186 | 9403.188 | 17195.572 | 9403.188 | 21007.634 |
| average | 12892.059 | 5238.199 | 12892.059 | 16767.735 | 12892.059 | 17842.260 |
| stdev | 9668.743 | 3492.797 | 9668.743 | 10930.672 | 9668.743 | 12369.055 |
| p (t-test) | | 0.019 | | 0.114 | | 0.383 |
| min | 525.489 | 701.419 | 525.489 | 773.810 | 525.489 | 4198.113 |
| max | 33763.353 | 9919.743 | 33763.353 | 32087.099 | 33763.353 | 28321.033 |
| n (Samp) | 154 | 9 | 154 | 18 | 154 | 3 |
| n (Pat) | 87 | 9 | 87 | 18 | 87 | 3 | sCr only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 9133.017 | 525.489 | 9133.017 | 27970.480 | 9133.017 | 10955.509 |
| average | 12693.458 | 25450.382 | 12693.458 | 27745.746 | 12693.458 | 10955.509 |
| stdev | 9616.679 | na | 9616.679 | 4106.649 | 9616.679 | 14215.851 |
| p (t-test) | | na | | 0.002 | | 0.800 |
| min | 525.489 | 25450.382 | 525.489 | 22954.925 | 525.489 | 903.384 |
| max | 33763.353 | 25450.382 | 33763.353 | 32087.099 | 33763.353 | 21007.634 |
| n (Samp) | 185 | 1 | 185 | 4 | 185 | 2 |
| n (Pat) | 106 | 1 | 106 | 4 | 106 | 2 |

UO only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 10719.557 | 4952.186 | 10719.557 | 14022.648 | 10719.557 | 22954.925 |
| average | 12822.638 | 5238.199 | 12822.638 | 15528.387 | 12822.638 | 18491.357 |
| stdev | 9463.640 | 3492.797 | 9463.640 | 10853.591 | 9463.640 | 12665.757 |
| p (t-test) | | 0.019 | | 0.292 | | 0.310 |
| min | 525.489 | 701.419 | 525.489 | 773.810 | 525.489 | 4198.113 |
| max | 30367.279 | 9919.743 | 30367.279 | 30129.151 | 30367.279 | 28321.033 |
| n (Samp) | 123 | 9 | 123 | 16 | 123 | 3 |
| n (Pat) | 70 | 9 | 70 | 16 | 70 | 3 | sCr or UO

| Time prior AKI stage | AUC | SE | nCohort 1 | nCohort 2 | p |
| --- | --- | --- | --- | --- | --- |
| 0 hours | 0.28 | 0.075 | 154 | 9 | 0.004 |
| 24 hours | 0.61 | 0.074 | 154 | 18 | 0.143 |
| 48 hours | 0.63 | 0.175 | 154 | 3 | 0.469 |

Fig. 2 Continued sCr only

| Time prior AKI stage | AUC | SE | nCohort 1 | nCohort 2 | p |
|---|---|---|---|---|---|
| 0 hours | 0.85 | 0.240 | 185 | 1 | 0.141 |
| 24 hours | 0.90 | 0.103 | 185 | 4 | 0.000 |
| 48 hours | 0.41 | 0.189 | 185 | 2 | 0.627 |

UO only

| Time prior AKI stage | AUC | SE | nCohort 1 | nCohort 2 | p |
|---|---|---|---|---|---|
| 0 hours | 0.28 | 0.074 | 123 | 9 | 0.003 |
| 24 hours | 0.58 | 0.079 | 123 | 16 | 0.321 |
| 48 hours | 0.64 | 0.175 | 123 | 3 | 0.430 | sCr or UO

| Time prior AKI stage | Cutoff value | sens | spec | Quartile | OR | 95% CI of OR | |
|---|---|---|---|---|---|---|---|
| 0 hours | 1919.95 | 78% | 10% | 1 | | | |
| | 1179.99 | 89% | 8% | 2 | na | na | na |
| | 619.703 | 100% | 4% | 3 | na | na | na |
| | 18848.1 | 0% | 70% | 4 | na | na | na |
| | 23956.6 | 0% | 81% | | | | |
| | 27878.2 | 0% | 90% | | | | |
| 24 hours | 8495.58 | 72% | 45% | 1 | | | |
| | 3620.22 | 83% | 21% | 2 | 0.7 | 0.2 | 2.5 |
| | 2961.54 | 94% | 19% | 3 | 1.0 | 0.3 | 2.9 |
| | 18848.1 | 44% | 70% | 4 | 1.9 | 0.8 | 4.5 |
| | 23956.6 | 39% | 81% | | | | |
| | 27878.2 | 22% | 90% | | | | |
| 48 hours | 4066.04 | 100% | 22% | 1 | | | |
| | 4066.04 | 100% | 22% | 2 | 0.0 | 0.0 | na |
| | 4066.04 | 100% | 22% | 3 | 1.0 | 0.0 | 55.9 |
| | 18848.1 | 67% | 70% | 4 | 1.0 | 0.0 | 54.4 |
| | 23956.6 | 33% | 81% | | | | |
| | 27878.2 | 33% | 90% | | | | | sCr only

| Time prior AKI stage | Cutoff value | sens | spec | Quartile | OR | 95% CI of OR | |
|---|---|---|---|---|---|---|---|
| 0 hours | 25258.8 | 100% | 85% | 1 | | | |
| | 25258.8 | 100% | 85% | 2 | na | na | na |
| | 25258.8 | 100% | 85% | 3 | na | na | na |
| | 18614.4 | 100% | 70% | 4 | na | na | na |
| | 23328.2 | 100% | 80% | | | | |
| | 27878.2 | 0% | 90% | | | | |
| 24 hours | 25848.7 | 75% | 86% | 1 | | | |
| | 22167.9 | 100% | 77% | 2 | na | na | na |
| | 22167.9 | 100% | 77% | 3 | na | na | na |
| | 18614.4 | 100% | 70% | 4 | na | na | na |
| | 23328.2 | 75% | 80% | | | | |
| | 27878.2 | 50% | 90% | | | | |
| 48 hours | 892.467 | 100% | 6% | 1 | | | |
| | 892.467 | 100% | 6% | 2 | 0.0 | 0.0 | na |
| | 892.467 | 100% | 6% | 3 | 0.0 | 0.0 | na |
| | 18614.4 | 50% | 70% | 4 | 1.0 | 0.0 | 56.2 |
| | 23328.2 | 0% | 80% | | | | |
| | 27878.2 | 0% | 90% | | | | |

Fig. 2 Continued

UO only

| Time prior AKI stage | Cutoff value | sens | spec | Quartile | OR | 95% CI of OR | |
|---|---|---|---|---|---|---|---|
| 0 hours | 1919.95 | 78% | 11% | 1 | | | |
| | 1056.22 | 89% | 9% | 2 | na | na | na |
| | 619.703 | 100% | 4% | 3 | na | na | na |
| | 18614.4 | 0% | 71% | 4 | na | na | na |
| | 23302.6 | 0% | 80% | | | | |
| | 27495.8 | 0% | 90% | | | | |
| 24 hours | 6990.37 | 75% | 37% | 1 | | | |
| | 3620.22 | 81% | 22% | 2 | 0.7 | 0.2 | 2.5 |
| | 2961.54 | 94% | 20% | 3 | 0.7 | 0.2 | 2.5 |
| | 18614.4 | 38% | 71% | 4 | 1.6 | 0.6 | 4.0 |
| | 23302.6 | 38% | 80% | | | | |
| | 27495.8 | 25% | 90% | | | | |
| 48 hours | 3620.22 | 100% | 22% | 1 | | | |
| | 3620.22 | 100% | 22% | 2 | 0.0 | 0.0 | na |
| | 3620.22 | 100% | 22% | 3 | 0.0 | 0.0 | na |
| | 18614.4 | 67% | 71% | 4 | 2.0 | 0.1 | 43.1 |
| | 23302.6 | 33% | 80% | | | | |
| | 27495.8 | 33% | 90% | | | | |

Stem cell factor sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 182.000 | 214.000 | 182.000 | 151.000 | 182.000 | 124.500 |
| average | 323.322 | 356.759 | 323.322 | 294.144 | 323.322 | 156.717 |
| stdev | 418.581 | 368.989 | 418.581 | 315.466 | 418.581 | 109.732 |
| p (t-test) | | 0.686 | | 0.683 | | 0.093 |
| min | 9.140 | 71.000 | 9.140 | 30.000 | 9.140 | 34.700 |
| max | 2940.000 | 1570.000 | 2940.000 | 1290.000 | 2940.000 | 368.000 |
| n (Samp) | 419 | 27 | 419 | 36 | 419 | 18 |
| n (Pat) | 164 | 27 | 164 | 36 | 164 | 18 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 182.000 | 190.000 | 182.000 | 175.000 | 182.000 | 155.000 |
| average | 336.284 | 421.800 | 336.284 | 410.411 | 336.284 | 153.814 |
| stdev | 433.076 | 572.221 | 433.076 | 528.796 | 433.076 | 75.483 |
| p (t-test) | | 0.661 | | 0.612 | | 0.266 |
| min | 9.140 | 71.000 | 9.140 | 59.700 | 9.140 | 34.700 |
| max | 3000.000 | 1440.000 | 3000.000 | 1720.000 | 3000.000 | 284.000 |
| n (Samp) | 518 | 5 | 518 | 9 | 518 | 7 |
| n (Pat) | 199 | 5 | 199 | 9 | 199 | 7 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 191.000 | 263.500 | 191.000 | 160.000 | 191.000 | 170.500 |
| average | 319.456 | 382.327 | 319.456 | 307.883 | 319.456 | 175.450 |
| stdev | 374.117 | 371.083 | 374.117 | 330.381 | 374.117 | 118.317 |
| p (t-test) | | 0.409 | | 0.870 | | 0.126 |
| min | 9.140 | 76.300 | 9.140 | 30.000 | 9.140 | 34.700 |
| max | 2420.000 | 1570.000 | 2420.000 | 1290.000 | 2420.000 | 368.000 |
| n (Samp) | 352 | 26 | 352 | 30 | 352 | 16 |
| n (Pat) | 133 | 26 | 133 | 30 | 133 | 16 |

Fig. 2 Continued sCr or UO

| Time prior AKI stage | AUC | SE | nCohort 1 | nCohort 2 | p |
|---|---|---|---|---|---|
| 0 hours | 0.58 | 0.059 | 419 | 27 | 0.191 |
| 24 hours | 0.50 | 0.050 | 419 | 36 | 0.930 |
| 48 hours | 0.38 | 0.062 | 419 | 18 | 0.064 | sCr only

| Time prior AKI stage | AUC | SE | nCohort 1 | nCohort 2 | p |
|---|---|---|---|---|---|
| 0 hours | 0.55 | 0.133 | 518 | 5 | 0.707 |
| 24 hours | 0.56 | 0.100 | 518 | 9 | 0.542 |
| 48 hours | 0.42 | 0.102 | 518 | 7 | 0.408 |

UO only

| Time prior AKI stage | AUC | SE | nCohort 1 | nCohort 2 | p |
|---|---|---|---|---|---|
| 0 hours | 0.58 | 0.060 | 352 | 26 | 0.160 |
| 24 hours | 0.49 | 0.054 | 352 | 30 | 0.784 |
| 48 hours | 0.40 | 0.067 | 352 | 16 | 0.125 | sCr or UO

| Time prior AKI stage | Cutoff value | sens | spec | Quartile | OR | 95% CI of OR | |
|---|---|---|---|---|---|---|---|
| 0 hours | 130 | 70% | 40% | 1 | | | |
| | 105 | 81% | 33% | 2 | 4.8 | 1.4 | 16.4 |
| | 87.6 | 93% | 27% | 3 | 4.8 | 1.4 | 16.5 |
| | 319 | 33% | 70% | 4 | 3.6 | 1.0 | 13.3 |
| | 460 | 22% | 80% | | | | |
| | 753 | 11% | 90% | | | | |
| 24 hours | 100 | 72% | 32% | 1 | | | |
| | 86 | 81% | 25% | 2 | 0.6 | 0.4 | 1.2 |
| | 53 | 92% | 11% | 3 | 1.6 | 1.1 | 2.4 |
| | 319 | 31% | 70% | 4 | 0.8 | 0.5 | 1.3 |
| | 460 | 22% | 80% | | | | |
| | 753 | 11% | 90% | | | | |
| 48 hours | 64.9 | 72% | 17% | 1 | | | |
| | 51 | 83% | 11% | 2 | 5.2 | 0.5 | 57.1 |
| | 34 | 100% | 5% | 3 | 6.3 | 0.6 | 64.8 |
| | 319 | 11% | 70% | 4 | 6.3 | 0.6 | 64.8 |
| | 460 | 0% | 80% | | | | |
| | 753 | 0% | 90% | | | | | sCr only

| Time prior AKI stage | Cutoff value | sens | spec | Quartile | OR | 95% CI of OR | |
|---|---|---|---|---|---|---|---|
| 0 hours | 176 | 80% | 49% | 1 | | | |
| | 176 | 80% | 49% | 2 | 1.0 | 0.0 | 51.5 |
| | 70 | 100% | 18% | 3 | 2.0 | 0.1 | 39.0 |
| | 324 | 20% | 70% | 4 | 1.0 | 0.0 | 51.5 |
| | 479 | 20% | 80% | | | | |
| | 813 | 20% | 90% | | | | |
| 24 hours | 133 | 78% | 41% | 1 | | | |
| | 117 | 89% | 36% | 2 | 4.1 | 0.3 | 48.5 |
| | 59.6 | 100% | 13% | 3 | 2.0 | 0.1 | 39.0 |
| | 324 | 33% | 70% | 4 | 2.0 | 0.1 | 39.0 |
| | 479 | 22% | 80% | | | | |
| | 813 | 11% | 90% | | | | |

Fig. 2 Continued

| | 48 hours | 126 | 71% | 39% | 1 | | | |
|---|---|---|---|---|---|---|---|---|
| | | 121 | 86% | 38% | 2 | na | na | na |
| | | 34 | 100% | 5% | 3 | na | na | na |
| | | 324 | 0% | 70% | 4 | na | na | na |
| | | 479 | 0% | 80% | | | | |
| | | 813 | 0% | 90% | | | | |

UO only

| Time prior AKI stage | Cutoff value | sens | spec | Quartile | OR | 95% CI of OR | |
|---|---|---|---|---|---|---|---|
| 0 hours | 120 | 73% | 33% | 1 | | | |
| | 107 | 81% | 30% | 2 | 2.8 | 1.1 | 7.2 |
| | 89.6 | 92% | 24% | 3 | 2.1 | 0.7 | 5.8 |
| | 333 | 38% | 70% | 4 | 3.2 | 1.3 | 7.9 |
| | 446 | 31% | 80% | | | | |
| | 729 | 12% | 90% | | | | |
| 24 hours | 99.7 | 70% | 28% | 1 | | | |
| | 86 | 80% | 21% | 2 | 0.4 | 0.2 | 0.9 |
| | 53 | 90% | 9% | 3 | 1.1 | 0.7 | 1.8 |
| | 333 | 33% | 70% | 4 | 0.8 | 0.4 | 1.3 |
| | 446 | 27% | 80% | | | | |
| | 729 | 13% | 90% | | | | |
| 48 hours | 64.9 | 75% | 14% | 1 | | | |
| | 56 | 81% | 10% | 2 | na | na | na |
| | 42.1 | 94% | 7% | 3 | na | na | na |
| | 333 | 19% | 70% | 4 | na | na | na |
| | 446 | 0% | 80% | | | | |
| | 729 | 0% | 90% | | | | |

Tissue inhibitor of metalloproteinase 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 2.290 | 7.880 | 2.290 | 7.470 | 2.290 | 6.455 |
| average | 11.372 | 7.749 | 11.372 | 28.504 | 11.372 | 11.860 |
| stdev | 31.858 | 6.777 | 31.858 | 59.224 | 31.858 | 14.660 |
| p (t-test) | | 0.556 | | 0.005 | | 0.948 |
| min | 0.034 | 0.069 | 0.034 | 0.169 | 0.034 | 0.153 |
| max | 302.000 | 25.200 | 302.000 | 302.000 | 302.000 | 52.000 |
| n (Samp) | 419 | 27 | 419 | 36 | 419 | 18 |
| n (Pat) | 164 | 27 | 164 | 36 | 164 | 18 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 2.840 | 10.100 | 2.840 | 11.400 | 2.840 | 3.310 |
| average | 12.002 | 34.581 | 12.002 | 26.707 | 12.002 | 22.679 |
| stdev | 32.161 | 64.690 | 32.161 | 50.635 | 32.161 | 36.736 |
| p (t-test) | | 0.123 | | 0.179 | | 0.384 |
| min | 0.034 | 0.256 | 0.034 | 0.169 | 0.034 | 0.326 |
| max | 302.000 | 150.000 | 302.000 | 159.000 | 302.000 | 102.000 |
| n (Samp) | 518 | 5 | 518 | 9 | 518 | 7 |
| n (Pat) | 199 | 5 | 199 | 9 | 199 | 7 |

Fig. 2 Continued

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 2.265 | 7.910 | 2.265 | 8.610 | 2.265 | 9.040 |
| average | 12.029 | 13.520 | 12.029 | 27.603 | 12.029 | 13.436 |
| stdev | 34.198 | 29.036 | 34.198 | 59.552 | 34.198 | 15.368 |
| p (t-test) |  | 0.829 |  | 0.026 |  | 0.870 |
| min | 0.034 | 0.069 | 0.034 | 0.239 | 0.034 | 0.153 |
| max | 302.000 | 152.000 | 302.000 | 302.000 | 302.000 | 52.000 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
|---|---|---|---|---|---|
| 0 hours | 0.60 | 0.059 | 419 | 27 | 0.101 |
| 24 hours | 0.64 | 0.052 | 419 | 36 | 0.008 |
| 48 hours | 0.58 | 0.072 | 419 | 18 | 0.248 | sCr only

| Time prior AKI stage | AUC | SE | nCohort 1 | nCohort 2 | p |
|---|---|---|---|---|---|
| 0 hours | 0.58 | 0.134 | 518 | 5 | 0.531 |
| 24 hours | 0.60 | 0.101 | 518 | 9 | 0.317 |
| 48 hours | 0.56 | 0.113 | 518 | 7 | 0.572 |

UO only

| Time prior AKI stage | AUC | SE | nCohort 1 | nCohort 2 | p |
|---|---|---|---|---|---|
| 0 hours | 0.62 | 0.060 | 352 | 26 | 0.043 |
| 24 hours | 0.66 | 0.056 | 352 | 30 | 0.005 |
| 48 hours | 0.62 | 0.076 | 352 | 16 | 0.102 | sCr or UO

| Time prior AKI stage | Cutoff value | sens | spec | Quartile | OR | 95% CI of OR | |
|---|---|---|---|---|---|---|---|
| 0 hours | 2.22 | 70% | 48% | 1 |  |  |  |
|  | 1.88 | 81% | 41% | 2 | 2.4 | 0.9 | 6.3 |
|  | 0.932 | 93% | 21% | 3 | 3.2 | 1.3 | 7.9 |
|  | 7.13 | 56% | 70% | 4 | 2.8 | 1.1 | 7.1 |
|  | 11.7 | 19% | 80% |  |  |  |  |
|  | 25.5 | 0% | 90% |  |  |  |  |
| 24 hours | 2.63 | 72% | 53% | 1 |  |  |  |
|  | 1.44 | 81% | 32% | 2 | 0.6 | 0.3 | 1.5 |
|  | 0.673 | 92% | 14% | 3 | 1.7 | 1.0 | 3.0 |
|  | 7.13 | 53% | 70% | 4 | 2.9 | 1.8 | 4.7 |
|  | 11.7 | 39% | 80% |  |  |  |  |
|  | 25.5 | 22% | 90% |  |  |  |  |
| 48 hours | 1.99 | 72% | 43% | 1 |  |  |  |
|  | 1.01 | 89% | 23% | 2 | 0.4 | 0.1 | 1.6 |
|  | 0.325 | 94% | 6% | 3 | 1.0 | 0.4 | 2.3 |
|  | 7.13 | 50% | 70% | 4 | 1.2 | 0.6 | 2.6 |
|  | 11.7 | 28% | 80% |  |  |  |  |
|  | 25.5 | 22% | 90% |  |  |  |  |

Fig. 2 Continued sCr only

| Time prior AKI stage | Cutoff value | sens | spec | Quartile | OR | 95% CI of OR | |
|---|---|---|---|---|---|---|---|
| 0 hours | 1.94 | 80% | 38% | 1 | | | |
| | 1.94 | 80% | 38% | 2 | 1.0 | 0.0 | 51.5 |
| | 0.25 | 100% | 5% | 3 | 1.0 | 0.0 | 51.5 |
| | 8.82 | 60% | 70% | 4 | 2.0 | 0.1 | 39.0 |
| | 13 | 20% | 80% | | | | |
| | 26.9 | 20% | 90% | | | | |
| 24 hours | 1.44 | 78% | 29% | 1 | | | |
| | 0.765 | 89% | 15% | 2 | 0.5 | 0.0 | 9.6 |
| | 0.168 | 100% | 2% | 3 | 0.5 | 0.0 | 9.6 |
| | 8.82 | 56% | 70% | 4 | 2.5 | 0.6 | 10.3 |
| | 13 | 33% | 80% | | | | |
| | 26.9 | 22% | 90% | | | | |
| 48 hours | 1.89 | 71% | 38% | 1 | | | |
| | 1.01 | 86% | 21% | 2 | 0.5 | 0.0 | 9.7 |
| | 0.325 | 100% | 6% | 3 | 0.5 | 0.0 | 9.7 |
| | 8.82 | 43% | 70% | 4 | 1.5 | 0.3 | 7.9 |
| | 13 | 43% | 80% | | | | |
| | 26.9 | 29% | 90% | | | | |

UO only

| Time prior AKI stage | Cutoff value | sens | spec | Quartile | OR | 95% CI of OR | |
|---|---|---|---|---|---|---|---|
| 0 hours | 2.22 | 73% | 49% | 1 | | | |
| | 1.99 | 81% | 43% | 2 | 3.7 | 1.0 | 13.5 |
| | 1.38 | 92% | 30% | 3 | 4.9 | 1.4 | 16.9 |
| | 7.58 | 58% | 70% | 4 | 4.2 | 1.2 | 15.0 |
| | 11.9 | 23% | 80% | | | | |
| | 25.5 | 4% | 90% | | | | |
| 24 hours | 3.84 | 70% | 61% | 1 | | | |
| | 2.04 | 80% | 44% | 2 | 0.7 | 0.2 | 2.4 |
| | 0.995 | 90% | 22% | 3 | 2.7 | 1.3 | 5.6 |
| | 7.58 | 53% | 70% | 4 | 3.6 | 1.8 | 7.1 |
| | 11.9 | 40% | 80% | | | | |
| | 25.5 | 20% | 90% | | | | |
| 48 hours | 1.99 | 75% | 43% | 1 | | | |
| | 1.94 | 81% | 41% | 2 | 0.7 | 0.1 | 3.5 |
| | 1.01 | 94% | 22% | 3 | 1.7 | 0.6 | 5.1 |
| | 7.58 | 56% | 70% | 4 | 2.1 | 0.7 | 5.8 |
| | 11.9 | 31% | 80% | | | | |
| | 25.5 | 25% | 90% | | | | |

Fig. 2 Continued

Tissue inhibitor of metalloproteinase 2 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 9044.741 | 16865.143 | 9044.741 | 17398.791 | 9044.741 | 14885.643 |
| average | 12995.451 | 16020.396 | 12995.451 | 30778.064 | 12995.451 | 19958.700 |
| stdev | 17809.885 | 8353.242 | 17809.885 | 41357.548 | 17809.885 | 17812.682 |
| p (t-test) |  | 0.421 |  | 0.000 |  | 0.110 |
| min | 52.566 | 1670.959 | 52.566 | 1052.146 | 52.566 | 746.215 |
| max | 210000.000 | 33679.652 | 210000.000 | 210000.000 | 210000.000 | 70571.053 |
| n (Samp) | 247 | 23 | 247 | 35 | 247 | 18 |
| n (Pat) | 159 | 23 | 159 | 35 | 159 | 18 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 10329.859 | 10423.015 | 10329.859 | 15534.342 | 10329.859 | 25613.325 |
| average | 14666.586 | 10423.015 | 14666.586 | 19701.839 | 14666.586 | 52050.461 |
| stdev | 18694.509 | 1904.764 | 18694.509 | 13576.451 | 18694.509 | 73178.705 |
| p (t-test) |  | 0.749 |  | 0.450 |  | 0.000 |
| min | 52.566 | 9076.144 | 52.566 | 6112.595 | 52.566 | 3877.712 |
| max | 210000.000 | 11769.887 | 210000.000 | 45799.450 | 210000.000 | 210000.000 |
| n (Samp) | 319 | 2 | 319 | 8 | 319 | 7 |
| n (Pat) | 188 | 2 | 188 | 8 | 188 | 7 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 9270.541 | 16992.272 | 9270.541 | 18520.128 | 9270.541 | 13830.893 |
| average | 14010.395 | 16552.297 | 14010.395 | 32472.372 | 14010.395 | 17273.988 |
| stdev | 19345.958 | 8166.528 | 19345.958 | 44095.165 | 19345.958 | 12588.393 |
| p (t-test) |  | 0.534 |  | 0.000 |  | 0.508 |
| min | 52.566 | 1670.959 | 52.566 | 1052.146 | 52.566 | 746.215 |
| max | 210000.000 | 33679.652 | 210000.000 | 210000.000 | 210000.000 | 49583.194 |
| n (Samp) | 213 | 23 | 213 | 30 | 213 | 16 |
| n (Pat) | 132 | 23 | 132 | 30 | 132 | 16 | sCr or UO

| Time prior AKI stage | AUC | SE | nCohort 1 | nCohort 2 | p |
| --- | --- | --- | --- | --- | --- |
| 0 hours | 0.67 | 0.064 | 247 | 23 | 0.007 |
| 24 hours | 0.74 | 0.050 | 247 | 35 | 0.000 |
| 48 hours | 0.65 | 0.072 | 247 | 18 | 0.040 | sCr only

| Time prior AKI stage | AUC | SE | nCohort 1 | nCohort 2 | p |
| --- | --- | --- | --- | --- | --- |
| 0 hours | 0.50 | 0.204 | 319 | 2 | 0.982 |
| 24 hours | 0.66 | 0.107 | 319 | 8 | 0.137 |
| 48 hours | 0.71 | 0.112 | 319 | 7 | 0.064 |

UO only

| Time prior AKI stage | AUC | SE | nCohort 1 | nCohort 2 | p |
| --- | --- | --- | --- | --- | --- |
| 0 hours | 0.67 | 0.064 | 213 | 23 | 0.007 |
| 24 hours | 0.73 | 0.054 | 213 | 30 | 0.000 |
| 48 hours | 0.64 | 0.077 | 213 | 16 | 0.075 |

Fig. 2 Continued sCr or UO

| Time prior AKI stage | Cutoff value | sens | spec | Quartile | OR | 95% CI of OR | |
|---|---|---|---|---|---|---|---|
| 0 hours | 9602.15 | 74% | 53% | 1 | | | |
| | 8004.08 | 83% | 43% | 2 | 2.0 | 0.4 | 9.4 |
| | 6975.51 | 91% | 36% | 3 | 3.2 | 0.8 | 12.6 |
| | 13880.1 | 61% | 70% | 4 | 6.3 | 1.8 | 21.3 |
| | 17585.4 | 39% | 80% | | | | |
| | 23054.6 | 17% | 90% | | | | |
| 24 hours | 10342.4 | 71% | 56% | 1 | | | |
| | 9234.93 | 80% | 51% | 2 | 7.5 | 0.8 | 75.2 |
| | 7056.32 | 91% | 37% | 3 | 10.2 | 1.1 | 95.5 |
| | 13880.1 | 66% | 70% | 4 | 23.4 | 2.8 | 198.0 |
| | 17585.4 | 49% | 80% | | | | |
| | 23054.6 | 37% | 90% | | | | |
| 48 hours | 9686.03 | 72% | 54% | 1 | | | |
| | 5554.22 | 83% | 29% | 2 | 0.7 | 0.1 | 3.6 |
| | 3395.45 | 94% | 16% | 3 | 2.1 | 0.7 | 6.0 |
| | 13880.1 | 56% | 70% | 4 | 2.5 | 0.9 | 6.6 |
| | 17585.4 | 39% | 80% | | | | |
| | 23054.6 | 39% | 90% | | | | | sCr only

| Time prior AKI stage | Cutoff value | sens | spec | Quartile | OR | 95% CI of OR | |
|---|---|---|---|---|---|---|---|
| 0 hours | 9044.74 | 100% | 44% | 1 | | | |
| | 9044.74 | 100% | 44% | 2 | na | na | na |
| | 9044.74 | 100% | 44% | 3 | na | na | na |
| | 16394.9 | 0% | 70% | 4 | na | na | na |
| | 20203.3 | 0% | 80% | | | | |
| | 27021.8 | 0% | 90% | | | | |
| 24 hours | 9745.48 | 75% | 48% | 1 | | | |
| | 8192.37 | 88% | 38% | 2 | na | na | na |
| | 6042.22 | 100% | 27% | 3 | na | na | na |
| | 16394.9 | 50% | 70% | 4 | na | na | na |
| | 20203.3 | 38% | 80% | | | | |
| | 27021.8 | 25% | 90% | | | | |
| 48 hours | 16394.9 | 71% | 70% | 1 | | | |
| | 5554.22 | 86% | 25% | 2 | 1.0 | 0.0 | 52.3 |
| | 3847.82 | 100% | 18% | 3 | 1.0 | 0.0 | 52.9 |
| | 16394.9 | 71% | 70% | 4 | 4.1 | 0.3 | 50.0 |
| | 20203.3 | 57% | 80% | | | | |
| | 27021.8 | 43% | 90% | | | | |

UO only

| Time prior AKI stage | Cutoff value | sens | spec | Quartile | OR | 95% CI of OR | |
|---|---|---|---|---|---|---|---|
| 0 hours | 10640 | 74% | 56% | 1 | | | |
| | 8004.08 | 83% | 40% | 2 | 2.1 | 0.4 | 9.7 |
| | 6975.51 | 91% | 34% | 3 | 3.8 | 1.0 | 14.5 |
| | 14816 | 61% | 70% | 4 | 5.8 | 1.7 | 20.3 |
| | 18281.5 | 39% | 80% | | | | |
| | 26183.6 | 17% | 90% | | | | |
| 24 hours | 14816 | 70% | 70% | 1 | | | |
| | 10329.9 | 80% | 54% | 2 | 5.3 | 0.5 | 59.3 |
| | 7066.27 | 90% | 35% | 3 | 10.2 | 1.1 | 96.8 |
| | 14816 | 70% | 70% | 4 | 19.2 | 2.2 | 167.9 |
| | 18281.5 | 50% | 80% | | | | |
| | 26183.6 | 33% | 90% | | | | |

Fig. 2 Continued

| 48 hours | 9684.33 | 75% | 52% | 1 | | | |
| | 9044.74 | 81% | 49% | 2 | 1.0 | 0.1 | 7.6 |
| | 3395.45 | 94% | 15% | 3 | 3.9 | 1.0 | 14.6 |
| | 14816 | 44% | 70% | 4 | 2.6 | 0.6 | 11.0 |
| | 18281.5 | 31% | 80% | | | | |
| | 26183.6 | 19% | 90% | | | | |

Tumor necrosis factor-alpha sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 3.190 | 2.780 | 3.190 | 3.425 | 3.190 | 2.570 |
| average | 9.487 | 6.722 | 9.487 | 7.450 | 9.487 | 8.398 |
| stdev | 22.747 | 7.888 | 22.747 | 8.235 | 22.747 | 9.680 |
| p (t-test) | | 0.530 | | 0.594 | | 0.840 |
| min | 0.016 | 0.016 | 0.016 | 0.016 | 0.016 | 0.016 |
| max | 300.000 | 30.600 | 300.000 | 30.200 | 300.000 | 28.500 |
| n (Samp) | 419 | 27 | 419 | 36 | 419 | 18 |
| n (Pat) | 164 | 27 | 164 | 36 | 164 | 18 | sCr only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 3.315 | 2.100 | 3.315 | 2.900 | 3.315 | 3.120 |
| average | 9.781 | 3.054 | 9.781 | 5.201 | 9.781 | 7.399 |
| stdev | 22.013 | 2.783 | 22.013 | 5.681 | 22.013 | 9.945 |
| p (t-test) | | 0.495 | | 0.533 | | 0.775 |
| min | 0.016 | 1.140 | 0.016 | 0.016 | 0.016 | 0.016 |
| max | 300.000 | 7.980 | 300.000 | 17.800 | 300.000 | 28.500 |
| n (Samp) | 518 | 5 | 518 | 9 | 518 | 7 |
| n (Pat) | 199 | 5 | 199 | 9 | 199 | 7 |

UO only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 3.310 | 3.475 | 3.310 | 4.035 | 3.310 | 3.825 |
| average | 9.520 | 6.949 | 9.520 | 7.733 | 9.520 | 8.153 |
| stdev | 23.836 | 7.973 | 23.836 | 8.562 | 23.836 | 8.514 |
| p (t-test) | | 0.585 | | 0.683 | | 0.819 |
| min | 0.016 | 0.016 | 0.016 | 0.016 | 0.016 | 0.016 |
| max | 300.000 | 30.600 | 300.000 | 30.200 | 300.000 | 25.000 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
| --- | --- | --- | --- | --- | --- |
| 0 hours | 0.49 | 0.057 | 419 | 27 | 0.849 |
| 24 hours | 0.51 | 0.051 | 419 | 36 | 0.809 |
| 48 hours | 0.51 | 0.070 | 419 | 18 | 0.871 | sCr only

| Time prior AKI stage | AUC | SE | nCohort 1 | nCohort 2 | p |
| --- | --- | --- | --- | --- | --- |
| 0 hours | 0.38 | 0.114 | 518 | 5 | 0.285 |
| 24 hours | 0.46 | 0.094 | 518 | 9 | 0.661 |
| 48 hours | 0.50 | 0.110 | 518 | 7 | 0.994 |

Fig. 2 Continued

UO only

| Time prior AKI stage | AUC | SE | nCohort 1 | nCohort 2 | p |
|---|---|---|---|---|---|
| 0 hours | 0.49 | 0.059 | 352 | 26 | 0.909 |
| 24 hours | 0.51 | 0.055 | 352 | 30 | 0.799 |
| 48 hours | 0.53 | 0.075 | 352 | 16 | 0.698 | sCr or UO

| Time prior AKI stage | Cutoff value | sens | spec | Quartile | OR | 95% CI of OR | |
|---|---|---|---|---|---|---|---|
| 0 hours | 1.72 | 70% | 30% | 1 | | | |
| | 1.18 | 81% | 21% | 2 | 0.9 | 0.5 | 1.6 |
| | 0.739 | 93% | 12% | 3 | 1.2 | 0.7 | 2.0 |
| | 9 | 30% | 70% | 4 | 0.9 | 0.5 | 1.6 |
| | 14.8 | 19% | 80% | | | | |
| | 20.6 | 7% | 90% | | | | |
| 24 hours | 1.64 | 72% | 29% | 1 | | | |
| | 1.09 | 81% | 20% | 2 | 1.3 | 0.8 | 2.0 |
| | 0.501 | 92% | 11% | 3 | 1.3 | 0.8 | 2.0 |
| | 9 | 33% | 70% | 4 | 1.0 | 0.6 | 1.7 |
| | 14.8 | 19% | 80% | | | | |
| | 20.6 | 8% | 90% | | | | |
| 48 hours | 1.68 | 72% | 29% | 1 | | | |
| | 1.29 | 83% | 24% | 2 | 1.5 | 0.7 | 3.6 |
| | 0 | 100% | 0% | 3 | 0.7 | 0.2 | 2.4 |
| | 9 | 33% | 70% | 4 | 1.3 | 0.5 | 3.1 |
| | 14.8 | 28% | 80% | | | | |
| | 20.6 | 17% | 90% | | | | | sCr only

| Time prior AKI stage | Cutoff value | sens | spec | Quartile | OR | 95% CI of OR | |
|---|---|---|---|---|---|---|---|
| 0 hours | 1.92 | 80% | 34% | 1 | | | |
| | 1.92 | 80% | 34% | 2 | na | na | na |
| | 1.09 | 100% | 19% | 3 | na | na | na |
| | 9.65 | 0% | 70% | 4 | na | na | na |
| | 15.4 | 0% | 80% | | | | |
| | 21.1 | 0% | 90% | | | | |
| 24 hours | 1.64 | 78% | 28% | 1 | | | |
| | 1.42 | 89% | 25% | 2 | 3.0 | 0.2 | 42.8 |
| | 0 | 100% | 0% | 3 | 4.1 | 0.3 | 48.9 |
| | 9.65 | 22% | 70% | 4 | 1.0 | 0.0 | 52.3 |
| | 15.4 | 11% | 80% | | | | |
| | 21.1 | 0% | 90% | | | | |
| 48 hours | 2.78 | 71% | 44% | 1 | | | |
| | 1.68 | 86% | 29% | 2 | 2.0 | 0.1 | 39.6 |
| | 0 | 100% | 0% | 3 | 3.1 | 0.2 | 43.2 |
| | 9.65 | 29% | 70% | 4 | 1.0 | 0.0 | 52.3 |
| | 15.4 | 14% | 80% | | | | |
| | 21.1 | 14% | 90% | | | | |

UO only

| Time prior AKI stage | Cutoff value | sens | spec | Quartile | OR | 95% CI of OR | |
|---|---|---|---|---|---|---|---|
| 0 hours | 1.64 | 73% | 27% | 1 | | | |
| | 1.17 | 81% | 20% | 2 | 0.9 | 0.4 | 1.6 |
| | 0.435 | 92% | 9% | 3 | 1.0 | 0.5 | 1.8 |
| | 8.95 | 31% | 70% | 4 | 0.9 | 0.4 | 1.6 |
| | 14.7 | 19% | 80% | | | | |
| | 20.1 | 8% | 90% | | | | |

Fig. 2 Continued

| 24 hours | 2.16 | 70% | 36% | 1 | | | |
| | 1.09 | 80% | 19% | 2 | 0.7 | 0.4 | 1.3 |
| | 0.583 | 90% | 10% | 3 | 1.1 | 0.7 | 1.9 |
| | 8.95 | 33% | 70% | 4 | 0.9 | 0.5 | 1.5 |
| | 14.7 | 20% | 80% | | | | |
| | 20.1 | 10% | 90% | | | | |
| 48 hours | 1.82 | 75% | 32% | 1 | | | |
| | 1.64 | 81% | 27% | 2 | 1.7 | 0.6 | 5.1 |
| | 0.739 | 94% | 11% | 3 | 1.3 | 0.4 | 4.4 |
| | 8.95 | 38% | 70% | 4 | 1.3 | 0.4 | 4.4 |
| | 14.7 | 25% | 80% | | | | |
| | 20.1 | 13% | 90% | | | | |

Vascular endothelial growth factor sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 633.000 | 727.000 | 633.000 | 956.000 | 633.000 | 589.000 |
| average | 2277.095 | 1981.822 | 2277.095 | 6929.669 | 2277.095 | 1561.578 |
| stdev | 6236.975 | 4222.324 | 6236.975 | 23297.538 | 6236.975 | 2024.383 |
| p (t-test) | | 0.809 | | 0.003 | | 0.628 |
| min | 33.400 | 34.600 | 33.400 | 93.100 | 33.400 | 58.400 |
| max | 61900.000 | 20800.000 | 61900.000 | 139000.000 | 61900.000 | 6620.000 |
| n (Samp) | 419 | 27 | 419 | 36 | 419 | 18 |
| n (Pat) | 164 | 27 | 164 | 36 | 164 | 18 | sCr only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 660.500 | 1100.000 | 660.500 | 2460.000 | 660.500 | 1770.000 |
| average | 2554.556 | 4397.400 | 2554.556 | 5519.456 | 2554.556 | 3736.143 |
| stdev | 8452.571 | 5240.937 | 8452.571 | 6250.495 | 8452.571 | 4049.560 |
| p (t-test) | | 0.627 | | 0.296 | | 0.712 |
| min | 33.400 | 180.000 | 33.400 | 93.100 | 33.400 | 213.000 |
| max | 139000.000 | 11600.000 | 139000.000 | 18100.000 | 139000.000 | 10400.000 |
| n (Samp) | 518 | 5 | 518 | 9 | 518 | 7 |
| n (Pat) | 199 | 5 | 199 | 9 | 199 | 7 |

UO only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 650.500 | 771.500 | 650.500 | 985.500 | 650.500 | 658.500 |
| average | 2135.791 | 1834.892 | 2135.791 | 7120.100 | 2135.791 | 1704.588 |
| stdev | 6193.768 | 4090.005 | 6193.768 | 25432.386 | 6193.768 | 2224.115 |
| p (t-test) | | 0.808 | | 0.005 | | 0.782 |
| min | 33.400 | 34.600 | 33.400 | 122.000 | 33.400 | 58.400 |
| max | 61900.000 | 20800.000 | 61900.000 | 139000.000 | 61900.000 | 6670.000 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
| --- | --- | --- | --- | --- | --- |
| 0 hours | 0.50 | 0.058 | 419 | 27 | 0.945 |
| 24 hours | 0.61 | 0.052 | 419 | 36 | 0.037 |
| 48 hours | 0.48 | 0.069 | 419 | 18 | 0.788 |

Fig. 2 Continued sCr only

| Time prior AKI stage | AUC | SE | nCohort 1 | nCohort 2 | p |
|---|---|---|---|---|---|
| 0 hours | 0.64 | 0.135 | 518 | 5 | 0.312 |
| 24 hours | 0.70 | 0.099 | 518 | 9 | 0.043 |
| 48 hours | 0.62 | 0.114 | 518 | 7 | 0.295 |

UO only

| Time prior AKI stage | AUC | SE | nCohort 1 | nCohort 2 | p |
|---|---|---|---|---|---|
| 0 hours | 0.52 | 0.059 | 352 | 26 | 0.776 |
| 24 hours | 0.59 | 0.057 | 352 | 30 | 0.104 |
| 48 hours | 0.50 | 0.074 | 352 | 16 | 0.974 | sCr or UO

| Time prior AKI stage | Cutoff value | sens | spec | Quartile | OR | 95% CI of OR | |
|---|---|---|---|---|---|---|---|
| 0 hours | 484 | 70% | 39% | 1 | | | |
| | 271 | 81% | 20% | 2 | 1.0 | 0.5 | 2.0 |
| | 96.9 | 93% | 3% | 3 | 1.7 | 1.0 | 3.0 |
| | 1180 | 30% | 70% | 4 | 0.8 | 0.4 | 1.7 |
| | 2080 | 11% | 81% | | | | |
| | 4640 | 11% | 90% | | | | |
| 24 hours | 661 | 72% | 53% | 1 | | | |
| | 438 | 81% | 35% | 2 | 0.6 | 0.3 | 1.5 |
| | 204 | 92% | 11% | 3 | 2.7 | 1.6 | 4.4 |
| | 1180 | 42% | 70% | 4 | 1.9 | 1.1 | 3.3 |
| | 2080 | 28% | 81% | | | | |
| | 4640 | 25% | 90% | | | | |
| 48 hours | 277 | 72% | 20% | 1 | | | |
| | 217 | 83% | 12% | 2 | 0.3 | 0.1 | 1.2 |
| | 129 | 94% | 4% | 3 | 0.7 | 0.3 | 1.6 |
| | 1180 | 39% | 70% | 4 | 1.0 | 0.5 | 2.0 |
| | 2080 | 22% | 81% | | | | |
| | 4640 | 11% | 90% | | | | | sCr only

| Time prior AKI stage | Cutoff value | sens | spec | Quartile | OR | 95% CI of OR | |
|---|---|---|---|---|---|---|---|
| 0 hours | 726 | 80% | 53% | 1 | | | |
| | 726 | 80% | 53% | 2 | 0.0 | 0.0 | na |
| | 179 | 100% | 8% | 3 | 2.0 | 0.1 | 39.0 |
| | 1260 | 40% | 70% | 4 | 2.0 | 0.1 | 39.0 |
| | 2080 | 40% | 80% | | | | |
| | 4930 | 40% | 90% | | | | |
| 24 hours | 695 | 78% | 52% | 1 | | | |
| | 661 | 89% | 50% | 2 | 1.0 | 0.0 | 51.5 |
| | 87.1 | 100% | 3% | 3 | 2.0 | 0.1 | 39.0 |
| | 1260 | 56% | 70% | 4 | 5.1 | 0.5 | 55.4 |
| | 2080 | 56% | 80% | | | | |
| | 4930 | 44% | 90% | | | | |
| 48 hours | 459 | 71% | 36% | 1 | | | |
| | 363 | 86% | 28% | 2 | 2.0 | 0.1 | 39.3 |
| | 211 | 100% | 12% | 3 | 0.0 | 0.0 | na |
| | 1260 | 57% | 70% | 4 | 4.1 | 0.3 | 48.5 |
| | 2080 | 43% | 80% | | | | |
| | 4930 | 43% | 90% | | | | |

Fig. 2 Continued

UO only

| Time prior AKI stage | Cutoff value | sens | spec | Quartile | OR | 95% CI of OR | |
|---|---|---|---|---|---|---|---|
| 0 hours | 484 | 73% | 39% | 1 | | | |
| | 349 | 81% | 27% | 2 | 1.4 | 0.7 | 2.9 |
| | 96.9 | 92% | 3% | 3 | 1.9 | 1.0 | 3.6 |
| | 1160 | 35% | 70% | 4 | 1.0 | 0.4 | 2.3 |
| | 2040 | 15% | 80% | | | | |
| | 3810 | 8% | 90% | | | | |
| 24 hours | 695 | 70% | 53% | 1 | | | |
| | 438 | 80% | 34% | 2 | 0.8 | 0.3 | 2.0 |
| | 227 | 90% | 11% | 3 | 3.1 | 1.7 | 5.5 |
| | 1160 | 37% | 70% | 4 | 1.4 | 0.7 | 2.9 |
| | 2040 | 20% | 80% | | | | |
| | 3810 | 20% | 90% | | | | |
| 48 hours | 277 | 75% | 19% | 1 | | | |
| | 220 | 81% | 11% | 2 | 0.6 | 0.2 | 1.7 |
| | 129 | 94% | 3% | 3 | 0.6 | 0.2 | 1.7 |
| | 1160 | 38% | 70% | 4 | 1.0 | 0.4 | 2.3 |
| | 2040 | 25% | 80% | | | | |
| | 3810 | 19% | 90% | | | | |

Fig. 2 Continued

EN-RAGE sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1.436 | 5.856 | 1.436 | 5.856 | 1.436 | 5.856 |
| average | 10.655 | 27.324 | 10.655 | 27.324 | 10.655 | 27.324 |
| stdev | 53.079 | 64.053 | 53.079 | 64.053 | 53.079 | 64.053 |
| p (t-test) |  | 0.240 |  | 0.240 |  | 0.240 |
| min | 0.077 | 0.223 | 0.077 | 0.223 | 0.077 | 0.223 |
| max | 391.452 | 307.987 | 391.452 | 307.987 | 391.452 | 307.987 |
| n (Samp) | 54 | 23 | 54 | 23 | 54 | 23 |
| n (Pat) | 54 | 23 | 54 | 23 | 54 | 23 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1.804 | 1.225 | 1.804 | 1.225 | 1.804 | 1.225 |
| average | 5.575 | 1.902 | 5.575 | 1.902 | 5.575 | 1.902 |
| stdev | 11.019 | 2.102 | 11.019 | 2.102 | 11.019 | 2.102 |
| p (t-test) |  | 0.521 |  | 0.521 |  | 0.521 |
| min | 0.077 | 0.307 | 0.077 | 0.307 | 0.077 | 0.307 |
| max | 49.126 | 4.853 | 49.126 | 4.853 | 49.126 | 4.853 |
| n (Samp) | 20 | 4 | 20 | 4 | 20 | 4 |
| n (Pat) | 20 | 4 | 20 | 4 | 20 | 4 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1.436 | 4.907 | 1.436 | 4.907 | 1.436 | 4.907 |
| average | 21.358 | 14.404 | 21.358 | 14.404 | 21.358 | 14.404 |
| stdev | 74.453 | 19.252 | 74.453 | 19.252 | 74.453 | 19.252 |
| p (t-test) |  | 0.698 |  | 0.698 |  | 0.698 |
| min | 0.142 | 0.281 | 0.142 | 0.281 | 0.142 | 0.281 |
| max | 391.452 | 76.160 | 391.452 | 76.160 | 391.452 | 76.160 |
| n (Samp) | 44 | 18 | 44 | 18 | 44 | 18 |
| n (Pat) | 44 | 18 | 44 | 18 | 44 | 18 | sCr or UO

| Time prior AKI stage | AUC | SE | nCohort 1 | nCohort 2 | p |
|---|---|---|---|---|---|
| 0 hours | 0.67 | 0.070 | 54 | 23 | 0.014 |
| 24 hours | 0.67 | 0.070 | 54 | 23 | 0.014 |
| 48 hours | 0.67 | 0.070 | 54 | 23 | 0.014 | sCr only

| Time prior AKI stage | AUC | SE | nCohort 1 | nCohort 2 | p |
|---|---|---|---|---|---|
| 0 hours | 0.43 | 0.154 | 20 | 4 | 0.626 |
| 24 hours | 0.43 | 0.154 | 20 | 4 | 0.626 |
| 48 hours | 0.43 | 0.154 | 20 | 4 | 0.626 |

UO only

| Time prior AKI stage | AUC | SE | nCohort 1 | nCohort 2 | p |
|---|---|---|---|---|---|
| 0 hours | 0.65 | 0.080 | 44 | 18 | 0.066 |
| 24 hours | 0.65 | 0.080 | 44 | 18 | 0.066 |
| 48 hours | 0.65 | 0.080 | 44 | 18 | 0.066 |

Fig. 3 sCr or UO

| Time prior AKI stage | Cutoff value | sens | spec | Quartile | OR | 95% CI of OR | |
|---|---|---|---|---|---|---|---|
| 0 hours | 0.91054 | 74% | 37% | 1 | | | |
| | 0.63129 | 83% | 24% | 2 | 0.3 | 0.1 | 1.7 |
| | 0.48001 | 91% | 17% | 3 | 1.0 | 0.3 | 2.9 |
| | 3.07933 | 57% | 70% | 4 | 3.4 | 1.4 | 8.7 |
| | 5.24957 | 52% | 81% | | | | |
| | 8.8999 | 48% | 91% | | | | |
| 24 hours | 0.91054 | 74% | 37% | 1 | | | |
| | 0.63129 | 83% | 24% | 2 | 0.3 | 0.1 | 1.7 |
| | 0.48001 | 91% | 17% | 3 | 1.0 | 0.3 | 2.9 |
| | 3.07933 | 57% | 70% | 4 | 3.4 | 1.4 | 8.7 |
| | 5.24957 | 52% | 81% | | | | |
| | 8.8999 | 48% | 91% | | | | |
| 48 hours | 0.91054 | 74% | 37% | 1 | | | |
| | 0.63129 | 83% | 24% | 2 | 0.3 | 0.1 | 1.7 |
| | 0.48001 | 91% | 17% | 3 | 1.0 | 0.3 | 2.9 |
| | 3.07933 | 57% | 70% | 4 | 3.4 | 1.4 | 8.7 |
| | 5.24957 | 52% | 81% | | | | |
| | 8.8999 | 48% | 91% | | | | | sCr only

| Time prior AKI stage | Cutoff value | sens | spec | Quartile | OR | 95% CI of OR | |
|---|---|---|---|---|---|---|---|
| 0 hours | 0.30654 | 75% | 20% | 1 | | | |
| | 0.25054 | 100% | 20% | 2 | 1.0 | 0.0 | 110.4 |
| | 0.25054 | 100% | 20% | 3 | 0.0 | 0.0 | na |
| | 3.07933 | 25% | 70% | 4 | 2.5 | 0.1 | 114.2 |
| | 7.78951 | 0% | 80% | | | | |
| | 11.3413 | 0% | 90% | | | | |
| 24 hours | 0.30654 | 75% | 20% | 1 | | | |
| | 0.25054 | 100% | 20% | 2 | 1.0 | 0.0 | 110.4 |
| | 0.25054 | 100% | 20% | 3 | 0.0 | 0.0 | na |
| | 3.07933 | 25% | 70% | 4 | 2.5 | 0.1 | 114.2 |
| | 7.78951 | 0% | 80% | | | | |
| | 11.3413 | 0% | 90% | | | | |
| 48 hours | 0.30654 | 75% | 20% | 1 | | | |
| | 0.25054 | 100% | 20% | 2 | 1.0 | 0.0 | 110.4 |
| | 0.25054 | 100% | 20% | 3 | 0.0 | 0.0 | na |
| | 3.07933 | 25% | 70% | 4 | 2.5 | 0.1 | 114.2 |
| | 7.78951 | 0% | 80% | | | | |
| | 11.3413 | 0% | 90% | | | | |

UO only

| Time prior AKI stage | Cutoff value | sens | spec | Quartile | OR | 95% CI of OR | |
|---|---|---|---|---|---|---|---|
| 0 hours | 1.96208 | 72% | 61% | 1 | | | |
| | 0.86575 | 83% | 32% | 2 | 0.6 | 0.1 | 4.0 |
| | 0.62996 | 94% | 20% | 3 | 2.0 | 0.5 | 8.1 |
| | 4.10153 | 50% | 70% | 4 | 4.0 | 1.1 | 14.8 |
| | 8.39546 | 44% | 82% | | | | |
| | 20.2268 | 33% | 91% | | | | |
| 24 hours | 1.96208 | 72% | 61% | 1 | | | |
| | 0.86575 | 83% | 32% | 2 | 0.6 | 0.1 | 4.0 |
| | 0.62996 | 94% | 20% | 3 | 2.0 | 0.5 | 8.1 |
| | 4.10153 | 50% | 70% | 4 | 4.0 | 1.1 | 14.8 |
| | 8.39546 | 44% | 82% | | | | |
| | 20.2268 | 33% | 91% | | | | |

Fig. 3 Continued

| 48 hours | 1.96208 | 72% | 61% | 1 | | | |
|---|---|---|---|---|---|---|---|
| | 0.86575 | 83% | 32% | 2 | 0.6 | 0.1 | 4.0 |
| | 0.62996 | 94% | 20% | 3 | 2.0 | 0.5 | 8.1 |
| | 4.10153 | 50% | 70% | 4 | 4.0 | 1.1 | 14.8 |
| | 8.39546 | 44% | 82% | | | | |
| | 20.2268 | 33% | 91% | | | | |

Eotaxin sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 36.000 | 48.300 | 36.000 | 48.300 | 36.000 | 48.300 |
| average | 52.830 | 92.050 | 52.830 | 92.050 | 52.830 | 92.050 |
| stdev | 43.401 | 134.609 | 43.401 | 134.609 | 43.401 | 134.609 |
| p (t-test) | | 0.058 | | 0.058 | | 0.058 |
| min | 10.800 | 12.100 | 10.800 | 12.100 | 10.800 | 12.100 |
| max | 229.000 | 535.000 | 229.000 | 535.000 | 229.000 | 535.000 |
| n (Samp) | 54 | 22 | 54 | 22 | 54 | 22 |
| n (Pat) | 54 | 22 | 54 | 22 | 54 | 22 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 31.300 | 120.000 | 31.300 | 120.000 | 31.300 | 120.000 |
| average | 88.265 | 118.740 | 88.265 | 118.740 | 88.265 | 118.740 |
| stdev | 137.507 | 72.223 | 137.507 | 72.223 | 137.507 | 72.223 |
| p (t-test) | | 0.640 | | 0.640 | | 0.640 |
| min | 12.300 | 18.700 | 12.300 | 18.700 | 12.300 | 18.700 |
| max | 535.000 | 221.000 | 535.000 | 221.000 | 535.000 | 221.000 |
| n (Samp) | 20 | 5 | 20 | 5 | 20 | 5 |
| n (Pat) | 20 | 5 | 20 | 5 | 20 | 5 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 35.250 | 47.300 | 35.250 | 47.300 | 35.250 | 47.300 |
| average | 51.782 | 49.547 | 51.782 | 49.547 | 51.782 | 49.547 |
| stdev | 45.589 | 30.475 | 45.589 | 30.475 | 45.589 | 30.475 |
| p (t-test) | | 0.853 | | 0.853 | | 0.853 |
| min | 10.800 | 12.100 | 10.800 | 12.100 | 10.800 | 12.100 |
| max | 229.000 | 135.000 | 229.000 | 135.000 | 229.000 | 135.000 |
| n (Samp) | 44 | 17 | 44 | 17 | 44 | 17 |
| n (Pat) | 44 | 17 | 44 | 17 | 44 | 17 | sCr or UO

| Time prior AKI stage | AUC | SE | nCohort 1 | nCohort 2 | p |
|---|---|---|---|---|---|
| 0 hours | 0.51 | 0.074 | 54 | 22 | 0.842 |
| 24 hours | 0.51 | 0.074 | 54 | 22 | 0.842 |
| 48 hours | 0.51 | 0.074 | 54 | 22 | 0.842 |

Fig. 3 Continued sCr only

| Time prior AKI stage | AUC | SE | nCohort 1 | nCohort 2 | p |
|---|---|---|---|---|---|
| 0 hours | 0.74 | 0.138 | 20 | 5 | 0.082 |
| 24 hours | 0.74 | 0.138 | 20 | 5 | 0.082 |
| 48 hours | 0.74 | 0.138 | 20 | 5 | 0.082 |

UO only

| Time prior AKI stage | AUC | SE | nCohort 1 | nCohort 2 | p |
|---|---|---|---|---|---|
| 0 hours | 0.53 | 0.084 | 44 | 17 | 0.695 |
| 24 hours | 0.53 | 0.084 | 44 | 17 | 0.695 |
| 48 hours | 0.53 | 0.084 | 44 | 17 | 0.695 | sCr or UO

| Time prior AKI stage | Cutoff value | sens | spec | Quartile | OR | 95% CI of OR | |
|---|---|---|---|---|---|---|---|
| 0 hours | 20.7 | 73% | 17% | 1 | | | |
| | 18.4 | 82% | 13% | 2 | 0.3 | 0.1 | 1.1 |
| | 15.5 | 91% | 7% | 3 | 0.8 | 0.3 | 2.0 |
| | 66.2 | 32% | 70% | 4 | 0.8 | 0.3 | 2.0 |
| | 76.5 | 23% | 81% | | | | |
| | 93 | 18% | 91% | | | | |
| 24 hours | 20.7 | 73% | 17% | 1 | | | |
| | 18.4 | 82% | 13% | 2 | 0.3 | 0.1 | 1.1 |
| | 15.5 | 91% | 7% | 3 | 0.8 | 0.3 | 2.0 |
| | 66.2 | 32% | 70% | 4 | 0.8 | 0.3 | 2.0 |
| | 76.5 | 23% | 81% | | | | |
| | 93 | 18% | 91% | | | | |
| 48 hours | 20.7 | 73% | 17% | 1 | | | |
| | 18.4 | 82% | 13% | 2 | 0.3 | 0.1 | 1.1 |
| | 15.5 | 91% | 7% | 3 | 0.8 | 0.3 | 2.0 |
| | 66.2 | 32% | 70% | 4 | 0.8 | 0.3 | 2.0 |
| | 76.5 | 23% | 81% | | | | |
| | 93 | 18% | 91% | | | | | sCr only

| Time prior AKI stage | Cutoff value | sens | spec | Quartile | OR | 95% CI of OR | |
|---|---|---|---|---|---|---|---|
| 0 hours | 88.1 | 80% | 85% | 1 | | | |
| | 88.1 | 80% | 85% | 2 | 0.0 | 0.0 | na |
| | 18.4 | 100% | 15% | 3 | 0.0 | 0.0 | na |
| | 74.9 | 80% | 70% | 4 | 6.7 | 0.2 | 219.7 |
| | 85.3 | 80% | 80% | | | | |
| | 110 | 60% | 90% | | | | |
| 24 hours | 88.1 | 80% | 85% | 1 | | | |
| | 88.1 | 80% | 85% | 2 | 0.0 | 0.0 | na |
| | 18.4 | 100% | 15% | 3 | 0.0 | 0.0 | na |
| | 74.9 | 80% | 70% | 4 | 6.7 | 0.2 | 219.7 |
| | 85.3 | 80% | 80% | | | | |
| | 110 | 60% | 90% | | | | |
| 48 hours | 88.1 | 80% | 85% | 1 | | | |
| | 88.1 | 80% | 85% | 2 | 0.0 | 0.0 | na |
| | 18.4 | 100% | 15% | 3 | 0.0 | 0.0 | na |
| | 74.9 | 80% | 70% | 4 | 6.7 | 0.2 | 219.7 |
| | 85.3 | 80% | 80% | | | | |
| | 110 | 60% | 90% | | | | |

Fig. 3 Continued

UO only

| Time prior AKI stage | Cutoff value | sens | spec | Quartile | OR | 95% CI of OR | |
|---|---|---|---|---|---|---|---|
| 0 hours | 35.4 | 71% | 52% | 1 | | | |
| | 18.7 | 82% | 16% | 2 | 0.3 | 0.1 | 1.7 |
| | 15.5 | 94% | 9% | 3 | 1.3 | 0.4 | 4.1 |
| | 62.4 | 29% | 70% | 4 | 0.7 | 0.2 | 2.3 |
| | 70.5 | 18% | 82% | | | | |
| | 93 | 6% | 91% | | | | |
| 24 hours | 35.4 | 71% | 52% | 1 | | | |
| | 18.7 | 82% | 16% | 2 | 0.3 | 0.1 | 1.7 |
| | 15.5 | 94% | 9% | 3 | 1.3 | 0.4 | 4.1 |
| | 62.4 | 29% | 70% | 4 | 0.7 | 0.2 | 2.3 |
| | 70.5 | 18% | 82% | | | | |
| | 93 | 6% | 91% | | | | |
| 48 hours | 35.4 | 71% | 52% | 1 | | | |
| | 18.7 | 82% | 16% | 2 | 0.3 | 0.1 | 1.7 |
| | 15.5 | 94% | 9% | 3 | 1.3 | 0.4 | 4.1 |
| | 62.4 | 29% | 70% | 4 | 0.7 | 0.2 | 2.3 |
| | 70.5 | 18% | 82% | | | | |
| | 93 | 6% | 91% | | | | |

Hepatocyte growth factor receptor sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 515.068 | 588.312 | 515.068 | 588.312 | 515.068 | 588.312 |
| average | 911.178 | 745.540 | 911.178 | 745.540 | 911.178 | 745.540 |
| stdev | 1003.635 | 671.390 | 1003.635 | 671.390 | 1003.635 | 671.390 |
| p (t-test) | | 0.615 | | 0.615 | | 0.615 |
| min | 5.678 | 5.678 | 5.678 | 5.678 | 5.678 | 5.678 |
| max | 3446.809 | 1907.850 | 3446.809 | 1907.850 | 3446.809 | 1907.850 |
| n (Samp) | 31 | 11 | 31 | 11 | 31 | 11 |
| n (Pat) | 31 | 11 | 31 | 11 | 31 | 11 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 366.909 | 383.572 | 366.909 | 383.572 | 366.909 | 383.572 |
| average | 722.651 | 688.094 | 722.651 | 688.094 | 722.651 | 688.094 |
| stdev | 1011.090 | 842.631 | 1011.090 | 842.631 | 1011.090 | 842.631 |
| p (t-test) | | 0.952 | | 0.952 | | 0.952 |
| min | 5.678 | 77.381 | 5.678 | 77.381 | 5.678 | 77.381 |
| max | 3306.220 | 1907.850 | 3306.220 | 1907.850 | 3306.220 | 1907.850 |
| n (Samp) | 12 | 4 | 12 | 4 | 12 | 4 |
| n (Pat) | 12 | 4 | 12 | 4 | 12 | 4 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 659.439 | 564.384 | 659.439 | 564.384 | 659.439 | 564.384 |
| average | 947.526 | 634.224 | 947.526 | 634.224 | 947.526 | 634.224 |
| stdev | 982.679 | 610.143 | 982.679 | 610.143 | 982.679 | 610.143 |
| p (t-test) | | 0.436 | | 0.436 | | 0.436 |
| min | 5.678 | 5.678 | 5.678 | 5.678 | 5.678 | 5.678 |
| max | 3446.809 | 1720.137 | 3446.809 | 1720.137 | 3446.809 | 1720.137 |
| n (Samp) | 22 | 7 | 22 | 7 | 22 | 7 |
| n (Pat) | 22 | 7 | 22 | 7 | 22 | 7 |

Fig. 3 Continued sCr or UO

| Time prior AKI stage | AUC | SE | nCohort 1 | nCohort 2 | p |
|---|---|---|---|---|---|
| 0 hours | 0.47 | 0.101 | 31 | 11 | 0.784 |
| 24 hours | 0.47 | 0.101 | 31 | 11 | 0.784 |
| 48 hours | 0.47 | 0.101 | 31 | 11 | 0.784 | sCr only

| Time prior AKI stage | AUC | SE | nCohort 1 | nCohort 2 | p |
|---|---|---|---|---|---|
| 0 hours | 0.54 | 0.173 | 12 | 4 | 0.810 |
| 24 hours | 0.54 | 0.173 | 12 | 4 | 0.810 |
| 48 hours | 0.54 | 0.173 | 12 | 4 | 0.810 |

UO only

| Time prior AKI stage | AUC | SE | nCohort 1 | nCohort 2 | p |
|---|---|---|---|---|---|
| 0 hours | 0.42 | 0.122 | 22 | 7 | 0.506 |
| 24 hours | 0.42 | 0.122 | 22 | 7 | 0.506 |
| 48 hours | 0.42 | 0.122 | 22 | 7 | 0.506 | sCr or UO

| Time prior AKI stage | Cutoff value | sens | spec | Quartile | OR | 95% CI of OR | |
|---|---|---|---|---|---|---|---|
| 0 hours | 218.75 | 73% | 42% | 1 | | | |
| | 37.4088 | 82% | 13% | 2 | 3.0 | 0.4 | 22.5 |
| | 0 | 100% | 0% | 3 | 1.0 | 0.1 | 11.0 |
| | 1233.12 | 27% | 71% | 4 | 1.9 | 0.2 | 16.2 |
| | 1843 | 9% | 81% | | | | |
| | 2406.53 | 0% | 90% | | | | |
| 24 hours | 218.75 | 73% | 42% | 1 | | | |
| | 37.4088 | 82% | 13% | 2 | 3.0 | 0.4 | 22.5 |
| | 0 | 100% | 0% | 3 | 1.0 | 0.1 | 11.0 |
| | 1233.12 | 27% | 71% | 4 | 1.9 | 0.2 | 16.2 |
| | 1843 | 9% | 81% | | | | |
| | 2406.53 | 0% | 90% | | | | |
| 48 hours | 218.75 | 73% | 42% | 1 | | | |
| | 37.4088 | 82% | 13% | 2 | 3.0 | 0.4 | 22.5 |
| | 0 | 100% | 0% | 3 | 1.0 | 0.1 | 11.0 |
| | 1233.12 | 27% | 71% | 4 | 1.9 | 0.2 | 16.2 |
| | 1843 | 9% | 81% | | | | |
| | 2406.53 | 0% | 90% | | | | |

UO only

| Time prior AKI stage | Cutoff value | sens | spec | Quartile | OR | 95% CI of OR | |
|---|---|---|---|---|---|---|---|
| 0 hours | 214.12 | 71% | 41% | 1 | | | |
| | 37.4088 | 86% | 9% | 2 | 5.3 | 0.2 | 154.7 |
| | 0 | 100% | 0% | 3 | 1.2 | 0.0 | 107.9 |
| | 1387.64 | 14% | 73% | 4 | 2.8 | 0.1 | 103.7 |
| | 1843 | 0% | 82% | | | | |
| | 2406.53 | 0% | 91% | | | | |
| 24 hours | 214.12 | 71% | 41% | 1 | | | |
| | 37.4088 | 86% | 9% | 2 | 5.3 | 0.2 | 154.7 |
| | 0 | 100% | 0% | 3 | 1.2 | 0.0 | 107.9 |
| | 1387.64 | 14% | 73% | 4 | 2.8 | 0.1 | 103.7 |
| | 1843 | 0% | 82% | | | | |
| | 2406.53 | 0% | 91% | | | | |

Fig. 3 Continued

| 48 hours | 214.12 | 71% | 41% | 1 | | | |
| | 37.4088 | 86% | 9% | 2 | 5.3 | 0.2 | 154.7 |
| | 0 | 100% | 0% | 3 | 1.2 | 0.0 | 107.9 |
| | 1387.64 | 14% | 73% | 4 | 2.8 | 0.1 | 103.7 |
| | 1843 | 0% | 82% | | | | |
| | 2406.53 | 0% | 91% | | | | |

Interleukin-1 beta sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 1.145 | 3.665 | 1.145 | 3.665 | 1.145 | 3.665 |
| average | 14.618 | 16.502 | 14.618 | 16.502 | 14.618 | 16.502 |
| stdev | 90.937 | 47.237 | 90.937 | 47.237 | 90.937 | 47.237 |
| p (t-test) | | 0.927 | | 0.927 | | 0.927 |
| min | 0.006 | 0.508 | 0.006 | 0.508 | 0.006 | 0.508 |
| max | 670.000 | 224.000 | 670.000 | 224.000 | 670.000 | 224.000 |
| n (Samp) | 54 | 22 | 54 | 22 | 54 | 22 |
| n (Pat) | 54 | 22 | 54 | 22 | 54 | 22 | sCr only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 1.001 | 4.030 | 1.001 | 4.030 | 1.001 | 4.030 |
| average | 3.114 | 10.864 | 3.114 | 10.864 | 3.114 | 10.864 |
| stdev | 6.824 | 12.949 | 6.824 | 12.949 | 6.824 | 12.949 |
| p (t-test) | | 0.072 | | 0.072 | | 0.072 |
| min | 0.006 | 2.290 | 0.006 | 2.290 | 0.006 | 2.290 |
| max | 31.300 | 32.800 | 31.300 | 32.800 | 31.300 | 32.800 |
| n (Samp) | 20 | 5 | 20 | 5 | 20 | 5 |
| n (Pat) | 20 | 5 | 20 | 5 | 20 | 5 |

UO only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 1.385 | 2.240 | 1.385 | 2.240 | 1.385 | 2.240 |
| average | 18.155 | 16.874 | 18.155 | 16.874 | 18.155 | 16.874 |
| stdev | 100.657 | 53.558 | 100.657 | 53.558 | 100.657 | 53.558 |
| p (t-test) | | 0.961 | | 0.961 | | 0.961 |
| min | 0.006 | 0.508 | 0.006 | 0.508 | 0.006 | 0.508 |
| max | 670.000 | 224.000 | 670.000 | 224.000 | 670.000 | 224.000 |
| n (Samp) | 44 | 17 | 44 | 17 | 44 | 17 |
| n (Pat) | 44 | 17 | 44 | 17 | 44 | 17 | sCr or UO

| Time prior AKI stage | AUC | SE | nCohort 1 | nCohort 2 | p |
| --- | --- | --- | --- | --- | --- |
| 0 hours | 0.72 | 0.069 | 54 | 22 | 0.002 |
| 24 hours | 0.72 | 0.069 | 54 | 22 | 0.002 |
| 48 hours | 0.72 | 0.069 | 54 | 22 | 0.002 | sCr only

| Time prior AKI stage | AUC | SE | nCohort 1 | nCohort 2 | p |
| --- | --- | --- | --- | --- | --- |
| 0 hours | 0.84 | 0.117 | 20 | 5 | 0.004 |
| 24 hours | 0.84 | 0.117 | 20 | 5 | 0.004 |
| 48 hours | 0.84 | 0.117 | 20 | 5 | 0.004 |

Fig. 3 Continued

UO only

| Time prior AKI stage | AUC | SE | nCohort 1 | nCohort 2 | p |
|---|---|---|---|---|---|
| 0 hours | 0.64 | 0.082 | 44 | 17 | 0.088 |
| 24 hours | 0.64 | 0.082 | 44 | 17 | 0.088 |
| 48 hours | 0.64 | 0.082 | 44 | 17 | 0.088 | sCr or UO

| Time prior AKI stage | Cutoff value | sens | spec | Quartile | OR | 95% CI of OR | |
|---|---|---|---|---|---|---|---|
| 0 hours | 1.17 | 73% | 52% | 1 | | | |
| | 0.783 | 82% | 44% | 2 | 3.0 | 0.6 | 15.5 |
| | 0.616 | 91% | 37% | 3 | 3.0 | 0.6 | 15.5 |
| | 1.93 | 68% | 70% | 4 | 9.4 | 2.1 | 42.7 |
| | 3.65 | 50% | 81% | | | | |
| | 6.66 | 23% | 91% | | | | |
| 24 hours | 1.17 | 73% | 52% | 1 | | | |
| | 0.783 | 82% | 44% | 2 | 3.0 | 0.6 | 15.5 |
| | 0.616 | 91% | 37% | 3 | 3.0 | 0.6 | 15.5 |
| | 1.93 | 68% | 70% | 4 | 9.4 | 2.1 | 42.7 |
| | 3.65 | 50% | 81% | | | | |
| | 6.66 | 23% | 91% | | | | |
| 48 hours | 1.17 | 73% | 52% | 1 | | | |
| | 0.783 | 82% | 44% | 2 | 3.0 | 0.6 | 15.5 |
| | 0.616 | 91% | 37% | 3 | 3.0 | 0.6 | 15.5 |
| | 1.93 | 68% | 70% | 4 | 9.4 | 2.1 | 42.7 |
| | 3.65 | 50% | 81% | | | | |
| | 6.66 | 23% | 91% | | | | |

UO only

| Time prior AKI stage | Cutoff value | sens | spec | Quartile | OR | 95% CI of OR | |
|---|---|---|---|---|---|---|---|
| 0 hours | 1.12 | 71% | 48% | 1 | | | |
| | 0.783 | 82% | 43% | 2 | 3.3 | 0.6 | 18.1 |
| | 0.508 | 94% | 30% | 3 | 2.4 | 0.4 | 14.3 |
| | 2.47 | 47% | 70% | 4 | 3.9 | 0.7 | 20.4 |
| | 6.01 | 24% | 82% | | | | |
| | 9.92 | 18% | 91% | | | | |
| 24 hours | 1.12 | 71% | 48% | 1 | | | |
| | 0.783 | 82% | 43% | 2 | 3.3 | 0.6 | 18.1 |
| | 0.508 | 94% | 30% | 3 | 2.4 | 0.4 | 14.3 |
| | 2.47 | 47% | 70% | 4 | 3.9 | 0.7 | 20.4 |
| | 6.01 | 24% | 82% | | | | |
| | 9.92 | 18% | 91% | | | | |
| 48 hours | 1.12 | 71% | 48% | 1 | | | |
| | 0.783 | 82% | 43% | 2 | 3.3 | 0.6 | 18.1 |
| | 0.508 | 94% | 30% | 3 | 2.4 | 0.4 | 14.3 |
| | 2.47 | 47% | 70% | 4 | 3.9 | 0.7 | 20.4 |
| | 6.01 | 24% | 82% | | | | |
| | 9.92 | 18% | 91% | | | | |

Fig. 3 Continued

Interleukin-10 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1.430 | 1.300 | 1.430 | 1.300 | 1.430 | 1.300 |
| average | 1.820 | 1.466 | 1.820 | 1.466 | 1.820 | 1.466 |
| stdev | 4.161 | 1.335 | 4.161 | 1.335 | 4.161 | 1.335 |
| p (t-test) |  | 0.698 |  | 0.698 |  | 0.698 |
| min | 0.062 | 0.062 | 0.062 | 0.062 | 0.062 | 0.062 |
| max | 30.900 | 3.930 | 30.900 | 3.930 | 30.900 | 3.930 |
| n (Samp) | 54 | 22 | 54 | 22 | 54 | 22 |
| n (Pat) | 54 | 22 | 54 | 22 | 54 | 22 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1.310 | 1.460 | 1.310 | 1.460 | 1.310 | 1.460 |
| average | 1.035 | 1.380 | 1.035 | 1.380 | 1.035 | 1.380 |
| stdev | 0.803 | 0.888 | 0.803 | 0.888 | 0.803 | 0.888 |
| p (t-test) |  | 0.407 |  | 0.407 |  | 0.407 |
| min | 0.062 | 0.062 | 0.062 | 0.062 | 0.062 | 0.062 |
| max | 2.330 | 2.540 | 2.330 | 2.540 | 2.330 | 2.540 |
| n (Samp) | 20 | 5 | 20 | 5 | 20 | 5 |
| n (Pat) | 20 | 5 | 20 | 5 | 20 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1.425 | 1.350 | 1.425 | 1.350 | 1.425 | 1.350 |
| average | 1.930 | 1.568 | 1.930 | 1.568 | 1.930 | 1.568 |
| stdev | 4.597 | 1.482 | 4.597 | 1.482 | 4.597 | 1.482 |
| p (t-test) |  | 0.752 |  | 0.752 |  | 0.752 |
| min | 0.062 | 0.062 | 0.062 | 0.062 | 0.062 | 0.062 |
| max | 30.900 | 3.930 | 30.900 | 3.930 | 30.900 | 3.930 |
| n (Samp) | 44 | 17 | 44 | 17 | 44 | 17 |
| n (Pat) | 44 | 17 | 44 | 17 | 44 | 17 | sCr or UO

| Time prior AKI stage | AUC | SE | nCohort 1 | nCohort 2 | p |
|---|---|---|---|---|---|
| 0 hours | 0.51 | 0.074 | 54 | 22 | 0.914 |
| 24 hours | 0.51 | 0.074 | 54 | 22 | 0.914 |
| 48 hours | 0.51 | 0.074 | 54 | 22 | 0.914 | sCr only

| Time prior AKI stage | AUC | SE | nCohort 1 | nCohort 2 | p |
|---|---|---|---|---|---|
| 0 hours | 0.61 | 0.149 | 20 | 5 | 0.460 |
| 24 hours | 0.61 | 0.149 | 20 | 5 | 0.460 |
| 48 hours | 0.61 | 0.149 | 20 | 5 | 0.460 |

UO only

| Time prior AKI stage | AUC | SE | nCohort 1 | nCohort 2 | p |
|---|---|---|---|---|---|
| 0 hours | 0.54 | 0.084 | 44 | 17 | 0.672 |
| 24 hours | 0.54 | 0.084 | 44 | 17 | 0.672 |
| 48 hours | 0.54 | 0.084 | 44 | 17 | 0.672 |

Fig. 3 Continued sCr or UO

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 2.7 | 1.0 | 7.7 |
| | 0 | 100% | 0% | 3 | 1.0 | 0.3 | 3.5 |
| | 1.91 | 27% | 72% | 4 | 1.7 | 0.6 | 5.2 |
| | 2.32 | 23% | 81% | | | | |
| | 2.72 | 23% | 91% | | | | |
| 24 hours | 0 | 100% | 0% | 1 | | | |
| | 0 | 100% | 0% | 2 | 2.7 | 1.0 | 7.7 |
| | 0 | 100% | 0% | 3 | 1.0 | 0.3 | 3.5 |
| | 1.91 | 27% | 72% | 4 | 1.7 | 0.6 | 5.2 |
| | 2.32 | 23% | 81% | | | | |
| | 2.72 | 23% | 91% | | | | |
| 48 hours | 0 | 100% | 0% | 1 | | | |
| | 0 | 100% | 0% | 2 | 2.7 | 1.0 | 7.7 |
| | 0 | 100% | 0% | 3 | 1.0 | 0.3 | 3.5 |
| | 1.91 | 27% | 72% | 4 | 1.7 | 0.6 | 5.2 |
| | 2.32 | 23% | 81% | | | | |
| | 2.72 | 23% | 91% | | | | |

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.7 | 0.2 | 2.6 |
| | 0 | 100% | 0% | 3 | 0.5 | 0.1 | 2.0 |
| | 1.91 | 35% | 73% | 4 | 0.9 | 0.3 | 2.9 |
| | 2.42 | 29% | 82% | | | | |
| | 2.93 | 29% | 91% | | | | |
| 24 hours | 0 | 100% | 0% | 1 | | | |
| | 0 | 100% | 0% | 2 | 0.7 | 0.2 | 2.6 |
| | 0 | 100% | 0% | 3 | 0.5 | 0.1 | 2.0 |
| | 1.91 | 35% | 73% | 4 | 0.9 | 0.3 | 2.9 |
| | 2.42 | 29% | 82% | | | | |
| | 2.93 | 29% | 91% | | | | |
| 48 hours | 0 | 100% | 0% | 1 | | | |
| | 0 | 100% | 0% | 2 | 0.7 | 0.2 | 2.6 |
| | 0 | 100% | 0% | 3 | 0.5 | 0.1 | 2.0 |
| | 1.91 | 35% | 73% | 4 | 0.9 | 0.3 | 2.9 |
| | 2.42 | 29% | 82% | | | | |
| | 2.93 | 29% | 91% | | | | |

Fig. 3 Continued

Nidogen-1 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 2325.581 | 1487.455 | 2325.581 | 1487.455 | 2325.581 | 1487.455 |
| average | 2340.874 | 1960.383 | 2340.874 | 1960.383 | 2340.874 | 1960.383 |
| stdev | 1616.976 | 1448.585 | 1616.976 | 1448.585 | 1616.976 | 1448.585 |
| p (t-test) |  | 0.499 |  | 0.499 |  | 0.499 |
| min | 95.536 | 662.526 | 95.536 | 662.526 | 95.536 | 662.526 |
| max | 4988.372 | 4569.767 | 4988.372 | 4569.767 | 4988.372 | 4569.767 |
| n (Samp) | 29 | 11 | 29 | 11 | 29 | 11 |
| n (Pat) | 29 | 11 | 29 | 11 | 29 | 11 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 939.840 | 3992.896 | 939.840 | 3992.896 | 939.840 | 3992.896 |
| average | 1875.887 | 4074.787 | 1875.887 | 4074.787 | 1875.887 | 4074.787 |
| stdev | 1678.686 | 390.809 | 1678.686 | 390.809 | 1678.686 | 390.809 |
| p (t-test) |  | 0.025 |  | 0.025 |  | 0.025 |
| min | 95.536 | 3743.590 | 95.536 | 3743.590 | 95.536 | 3743.590 |
| max | 4273.504 | 4569.767 | 4273.504 | 4569.767 | 4273.504 | 4569.767 |
| n (Samp) | 11 | 4 | 11 | 4 | 11 | 4 |
| n (Pat) | 11 | 4 | 11 | 4 | 11 | 4 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 2325.581 | 981.366 | 2325.581 | 981.366 | 2325.581 | 981.366 |
| average | 2498.939 | 1176.300 | 2498.939 | 1176.300 | 2498.939 | 1176.300 |
| stdev | 1606.892 | 441.686 | 1606.892 | 441.686 | 1606.892 | 441.686 |
| p (t-test) |  | 0.043 |  | 0.043 |  | 0.043 |
| min | 259.783 | 662.526 | 259.783 | 662.526 | 259.783 | 662.526 |
| max | 4988.372 | 1857.143 | 4988.372 | 1857.143 | 4988.372 | 1857.143 |
| n (Samp) | 21 | 7 | 21 | 7 | 21 | 7 |
| n (Pat) | 21 | 7 | 21 | 7 | 21 | 7 | sCr or UO

| Time prior AKI stage | AUC | SE | nCohort 1 | nCohort 2 | p |
|---|---|---|---|---|---|
| 0 hours | 0.47 | 0.102 | 29 | 11 | 0.759 |
| 24 hours | 0.47 | 0.102 | 29 | 11 | 0.759 |
| 48 hours | 0.47 | 0.102 | 29 | 11 | 0.759 | sCr only

| Time prior AKI stage | AUC | SE | nCohort 1 | nCohort 2 | p |
|---|---|---|---|---|---|
| 0 hours | 0.84 | 0.135 | 11 | 4 | 0.011 |
| 24 hours | 0.84 | 0.135 | 11 | 4 | 0.011 |
| 48 hours | 0.84 | 0.135 | 11 | 4 | 0.011 |

UO only

| Time prior AKI stage | AUC | SE | nCohort 1 | nCohort 2 | p |
|---|---|---|---|---|---|
| 0 hours | 0.28 | 0.104 | 21 | 7 | 0.037 |
| 24 hours | 0.28 | 0.104 | 21 | 7 | 0.037 |
| 48 hours | 0.28 | 0.104 | 21 | 7 | 0.037 |

Fig. 3 Continued sCr or UO

| Time prior AKI stage | Cutoff value | sens | spec | Quartile | OR | 95% CI of OR | |
|---|---|---|---|---|---|---|---|
| 0 hours | 875.668 | 73% | 34% | 1 | | | |
| | 855.072 | 82% | 34% | 2 | 0.0 | 0.0 | na |
| | 850.932 | 91% | 34% | 3 | 5.4 | 0.8 | 35.2 |
| | 3487.18 | 27% | 72% | 4 | 0.3 | 0.0 | 5.8 |
| | 4273.5 | 9% | 83% | | | | |
| | 4662.79 | 0% | 93% | | | | |
| 24 hours | 875.668 | 73% | 34% | 1 | | | |
| | 855.072 | 82% | 34% | 2 | 0.0 | 0.0 | na |
| | 850.932 | 91% | 34% | 3 | 5.4 | 0.8 | 35.2 |
| | 3487.18 | 27% | 72% | 4 | 0.3 | 0.0 | 5.8 |
| | 4273.5 | 9% | 83% | | | | |
| | 4662.79 | 0% | 93% | | | | |
| 48 hours | 875.668 | 73% | 34% | 1 | | | |
| | 855.072 | 82% | 34% | 2 | 0.0 | 0.0 | na |
| | 850.932 | 91% | 34% | 3 | 5.4 | 0.8 | 35.2 |
| | 3487.18 | 27% | 72% | 4 | 0.3 | 0.0 | 5.8 |
| | 4273.5 | 9% | 83% | | | | |
| | 4662.79 | 0% | 93% | | | | |

Oxidized low-density lipoprotein receptor 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 25.394 | 52.327 | 25.394 | 52.327 | 25.394 | 52.327 |
| average | 33.728 | 61.365 | 33.728 | 61.365 | 33.728 | 61.365 |
| stdev | 30.299 | 62.559 | 30.299 | 62.559 | 30.299 | 62.559 |
| p (t-test) | | 0.011 | | 0.011 | | 0.011 |
| min | 1.212 | 1.735 | 1.212 | 1.735 | 1.212 | 1.735 |
| max | 139.836 | 214.368 | 139.836 | 214.368 | 139.836 | 214.368 |
| n (Samp) | 54 | 23 | 54 | 23 | 54 | 23 |
| n (Pat) | 54 | 23 | 54 | 23 | 54 | 23 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 12.015 | 22.855 | 12.015 | 22.855 | 12.015 | 22.855 |
| average | 35.267 | 28.687 | 35.267 | 28.687 | 35.267 | 28.687 |
| stdev | 52.327 | 25.404 | 52.327 | 25.404 | 52.327 | 25.404 |
| p (t-test) | | 0.811 | | 0.811 | | 0.811 |
| min | 1.212 | 4.749 | 1.212 | 4.749 | 1.212 | 4.749 |
| max | 187.486 | 64.291 | 187.486 | 64.291 | 187.486 | 64.291 |
| n (Samp) | 20 | 4 | 20 | 4 | 20 | 4 |
| n (Pat) | 20 | 4 | 20 | 4 | 20 | 4 |

Fig. 3 Continued

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 27.472 | 55.471 | 27.472 | 55.471 | 27.472 | 55.471 |
| average | 33.894 | 62.449 | 33.894 | 62.449 | 33.894 | 62.449 |
| stdev | 23.779 | 60.581 | 23.779 | 60.581 | 23.779 | 60.581 |
| p (t-test) |  | 0.009 |  | 0.009 |  | 0.009 |
| min | 4.239 | 2.639 | 4.239 | 2.639 | 4.239 | 2.639 |
| max | 92.283 | 214.368 | 92.283 | 214.368 | 92.283 | 214.368 |
| n (Samp) | 44 | 18 | 44 | 18 | 44 | 18 |
| n (Pat) | 44 | 18 | 44 | 18 | 44 | 18 | sCr or UO

| Time prior AKI stage | AUC | SE | nCohort 1 | nCohort 2 | p |
|---|---|---|---|---|---|
| 0 hours | 0.60 | 0.072 | 54 | 23 | 0.153 |
| 24 hours | 0.60 | 0.072 | 54 | 23 | 0.153 |
| 48 hours | 0.60 | 0.072 | 54 | 23 | 0.153 | sCr only

| Time prior AKI stage | AUC | SE | nCohort 1 | nCohort 2 | p |
|---|---|---|---|---|---|
| 0 hours | 0.59 | 0.164 | 20 | 4 | 0.594 |
| 24 hours | 0.59 | 0.164 | 20 | 4 | 0.594 |
| 48 hours | 0.59 | 0.164 | 20 | 4 | 0.594 |

UO only

| Time prior AKI stage | AUC | SE | nCohort 1 | nCohort 2 | p |
|---|---|---|---|---|---|
| 0 hours | 0.61 | 0.081 | 44 | 18 | 0.172 |
| 24 hours | 0.61 | 0.081 | 44 | 18 | 0.172 |
| 48 hours | 0.61 | 0.081 | 44 | 18 | 0.172 | sCr or UO

| Time prior AKI stage | Cutoff value | sens | spec | Quartile | OR | 95% CI of OR | |
|---|---|---|---|---|---|---|---|
| 0 hours | 16.1385 | 74% | 37% | 1 |  |  |  |
|  | 10.083 | 83% | 26% | 2 | 1.0 | 0.3 | 2.9 |
|  | 4.23945 | 91% | 6% | 3 | 0.3 | 0.1 | 1.7 |
|  | 39.3184 | 52% | 70% | 4 | 3.4 | 1.4 | 8.7 |
|  | 54.8111 | 48% | 81% |  |  |  |  |
|  | 77.6918 | 26% | 91% |  |  |  |  |
| 24 hours | 16.1385 | 74% | 37% | 1 |  |  |  |
|  | 10.083 | 83% | 26% | 2 | 1.0 | 0.3 | 2.9 |
|  | 4.23945 | 91% | 6% | 3 | 0.3 | 0.1 | 1.7 |
|  | 39.3184 | 52% | 70% | 4 | 3.4 | 1.4 | 8.7 |
|  | 54.8111 | 48% | 81% |  |  |  |  |
|  | 77.6918 | 26% | 91% |  |  |  |  |
| 48 hours | 16.1385 | 74% | 37% | 1 |  |  |  |
|  | 10.083 | 83% | 26% | 2 | 1.0 | 0.3 | 2.9 |
|  | 4.23945 | 91% | 6% | 3 | 0.3 | 0.1 | 1.7 |
|  | 39.3184 | 52% | 70% | 4 | 3.4 | 1.4 | 8.7 |
|  | 54.8111 | 48% | 81% |  |  |  |  |
|  | 77.6918 | 26% | 91% |  |  |  |  |

Fig. 3 Continued sCr only

| Time prior AKI stage | Cutoff value | sens | spec | Quartile | OR | 95% CI of OR | |
|---|---|---|---|---|---|---|---|
| 0 hours | 14.8506 | 75% | 65% | 1 | | | |
| | 3.32291 | 100% | 15% | 2 | 0.0 | 0.0 | na |
| | 3.32291 | 100% | 15% | 3 | 2.5 | 0.1 | 114.2 |
| | 21.4101 | 50% | 70% | 4 | 1.0 | 0.0 | 110.4 |
| | 39.3184 | 25% | 80% | | | | |
| | 118.591 | 0% | 90% | | | | |
| 24 hours | 14.8506 | 75% | 65% | 1 | | | |
| | 3.32291 | 100% | 15% | 2 | 0.0 | 0.0 | na |
| | 3.32291 | 100% | 15% | 3 | 2.5 | 0.1 | 114.2 |
| | 21.4101 | 50% | 70% | 4 | 1.0 | 0.0 | 110.4 |
| | 39.3184 | 25% | 80% | | | | |
| | 118.591 | 0% | 90% | | | | |
| 48 hours | 14.8506 | 75% | 65% | 1 | | | |
| | 3.32291 | 100% | 15% | 2 | 0.0 | 0.0 | na |
| | 3.32291 | 100% | 15% | 3 | 2.5 | 0.1 | 114.2 |
| | 21.4101 | 50% | 70% | 4 | 1.0 | 0.0 | 110.4 |
| | 39.3184 | 25% | 80% | | | | |
| | 118.591 | 0% | 90% | | | | |

UO only

| Time prior AKI stage | Cutoff value | sens | spec | Quartile | OR | 95% CI of OR | |
|---|---|---|---|---|---|---|---|
| 0 hours | 17.0311 | 72% | 30% | 1 | | | |
| | 9.74574 | 83% | 16% | 2 | 0.3 | 0.1 | 1.6 |
| | 6.7825 | 94% | 9% | 3 | 0.3 | 0.1 | 1.7 |
| | 40.7225 | 56% | 70% | 4 | 2.6 | 0.9 | 7.6 |
| | 54.8111 | 50% | 82% | | | | |
| | 69.1111 | 33% | 91% | | | | |
| 24 hours | 17.0311 | 72% | 30% | 1 | | | |
| | 9.74574 | 83% | 16% | 2 | 0.3 | 0.1 | 1.6 |
| | 6.7825 | 94% | 9% | 3 | 0.3 | 0.1 | 1.7 |
| | 40.7225 | 56% | 70% | 4 | 2.6 | 0.9 | 7.6 |
| | 54.8111 | 50% | 82% | | | | |
| | 69.1111 | 33% | 91% | | | | |
| 48 hours | 17.0311 | 72% | 30% | 1 | | | |
| | 9.74574 | 83% | 16% | 2 | 0.3 | 0.1 | 1.6 |
| | 6.7825 | 94% | 9% | 3 | 0.3 | 0.1 | 1.7 |
| | 40.7225 | 56% | 70% | 4 | 2.6 | 0.9 | 7.6 |
| | 54.8111 | 50% | 82% | | | | |
| | 69.1111 | 33% | 91% | | | | |

Fig. 3 Continued

P-selectin glycoprotein ligand 1 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 1.216 | 0.599 | 1.216 | 0.599 | 1.216 | 0.599 |
| average | 3.851 | 3.665 | 3.851 | 3.665 | 3.851 | 3.665 |
| stdev | 5.828 | 9.924 | 5.828 | 9.924 | 5.828 | 9.924 |
| p (t-test) |  | 0.918 |  | 0.918 |  | 0.918 |
| min | 0.001 | 0.016 | 0.001 | 0.016 | 0.001 | 0.016 |
| max | 22.914 | 47.674 | 22.914 | 47.674 | 22.914 | 47.674 |
| n (Samp) | 54 | 23 | 54 | 23 | 54 | 23 |
| n (Pat) | 54 | 23 | 54 | 23 | 54 | 23 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 1.426 | 0.018 | 1.426 | 0.018 | 1.426 | 0.018 |
| average | 3.661 | 0.223 | 3.661 | 0.223 | 3.661 | 0.223 |
| stdev | 5.574 | 0.458 | 5.574 | 0.458 | 5.574 | 0.458 |
| p (t-test) |  | 0.188 |  | 0.188 |  | 0.188 |
| min | 0.018 | 0.016 | 0.018 | 0.016 | 0.018 | 0.016 |
| max | 19.906 | 1.042 | 19.906 | 1.042 | 19.906 | 1.042 |
| n (Samp) | 20 | 5 | 20 | 5 | 20 | 5 |
| n (Pat) | 20 | 5 | 20 | 5 | 20 | 5 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 1.216 | 0.725 | 1.216 | 0.725 | 1.216 | 0.725 |
| average | 3.658 | 4.095 | 3.658 | 4.095 | 3.658 | 4.095 |
| stdev | 5.490 | 11.142 | 5.490 | 11.142 | 5.490 | 11.142 |
| p (t-test) |  | 0.836 |  | 0.836 |  | 0.836 |
| min | 0.001 | 0.018 | 0.001 | 0.018 | 0.001 | 0.018 |
| max | 22.914 | 47.674 | 22.914 | 47.674 | 22.914 | 47.674 |
| n (Samp) | 44 | 18 | 44 | 18 | 44 | 18 |
| n (Pat) | 44 | 18 | 44 | 18 | 44 | 18 | sCr or UO

| Time prior AKI stage | AUC | SE | nCohort 1 | nCohort 2 | p |
| --- | --- | --- | --- | --- | --- |
| 0 hours | 0.39 | 0.068 | 54 | 23 | 0.093 |
| 24 hours | 0.39 | 0.068 | 54 | 23 | 0.093 |
| 48 hours | 0.39 | 0.068 | 54 | 23 | 0.093 | sCr only

| Time prior AKI stage | AUC | SE | nCohort 1 | nCohort 2 | p |
| --- | --- | --- | --- | --- | --- |
| 0 hours | 0.12 | 0.072 | 20 | 5 | 0.000 |
| 24 hours | 0.12 | 0.072 | 20 | 5 | 0.000 |
| 48 hours | 0.12 | 0.072 | 20 | 5 | 0.000 |

UO only

| Time prior AKI stage | AUC | SE | nCohort 1 | nCohort 2 | p |
| --- | --- | --- | --- | --- | --- |
| 0 hours | 0.40 | 0.077 | 44 | 18 | 0.187 |
| 24 hours | 0.40 | 0.077 | 44 | 18 | 0.187 |
| 48 hours | 0.40 | 0.077 | 44 | 18 | 0.187 |

Fig. 3 Continued sCr or UO

| Time prior AKI stage | Cutoff value | sens | spec | Quartile | OR | 95% CI of OR | |
|---|---|---|---|---|---|---|---|
| 0 hours | 0.01619 | 96% | 2% | 1 | | | |
| | 0.01619 | 96% | 2% | 2 | 1.8 | 0.6 | 5.5 |
| | 0.01619 | 96% | 2% | 3 | 1.1 | 0.3 | 3.7 |
| | 3.12755 | 17% | 70% | 4 | 3.6 | 1.3 | 10.0 |
| | 6.11213 | 17% | 81% | | | | |
| | 14.6669 | 4% | 91% | | | | |
| 24 hours | 0.01619 | 96% | 2% | 1 | | | |
| | 0.01619 | 96% | 2% | 2 | 1.8 | 0.6 | 5.5 |
| | 0.01619 | 96% | 2% | 3 | 1.1 | 0.3 | 3.7 |
| | 3.12755 | 17% | 70% | 4 | 3.6 | 1.3 | 10.0 |
| | 6.11213 | 17% | 81% | | | | |
| | 14.6669 | 4% | 91% | | | | |
| 48 hours | 0.01619 | 96% | 2% | 1 | | | |
| | 0.01619 | 96% | 2% | 2 | 1.8 | 0.6 | 5.5 |
| | 0.01619 | 96% | 2% | 3 | 1.1 | 0.3 | 3.7 |
| | 3.12755 | 17% | 70% | 4 | 3.6 | 1.3 | 10.0 |
| | 6.11213 | 17% | 81% | | | | |
| | 14.6669 | 4% | 91% | | | | |

UO only

| Time prior AKI stage | Cutoff value | sens | spec | Quartile | OR | 95% CI of OR | |
|---|---|---|---|---|---|---|---|
| 0 hours | 0.01822 | 72% | 16% | 1 | | | |
| | 0.00132 | 100% | 2% | 2 | 2.2 | 0.5 | 8.7 |
| | 0.00132 | 100% | 2% | 3 | 1.0 | 0.2 | 5.0 |
| | 2.61628 | 17% | 70% | 4 | 3.8 | 1.0 | 14.3 |
| | 7.08225 | 17% | 82% | | | | |
| | 12.7911 | 6% | 91% | | | | |
| 24 hours | 0.01822 | 72% | 16% | 1 | | | |
| | 0.00132 | 100% | 2% | 2 | 2.2 | 0.5 | 8.7 |
| | 0.00132 | 100% | 2% | 3 | 1.0 | 0.2 | 5.0 |
| | 2.61628 | 17% | 70% | 4 | 3.8 | 1.0 | 14.3 |
| | 7.08225 | 17% | 82% | | | | |
| | 12.7911 | 6% | 91% | | | | |
| 48 hours | 0.01822 | 72% | 16% | 1 | | | |
| | 0.00132 | 100% | 2% | 2 | 2.2 | 0.5 | 8.7 |
| | 0.00132 | 100% | 2% | 3 | 1.0 | 0.2 | 5.0 |
| | 2.61628 | 17% | 70% | 4 | 3.8 | 1.0 | 14.3 |
| | 7.08225 | 17% | 82% | | | | |
| | 12.7911 | 6% | 91% | | | | |

Fig. 3 Continued

Stem cell factor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 212.000 | 116.000 | 212.000 | 116.000 | 212.000 | 116.000 |
| average | 325.950 | 179.641 | 325.950 | 179.641 | 325.950 | 179.641 |
| stdev | 357.718 | 148.948 | 357.718 | 148.948 | 357.718 | 148.948 |
| p (t-test) |  | 0.069 |  | 0.069 |  | 0.069 |
| min | 11.400 | 30.000 | 11.400 | 30.000 | 11.400 | 30.000 |
| max | 1610.000 | 519.000 | 1610.000 | 519.000 | 1610.000 | 519.000 |
| n (Samp) | 54 | 22 | 54 | 22 | 54 | 22 |
| n (Pat) | 54 | 22 | 54 | 22 | 54 | 22 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 116.100 | 188.000 | 116.100 | 188.000 | 116.100 | 188.000 |
| average | 194.570 | 216.220 | 194.570 | 216.220 | 194.570 | 216.220 |
| stdev | 195.777 | 113.554 | 195.777 | 113.554 | 195.777 | 113.554 |
| p (t-test) |  | 0.816 |  | 0.816 |  | 0.816 |
| min | 14.300 | 93.100 | 14.300 | 93.100 | 14.300 | 93.100 |
| max | 813.000 | 364.000 | 813.000 | 364.000 | 813.000 | 364.000 |
| n (Samp) | 20 | 5 | 20 | 5 | 20 | 5 |
| n (Pat) | 20 | 5 | 20 | 5 | 20 | 5 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 233.500 | 129.000 | 233.500 | 129.000 | 233.500 | 129.000 |
| average | 366.466 | 182.612 | 366.466 | 182.612 | 366.466 | 182.612 |
| stdev | 380.110 | 155.525 | 380.110 | 155.525 | 380.110 | 155.525 |
| p (t-test) |  | 0.059 |  | 0.059 |  | 0.059 |
| min | 11.400 | 30.000 | 11.400 | 30.000 | 11.400 | 30.000 |
| max | 1610.000 | 519.000 | 1610.000 | 519.000 | 1610.000 | 519.000 |
| n (Samp) | 44 | 17 | 44 | 17 | 44 | 17 |
| n (Pat) | 44 | 17 | 44 | 17 | 44 | 17 | sCr or UO

| Time prior AKI stage | AUC | SE | nCohort 1 | nCohort 2 | p |
|---|---|---|---|---|---|
| 0 hours | 0.41 | 0.070 | 54 | 22 | 0.193 |
| 24 hours | 0.41 | 0.070 | 54 | 22 | 0.193 |
| 48 hours | 0.41 | 0.070 | 54 | 22 | 0.193 | sCr only

| Time prior AKI stage | AUC | SE | nCohort 1 | nCohort 2 | p |
|---|---|---|---|---|---|
| 0 hours | 0.64 | 0.148 | 20 | 5 | 0.343 |
| 24 hours | 0.64 | 0.148 | 20 | 5 | 0.343 |
| 48 hours | 0.64 | 0.148 | 20 | 5 | 0.343 |

UO only

| Time prior AKI stage | AUC | SE | nCohort 1 | nCohort 2 | p |
|---|---|---|---|---|---|
| 0 hours | 0.37 | 0.076 | 44 | 17 | 0.078 |
| 24 hours | 0.37 | 0.076 | 44 | 17 | 0.078 |
| 48 hours | 0.37 | 0.076 | 44 | 17 | 0.078 |

Fig. 3 Continued sCr or UO

| Time prior AKI stage | Cutoff value | sens | spec | Quartile | OR | 95% CI of OR | |
|---|---|---|---|---|---|---|---|
| 0 hours | 88 | 73% | 33% | 1 | | | |
| | 64.5 | 82% | 15% | 2 | 1.9 | 0.5 | 7.0 |
| | 34.7 | 91% | 6% | 3 | 4.8 | 1.5 | 15.8 |
| | 357 | 18% | 70% | 4 | 1.9 | 0.5 | 7.0 |
| | 510 | 5% | 81% | | | | |
| | 785 | 0% | 91% | | | | |
| 24 hours | 88 | 73% | 33% | 1 | | | |
| | 64.5 | 82% | 15% | 2 | 1.9 | 0.5 | 7.0 |
| | 34.7 | 91% | 6% | 3 | 4.8 | 1.5 | 15.8 |
| | 357 | 18% | 70% | 4 | 1.9 | 0.5 | 7.0 |
| | 510 | 5% | 81% | | | | |
| | 785 | 0% | 91% | | | | |
| 48 hours | 88 | 73% | 33% | 1 | | | |
| | 64.5 | 82% | 15% | 2 | 1.9 | 0.5 | 7.0 |
| | 34.7 | 91% | 6% | 3 | 4.8 | 1.5 | 15.8 |
| | 357 | 18% | 70% | 4 | 1.9 | 0.5 | 7.0 |
| | 510 | 5% | 81% | | | | |
| | 785 | 0% | 91% | | | | |

UO only

| Time prior AKI stage | Cutoff value | sens | spec | Quartile | OR | 95% CI of OR | |
|---|---|---|---|---|---|---|---|
| 0 hours | 88 | 71% | 30% | 1 | | | |
| | 63.5 | 82% | 11% | 2 | 1.8 | 0.3 | 12.1 |
| | 30 | 94% | 5% | 3 | 6.1 | 1.2 | 31.7 |
| | 446 | 12% | 70% | 4 | 3.5 | 0.6 | 19.3 |
| | 591 | 0% | 82% | | | | |
| | 785 | 0% | 91% | | | | |
| 24 hours | 88 | 71% | 30% | 1 | | | |
| | 63.5 | 82% | 11% | 2 | 1.8 | 0.3 | 12.1 |
| | 30 | 94% | 5% | 3 | 6.1 | 1.2 | 31.7 |
| | 446 | 12% | 70% | 4 | 3.5 | 0.6 | 19.3 |
| | 591 | 0% | 82% | | | | |
| | 785 | 0% | 91% | | | | |
| 48 hours | 88 | 71% | 30% | 1 | | | |
| | 63.5 | 82% | 11% | 2 | 1.8 | 0.3 | 12.1 |
| | 30 | 94% | 5% | 3 | 6.1 | 1.2 | 31.7 |
| | 446 | 12% | 70% | 4 | 3.5 | 0.6 | 19.3 |
| | 591 | 0% | 82% | | | | |
| | 785 | 0% | 91% | | | | |

Fig. 3 Continued

Aspartate aminotransferase, cytoplasmic sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 8.305 | 12.500 | 8.305 | 12.550 | 8.305 | 12.950 |
| average | 10.627 | 13.354 | 10.627 | 13.691 | 10.627 | 15.835 |
| stdev | 12.621 | 9.996 | 12.621 | 10.223 | 12.621 | 12.149 |
| p (t-test) |  | 0.398 |  | 0.357 |  | 0.214 |
| min | 0.527 | 1.430 | 0.527 | 1.430 | 0.527 | 0.974 |
| max | 104.000 | 41.400 | 104.000 | 41.400 | 104.000 | 41.400 |
| n (Samp) | 104 | 17 | 104 | 16 | 104 | 10 |
| n (Pat) | 104 | 17 | 104 | 16 | 104 | 10 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 8.610 | 13.000 | 8.610 | 13.000 | 8.610 | 13.400 |
| average | 11.629 | 15.518 | 11.629 | 15.518 | 11.629 | 17.396 |
| stdev | 15.749 | 10.878 | 15.749 | 10.878 | 15.749 | 13.831 |
| p (t-test) |  | 0.491 |  | 0.491 |  | 0.420 |
| min | 0.527 | 6.690 | 0.527 | 6.690 | 0.527 | 5.980 |
| max | 142.000 | 41.400 | 142.000 | 41.400 | 142.000 | 41.400 |
| n (Samp) | 170 | 8 | 170 | 8 | 170 | 5 |
| n (Pat) | 170 | 8 | 170 | 8 | 170 | 5 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 7.730 | 11.400 | 7.730 | 11.950 | 7.730 | 12.500 |
| average | 9.109 | 11.735 | 9.109 | 12.111 | 9.109 | 13.939 |
| stdev | 7.647 | 8.426 | 7.647 | 8.783 | 7.647 | 9.544 |
| p (t-test) |  | 0.292 |  | 0.250 |  | 0.118 |
| min | 0.527 | 1.430 | 0.527 | 1.430 | 0.527 | 0.974 |
| max | 39.200 | 30.800 | 39.200 | 30.800 | 39.200 | 30.800 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
| --- | --- | --- | --- | --- | --- |
| 0 hours | 0.63 | 0.077 | 104 | 17 | 0.095 |
| 24 hours | 0.64 | 0.079 | 104 | 16 | 0.080 |
| 48 hours | 0.66 | 0.098 | 104 | 10 | 0.091 | sCr only

| Time prior AKI stage | AUC | SE | nCohort 1 | nCohort 2 | p |
| --- | --- | --- | --- | --- | --- |
| 0 hours | 0.71 | 0.105 | 170 | 8 | 0.051 |
| 24 hours | 0.71 | 0.105 | 170 | 8 | 0.051 |
| 48 hours | 0.71 | 0.132 | 170 | 5 | 0.112 |

UO only

| Time prior AKI stage | AUC | SE | nCohort 1 | nCohort 2 | p |
| --- | --- | --- | --- | --- | --- |
| 0 hours | 0.60 | 0.095 | 85 | 11 | 0.271 |
| 24 hours | 0.61 | 0.099 | 85 | 10 | 0.251 |
| 48 hours | 0.66 | 0.116 | 85 | 7 | 0.161 |

Fig. 4 sCr or UO

| Time prior AKI stage | Cutoff value | sens | spec | Quartile | OR | 95% CI of OR | |
|---|---|---|---|---|---|---|---|
| 0 hours | 7.73 | 71% | 47% | 1 | | | |
| | 6.44 | 82% | 38% | 2 | 1.0 | 0.2 | 4.3 |
| | 3.91 | 94% | 26% | 3 | 1.4 | 0.4 | 5.0 |
| | 12.1 | 53% | 71% | 4 | 2.6 | 0.9 | 7.8 |
| | 14.2 | 35% | 81% | | | | |
| | 20.8 | 12% | 90% | | | | |
| 24 hours | 6.6 | 75% | 38% | 1 | | | |
| | 6.44 | 81% | 38% | 2 | 0.6 | 0.1 | 3.8 |
| | 3.91 | 94% | 26% | 3 | 1.4 | 0.4 | 5.0 |
| | 12.1 | 56% | 71% | 4 | 2.7 | 0.9 | 8.2 |
| | 14.2 | 38% | 81% | | | | |
| | 20.8 | 13% | 90% | | | | |
| 48 hours | 11.3 | 70% | 68% | 1 | | | |
| | 6.44 | 80% | 38% | 2 | 2.0 | 0.1 | 43.7 |
| | 5.92 | 90% | 33% | 3 | 2.1 | 0.1 | 45.6 |
| | 12.1 | 60% | 71% | 4 | 5.6 | 0.5 | 69.0 |
| | 14.2 | 40% | 81% | | | | |
| | 20.8 | 20% | 90% | | | | |

UO only

| Time prior AKI stage | Cutoff value | sens | spec | Quartile | OR | 95% CI of OR | |
|---|---|---|---|---|---|---|---|
| 0 hours | 6.44 | 73% | 40% | 1 | | | |
| | 3.95 | 82% | 28% | 2 | 3.3 | 0.2 | 53.6 |
| | 3.91 | 91% | 28% | 3 | 3.3 | 0.2 | 53.6 |
| | 11.8 | 45% | 71% | 4 | 4.6 | 0.3 | 64.0 |
| | 13.8 | 36% | 80% | | | | |
| | 20.5 | 9% | 91% | | | | |
| 24 hours | 6.44 | 70% | 40% | 1 | | | |
| | 3.95 | 80% | 28% | 2 | 3.1 | 0.2 | 51.5 |
| | 3.91 | 90% | 28% | 3 | 2.0 | 0.1 | 45.2 |
| | 11.8 | 50% | 71% | 4 | 4.4 | 0.3 | 61.5 |
| | 13.8 | 40% | 80% | | | | |
| | 20.5 | 10% | 91% | | | | |
| 48 hours | 10.2 | 71% | 69% | 1 | | | |
| | 6.44 | 86% | 40% | 2 | 1.0 | 0.0 | 60.2 |
| | 0.968 | 100% | 11% | 3 | 2.1 | 0.1 | 47.6 |
| | 11.8 | 57% | 71% | 4 | 3.3 | 0.2 | 54.3 |
| | 13.8 | 43% | 80% | | | | |
| | 20.5 | 14% | 91% | | | | |

CD40 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 34.100 | 61.000 | 34.100 | 58.700 | 34.100 | 59.500 |
| average | 54.583 | 93.427 | 54.583 | 84.985 | 54.583 | 72.793 |
| stdev | 59.803 | 77.753 | 59.803 | 73.900 | 59.803 | 52.113 |
| p (t-test) | | 0.019 | | 0.069 | | 0.355 |
| min | 2.560 | 8.250 | 2.560 | 8.250 | 2.560 | 4.430 |
| max | 326.000 | 243.000 | 326.000 | 243.000 | 326.000 | 143.000 |
| n (Samp) | 104 | 17 | 104 | 16 | 104 | 10 |
| n (Pat) | 104 | 17 | 104 | 16 | 104 | 10 |

Fig. 4 Continued sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 46.500 | 59.500 | 46.500 | 59.500 | 46.500 | 58.000 |
| average | 61.685 | 101.394 | 61.685 | 100.181 | 61.685 | 62.646 |
| stdev | 59.651 | 87.642 | 59.651 | 88.719 | 59.651 | 50.302 |
| p (t-test) | | 0.074 | | 0.083 | | 0.972 |
| min | 2.410 | 8.250 | 2.410 | 8.250 | 2.410 | 4.430 |
| max | 326.000 | 243.000 | 326.000 | 243.000 | 326.000 | 143.000 |
| n (Samp) | 170 | 8 | 170 | 8 | 170 | 5 |
| n (Pat) | 170 | 8 | 170 | 8 | 170 | 5 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 32.800 | 61.000 | 32.800 | 57.150 | 32.800 | 61.000 |
| average | 44.141 | 80.446 | 44.141 | 66.611 | 44.141 | 74.643 |
| stdev | 35.511 | 66.200 | 35.511 | 51.240 | 35.511 | 49.323 |
| p (t-test) | | 0.006 | | 0.075 | | 0.037 |
| min | 2.560 | 8.410 | 2.560 | 8.410 | 2.560 | 16.700 |
| max | 174.000 | 239.000 | 174.000 | 163.000 | 174.000 | 137.000 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
|---|---|---|---|---|---|
| 0 hours | 0.68 | 0.076 | 104 | 17 | 0.017 |
| 24 hours | 0.63 | 0.079 | 104 | 16 | 0.113 |
| 48 hours | 0.62 | 0.099 | 104 | 10 | 0.223 | sCr only

| Time prior AKI stage | AUC | SE | nCohort 1 | nCohort 2 | p |
|---|---|---|---|---|---|
| 0 hours | 0.64 | 0.108 | 170 | 8 | 0.196 |
| 24 hours | 0.62 | 0.108 | 170 | 8 | 0.271 |
| 48 hours | 0.54 | 0.134 | 170 | 5 | 0.746 |

UO only

| Time prior AKI stage | AUC | SE | nCohort 1 | nCohort 2 | p |
|---|---|---|---|---|---|
| 0 hours | 0.70 | 0.092 | 85 | 11 | 0.027 |
| 24 hours | 0.63 | 0.099 | 85 | 10 | 0.188 |
| 48 hours | 0.68 | 0.115 | 85 | 7 | 0.114 | sCr or UO

| Time prior AKI stage | Cutoff value | sens | spec | Quartile | OR | 95% CI of OR | |
|---|---|---|---|---|---|---|---|
| 0 hours | 55.3 | 71% | 67% | 1 | | | |
| | 36.5 | 82% | 55% | 2 | 0.5 | 0.0 | 10.5 |
| | 8.37 | 94% | 10% | 3 | 5.1 | 1.3 | 20.3 |
| | 58 | 59% | 70% | 4 | 3.4 | 0.8 | 14.4 |
| | 77.5 | 35% | 81% | | | | |
| | 119 | 29% | 90% | | | | |
| 24 hours | 27.3 | 75% | 36% | 1 | | | |
| | 21.3 | 81% | 27% | 2 | 0.6 | 0.1 | 3.8 |
| | 8.37 | 94% | 10% | 3 | 1.8 | 0.5 | 6.0 |
| | 58 | 50% | 70% | 4 | 2.3 | 0.7 | 7.0 |
| | 77.5 | 38% | 81% | | | | |
| | 119 | 31% | 90% | | | | |

Fig. 4 Continued

|  | 48 hours | 51.8 | 70% | 65% | 1 |  |  |  |
|---|---|---|---|---|---|---|---|---|
|  |  | 21.3 | 80% | 27% | 2 | 0.5 | 0.0 | 10.2 |
|  |  | 16 | 90% | 21% | 3 | 1.6 | 0.3 | 9.3 |
|  |  | 58 | 50% | 70% | 4 | 2.1 | 0.4 | 10.6 |
|  |  | 77.5 | 40% | 81% |  |  |  |  |
|  |  | 119 | 30% | 90% |  |  |  |  | sCr only

| Time prior AKI stage | Cutoff value | sens | spec | Quartile | OR | 95% CI of OR | |
|---|---|---|---|---|---|---|---|
| 0 hours | 45.9 | 75% | 50% | 1 |  |  |  |
|  | 36.5 | 88% | 44% | 2 | 2.0 | 0.1 | 41.4 |
|  | 8.06 | 100% | 7% | 3 | 2.0 | 0.1 | 42.5 |
|  | 71.2 | 38% | 70% | 4 | 3.1 | 0.2 | 46.0 |
|  | 88.8 | 38% | 80% |  |  |  |  |
|  | 119 | 38% | 90% |  |  |  |  |
| 24 hours | 45.9 | 75% | 50% | 1 |  |  |  |
|  | 27.3 | 88% | 27% | 2 | 2.0 | 0.1 | 41.4 |
|  | 8.06 | 100% | 7% | 3 | 2.0 | 0.1 | 42.5 |
|  | 71.2 | 38% | 70% | 4 | 3.1 | 0.2 | 46.0 |
|  | 88.8 | 38% | 80% |  |  |  |  |
|  | 119 | 38% | 90% |  |  |  |  |
| 48 hours | 45.9 | 80% | 50% | 1 |  |  |  |
|  | 45.9 | 80% | 50% | 2 | 1.0 | 0.0 | 54.0 |
|  | 4.18 | 100% | 3% | 3 | 2.0 | 0.1 | 41.5 |
|  | 71.2 | 20% | 70% | 4 | 1.0 | 0.0 | 54.0 |
|  | 88.8 | 20% | 80% |  |  |  |  |
|  | 119 | 20% | 90% |  |  |  |  |

UO only

| Time prior AKI stage | Cutoff value | sens | spec | Quartile | OR | 95% CI of OR | |
|---|---|---|---|---|---|---|---|
| 0 hours | 55.3 | 73% | 71% | 1 |  |  |  |
|  | 44.5 | 82% | 64% | 2 | 1.0 | 0.0 | 59.8 |
|  | 21.3 | 91% | 28% | 3 | 4.6 | 0.3 | 64.0 |
|  | 55.3 | 73% | 71% | 4 | 6.1 | 0.5 | 76.8 |
|  | 64.1 | 36% | 80% |  |  |  |  |
|  | 88.8 | 27% | 91% |  |  |  |  |
| 24 hours | 44.5 | 70% | 64% | 1 |  |  |  |
|  | 21.3 | 80% | 28% | 2 | 0.5 | 0.0 | 10.3 |
|  | 16.4 | 90% | 21% | 3 | 1.5 | 0.2 | 9.3 |
|  | 55.3 | 50% | 71% | 4 | 2.1 | 0.4 | 11.1 |
|  | 64.1 | 30% | 80% |  |  |  |  |
|  | 88.8 | 30% | 91% |  |  |  |  |
| 48 hours | 51.8 | 71% | 68% | 1 |  |  |  |
|  | 21.3 | 86% | 28% | 2 | 1.0 | 0.0 | 60.2 |
|  | 16.4 | 100% | 21% | 3 | 2.1 | 0.1 | 47.6 |
|  | 55.3 | 57% | 71% | 4 | 3.3 | 0.2 | 54.3 |
|  | 64.1 | 43% | 80% |  |  |  |  |
|  | 88.8 | 43% | 91% |  |  |  |  |

Fig. 4 Continued

CD40 Ligand sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.237 | 0.376 | 0.237 | 0.370 | 0.237 | 0.323 |
| average | 0.267 | 0.385 | 0.267 | 0.358 | 0.267 | 0.324 |
| stdev | 0.185 | 0.151 | 0.185 | 0.160 | 0.185 | 0.159 |
| p (t-test) |  | 0.014 |  | 0.064 |  | 0.353 |
| min | 0.011 | 0.095 | 0.011 | 0.088 | 0.011 | 0.063 |
| max | 0.869 | 0.640 | 0.869 | 0.640 | 0.869 | 0.562 |
| n (Samp) | 104 | 17 | 104 | 16 | 104 | 10 |
| n (Pat) | 104 | 17 | 104 | 16 | 104 | 10 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.269 | 0.405 | 0.269 | 0.405 | 0.269 | 0.376 |
| average | 0.289 | 0.405 | 0.289 | 0.404 | 0.289 | 0.342 |
| stdev | 0.191 | 0.165 | 0.191 | 0.167 | 0.191 | 0.162 |
| p (t-test) |  | 0.095 |  | 0.097 |  | 0.543 |
| min | 0.011 | 0.095 | 0.011 | 0.088 | 0.011 | 0.063 |
| max | 0.891 | 0.640 | 0.891 | 0.640 | 0.891 | 0.475 |
| n (Samp) | 170 | 8 | 170 | 8 | 170 | 5 |
| n (Pat) | 170 | 8 | 170 | 8 | 170 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.235 | 0.376 | 0.235 | 0.329 | 0.235 | 0.282 |
| average | 0.252 | 0.379 | 0.252 | 0.336 | 0.252 | 0.340 |
| stdev | 0.174 | 0.134 | 0.174 | 0.142 | 0.174 | 0.155 |
| p (t-test) |  | 0.022 |  | 0.146 |  | 0.199 |
| min | 0.011 | 0.165 | 0.011 | 0.165 | 0.011 | 0.167 |
| max | 0.659 | 0.562 | 0.659 | 0.562 | 0.659 | 0.562 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
|---|---|---|---|---|---|
| 0 hours | 0.70 | 0.075 | 104 | 17 | 0.006 |
| 24 hours | 0.66 | 0.078 | 104 | 16 | 0.039 |
| 48 hours | 0.61 | 0.099 | 104 | 10 | 0.286 | sCr only

| Time prior AKI stage | AUC | SE | nCohort 1 | nCohort 2 | p |
|---|---|---|---|---|---|
| 0 hours | 0.69 | 0.106 | 170 | 8 | 0.080 |
| 24 hours | 0.68 | 0.107 | 170 | 8 | 0.086 |
| 48 hours | 0.58 | 0.136 | 170 | 5 | 0.533 |

UO only

| Time prior AKI stage | AUC | SE | nCohort 1 | nCohort 2 | p |
|---|---|---|---|---|---|
| 0 hours | 0.73 | 0.090 | 85 | 11 | 0.012 |
| 24 hours | 0.66 | 0.098 | 85 | 10 | 0.104 |
| 48 hours | 0.66 | 0.116 | 85 | 7 | 0.170 |

Fig. 4 Continued sCr or UO

| Time prior AKI stage | Cutoff value | sens | spec | Quartile | OR | 95% CI of OR | |
|---|---|---|---|---|---|---|---|
| 0 hours | 0.35 | 71% | 70% | 1 | | | |
| | 0.26 | 82% | 55% | 2 | 2.1 | 0.1 | 45.0 |
| | 0.164 | 94% | 39% | 3 | 8.8 | 0.8 | 96.6 |
| | 0.35 | 71% | 70% | 4 | 8.5 | 0.8 | 92.2 |
| | 0.456 | 35% | 81% | | | | |
| | 0.531 | 24% | 90% | | | | |
| 24 hours | 0.26 | 75% | 55% | 1 | | | |
| | 0.176 | 81% | 40% | 2 | 3.2 | 0.2 | 50.6 |
| | 0.164 | 94% | 39% | 3 | 5.8 | 0.5 | 70.5 |
| | 0.35 | 56% | 70% | 4 | 8.8 | 0.8 | 96.6 |
| | 0.456 | 25% | 81% | | | | |
| | 0.531 | 19% | 90% | | | | |
| 48 hours | 0.26 | 70% | 55% | 1 | | | |
| | 0.172 | 80% | 40% | 2 | 2.0 | 0.1 | 43.7 |
| | 0.164 | 90% | 39% | 3 | 3.2 | 0.2 | 51.4 |
| | 0.35 | 50% | 70% | 4 | 4.3 | 0.3 | 58.2 |
| | 0.456 | 20% | 81% | | | | |
| | 0.531 | 10% | 90% | | | | | sCr only

| Time prior AKI stage | Cutoff value | sens | spec | Quartile | OR | 95% CI of OR | |
|---|---|---|---|---|---|---|---|
| 0 hours | 0.361 | 75% | 64% | 1 | | | |
| | 0.301 | 88% | 56% | 2 | 0.0 | 0.0 | na |
| | 0.0916 | 100% | 21% | 3 | 4.3 | 0.3 | 54.8 |
| | 0.41 | 50% | 70% | 4 | 3.1 | 0.2 | 46.0 |
| | 0.487 | 25% | 80% | | | | |
| | 0.536 | 25% | 90% | | | | |
| 24 hours | 0.361 | 75% | 64% | 1 | | | |
| | 0.301 | 88% | 56% | 2 | 0.0 | 0.0 | na |
| | 0.0874 | 100% | 19% | 3 | 4.3 | 0.3 | 54.8 |
| | 0.41 | 50% | 70% | 4 | 3.1 | 0.2 | 46.0 |
| | 0.487 | 25% | 80% | | | | |
| | 0.536 | 25% | 90% | | | | |
| 48 hours | 0.361 | 80% | 64% | 1 | | | |
| | 0.361 | 80% | 64% | 2 | 0.0 | 0.0 | na |
| | 0.0606 | 100% | 8% | 3 | 3.1 | 0.2 | 46.1 |
| | 0.41 | 40% | 70% | 4 | 1.0 | 0.0 | 54.0 |
| | 0.487 | 0% | 80% | | | | |
| | 0.536 | 0% | 90% | | | | |

Fig. 4 Continued

CXCL16 (C-X-C Motif chemokine 16)

sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.160 | 3.144 | 0.160 | 1.832 | 0.160 | 0.291 |
| average | 0.919 | 4.232 | 0.919 | 3.540 | 0.919 | 1.616 |
| stdev | 1.927 | 4.091 | 1.927 | 3.773 | 1.927 | 2.520 |
| p (t-test) |  | 0.000 |  | 0.000 |  | 0.290 |
| min | 0.000 | 0.005 | 0.000 | 0.005 | 0.000 | 0.005 |
| max | 10.210 | 10.538 | 10.210 | 9.861 | 10.210 | 7.568 |
| n (Samp) | 103 | 15 | 103 | 15 | 103 | 10 |
| n (Pat) | 103 | 15 | 103 | 15 | 103 | 10 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.210 | 6.398 | 0.210 | 6.398 | 0.210 | 3.144 |
| average | 1.111 | 5.661 | 1.111 | 5.576 | 1.111 | 3.294 |
| stdev | 2.180 | 3.694 | 2.180 | 3.572 | 2.180 | 2.813 |
| p (t-test) |  | 0.000 |  | 0.000 |  | 0.030 |
| min | 0.000 | 0.005 | 0.000 | 0.005 | 0.000 | 0.005 |
| max | 10.210 | 10.538 | 10.210 | 9.861 | 10.210 | 7.568 |
| n (Samp) | 167 | 8 | 167 | 8 | 167 | 5 |
| n (Pat) | 167 | 8 | 167 | 8 | 167 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.157 | 0.715 | 0.157 | 0.393 | 0.157 | 0.189 |
| average | 0.830 | 2.575 | 0.830 | 1.496 | 0.830 | 0.667 |
| stdev | 1.628 | 3.616 | 1.628 | 2.300 | 1.628 | 1.118 |
| p (t-test) |  | 0.010 |  | 0.266 |  | 0.796 |
| min | 0.000 | 0.021 | 0.000 | 0.021 | 0.000 | 0.021 |
| max | 9.383 | 10.098 | 9.383 | 6.964 | 9.383 | 3.144 |
| n (Samp) | 84 | 9 | 84 | 9 | 84 | 7 |
| n (Pat) | 84 | 9 | 84 | 9 | 84 | 7 | sCr or UO

| Time prior AKI stage | AUC | SE | nCohort 1 | nCohort 2 | p |
|---|---|---|---|---|---|
| 0 hours | 0.71 | 0.078 | 103 | 15 | 0.006 |
| 24 hours | 0.69 | 0.080 | 103 | 15 | 0.017 |
| 48 hours | 0.56 | 0.098 | 103 | 10 | 0.563 | sCr only

| Time prior AKI stage | AUC | SE | nCohort 1 | nCohort 2 | p |
|---|---|---|---|---|---|
| 0 hours | 0.82 | 0.093 | 167 | 8 | 0.001 |
| 24 hours | 0.82 | 0.093 | 167 | 8 | 0.001 |
| 48 hours | 0.72 | 0.131 | 167 | 5 | 0.096 |

UO only

| Time prior AKI stage | AUC | SE | nCohort 1 | nCohort 2 | p |
|---|---|---|---|---|---|
| 0 hours | 0.65 | 0.104 | 84 | 9 | 0.146 |
| 24 hours | 0.61 | 0.104 | 84 | 9 | 0.299 |
| 48 hours | 0.52 | 0.115 | 84 | 7 | 0.883 |

Fig. 4 Continued sCr or UO

| Time prior AKI stage | Cutoff value | sens | spec | Quartile | OR | 95% CI of OR | |
|---|---|---|---|---|---|---|---|
| 0 hours | 0.18261 | 73% | 52% | 1 | | | |
| | 0.16002 | 80% | 50% | 2 | 0.6 | 0.1 | 3.7 |
| | 0.01984 | 93% | 12% | 3 | 0.3 | 0.0 | 4.9 |
| | 0.53464 | 67% | 71% | 4 | 3.7 | 1.3 | 10.5 |
| | 1.04015 | 60% | 81% | | | | |
| | 3.14297 | 53% | 90% | | | | |
| 24 hours | 0.18261 | 73% | 52% | 1 | | | |
| | 0.16002 | 80% | 50% | 2 | 0.6 | 0.1 | 3.7 |
| | 0.01984 | 93% | 12% | 3 | 0.6 | 0.1 | 3.8 |
| | 0.53464 | 60% | 71% | 4 | 3.2 | 1.1 | 9.1 |
| | 1.04015 | 53% | 81% | | | | |
| | 3.14297 | 47% | 90% | | | | |
| 48 hours | 0.16002 | 70% | 50% | 1 | | | |
| | 0.03878 | 80% | 19% | 2 | 0.3 | 0.0 | 4.9 |
| | 0.01984 | 90% | 12% | 3 | 1.0 | 0.2 | 4.3 |
| | 0.53464 | 40% | 71% | 4 | 1.0 | 0.2 | 4.1 |
| | 1.04015 | 30% | 81% | | | | |
| | 3.14297 | 30% | 90% | | | | | sCr only

| Time prior AKI stage | Cutoff value | sens | spec | Quartile | OR | 95% CI of OR | |
|---|---|---|---|---|---|---|---|
| 0 hours | 3.14297 | 75% | 88% | 1 | | | |
| | 1.81572 | 88% | 84% | 2 | 0.0 | 0.0 | na |
| | 0.00024 | 100% | 1% | 3 | 0.0 | 0.0 | na |
| | 0.57229 | 88% | 70% | 4 | 7.9 | 0.8 | 82.5 |
| | 1.25962 | 88% | 80% | | | | |
| | 3.47902 | 63% | 90% | | | | |
| 24 hours | 3.14297 | 75% | 88% | 1 | | | |
| | 1.81572 | 88% | 84% | 2 | 0.0 | 0.0 | na |
| | 0.00024 | 100% | 1% | 3 | 0.0 | 0.0 | na |
| | 0.57229 | 88% | 70% | 4 | 7.9 | 0.8 | 82.5 |
| | 1.25962 | 88% | 80% | | | | |
| | 3.47902 | 63% | 90% | | | | |
| 48 hours | 1.81572 | 80% | 84% | 1 | | | |
| | 1.81572 | 80% | 84% | 2 | 0.0 | 0.0 | na |
| | 0.00024 | 100% | 1% | 3 | 0.0 | 0.0 | na |
| | 0.57229 | 80% | 70% | 4 | 4.3 | 0.3 | 55.0 |
| | 1.25962 | 80% | 80% | | | | |
| | 3.47902 | 40% | 90% | | | | |

UO only

| Time prior AKI stage | Cutoff value | sens | spec | Quartile | OR | 95% CI of OR | |
|---|---|---|---|---|---|---|---|
| 0 hours | 0.16002 | 78% | 51% | 1 | | | |
| | 0.03878 | 89% | 20% | 2 | 0.5 | 0.0 | 10.8 |
| | 0.01984 | 100% | 10% | 3 | 1.0 | 0.1 | 8.6 |
| | 0.53464 | 56% | 70% | 4 | 2.1 | 0.4 | 11.1 |
| | 1.1193 | 44% | 81% | | | | |
| | 2.0393 | 33% | 90% | | | | |
| 24 hours | 0.16002 | 78% | 51% | 1 | | | |
| | 0.03878 | 89% | 20% | 2 | 0.5 | 0.0 | 10.8 |
| | 0.01984 | 100% | 10% | 3 | 1.6 | 0.3 | 9.8 |
| | 0.53464 | 44% | 70% | 4 | 1.5 | 0.2 | 9.3 |
| | 1.1193 | 33% | 81% | | | | |
| | 2.0393 | 22% | 90% | | | | |

Fig. 4 Continued

| 48 hours | 0.16002 | 71% | 51% | 1 | | | |
|---|---|---|---|---|---|---|---|
| | 0.03878 | 86% | 20% | 2 | 0.0 | 0.0 | na |
| | 0.01984 | 100% | 10% | 3 | 2.1 | 0.4 | 11.2 |
| | 0.53464 | 29% | 70% | 4 | 0.5 | 0.0 | 10.4 |
| | 1.1193 | 14% | 81% | | | | |
| | 2.0393 | 14% | 90% | | | | |

EN-RAGE sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1.148 | 5.127 | 1.148 | 3.631 | 1.148 | 10.904 |
| average | 7.744 | 29.048 | 7.744 | 28.549 | 7.744 | 38.322 |
| stdev | 23.908 | 46.593 | 23.908 | 46.896 | 23.908 | 55.130 |
| p (t-test) | | 0.011 | | 0.014 | | 0.003 |
| min | 0.002 | 0.065 | 0.002 | 0.065 | 0.002 | 0.065 |
| max | 197.971 | 150.844 | 197.971 | 150.844 | 197.971 | 150.844 |
| n (Samp) | 99 | 12 | 99 | 12 | 99 | 8 |
| n (Pat) | 99 | 12 | 99 | 12 | 99 | 8 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 1.648 | 3.635 | 1.648 | 3.494 | 1.648 | 2.579 |
| average | 14.609 | 5.509 | 14.609 | 5.157 | 14.609 | 5.852 |
| stdev | 60.292 | 6.507 | 60.292 | 6.759 | 60.292 | 8.350 |
| p (t-test) | | 0.713 | | 0.702 | | 0.773 |
| min | 0.002 | 0.065 | 0.002 | 0.065 | 0.002 | 0.065 |
| max | 675.017 | 18.184 | 675.017 | 18.184 | 675.017 | 18.184 |
| n (Samp) | 160 | 6 | 160 | 6 | 160 | 4 |
| n (Pat) | 160 | 6 | 160 | 6 | 160 | 4 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 1.257 | 24.342 | 1.257 | 24.342 | 1.257 | 28.751 |
| average | 9.172 | 42.388 | 9.172 | 41.904 | 9.172 | 50.482 |
| stdev | 25.822 | 52.912 | 25.822 | 53.314 | 25.822 | 59.533 |
| p (t-test) | | 0.002 | | 0.003 | | 0.001 |
| min | 0.002 | 0.930 | 0.002 | 0.930 | 0.002 | 0.621 |
| max | 197.971 | 150.844 | 197.971 | 150.844 | 197.971 | 150.844 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
|---|---|---|---|---|---|
| 0 hours | 0.74 | 0.085 | 99 | 12 | 0.004 |
| 24 hours | 0.68 | 0.089 | 99 | 12 | 0.045 |
| 48 hours | 0.70 | 0.107 | 99 | 8 | 0.058 | sCr only

| Time prior AKI stage | AUC | SE | nCohort 1 | nCohort 2 | p |
|---|---|---|---|---|---|
| 0 hours | 0.58 | 0.124 | 160 | 6 | 0.503 |
| 24 hours | 0.50 | 0.120 | 160 | 6 | 0.993 |
| 48 hours | 0.50 | 0.147 | 160 | 4 | 0.975 |

Fig. 4 Continued

UO only

| Time prior AKI stage | AUC | SE | nCohort 1 | nCohort 2 | p |
|---|---|---|---|---|---|
| 0 hours | 0.82 | 0.093 | 84 | 8 | 0.001 |
| 24 hours | 0.79 | 0.098 | 84 | 8 | 0.003 |
| 48 hours | 0.79 | 0.112 | 84 | 6 | 0.009 | sCr or UO

| Time prior AKI stage | Cutoff value | sens | spec | Quartile | OR | 95% CI of OR | |
|---|---|---|---|---|---|---|---|
| 0 hours | 2.3998 | 75% | 72% | 1 | | | |
| | 2.02601 | 83% | 67% | 2 | 1.0 | 0.0 | 56.3 |
| | 0.92777 | 92% | 43% | 3 | 3.1 | 0.2 | 49.6 |
| | 2.3998 | 75% | 72% | 4 | 8.7 | 0.8 | 96.4 |
| | 3.89368 | 58% | 81% | | | | |
| | 21.6311 | 33% | 91% | | | | |
| 24 hours | 1.50846 | 75% | 60% | 1 | | | |
| | 0.92777 | 83% | 43% | 2 | 0.5 | 0.0 | 10.2 |
| | 0.28358 | 92% | 16% | 3 | 1.5 | 0.3 | 9.0 |
| | 2.3998 | 58% | 72% | 4 | 3.4 | 0.8 | 14.9 |
| | 3.89368 | 50% | 81% | | | | |
| | 21.6311 | 33% | 91% | | | | |
| 48 hours | 2.3998 | 75% | 72% | 1 | | | |
| | 0.59513 | 88% | 29% | 2 | 1.0 | 0.0 | 56.5 |
| | 0.00184 | 100% | 1% | 3 | 2.0 | 0.1 | 44.3 |
| | 2.3998 | 75% | 72% | 4 | 4.3 | 0.3 | 59.3 |
| | 3.89368 | 50% | 81% | | | | |
| | 21.6311 | 38% | 91% | | | | | sCr only

| Time prior AKI stage | Cutoff value | sens | spec | Quartile | OR | 95% CI of OR | |
|---|---|---|---|---|---|---|---|
| 0 hours | 2.06204 | 83% | 56% | 1 | | | |
| | 2.06204 | 83% | 56% | 2 | 0.0 | 0.0 | na |
| | 0.00184 | 100% | 1% | 3 | 4.3 | 0.3 | 55.5 |
| | 3.95805 | 50% | 70% | 4 | 1.0 | 0.0 | 54.2 |
| | 7.35633 | 17% | 80% | | | | |
| | 30.5 | 0% | 91% | | | | |
| 24 hours | 0.28358 | 83% | 11% | 1 | | | |
| | 0.28358 | 83% | 11% | 2 | 0.0 | 0.0 | na |
| | 0.00184 | 100% | 1% | 3 | 1.5 | 0.3 | 8.7 |
| | 3.95805 | 50% | 70% | 4 | 0.5 | 0.0 | 9.9 |
| | 7.35633 | 17% | 80% | | | | |
| | 30.5 | 0% | 91% | | | | |
| 48 hours | 1.50846 | 75% | 48% | 1 | | | |
| | 0.00184 | 100% | 1% | 2 | 1.0 | 0.0 | 55.6 |
| | 0.00184 | 100% | 1% | 3 | 1.0 | 0.0 | 55.6 |
| | 3.95805 | 25% | 70% | 4 | 1.0 | 0.0 | 55.6 |
| | 7.35633 | 25% | 80% | | | | |
| | 30.5 | 0% | 91% | | | | |

Fig. 4 Continued

Eotaxin sCr or UO

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 34.900   | 95.300   | 34.900   | 67.300   | 34.900   | 55.550   |
| average  | 47.658   | 117.159  | 47.658   | 112.206  | 47.658   | 85.390   |
| stdev    | 35.799   | 81.240   | 35.799   | 84.794   | 35.799   | 92.433   |
| p (t-test) |        | 0.000    |          | 0.000    |          | 0.010    |
| min      | 5.080    | 33.700   | 5.080    | 30.100   | 5.080    | 27.200   |
| max      | 185.000  | 333.000  | 185.000  | 333.000  | 185.000  | 333.000  |
| n (Samp) | 104      | 17       | 104      | 16       | 104      | 10       |
| n (Pat)  | 104      | 17       | 104      | 16       | 104      | 10       | sCr only

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 42.900   | 154.000  | 42.900   | 153.500  | 42.900   | 128.000  |
| average  | 54.268   | 161.063  | 54.268   | 152.863  | 54.268   | 149.340  |
| stdev    | 41.819   | 92.895   | 41.819   | 98.835   | 41.819   | 120.457  |
| p (t-test) |        | 0.000    |          | 0.000    |          | 0.000    |
| min      | 5.080    | 40.000   | 5.080    | 40.000   | 5.080    | 27.200   |
| max      | 270.000  | 333.000  | 270.000  | 333.000  | 270.000  | 333.000  |
| n (Samp) | 170      | 8        | 170      | 8        | 170      | 5        |
| n (Pat)  | 170      | 8        | 170      | 8        | 170      | 5        |

UO only

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 35.100   | 69.100   | 35.100   | 65.450   | 35.100   | 49.300   |
| average  | 48.520   | 93.109   | 48.520   | 89.340   | 48.520   | 61.171   |
| stdev    | 36.504   | 54.112   | 36.504   | 55.574   | 36.504   | 35.815   |
| p (t-test) |        | 0.001    |          | 0.002    |          | 0.380    |
| min      | 7.220    | 33.700   | 7.220    | 30.100   | 7.220    | 28.300   |
| max      | 185.000  | 193.000  | 185.000  | 193.000  | 185.000  | 128.000  |
| n (Samp) | 85       | 11       | 85       | 10       | 85       | 7        |
| n (Pat)  | 85       | 11       | 85       | 10       | 85       | 7        | sCr or UO

| Time prior AKI stage | AUC | SE | nCohort 1 | nCohort 2 | p |
|---|---|---|---|---|---|
| 0 hours  | 0.83 | 0.064 | 104 | 17 | 0.000 |
| 24 hours | 0.80 | 0.069 | 104 | 16 | 0.000 |
| 48 hours | 0.67 | 0.097 | 104 | 10 | 0.073 | sCr only

| Time prior AKI stage | AUC | SE | nCohort 1 | nCohort 2 | p |
|---|---|---|---|---|---|
| 0 hours  | 0.88 | 0.080 | 170 | 8 | 0.000 |
| 24 hours | 0.85 | 0.087 | 170 | 8 | 0.000 |
| 48 hours | 0.78 | 0.123 | 170 | 5 | 0.021 |

UO only

| Time prior AKI stage | AUC | SE | nCohort 1 | nCohort 2 | p |
|---|---|---|---|---|---|
| 0 hours  | 0.79 | 0.083 | 85 | 11 | 0.000 |
| 24 hours | 0.77 | 0.090 | 85 | 10 | 0.003 |
| 48 hours | 0.65 | 0.117 | 85 | 7  | 0.192 |

Fig. 4 Continued

E-selectin sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.148 | 0.755 | 0.148 | 0.755 | 0.148 | 0.496 |
| average | 0.273 | 1.217 | 0.273 | 1.217 | 0.273 | 0.872 |
| stdev | 0.311 | 1.507 | 0.311 | 1.507 | 0.311 | 0.931 |
| p (t-test) |  | 0.000 |  | 0.000 |  | 0.000 |
| min | 0.000 | 0.000 | 0.000 | 0.000 | 0.000 | 0.000 |
| max | 1.605 | 5.381 | 1.605 | 5.381 | 1.605 | 2.323 |
| n (Samp) | 99 | 12 | 99 | 12 | 99 | 8 |
| n (Pat) | 99 | 12 | 99 | 12 | 99 | 8 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 0.212 | 0.755 | 0.212 | 0.755 | 0.212 | 0.826 |
| average | 0.428 | 0.757 | 0.428 | 0.757 | 0.428 | 0.808 |
| stdev | 0.689 | 0.509 | 0.689 | 0.509 | 0.689 | 0.646 |
| p (t-test) |  | 0.250 |  | 0.250 |  | 0.278 |
| min | 0.000 | 0.000 | 0.000 | 0.000 | 0.000 | 0.000 |
| max | 5.381 | 1.579 | 5.381 | 1.579 | 5.381 | 1.579 |
| n (Samp) | 160 | 6 | 160 | 6 | 160 | 4 |
| n (Pat) | 160 | 6 | 160 | 6 | 160 | 4 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 0.146 | 1.227 | 0.146 | 1.227 | 0.146 | 0.898 |
| average | 0.281 | 1.565 | 0.281 | 1.565 | 0.281 | 1.033 |
| stdev | 0.358 | 1.760 | 0.358 | 1.760 | 0.358 | 1.014 |
| p (t-test) |  | 0.000 |  | 0.000 |  | 0.000 |
| min | 0.000 | 0.023 | 0.000 | 0.023 | 0.000 | 0.023 |
| max | 2.158 | 5.381 | 2.158 | 5.381 | 2.158 | 2.323 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
| --- | --- | --- | --- | --- | --- |
| 0 hours | 0.75 | 0.084 | 99 | 12 | 0.003 |
| 24 hours | 0.75 | 0.084 | 99 | 12 | 0.003 |
| 48 hours | 0.65 | 0.109 | 99 | 8 | 0.172 | sCr only

| Time prior AKI stage | AUC | SE | nCohort 1 | nCohort 2 | p |
| --- | --- | --- | --- | --- | --- |
| 0 hours | 0.74 | 0.118 | 160 | 6 | 0.040 |
| 24 hours | 0.74 | 0.118 | 160 | 6 | 0.040 |
| 48 hours | 0.69 | 0.149 | 160 | 4 | 0.203 |

UO only

| Time prior AKI stage | AUC | SE | nCohort 1 | nCohort 2 | p |
| --- | --- | --- | --- | --- | --- |
| 0 hours | 0.79 | 0.098 | 84 | 8 | 0.003 |
| 24 hours | 0.79 | 0.098 | 84 | 8 | 0.003 |
| 48 hours | 0.71 | 0.123 | 84 | 6 | 0.092 |

Fig. 4 Continued sCr or UO

| Time prior AKI stage | Cutoff value | sens | spec | Quartile | OR | 95% CI of OR | |
|---|---|---|---|---|---|---|---|
| 0 hours | 0.22403 | 75% | 63% | 1 | | | |
| | 0.21237 | 83% | 61% | 2 | 0.0 | 0.0 | na |
| | 0.01715 | 92% | 11% | 3 | 1.0 | 0.1 | 8.0 |
| | 0.29473 | 67% | 71% | 4 | 5.0 | 1.2 | 20.3 |
| | 0.46344 | 67% | 81% | | | | |
| | 0.69543 | 58% | 91% | | | | |
| 24 hours | 0.22403 | 75% | 63% | 1 | | | |
| | 0.21237 | 83% | 61% | 2 | 0.0 | 0.0 | na |
| | 0.01715 | 92% | 11% | 3 | 1.0 | 0.1 | 8.0 |
| | 0.29473 | 67% | 71% | 4 | 5.0 | 1.2 | 20.3 |
| | 0.46344 | 67% | 81% | | | | |
| | 0.69543 | 58% | 91% | | | | |
| 48 hours | 0.15842 | 75% | 52% | 1 | | | |
| | 0.01715 | 88% | 11% | 2 | 0.0 | 0.0 | na |
| | 0 | 100% | 0% | 3 | 1.0 | 0.1 | 8.0 |
| | 0.29473 | 50% | 71% | 4 | 2.1 | 0.4 | 10.7 |
| | 0.46344 | 50% | 81% | | | | |
| | 0.69543 | 50% | 91% | | | | | sCr only

| Time prior AKI stage | Cutoff value | sens | spec | Quartile | OR | 95% CI of OR | |
|---|---|---|---|---|---|---|---|
| 0 hours | 0.56592 | 83% | 82% | 1 | | | |
| | 0.56592 | 83% | 82% | 2 | 0.0 | 0.0 | na |
| | 0 | 100% | 0% | 3 | 0.0 | 0.0 | na |
| | 0.38703 | 83% | 70% | 4 | 5.4 | 0.5 | 62.9 |
| | 0.50393 | 83% | 80% | | | | |
| | 0.86208 | 33% | 90% | | | | |
| 24 hours | 0.56592 | 83% | 82% | 1 | | | |
| | 0.56592 | 83% | 82% | 2 | 0.0 | 0.0 | na |
| | 0 | 100% | 0% | 3 | 0.0 | 0.0 | na |
| | 0.38703 | 83% | 70% | 4 | 5.4 | 0.5 | 62.9 |
| | 0.50393 | 83% | 80% | | | | |
| | 0.86208 | 33% | 90% | | | | |
| 48 hours | 0.75187 | 75% | 89% | 1 | | | |
| | 0 | 100% | 0% | 2 | 0.0 | 0.0 | na |
| | 0 | 100% | 0% | 3 | 0.0 | 0.0 | na |
| | 0.38703 | 75% | 70% | 4 | 3.2 | 0.2 | 47.6 |
| | 0.50393 | 75% | 80% | | | | |
| | 0.86208 | 50% | 90% | | | | |

UO only

| Time prior AKI stage | Cutoff value | sens | spec | Quartile | OR | 95% CI of OR | |
|---|---|---|---|---|---|---|---|
| 0 hours | 0.22403 | 75% | 67% | 1 | | | |
| | 0.21237 | 88% | 64% | 2 | 0.0 | 0.0 | na |
| | 0.01302 | 100% | 10% | 3 | 2.1 | 0.1 | 47.6 |
| | 0.25913 | 63% | 70% | 4 | 6.1 | 0.5 | 78.3 |
| | 0.46527 | 63% | 81% | | | | |
| | 0.66092 | 63% | 90% | | | | |
| 24 hours | 0.22403 | 75% | 67% | 1 | | | |
| | 0.21237 | 88% | 64% | 2 | 0.0 | 0.0 | na |
| | 0.01302 | 100% | 10% | 3 | 2.1 | 0.1 | 47.6 |
| | 0.25913 | 63% | 70% | 4 | 6.1 | 0.5 | 78.3 |
| | 0.46527 | 63% | 81% | | | | |
| | 0.66092 | 63% | 90% | | | | |

Fig. 4 Continued

| 48 hours | 0.15842 | 83% | 54% | 1 | | | |
| | 0.15842 | 83% | 54% | 2 | 0.0 | 0.0 | na |
| | 0.01302 | 100% | 10% | 3 | 2.1 | 0.1 | 48.1 |
| | 0.25913 | 50% | 70% | 4 | 3.2 | 0.2 | 52.0 |
| | 0.46527 | 50% | 81% | | | | |
| | 0.66092 | 50% | 90% | | | | |

Fibronectin sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 22.340 | 105.568 | 22.340 | 105.568 | 22.340 | 79.237 |
| average | 88.644 | 203.524 | 88.644 | 190.977 | 88.644 | 78.598 |
| stdev | 172.416 | 234.580 | 172.416 | 229.924 | 172.416 | 43.536 |
| p (t-test) | | 0.039 | | 0.064 | | 0.870 |
| min | 0.276 | 0.040 | 0.276 | 0.040 | 0.276 | 0.040 |
| max | 1020.452 | 810.740 | 1020.452 | 810.740 | 1020.452 | 125.995 |
| n (Samp) | 99 | 12 | 99 | 12 | 99 | 8 |
| n (Pat) | 99 | 12 | 99 | 12 | 99 | 8 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 31.058 | 105.568 | 31.058 | 105.568 | 31.058 | 105.568 |
| average | 110.031 | 162.901 | 110.031 | 162.901 | 110.031 | 103.036 |
| stdev | 231.070 | 164.581 | 231.070 | 164.581 | 231.070 | 83.043 |
| p (t-test) | | 0.580 | | 0.580 | | 0.952 |
| min | 0.276 | 0.040 | 0.276 | 0.040 | 0.276 | 0.040 |
| max | 2177.715 | 383.874 | 2177.715 | 383.874 | 2177.715 | 200.967 |
| n (Samp) | 160 | 6 | 160 | 6 | 160 | 4 |
| n (Pat) | 160 | 6 | 160 | 6 | 160 | 4 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 24.434 | 123.504 | 24.434 | 123.504 | 24.434 | 91.823 |
| average | 104.482 | 242.180 | 104.482 | 223.358 | 104.482 | 89.770 |
| stdev | 184.561 | 260.969 | 184.561 | 257.360 | 184.561 | 35.256 |
| p (t-test) | | 0.055 | | 0.096 | | 0.847 |
| min | 0.000 | 42.703 | 0.000 | 42.703 | 0.000 | 42.703 |
| max | 1020.452 | 810.740 | 1020.452 | 810.740 | 1020.452 | 125.995 |
| n (Samp) | 84 | 8 | 84 | 8 | 84 | 6 |
| n (Pat) | 84 | 8 | 84 | 8 | 84 | 6 |

Fig. 4 Continued sCr or UO

| Time prior AKI stage | AUC | SE | nCohort 1 | nCohort 2 | p |
|---|---|---|---|---|---|
| 0 hours | 0.74 | 0.086 | 99 | 12 | 0.006 |
| 24 hours | 0.73 | 0.086 | 99 | 12 | 0.008 |
| 48 hours | 0.66 | 0.109 | 99 | 8 | 0.140 | sCr only

| Time prior AKI stage | AUC | SE | nCohort 1 | nCohort 2 | p |
|---|---|---|---|---|---|
| 0 hours | 0.64 | 0.124 | 160 | 6 | 0.269 |
| 24 hours | 0.64 | 0.124 | 160 | 6 | 0.269 |
| 48 hours | 0.58 | 0.151 | 160 | 4 | 0.620 |

UO only

| Time prior AKI stage | AUC | SE | nCohort 1 | nCohort 2 | p |
|---|---|---|---|---|---|
| 0 hours | 0.79 | 0.099 | 84 | 8 | 0.004 |
| 24 hours | 0.77 | 0.100 | 84 | 8 | 0.007 |
| 48 hours | 0.70 | 0.123 | 84 | 6 | 0.096 | sCr or UO

| Time prior AKI stage | Cutoff value | sens | spec | Quartile | OR | 95% CI of OR | |
|---|---|---|---|---|---|---|---|
| 0 hours | 54.8878 | 75% | 72% | 1 | | | |
| | 40.343 | 83% | 65% | 2 | 0.0 | 0.0 | na |
| | 29.5388 | 92% | 58% | 3 | 5.7 | 0.5 | 69.7 |
| | 52.5309 | 75% | 71% | 4 | 7.1 | 0.6 | 82.3 |
| | 107.409 | 50% | 81% | | | | |
| | 250 | 33% | 91% | | | | |
| 24 hours | 54.8878 | 75% | 72% | 1 | | | |
| | 40.343 | 83% | 65% | 2 | 0.0 | 0.0 | na |
| | 29.5388 | 92% | 58% | 3 | 5.7 | 0.5 | 69.7 |
| | 52.5309 | 75% | 71% | 4 | 7.1 | 0.6 | 82.3 |
| | 107.409 | 50% | 81% | | | | |
| | 250 | 25% | 91% | | | | |
| 48 hours | 54.8878 | 75% | 72% | 1 | | | |
| | 40.343 | 88% | 65% | 2 | 0.0 | 0.0 | na |
| | 0 | 100% | 0% | 3 | 4.3 | 0.3 | 59.3 |
| | 52.5309 | 75% | 71% | 4 | 3.1 | 0.2 | 50.0 |
| | 107.409 | 38% | 81% | | | | |
| | 250 | 0% | 91% | | | | | sCr only

| Time prior AKI stage | Cutoff value | sens | spec | Quartile | OR | 95% CI of OR | |
|---|---|---|---|---|---|---|---|
| 0 hours | 30.1485 | 83% | 50% | 1 | | | |
| | 30.1485 | 83% | 50% | 2 | 1.0 | 0.0 | 54.2 |
| | 0 | 100% | 0% | 3 | 1.0 | 0.0 | 55.6 |
| | 85.4884 | 67% | 70% | 4 | 3.1 | 0.2 | 46.4 |
| | 137.292 | 33% | 80% | | | | |
| | 250 | 33% | 90% | | | | |
| 24 hours | 30.1485 | 83% | 50% | 1 | | | |
| | 30.1485 | 83% | 50% | 2 | 1.0 | 0.0 | 54.2 |
| | 0 | 100% | 0% | 3 | 1.0 | 0.0 | 55.6 |
| | 85.4884 | 67% | 70% | 4 | 3.1 | 0.2 | 46.4 |
| | 137.292 | 33% | 80% | | | | |
| | 250 | 33% | 90% | | | | |

Fig. 4 Continued

| 48 hours | 85.4884 | 75% | 70% | 1 | | | |
| --- | --- | --- | --- | --- | --- | --- | --- |
| | 0 | 100% | 0% | 2 | 0.0 | 0.0 | na |
| | 0 | 100% | 0% | 3 | 1.0 | 0.0 | 55.6 |
| | 85.4884 | 75% | 70% | 4 | 2.1 | 0.1 | 42.9 |
| | 137.292 | 25% | 80% | | | | |
| | 250 | 0% | 90% | | | | |

Granulocyte colony-stimulating factor sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 31.900 | 85.300 | 31.900 | 87.700 | 31.900 | 77.500 |
| average | 59.293 | 468.006 | 59.293 | 490.544 | 59.293 | 182.334 |
| stdev | 89.020 | 917.287 | 89.020 | 942.638 | 89.020 | 327.238 |
| p (t-test) | | 0.000 | | 0.000 | | 0.004 |
| min | 1.020 | 12.400 | 1.020 | 12.400 | 1.020 | 8.040 |
| max | 521.000 | 3010.000 | 521.000 | 3010.000 | 521.000 | 1090.000 |
| n (Samp) | 104 | 17 | 104 | 16 | 104 | 10 |
| n (Pat) | 104 | 17 | 104 | 16 | 104 | 10 | sCr only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 37.350 | 122.150 | 37.350 | 122.150 | 37.350 | 85.300 |
| average | 1074.646 | 780.338 | 1074.646 | 780.338 | 1074.646 | 665.408 |
| stdev | 9479.458 | 1255.939 | 9479.458 | 1255.939 | 9479.458 | 1311.695 |
| p (t-test) | | 0.930 | | 0.930 | | 0.923 |
| min | 0.879 | 12.400 | 0.879 | 12.400 | 0.879 | 8.040 |
| max | 103844.000 | 3010.000 | 103844.000 | 3010.000 | 103844.000 | 3010.000 |
| n (Samp) | 170 | 8 | 170 | 8 | 170 | 5 |
| n (Pat) | 170 | 8 | 170 | 8 | 170 | 5 |

UO only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 30.600 | 69.700 | 30.600 | 65.900 | 30.600 | 69.700 |
| average | 77.244 | 435.736 | 77.244 | 468.570 | 77.244 | 225.143 |
| stdev | 193.995 | 908.267 | 193.995 | 950.726 | 193.995 | 389.516 |
| p (t-test) | | 0.002 | | 0.001 | | 0.080 |
| min | 1.020 | 30.400 | 1.020 | 17.700 | 1.020 | 17.700 |
| max | 1610.000 | 3010.000 | 1610.000 | 3010.000 | 1610.000 | 1090.000 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
| --- | --- | --- | --- | --- | --- |
| 0 hours | 0.77 | 0.070 | 104 | 17 | 0.000 |
| 24 hours | 0.74 | 0.074 | 104 | 16 | 0.001 |
| 48 hours | 0.67 | 0.097 | 104 | 10 | 0.075 | sCr only

| Time prior AKI stage | AUC | SE | nCohort 1 | nCohort 2 | p |
| --- | --- | --- | --- | --- | --- |
| 0 hours | 0.80 | 0.096 | 170 | 8 | 0.002 |
| 24 hours | 0.80 | 0.096 | 170 | 8 | 0.002 |
| 48 hours | 0.71 | 0.132 | 170 | 5 | 0.103 |

Fig. 4 Continued

UO only

| Time prior AKI stage | AUC | SE | nCohort 1 | nCohort 2 | p |
|---|---|---|---|---|---|
| 0 hours | 0.77 | 0.086 | 85 | 11 | 0.001 |
| 24 hours | 0.72 | 0.095 | 85 | 10 | 0.019 |
| 48 hours | 0.70 | 0.115 | 85 | 7 | 0.087 | sCr or UO

| Time prior AKI stage | Cutoff value | sens | spec | Quartile | OR | 95% CI of OR | |
|---|---|---|---|---|---|---|---|
| 0 hours | 58.9 | 71% | 76% | 1 | | | |
| | 40.4 | 82% | 62% | 2 | 2.1 | 0.1 | 45.0 |
| | 29.9 | 94% | 49% | 3 | 4.5 | 0.3 | 59.6 |
| | 48.3 | 71% | 70% | 4 | 13.8 | 1.4 | 140.1 |
| | 73.8 | 53% | 81% | | | | |
| | 116 | 35% | 90% | | | | |
| 24 hours | 33.5 | 75% | 53% | 1 | | | |
| | 30.7 | 81% | 50% | 2 | 4.5 | 0.3 | 59.6 |
| | 17.1 | 94% | 30% | 3 | 2.1 | 0.1 | 45.0 |
| | 48.3 | 69% | 70% | 4 | 12.4 | 1.2 | 128.9 |
| | 73.8 | 56% | 81% | | | | |
| | 116 | 38% | 90% | | | | |
| 48 hours | 29.9 | 70% | 49% | 1 | | | |
| | 28.8 | 80% | 48% | 2 | 3.1 | 0.2 | 49.3 |
| | 17.1 | 90% | 30% | 3 | 0.0 | 0.0 | na |
| | 48.3 | 60% | 70% | 4 | 7.0 | 0.6 | 81.2 |
| | 73.8 | 50% | 81% | | | | |
| | 116 | 30% | 90% | | | | | sCr only

| Time prior AKI stage | Cutoff value | sens | spec | Quartile | OR | 95% CI of OR | |
|---|---|---|---|---|---|---|---|
| 0 hours | 84.8 | 75% | 82% | 1 | | | |
| | 67.1 | 88% | 75% | 2 | 0.0 | 0.0 | na |
| | 12 | 100% | 16% | 3 | 1.0 | 0.0 | 55.2 |
| | 58.9 | 88% | 70% | 4 | 6.6 | 0.6 | 71.7 |
| | 82.6 | 75% | 81% | | | | |
| | 141 | 50% | 90% | | | | |
| 24 hours | 84.8 | 75% | 82% | 1 | | | |
| | 67.1 | 88% | 75% | 2 | 0.0 | 0.0 | na |
| | 12 | 100% | 16% | 3 | 1.0 | 0.0 | 55.2 |
| | 58.9 | 88% | 70% | 4 | 6.6 | 0.6 | 71.7 |
| | 82.6 | 75% | 81% | | | | |
| | 141 | 50% | 90% | | | | |
| 48 hours | 67.1 | 80% | 75% | 1 | | | |
| | 67.1 | 80% | 75% | 2 | 0.0 | 0.0 | na |
| | 7.82 | 100% | 11% | 3 | 1.0 | 0.0 | 54.0 |
| | 58.9 | 80% | 70% | 4 | 3.1 | 0.2 | 46.1 |
| | 82.6 | 60% | 81% | | | | |
| | 141 | 40% | 90% | | | | |

Fig. 4 Continued

Granulocyte-macrophage colony-stimulating factor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 9.120 | 9.940 | 9.120 | 9.730 | 9.120 | 9.730 |
| average | 9.505 | 12.998 | 9.505 | 13.185 | 9.505 | 13.136 |
| stdev | 5.741 | 10.912 | 5.741 | 10.375 | 5.741 | 10.913 |
| p (t-test) |  | 0.048 |  | 0.038 |  | 0.085 |
| min | 0.230 | 0.230 | 0.230 | 0.230 | 0.230 | 0.230 |
| max | 29.400 | 39.800 | 29.400 | 39.800 | 29.400 | 39.800 |
| n (Samp) | 104 | 17 | 104 | 16 | 104 | 10 |
| n (Pat) | 104 | 17 | 104 | 16 | 104 | 10 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 9.940 | 12.500 | 9.940 | 12.500 | 9.940 | 14.500 |
| average | 13.591 | 15.280 | 13.591 | 14.893 | 13.591 | 13.248 |
| stdev | 35.070 | 10.107 | 35.070 | 9.147 | 35.070 | 5.608 |
| p (t-test) |  | 0.892 |  | 0.917 |  | 0.983 |
| min | 0.230 | 5.140 | 0.230 | 5.140 | 0.230 | 5.140 |
| max | 453.000 | 37.500 | 453.000 | 34.400 | 453.000 | 19.600 |
| n (Samp) | 170 | 8 | 170 | 8 | 170 | 5 |
| n (Pat) | 170 | 8 | 170 | 8 | 170 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 9.520 | 9.520 | 9.520 | 9.075 | 9.520 | 9.520 |
| average | 9.780 | 11.247 | 9.780 | 11.682 | 9.780 | 12.874 |
| stdev | 5.523 | 10.599 | 5.523 | 10.498 | 5.523 | 12.611 |
| p (t-test) |  | 0.466 |  | 0.360 |  | 0.211 |
| min | 0.230 | 0.230 | 0.230 | 0.230 | 0.230 | 0.230 |
| max | 29.400 | 39.800 | 29.400 | 39.800 | 29.400 | 39.800 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
|---|---|---|---|---|---|
| 0 hours | 0.57 | 0.077 | 104 | 17 | 0.337 |
| 24 hours | 0.58 | 0.080 | 104 | 16 | 0.306 |
| 48 hours | 0.59 | 0.099 | 104 | 10 | 0.375 | sCr only

| Time prior AKI stage | AUC | SE | nCohort 1 | nCohort 2 | p |
|---|---|---|---|---|---|
| 0 hours | 0.64 | 0.108 | 170 | 8 | 0.207 |
| 24 hours | 0.64 | 0.108 | 170 | 8 | 0.207 |
| 48 hours | 0.64 | 0.136 | 170 | 5 | 0.302 |

UO only

| Time prior AKI stage | AUC | SE | nCohort 1 | nCohort 2 | p |
|---|---|---|---|---|---|
| 0 hours | 0.50 | 0.093 | 85 | 11 | 0.968 |
| 24 hours | 0.49 | 0.097 | 85 | 10 | 0.942 |
| 48 hours | 0.52 | 0.115 | 85 | 7 | 0.861 |

Fig. 4 Continued sCr or UO

| Time prior AKI stage | Cutoff value | sens | spec | Quartile | OR | 95% CI of OR | |
|---|---|---|---|---|---|---|---|
| 0 hours | 8.11 | 71% | 43% | 1 | | | |
| | 6.91 | 82% | 33% | 2 | 1.4 | 0.4 | 5.0 |
| | 0 | 100% | 0% | 3 | 1.4 | 0.4 | 5.0 |
| | 12.2 | 35% | 71% | 4 | 2.2 | 0.7 | 6.7 |
| | 14.1 | 35% | 81% | | | | |
| | 16.2 | 24% | 90% | | | | |
| 24 hours | 8.11 | 75% | 43% | 1 | | | |
| | 7.83 | 81% | 37% | 2 | 2.8 | 0.6 | 12.8 |
| | 5.01 | 94% | 22% | 3 | 2.2 | 0.4 | 10.8 |
| | 12.2 | 31% | 71% | 4 | 2.8 | 0.6 | 12.8 |
| | 14.1 | 31% | 81% | | | | |
| | 16.2 | 25% | 90% | | | | |
| 48 hours | 8.2 | 70% | 46% | 1 | | | |
| | 7.4 | 80% | 34% | 2 | 1.0 | 0.1 | 7.9 |
| | 5.01 | 90% | 22% | 3 | 1.0 | 0.1 | 8.3 |
| | 12.2 | 40% | 71% | 4 | 2.1 | 0.4 | 10.6 |
| | 14.1 | 40% | 81% | | | | |
| | 16.2 | 30% | 90% | | | | | sCr only

| Time prior AKI stage | Cutoff value | sens | spec | Quartile | OR | 95% CI of OR | |
|---|---|---|---|---|---|---|---|
| 0 hours | 9.94 | 75% | 51% | 1 | | | |
| | 8.11 | 88% | 39% | 2 | 2.0 | 0.1 | 41.4 |
| | 5.01 | 100% | 18% | 3 | 1.0 | 0.0 | 55.2 |
| | 13.2 | 50% | 71% | 4 | 4.2 | 0.3 | 53.4 |
| | 15.2 | 38% | 81% | | | | |
| | 19.8 | 13% | 90% | | | | |
| 24 hours | 9.94 | 75% | 51% | 1 | | | |
| | 8.11 | 88% | 39% | 2 | 2.0 | 0.1 | 41.4 |
| | 5.01 | 100% | 18% | 3 | 1.0 | 0.0 | 55.2 |
| | 13.2 | 50% | 71% | 4 | 4.2 | 0.3 | 53.4 |
| | 15.2 | 38% | 81% | | | | |
| | 19.8 | 13% | 90% | | | | |
| 48 hours | 10.3 | 80% | 52% | 1 | | | |
| | 10.3 | 80% | 52% | 2 | 0.0 | 0.0 | na |
| | 5.01 | 100% | 18% | 3 | 2.0 | 0.1 | 41.5 |
| | 13.2 | 60% | 71% | 4 | 2.0 | 0.1 | 41.5 |
| | 15.2 | 40% | 81% | | | | |
| | 19.8 | 0% | 90% | | | | |

UO only

| Time prior AKI stage | Cutoff value | sens | spec | Quartile | OR | 95% CI of OR | |
|---|---|---|---|---|---|---|---|
| 0 hours | 7.83 | 73% | 33% | 1 | | | |
| | 6.91 | 82% | 29% | 2 | 1.0 | 0.2 | 4.5 |
| | 0 | 100% | 0% | 3 | 1.0 | 0.2 | 4.5 |
| | 12.5 | 27% | 72% | 4 | 0.6 | 0.1 | 3.9 |
| | 13.7 | 27% | 80% | | | | |
| | 16.2 | 9% | 92% | | | | |
| 24 hours | 8.43 | 70% | 41% | 1 | | | |
| | 7.83 | 80% | 33% | 2 | 1.6 | 0.3 | 9.7 |
| | 6.91 | 90% | 29% | 3 | 2.2 | 0.4 | 11.5 |
| | 12.5 | 20% | 72% | 4 | 0.5 | 0.0 | 11.3 |
| | 13.7 | 20% | 80% | | | | |
| | 16.2 | 10% | 92% | | | | |

Fig. 4 Continued

| 48 hours | 8.43 | 71% | 41% | 1 | | | |
| | 7.4 | 86% | 31% | 2 | 3.3 | 0.2 | 54.3 |
| | 0 | 100% | 0% | 3 | 1.0 | 0.0 | 60.2 |
| | 12.5 | 29% | 72% | 4 | 2.1 | 0.1 | 47.6 |
| | 13.7 | 29% | 80% | | | | |
| | 16.2 | 14% | 92% | | | | |

Heparin-binding growth factor 2 sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 241.000 | 496.000 | 241.000 | 534.500 | 241.000 | 310.500 |
| average | 298.408 | 739.982 | 298.408 | 734.481 | 298.408 | 432.870 |
| stdev | 244.741 | 847.967 | 244.741 | 839.845 | 244.741 | 309.453 |
| p (t-test) | | 0.000 | | 0.000 | | 0.108 |
| min | 0.392 | 84.700 | 0.392 | 84.700 | 0.392 | 84.700 |
| max | 1320.000 | 3610.000 | 1320.000 | 3610.000 | 1320.000 | 997.000 |
| n (Samp) | 104 | 17 | 104 | 16 | 104 | 10 |
| n (Pat) | 104 | 17 | 104 | 16 | 104 | 10 | sCr only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 245.000 | 802.500 | 245.000 | 802.500 | 245.000 | 903.000 |
| average | 337.579 | 836.588 | 337.579 | 836.588 | 337.579 | 739.540 |
| stdev | 382.525 | 457.469 | 382.525 | 457.469 | 382.525 | 421.285 |
| p (t-test) | | 0.000 | | 0.000 | | 0.022 |
| min | 0.392 | 84.700 | 0.392 | 84.700 | 0.392 | 84.700 |
| max | 3610.000 | 1680.000 | 3610.000 | 1680.000 | 3610.000 | 1140.000 |
| n (Samp) | 170 | 8 | 170 | 8 | 170 | 5 |
| n (Pat) | 170 | 8 | 170 | 8 | 170 | 5 |

UO only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 225.000 | 307.000 | 225.000 | 310.500 | 225.000 | 307.000 |
| average | 289.233 | 778.545 | 289.233 | 773.600 | 289.233 | 395.429 |
| stdev | 242.056 | 1043.958 | 242.056 | 1053.004 | 242.056 | 285.819 |
| p (t-test) | | 0.000 | | 0.000 | | 0.274 |
| min | 0.392 | 165.000 | 0.392 | 166.000 | 0.392 | 166.000 |
| max | 1320.000 | 3610.000 | 1320.000 | 3610.000 | 1320.000 | 997.000 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
| --- | --- | --- | --- | --- | --- |
| 0 hours | 0.73 | 0.073 | 104 | 17 | 0.002 |
| 24 hours | 0.73 | 0.075 | 104 | 16 | 0.002 |
| 48 hours | 0.65 | 0.098 | 104 | 10 | 0.130 | sCr only

| Time prior AKI stage | AUC | SE | nCohort 1 | nCohort 2 | p |
| --- | --- | --- | --- | --- | --- |
| 0 hours | 0.83 | 0.091 | 170 | 8 | 0.000 |
| 24 hours | 0.83 | 0.091 | 170 | 8 | 0.000 |
| 48 hours | 0.76 | 0.126 | 170 | 5 | 0.038 |

Fig. 4 Continued

UO only

| Time prior AKI stage | AUC | SE | nCohort 1 | nCohort 2 | p |
|---|---|---|---|---|---|
| 0 hours | 0.72 | 0.091 | 85 | 11 | 0.016 |
| 24 hours | 0.71 | 0.096 | 85 | 10 | 0.026 |
| 48 hours | 0.67 | 0.116 | 85 | 7 | 0.150 | sCr or UO

| Time prior AKI stage | Cutoff value | sens | spec | Quartile | OR | 95% CI of OR | |
|---|---|---|---|---|---|---|---|
| 0 hours | 285 | 71% | 69% | 1 | | | |
| | 218 | 82% | 41% | 2 | 1.0 | 0.1 | 8.2 |
| | 158 | 94% | 21% | 3 | 2.2 | 0.4 | 10.8 |
| | 295 | 65% | 70% | 4 | 5.7 | 1.5 | 22.2 |
| | 348 | 53% | 81% | | | | |
| | 501 | 47% | 91% | | | | |
| 24 hours | 285 | 75% | 69% | 1 | | | |
| | 208 | 81% | 41% | 2 | 1.0 | 0.1 | 8.2 |
| | 165 | 94% | 22% | 3 | 1.6 | 0.3 | 9.2 |
| | 295 | 69% | 70% | 4 | 6.0 | 1.5 | 23.4 |
| | 348 | 56% | 81% | | | | |
| | 501 | 50% | 91% | | | | |
| 48 hours | 285 | 70% | 69% | 1 | | | |
| | 192 | 80% | 29% | 2 | 0.5 | 0.0 | 10.2 |
| | 165 | 90% | 22% | 3 | 1.6 | 0.3 | 9.3 |
| | 295 | 60% | 70% | 4 | 2.1 | 0.4 | 10.6 |
| | 348 | 40% | 81% | | | | |
| | 501 | 30% | 91% | | | | | sCr only

| Time prior AKI stage | Cutoff value | sens | spec | Quartile | OR | 95% CI of OR | |
|---|---|---|---|---|---|---|---|
| 0 hours | 691 | 75% | 91% | 1 | | | |
| | 522 | 88% | 89% | 2 | 0.0 | 0.0 | na |
| | 75.8 | 100% | 8% | 3 | 0.0 | 0.0 | na |
| | 307 | 88% | 70% | 4 | 7.9 | 0.8 | 82.0 |
| | 421 | 88% | 80% | | | | |
| | 629 | 75% | 90% | | | | |
| 24 hours | 691 | 75% | 91% | 1 | | | |
| | 522 | 88% | 89% | 2 | 0.0 | 0.0 | na |
| | 75.8 | 100% | 8% | 3 | 0.0 | 0.0 | na |
| | 307 | 88% | 70% | 4 | 7.9 | 0.8 | 82.0 |
| | 421 | 88% | 80% | | | | |
| | 629 | 75% | 90% | | | | |
| 48 hours | 522 | 80% | 89% | 1 | | | |
| | 522 | 80% | 89% | 2 | 0.0 | 0.0 | na |
| | 75.8 | 100% | 8% | 3 | 0.0 | 0.0 | na |
| | 307 | 80% | 70% | 4 | 4.2 | 0.3 | 53.6 |
| | 421 | 80% | 80% | | | | |
| | 629 | 60% | 90% | | | | |

UO only

| Time prior AKI stage | Cutoff value | sens | spec | Quartile | OR | 95% CI of OR | |
|---|---|---|---|---|---|---|---|
| 0 hours | 258 | 73% | 62% | 1 | | | |
| | 218 | 82% | 47% | 2 | 2.1 | 0.1 | 47.1 |
| | 208 | 91% | 47% | 3 | 3.3 | 0.2 | 53.6 |
| | 272 | 64% | 71% | 4 | 6.1 | 0.5 | 76.8 |
| | 323 | 36% | 80% | | | | |
| | 492 | 36% | 91% | | | | |

Fig. 4 Continued

| | | | | | | | |
|---|---|---|---|---|---|---|---|
| 24 hours | 285 | 70% | 73% | 1 | | | |
| | 208 | 80% | 47% | 2 | 2.0 | 0.1 | 45.2 |
| | 192 | 90% | 32% | 3 | 2.0 | 0.1 | 45.2 |
| | 272 | 70% | 71% | 4 | 5.8 | 0.5 | 73.7 |
| | 323 | 40% | 80% | | | | |
| | 492 | 40% | 91% | | | | |
| 48 hours | 285 | 71% | 73% | 1 | | | |
| | 192 | 86% | 32% | 2 | 1.0 | 0.0 | 60.2 |
| | 165 | 100% | 24% | 3 | 2.1 | 0.1 | 47.6 |
| | 272 | 71% | 71% | 4 | 3.3 | 0.2 | 54.3 |
| | 323 | 29% | 80% | | | | |
| | 492 | 29% | 91% | | | | |

Interleukin-1 receptor antagonist sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 5705.000 | 33900.000 | 5705.000 | 31750.000 | 5705.000 | 19765.000 |
| average | 30642.702 | 71077.765 | 30642.702 | 72423.875 | 30642.702 | 34942.100 |
| stdev | 89701.395 | 108638.515 | 89701.395 | 112085.320 | 89701.395 | 43174.851 |
| p (t-test) | | 0.097 | | 0.096 | | 0.881 |
| min | 337.000 | 1560.000 | 337.000 | 1560.000 | 337.000 | 801.000 |
| max | 520726.000 | 439392.000 | 520726.000 | 439392.000 | 520726.000 | 127000.000 |
| n (Samp) | 104 | 17 | 104 | 16 | 104 | 10 |
| n (Pat) | 104 | 17 | 104 | 16 | 104 | 10 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 7360.000 | 32650.000 | 7360.000 | 32650.000 | 7360.000 | 29600.000 |
| average | 32869.000 | 104837.750 | 32869.000 | 104837.750 | 32869.000 | 38470.200 |
| stdev | 91427.456 | 149476.699 | 91427.456 | 149476.699 | 91427.456 | 46168.368 |
| p (t-test) | | 0.037 | | 0.037 | | 0.892 |
| min | 207.000 | 1560.000 | 207.000 | 1560.000 | 207.000 | 801.000 |
| max | 598080.000 | 439392.000 | 598080.000 | 439392.000 | 598080.000 | 117000.000 |
| n (Samp) | 170 | 8 | 170 | 8 | 170 | 5 |
| n (Pat) | 170 | 8 | 170 | 8 | 170 | 5 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 5440.000 | 33900.000 | 5440.000 | 22850.000 | 5440.000 | 9930.000 |
| average | 30525.071 | 45079.091 | 30525.071 | 44633.000 | 30525.071 | 40474.286 |
| stdev | 89350.938 | 46703.999 | 89350.938 | 49321.134 | 89350.938 | 50609.035 |
| p (t-test) | | 0.598 | | 0.626 | | 0.773 |
| min | 337.000 | 3360.000 | 337.000 | 3290.000 | 337.000 | 2980.000 |
| max | 520726.000 | 127000.000 | 520726.000 | 127000.000 | 520726.000 | 127000.000 |
| n (Samp) | 85 | 11 | 85 | 10 | 85 | 7 |
| n (Pat) | 85 | 11 | 85 | 10 | 85 | 7 |

Fig. 4 Continued sCr or UO

| Time prior AKI stage | AUC | SE | nCohort 1 | nCohort 2 | p |
|---|---|---|---|---|---|
| 0 hours | 0.76 | 0.071 | 104 | 17 | 0.000 |
| 24 hours | 0.74 | 0.074 | 104 | 16 | 0.001 |
| 48 hours | 0.65 | 0.098 | 104 | 10 | 0.131 | sCr only

| Time prior AKI stage | AUC | SE | nCohort 1 | nCohort 2 | p |
|---|---|---|---|---|---|
| 0 hours | 0.76 | 0.101 | 170 | 8 | 0.011 |
| 24 hours | 0.76 | 0.101 | 170 | 8 | 0.011 |
| 48 hours | 0.65 | 0.135 | 170 | 5 | 0.255 |

UO only

| Time prior AKI stage | AUC | SE | nCohort 1 | nCohort 2 | p |
|---|---|---|---|---|---|
| 0 hours | 0.75 | 0.088 | 85 | 11 | 0.004 |
| 24 hours | 0.73 | 0.095 | 85 | 10 | 0.016 |
| 48 hours | 0.67 | 0.116 | 85 | 7 | 0.133 | sCr or UO

| Time prior AKI stage | Cutoff value | sens | spec | Quartile | OR | 95% CI of OR | |
|---|---|---|---|---|---|---|---|
| 0 hours | 11600 | 71% | 67% | 1 | | | |
| | 9110 | 82% | 63% | 2 | 2.1 | 0.1 | 45.0 |
| | 3270 | 94% | 38% | 3 | 3.2 | 0.2 | 50.6 |
| | 13200 | 65% | 70% | 4 | 16.0 | 1.6 | 159.7 |
| | 17200 | 65% | 81% | | | | |
| | 40400 | 35% | 90% | | | | |
| 24 hours | 9250 | 75% | 63% | 1 | | | |
| | 9110 | 81% | 63% | 2 | 2.1 | 0.1 | 45.0 |
| | 3270 | 94% | 38% | 3 | 3.2 | 0.2 | 50.6 |
| | 13200 | 63% | 70% | 4 | 14.5 | 1.4 | 147.8 |
| | 17200 | 63% | 81% | | | | |
| | 40400 | 31% | 90% | | | | |
| 48 hours | 9110 | 70% | 63% | 1 | | | |
| | 3270 | 80% | 38% | 2 | 2.0 | 0.1 | 43.7 |
| | 2870 | 90% | 32% | 3 | 2.1 | 0.1 | 45.6 |
| | 13200 | 50% | 70% | 4 | 5.6 | 0.5 | 69.0 |
| | 17200 | 50% | 81% | | | | |
| | 40400 | 20% | 90% | | | | | sCr only

| Time prior AKI stage | Cutoff value | sens | spec | Quartile | OR | 95% CI of OR | |
|---|---|---|---|---|---|---|---|
| 0 hours | 19000 | 75% | 76% | 1 | | | |
| | 9110 | 88% | 58% | 2 | 0.0 | 0.0 | na |
| | 1520 | 100% | 12% | 3 | 2.0 | 0.1 | 42.5 |
| | 15500 | 75% | 70% | 4 | 5.4 | 0.5 | 62.1 |
| | 22400 | 63% | 80% | | | | |
| | 42300 | 38% | 90% | | | | |
| 24 hours | 19000 | 75% | 76% | 1 | | | |
| | 9110 | 88% | 58% | 2 | 0.0 | 0.0 | na |
| | 1520 | 100% | 12% | 3 | 2.0 | 0.1 | 42.5 |
| | 15500 | 75% | 70% | 4 | 5.4 | 0.5 | 62.1 |
| | 22400 | 63% | 80% | | | | |
| | 42300 | 38% | 90% | | | | |

Fig. 4 Continued

| 48 hours | 9110 | 80% | 58% | 1 | | | |
| --- | --- | --- | --- | --- | --- | --- | --- |
| | 9110 | 80% | 58% | 2 | 0.0 | 0.0 | na |
| | 715 | 100% | 4% | 3 | 1.0 | 0.0 | 54.0 |
| | 15500 | 60% | 70% | 4 | 3.1 | 0.2 | 46.1 |
| | 22400 | 60% | 80% | | | | |
| | 42300 | 20% | 90% | | | | |

Interleukin-1 beta sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 1.285 | 10.200 | 1.285 | 7.625 | 1.285 | 6.870 |
| average | 4.632 | 14.897 | 4.632 | 14.947 | 4.632 | 12.108 |
| stdev | 12.238 | 13.030 | 12.238 | 13.440 | 12.238 | 13.845 |
| p (t-test) | | 0.002 | | 0.002 | | 0.071 |
| min | 0.006 | 0.513 | 0.006 | 0.366 | 0.006 | 0.006 |
| max | 109.000 | 38.200 | 109.000 | 38.200 | 109.000 | 38.200 |
| n (Samp) | 104 | 17 | 104 | 16 | 104 | 10 |
| n (Pat) | 104 | 17 | 104 | 16 | 104 | 10 | sCr only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 1.625 | 7.625 | 1.625 | 7.240 | 1.625 | 7.130 |
| average | 10.950 | 10.388 | 10.950 | 9.940 | 10.950 | 6.361 |
| stdev | 54.876 | 9.563 | 54.876 | 9.635 | 54.876 | 3.556 |
| p (t-test) | | 0.977 | | 0.959 | | 0.852 |
| min | 0.006 | 0.513 | 0.006 | 0.513 | 0.006 | 0.513 |
| max | 670.000 | 32.800 | 670.000 | 32.800 | 670.000 | 10.200 |
| n (Samp) | 170 | 8 | 170 | 8 | 170 | 5 |
| n (Pat) | 170 | 8 | 170 | 8 | 170 | 5 |

UO only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 1.290 | 12.500 | 1.290 | 12.500 | 1.290 | 7.130 |
| average | 4.224 | 17.044 | 4.224 | 17.697 | 4.224 | 15.229 |
| stdev | 12.312 | 13.948 | 12.312 | 14.404 | 12.312 | 15.651 |
| p (t-test) | | 0.002 | | 0.002 | | 0.028 |
| min | 0.006 | 0.539 | 0.006 | 0.366 | 0.006 | 0.006 |
| max | 109.000 | 38.200 | 109.000 | 38.200 | 109.000 | 38.200 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
| --- | --- | --- | --- | --- | --- |
| 0 hours | 0.82 | 0.065 | 104 | 17 | 0.000 |
| 24 hours | 0.81 | 0.067 | 104 | 16 | 0.000 |
| 48 hours | 0.73 | 0.093 | 104 | 10 | 0.012 | sCr only

| Time prior AKI stage | AUC | SE | nCohort 1 | nCohort 2 | p |
| --- | --- | --- | --- | --- | --- |
| 0 hours | 0.76 | 0.101 | 170 | 8 | 0.010 |
| 24 hours | 0.75 | 0.101 | 170 | 8 | 0.012 |
| 48 hours | 0.69 | 0.134 | 170 | 5 | 0.165 |

Fig. 4 Continued

UO only

| Time prior AKI stage | AUC | SE | nCohort 1 | nCohort 2 | p |
|---|---|---|---|---|---|
| 0 hours | 0.84 | 0.076 | 85 | 11 | 0.000 |
| 24 hours | 0.85 | 0.079 | 85 | 10 | 0.000 |
| 48 hours | 0.78 | 0.106 | 85 | 7 | 0.007 | sCr or UO

| Time prior AKI stage | Cutoff value | sens | spec | Quartile | OR | 95% CI of OR | |
|---|---|---|---|---|---|---|---|
| 0 hours | 6.97 | 71% | 88% | 1 | | | |
| | 5.8 | 82% | 84% | 2 | 0.0 | 0.0 | na |
| | 0.518 | 94% | 17% | 3 | 0.5 | 0.0 | 10.5 |
| | 3.11 | 82% | 73% | 4 | 11.5 | 3.1 | 42.5 |
| | 4.1 | 82% | 81% | | | | |
| | 8.67 | 53% | 90% | | | | |
| 24 hours | 6.59 | 75% | 87% | 1 | | | |
| | 5.8 | 81% | 84% | 2 | 0.0 | 0.0 | na |
| | 0.496 | 94% | 16% | 3 | 0.5 | 0.0 | 10.5 |
| | 3.11 | 88% | 73% | 4 | 10.7 | 2.9 | 39.9 |
| | 4.1 | 88% | 81% | | | | |
| | 8.67 | 44% | 90% | | | | |
| 48 hours | 5.8 | 70% | 84% | 1 | | | |
| | 4.1 | 80% | 81% | 2 | 0.0 | 0.0 | na |
| | 0.496 | 90% | 16% | 3 | 0.0 | 0.0 | na |
| | 3.11 | 80% | 73% | 4 | 5.0 | 1.2 | 20.0 |
| | 4.1 | 80% | 81% | | | | |
| | 8.67 | 30% | 90% | | | | | sCr only

| Time prior AKI stage | Cutoff value | sens | spec | Quartile | OR | 95% CI of OR | |
|---|---|---|---|---|---|---|---|
| 0 hours | 6.97 | 75% | 82% | 1 | | | |
| | 6.59 | 88% | 81% | 2 | 0.0 | 0.0 | na |
| | 0.508 | 100% | 15% | 3 | 0.0 | 0.0 | na |
| | 3.14 | 88% | 70% | 4 | 7.9 | 0.8 | 82.0 |
| | 6.44 | 88% | 80% | | | | |
| | 14.3 | 13% | 90% | | | | |
| 24 hours | 6.97 | 75% | 82% | 1 | | | |
| | 6.59 | 88% | 81% | 2 | 0.0 | 0.0 | na |
| | 0.508 | 100% | 15% | 3 | 0.0 | 0.0 | na |
| | 3.14 | 88% | 70% | 4 | 7.9 | 0.8 | 82.0 |
| | 6.44 | 88% | 80% | | | | |
| | 14.3 | 13% | 90% | | | | |
| 48 hours | 6.59 | 80% | 81% | 1 | | | |
| | 6.59 | 80% | 81% | 2 | 0.0 | 0.0 | na |
| | 0.508 | 100% | 15% | 3 | 0.0 | 0.0 | na |
| | 3.14 | 80% | 70% | 4 | 4.2 | 0.3 | 53.6 |
| | 6.44 | 80% | 80% | | | | |
| | 14.3 | 0% | 90% | | | | |

UO only

| Time prior AKI stage | Cutoff value | sens | spec | Quartile | OR | 95% CI of OR | |
|---|---|---|---|---|---|---|---|
| 0 hours | 6.97 | 73% | 87% | 1 | | | |
| | 5.8 | 82% | 84% | 2 | 0.0 | 0.0 | na |
| | 2.03 | 91% | 65% | 3 | 1.0 | 0.0 | 59.8 |
| | 3.11 | 82% | 72% | 4 | 13.8 | 1.3 | 151.2 |
| | 4.04 | 82% | 80% | | | | |
| | 7.68 | 64% | 91% | | | | |

Fig. 4 Continued

| 24 hours | 6.97 | 70% | 87% | 1 | | | |
| --- | --- | --- | --- | --- | --- | --- | --- |
| | 5.8 | 80% | 84% | 2 | 0.0 | 0.0 | na |
| | 4.12 | 90% | 81% | 3 | 1.0 | 0.0 | 57.4 |
| | 3.11 | 90% | 72% | 4 | 11.0 | 1.0 | 123.3 |
| | 4.04 | 90% | 80% | | | | |
| | 7.68 | 60% | 91% | | | | |
| 48 hours | 5.8 | 71% | 84% | 1 | | | |
| | 4.12 | 86% | 81% | 2 | 0.0 | 0.0 | na |
| | 0 | 100% | 0% | 3 | 0.0 | 0.0 | na |
| | 3.11 | 86% | 72% | 4 | 7.8 | 0.6 | 93.8 |
| | 4.04 | 86% | 80% | | | | |
| | 7.68 | 43% | 91% | | | | |

Interleukin-10 sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 1.765 | 2.020 | 1.765 | 1.985 | 1.765 | 2.545 |
| average | 3.561 | 8.180 | 3.561 | 8.668 | 3.561 | 2.177 |
| stdev | 18.712 | 26.263 | 18.712 | 27.043 | 18.712 | 1.269 |
| p (t-test) | | 0.377 | | 0.343 | | 0.816 |
| min | 0.062 | 0.062 | 0.062 | 0.062 | 0.062 | 0.062 |
| max | 192.000 | 110.000 | 192.000 | 110.000 | 192.000 | 4.000 |
| n (Samp) | 104 | 17 | 104 | 16 | 104 | 10 |
| n (Pat) | 104 | 17 | 104 | 16 | 104 | 10 | sCr only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 1.870 | 1.985 | 1.870 | 1.945 | 1.870 | 1.940 |
| average | 5.103 | 1.808 | 5.103 | 1.770 | 5.103 | 2.074 |
| stdev | 24.237 | 0.837 | 24.237 | 0.822 | 24.237 | 0.553 |
| p (t-test) | | 0.702 | | 0.699 | | 0.781 |
| min | 0.062 | 0.062 | 0.062 | 0.062 | 0.062 | 1.350 |
| max | 230.000 | 2.710 | 230.000 | 2.710 | 230.000 | 2.710 |
| n (Samp) | 170 | 8 | 170 | 8 | 170 | 5 |
| n (Pat) | 170 | 8 | 170 | 8 | 170 | 5 |

UO only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 1.910 | 2.540 | 1.910 | 2.545 | 1.910 | 2.550 |
| average | 4.052 | 11.680 | 4.052 | 12.842 | 4.052 | 2.185 |
| stdev | 20.680 | 32.635 | 20.680 | 34.159 | 20.680 | 1.529 |
| p (t-test) | | 0.288 | | 0.242 | | 0.813 |
| min | 0.062 | 0.062 | 0.062 | 0.062 | 0.062 | 0.062 |
| max | 192.000 | 110.000 | 192.000 | 110.000 | 192.000 | 4.000 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
| --- | --- | --- | --- | --- | --- |
| 0 hours | 0.56 | 0.077 | 104 | 17 | 0.413 |
| 24 hours | 0.58 | 0.080 | 104 | 16 | 0.287 |
| 48 hours | 0.64 | 0.098 | 104 | 10 | 0.166 |

Fig. 4 Continued sCr only

| Time prior AKI stage | AUC | SE | nCohort 1 | nCohort 2 | p |
|---|---|---|---|---|---|
| 0 hours | 0.51 | 0.105 | 170 | 8 | 0.936 |
| 24 hours | 0.50 | 0.105 | 170 | 8 | 0.983 |
| 48 hours | 0.56 | 0.135 | 170 | 5 | 0.644 |

UO only

| Time prior AKI stage | AUC | SE | nCohort 1 | nCohort 2 | p |
|---|---|---|---|---|---|
| 0 hours | 0.56 | 0.095 | 85 | 11 | 0.521 |
| 24 hours | 0.60 | 0.099 | 85 | 10 | 0.293 |
| 48 hours | 0.62 | 0.117 | 85 | 7 | 0.296 | sCr or UO

| Time prior AKI stage | Cutoff value | sens | spec | Quartile | OR | 95% CI of OR | |
|---|---|---|---|---|---|---|---|
| 0 hours | 1.32 | 71% | 37% | 1 | | | |
| | 0.0616 | 82% | 25% | 2 | 0.7 | 0.2 | 2.6 |
| | 0 | 100% | 0% | 3 | 1.0 | 0.3 | 3.1 |
| | 2.32 | 41% | 70% | 4 | 1.6 | 0.6 | 4.1 |
| | 2.78 | 24% | 82% | | | | |
| | 3.22 | 12% | 90% | | | | |
| 24 hours | 1.32 | 75% | 37% | 1 | | | |
| | 0.912 | 81% | 25% | 2 | 0.5 | 0.1 | 2.3 |
| | 0 | 100% | 0% | 3 | 1.0 | 0.3 | 3.1 |
| | 2.32 | 44% | 70% | 4 | 1.6 | 0.6 | 4.3 |
| | 2.78 | 25% | 82% | | | | |
| | 3.22 | 13% | 90% | | | | |
| 48 hours | 1.93 | 70% | 59% | 1 | | | |
| | 1.82 | 80% | 53% | 2 | 0.0 | 0.0 | na |
| | 0 | 100% | 0% | 3 | 1.6 | 0.3 | 9.3 |
| | 2.32 | 60% | 70% | 4 | 2.7 | 0.6 | 12.5 |
| | 2.78 | 30% | 82% | | | | |
| | 3.22 | 10% | 90% | | | | | sCr only

| Time prior AKI stage | Cutoff value | sens | spec | Quartile | OR | 95% CI of OR | |
|---|---|---|---|---|---|---|---|
| 0 hours | 1.57 | 75% | 41% | 1 | | | |
| | 1.32 | 88% | 34% | 2 | 2.0 | 0.1 | 41.4 |
| | 0 | 100% | 0% | 3 | 5.5 | 0.5 | 63.7 |
| | 2.54 | 13% | 71% | 4 | 0.0 | 0.0 | na |
| | 2.93 | 0% | 80% | | | | |
| | 3.74 | 0% | 91% | | | | |
| 24 hours | 1.57 | 75% | 41% | 1 | | | |
| | 1.32 | 88% | 34% | 2 | na | na | na |
| | 0 | 100% | 0% | 3 | na | na | na |
| | 2.54 | 13% | 71% | 4 | na | na | na |
| | 2.93 | 0% | 80% | | | | |
| | 3.74 | 0% | 91% | | | | |
| 48 hours | 1.82 | 80% | 49% | 1 | | | |
| | 1.82 | 80% | 49% | 2 | na | na | na |
| | 1.32 | 100% | 34% | 3 | na | na | na |
| | 2.54 | 20% | 71% | 4 | na | na | na |
| | 2.93 | 0% | 80% | | | | |
| | 3.74 | 0% | 91% | | | | |

Fig. 4 Continued

UO only

| Time prior AKI stage | Cutoff value | sens | spec | Quartile | OR | 95% CI of OR | |
|---|---|---|---|---|---|---|---|
| 0 hours | 0.912 | 73% | 25% | 1 | | | |
| | 0.0616 | 82% | 25% | 2 | 0.6 | 0.1 | 3.9 |
| | 0 | 100% | 0% | 3 | 0.6 | 0.1 | 3.9 |
| | 2.42 | 55% | 71% | 4 | 1.4 | 0.4 | 5.3 |
| | 2.82 | 36% | 80% | | | | |
| | 3.22 | 18% | 91% | | | | |
| 24 hours | 1.32 | 70% | 33% | 1 | | | |
| | 0.912 | 80% | 25% | 2 | 1.0 | 0.1 | 8.1 |
| | 0.0616 | 90% | 25% | 3 | 1.0 | 0.1 | 8.1 |
| | 2.42 | 60% | 71% | 4 | 2.1 | 0.4 | 11.1 |
| | 2.82 | 40% | 80% | | | | |
| | 3.22 | 20% | 91% | | | | |
| 48 hours | 2.51 | 71% | 72% | 1 | | | |
| | 0 | 100% | 0% | 2 | 0.0 | 0.0 | na |
| | 0 | 100% | 0% | 3 | 1.0 | 0.1 | 8.6 |
| | 2.42 | 71% | 71% | 4 | 1.6 | 0.3 | 9.8 |
| | 2.82 | 43% | 80% | | | | |
| | 3.22 | 14% | 91% | | | | |

Interleukin-3 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.030 | 0.049 | 0.030 | 0.050 | 0.030 | 0.048 |
| average | 0.032 | 0.064 | 0.032 | 0.061 | 0.032 | 0.042 |
| stdev | 0.026 | 0.052 | 0.026 | 0.050 | 0.026 | 0.024 |
| p (t-test) | | 0.000 | | 0.000 | | 0.203 |
| min | 0.001 | 0.006 | 0.001 | 0.006 | 0.001 | 0.006 |
| max | 0.128 | 0.227 | 0.128 | 0.227 | 0.128 | 0.077 |
| n (Samp) | 104 | 17 | 104 | 16 | 104 | 10 |
| n (Pat) | 104 | 17 | 104 | 16 | 104 | 10 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.035 | 0.066 | 0.035 | 0.066 | 0.035 | 0.061 |
| average | 0.037 | 0.069 | 0.037 | 0.062 | 0.037 | 0.058 |
| stdev | 0.033 | 0.037 | 0.033 | 0.022 | 0.033 | 0.020 |
| p (t-test) | | 0.011 | | 0.043 | | 0.169 |
| min | 0.001 | 0.027 | 0.001 | 0.027 | 0.001 | 0.027 |
| max | 0.227 | 0.147 | 0.227 | 0.091 | 0.227 | 0.077 |
| n (Samp) | 170 | 8 | 170 | 8 | 170 | 5 |
| n (Pat) | 170 | 8 | 170 | 8 | 170 | 5 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.029 | 0.049 | 0.029 | 0.049 | 0.029 | 0.047 |
| average | 0.031 | 0.061 | 0.031 | 0.063 | 0.031 | 0.039 |
| stdev | 0.025 | 0.058 | 0.025 | 0.061 | 0.025 | 0.025 |
| p (t-test) | | 0.002 | | 0.002 | | 0.424 |
| min | 0.001 | 0.006 | 0.001 | 0.006 | 0.001 | 0.006 |
| max | 0.128 | 0.227 | 0.128 | 0.227 | 0.128 | 0.077 |
| n (Samp) | 85 | 11 | 85 | 10 | 85 | 7 |
| n (Pat) | 85 | 11 | 85 | 10 | 85 | 7 |

Fig. 4 Continued sCr or UO

| Time prior AKI stage | AUC | SE | nCohort 1 | nCohort 2 | p |
|---|---|---|---|---|---|
| 0 hours | 0.75 | 0.071 | 104 | 17 | 0.000 |
| 24 hours | 0.75 | 0.073 | 104 | 16 | 0.001 |
| 48 hours | 0.66 | 0.098 | 104 | 10 | 0.108 | sCr only

| Time prior AKI stage | AUC | SE | nCohort 1 | nCohort 2 | p |
|---|---|---|---|---|---|
| 0 hours | 0.77 | 0.099 | 170 | 8 | 0.007 |
| 24 hours | 0.77 | 0.100 | 170 | 8 | 0.008 |
| 48 hours | 0.76 | 0.127 | 170 | 5 | 0.045 |

UO only

| Time prior AKI stage | AUC | SE | nCohort 1 | nCohort 2 | p |
|---|---|---|---|---|---|
| 0 hours | 0.72 | 0.091 | 85 | 11 | 0.013 |
| 24 hours | 0.73 | 0.095 | 85 | 10 | 0.017 |
| 48 hours | 0.62 | 0.117 | 85 | 7 | 0.303 | sCr or UO

| Time prior AKI stage | Cutoff value | sens | spec | Quartile | OR | 95% CI of OR | |
|---|---|---|---|---|---|---|---|
| 0 hours | 0.0466 | 71% | 75% | 1 | | | |
| | 0.0321 | 82% | 54% | 2 | 2.1 | 0.1 | 45.0 |
| | 0.014 | 94% | 34% | 3 | 4.5 | 0.3 | 59.6 |
| | 0.0455 | 76% | 71% | 4 | 13.8 | 1.4 | 140.1 |
| | 0.0495 | 47% | 81% | | | | |
| | 0.0626 | 29% | 90% | | | | |
| 24 hours | 0.0466 | 75% | 75% | 1 | | | |
| | 0.0321 | 81% | 54% | 2 | 2.1 | 0.1 | 45.0 |
| | 0.014 | 94% | 34% | 3 | 4.5 | 0.3 | 59.6 |
| | 0.0455 | 75% | 71% | 4 | 12.4 | 1.2 | 128.9 |
| | 0.0495 | 50% | 81% | | | | |
| | 0.0626 | 31% | 90% | | | | |
| 48 hours | 0.0315 | 70% | 52% | 1 | | | |
| | 0.0251 | 80% | 41% | 2 | 2.0 | 0.1 | 43.7 |
| | 0.00681 | 90% | 27% | 3 | 2.1 | 0.1 | 45.6 |
| | 0.0455 | 60% | 71% | 4 | 5.6 | 0.5 | 69.0 |
| | 0.0495 | 40% | 81% | | | | |
| | 0.0626 | 20% | 90% | | | | |

UO only

| Time prior AKI stage | Cutoff value | sens | spec | Quartile | OR | 95% CI of OR | |
|---|---|---|---|---|---|---|---|
| 0 hours | 0.0466 | 73% | 73% | 1 | | | |
| | 0.0463 | 82% | 71% | 2 | 1.0 | 0.0 | 59.8 |
| | 0.014 | 91% | 35% | 3 | 4.6 | 0.3 | 64.0 |
| | 0.0463 | 82% | 71% | 4 | 6.1 | 0.5 | 76.8 |
| | 0.0495 | 36% | 80% | | | | |
| | 0.0626 | 18% | 91% | | | | |
| 24 hours | 0.0466 | 80% | 73% | 1 | | | |
| | 0.0466 | 80% | 73% | 2 | 1.0 | 0.0 | 57.4 |
| | 0.014 | 90% | 35% | 3 | 3.1 | 0.2 | 51.5 |
| | 0.0463 | 80% | 71% | 4 | 5.8 | 0.5 | 73.7 |
| | 0.0495 | 40% | 80% | | | | |
| | 0.0626 | 20% | 91% | | | | |

Fig. 4 Continued

| 48 hours | | | | | | | |
|---|---|---|---|---|---|---|---|
| | 0.0315 | 71% | 56% | 1 | | | |
| | 0.00681 | 86% | 27% | 2 | 1.0 | 0.0 | 60.2 |
| | 0.00616 | 100% | 22% | 3 | 2.1 | 0.1 | 47.6 |
| | 0.0463 | 57% | 71% | 4 | 3.3 | 0.2 | 54.3 |
| | 0.0495 | 29% | 80% | | | | |
| | 0.0626 | 14% | 91% | | | | |

Myeloperoxidase sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1087.757 | 1814.853 | 1087.757 | 1814.853 | 1087.757 | 2374.882 |
| average | 1517.531 | 5244.497 | 1517.531 | 5211.500 | 1517.531 | 5368.282 |
| stdev | 1587.956 | 7706.197 | 1587.956 | 7725.839 | 1587.956 | 8287.124 |
| p (t-test) | | 0.000 | | 0.000 | | 0.000 |
| min | 0.000 | 755.054 | 0.000 | 755.054 | 0.000 | 863.219 |
| max | 9348.967 | 25446.740 | 9348.967 | 25446.740 | 9348.967 | 25446.740 |
| n (Samp) | 99 | 12 | 99 | 12 | 99 | 8 |
| n (Pat) | 99 | 12 | 99 | 12 | 99 | 8 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1302.118 | 1443.616 | 1302.118 | 1267.337 | 1302.118 | 1814.853 |
| average | 2495.233 | 1542.545 | 2495.233 | 1476.552 | 2495.233 | 1821.109 |
| stdev | 4695.709 | 766.518 | 4695.709 | 815.742 | 4695.709 | 795.914 |
| p (t-test) | | 0.621 | | 0.597 | | 0.775 |
| min | 0.000 | 755.054 | 0.000 | 755.054 | 0.000 | 863.219 |
| max | 40151.357 | 2791.511 | 40151.357 | 2791.511 | 40151.357 | 2791.511 |
| n (Samp) | 160 | 6 | 160 | 6 | 160 | 4 |
| n (Pat) | 160 | 6 | 160 | 6 | 160 | 4 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1092.221 | 3288.714 | 1092.221 | 3288.714 | 1092.221 | 3288.714 |
| average | 1770.249 | 7267.707 | 1770.249 | 7267.707 | 1770.249 | 6687.464 |
| stdev | 1947.791 | 8897.131 | 1947.791 | 8897.131 | 1947.791 | 9363.435 |
| p (t-test) | | 0.000 | | 0.000 | | 0.000 |
| min | 0.000 | 923.333 | 0.000 | 923.333 | 0.000 | 923.333 |
| max | 10821.990 | 25446.740 | 10821.990 | 25446.740 | 10821.990 | 25446.740 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
|---|---|---|---|---|---|
| 0 hours | 0.71 | 0.088 | 99 | 12 | 0.017 |
| 24 hours | 0.69 | 0.089 | 99 | 12 | 0.037 |
| 48 hours | 0.74 | 0.104 | 99 | 8 | 0.021 | sCr only

| Time prior AKI stage | AUC | SE | nCohort 1 | nCohort 2 | p |
|---|---|---|---|---|---|
| 0 hours | 0.50 | 0.120 | 160 | 6 | 0.979 |
| 24 hours | 0.45 | 0.116 | 160 | 6 | 0.694 |
| 48 hours | 0.58 | 0.151 | 160 | 4 | 0.592 |

Fig. 4 Continued

UO only

| Time prior AKI stage | AUC | SE | nCohort 1 | nCohort 2 | p |
|---|---|---|---|---|---|
| 0 hours | 0.79 | 0.099 | 84 | 8 | 0.004 |
| 24 hours | 0.79 | 0.099 | 84 | 8 | 0.004 |
| 48 hours | 0.77 | 0.116 | 84 | 6 | 0.020 | sCr only

| Time prior AKI stage | Cutoff value | sens | spec | Quartile | OR | 95% CI of OR | |
|---|---|---|---|---|---|---|---|
| 0 hours | 841.799 | 83% | 23% | 1 | | | |
| | 841.799 | 83% | 23% | 2 | 2.1 | 0.1 | 43.9 |
| | 744.986 | 100% | 19% | 3 | 1.0 | 0.0 | 55.5 |
| | 1902.02 | 33% | 70% | 4 | 2.1 | 0.1 | 43.9 |
| | 2875.83 | 0% | 81% | | | | |
| | 3866.7 | 0% | 90% | | | | |
| 24 hours | 803.653 | 83% | 21% | 1 | | | |
| | 803.653 | 83% | 21% | 2 | 2.1 | 0.1 | 43.9 |
| | 744.986 | 100% | 19% | 3 | 0.0 | 0.0 | na |
| | 1902.02 | 33% | 70% | 4 | 3.2 | 0.2 | 48.8 |
| | 2875.83 | 0% | 81% | | | | |
| | 3866.7 | 0% | 90% | | | | |
| 48 hours | 1540.62 | 75% | 61% | 1 | | | |
| | 841.799 | 100% | 23% | 2 | 0.0 | 0.0 | na |
| | 841.799 | 100% | 23% | 3 | 2.1 | 0.1 | 42.9 |
| | 1902.02 | 50% | 70% | 4 | 1.0 | 0.0 | 55.6 |
| | 2875.83 | 0% | 81% | | | | |
| | 3866.7 | 0% | 90% | | | | |

Oxidized low-density lipoprotein receptor 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 20.886 | 31.078 | 20.886 | 27.608 | 20.886 | 32.654 |
| average | 29.165 | 39.600 | 29.165 | 38.691 | 29.165 | 38.812 |
| stdev | 27.369 | 32.577 | 27.369 | 33.016 | 27.369 | 37.031 |
| p (t-test) | | 0.224 | | 0.268 | | 0.353 |
| min | 0.150 | 4.511 | 0.150 | 4.511 | 0.150 | 4.511 |
| max | 148.195 | 121.257 | 148.195 | 121.257 | 148.195 | 121.257 |
| n (Samp) | 99 | 12 | 99 | 12 | 99 | 8 |
| n (Pat) | 99 | 12 | 99 | 12 | 99 | 8 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 27.978 | 37.780 | 27.978 | 37.780 | 27.978 | 61.731 |
| average | 39.150 | 51.898 | 39.150 | 50.079 | 39.150 | 62.307 |
| stdev | 35.731 | 41.918 | 35.731 | 43.270 | 35.731 | 49.944 |
| p (t-test) | | 0.395 | | 0.466 | | 0.206 |
| min | 0.150 | 4.511 | 0.150 | 4.511 | 0.150 | 4.511 |
| max | 214.368 | 121.257 | 214.368 | 121.257 | 214.368 | 121.257 |
| n (Samp) | 160 | 6 | 160 | 6 | 160 | 4 |
| n (Pat) | 160 | 6 | 160 | 6 | 160 | 4 |

Fig. 4 Continued

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 20.720 | 32.654 | 20.720 | 32.654 | 20.720 | 32.654 |
| average | 27.595 | 35.910 | 27.595 | 35.910 | 27.595 | 30.788 |
| stdev | 25.320 | 22.419 | 25.320 | 22.419 | 25.320 | 15.744 |
| p (t-test) | | 0.373 | | 0.373 | | 0.762 |
| min | 0.150 | 6.860 | 0.150 | 6.860 | 0.150 | 6.860 |
| max | 134.298 | 79.995 | 134.298 | 79.995 | 134.298 | 46.568 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
|---|---|---|---|---|---|
| 0 hours | 0.63 | 0.091 | 99 | 12 | 0.167 |
| 24 hours | 0.60 | 0.091 | 99 | 12 | 0.257 |
| 48 hours | 0.58 | 0.110 | 99 | 8 | 0.451 | sCr only

| Time prior AKI stage | AUC | SE | nCohort 1 | nCohort 2 | p |
|---|---|---|---|---|---|
| 0 hours | 0.61 | 0.125 | 160 | 6 | 0.369 |
| 24 hours | 0.57 | 0.124 | 160 | 6 | 0.557 |
| 48 hours | 0.64 | 0.152 | 160 | 4 | 0.343 |

UO only

| Time prior AKI stage | AUC | SE | nCohort 1 | nCohort 2 | p |
|---|---|---|---|---|---|
| 0 hours | 0.65 | 0.110 | 84 | 8 | 0.170 |
| 24 hours | 0.65 | 0.110 | 84 | 8 | 0.170 | sCr or UO

| Time prior AKI stage | Cutoff value | sens | spec | Quartile | OR | 95% CI of OR | |
|---|---|---|---|---|---|---|---|
| 0 hours | 22.5228 | 75% | 52% | 1 | | | |
| | 22.1625 | 83% | 52% | 2 | 1.0 | 0.1 | 8.0 |
| | 6.43176 | 92% | 13% | 3 | 1.5 | 0.3 | 9.0 |
| | 32.0928 | 42% | 71% | 4 | 2.7 | 0.6 | 12.6 |
| | 42.9453 | 33% | 81% | | | | |
| | 64.4382 | 17% | 91% | | | | |
| 24 hours | 22.1625 | 75% | 52% | 1 | | | |
| | 18.3377 | 83% | 41% | 2 | 1.0 | 0.1 | 8.0 |
| | 6.43176 | 92% | 13% | 3 | 1.5 | 0.3 | 9.0 |
| | 32.0928 | 42% | 71% | 4 | 2.7 | 0.6 | 12.6 |
| | 42.9453 | 33% | 81% | | | | |
| | 64.4382 | 17% | 91% | | | | |
| 48 hours | 22.1625 | 75% | 52% | 1 | | | |
| | 6.43176 | 88% | 13% | 2 | 0.0 | 0.0 | na |
| | 3.32291 | 100% | 7% | 3 | 1.0 | 0.1 | 8.0 |
| | 32.0928 | 50% | 71% | 4 | 2.1 | 0.4 | 10.7 |
| | 42.9453 | 38% | 81% | | | | |
| | 64.4382 | 13% | 91% | | | | |

Fig. 4 Continued sCr only

| Time prior AKI stage | Cutoff value | sens | spec | Quartile | OR | 95% CI of OR | |
|---|---|---|---|---|---|---|---|
| 0 hours | 29.9079 | 83% | 54% | 1 | | | |
| | 29.9079 | 83% | 54% | 2 | 0.0 | 0.0 | na |
| | 4.23945 | 100% | 5% | 3 | 3.2 | 0.2 | 47.6 |
| | 45.0352 | 33% | 70% | 4 | 2.0 | 0.1 | 41.7 |
| | 60.4304 | 33% | 80% | | | | |
| | 84.6671 | 17% | 90% | | | | |
| 24 hours | 18.3377 | 83% | 31% | 1 | | | |
| | 18.3377 | 83% | 31% | 2 | 1.0 | 0.0 | 54.2 |
| | 4.23945 | 100% | 5% | 3 | 2.1 | 0.1 | 42.9 |
| | 45.0352 | 33% | 70% | 4 | 2.0 | 0.1 | 41.7 |
| | 60.4304 | 33% | 80% | | | | |
| | 84.6671 | 17% | 90% | | | | |
| 48 hours | 42.9453 | 75% | 68% | 1 | | | |
| | 4.23945 | 100% | 5% | 2 | 0.0 | 0.0 | na |
| | 4.23945 | 100% | 5% | 3 | 1.0 | 0.0 | 55.6 |
| | 45.0352 | 50% | 70% | 4 | 2.1 | 0.1 | 42.9 |
| | 60.4304 | 50% | 80% | | | | |
| | 84.6671 | 25% | 90% | | | | |

UO only

| Time prior AKI stage | Cutoff value | sens | spec | Quartile | OR | 95% CI of OR | |
|---|---|---|---|---|---|---|---|
| 0 hours | 22.5228 | 75% | 52% | 1 | | | |
| | 22.1625 | 88% | 52% | 2 | 1.0 | 0.0 | 60.2 |
| | 6.43176 | 100% | 12% | 3 | 2.1 | 0.1 | 47.6 |
| | 29.8385 | 50% | 70% | 4 | 4.6 | 0.3 | 65.0 |
| | 38.7783 | 50% | 81% | | | | |
| | 61.2343 | 13% | 90% | | | | |
| 24 hours | 22.5228 | 75% | 52% | 1 | | | |
| | 22.1625 | 88% | 52% | 2 | 1.0 | 0.0 | 60.2 |
| | 6.43176 | 100% | 12% | 3 | 2.1 | 0.1 | 47.6 |
| | 29.8385 | 50% | 70% | 4 | 4.6 | 0.3 | 65.0 |
| | 38.7783 | 50% | 81% | | | | |
| | 61.2343 | 13% | 90% | | | | |
| 48 hours | 22.1625 | 83% | 52% | 1 | | | |
| | 22.1625 | 83% | 52% | 2 | 0.0 | 0.0 | na |
| | 6.43176 | 100% | 12% | 3 | 2.1 | 0.1 | 48.1 |
| | 29.8385 | 50% | 70% | 4 | 3.2 | 0.2 | 52.0 |
| | 38.7783 | 50% | 81% | | | | |
| | 61.2343 | 0% | 90% | | | | |

Pappalysin-1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.032 | 0.061 | 0.032 | 0.054 | 0.032 | 0.040 |
| average | 0.043 | 0.462 | 0.043 | 0.479 | 0.043 | 0.045 |
| stdev | 0.035 | 1.626 | 0.035 | 1.678 | 0.035 | 0.020 |
| p (t-test) | | 0.008 | | 0.008 | | 0.863 |
| min | 0.003 | 0.017 | 0.003 | 0.017 | 0.003 | 0.011 |
| max | 0.193 | 6.770 | 0.193 | 6.770 | 0.193 | 0.080 |
| n (Samp) | 104 | 17 | 104 | 16 | 104 | 10 |
| n (Pat) | 104 | 17 | 104 | 16 | 104 | 10 |

Fig. 4 Continued sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.040 | 0.058 | 0.040 | 0.056 | 0.040 | 0.046 |
| average | 0.088 | 0.067 | 0.088 | 0.066 | 0.088 | 0.044 |
| stdev | 0.517 | 0.036 | 0.517 | 0.036 | 0.517 | 0.020 |
| p (t-test) | | 0.908 | | 0.906 | | 0.849 |
| min | 0.003 | 0.017 | 0.003 | 0.017 | 0.003 | 0.011 |
| max | 6.770 | 0.124 | 6.770 | 0.124 | 6.770 | 0.061 |
| n (Samp) | 170 | 8 | 170 | 8 | 170 | 5 |
| n (Pat) | 170 | 8 | 170 | 8 | 170 | 5 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.030 | 0.065 | 0.030 | 0.059 | 0.030 | 0.037 |
| average | 0.039 | 0.676 | 0.039 | 0.727 | 0.039 | 0.050 |
| stdev | 0.029 | 2.021 | 0.029 | 2.124 | 0.029 | 0.019 |
| p (t-test) | | 0.003 | | 0.002 | | 0.341 |
| min | 0.003 | 0.035 | 0.003 | 0.031 | 0.003 | 0.031 |
| max | 0.142 | 6.770 | 0.142 | 6.770 | 0.142 | 0.080 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
|---|---|---|---|---|---|
| 0 hours | 0.75 | 0.072 | 104 | 17 | 0.000 |
| 24 hours | 0.71 | 0.076 | 104 | 16 | 0.006 |
| 48 hours | 0.59 | 0.099 | 104 | 10 | 0.347 | sCr only

| Time prior AKI stage | AUC | SE | nCohort 1 | nCohort 2 | p |
|---|---|---|---|---|---|
| 0 hours | 0.68 | 0.107 | 170 | 8 | 0.086 |
| 24 hours | 0.68 | 0.107 | 170 | 8 | 0.099 |
| 48 hours | 0.54 | 0.134 | 170 | 5 | 0.792 |

UO only

| Time prior AKI stage | AUC | SE | nCohort 1 | nCohort 2 | p |
|---|---|---|---|---|---|
| 0 hours | 0.80 | 0.083 | 85 | 11 | 0.000 |
| 24 hours | 0.74 | 0.093 | 85 | 10 | 0.009 |
| 48 hours | 0.67 | 0.116 | 85 | 7 | 0.133 | sCr or UO

| Time prior AKI stage | Cutoff value | sens | spec | Quartile | OR | 95% CI of OR | |
|---|---|---|---|---|---|---|---|
| 0 hours | 0.0506 | 71% | 70% | 1 | | | |
| | 0.0433 | 82% | 62% | 2 | 2.1 | 0.1 | 45.0 |
| | 0.0334 | 94% | 52% | 3 | 7.3 | 0.6 | 82.8 |
| | 0.0506 | 71% | 70% | 4 | 10.1 | 1.0 | 106.6 |
| | 0.0686 | 35% | 81% | | | | |
| | 0.0822 | 29% | 90% | | | | |
| 24 hours | 0.0354 | 75% | 52% | 1 | | | |
| | 0.0353 | 81% | 52% | 2 | 4.5 | 0.3 | 59.6 |
| | 0.031 | 94% | 50% | 3 | 5.8 | 0.5 | 70.5 |
| | 0.0506 | 63% | 70% | 4 | 7.3 | 0.6 | 82.8 |
| | 0.0686 | 31% | 81% | | | | |
| | 0.0822 | 25% | 90% | | | | |

Fig. 4 Continued

| | | | | | | | |
|---|---|---|---|---|---|---|---|
| 48 hours | 0.0353 | 70% | 52% | 1 | | | |
| | 0.0334 | 80% | 52% | 2 | 2.0 | 0.1 | 43.7 |
| | 0.031 | 90% | 50% | 3 | 4.5 | 0.3 | 60.8 |
| | 0.0506 | 30% | 70% | 4 | 3.1 | 0.2 | 49.3 |
| | 0.0686 | 10% | 81% | | | | |
| | 0.0822 | 0% | 90% | | | | | sCr only

| Time prior AKI stage | Cutoff value | sens | spec | Quartile | OR | 95% CI of OR | |
|---|---|---|---|---|---|---|---|
| 0 hours | 0.0506 | 75% | 64% | 1 | | | |
| | 0.0441 | 88% | 57% | 2 | 0.0 | 0.0 | na |
| | 0.0164 | 100% | 21% | 3 | 4.3 | 0.3 | 54.8 |
| | 0.0564 | 50% | 70% | 4 | 3.1 | 0.2 | 46.0 |
| | 0.0695 | 25% | 80% | | | | |
| | 0.104 | 25% | 91% | | | | |
| 24 hours | 0.0506 | 75% | 64% | 1 | | | |
| | 0.0441 | 88% | 57% | 2 | 0.0 | 0.0 | na |
| | 0.0164 | 100% | 21% | 3 | 4.3 | 0.3 | 54.8 |
| | 0.0564 | 50% | 70% | 4 | 3.1 | 0.2 | 46.0 |
| | 0.0695 | 25% | 80% | | | | |
| | 0.104 | 25% | 91% | | | | |
| 48 hours | 0.0441 | 80% | 57% | 1 | | | |
| | 0.0441 | 80% | 57% | 2 | 0.0 | 0.0 | na |
| | 0.0101 | 100% | 9% | 3 | 4.2 | 0.3 | 53.6 |
| | 0.0564 | 40% | 70% | 4 | 0.0 | 0.0 | na |
| | 0.0695 | 0% | 80% | | | | |
| | 0.104 | 0% | 91% | | | | |

P-selectin glycoprotein ligand 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 2.554 | 1.185 | 2.554 | 1.185 | 2.554 | 1.447 |
| average | 5.234 | 2.324 | 5.234 | 2.218 | 5.234 | 2.115 |
| stdev | 8.867 | 2.495 | 8.867 | 2.581 | 8.867 | 2.063 |
| p (t-test) | | 0.226 | | 0.210 | | 0.271 |
| min | 0.001 | 0.018 | 0.001 | 0.016 | 0.001 | 0.018 |
| max | 67.069 | 7.263 | 67.069 | 7.263 | 67.069 | 6.962 |
| n (Samp) | 104 | 14 | 104 | 14 | 104 | 10 |
| n (Pat) | 104 | 14 | 104 | 14 | 104 | 10 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 2.552 | 0.923 | 2.552 | 0.418 | 2.552 | 1.713 |
| average | 5.117 | 1.828 | 5.117 | 1.639 | 5.117 | 2.254 |
| stdev | 8.342 | 2.378 | 8.342 | 2.499 | 8.342 | 2.776 |
| p (t-test) | | 0.300 | | 0.274 | | 0.446 |
| min | 0.001 | 0.188 | 0.001 | 0.016 | 0.001 | 0.018 |
| max | 67.069 | 6.962 | 67.069 | 6.962 | 67.069 | 6.962 |
| n (Samp) | 168 | 7 | 168 | 7 | 168 | 5 |
| n (Pat) | 168 | 7 | 168 | 7 | 168 | 5 |

Fig. 4 Continued

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 2.662 | 1.189 | 2.662 | 1.189 | 2.662 | 1.181 |
| average | 5.711 | 2.988 | 5.711 | 2.969 | 5.711 | 2.408 |
| stdev | 9.664 | 2.902 | 9.664 | 2.923 | 9.664 | 2.403 |
| p (t-test) | | 0.404 | | 0.401 | | 0.372 |
| min | 0.001 | 0.018 | 0.001 | 0.018 | 0.001 | 0.018 |
| max | 67.069 | 7.263 | 67.069 | 7.263 | 67.069 | 6.962 |
| n (Samp) | 85 | 9 | 85 | 9 | 85 | 7 |
| n (Pat) | 85 | 9 | 85 | 9 | 85 | 7 | sCr or UO

| Time prior AKI stage | AUC | SE | nCohort 1 | nCohort 2 | p |
|---|---|---|---|---|---|
| 0 hours | 0.40 | 0.076 | 104 | 14 | 0.169 |
| 24 hours | 0.37 | 0.073 | 104 | 14 | 0.067 |
| 48 hours | 0.40 | 0.088 | 104 | 10 | 0.247 | sCr only

| Time prior AKI stage | AUC | SE | nCohort 1 | nCohort 2 | p |
|---|---|---|---|---|---|
| 0 hours | 0.33 | 0.093 | 168 | 7 | 0.073 |
| 24 hours | 0.28 | 0.083 | 168 | 7 | 0.009 |
| 48 hours | 0.37 | 0.115 | 168 | 5 | 0.265 |

UO only

| Time prior AKI stage | AUC | SE | nCohort 1 | nCohort 2 | p |
|---|---|---|---|---|---|
| 0 hours | 0.43 | 0.097 | 85 | 9 | 0.474 |
| 24 hours | 0.43 | 0.096 | 85 | 9 | 0.443 |
| 48 hours | 0.40 | 0.105 | 85 | 7 | 0.354 | sCr or UO

| Time prior AKI stage | Cutoff value | sens | spec | Quartile | OR | 95% CI of OR | |
|---|---|---|---|---|---|---|---|
| 0 hours | 0.91712 | 71% | 28% | 1 | | | |
| | 0.40965 | 86% | 17% | 2 | 1.0 | 0.1 | 8.5 |
| | 0.01822 | 93% | 12% | 3 | 3.5 | 0.8 | 15.0 |
| | 4.87351 | 21% | 70% | 4 | 2.2 | 0.4 | 11.3 |
| | 7.69299 | 0% | 81% | | | | |
| | 12.0757 | 0% | 90% | | | | |
| 24 hours | 0.40965 | 71% | 17% | 1 | | | |
| | 0.01619 | 93% | 2% | 2 | 1.0 | 0.1 | 8.5 |
| | 0.01619 | 93% | 2% | 3 | 2.8 | 0.6 | 12.8 |
| | 4.87351 | 21% | 70% | 4 | 2.9 | 0.6 | 13.4 |
| | 7.69299 | 0% | 81% | | | | |
| | 12.0757 | 0% | 90% | | | | |
| 48 hours | 0.91712 | 70% | 28% | 1 | | | |
| | 0.83513 | 80% | 26% | 2 | 2.2 | 0.1 | 47.1 |
| | 0.40965 | 90% | 17% | 3 | 5.8 | 0.5 | 71.3 |
| | 4.87351 | 10% | 70% | 4 | 2.2 | 0.1 | 47.1 |
| | 7.69299 | 0% | 81% | | | | |
| | 12.0757 | 0% | 90% | | | | | sCr only

| Time prior AKI stage | Cutoff value | sens | spec | Quartile | OR | 95% CI of OR | |
|---|---|---|---|---|---|---|---|
| 0 hours | 0.41788 | 71% | 16% | 1 | | | |
| | 0.40965 | 86% | 16% | 2 | 0.0 | 0.0 | na |
| | 0.11161 | 100% | 11% | 3 | 3.1 | 0.2 | 47.1 |
| | 4.41089 | 14% | 70% | 4 | 3.2 | 0.2 | 48.4 |

Fig. 4 Continued

|  | 7.47389 | 0% | 80% |  |  |  |  |
|---|---|---|---|---|---|---|---|
|  | 12.7911 | 0% | 90% |  |  |  |  |
| 24 hours | 0.11161 | 71% | 11% | 1 |  |  |  |
|  | 0.01619 | 86% | 1% | 2 | 0.0 | 0.0 | na |
|  | 0.00132 | 100% | 1% | 3 | 2.0 | 0.1 | 42.5 |
|  | 4.41089 | 14% | 70% | 4 | 4.4 | 0.3 | 56.2 |
|  | 7.47389 | 0% | 80% |  |  |  |  |
|  | 12.7911 | 0% | 90% |  |  |  |  |
| 48 hours | 0.40965 | 80% | 16% | 1 |  |  |  |
|  | 0.40965 | 80% | 16% | 2 | 0.0 | 0.0 | na |
|  | 0.00132 | 100% | 1% | 3 | 2.1 | 0.1 | 43.6 |
|  | 4.41089 | 20% | 70% | 4 | 2.1 | 0.1 | 43.6 |
|  | 7.47389 | 0% | 80% |  |  |  |  |
|  | 12.7911 | 0% | 90% |  |  |  |  |

UO only

| Time prior AKI stage | Cutoff value | sens | spec | Quartile | OR | 95% CI of OR | |
|---|---|---|---|---|---|---|---|
| 0 hours | 0.95625 | 78% | 27% | 1 |  |  |  |
|  | 0.01822 | 89% | 11% | 2 | 3.5 | 0.2 | 56.5 |
|  | 0.00132 | 100% | 2% | 3 | 3.3 | 0.2 | 53.6 |
|  | 5.09673 | 33% | 71% | 4 | 2.2 | 0.1 | 49.5 |
|  | 8.19191 | 0% | 80% |  |  |  |  |
|  | 14.8279 | 0% | 91% |  |  |  |  |
| 24 hours | 0.95625 | 78% | 27% | 1 |  |  |  |
|  | 0.00132 | 100% | 2% | 2 | 3.5 | 0.2 | 56.5 |
|  | 0.00132 | 100% | 2% | 3 | 3.3 | 0.2 | 53.6 |
|  | 5.09673 | 33% | 71% | 4 | 2.2 | 0.1 | 49.5 |
|  | 8.19191 | 0% | 80% |  |  |  |  |
|  | 14.8279 | 0% | 91% |  |  |  |  |
| 48 hours | 0.95625 | 71% | 27% | 1 |  |  |  |
|  | 0.83513 | 86% | 25% | 2 | na | na | na |
|  | 0.00132 | 100% | 2% | 3 | na | na | na |
|  | 5.09673 | 14% | 71% | 4 | na | na | na |
|  | 8.19191 | 0% | 80% |  |  |  |  |
|  | 14.8279 | 0% | 91% |  |  |  |  |

Secretory leukocyte peptidase inhibitor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 14123.539 | 20780.608 | 14123.539 | 21867.766 | 14123.539 | 19419.847 |
| average | 15206.496 | 19724.468 | 15206.496 | 20706.543 | 15206.496 | 16739.251 |
| stdev | 9544.648 | 9761.736 | 9544.648 | 9349.930 | 9544.648 | 9726.830 |
| p (t-test) |  | 0.137 |  | 0.078 |  | 0.694 |
| min | 579.609 | 903.384 | 579.609 | 903.384 | 579.609 | 903.384 |
| max | 33763.353 | 32087.099 | 33763.353 | 32087.099 | 33763.353 | 30129.151 |
| n (Samp) | 48 | 13 | 48 | 12 | 48 | 7 |
| n (Pat) | 48 | 13 | 48 | 12 | 48 | 7 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 15442.804 | 22954.925 | 15442.804 | 24420.267 | 15442.804 | 19419.847 |
| average | 15819.141 | 20568.402 | 15819.141 | 22903.639 | 15819.141 | 15815.494 |
| stdev | 9590.646 | 10310.804 | 9590.646 | 9042.524 | 9590.646 | 7659.241 |
| p (t-test) |  | 0.212 |  | 0.082 |  | 0.999 |
| min | 579.609 | 6556.982 | 579.609 | 7019.002 | 579.609 | 7019.002 |

Fig. 4 Continued

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| max | 33763.353 | 32087.099 | 33763.353 | 32087.099 | 33763.353 | 21007.634 |
| n (Samp) | 90 | 7 | 90 | 6 | 90 | 3 |
| n (Pat) | 90 | 7 | 90 | 6 | 90 | 3 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 14407.346 | 19297.710 | 14407.346 | 17915.129 | 14407.346 | 17915.129 |
| average | 15386.285 | 17065.467 | 15386.285 | 16867.955 | 15386.285 | 15349.455 |
| stdev | 9150.675 | 10104.233 | 9150.675 | 10066.770 | 9150.675 | 11539.117 |
| p (t-test) | | 0.663 | | 0.701 | | 0.993 |
| min | 1017.287 | 903.384 | 1017.287 | 903.384 | 1017.287 | 903.384 |
| max | 30367.279 | 30129.151 | 30367.279 | 30129.151 | 30367.279 | 30129.151 |
| n (Samp) | 37 | 7 | 37 | 7 | 37 | 5 |
| n (Pat) | 37 | 7 | 37 | 7 | 37 | 5 | sCr or UO

| Time prior AKI stage | AUC | SE | nCohort 1 | nCohort 2 | p |
|---|---|---|---|---|---|
| 0 hours | 0.63 | 0.091 | 48 | 13 | 0.156 |
| 24 hours | 0.66 | 0.094 | 48 | 12 | 0.088 |
| 48 hours | 0.55 | 0.120 | 48 | 7 | 0.691 | sCr only

| Time prior AKI stage | AUC | SE | nCohort 1 | nCohort 2 | p |
|---|---|---|---|---|---|
| 0 hours | 0.65 | 0.117 | 90 | 7 | 0.211 |
| 24 hours | 0.71 | 0.122 | 90 | 6 | 0.077 |
| 48 hours | 0.51 | 0.171 | 90 | 3 | 0.965 |

UO only

| Time prior AKI stage | AUC | SE | nCohort 1 | nCohort 2 | p |
|---|---|---|---|---|---|
| 0 hours | 0.55 | 0.122 | 37 | 7 | 0.670 |
| 24 hours | 0.54 | 0.122 | 37 | 7 | 0.716 |
| 48 hours | 0.50 | 0.139 | 37 | 5 | 0.985 | sCr or UO

| Time prior AKI stage | Cutoff value | sens | spec | Quartile | OR | 95% CI of OR | |
|---|---|---|---|---|---|---|---|
| 0 hours | 15976.6 | 77% | 60% | 1 | | | |
| | 6556.98 | 85% | 25% | 2 | 0.0 | 0.0 | na |
| | 6452.65 | 92% | 25% | 3 | 2.7 | 0.7 | 10.4 |
| | 23088.5 | 38% | 71% | 4 | 1.3 | 0.3 | 5.8 |
| | 25848.7 | 31% | 81% | | | | |
| | 28173.4 | 23% | 92% | | | | |
| 24 hours | 16611 | 75% | 63% | 1 | | | |
| | 15976.6 | 83% | 60% | 2 | 0.0 | 0.0 | na |
| | 6452.65 | 92% | 25% | 3 | 4.3 | 0.8 | 23.1 |
| | 23088.5 | 42% | 71% | 4 | 2.4 | 0.4 | 14.3 |
| | 25848.7 | 33% | 81% | | | | |
| | 28173.4 | 25% | 92% | | | | |
| 48 hours | 16611 | 71% | 63% | 1 | | | |
| | 6452.65 | 86% | 25% | 2 | 0.9 | 0.0 | 63.7 |
| | 579.609 | 100% | 2% | 3 | 4.8 | 0.3 | 79.7 |
| | 23088.5 | 14% | 71% | 4 | 0.9 | 0.0 | 63.7 |
| | 25848.7 | 14% | 81% | | | | |
| | 28173.4 | 14% | 92% | | | | |

Fig. 4 Continued sCr only

| Time prior AKI stage | Cutoff value | sens | spec | Quartile | OR | 95% CI of OR | |
|---|---|---|---|---|---|---|---|
| 0 hours | 19297.7 | 71% | 62% | 1 | | | |
| | 6829.86 | 86% | 26% | 2 | 1.0 | 0.0 | 59.8 |
| | 6452.65 | 100% | 23% | 3 | 2.1 | 0.1 | 47.1 |
| | 23389 | 43% | 70% | 4 | 3.1 | 0.2 | 50.9 |
| | 25848.7 | 43% | 80% | | | | |
| | 28731.2 | 29% | 90% | | | | |
| 24 hours | 19297.7 | 83% | 62% | 1 | | | |
| | 19297.7 | 83% | 62% | 2 | 0.0 | 0.0 | na |
| | 6829.86 | 100% | 26% | 3 | 2.1 | 0.1 | 47.1 |
| | 23389 | 50% | 70% | 4 | 3.3 | 0.2 | 53.6 |
| | 25848.7 | 50% | 80% | | | | |
| | 28731.2 | 33% | 90% | | | | |
| 48 hours | 6829.86 | 100% | 26% | 1 | | | |
| | 6829.86 | 100% | 26% | 2 | na | na | na |
| | 6829.86 | 100% | 26% | 3 | na | na | na |
| | 23389 | 0% | 70% | 4 | na | na | na |
| | 25848.7 | 0% | 80% | | | | |
| | 28731.2 | 0% | 90% | | | | |

UO only

| Time prior AKI stage | Cutoff value | sens | spec | Quartile | OR | 95% CI of OR | |
|---|---|---|---|---|---|---|---|
| 0 hours | 15442.8 | 71% | 57% | 1 | | | |
| | 6452.65 | 86% | 27% | 2 | 1.0 | 0.0 | 74.6 |
| | 0 | 100% | 0% | 3 | 5.7 | 0.3 | 106.6 |
| | 21619.4 | 29% | 70% | 4 | 1.0 | 0.0 | 74.6 |
| | 25492.5 | 14% | 81% | | | | |
| | 28173.4 | 14% | 92% | | | | |
| 24 hours | 15442.8 | 71% | 57% | 1 | | | |
| | 6452.65 | 86% | 27% | 2 | 1.0 | 0.0 | 74.6 |
| | 0 | 100% | 0% | 3 | 5.7 | 0.3 | 106.6 |
| | 21619.4 | 29% | 70% | 4 | 1.0 | 0.0 | 74.6 |
| | 25492.5 | 14% | 81% | | | | |
| | 28173.4 | 14% | 92% | | | | |
| 48 hours | 6452.65 | 80% | 27% | 1 | | | |
| | 6452.65 | 80% | 27% | 2 | 0.9 | 0.0 | 68.6 |
| | 0 | 100% | 0% | 3 | 2.3 | 0.1 | 67.6 |
| | 21619.4 | 20% | 70% | 4 | 0.9 | 0.0 | 68.6 |
| | 25492.5 | 20% | 81% | | | | |
| | 28173.4 | 20% | 92% | | | | |

Fig. 4 Continued

Stem cell factor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 216.500 | 364.000 | 216.500 | 498.500 | 216.500 | 439.000 |
| average | 400.384 | 808.100 | 400.384 | 773.169 | 400.384 | 807.070 |
| stdev | 473.635 | 867.618 | 473.635 | 726.913 | 473.635 | 817.894 |
| p (t-test) |  | 0.005 |  | 0.008 |  | 0.018 |
| min | 9.140 | 51.400 | 9.140 | 51.400 | 9.140 | 51.400 |
| max | 2900.000 | 3000.000 | 2900.000 | 2190.000 | 2900.000 | 2190.000 |
| n (Samp) | 104 | 17 | 104 | 16 | 104 | 10 |
| n (Pat) | 104 | 17 | 104 | 16 | 104 | 10 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 271.500 | 671.500 | 271.500 | 671.500 | 271.500 | 633.000 |
| average | 435.504 | 907.625 | 435.504 | 907.625 | 435.504 | 893.400 |
| stdev | 479.531 | 764.629 | 479.531 | 764.629 | 479.531 | 879.922 |
| p (t-test) |  | 0.009 |  | 0.009 |  | 0.042 |
| min | 9.140 | 118.000 | 9.140 | 118.000 | 9.140 | 118.000 |
| max | 2900.000 | 2190.000 | 2900.000 | 2190.000 | 2900.000 | 2190.000 |
| n (Samp) | 170 | 8 | 170 | 8 | 170 | 5 |
| n (Pat) | 170 | 8 | 170 | 8 | 170 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 235.000 | 173.000 | 235.000 | 209.000 | 235.000 | 245.000 |
| average | 402.698 | 727.518 | 402.698 | 663.570 | 402.698 | 732.814 |
| stdev | 431.931 | 922.919 | 431.931 | 689.743 | 431.931 | 770.751 |
| p (t-test) |  | 0.049 |  | 0.095 |  | 0.073 |
| min | 9.140 | 51.400 | 9.140 | 51.400 | 9.140 | 51.400 |
| max | 1890.000 | 3000.000 | 1890.000 | 1850.000 | 1890.000 | 1850.000 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
|---|---|---|---|---|---|
| 0 hours | 0.62 | 0.077 | 104 | 17 | 0.111 |
| 24 hours | 0.64 | 0.079 | 104 | 16 | 0.080 |
| 48 hours | 0.60 | 0.099 | 104 | 10 | 0.323 | sCr only

| Time prior AKI stage | AUC | SE | nCohort 1 | nCohort 2 | p |
|---|---|---|---|---|---|
| 0 hours | 0.71 | 0.105 | 170 | 8 | 0.045 |
| 24 hours | 0.71 | 0.105 | 170 | 8 | 0.045 |
| 48 hours | 0.65 | 0.135 | 170 | 5 | 0.264 |

UO only

| Time prior AKI stage | AUC | SE | nCohort 1 | nCohort 2 | p |
|---|---|---|---|---|---|
| 0 hours | 0.54 | 0.094 | 85 | 11 | 0.671 |
| 24 hours | 0.56 | 0.099 | 85 | 10 | 0.561 |
| 48 hours | 0.55 | 0.117 | 85 | 7 | 0.671 |

Fig. 4 Continued sCr or UO

| Time prior AKI stage | Cutoff value | sens | spec | Quartile | OR | 95% CI of OR | |
|---|---|---|---|---|---|---|---|
| 0 hours | 165 | 71% | 37% | 1 | | | |
| | 116 | 82% | 25% | 2 | 0.7 | 0.2 | 2.6 |
| | 92.5 | 94% | 19% | 3 | 0.5 | 0.1 | 2.3 |
| | 372 | 47% | 70% | 4 | 2.3 | 0.9 | 5.5 |
| | 630 | 47% | 81% | | | | |
| | 829 | 35% | 90% | | | | |
| 24 hours | 165 | 75% | 37% | 1 | | | |
| | 150 | 81% | 36% | 2 | 1.0 | 0.2 | 4.3 |
| | 92.5 | 94% | 19% | 3 | 0.6 | 0.1 | 3.8 |
| | 372 | 50% | 70% | 4 | 3.3 | 1.1 | 9.4 |
| | 630 | 50% | 81% | | | | |
| | 829 | 38% | 90% | | | | |
| 48 hours | 150 | 70% | 36% | 1 | | | |
| | 116 | 80% | 25% | 2 | 1.0 | 0.1 | 7.9 |
| | 61.5 | 90% | 11% | 3 | 0.5 | 0.0 | 10.6 |
| | 372 | 50% | 70% | 4 | 2.7 | 0.6 | 12.5 |
| | 630 | 50% | 81% | | | | |
| | 829 | 40% | 90% | | | | | sCr only

| Time prior AKI stage | Cutoff value | sens | spec | Quartile | OR | 95% CI of OR | |
|---|---|---|---|---|---|---|---|
| 0 hours | 357 | 75% | 63% | 1 | | | |
| | 165 | 88% | 31% | 2 | 1.0 | 0.0 | 53.9 |
| | 116 | 100% | 23% | 3 | 1.0 | 0.0 | 55.2 |
| | 487 | 63% | 70% | 4 | 5.4 | 0.5 | 62.1 |
| | 633 | 50% | 80% | | | | |
| | 1050 | 38% | 90% | | | | |
| 24 hours | 357 | 75% | 63% | 1 | | | |
| | 165 | 88% | 31% | 2 | 1.0 | 0.0 | 53.9 |
| | 116 | 100% | 23% | 3 | 1.0 | 0.0 | 55.2 |
| | 487 | 63% | 70% | 4 | 5.4 | 0.5 | 62.1 |
| | 633 | 50% | 80% | | | | |
| | 1050 | 38% | 90% | | | | |
| 48 hours | 165 | 80% | 31% | 1 | | | |
| | 165 | 80% | 31% | 2 | 1.0 | 0.0 | 54.0 |
| | 116 | 100% | 23% | 3 | 0.0 | 0.0 | na |
| | 487 | 60% | 70% | 4 | 3.1 | 0.2 | 46.1 |
| | 633 | 40% | 80% | | | | |
| | 1050 | 40% | 90% | | | | |

UO only

| Time prior AKI stage | Cutoff value | sens | spec | Quartile | OR | 95% CI of OR | |
|---|---|---|---|---|---|---|---|
| 0 hours | 150 | 73% | 33% | 1 | | | |
| | 99.7 | 82% | 21% | 2 | 1.0 | 0.2 | 4.5 |
| | 92.8 | 91% | 20% | 3 | 0.3 | 0.0 | 5.0 |
| | 421 | 36% | 71% | 4 | 1.4 | 0.4 | 5.3 |
| | 593 | 36% | 80% | | | | |
| | 829 | 36% | 91% | | | | |
| 24 hours | 165 | 70% | 35% | 1 | | | |
| | 150 | 80% | 33% | 2 | 1.5 | 0.2 | 9.3 |
| | 92.8 | 90% | 20% | 3 | 0.5 | 0.0 | 10.3 |
| | 421 | 40% | 71% | 4 | 2.1 | 0.4 | 11.1 |
| | 593 | 40% | 80% | | | | |
| | 829 | 40% | 91% | | | | |

Fig. 4 Continued

| 48 hours | 150 | 71% | 33% | 1 | | | |
| | 61.5 | 86% | 11% | 2 | 0.5 | 0.0 | 10.8 |
| | 51 | 100% | 7% | 3 | 0.5 | 0.0 | 10.8 |
| | 421 | 43% | 71% | 4 | 1.6 | 0.3 | 9.8 |
| | 593 | 43% | 80% | | | | |
| | 829 | 43% | 91% | | | | |

Tissue inhibitor of metalloproteinase 1 sCr or UO

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 3.975 | 32.300 | 3.975 | 30.350 | 3.975 | 13.240 |
| average | 15.936 | 75.903 | 15.936 | 53.375 | 15.936 | 20.705 |
| stdev | 39.829 | 89.651 | 39.829 | 78.371 | 39.829 | 21.532 |
| p (t-test) | | 0.000 | | 0.003 | | 0.710 |
| min | 0.104 | 0.256 | 0.104 | 0.256 | 0.104 | 0.169 |
| max | 302.000 | 302.000 | 302.000 | 302.000 | 302.000 | 57.400 |
| n (Samp) | 104 | 17 | 104 | 16 | 104 | 10 |
| n (Pat) | 104 | 17 | 104 | 16 | 104 | 10 | sCr only

| | 0 hr prior toAKI stage | | 24 hr prior toAKI stage | | 48 hr prior toAKI stage | |
| | Cohort 1 | Cohort 2 | Cohort 1 | Cohort 2 | Cohort 1 | Cohort 2 |
|---|---|---|---|---|---|---|
| median | 7.065 | 44.850 | 7.065 | 27.200 | 7.065 | 22.100 |
| average | 19.289 | 82.832 | 19.289 | 65.653 | 19.289 | 36.996 |
| stdev | 45.763 | 85.517 | 45.763 | 83.933 | 45.763 | 42.880 |
| p (t-test) | | 0.000 | | 0.008 | | 0.394 |
| min | 0.104 | 0.256 | 0.104 | 0.256 | 0.104 | 0.169 |
| max | 302.000 | 231.000 | 302.000 | 231.000 | 302.000 | 102.000 |
| n (Samp) | 170 | 8 | 170 | 8 | 170 | 5 |
| n (Pat) | 170 | 8 | 170 | 8 | 170 | 5 |

UO only

| | 0 hr prior toAKI stage | | 24 hr prior toAKI stage | | 48 hr prior toAKI stage | |
| | Cohort 1 | Cohort 2 | Cohort 1 | Cohort 2 | Cohort 1 | Cohort 2 |
|---|---|---|---|---|---|---|
| median | 3.420 | 31.700 | 3.420 | 30.350 | 3.420 | 22.100 |
| average | 17.225 | 80.072 | 17.225 | 58.187 | 17.225 | 20.881 |
| stdev | 43.625 | 101.872 | 43.625 | 90.621 | 43.625 | 18.715 |
| p (t-test) | | 0.000 | | 0.016 | | 0.827 |
| min | 0.104 | 1.900 | 0.104 | 1.900 | 0.104 | 1.900 |
| max | 302.000 | 302.000 | 302.000 | 302.000 | 302.000 | 52.000 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
|---|---|---|---|---|---|
| 0 hours | 0.80 | 0.067 | 104 | 17 | 0.000 |
| 24 hours | 0.75 | 0.074 | 104 | 16 | 0.001 |
| 48 hours | 0.63 | 0.098 | 104 | 10 | 0.186 | sCr only

| Time prior AKI stage | AUC | SE | nCohort 1 | nCohort 2 | p |
|---|---|---|---|---|---|
| 0 hours | 0.78 | 0.099 | 170 | 8 | 0.005 |
| 24 hours | 0.73 | 0.103 | 170 | 8 | 0.025 |
| 48 hours | 0.63 | 0.136 | 170 | 5 | 0.357 |

Fig. 4 Continued

UO only

| Time prior AKI stage | AUC | SE | nCohort 1 | nCohort 2 | p |
|---|---|---|---|---|---|
| 0 hours | 0.82 | 0.080 | 85 | 11 | 0.000 |
| 24 hours | 0.78 | 0.089 | 85 | 10 | 0.002 |
| 48 hours | 0.70 | 0.114 | 85 | 7 | 0.074 | sCr or UO

| Time prior AKI stage | Cutoff value | sens | spec | Quartile | OR | 95% CI of OR | |
|---|---|---|---|---|---|---|---|
| 0 hours | 22.1 | 71% | 83% | 1 | | | |
| | 10.4 | 82% | 71% | 2 | 2.1 | 0.1 | 45.0 |
| | 1.8 | 94% | 32% | 3 | 1.0 | 0.0 | 57.7 |
| | 10.3 | 82% | 70% | 4 | 20.9 | 2.1 | 206.3 |
| | 15.9 | 76% | 81% | | | | |
| | 31.3 | 59% | 90% | | | | |
| 24 hours | 5.95 | 75% | 57% | 1 | | | |
| | 4.22 | 81% | 54% | 2 | 3.2 | 0.2 | 50.6 |
| | 1.8 | 94% | 32% | 3 | 2.1 | 0.1 | 45.0 |
| | 10.3 | 69% | 70% | 4 | 14.5 | 1.4 | 147.8 |
| | 15.9 | 69% | 81% | | | | |
| | 31.3 | 50% | 90% | | | | |
| 48 hours | 3.57 | 70% | 48% | 1 | | | |
| | 3.03 | 80% | 46% | 2 | 3.1 | 0.2 | 49.3 |
| | 1.8 | 90% | 32% | 3 | 1.0 | 0.0 | 58.3 |
| | 10.3 | 50% | 70% | 4 | 5.6 | 0.5 | 69.0 |
| | 15.9 | 50% | 81% | | | | |
| | 31.3 | 30% | 90% | | | | | sCr only

| Time prior AKI stage | Cutoff value | sens | spec | Quartile | OR | 95% CI of OR | |
|---|---|---|---|---|---|---|---|
| 0 hours | 21.5 | 75% | 81% | 1 | | | |
| | 10.4 | 88% | 64% | 2 | 0.0 | 0.0 | na |
| | 0.216 | 100% | 2% | 3 | 1.0 | 0.0 | 55.2 |
| | 14 | 75% | 70% | 4 | 6.6 | 0.6 | 71.7 |
| | 20.9 | 75% | 80% | | | | |
| | 38.2 | 50% | 90% | | | | |
| 24 hours | 16.9 | 75% | 77% | 1 | | | |
| | 5.95 | 88% | 49% | 2 | 1.0 | 0.0 | 53.9 |
| | 0.216 | 100% | 2% | 3 | 0.0 | 0.0 | na |
| | 14 | 75% | 70% | 4 | 6.6 | 0.6 | 71.7 |
| | 20.9 | 63% | 80% | | | | |
| | 38.2 | 38% | 90% | | | | |
| 48 hours | 3.03 | 80% | 41% | 1 | | | |
| | 3.03 | 80% | 41% | 2 | 1.0 | 0.0 | 54.0 |
| | 0.157 | 100% | 1% | 3 | 0.0 | 0.0 | na |
| | 14 | 60% | 70% | 4 | 3.1 | 0.2 | 46.1 |
| | 20.9 | 60% | 80% | | | | |
| | 38.2 | 40% | 90% | | | | |

Fig. 4 Continued

Tissue inhibitor of metalloproteinase 2 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 8885.843 | 28006.563 | 8885.843 | 26058.107 | 8885.843 | 23748.947 |
| average | 13900.106 | 54466.502 | 13900.106 | 53146.474 | 13900.106 | 26765.638 |
| stdev | 23828.650 | 62915.343 | 23828.650 | 63648.454 | 23828.650 | 16045.772 |
| p (t-test) |  | 0.000 |  | 0.000 |  | 0.138 |
| min | 759.402 | 6112.595 | 759.402 | 6112.595 | 759.402 | 6112.595 |
| max | 210000.000 | 210000.000 | 210000.000 | 210000.000 | 210000.000 | 49583.194 |
| n (Samp) | 99 | 12 | 99 | 12 | 99 | 8 |
| n (Pat) | 99 | 12 | 99 | 12 | 99 | 8 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 12684.303 | 28006.563 | 12684.303 | 26058.107 | 12684.303 | 37016.656 |
| average | 17466.777 | 57693.172 | 17466.777 | 55053.115 | 17466.777 | 72536.477 |
| stdev | 23800.455 | 75815.758 | 23800.455 | 77255.547 | 23800.455 | 93259.029 |
| p (t-test) |  | 0.000 |  | 0.001 |  | 0.000 |
| min | 759.402 | 6112.595 | 759.402 | 6112.595 | 759.402 | 6112.595 |
| max | 210000.000 | 210000.000 | 210000.000 | 210000.000 | 210000.000 | 210000.000 |
| n (Samp) | 160 | 6 | 160 | 6 | 160 | 4 |
| n (Pat) | 160 | 6 | 160 | 6 | 160 | 4 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 8878.783 | 41049.819 | 8878.783 | 41049.819 | 8878.783 | 27782.110 |
| average | 14653.718 | 70732.373 | 14653.718 | 70732.373 | 14653.718 | 30399.864 |
| stdev | 25814.293 | 72555.132 | 25814.293 | 72555.132 | 25814.293 | 16094.384 |
| p (t-test) |  | 0.000 |  | 0.000 |  | 0.145 |
| min | 759.402 | 12393.647 | 759.402 | 12393.647 | 759.402 | 12393.647 |
| max | 210000.000 | 210000.000 | 210000.000 | 210000.000 | 210000.000 | 49583.194 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
|---|---|---|---|---|---|
| 0 hours | 0.86 | 0.069 | 99 | 12 | 0.000 |
| 24 hours | 0.84 | 0.073 | 99 | 12 | 0.000 |
| 48 hours | 0.81 | 0.094 | 99 | 8 | 0.001 | sCr only

| Time prior AKI stage | AUC | SE | nCohort 1 | nCohort 2 | p |
|---|---|---|---|---|---|
| 0 hours | 0.80 | 0.110 | 160 | 6 | 0.006 |
| 24 hours | 0.74 | 0.118 | 160 | 6 | 0.042 |
| 48 hours | 0.76 | 0.142 | 160 | 4 | 0.068 |

UO only

| Time prior AKI stage | AUC | SE | nCohort 1 | nCohort 2 | p |
|---|---|---|---|---|---|
| 0 hours | 0.90 | 0.075 | 84 | 8 | 0.000 |
| 24 hours | 0.90 | 0.075 | 84 | 8 | 0.000 |
| 48 hours | 0.87 | 0.096 | 84 | 6 | 0.000 |

Fig. 4 Continued sCr only

| Time prior AKI stage | Cutoff value | sens | spec | Quartile | OR | 95% CI of OR | |
|---|---|---|---|---|---|---|---|
| 0 hours | 24404.5 | 83% | 87% | 1 | | | |
| | 24404.5 | 83% | 87% | 2 | 0.0 | 0.0 | na |
| | 5722.8 | 100% | 21% | 3 | 0.0 | 0.0 | na |
| | 17995.5 | 83% | 70% | 4 | 5.4 | 0.5 | 62.9 |
| | 22143.4 | 83% | 81% | | | | |
| | 29949 | 33% | 90% | | | | |
| 24 hours | 13642.1 | 83% | 54% | 1 | | | |
| | 13642.1 | 83% | 54% | 2 | 0.0 | 0.0 | na |
| | 5722.8 | 100% | 21% | 3 | 1.0 | 0.0 | 55.6 |
| | 17995.5 | 67% | 70% | 4 | 4.2 | 0.3 | 54.0 |
| | 22143.4 | 67% | 81% | | | | |
| | 29949 | 33% | 90% | | | | |
| 48 hours | 24404.5 | 75% | 87% | 1 | | | |
| | 5722.8 | 100% | 21% | 2 | 0.0 | 0.0 | na |
| | 5722.8 | 100% | 21% | 3 | 0.0 | 0.0 | na |
| | 17995.5 | 75% | 70% | 4 | 3.2 | 0.2 | 47.6 |
| | 22143.4 | 75% | 81% | | | | |
| | 29949 | 50% | 90% | | | | |

Tumor necrosis factor-alpha sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 6.930 | 6.810 | 6.930 | 5.675 | 6.930 | 4.280 |
| average | 10.947 | 18.227 | 10.947 | 18.871 | 10.947 | 22.519 |
| stdev | 13.503 | 36.743 | 13.503 | 37.849 | 13.503 | 47.866 |
| p (t-test) | | 0.133 | | 0.113 | | 0.065 |
| min | 0.016 | 1.530 | 0.016 | 1.530 | 0.016 | 0.016 |
| max | 86.200 | 156.000 | 86.200 | 156.000 | 86.200 | 156.000 |
| n (Samp) | 104 | 17 | 104 | 16 | 104 | 10 |
| n (Pat) | 104 | 17 | 104 | 16 | 104 | 10 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 8.435 | 9.190 | 8.435 | 8.605 | 8.435 | 11.100 |
| average | 15.362 | 11.001 | 15.362 | 10.419 | 15.362 | 12.564 |
| stdev | 32.316 | 9.521 | 32.316 | 9.869 | 32.316 | 12.199 |
| p (t-test) | | 0.704 | | 0.667 | | 0.847 |
| min | 0.016 | 2.900 | 0.016 | 2.900 | 0.016 | 2.900 |
| max | 300.000 | 33.200 | 300.000 | 33.200 | 300.000 | 33.200 |
| n (Samp) | 170 | 8 | 170 | 8 | 170 | 5 |
| n (Pat) | 170 | 8 | 170 | 8 | 170 | 5 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 5.330 | 4.540 | 5.330 | 7.820 | 5.330 | 4.540 |
| average | 9.767 | 22.232 | 9.767 | 24.129 | 9.767 | 26.438 |
| stdev | 11.919 | 45.241 | 11.919 | 47.224 | 11.919 | 57.259 |
| p (t-test) | | 0.039 | | 0.023 | | 0.026 |
| min | 0.016 | 1.530 | 0.016 | 1.530 | 0.016 | 0.016 |
| max | 72.000 | 156.000 | 72.000 | 156.000 | 72.000 | 156.000 |
| n (Samp) | 85 | 11 | 85 | 10 | 85 | 7 |
| n (Pat) | 85 | 11 | 85 | 10 | 85 | 7 |

Fig. 4 Continued sCr or UO

| Time prior AKI stage | AUC | SE | nCohort 1 | nCohort 2 | p |
|---|---|---|---|---|---|
| 0 hours | 0.53 | 0.077 | 104 | 17 | 0.743 |
| 24 hours | 0.52 | 0.079 | 104 | 16 | 0.763 |
| 48 hours | 0.47 | 0.094 | 104 | 10 | 0.768 | sCr only

| Time prior AKI stage | AUC | SE | nCohort 1 | nCohort 2 | p |
|---|---|---|---|---|---|
| 0 hours | 0.53 | 0.106 | 170 | 8 | 0.798 |
| 24 hours | 0.50 | 0.105 | 170 | 8 | 0.994 |
| 48 hours | 0.54 | 0.134 | 170 | 5 | 0.756 |

UO only

| Time prior AKI stage | AUC | SE | nCohort 1 | nCohort 2 | p |
|---|---|---|---|---|---|
| 0 hours | 0.54 | 0.094 | 85 | 11 | 0.679 |
| 24 hours | 0.56 | 0.099 | 85 | 10 | 0.553 |
| 48 hours | 0.47 | 0.112 | 85 | 7 | 0.787 | sCr or UO

| Time prior AKI stage | Cutoff value | sens | spec | Quartile | OR | 95% CI of OR | |
|---|---|---|---|---|---|---|---|
| 0 hours | 3.6 | 71% | 37% | 1 | | | |
| | 2.68 | 82% | 28% | 2 | 2.3 | 0.7 | 7.0 |
| | 1.53 | 94% | 13% | 3 | 1.4 | 0.4 | 5.0 |
| | 13.8 | 24% | 71% | 4 | 1.3 | 0.4 | 4.8 |
| | 17.3 | 24% | 82% | | | | |
| | 22.1 | 18% | 90% | | | | |
| 24 hours | 3.19 | 75% | 31% | 1 | | | |
| | 2.68 | 81% | 28% | 2 | 2.3 | 0.7 | 7.0 |
| | 1.53 | 94% | 13% | 3 | 1.0 | 0.2 | 4.3 |
| | 13.8 | 25% | 71% | 4 | 1.4 | 0.4 | 5.0 |
| | 17.3 | 25% | 82% | | | | |
| | 22.1 | 19% | 90% | | | | |
| 48 hours | 3.6 | 70% | 37% | 1 | | | |
| | 2.68 | 80% | 28% | 2 | 1.0 | 0.1 | 8.5 |
| | 1.51 | 90% | 13% | 3 | 2.2 | 0.4 | 10.9 |
| | 13.8 | 20% | 71% | 4 | 1.0 | 0.1 | 8.5 |
| | 17.3 | 20% | 82% | | | | |
| | 22.1 | 20% | 90% | | | | | sCr only

| Time prior AKI stage | Cutoff value | sens | spec | Quartile | OR | 95% CI of OR | |
|---|---|---|---|---|---|---|---|
| 0 hours | 6.73 | 75% | 45% | 1 | | | |
| | 4.01 | 88% | 35% | 2 | 3.1 | 0.2 | 46.0 |
| | 2.68 | 100% | 23% | 3 | 3.1 | 0.2 | 47.1 |
| | 15.4 | 13% | 70% | 4 | 1.0 | 0.0 | 53.9 |
| | 19 | 13% | 80% | | | | |
| | 25.8 | 13% | 90% | | | | |
| 24 hours | 4.01 | 75% | 35% | 1 | | | |
| | 3.31 | 88% | 28% | 2 | 3.1 | 0.2 | 46.0 |
| | 2.68 | 100% | 23% | 3 | 3.1 | 0.2 | 47.1 |
| | 15.4 | 13% | 70% | 4 | 1.0 | 0.0 | 53.9 |
| | 19 | 13% | 80% | | | | |
| | 25.8 | 13% | 90% | | | | |

Fig. 4 Continued

| 48 hours | 4.01 | 80% | 35% | 1 | | | |
| | 4.01 | 80% | 35% | 2 | 1.0 | 0.0 | 54.0 |
| | 2.68 | 100% | 23% | 3 | 2.0 | 0.1 | 41.5 |
| | 15.4 | 20% | 70% | 4 | 1.0 | 0.0 | 54.0 |
| | 19 | 20% | 80% | | | | |
| | 25.8 | 20% | 90% | | | | |

UO only

| Time prior AKI stage | Cutoff value | sens | spec | Quartile | OR | 95% CI of OR | |
|---|---|---|---|---|---|---|---|
| 0 hours | 3.19 | 73% | 34% | 1 | | | |
| | 2.41 | 82% | 28% | 2 | 2.2 | 0.4 | 11.5 |
| | 1.53 | 91% | 14% | 3 | 1.0 | 0.1 | 8.5 |
| | 12.1 | 27% | 71% | 4 | 1.6 | 0.3 | 9.7 |
| | 16.5 | 27% | 80% | | | | |
| | 20.6 | 18% | 91% | | | | |
| 24 hours | 3.6 | 70% | 40% | 1 | | | |
| | 2.41 | 80% | 28% | 2 | 1.5 | 0.2 | 9.3 |
| | 1.53 | 90% | 14% | 3 | 1.0 | 0.1 | 8.1 |
| | 12.1 | 30% | 71% | 4 | 1.5 | 0.2 | 9.3 |
| | 16.5 | 30% | 80% | | | | |
| | 20.6 | 20% | 91% | | | | |
| 48 hours | 3.6 | 71% | 40% | 1 | | | |
| | 1.51 | 86% | 14% | 2 | 2.1 | 0.1 | 47.6 |
| | 0 | 100% | 0% | 3 | 2.1 | 0.1 | 47.6 |
| | 12.1 | 14% | 71% | 4 | 2.1 | 0.1 | 47.6 |
| | 16.5 | 14% | 80% | | | | |
| | 20.6 | 14% | 91% | | | | |

Vascular cell adhesion molecule 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 50.502 | 71.906 | 50.502 | 71.906 | 50.502 | 71.906 |
| average | 61.614 | 75.426 | 61.614 | 74.870 | 61.614 | 60.603 |
| stdev | 46.472 | 62.899 | 46.472 | 63.273 | 46.472 | 41.126 |
| p (t-test) | | 0.352 | | 0.373 | | 0.953 |
| min | 0.475 | 3.048 | 0.475 | 3.048 | 0.475 | 3.048 |
| max | 322.684 | 240.000 | 322.684 | 240.000 | 322.684 | 118.181 |
| n (Samp) | 99 | 12 | 99 | 12 | 99 | 8 |
| n (Pat) | 99 | 12 | 99 | 12 | 99 | 8 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 66.132 | 58.366 | 66.132 | 58.366 | 66.132 | 57.364 |
| average | 71.467 | 61.114 | 71.467 | 60.335 | 71.467 | 58.989 |
| stdev | 47.918 | 41.906 | 47.918 | 42.581 | 47.918 | 47.470 |
| p (t-test) | | 0.603 | | 0.576 | | 0.608 |
| min | 0.475 | 3.048 | 0.475 | 3.048 | 0.475 | 3.048 |
| max | 322.684 | 118.181 | 322.684 | 118.181 | 322.684 | 118.181 |
| n (Samp) | 160 | 6 | 160 | 6 | 160 | 4 |
| n (Pat) | 160 | 6 | 160 | 6 | 160 | 4 |

Fig. 4 Continued

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 54.959 | 83.564 | 54.959 | 83.564 | 54.959 | 83.564 |
| average | 65.536 | 88.523 | 65.536 | 88.272 | 65.536 | 69.435 |
| stdev | 48.733 | 70.239 | 48.733 | 70.393 | 48.733 | 40.095 |
| p (t-test) | | 0.224 | | 0.229 | | 0.849 |
| min | 0.475 | 20.469 | 0.475 | 20.469 | 0.475 | 20.469 |
| max | 322.684 | 240.000 | 322.684 | 240.000 | 322.684 | 118.181 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
|---|---|---|---|---|---|
| 0 hours | 0.56 | 0.091 | 99 | 12 | 0.527 |
| 24 hours | 0.55 | 0.090 | 99 | 12 | 0.558 |
| 48 hours | 0.51 | 0.107 | 99 | 8 | 0.897 | sCr only

| Time prior AKI stage | AUC | SE | nCohort 1 | nCohort 2 | p |
|---|---|---|---|---|---|
| 0 hours | 0.45 | 0.116 | 160 | 6 | 0.673 |
| 24 hours | 0.45 | 0.116 | 160 | 6 | 0.653 |
| 48 hours | 0.43 | 0.138 | 160 | 4 | 0.619 |

UO only

| Time prior AKI stage | AUC | SE | nCohort 1 | nCohort 2 | p |
|---|---|---|---|---|---|
| 0 hours | 0.60 | 0.110 | 84 | 8 | 0.381 |
| 24 hours | 0.60 | 0.110 | 84 | 8 | 0.388 |
| 48 hours | 0.55 | 0.125 | 84 | 6 | 0.669 | sCr or UO

| Time prior AKI stage | Cutoff value | sens | spec | Quartile | OR | 95% CI of OR | |
|---|---|---|---|---|---|---|---|
| 0 hours | 31.3604 | 75% | 27% | 1 | | | |
| | 20.4689 | 83% | 14% | 2 | 0.6 | 0.1 | 3.7 |
| | 20.0671 | 92% | 14% | 3 | 0.6 | 0.1 | 3.7 |
| | 75.6644 | 50% | 71% | 4 | 1.7 | 0.5 | 5.8 |
| | 94.8499 | 25% | 81% | | | | |
| | 121.836 | 8% | 91% | | | | |
| 24 hours | 27.807 | 75% | 24% | 1 | | | |
| | 20.4689 | 83% | 14% | 2 | 0.6 | 0.1 | 3.7 |
| | 20.0671 | 92% | 14% | 3 | 0.6 | 0.1 | 3.7 |
| | 75.6644 | 50% | 71% | 4 | 1.7 | 0.5 | 5.8 |
| | 94.8499 | 25% | 81% | | | | |
| | 121.836 | 8% | 91% | | | | |
| 48 hours | 20.4689 | 75% | 14% | 1 | | | |
| | 20.0671 | 88% | 14% | 2 | 0.0 | 0.0 | na |
| | 0.47523 | 100% | 1% | 3 | 0.6 | 0.1 | 3.7 |
| | 75.6644 | 50% | 71% | 4 | 1.0 | 0.2 | 4.2 |
| | 94.8499 | 13% | 81% | | | | |
| | 121.836 | 0% | 91% | | | | |

Fig. 4 Continued sCr only

| Time prior AKI stage | Cutoff value | sens | spec | Quartile | OR | 95% CI of OR | |
|---|---|---|---|---|---|---|---|
| 0 hours | 31.3604 | 83% | 19% | 1 | | | |
| | 31.3604 | 83% | 19% | 2 | 0.5 | 0.0 | 10.4 |
| | 0.47523 | 100% | 1% | 3 | 0.5 | 0.0 | 10.2 |
| | 88.48 | 33% | 70% | 4 | 1.0 | 0.1 | 8.0 |
| | 103.319 | 17% | 80% | | | | |
| | 127.565 | 0% | 90% | | | | |
| 24 hours | 27.807 | 83% | 18% | 1 | | | |
| | 27.807 | 83% | 18% | 2 | 0.5 | 0.0 | 10.4 |
| | 0.47523 | 100% | 1% | 3 | 0.5 | 0.0 | 10.2 |
| | 88.48 | 33% | 70% | 4 | 1.0 | 0.1 | 8.0 |
| | 103.319 | 17% | 80% | | | | |
| | 127.565 | 0% | 90% | | | | |
| 48 hours | 49.3582 | 75% | 36% | 1 | | | |
| | 0.47523 | 100% | 1% | 2 | 1.0 | 0.0 | 55.6 |
| | 0.47523 | 100% | 1% | 3 | 1.0 | 0.0 | 55.6 |
| | 88.48 | 25% | 70% | 4 | 1.0 | 0.0 | 55.6 |
| | 103.319 | 25% | 80% | | | | |
| | 127.565 | 0% | 90% | | | | |

UO only

| Time prior AKI stage | Cutoff value | sens | spec | Quartile | OR | 95% CI of OR | |
|---|---|---|---|---|---|---|---|
| 0 hours | 50.5017 | 75% | 46% | 1 | | | |
| | 20.4689 | 88% | 13% | 2 | 0.5 | 0.0 | 10.8 |
| | 20.0671 | 100% | 13% | 3 | 1.0 | 0.1 | 8.6 |
| | 80.5035 | 50% | 70% | 4 | 1.6 | 0.3 | 9.8 |
| | 100.474 | 25% | 81% | | | | |
| | 126.58 | 13% | 90% | | | | |
| 24 hours | 49.3582 | 75% | 45% | 1 | | | |
| | 20.4689 | 88% | 13% | 2 | 0.5 | 0.0 | 10.8 |
| | 20.0671 | 100% | 13% | 3 | 1.0 | 0.1 | 8.6 |
| | 80.5035 | 50% | 70% | 4 | 1.6 | 0.3 | 9.8 |
| | 100.474 | 25% | 81% | | | | |
| | 126.58 | 13% | 90% | | | | |
| 48 hours | 20.4689 | 83% | 13% | 1 | | | |
| | 20.4689 | 83% | 13% | 2 | 0.0 | 0.0 | na |
| | 20.0671 | 100% | 13% | 3 | 1.0 | 0.1 | 8.6 |
| | 80.5035 | 50% | 70% | 4 | 1.0 | 0.1 | 8.2 |
| | 100.474 | 17% | 81% | | | | |
| | 126.58 | 0% | 90% | | | | |

Fig. 4 Continued

Vascular endothelial growth factor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 982.500 | 7060.000 | 982.500 | 6865.000 | 982.500 | 2415.000 |
| average | 2862.470 | 14645.706 | 2862.470 | 14563.625 | 2862.470 | 4167.110 |
| stdev | 5408.538 | 32646.449 | 5408.538 | 33648.820 | 5408.538 | 4889.298 |
| p (t-test) |  | 0.001 |  | 0.001 |  | 0.464 |
| min | 73.000 | 180.000 | 73.000 | 180.000 | 73.000 | 93.100 |
| max | 32200.000 | 139000.000 | 32200.000 | 139000.000 | 32200.000 | 15700.000 |
| n (Samp) | 104 | 17 | 104 | 16 | 104 | 10 |
| n (Pat) | 104 | 17 | 104 | 16 | 104 | 10 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 1110.000 | 10040.000 | 1110.000 | 10030.000 | 1110.000 | 7060.000 |
| average | 4259.770 | 10911.250 | 4259.770 | 10908.750 | 4259.770 | 7826.620 |
| stdev | 13068.126 | 6583.380 | 13068.126 | 6584.483 | 13068.126 | 5761.874 |
| p (t-test) |  | 0.155 |  | 0.155 |  | 0.545 |
| min | 73.000 | 180.000 | 73.000 | 180.000 | 73.000 | 93.100 |
| max | 139000.000 | 19500.000 | 139000.000 | 19500.000 | 139000.000 | 15700.000 |
| n (Samp) | 170 | 8 | 170 | 8 | 170 | 5 |
| n (Pat) | 170 | 8 | 170 | 8 | 170 | 5 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 851.000 | 2320.000 | 851.000 | 2750.000 | 851.000 | 1510.000 |
| average | 2419.164 | 17113.364 | 2419.164 | 17230.800 | 2419.164 | 2856.857 |
| stdev | 4246.719 | 40806.641 | 4246.719 | 42924.776 | 4246.719 | 2903.752 |
| p (t-test) |  | 0.001 |  | 0.002 |  | 0.790 |
| min | 96.900 | 461.000 | 96.900 | 437.000 | 96.900 | 437.000 |
| max | 25700.000 | 139000.000 | 25700.000 | 139000.000 | 25700.000 | 7060.000 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
| --- | --- | --- | --- | --- | --- |
| 0 hours | 0.74 | 0.073 | 104 | 17 | 0.001 |
| 24 hours | 0.71 | 0.076 | 104 | 16 | 0.005 |
| 48 hours | 0.59 | 0.099 | 104 | 10 | 0.370 | sCr only

| Time prior AKI stage | AUC | SE | nCohort 1 | nCohort 2 | p |
| --- | --- | --- | --- | --- | --- |
| 0 hours | 0.82 | 0.093 | 170 | 8 | 0.001 |
| 24 hours | 0.82 | 0.093 | 170 | 8 | 0.001 |
| 48 hours | 0.73 | 0.130 | 170 | 5 | 0.076 |

UO only

| Time prior AKI stage | AUC | SE | nCohort 1 | nCohort 2 | p |
| --- | --- | --- | --- | --- | --- |
| 0 hours | 0.72 | 0.091 | 85 | 11 | 0.015 |
| 24 hours | 0.68 | 0.098 | 85 | 10 | 0.069 |
| 48 hours | 0.59 | 0.117 | 85 | 7 | 0.452 |

Fig. 4 Continued sCr or UO

| Time prior AKI stage | Cutoff value | sens | spec | Quartile | OR | 95% CI of OR | |
|---|---|---|---|---|---|---|---|
| 0 hours | 2080 | 71% | 67% | 1 | | | |
| | 851 | 82% | 48% | 2 | 1.0 | 0.1 | 8.2 |
| | 457 | 94% | 23% | 3 | 1.6 | 0.3 | 9.2 |
| | 2240 | 65% | 70% | 4 | 6.7 | 1.7 | 25.4 |
| | 3530 | 59% | 81% | | | | |
| | 5860 | 59% | 90% | | | | |
| 24 hours | 1470 | 75% | 61% | 1 | | | |
| | 571 | 81% | 35% | 2 | 0.3 | 0.0 | 4.9 |
| | 372 | 94% | 20% | 3 | 1.0 | 0.2 | 4.3 |
| | 2240 | 63% | 70% | 4 | 3.9 | 1.4 | 10.9 |
| | 3530 | 56% | 81% | | | | |
| | 5860 | 56% | 90% | | | | |
| 48 hours | 571 | 70% | 35% | 1 | | | |
| | 457 | 80% | 23% | 2 | 0.3 | 0.0 | 4.7 |
| | 372 | 90% | 20% | 3 | 0.3 | 0.0 | 4.9 |
| | 2240 | 50% | 70% | 4 | 1.7 | 0.5 | 5.8 |
| | 3530 | 40% | 81% | | | | |
| | 5860 | 40% | 90% | | | | | sCr only

| Time prior AKI stage | Cutoff value | sens | spec | Quartile | OR | 95% CI of OR | |
|---|---|---|---|---|---|---|---|
| 0 hours | 7040 | 75% | 91% | 1 | | | |
| | 6580 | 88% | 89% | 2 | 0.0 | 0.0 | na |
| | 175 | 100% | 4% | 3 | 0.0 | 0.0 | na |
| | 2240 | 88% | 70% | 4 | 7.9 | 0.8 | 82.0 |
| | 3260 | 88% | 80% | | | | |
| | 6910 | 75% | 90% | | | | |
| 24 hours | 7040 | 75% | 91% | 1 | | | |
| | 6580 | 88% | 89% | 2 | 0.0 | 0.0 | na |
| | 175 | 100% | 4% | 3 | 0.0 | 0.0 | na |
| | 2240 | 88% | 70% | 4 | 7.9 | 0.8 | 82.0 |
| | 3260 | 88% | 80% | | | | |
| | 6910 | 75% | 90% | | | | |
| 48 hours | 5860 | 80% | 87% | 1 | | | |
| | 5860 | 80% | 87% | 2 | 0.0 | 0.0 | na |
| | 73 | 100% | 1% | 3 | 0.0 | 0.0 | na |
| | 2240 | 80% | 70% | 4 | 4.2 | 0.3 | 53.6 |
| | 3260 | 80% | 80% | | | | |
| | 6910 | 60% | 90% | | | | |

UO only

| Time prior AKI stage | Cutoff value | sens | spec | Quartile | OR | 95% CI of OR | |
|---|---|---|---|---|---|---|---|
| 0 hours | 1370 | 73% | 62% | 1 | | | |
| | 851 | 82% | 51% | 2 | 2.1 | 0.1 | 47.1 |
| | 571 | 91% | 38% | 3 | 3.3 | 0.2 | 53.6 |
| | 2220 | 55% | 71% | 4 | 6.1 | 0.5 | 76.8 |
| | 2830 | 45% | 80% | | | | |
| | 5230 | 45% | 91% | | | | |
| 24 hours | 1370 | 70% | 62% | 1 | | | |
| | 571 | 80% | 38% | 2 | 0.5 | 0.0 | 10.3 |
| | 457 | 90% | 25% | 3 | 1.0 | 0.1 | 8.1 |
| | 2220 | 50% | 71% | 4 | 2.8 | 0.6 | 13.3 |
| | 2830 | 50% | 80% | | | | |
| | 5230 | 40% | 91% | | | | |

Fig. 4 Continued

| 48 hours | 571 | 71% | 38% | 1 | | | |
| --- | --- | --- | --- | --- | --- | --- | --- |
| | 457 | 86% | 25% | 2 | 0.5 | 0.0 | 10.8 |
| | 378 | 100% | 21% | 3 | 0.5 | 0.0 | 10.8 |
| | 2220 | 43% | 71% | 4 | 1.6 | 0.3 | 9.8 |
| | 2830 | 43% | 80% | | | | |
| | 5230 | 29% | 91% | | | | |

Fig. 4 Continued

Aspartate aminotransferase, cytoplasmic sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 16.400 | 16.450 | 16.400 | 21.500 | 16.400 | 21.750 |
| average | 18.403 | 15.180 | 18.403 | 19.625 | 18.403 | 19.997 |
| stdev | 19.998 | 11.430 | 19.998 | 9.203 | 19.998 | 8.739 |
| p (t-test) |  | 0.245 |  | 0.642 |  | 0.688 |
| min | 2.080 | 1.810 | 2.080 | 0.943 | 2.080 | 2.780 |
| max | 251.000 | 41.100 | 251.000 | 39.600 | 251.000 | 32.100 |
| n (Samp) | 257 | 56 | 257 | 61 | 257 | 26 |
| n (Pat) | 112 | 56 | 112 | 61 | 112 | 26 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 16.600 | 21.000 | 16.600 | 19.550 | 16.600 | 22.300 |
| average | 17.456 | 16.996 | 17.456 | 19.822 | 17.456 | 18.210 |
| stdev | 16.068 | 11.307 | 16.068 | 9.203 | 16.068 | 10.336 |
| p (t-test) |  | 0.892 |  | 0.457 |  | 0.862 |
| min | 1.810 | 2.090 | 1.810 | 0.943 | 1.810 | 2.820 |
| max | 251.000 | 39.800 | 251.000 | 36.600 | 251.000 | 29.800 |
| n (Samp) | 459 | 23 | 459 | 26 | 459 | 14 |
| n (Pat) | 180 | 23 | 180 | 26 | 180 | 14 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 16.800 | 17.800 | 16.800 | 21.300 | 16.800 | 21.300 |
| average | 19.345 | 14.855 | 19.345 | 19.057 | 19.345 | 21.206 |
| stdev | 21.614 | 10.311 | 21.614 | 8.625 | 21.614 | 8.483 |
| p (t-test) |  | 0.150 |  | 0.924 |  | 0.683 |
| min | 1.890 | 1.810 | 1.890 | 2.170 | 1.890 | 2.780 |
| max | 251.000 | 41.100 | 251.000 | 39.600 | 251.000 | 39.800 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
| --- | --- | --- | --- | --- | --- |
| 0 hours | 0.47 | 0.042 | 257 | 56 | 0.486 |
| 24 hours | 0.65 | 0.041 | 257 | 61 | 0.000 |
| 48 hours | 0.66 | 0.061 | 257 | 26 | 0.010 | sCr only

| Time prior AKI stage | AUC | SE | nCohort 1 | nCohort 2 | p |
| --- | --- | --- | --- | --- | --- |
| 0 hours | 0.53 | 0.063 | 459 | 23 | 0.585 |
| 24 hours | 0.64 | 0.060 | 459 | 26 | 0.024 |
| 48 hours | 0.61 | 0.081 | 459 | 14 | 0.172 |

UO only

| Time prior AKI stage | AUC | SE | nCohort 1 | nCohort 2 | p |
| --- | --- | --- | --- | --- | --- |
| 0 hours | 0.45 | 0.044 | 213 | 51 | 0.250 |
| 24 hours | 0.61 | 0.045 | 213 | 53 | 0.019 |
| 48 hours | 0.66 | 0.065 | 213 | 23 | 0.014 |

Fig. 5 sCr or UO

| Time prior AKI stage | Cutoff value | sens | spec | Quartile | OR | 95% CI of OR | |
|---|---|---|---|---|---|---|---|
| 0 hours | 3.16 | 71% | 10% | 1 | | | |
| | 2.59 | 80% | 4% | 2 | 0.3 | 0.2 | 0.5 |
| | 2.08 | 91% | 0% | 3 | 0.2 | 0.1 | 0.4 |
| | 19.6 | 45% | 70% | 4 | 1.2 | 1.0 | 1.6 |
| | 22.8 | 32% | 81% | | | | |
| | 27.1 | 13% | 90% | | | | |
| 24 hours | 17.9 | 70% | 61% | 1 | | | |
| | 14.4 | 80% | 35% | 2 | 0.4 | 0.2 | 0.8 |
| | 3.12 | 90% | 9% | 3 | 1.8 | 1.3 | 2.6 |
| | 19.6 | 56% | 70% | 4 | 3.1 | 2.3 | 4.3 |
| | 22.8 | 44% | 81% | | | | |
| | 27.1 | 20% | 90% | | | | |
| 48 hours | 17.9 | 73% | 61% | 1 | | | |
| | 15.5 | 81% | 44% | 2 | 0.4 | 0.1 | 1.6 |
| | 3.47 | 92% | 12% | 3 | 1.4 | 0.7 | 3.0 |
| | 19.6 | 65% | 70% | 4 | 2.6 | 1.4 | 4.9 |
| | 22.8 | 35% | 81% | | | | |
| | 27.1 | 27% | 90% | | | | | sCr only

| Time prior AKI stage | Cutoff value | sens | spec | Quartile | OR | 95% CI of OR | |
|---|---|---|---|---|---|---|---|
| 0 hours | 4.27 | 74% | 17% | 1 | | | |
| | 3.66 | 83% | 15% | 2 | 0.2 | 0.1 | 0.7 |
| | 2.6 | 91% | 6% | 3 | 0.1 | 0.0 | 0.9 |
| | 20.5 | 52% | 70% | 4 | 1.2 | 0.8 | 1.9 |
| | 23.4 | 30% | 80% | | | | |
| | 27.4 | 17% | 90% | | | | |
| 24 hours | 17.5 | 73% | 54% | 1 | | | |
| | 17.1 | 81% | 53% | 2 | 0.2 | 0.0 | 2.9 |
| | 3.12 | 92% | 12% | 3 | 2.9 | 1.4 | 5.9 |
| | 20.5 | 46% | 70% | 4 | 2.6 | 1.3 | 5.4 |
| | 23.4 | 38% | 80% | | | | |
| | 27.4 | 19% | 90% | | | | |
| 48 hours | 18.3 | 71% | 59% | 1 | | | |
| | 3.37 | 86% | 14% | 2 | 0.0 | 0.0 | na |
| | 3.16 | 93% | 12% | 3 | 0.5 | 0.1 | 2.2 |
| | 20.5 | 57% | 70% | 4 | 2.1 | 1.0 | 4.4 |
| | 23.4 | 36% | 80% | | | | |
| | 27.4 | 21% | 90% | | | | |

UO only

| Time prior AKI stage | Cutoff value | sens | spec | Quartile | OR | 95% CI of OR | |
|---|---|---|---|---|---|---|---|
| 0 hours | 3.32 | 71% | 11% | 1 | | | |
| | 3.06 | 80% | 7% | 2 | 0.8 | 0.6 | 1.2 |
| | 2.08 | 90% | 0% | 3 | 0.4 | 0.2 | 0.6 |
| | 20.6 | 35% | 70% | 4 | 1.5 | 1.1 | 2.1 |
| | 22.9 | 25% | 80% | | | | |
| | 27.8 | 8% | 91% | | | | |
| 24 hours | 16.6 | 72% | 49% | 1 | | | |
| | 13.8 | 81% | 29% | 2 | 0.8 | 0.5 | 1.3 |
| | 3.47 | 91% | 11% | 3 | 1.4 | 0.9 | 2.1 |
| | 20.6 | 51% | 70% | 4 | 2.7 | 1.9 | 3.9 |
| | 22.9 | 42% | 80% | | | | |
| | 27.8 | 9% | 91% | | | | |

Fig. 5 Continued

| 48 hours | 17.9 | 74% | 56% | 1 | | | |
| | 15.5 | 83% | 40% | 2 | 1.0 | 0.3 | 4.0 |
| | 12.7 | 91% | 22% | 3 | 2.9 | 1.1 | 7.7 |
| | 20.6 | 61% | 70% | 4 | 3.4 | 1.3 | 8.6 |
| | 22.9 | 30% | 80% | | | | |
| | 27.8 | 22% | 91% | | | | |

CD40 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1.650 | 1.780 | 1.650 | 1.700 | 1.650 | 1.735 |
| average | 2.071 | 2.202 | 2.071 | 2.660 | 2.071 | 2.171 |
| stdev | 2.138 | 1.445 | 2.138 | 3.608 | 2.138 | 1.345 |
| p (t-test) | | 0.662 | | 0.097 | | 0.814 |
| min | 0.446 | 0.748 | 0.446 | 0.798 | 0.446 | 0.793 |
| max | 28.000 | 6.510 | 28.000 | 28.100 | 28.000 | 5.430 |
| n (Samp) | 257 | 56 | 257 | 61 | 257 | 26 |
| n (Pat) | 112 | 56 | 112 | 61 | 112 | 26 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1.610 | 2.470 | 1.610 | 2.090 | 1.610 | 1.995 |
| average | 2.076 | 3.101 | 2.076 | 3.507 | 2.076 | 2.468 |
| stdev | 1.883 | 1.798 | 1.883 | 5.192 | 1.883 | 1.246 |
| p (t-test) | | 0.011 | | 0.001 | | 0.440 |
| min | 0.446 | 0.959 | 0.446 | 1.060 | 0.446 | 1.240 |
| max | 28.000 | 6.650 | 28.000 | 28.100 | 28.000 | 5.430 |
| n (Samp) | 459 | 23 | 459 | 26 | 459 | 14 |
| n (Pat) | 180 | 23 | 180 | 26 | 180 | 14 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 1.610 | 1.770 | 1.610 | 1.700 | 1.610 | 1.690 |
| average | 1.946 | 2.235 | 1.946 | 2.287 | 1.946 | 2.135 |
| stdev | 1.153 | 1.457 | 1.153 | 1.479 | 1.153 | 1.436 |
| p (t-test) | | 0.129 | | 0.070 | | 0.467 |
| min | 0.541 | 0.748 | 0.541 | 0.798 | 0.541 | 0.793 |
| max | 6.610 | 6.510 | 6.610 | 6.600 | 6.610 | 6.350 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
|---|---|---|---|---|---|
| 0 hours | 0.54 | 0.043 | 257 | 56 | 0.299 |
| 24 hours | 0.56 | 0.042 | 257 | 61 | 0.174 |
| 48 hours | 0.54 | 0.061 | 257 | 26 | 0.511 | sCr only

| Time prior AKI stage | AUC | SE | nCohort 1 | nCohort 2 | p |
|---|---|---|---|---|---|
| 0 hours | 0.71 | 0.062 | 459 | 23 | 0.001 |
| 24 hours | 0.66 | 0.060 | 459 | 26 | 0.008 |
| 48 hours | 0.66 | 0.081 | 459 | 14 | 0.046 |

Fig. 5 Continued

UO only

| Time prior AKI stage | AUC | SE | nCohort 1 | nCohort 2 | p |
|---|---|---|---|---|---|
| 0 hours | 0.55 | 0.046 | 213 | 51 | 0.290 |
| 24 hours | 0.56 | 0.045 | 213 | 53 | 0.216 |
| 48 hours | 0.52 | 0.064 | 213 | 23 | 0.799 | sCr or UO

| Time prior AKI stage | Cutoff value | sens | spec | Quartile | OR | 95% CI of OR | |
|---|---|---|---|---|---|---|---|
| 0 hours | 1.28 | 71% | 33% | 1 | | | |
| | 1.13 | 80% | 28% | 2 | 1.5 | 1.0 | 2.1 |
| | 0.926 | 91% | 16% | 3 | 1.6 | 1.1 | 2.3 |
| | 2.22 | 32% | 70% | 4 | 1.3 | 0.9 | 1.9 |
| | 2.59 | 23% | 81% | | | | |
| | 3.31 | 16% | 90% | | | | |
| 24 hours | 1.37 | 70% | 38% | 1 | | | |
| | 1.23 | 80% | 32% | 2 | 2.3 | 1.6 | 3.3 |
| | 1.04 | 90% | 22% | 3 | 1.5 | 1.0 | 2.2 |
| | 2.22 | 28% | 70% | 4 | 1.9 | 1.3 | 2.7 |
| | 2.59 | 25% | 81% | | | | |
| | 3.31 | 20% | 90% | | | | |
| 48 hours | 1.16 | 73% | 28% | 1 | | | |
| | 1.13 | 81% | 28% | 2 | 2.1 | 0.9 | 4.6 |
| | 0.928 | 92% | 16% | 3 | 1.5 | 0.6 | 3.7 |
| | 2.22 | 35% | 70% | 4 | 2.1 | 0.9 | 4.6 |
| | 2.59 | 31% | 81% | | | | |
| | 3.31 | 19% | 90% | | | | | sCr only

| Time prior AKI stage | Cutoff value | sens | spec | Quartile | OR | 95% CI of OR | |
|---|---|---|---|---|---|---|---|
| 0 hours | 1.78 | 74% | 57% | 1 | | | |
| | 1.57 | 83% | 49% | 2 | 4.1 | 0.3 | 48.7 |
| | 1.2 | 91% | 30% | 3 | 6.3 | 0.6 | 63.8 |
| | 2.17 | 61% | 70% | 4 | 13.1 | 1.5 | 113.3 |
| | 2.63 | 43% | 80% | | | | |
| | 3.82 | 26% | 90% | | | | |
| 24 hours | 1.55 | 73% | 47% | 1 | | | |
| | 1.48 | 81% | 44% | 2 | 8.5 | 0.9 | 79.7 |
| | 1.29 | 92% | 35% | 3 | 7.4 | 0.8 | 71.6 |
| | 2.17 | 46% | 70% | 4 | 10.7 | 1.2 | 95.7 |
| | 2.63 | 38% | 80% | | | | |
| | 3.82 | 23% | 90% | | | | |
| 48 hours | 1.77 | 71% | 56% | 1 | | | |
| | 1.56 | 86% | 48% | 2 | na | na | na |
| | 1.31 | 93% | 36% | 3 | na | na | na |
| | 2.17 | 43% | 70% | 4 | na | na | na |
| | 2.63 | 29% | 80% | | | | |
| | 3.82 | 14% | 90% | | | | |

UO only

| Time prior AKI stage | Cutoff value | sens | spec | Quartile | OR | 95% CI of OR | |
|---|---|---|---|---|---|---|---|
| 0 hours | 1.41 | 71% | 38% | 1 | | | |
| | 1.13 | 80% | 26% | 2 | 1.1 | 0.7 | 1.7 |
| | 0.926 | 90% | 15% | 3 | 1.3 | 0.9 | 2.0 |
| | 2.2 | 31% | 70% | 4 | 1.3 | 0.9 | 2.0 |
| | 2.56 | 27% | 80% | | | | |
| | 3.3 | 18% | 90% | | | | |

Fig. 5 Continued

| 24 hours | 1.38 | 72% | 35% | 1 | | | |
|---|---|---|---|---|---|---|---|
| | 1.12 | 81% | 25% | 2 | 1.3 | 0.9 | 2.0 |
| | 1.03 | 91% | 21% | 3 | 1.2 | 0.8 | 1.8 |
| | 2.2 | 30% | 70% | 4 | 1.4 | 1.0 | 2.1 |
| | 2.56 | 26% | 80% | | | | |
| | 3.3 | 19% | 90% | | | | |
| 48 hours | 1.13 | 74% | 26% | 1 | | | |
| | 1.03 | 83% | 21% | 2 | 0.8 | 0.4 | 1.8 |
| | 0.905 | 91% | 14% | 3 | 0.8 | 0.4 | 1.8 |
| | 2.2 | 35% | 70% | 4 | 1.2 | 0.6 | 2.4 |
| | 2.56 | 30% | 80% | | | | |
| | 3.3 | 17% | 90% | | | | |

CD40 Ligand sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.324 | 0.259 | 0.324 | 0.281 | 0.324 | 0.304 |
| average | 0.492 | 0.381 | 0.492 | 0.347 | 0.492 | 0.370 |
| stdev | 0.501 | 0.343 | 0.501 | 0.356 | 0.501 | 0.300 |
| p (t-test) | | 0.118 | | 0.033 | | 0.224 |
| min | 0.019 | 0.025 | 0.019 | 0.000 | 0.019 | 0.063 |
| max | 4.030 | 1.280 | 4.030 | 2.510 | 4.030 | 1.280 |
| n (Samp) | 257 | 56 | 257 | 61 | 257 | 26 |
| n (Pat) | 112 | 56 | 112 | 61 | 112 | 26 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 0.290 | 0.283 | 0.290 | 0.332 | 0.290 | 0.316 |
| average | 0.446 | 0.453 | 0.446 | 0.353 | 0.446 | 0.442 |
| stdev | 0.463 | 0.456 | 0.463 | 0.260 | 0.463 | 0.317 |
| p (t-test) | | 0.947 | | 0.309 | | 0.974 |
| min | 0.000 | 0.028 | 0.000 | 0.020 | 0.000 | 0.069 |
| max | 4.030 | 1.810 | 4.030 | 1.110 | 4.030 | 1.060 |
| n (Samp) | 459 | 23 | 459 | 26 | 459 | 14 |
| n (Pat) | 180 | 23 | 180 | 26 | 180 | 14 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 0.319 | 0.220 | 0.319 | 0.261 | 0.319 | 0.301 |
| average | 0.503 | 0.339 | 0.503 | 0.378 | 0.503 | 0.324 |
| stdev | 0.525 | 0.308 | 0.525 | 0.393 | 0.525 | 0.276 |
| p (t-test) | | 0.033 | | 0.105 | | 0.109 |
| min | 0.019 | 0.025 | 0.019 | 0.000 | 0.019 | 0.063 |
| max | 4.030 | 1.260 | 4.030 | 2.510 | 4.030 | 1.280 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
|---|---|---|---|---|---|
| 0 hours | 0.42 | 0.041 | 257 | 56 | 0.064 |
| 24 hours | 0.41 | 0.039 | 257 | 61 | 0.019 |
| 48 hours | 0.44 | 0.057 | 257 | 26 | 0.270 |

Fig. 5 Continued sCr only

| Time prior AKI stage | AUC | SE | nCohort 1 | nCohort 2 | p |
|---|---|---|---|---|---|
| 0 hours | 0.50 | 0.062 | 459 | 23 | 0.996 |
| 24 hours | 0.47 | 0.057 | 459 | 26 | 0.607 |
| 48 hours | 0.55 | 0.080 | 459 | 14 | 0.544 |

UO only

| Time prior AKI stage | AUC | SE | nCohort 1 | nCohort 2 | p |
|---|---|---|---|---|---|
| 0 hours | 0.38 | 0.041 | 213 | 51 | 0.005 |
| 24 hours | 0.42 | 0.042 | 213 | 53 | 0.056 |
| 48 hours | 0.39 | 0.058 | 213 | 23 | 0.050 | sCr or UO

| Time prior AKI stage | Cutoff value | sens | spec | Quartile | OR | 95% CI of OR | |
|---|---|---|---|---|---|---|---|
| 0 hours | 0.13 | 71% | 16% | 1 | | | |
| | 0.0983 | 80% | 10% | 2 | 1.1 | 0.8 | 1.7 |
| | 0.0662 | 91% | 4% | 3 | 1.4 | 0.9 | 2.0 |
| | 0.579 | 25% | 70% | 4 | 2.0 | 1.4 | 2.8 |
| | 0.754 | 18% | 80% | | | | |
| | 1.02 | 9% | 90% | | | | |
| 24 hours | 0.162 | 70% | 21% | 1 | | | |
| | 0.116 | 80% | 14% | 2 | 4.8 | 3.0 | 7.7 |
| | 0.0728 | 90% | 4% | 3 | 2.4 | 1.4 | 4.1 |
| | 0.579 | 11% | 70% | 4 | 4.2 | 2.6 | 6.8 |
| | 0.754 | 5% | 80% | | | | |
| | 1.02 | 3% | 90% | | | | |
| 48 hours | 0.137 | 73% | 17% | 1 | | | |
| | 0.115 | 81% | 14% | 2 | 3.3 | 1.3 | 8.4 |
| | 0.0936 | 92% | 10% | 3 | 1.7 | 0.6 | 5.2 |
| | 0.579 | 19% | 70% | 4 | 3.3 | 1.3 | 8.5 |
| | 0.754 | 12% | 80% | | | | |
| | 1.02 | 4% | 90% | | | | | sCr only

| Time prior AKI stage | Cutoff value | sens | spec | Quartile | OR | 95% CI of OR | |
|---|---|---|---|---|---|---|---|
| 0 hours | 0.182 | 74% | 30% | 1 | | | |
| | 0.137 | 83% | 22% | 2 | 0.7 | 0.3 | 1.5 |
| | 0.0705 | 91% | 6% | 3 | 1.4 | 0.7 | 2.5 |
| | 0.508 | 26% | 70% | 4 | 0.8 | 0.4 | 1.8 |
| | 0.69 | 22% | 80% | | | | |
| | 0.995 | 13% | 90% | | | | |
| 24 hours | 0.151 | 73% | 25% | 1 | | | |
| | 0.115 | 81% | 17% | 2 | 4.0 | 1.7 | 9.4 |
| | 0.0587 | 92% | 4% | 3 | 1.7 | 0.6 | 5.0 |
| | 0.508 | 15% | 70% | 4 | 2.4 | 0.9 | 6.4 |
| | 0.69 | 12% | 80% | | | | |
| | 0.995 | 4% | 90% | | | | |
| 48 hours | 0.263 | 71% | 46% | 1 | | | |
| | 0.165 | 86% | 27% | 2 | 2.0 | 0.5 | 9.2 |
| | 0.0936 | 93% | 12% | 3 | 2.0 | 0.5 | 9.2 |
| | 0.508 | 36% | 70% | 4 | 2.0 | 0.4 | 9.1 |
| | 0.69 | 21% | 80% | | | | |
| | 0.995 | 7% | 90% | | | | |

Fig. 5 Continued

UO only

| Time prior AKI stage | Cutoff value | sens | spec | Quartile | OR | 95% CI of OR | |
|---|---|---|---|---|---|---|---|
| 0 hours | 0.114 | 71% | 11% | 1 | | | |
| | 0.0976 | 82% | 8% | 2 | 1.3 | 0.8 | 2.0 |
| | 0.0722 | 90% | 4% | 3 | 1.3 | 0.8 | 2.0 |
| | 0.579 | 20% | 71% | 4 | 2.8 | 1.9 | 4.1 |
| | 0.754 | 14% | 80% | | | | |
| | 1 | 8% | 90% | | | | |
| 24 hours | 0.164 | 72% | 21% | 1 | | | |
| | 0.116 | 81% | 11% | 2 | 2.4 | 1.5 | 3.7 |
| | 0.0871 | 91% | 7% | 3 | 1.8 | 1.1 | 2.8 |
| | 0.579 | 17% | 71% | 4 | 2.4 | 1.5 | 3.7 |
| | 0.754 | 9% | 80% | | | | |
| | 1 | 4% | 90% | | | | |
| 48 hours | 0.111 | 74% | 11% | 1 | | | |
| | 0.0976 | 83% | 8% | 2 | 4.5 | 1.2 | 16.4 |
| | 0.0794 | 91% | 5% | 3 | 2.1 | 0.4 | 9.7 |
| | 0.579 | 13% | 71% | 4 | 5.1 | 1.4 | 18.3 |
| | 0.754 | 4% | 80% | | | | |
| | 1 | 4% | 90% | | | | |

CXCL16 (C-X-C Motif chemokine 16)

sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 3.852 | 4.618 | 3.852 | 4.317 | 3.852 | 4.307 |
| average | 5.186 | 5.042 | 5.186 | 5.544 | 5.186 | 5.133 |
| stdev | 5.591 | 2.203 | 5.591 | 3.968 | 5.591 | 2.404 |
| p (t-test) | | 0.853 | | 0.657 | | 0.963 |
| min | 1.242 | 1.592 | 1.242 | 2.141 | 1.242 | 2.076 |
| max | 45.787 | 12.320 | 45.787 | 29.157 | 45.787 | 11.674 |
| n (Samp) | 158 | 55 | 158 | 57 | 158 | 25 |
| n (Pat) | 107 | 55 | 107 | 57 | 107 | 25 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 4.058 | 5.839 | 4.058 | 5.047 | 4.058 | 4.307 |
| average | 5.036 | 6.072 | 5.036 | 6.376 | 5.036 | 5.063 |
| stdev | 4.230 | 2.922 | 4.230 | 5.305 | 4.230 | 2.105 |
| p (t-test) | | 0.270 | | 0.143 | | 0.982 |
| min | 1.242 | 1.592 | 1.242 | 2.141 | 1.242 | 2.076 |
| max | 45.787 | 12.185 | 45.787 | 29.157 | 45.787 | 8.611 |
| n (Samp) | 320 | 21 | 320 | 24 | 320 | 13 |
| n (Pat) | 172 | 21 | 172 | 24 | 172 | 13 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 3.982 | 4.618 | 3.982 | 4.295 | 3.982 | 4.598 |
| average | 4.613 | 5.150 | 4.613 | 5.061 | 4.613 | 5.308 |
| stdev | 2.598 | 2.305 | 2.598 | 2.512 | 2.598 | 2.417 |
| p (t-test) | | 0.204 | | 0.310 | | 0.252 |
| min | 1.535 | 1.987 | 1.535 | 1.969 | 1.535 | 2.931 |
| max | 18.483 | 12.320 | 18.483 | 14.552 | 18.483 | 11.674 |
| n (Samp) | 134 | 49 | 134 | 46 | 134 | 21 |
| n (Pat) | 86 | 49 | 86 | 46 | 86 | 21 |

Fig. 5 Continued sCr or UO

| Time prior AKI stage | AUC | SE | nCohort 1 | nCohort 2 | p |
|---|---|---|---|---|---|
| 0 hours | 0.60 | 0.046 | 158 | 55 | 0.027 |
| 24 hours | 0.61 | 0.045 | 158 | 57 | 0.013 |
| 48 hours | 0.61 | 0.064 | 158 | 25 | 0.081 | sCr only

| Time prior AKI stage | AUC | SE | nCohort 1 | nCohort 2 | p |
|---|---|---|---|---|---|
| 0 hours | 0.66 | 0.067 | 320 | 21 | 0.020 |
| 24 hours | 0.63 | 0.063 | 320 | 24 | 0.039 |
| 48 hours | 0.56 | 0.084 | 320 | 13 | 0.448 |

UO only

| Time prior AKI stage | AUC | SE | nCohort 1 | nCohort 2 | p |
|---|---|---|---|---|---|
| 0 hours | 0.60 | 0.049 | 134 | 49 | 0.038 |
| 24 hours | 0.58 | 0.050 | 134 | 46 | 0.097 |
| 48 hours | 0.63 | 0.069 | 134 | 21 | 0.054 | sCr or UO

| Time prior AKI stage | Cutoff value | sens | spec | Quartile | OR | 95% CI of OR | |
|---|---|---|---|---|---|---|---|
| 0 hours | 3.90377 | 71% | 51% | 1 | | | |
| | 3.24708 | 80% | 37% | 2 | 1.5 | 0.9 | 2.5 |
| | 2.77434 | 91% | 23% | 3 | 2.7 | 1.7 | 4.2 |
| | 4.8617 | 44% | 70% | 4 | 3.1 | 2.0 | 4.8 |
| | 6.13027 | 25% | 80% | | | | |
| | 9.14286 | 4% | 91% | | | | |
| 24 hours | 3.82304 | 70% | 49% | 1 | | | |
| | 3.27035 | 81% | 39% | 2 | 4.0 | 2.2 | 7.4 |
| | 3.01327 | 91% | 32% | 3 | 4.8 | 2.6 | 8.7 |
| | 4.8617 | 35% | 70% | 4 | 4.8 | 2.6 | 8.7 |
| | 6.13027 | 26% | 80% | | | | |
| | 9.14286 | 9% | 91% | | | | |
| 48 hours | 3.90377 | 72% | 51% | 1 | | | |
| | 3.35756 | 80% | 41% | 2 | 7.9 | 0.8 | 81.6 |
| | 2.94658 | 92% | 29% | 3 | 13.8 | 1.5 | 129.7 |
| | 4.8617 | 28% | 70% | 4 | 6.6 | 0.6 | 71.3 |
| | 6.13027 | 24% | 80% | | | | |
| | 9.14286 | 12% | 91% | | | | | sCr only

| Time prior AKI stage | Cutoff value | sens | spec | Quartile | OR | 95% CI of OR | |
|---|---|---|---|---|---|---|---|
| 0 hours | 4.38298 | 71% | 59% | 1 | | | |
| | 3.90708 | 81% | 45% | 2 | 0.7 | 0.1 | 3.5 |
| | 1.98492 | 90% | 3% | 3 | 1.7 | 0.6 | 5.1 |
| | 4.91653 | 67% | 70% | 4 | 4.0 | 1.7 | 9.7 |
| | 6.13027 | 43% | 80% | | | | |
| | 8.44643 | 24% | 90% | | | | |
| 24 hours | 4.07242 | 71% | 51% | 1 | | | |
| | 3.74074 | 83% | 41% | 2 | 1.0 | 0.4 | 2.8 |
| | 2.88815 | 92% | 18% | 3 | 1.5 | 0.6 | 3.7 |
| | 4.91653 | 54% | 70% | 4 | 2.7 | 1.3 | 5.6 |
| | 6.13027 | 38% | 80% | | | | |
| | 8.44643 | 8% | 90% | | | | |

Fig. 5 Continued

| | | | | | | | |
|---|---|---|---|---|---|---|---|
| 48 hours | 3.44681 | 77% | 34% | 1 | | | |
| | 3.38663 | 85% | 34% | 2 | 1.5 | 0.3 | 8.2 |
| | 2.90484 | 92% | 19% | 3 | 1.5 | 0.3 | 8.2 |
| | 4.91653 | 38% | 70% | 4 | 2.6 | 0.6 | 10.6 |
| | 6.13027 | 31% | 80% | | | | |
| | 8.44643 | 8% | 90% | | | | |

UO only

| Time prior AKI stage | Cutoff value | sens | spec | Quartile | OR | 95% CI of OR | |
|---|---|---|---|---|---|---|---|
| 0 hours | 3.69783 | 71% | 43% | 1 | | | |
| | 3.16667 | 82% | 33% | 2 | 1.3 | 0.7 | 2.2 |
| | 2.77434 | 92% | 19% | 3 | 1.8 | 1.1 | 3.0 |
| | 4.85106 | 43% | 70% | 4 | 3.0 | 1.8 | 4.8 |
| | 5.86207 | 33% | 81% | | | | |
| | 7.75 | 14% | 90% | | | | |
| 24 hours | 3.44681 | 72% | 38% | 1 | | | |
| | 3.24708 | 83% | 34% | 2 | 3.6 | 1.9 | 6.9 |
| | 3.01327 | 91% | 28% | 3 | 3.6 | 1.9 | 6.9 |
| | 4.85106 | 33% | 70% | 4 | 3.3 | 1.7 | 6.2 |
| | 5.86207 | 26% | 81% | | | | |
| | 7.75 | 15% | 90% | | | | |
| 48 hours | 4.11111 | 71% | 56% | 1 | | | |
| | 3.85174 | 81% | 47% | 2 | 1.5 | 0.3 | 8.6 |
| | 3.125 | 90% | 32% | 3 | 7.1 | 2.0 | 25.5 |
| | 4.85106 | 29% | 70% | 4 | 2.6 | 0.6 | 11.7 |
| | 5.86207 | 24% | 81% | | | | |
| | 7.75 | 19% | 90% | | | | |

EN-RAGE sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 30.036 | 31.568 | 30.036 | 35.344 | 30.036 | 33.057 |
| average | 59.344 | 56.303 | 59.344 | 69.741 | 59.344 | 60.958 |
| stdev | 80.467 | 79.390 | 80.467 | 94.106 | 80.467 | 102.186 |
| p (t-test) | | 0.828 | | 0.465 | | 0.932 |
| min | 0.000 | 1.616 | 0.000 | 2.110 | 0.000 | 10.808 |
| max | 582.406 | 382.303 | 582.406 | 459.659 | 582.406 | 495.754 |
| n (Samp) | 105 | 48 | 105 | 55 | 105 | 25 |
| n (Pat) | 99 | 48 | 99 | 55 | 99 | 25 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 31.141 | 31.801 | 31.141 | 35.072 | 31.141 | 35.344 |
| average | 58.323 | 120.455 | 58.323 | 125.557 | 58.323 | 93.910 |
| stdev | 74.620 | 290.447 | 74.620 | 244.464 | 74.620 | 149.319 |
| p (t-test) | | 0.018 | | 0.003 | | 0.131 |
| min | 0.000 | 14.106 | 0.000 | 7.818 | 0.000 | 10.808 |
| max | 582.406 | 1187.203 | 582.406 | 1063.972 | 582.406 | 495.754 |
| n (Samp) | 241 | 16 | 241 | 20 | 241 | 12 |
| n (Pat) | 160 | 16 | 160 | 20 | 160 | 12 |

Fig. 5 Continued

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 31.141 | 33.225 | 31.141 | 35.344 | 31.141 | 30.771 |
| average | 50.562 | 61.845 | 50.562 | 65.595 | 50.562 | 44.883 |
| stdev | 54.476 | 86.260 | 54.476 | 84.886 | 54.476 | 52.186 |
| p (t-test) |  | 0.360 |  | 0.209 |  | 0.664 |
| min | 0.000 | 1.616 | 0.000 | 2.110 | 0.000 | 2.110 |
| max | 328.866 | 382.303 | 328.866 | 402.412 | 328.866 | 260.355 |
| n (Samp) | 96 | 40 | 96 | 44 | 96 | 21 |
| n (Pat) | 84 | 40 | 84 | 44 | 84 | 21 | sCr or UO

| Time prior AKI stage | AUC | SE | nCohort 1 | nCohort 2 | p |
| --- | --- | --- | --- | --- | --- |
| 0 hours | 0.52 | 0.051 | 105 | 48 | 0.721 |
| 24 hours | 0.54 | 0.048 | 105 | 55 | 0.396 |
| 48 hours | 0.54 | 0.065 | 105 | 25 | 0.583 | sCr only

| Time prior AKI stage | AUC | SE | nCohort 1 | nCohort 2 | p |
| --- | --- | --- | --- | --- | --- |
| 0 hours | 0.53 | 0.076 | 241 | 16 | 0.703 |
| 24 hours | 0.57 | 0.069 | 241 | 20 | 0.316 |
| 48 hours | 0.55 | 0.088 | 241 | 12 | 0.541 |

UO only

| Time prior AKI stage | AUC | SE | nCohort 1 | nCohort 2 | p |
| --- | --- | --- | --- | --- | --- |
| 0 hours | 0.53 | 0.055 | 96 | 40 | 0.569 |
| 24 hours | 0.54 | 0.053 | 96 | 44 | 0.503 |
| 48 hours | 0.51 | 0.070 | 96 | 21 | 0.838 | sCr or UO

| Time prior AKI stage | Cutoff value | sens | spec | Quartile | OR | 95% CI of OR | |
| --- | --- | --- | --- | --- | --- | --- | --- |
| 0 hours | 19.6509 | 71% | 36% | 1 |  |  |  |
|  | 16.8608 | 83% | 27% | 2 | 2.4 | 1.4 | 4.1 |
|  | 14.0877 | 92% | 19% | 3 | 2.7 | 1.6 | 4.6 |
|  | 58.6806 | 29% | 70% | 4 | 1.1 | 0.6 | 2.0 |
|  | 84.9421 | 10% | 80% |  |  |  |  |
|  | 134.68 | 6% | 90% |  |  |  |  |
| 24 hours | 21.5526 | 71% | 39% | 1 |  |  |  |
|  | 16.3715 | 80% | 26% | 2 | 0.9 | 0.5 | 1.4 |
|  | 9.71827 | 91% | 10% | 3 | 1.9 | 1.2 | 2.9 |
|  | 58.6806 | 33% | 70% | 4 | 1.3 | 0.8 | 2.0 |
|  | 84.9421 | 22% | 80% |  |  |  |  |
|  | 134.68 | 13% | 90% |  |  |  |  |
| 48 hours | 26.0385 | 72% | 44% | 1 |  |  |  |
|  | 22.4747 | 80% | 40% | 2 | 3.1 | 1.1 | 8.8 |
|  | 16.3715 | 92% | 26% | 3 | 5.1 | 1.9 | 13.7 |
|  | 58.6806 | 12% | 70% | 4 | 1.0 | 0.2 | 4.1 |
|  | 84.9421 | 8% | 80% |  |  |  |  |
|  | 134.68 | 8% | 90% |  |  |  |  |

Fig. 5 Continued sCr only

| Time prior AKI stage | Cutoff value | sens | spec | Quartile | OR | 95% CI of OR | |
|---|---|---|---|---|---|---|---|
| 0 hours | 22.3226 | 75% | 34% | 1 | | | |
| | 19.1976 | 81% | 30% | 2 | 1.7 | 0.6 | 5.2 |
| | 15.5297 | 94% | 17% | 3 | 1.4 | 0.4 | 4.5 |
| | 58.0358 | 25% | 70% | 4 | 1.3 | 0.4 | 4.5 |
| | 78.2277 | 19% | 80% | | | | |
| | 134.68 | 13% | 90% | | | | |
| 24 hours | 25.3309 | 70% | 38% | 1 | | | |
| | 18.7129 | 80% | 28% | 2 | 1.7 | 0.6 | 5.2 |
| | 11.7707 | 90% | 11% | 3 | 1.0 | 0.3 | 3.9 |
| | 58.0358 | 45% | 70% | 4 | 3.3 | 1.3 | 8.3 |
| | 78.2277 | 35% | 80% | | | | |
| | 134.68 | 15% | 90% | | | | |
| 48 hours | 25.3309 | 75% | 38% | 1 | | | |
| | 21.107 | 83% | 34% | 2 | 4.2 | 0.3 | 52.0 |
| | 20.0521 | 92% | 32% | 3 | 4.2 | 0.3 | 52.0 |
| | 58.0358 | 25% | 70% | 4 | 3.0 | 0.2 | 44.3 |
| | 78.2277 | 17% | 80% | | | | |
| | 134.68 | 17% | 90% | | | | |

UO only

| Time prior AKI stage | Cutoff value | sens | spec | Quartile | OR | 95% CI of OR | |
|---|---|---|---|---|---|---|---|
| 0 hours | 19.6509 | 70% | 34% | 1 | | | |
| | 16.8608 | 83% | 26% | 2 | 1.6 | 0.9 | 2.8 |
| | 15.5297 | 90% | 23% | 3 | 1.8 | 1.0 | 3.1 |
| | 50.1062 | 38% | 71% | 4 | 1.2 | 0.6 | 2.2 |
| | 73.4569 | 15% | 80% | | | | |
| | 130.779 | 8% | 91% | | | | |
| 24 hours | 21.5526 | 70% | 36% | 1 | | | |
| | 15.5297 | 86% | 23% | 2 | 1.0 | 0.6 | 1.7 |
| | 9.71827 | 91% | 9% | 3 | 1.5 | 0.9 | 2.5 |
| | 50.1062 | 34% | 71% | 4 | 1.1 | 0.7 | 2.0 |
| | 73.4569 | 23% | 80% | | | | |
| | 130.779 | 14% | 91% | | | | |
| 48 hours | 26.0385 | 71% | 41% | 1 | | | |
| | 21.107 | 81% | 36% | 2 | 3.3 | 1.1 | 9.6 |
| | 16.3715 | 90% | 25% | 3 | 2.8 | 0.9 | 8.3 |
| | 50.1062 | 19% | 71% | 4 | 1.0 | 0.2 | 4.1 |
| | 73.4569 | 5% | 80% | | | | |
| | 130.779 | 5% | 91% | | | | |

Fig. 5 Continued

Eotaxin sCr or UO

|         | 0 hr prior to AKI stage | | 24 hr prior to AKI stage | | 48 hr prior to AKI stage | |
|---|---|---|---|---|---|---|
|         | Cohort 1 | Cohort 2 | Cohort 1 | Cohort 2 | Cohort 1 | Cohort 2 |
| median  | 49.900 | 66.000 | 49.900 | 64.700 | 49.900 | 60.000 |
| average | 71.683 | 83.606 | 71.683 | 75.930 | 71.683 | 79.620 |
| stdev   | 69.575 | 68.019 | 69.575 | 55.806 | 69.575 | 56.883 |
| p (t-test) |     | 0.244 |        | 0.657 |        | 0.574 |
| min     | 0.410 | 0.410 | 0.410 | 0.410 | 0.410 | 0.410 |
| max     | 441.000 | 373.000 | 441.000 | 335.000 | 441.000 | 239.000 |
| n (Samp) | 257 | 56 | 257 | 61 | 257 | 26 |
| n (Pat) | 112 | 56 | 112 | 61 | 112 | 26 | sCr only

|         | 0 hr prior to AKI stage | | 24 hr prior to AKI stage | | 48 hr prior to AKI stage | |
|---|---|---|---|---|---|---|
|         | Cohort 1 | Cohort 2 | Cohort 1 | Cohort 2 | Cohort 1 | Cohort 2 |
| median  | 56.800 | 64.400 | 56.800 | 48.250 | 56.800 | 90.800 |
| average | 76.222 | 74.500 | 76.222 | 73.569 | 76.222 | 106.486 |
| stdev   | 86.693 | 41.650 | 86.693 | 56.158 | 86.693 | 91.355 |
| p (t-test) |     | 0.925 |        | 0.878 |        | 0.200 |
| min     | 0.410 | 25.100 | 0.410 | 11.500 | 0.410 | 25.100 |
| max     | 1240.000 | 197.000 | 1240.000 | 212.000 | 1240.000 | 391.000 |
| n (Samp) | 459 | 23 | 459 | 26 | 459 | 14 |
| n (Pat) | 180 | 23 | 180 | 26 | 180 | 14 |

UO only

|         | 0 hr prior to AKI stage | | 24 hr prior to AKI stage | | 48 hr prior to AKI stage | |
|---|---|---|---|---|---|---|
|         | Cohort 1 | Cohort 2 | Cohort 1 | Cohort 2 | Cohort 1 | Cohort 2 |
| median  | 53.100 | 71.600 | 53.100 | 65.300 | 53.100 | 60.000 |
| average | 74.094 | 88.906 | 74.094 | 81.127 | 74.094 | 83.474 |
| stdev   | 71.367 | 69.790 | 71.367 | 59.419 | 71.367 | 61.817 |
| p (t-test) |     | 0.182 |        | 0.508 |        | 0.545 |
| min     | 0.410 | 0.410 | 0.410 | 0.410 | 0.410 | 0.410 |
| max     | 441.000 | 373.000 | 441.000 | 335.000 | 441.000 | 239.000 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
|---|---|---|---|---|---|
| 0 hours  | 0.59 | 0.043 | 257 | 56 | 0.039 |
| 24 hours | 0.57 | 0.042 | 257 | 61 | 0.111 |
| 48 hours | 0.59 | 0.061 | 257 | 26 | 0.143 | sCr only

| Time prior AKI stage | AUC | SE | nCohort 1 | nCohort 2 | p |
|---|---|---|---|---|---|
| 0 hours  | 0.57 | 0.063 | 459 | 23 | 0.301 |
| 24 hours | 0.51 | 0.058 | 459 | 26 | 0.926 |
| 48 hours | 0.66 | 0.081 | 459 | 14 | 0.046 |

UO only

| Time prior AKI stage | AUC | SE | nCohort 1 | nCohort 2 | p |
|---|---|---|---|---|---|
| 0 hours  | 0.60 | 0.046 | 213 | 51 | 0.023 |
| 24 hours | 0.58 | 0.045 | 213 | 53 | 0.087 |
| 48 hours | 0.58 | 0.065 | 213 | 23 | 0.239 |

Fig. 5 Continued sCr or UO

| Time prior AKI stage | Cutoff value | sens | spec | Quartile | OR | 95% CI of OR | |
|---|---|---|---|---|---|---|---|
| 0 hours | 47.5 | 71% | 46% | 1 | | | |
| | 39.5 | 80% | 39% | 2 | 1.8 | 1.1 | 2.8 |
| | 24.9 | 93% | 18% | 3 | 2.6 | 1.7 | 4.0 |
| | 77.9 | 38% | 71% | 4 | 2.4 | 1.6 | 3.7 |
| | 99.9 | 27% | 80% | | | | |
| | 158 | 11% | 90% | | | | |
| 24 hours | 46.5 | 72% | 45% | 1 | | | |
| | 31.9 | 80% | 29% | 2 | 1.6 | 1.1 | 2.3 |
| | 20.2 | 90% | 16% | 3 | 2.0 | 1.4 | 2.9 |
| | 77.9 | 36% | 71% | 4 | 2.0 | 1.4 | 2.9 |
| | 99.9 | 25% | 80% | | | | |
| | 158 | 5% | 90% | | | | |
| 48 hours | 43.5 | 73% | 42% | 1 | | | |
| | 39.5 | 81% | 39% | 2 | 3.7 | 1.0 | 13.9 |
| | 30.6 | 92% | 28% | 3 | 3.7 | 1.0 | 13.9 |
| | 77.9 | 42% | 71% | 4 | 5.6 | 1.6 | 19.2 |
| | 99.9 | 31% | 80% | | | | |
| | 158 | 8% | 90% | | | | | sCr only

| Time prior AKI stage | Cutoff value | sens | spec | Quartile | OR | 95% CI of OR | |
|---|---|---|---|---|---|---|---|
| 0 hours | 47.5 | 74% | 41% | 1 | | | |
| | 46.5 | 83% | 40% | 2 | 10.7 | 1.2 | 95.8 |
| | 32.8 | 96% | 27% | 3 | 7.4 | 0.8 | 71.6 |
| | 81.5 | 35% | 70% | 4 | 5.1 | 0.5 | 55.7 |
| | 104 | 17% | 80% | | | | |
| | 156 | 9% | 90% | | | | |
| 24 hours | 31.8 | 77% | 26% | 1 | | | |
| | 27.3 | 92% | 19% | 2 | 1.4 | 0.7 | 2.5 |
| | 27.3 | 92% | 19% | 3 | 0.8 | 0.4 | 1.8 |
| | 81.5 | 31% | 70% | 4 | 1.2 | 0.6 | 2.2 |
| | 104 | 27% | 80% | | | | |
| | 156 | 12% | 90% | | | | |
| 48 hours | 60 | 71% | 53% | 1 | | | |
| | 43.5 | 86% | 37% | 2 | 2.0 | 0.1 | 39.5 |
| | 39.5 | 93% | 34% | 3 | 4.1 | 0.3 | 49.2 |
| | 81.5 | 57% | 70% | 4 | 7.3 | 0.8 | 71.1 |
| | 104 | 36% | 80% | | | | |
| | 156 | 14% | 90% | | | | |

UO only

| Time prior AKI stage | Cutoff value | sens | spec | Quartile | OR | 95% CI of OR | |
|---|---|---|---|---|---|---|---|
| 0 hours | 57.1 | 71% | 54% | 1 | | | |
| | 46.4 | 80% | 43% | 2 | 1.3 | 0.8 | 2.3 |
| | 24.9 | 92% | 17% | 3 | 3.9 | 2.5 | 6.2 |
| | 85.7 | 37% | 70% | 4 | 2.3 | 1.4 | 3.7 |
| | 107 | 22% | 80% | | | | |
| | 154 | 12% | 90% | | | | |
| 24 hours | 49.6 | 74% | 49% | 1 | | | |
| | 38.4 | 81% | 31% | 2 | 1.4 | 0.9 | 2.3 |
| | 20.2 | 91% | 16% | 3 | 2.7 | 1.8 | 4.2 |
| | 85.7 | 34% | 70% | 4 | 2.3 | 1.5 | 3.5 |
| | 107 | 26% | 80% | | | | |
| | 154 | 9% | 90% | | | | |

Fig. 5 Continued

| 48 hours | 46.5 | 74% | 43% | 1 | | | |
| | 30.6 | 91% | 26% | 2 | 2.1 | 0.7 | 6.1 |
| | 30.6 | 91% | 26% | 3 | 2.1 | 0.7 | 6.1 |
| | 85.7 | 39% | 70% | 4 | 2.9 | 1.1 | 7.7 |
| | 107 | 35% | 80% | | | | |
| | 154 | 9% | 90% | | | | |

E-selectin sCr or UO

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 8.249 | 11.058 | 8.249 | 9.903 | 8.249 | na |
| average | 9.294 | 13.658 | 9.294 | 12.397 | 9.294 | na |
| stdev | 4.547 | 12.009 | 4.547 | 9.779 | 4.547 | na |
| p (t-test) | | 0.128 | | 0.167 | | na |
| min | 3.422 | 4.738 | 3.422 | 2.991 | 3.422 | na |
| max | 18.492 | 42.140 | 18.492 | 46.625 | 18.492 | na |
| n (Samp) | 26 | 8 | 26 | 17 | 26 | 0 |
| n (Pat) | 25 | 8 | 25 | 17 | 25 | 0 | sCr only

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 8.873 | 8.860 | 8.873 | 9.903 | 8.873 | 1.155 |
| average | 11.125 | 8.860 | 11.125 | 11.525 | 11.125 | 12.197 |
| stdev | 9.118 | 2.367 | 9.118 | 6.821 | 9.118 | na |
| p (t-test) | | 0.730 | | 0.901 | | na |
| min | 1.155 | 7.186 | 1.155 | 2.991 | 1.155 | 12.197 |
| max | 46.625 | 10.534 | 46.625 | 23.028 | 46.625 | 12.197 |
| n (Samp) | 47 | 2 | 47 | 9 | 47 | 1 |
| n (Pat) | 44 | 2 | 44 | 9 | 44 | 1 |

UO only

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 7.319 | 11.583 | 7.319 | 11.364 | 7.319 | 3.422 |
| average | 8.665 | 14.583 | 8.665 | 13.640 | 8.665 | 19.984 |
| stdev | 4.060 | 12.660 | 4.060 | 11.375 | 4.060 | na |
| p (t-test) | | 0.042 | | 0.052 | | na |
| min | 3.422 | 4.738 | 3.422 | 5.709 | 3.422 | 19.984 |
| max | 18.141 | 42.140 | 18.141 | 46.625 | 18.141 | 19.984 |
| n (Samp) | 27 | 7 | 27 | 11 | 27 | 1 |
| n (Pat) | 25 | 7 | 25 | 11 | 25 | 1 | sCr or UO

| Time prior AKI stage | AUC | SE | nCohort 1 | nCohort 2 | p |
|---|---|---|---|---|---|
| 0 hours | 0.60 | 0.119 | 26 | 8 | 0.398 |
| 24 hours | 0.60 | 0.090 | 26 | 17 | 0.247 |
| 48 hours | nd | nd | 26 | 0 | nd | sCr only

| Time prior AKI stage | AUC | SE | nCohort 1 | nCohort 2 | p |
|---|---|---|---|---|---|
| 0 hours | 0.50 | 0.211 | 47 | 2 | 1.000 |
| 24 hours | 0.56 | 0.108 | 47 | 9 | 0.606 |
| 48 hours | 0.68 | 0.301 | 47 | 1 | 0.548 |

Fig. 5 Continued

UO only

| Time prior AKI stage | AUC | SE | nCohort 1 | nCohort 2 | p |
|---|---|---|---|---|---|
| 0 hours | 0.66 | 0.124 | 27 | 7 | 0.207 |
| 24 hours | 0.69 | 0.101 | 27 | 11 | 0.063 |
| 48 hours | 1.00 | 0.000 | 27 | 1 | nd | sCr or UO

| Time prior AKI stage | Cutoff value | sens | spec | Quartile | OR | 95% CI of OR | |
|---|---|---|---|---|---|---|---|
| 0 hours | 6.92209 | 75% | 42% | 1 | | | |
| | 5.50832 | 88% | 31% | 2 | 2.0 | 0.1 | 66.2 |
| | 4.19113 | 100% | 12% | 3 | 2.3 | 0.1 | 81.0 |
| | 12.1661 | 38% | 73% | 4 | 3.5 | 0.1 | 87.6 |
| | 13.0751 | 25% | 81% | | | | |
| | 17.2592 | 13% | 92% | | | | |
| 24 hours | 8.15542 | 71% | 50% | 1 | | | |
| | 5.92073 | 82% | 31% | 2 | 3.3 | 0.5 | 23.3 |
| | 5.50832 | 94% | 31% | 3 | 3.3 | 0.5 | 23.3 |
| | 12.1661 | 35% | 73% | 4 | 3.3 | 0.5 | 23.3 |
| | 13.0751 | 29% | 81% | | | | |
| | 17.2592 | 12% | 92% | | | | |
| 48 hours | na | na | na | 1 | | | |
| | na | na | na | 2 | na | na | na |
| | na | na | na | 3 | na | na | na |
| | na | na | na | 4 | na | na | na |
| | na | na | na | | | | |
| | na | na | na | | | | | sCr only

| Time prior AKI stage | Cutoff value | sens | spec | Quartile | OR | 95% CI of OR | |
|---|---|---|---|---|---|---|---|
| 0 hours | 7.17611 | 100% | 40% | 1 | | | |
| | 7.17611 | 100% | 40% | 2 | na | na | na |
| | 7.17611 | 100% | 40% | 3 | na | na | na |
| | 12.427 | 0% | 70% | 4 | na | na | na |
| | 14.0922 | 0% | 81% | | | | |
| | 18.1406 | 0% | 91% | | | | |
| 24 hours | 5.78981 | 78% | 28% | 1 | | | |
| | 5.77974 | 89% | 28% | 2 | 3.5 | 0.2 | 67.2 |
| | 1.15465 | 100% | 2% | 3 | 2.2 | 0.1 | 56.1 |
| | 12.427 | 33% | 70% | 4 | 3.5 | 0.2 | 67.2 |
| | 14.0922 | 33% | 81% | | | | |
| | 18.1406 | 22% | 91% | | | | |
| 48 hours | 12.1661 | 100% | 68% | 1 | | | |
| | 12.1661 | 100% | 68% | 2 | na | na | na |
| | 12.1661 | 100% | 68% | 3 | na | na | na |
| | 12.427 | 0% | 70% | 4 | na | na | na |
| | 14.0922 | 0% | 81% | | | | |
| | 18.1406 | 0% | 91% | | | | |

UO only

| Time prior AKI stage | Cutoff value | sens | spec | Quartile | OR | 95% CI of OR | |
|---|---|---|---|---|---|---|---|
| 0 hours | 9.84124 | 71% | 70% | 1 | | | |
| | 5.50832 | 86% | 30% | 2 | 0.9 | 0.0 | 74.5 |
| | 4.19113 | 100% | 11% | 3 | 2.3 | 0.1 | 81.0 |
| | 9.84124 | 71% | 70% | 4 | 3.5 | 0.1 | 87.6 |
| | 12.1661 | 43% | 81% | | | | |
| | 14.7546 | 14% | 93% | | | | |

Fig. 5 Continued

| 24 hours | | 8.15542 | 73% | 56% | 1 | | | |
|---|---|---|---|---|---|---|---|---|
| | | 7.62421 | 82% | 56% | 2 | 3.4 | 0.1 | 79.1 |
| | | 5.92073 | 91% | 33% | 3 | 2.3 | 0.1 | 73.1 |
| | | 9.84124 | 55% | 70% | 4 | 8.0 | 0.4 | 158.9 |
| | | 12.1661 | 45% | 81% | | | | |
| | | 14.7546 | 9% | 93% | | | | |
| 48 hours | | 18.1406 | 100% | 100% | 1 | | | |
| | | 18.1406 | 100% | 100% | 2 | na | na | na |
| | | 18.1406 | 100% | 100% | 3 | na | na | na |
| | | 9.84124 | 100% | 70% | 4 | na | na | na |
| | | 12.1661 | 100% | 81% | | | | |
| | | 14.7546 | 100% | 93% | | | | |

Fibronectin sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 270138.890 | 233942.280 | 270138.890 | 227286.327 | 270138.890 | na |
| average | 275736.272 | 269443.010 | 275736.272 | 231194.180 | 275736.272 | na |
| stdev | 96995.024 | 169671.512 | 96995.024 | 85217.221 | 96995.024 | na |
| p (t-test) | | 0.895 | | 0.131 | | na |
| min | 56713.581 | 123404.707 | 56713.581 | 98880.874 | 56713.581 | na |
| max | 467390.708 | 620512.175 | 467390.708 | 389123.937 | 467390.708 | na |
| n (Samp) | 26 | 8 | 26 | 17 | 26 | 0 |
| n (Pat) | 25 | 8 | 25 | 17 | 25 | 0 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 238191.877 | 311320.553 | 238191.877 | 336115.111 | 238191.877 | 56713.581 |
| average | 255705.979 | 311320.553 | 255705.979 | 296245.196 | 255705.979 | 375418.393 |
| stdev | 117051.065 | 115439.239 | 117051.065 | 85659.532 | 117051.065 | na |
| p (t-test) | | 0.514 | | 0.328 | | na |
| min | 56713.581 | 229692.684 | 56713.581 | 128509.435 | 56713.581 | 375418.393 |
| max | 620512.175 | 392948.422 | 620512.175 | 389123.937 | 620512.175 | 375418.393 |
| n (Samp) | 47 | 2 | 47 | 9 | 47 | 1 |
| n (Pat) | 44 | 2 | 44 | 9 | 44 | 1 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 259659.017 | 238191.877 | 259659.017 | 182445.159 | 259659.017 | 56713.581 |
| average | 268537.793 | 275121.628 | 268537.793 | 177628.468 | 268537.793 | 185343.308 |
| stdev | 88409.373 | 182443.206 | 88409.373 | 43351.547 | 88409.373 | na |
| p (t-test) | | 0.891 | | 0.003 | | na |
| min | 56713.581 | 123404.707 | 56713.581 | 98880.874 | 56713.581 | 185343.308 |
| max | 413982.406 | 620512.175 | 413982.406 | 229692.684 | 413982.406 | 185343.308 |
| n (Samp) | 27 | 7 | 27 | 11 | 27 | 1 |
| n (Pat) | 25 | 7 | 25 | 11 | 25 | 1 | sCr or UO

| Time prior AKI stage | AUC | SE | nCohort 1 | nCohort 2 | p |
|---|---|---|---|---|---|
| 0 hours | 0.40 | 0.112 | 26 | 8 | 0.390 |
| 24 hours | 0.35 | 0.084 | 26 | 17 | 0.071 |
| 48 hours | nd | nd | 26 | 0 | nd |

Fig. 5 Continued sCr only

| Time prior AKI stage | AUC | SE | nCohort 1 | nCohort 2 | p |
|---|---|---|---|---|---|
| 0 hours | 0.66 | 0.216 | 47 | 2 | 0.460 |
| 24 hours | 0.65 | 0.107 | 47 | 9 | 0.174 |
| 48 hours | 0.85 | 0.244 | 47 | 1 | 0.151 |

UO only

| Time prior AKI stage | AUC | SE | nCohort 1 | nCohort 2 | p |
|---|---|---|---|---|---|
| 0 hours | 0.43 | 0.119 | 27 | 7 | 0.549 |
| 24 hours | 0.16 | 0.065 | 27 | 11 | 0.000 |
| 48 hours | 0.15 | 0.143 | 27 | 1 | 0.014 | sCr or UO

| Time prior AKI stage | Cutoff value | sens | spec | Quartile | OR | 95% CI of OR | |
|---|---|---|---|---|---|---|---|
| 0 hours | 130291 | 75% | 8% | 1 | | | |
| | 126889 | 88% | 8% | 2 | 0.5 | 0.0 | 16.6 |
| | 56713.6 | 100% | 4% | 3 | 1.0 | 0.1 | 12.4 |
| | 326303 | 25% | 73% | 4 | 2.1 | 0.2 | 21.1 |
| | 355014 | 25% | 81% | | | | |
| | 406971 | 13% | 92% | | | | |
| 24 hours | 175438 | 71% | 15% | 1 | | | |
| | 154791 | 82% | 15% | 2 | 0.2 | 0.0 | 3.3 |
| | 98880.9 | 94% | 4% | 3 | 2.1 | 0.5 | 9.3 |
| | 326303 | 24% | 73% | 4 | 2.6 | 0.5 | 12.8 |
| | 355014 | 6% | 81% | | | | |
| | 406971 | 0% | 92% | | | | |
| 48 hours | na | na | na | 1 | | | |
| | na | na | na | 2 | na | na | na |
| | na | na | na | 3 | na | na | na |
| | na | na | na | 4 | na | na | na |
| | na | na | na | | | | |
| | na | na | na | | | | | sCr only

| Time prior AKI stage | Cutoff value | sens | spec | Quartile | OR | 95% CI of OR | |
|---|---|---|---|---|---|---|---|
| 0 hours | 228409 | 100% | 47% | 1 | | | |
| | 228409 | 100% | 47% | 2 | na | na | na |
| | 228409 | 100% | 47% | 3 | na | na | na |
| | 301476 | 50% | 70% | 4 | na | na | na |
| | 344569 | 50% | 81% | | | | |
| | 413982 | 0% | 91% | | | | |
| 24 hours | 228409 | 78% | 47% | 1 | | | |
| | 222232 | 89% | 45% | 2 | 2.2 | 0.1 | 56.1 |
| | 126889 | 100% | 13% | 3 | 2.2 | 0.1 | 56.1 |
| | 301476 | 56% | 70% | 4 | 5.2 | 0.3 | 85.2 |
| | 344569 | 44% | 81% | | | | |
| | 413982 | 0% | 91% | | | | |
| 48 hours | 362587 | 100% | 85% | 1 | | | |
| | 362587 | 100% | 85% | 2 | na | na | na |
| | 362587 | 100% | 85% | 3 | na | na | na |
| | 301476 | 100% | 70% | 4 | na | na | na |
| | 344569 | 100% | 81% | | | | |
| | 413982 | 0% | 91% | | | | |

Fig. 5 Continued

UO only

| Time prior AKI stage | Cutoff value | sens | spec | Quartile | OR | 95% CI of OR | |
|---|---|---|---|---|---|---|---|
| 0 hours | 130291 | 71% | 7% | 1 | | | |
| | 126889 | 86% | 7% | 2 | 0.5 | 0.0 | 16.6 |
| | 56713.6 | 100% | 4% | 3 | 0.4 | 0.0 | 14.0 |
| | 311697 | 29% | 70% | 4 | 2.1 | 0.2 | 21.1 |
| | 351984 | 29% | 81% | | | | |
| | 398685 | 14% | 93% | | | | |
| 24 hours | 154791 | 73% | 15% | 1 | | | |
| | 126889 | 82% | 7% | 2 | na | na | na |
| | 98880.9 | 91% | 4% | 3 | na | na | na |
| | 311697 | 0% | 70% | 4 | na | na | na |
| | 351984 | 0% | 81% | | | | |
| | 398685 | 0% | 93% | | | | |
| 48 hours | 154791 | 100% | 15% | 1 | | | |
| | 154791 | 100% | 15% | 2 | na | na | na |
| | 154791 | 100% | 15% | 3 | na | na | na |
| | 311697 | 0% | 70% | 4 | na | na | na |
| | 351984 | 0% | 81% | | | | |
| | 398685 | 0% | 93% | | | | |

Granulocyte colony-stimulating factor sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 17.800 | 27.600 | 17.800 | 30.700 | 17.800 | 34.800 |
| average | 57.285 | 89.398 | 57.285 | 238.639 | 57.285 | 749.138 |
| stdev | 263.830 | 294.771 | 263.830 | 619.325 | 263.830 | 2338.868 |
| p (t-test) | | 0.420 | | 0.000 | | 0.000 |
| min | 0.050 | 2.130 | 0.050 | 2.490 | 0.050 | 4.400 |
| max | 3280.000 | 2200.000 | 3280.000 | 3330.000 | 3280.000 | 11103.000 |
| n (Samp) | 257 | 56 | 257 | 61 | 257 | 26 |
| n (Pat) | 112 | 56 | 112 | 61 | 112 | 26 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 20.700 | 23.800 | 20.700 | 22.000 | 20.700 | 16.000 |
| average | 158.817 | 48.129 | 158.817 | 202.845 | 158.817 | 372.577 |
| stdev | 932.655 | 62.474 | 932.655 | 437.559 | 932.655 | 1323.290 |
| p (t-test) | | 0.570 | | 0.811 | | 0.405 |
| min | 0.050 | 2.130 | 0.050 | 2.490 | 0.050 | 4.400 |
| max | 11103.000 | 296.000 | 11103.000 | 1870.000 | 11103.000 | 4970.000 |
| n (Samp) | 459 | 23 | 459 | 26 | 459 | 14 |
| n (Pat) | 180 | 23 | 180 | 26 | 180 | 14 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 20.200 | 25.000 | 20.200 | 30.400 | 20.200 | 34.900 |
| average | 88.576 | 90.326 | 88.576 | 346.606 | 88.576 | 636.291 |
| stdev | 446.150 | 307.321 | 446.150 | 1051.479 | 446.150 | 2309.734 |
| p (t-test) | | 0.979 | | 0.007 | | 0.003 |
| min | 0.050 | 2.750 | 0.050 | 6.110 | 0.050 | 9.100 |
| max | 4970.000 | 2200.000 | 4970.000 | 6280.000 | 4970.000 | 11103.000 |
| n (Samp) | 213 | 51 | 213 | 53 | 213 | 23 |
| n (Pat) | 89 | 51 | 89 | 53 | 89 | 23 |

Fig. 5 Continued sCr or UO

| Time prior AKI stage | AUC | SE | nCohort 1 | nCohort 2 | p |
|---|---|---|---|---|---|
| 0 hours | 0.61 | 0.043 | 257 | 56 | 0.012 |
| 24 hours | 0.66 | 0.041 | 257 | 61 | 0.000 |
| 48 hours | 0.66 | 0.061 | 257 | 26 | 0.010 | sCr only

| Time prior AKI stage | AUC | SE | nCohort 1 | nCohort 2 | p |
|---|---|---|---|---|---|
| 0 hours | 0.54 | 0.063 | 459 | 23 | 0.576 |
| 24 hours | 0.57 | 0.060 | 459 | 26 | 0.244 |
| 48 hours | 0.41 | 0.073 | 459 | 14 | 0.241 |

UO only

| Time prior AKI stage | AUC | SE | nCohort 1 | nCohort 2 | p |
|---|---|---|---|---|---|
| 0 hours | 0.59 | 0.046 | 213 | 51 | 0.055 |
| 24 hours | 0.63 | 0.045 | 213 | 53 | 0.003 |
| 48 hours | 0.67 | 0.064 | 213 | 23 | 0.008 | sCr or UO

| Time prior AKI stage | Cutoff value | sens | spec | Quartile | OR | 95% CI of OR | |
|---|---|---|---|---|---|---|---|
| 0 hours | 16.5 | 71% | 46% | 1 | | | |
| | 13.6 | 82% | 39% | 2 | 1.0 | 0.6 | 1.6 |
| | 7.29 | 91% | 14% | 3 | 1.4 | 0.9 | 2.0 |
| | 30.7 | 48% | 70% | 4 | 2.8 | 2.0 | 3.9 |
| | 39.2 | 39% | 80% | | | | |
| | 80.1 | 20% | 90% | | | | |
| 24 hours | 16.5 | 70% | 46% | 1 | | | |
| | 13.6 | 80% | 39% | 2 | 2.4 | 1.5 | 3.8 |
| | 11 | 90% | 28% | 3 | 1.7 | 1.0 | 2.8 |
| | 30.7 | 49% | 70% | 4 | 5.5 | 3.7 | 8.4 |
| | 39.2 | 46% | 80% | | | | |
| | 80.1 | 30% | 90% | | | | |
| 48 hours | 17.4 | 73% | 49% | 1 | | | |
| | 13.7 | 81% | 39% | 2 | 1.7 | 0.6 | 5.1 |
| | 9.36 | 92% | 21% | 3 | 2.1 | 0.7 | 5.8 |
| | 30.7 | 54% | 70% | 4 | 4.5 | 1.9 | 10.9 |
| | 39.2 | 46% | 80% | | | | |
| | 80.1 | 23% | 90% | | | | | sCr only

| Time prior AKI stage | Cutoff value | sens | spec | Quartile | OR | 95% CI of OR | |
|---|---|---|---|---|---|---|---|
| 0 hours | 15.2 | 74% | 36% | 1 | | | |
| | 8.73 | 83% | 13% | 2 | 0.6 | 0.3 | 1.5 |
| | 6.11 | 91% | 7% | 3 | 0.8 | 0.4 | 1.8 |
| | 37.9 | 48% | 70% | 4 | 1.3 | 0.7 | 2.5 |
| | 57.9 | 26% | 80% | | | | |
| | 117 | 4% | 90% | | | | |
| 24 hours | 14.5 | 73% | 34% | 1 | | | |
| | 13.6 | 81% | 30% | 2 | 1.4 | 0.7 | 2.9 |
| | 8.43 | 92% | 12% | 3 | 0.8 | 0.3 | 2.0 |
| | 37.9 | 42% | 70% | 4 | 2.1 | 1.1 | 3.9 |
| | 57.9 | 38% | 80% | | | | |
| | 117 | 23% | 90% | | | | |

Fig. 5 Continued

| | | | | | | | | |
|---|---|---|---|---|---|---|---|---|
| 48 hours | | 11.6 | 71% | 23% | 1 | | | |
| | | 9.38 | 86% | 16% | 2 | 2.1 | 0.5 | 9.2 |
| | | 7.73 | 93% | 11% | 3 | 1.5 | 0.3 | 8.1 |
| | | 37.9 | 21% | 70% | 4 | 2.6 | 0.6 | 10.6 |
| | | 57.9 | 7% | 80% | | | | |
| | | 117 | 7% | 90% | | | | |

UO only

| Time prior AKI stage | Cutoff value | sens | spec | Quartile | OR | 95% CI of OR | |
|---|---|---|---|---|---|---|---|
| 0 hours | 16.5 | 71% | 40% | 1 | | | |
| | 13.5 | 82% | 34% | 2 | 1.6 | 1.0 | 2.4 |
| | 10.3 | 90% | 23% | 3 | 1.3 | 0.8 | 2.0 |
| | 34.5 | 41% | 70% | 4 | 2.4 | 1.6 | 3.5 |
| | 45.3 | 33% | 81% | | | | |
| | 98 | 18% | 90% | | | | |
| 24 hours | 16.2 | 74% | 39% | 1 | | | |
| | 13.5 | 81% | 34% | 2 | 2.4 | 1.5 | 3.9 |
| | 11 | 91% | 25% | 3 | 1.2 | 0.6 | 2.1 |
| | 34.5 | 45% | 70% | 4 | 4.4 | 2.8 | 6.9 |
| | 45.3 | 40% | 81% | | | | |
| | 98 | 23% | 90% | | | | |
| 48 hours | 18.5 | 74% | 47% | 1 | | | |
| | 13.8 | 83% | 35% | 2 | 3.2 | 0.8 | 12.8 |
| | 12.3 | 91% | 30% | 3 | 2.1 | 0.4 | 9.7 |
| | 34.5 | 57% | 70% | 4 | 6.5 | 1.9 | 22.4 |
| | 45.3 | 48% | 81% | | | | |
| | 98 | 22% | 90% | | | | |

Granulocyte-macrophage colony-stimulating factor sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.574 | 0.574 | 0.574 | 0.574 | 0.574 | 0.574 |
| average | 5.126 | 2.404 | 5.126 | 4.591 | 5.126 | 2.681 |
| stdev | 18.333 | 4.680 | 18.333 | 6.381 | 18.333 | 4.081 |
| p (t-test) | | 0.271 | | 0.822 | | 0.499 |
| min | 0.574 | 0.574 | 0.574 | 0.574 | 0.574 | 0.574 |
| max | 277.000 | 21.700 | 277.000 | 26.700 | 277.000 | 13.600 |
| n (Samp) | 257 | 56 | 257 | 61 | 257 | 26 |
| n (Pat) | 112 | 56 | 112 | 61 | 112 | 26 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.574 | 0.574 | 0.574 | 0.574 | 0.574 | 0.574 |
| average | 4.952 | 4.564 | 4.952 | 4.965 | 4.952 | 3.358 |
| stdev | 15.307 | 6.977 | 15.307 | 5.825 | 15.307 | 5.660 |
| p (t-test) | | 0.904 | | 0.997 | | 0.698 |
| min | 0.574 | 0.574 | 0.574 | 0.574 | 0.574 | 0.574 |
| max | 277.000 | 21.500 | 277.000 | 19.900 | 277.000 | 16.600 |
| n (Samp) | 459 | 23 | 459 | 26 | 459 | 14 |
| n (Pat) | 180 | 23 | 180 | 26 | 180 | 14 |

Fig. 5 Continued

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.574 | 0.574 | 0.574 | 0.574 | 0.574 | 0.574 |
| average | 5.536 | 2.960 | 5.536 | 4.714 | 5.536 | 2.318 |
| stdev | 19.941 | 5.093 | 19.941 | 6.206 | 19.941 | 3.452 |
| p (t-test) |  | 0.362 |  | 0.767 |  | 0.441 |
| min | 0.574 | 0.574 | 0.574 | 0.574 | 0.574 | 0.574 |
| max | 277.000 | 21.700 | 277.000 | 26.700 | 277.000 | 11.100 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
| --- | --- | --- | --- | --- | --- |
| 0 hours | 0.42 | 0.041 | 257 | 56 | 0.056 |
| 24 hours | 0.52 | 0.042 | 257 | 61 | 0.549 |
| 48 hours | 0.45 | 0.058 | 257 | 26 | 0.399 | sCr only

| Time prior AKI stage | AUC | SE | nCohort 1 | nCohort 2 | p |
| --- | --- | --- | --- | --- | --- |
| 0 hours | 0.50 | 0.062 | 459 | 23 | 0.985 |
| 24 hours | 0.56 | 0.060 | 459 | 26 | 0.349 |
| 48 hours | 0.45 | 0.076 | 459 | 14 | 0.530 |

UO only

| Time prior AKI stage | AUC | SE | nCohort 1 | nCohort 2 | p |
| --- | --- | --- | --- | --- | --- |
| 0 hours | 0.44 | 0.044 | 213 | 51 | 0.207 |
| 24 hours | 0.53 | 0.045 | 213 | 53 | 0.490 |
| 48 hours | 0.43 | 0.060 | 213 | 23 | 0.268 | sCr or UO

| Time prior AKI stage | Cutoff value | sens | spec | Quartile | OR | 95% CI of OR | |
| --- | --- | --- | --- | --- | --- | --- | --- |
| 0 hours | 0 | 100% | 0% | 1 |  |  |  |
|  | 0 | 100% | 0% | 2 | 1.7 | 1.1 | 2.6 |
|  | 0 | 100% | 0% | 3 | 2.3 | 1.6 | 3.4 |
|  | 5 | 16% | 71% | 4 | 1.9 | 1.2 | 2.8 |
|  | 7.28 | 9% | 81% |  |  |  |  |
|  | 12.1 | 5% | 91% |  |  |  |  |
| 24 hours | 0 | 100% | 0% | 1 |  |  |  |
|  | 0 | 100% | 0% | 2 | 1.5 | 1.1 | 2.1 |
|  | 0 | 100% | 0% | 3 | 1.3 | 0.9 | 1.9 |
|  | 5 | 28% | 71% | 4 | 1.5 | 1.1 | 2.1 |
|  | 7.28 | 26% | 81% |  |  |  |  |
|  | 12.1 | 11% | 91% |  |  |  |  |
| 48 hours | 0 | 100% | 0% | 1 |  |  |  |
|  | 0 | 100% | 0% | 2 | 0.0 | 0.0 | na |
|  | 0 | 100% | 0% | 3 | 2.9 | 1.7 | 4.9 |
|  | 5 | 23% | 71% | 4 | 0.8 | 0.4 | 1.8 |
|  | 7.28 | 15% | 81% |  |  |  |  |
|  | 12.1 | 4% | 91% |  |  |  |  |

Fig. 5 Continued sCr only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 1.5 | 0.9 | 2.5 |
| | 0 | 100% | 0% | 3 | 0.8 | 0.4 | 1.6 |
| | 5.53 | 30% | 70% | 4 | 0.0 | 0.0 | na |
| | 7.28 | 26% | 81% | | | | |
| | 12.1 | 13% | 92% | | | | |
| 24 hours | 0 | 100% | 0% | 1 | | | |
| | 0 | 100% | 0% | 2 | na | na | na |
| | 0 | 100% | 0% | 3 | na | na | na |
| | 5.53 | 38% | 70% | 4 | na | na | na |
| | 7.28 | 23% | 81% | | | | |
| | 12.1 | 15% | 92% | | | | |
| 48 hours | 0 | 100% | 0% | 1 | | | |
| | 0 | 100% | 0% | 2 | 0.0 | 0.0 | na |
| | 0 | 100% | 0% | 3 | 4.0 | 1.7 | 9.5 |
| | 5.53 | 21% | 70% | 4 | 0.0 | 0.0 | na |
| | 7.28 | 21% | 81% | | | | |
| | 12.1 | 14% | 92% | | | | |

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.1 | 0.0 | 0.7 |
| | 0 | 100% | 0% | 3 | 4.2 | 3.0 | 5.8 |
| | 5 | 22% | 70% | 4 | 0.8 | 0.5 | 1.3 |
| | 7.28 | 12% | 81% | | | | |
| | 12.4 | 6% | 91% | | | | |
| 24 hours | 0 | 100% | 0% | 1 | | | |
| | 0 | 100% | 0% | 2 | 2.1 | 1.5 | 3.0 |
| | 0 | 100% | 0% | 3 | 0.6 | 0.4 | 1.0 |
| | 5 | 28% | 70% | 4 | 1.4 | 1.0 | 2.1 |
| | 7.28 | 28% | 81% | | | | |
| | 12.4 | 9% | 91% | | | | |
| 48 hours | 0 | 100% | 0% | 1 | | | |
| | 0 | 100% | 0% | 2 | 0.0 | 0.0 | na |
| | 0 | 100% | 0% | 3 | 3.1 | 1.6 | 5.7 |
| | 5 | 22% | 70% | 4 | 1.0 | 0.4 | 2.4 |
| | 7.28 | 13% | 81% | | | | |
| | 12.4 | 0% | 91% | | | | |

Fig. 5 Continued

Heparin-binding growth factor 2 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 72.800 | 83.800 | 72.800 | 190.000 | 72.800 | 117.000 |
| average | 114.544 | 252.314 | 114.544 | 324.423 | 114.544 | 160.440 |
| stdev | 167.455 | 1115.593 | 167.455 | 1103.034 | 167.455 | 155.678 |
| p (t-test) |  | 0.059 |  | 0.004 |  | 0.181 |
| min | 0.980 | 0.980 | 0.980 | 0.980 | 0.980 | 0.980 |
| max | 1280.000 | 8410.000 | 1280.000 | 8750.000 | 1280.000 | 489.000 |
| n (Samp) | 257 | 56 | 257 | 61 | 257 | 26 |
| n (Pat) | 112 | 56 | 112 | 61 | 112 | 26 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 90.600 | 117.000 | 90.600 | 158.000 | 90.600 | 111.500 |
| average | 138.276 | 278.217 | 138.276 | 527.932 | 138.276 | 452.310 |
| stdev | 221.207 | 762.147 | 221.207 | 1826.294 | 221.207 | 1082.141 |
| p (t-test) |  | 0.016 |  | 0.000 |  | 0.000 |
| min | 0.980 | 0.980 | 0.980 | 0.980 | 0.980 | 0.980 |
| max | 2520.000 | 3720.000 | 2520.000 | 9460.000 | 2520.000 | 4170.000 |
| n (Samp) | 459 | 23 | 459 | 26 | 459 | 14 |
| n (Pat) | 180 | 23 | 180 | 26 | 180 | 14 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 76.300 | 117.000 | 76.300 | 201.000 | 76.300 | 141.000 |
| average | 128.644 | 281.775 | 128.644 | 356.027 | 128.644 | 165.098 |
| stdev | 177.941 | 1166.816 | 177.941 | 1181.814 | 177.941 | 149.401 |
| p (t-test) |  | 0.067 |  | 0.007 |  | 0.345 |
| min | 0.980 | 0.980 | 0.980 | 0.980 | 0.980 | 0.980 |
| max | 1280.000 | 8410.000 | 1280.000 | 8750.000 | 1280.000 | 428.000 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
| --- | --- | --- | --- | --- | --- |
| 0 hours | 0.51 | 0.043 | 257 | 56 | 0.745 |
| 24 hours | 0.71 | 0.040 | 257 | 61 | 0.000 |
| 48 hours | 0.60 | 0.061 | 257 | 26 | 0.097 | sCr only

| Time prior AKI stage | AUC | SE | nCohort 1 | nCohort 2 | p |
| --- | --- | --- | --- | --- | --- |
| 0 hours | 0.51 | 0.062 | 459 | 23 | 0.885 |
| 24 hours | 0.64 | 0.060 | 459 | 26 | 0.023 |
| 48 hours | 0.60 | 0.081 | 459 | 14 | 0.238 |

UO only

| Time prior AKI stage | AUC | SE | nCohort 1 | nCohort 2 | p |
| --- | --- | --- | --- | --- | --- |
| 0 hours | 0.53 | 0.046 | 213 | 51 | 0.509 |
| 24 hours | 0.69 | 0.043 | 213 | 53 | 0.000 |
| 48 hours | 0.59 | 0.065 | 213 | 23 | 0.149 |

Fig. 5 Continued sCr or UO

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | na | na | na |
| | 0 | 100% | 0% | 3 | na | na | na |
| | 138 | 38% | 70% | 4 | na | na | na |
| | 179 | 27% | 80% | | | | |
| | 282 | 13% | 91% | | | | |
| 24 hours | 131 | 75% | 67% | 1 | | | |
| | 76.3 | 80% | 54% | 2 | 6.8 | 2.1 | 22.5 |
| | 0 | 100% | 0% | 3 | 11.4 | 3.6 | 35.8 |
| | 138 | 64% | 70% | 4 | 21.9 | 7.2 | 66.5 |
| | 179 | 51% | 80% | | | | |
| | 282 | 20% | 91% | | | | |
| 48 hours | 0 | 100% | 0% | 1 | | | |
| | 0 | 100% | 0% | 2 | na | na | na |
| | 0 | 100% | 0% | 3 | na | na | na |
| | 138 | 46% | 70% | 4 | na | na | na |
| | 179 | 38% | 80% | | | | |
| | 282 | 27% | 91% | | | | | sCr only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | na | na | na |
| | 0 | 100% | 0% | 3 | na | na | na |
| | 162 | 35% | 72% | 4 | na | na | na |
| | 216 | 30% | 81% | | | | |
| | 296 | 17% | 90% | | | | |
| 24 hours | 78.2 | 73% | 47% | 1 | | | |
| | 58.2 | 85% | 40% | 2 | na | na | na |
| | 0 | 100% | 0% | 3 | na | na | na |
| | 162 | 38% | 72% | 4 | na | na | na |
| | 216 | 35% | 81% | | | | |
| | 296 | 15% | 90% | | | | |
| 48 hours | 90.6 | 71% | 50% | 1 | | | |
| | 0 | 100% | 0% | 2 | 0.7 | 0.1 | 3.5 |
| | 0 | 100% | 0% | 3 | 1.3 | 0.4 | 4.4 |
| | 162 | 36% | 72% | 4 | 1.7 | 0.6 | 4.9 |
| | 216 | 36% | 81% | | | | |
| | 296 | 29% | 90% | | | | |

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.8 | 0.5 | 1.2 |
| | 0 | 100% | 0% | 3 | 1.2 | 0.8 | 1.8 |
| | 158 | 39% | 71% | 4 | 1.3 | 0.9 | 1.9 |
| | 217 | 22% | 80% | | | | |
| | 319 | 8% | 91% | | | | |
| 24 hours | 133 | 72% | 66% | 1 | | | |
| | 76.3 | 83% | 51% | 2 | 1.8 | 0.8 | 4.2 |
| | 0 | 100% | 0% | 3 | 6.3 | 3.2 | 12.2 |
| | 158 | 62% | 71% | 4 | 8.1 | 4.2 | 15.5 |
| | 217 | 43% | 80% | | | | |
| | 319 | 15% | 91% | | | | |

Fig. 5 Continued

| 48 hours | | 0 | 100% | 0% | 1 | | | |
|---|---|---|---|---|---|---|---|---|
| | | 0 | 100% | 0% | 2 | na | na | na |
| | | 0 | 100% | 0% | 3 | na | na | na |
| | | 158 | 43% | 71% | 4 | na | na | na |
| | | 217 | 35% | 80% | | | | |
| | | 319 | 26% | 91% | | | | |

Interleukin-1 receptor antagonist sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 239.000 | 249.500 | 239.000 | 269.000 | 239.000 | 284.000 |
| average | 806.606 | 457.437 | 806.606 | 1039.672 | 806.606 | 1002.346 |
| stdev | 3314.991 | 584.337 | 3314.991 | 3999.227 | 3314.991 | 2238.945 |
| p (t-test) | | 0.433 | | 0.636 | | 0.769 |
| min | 0.150 | 0.150 | 0.150 | 35.100 | 0.150 | 101.000 |
| max | 43939.000 | 2720.000 | 43939.000 | 31100.000 | 43939.000 | 11500.000 |
| n (Samp) | 257 | 56 | 257 | 61 | 257 | 26 |
| n (Pat) | 112 | 56 | 112 | 61 | 112 | 26 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 230.000 | 356.000 | 230.000 | 339.000 | 230.000 | 274.000 |
| average | 860.167 | 997.280 | 860.167 | 946.769 | 860.167 | 1243.571 |
| stdev | 3990.748 | 1747.003 | 3990.748 | 1518.849 | 3990.748 | 2996.860 |
| p (t-test) | | 0.870 | | 0.912 | | 0.722 |
| min | 0.150 | 0.150 | 0.150 | 120.000 | 0.150 | 114.000 |
| max | 58400.000 | 8150.000 | 58400.000 | 7350.000 | 58400.000 | 11500.000 |
| n (Samp) | 459 | 23 | 459 | 26 | 459 | 14 |
| n (Pat) | 180 | 23 | 180 | 26 | 180 | 14 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 255.000 | 250.000 | 255.000 | 269.000 | 255.000 | 287.000 |
| average | 770.500 | 493.253 | 770.500 | 1912.062 | 770.500 | 600.552 |
| stdev | 3251.168 | 836.021 | 3251.168 | 7115.248 | 3251.168 | 690.211 |
| p (t-test) | | 0.547 | | 0.085 | | 0.803 |
| min | 0.150 | 23.500 | 0.150 | 35.100 | 0.150 | 51.700 |
| max | 43939.000 | 5550.000 | 43939.000 | 42500.000 | 43939.000 | 2160.000 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
|---|---|---|---|---|---|
| 0 hours | 0.50 | 0.043 | 257 | 56 | 0.982 |
| 24 hours | 0.53 | 0.042 | 257 | 61 | 0.468 |
| 48 hours | 0.57 | 0.061 | 257 | 26 | 0.267 | sCr only

| Time prior AKI stage | AUC | SE | nCohort 1 | nCohort 2 | p |
|---|---|---|---|---|---|
| 0 hours | 0.61 | 0.064 | 459 | 23 | 0.085 |
| 24 hours | 0.63 | 0.060 | 459 | 26 | 0.030 |
| 48 hours | 0.56 | 0.081 | 459 | 14 | 0.437 |

Fig. 5 Continued

UO only

| Time prior AKI stage | AUC | SE | nCohort 1 | nCohort 2 | p |
|---|---|---|---|---|---|
| 0 hours | 0.50 | 0.045 | 213 | 51 | 0.998 |
| 24 hours | 0.53 | 0.045 | 213 | 53 | 0.540 |
| 48 hours | 0.54 | 0.065 | 213 | 23 | 0.503 | sCr or UO

| Time prior AKI stage | Cutoff value | sens | spec | Quartile | OR | 95% CI of OR | |
|---|---|---|---|---|---|---|---|
| 0 hours | 175 | 71% | 33% | 1 | | | |
| | 126 | 80% | 17% | 2 | 0.9 | 0.6 | 1.3 |
| | 74.4 | 93% | 5% | 3 | 0.9 | 0.6 | 1.3 |
| | 363 | 34% | 70% | 4 | 1.2 | 0.8 | 1.6 |
| | 531 | 18% | 80% | | | | |
| | 985 | 11% | 90% | | | | |
| 24 hours | 175 | 70% | 33% | 1 | | | |
| | 143 | 82% | 21% | 2 | 0.7 | 0.5 | 1.0 |
| | 118 | 90% | 15% | 3 | 1.4 | 1.1 | 1.9 |
| | 363 | 31% | 70% | 4 | 1.0 | 0.7 | 1.4 |
| | 531 | 23% | 80% | | | | |
| | 985 | 16% | 90% | | | | |
| 48 hours | 195 | 73% | 39% | 1 | | | |
| | 142 | 81% | 20% | 2 | 0.5 | 0.2 | 1.2 |
| | 114 | 92% | 14% | 3 | 0.7 | 0.3 | 1.4 |
| | 363 | 38% | 70% | 4 | 1.5 | 0.9 | 2.5 |
| | 531 | 31% | 80% | | | | |
| | 985 | 23% | 90% | | | | | sCr only

| Time prior AKI stage | Cutoff value | sens | spec | Quartile | OR | 95% CI of OR | |
|---|---|---|---|---|---|---|---|
| 0 hours | 219 | 74% | 47% | 1 | | | |
| | 173 | 83% | 34% | 2 | 0.7 | 0.2 | 2.4 |
| | 99.7 | 91% | 10% | 3 | 2.4 | 1.1 | 4.9 |
| | 348 | 52% | 70% | 4 | 1.8 | 0.8 | 4.0 |
| | 514 | 30% | 80% | | | | |
| | 1020 | 26% | 90% | | | | |
| 24 hours | 180 | 73% | 36% | 1 | | | |
| | 158 | 81% | 28% | 2 | 1.0 | 0.4 | 2.8 |
| | 143 | 92% | 22% | 3 | 2.1 | 1.0 | 4.5 |
| | 348 | 46% | 70% | 4 | 2.6 | 1.3 | 5.4 |
| | 514 | 35% | 80% | | | | |
| | 1020 | 31% | 90% | | | | |
| 48 hours | 199 | 71% | 42% | 1 | | | |
| | 142 | 86% | 22% | 2 | 0.7 | 0.1 | 3.5 |
| | 113 | 100% | 13% | 3 | 1.7 | 0.6 | 5.0 |
| | 348 | 29% | 70% | 4 | 1.3 | 0.4 | 4.3 |
| | 514 | 29% | 80% | | | | |
| | 1020 | 21% | 90% | | | | |

UO only

| Time prior AKI stage | Cutoff value | sens | spec | Quartile | OR | 95% CI of OR | |
|---|---|---|---|---|---|---|---|
| 0 hours | 190 | 71% | 35% | 1 | | | |
| | 126 | 82% | 13% | 2 | 0.7 | 0.5 | 1.1 |
| | 73.8 | 92% | 2% | 3 | 1.1 | 0.8 | 1.5 |
| | 364 | 35% | 70% | 4 | 0.7 | 0.5 | 1.1 |
| | 537 | 18% | 80% | | | | |
| | 873 | 12% | 90% | | | | |

Fig. 5 Continued

| 24 hours |     | 175 | 72% | 30% | 1 |     |     |     |
|----------|-----|-----|-----|-----|---|-----|-----|-----|
|          |     | 132 | 81% | 15% | 2 | 0.9 | 0.6 | 1.3 |
|          |     | 108 | 92% | 9%  | 3 | 0.9 | 0.6 | 1.3 |
|          |     | 364 | 34% | 70% | 4 | 1.3 | 0.9 | 1.8 |
|          |     | 537 | 26% | 80% |   |     |     |     |
|          |     | 873 | 17% | 90% |   |     |     |     |
| 48 hours |     | 195 | 74% | 37% | 1 |     |     |     |
|          |     | 138 | 83% | 17% | 2 | 0.6 | 0.3 | 1.6 |
|          |     | 114 | 91% | 11% | 3 | 0.8 | 0.4 | 1.8 |
|          |     | 364 | 35% | 70% | 4 | 1.4 | 0.7 | 2.6 |
|          |     | 537 | 26% | 80% |   |     |     |     |
|          |     | 873 | 22% | 90% |   |     |     |     |

Interleukin-1 beta sCr or UO

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 0.015    | 0.015    | 0.015    | 0.015    | 0.015    | 0.015    |
| average  | 0.189    | 0.191    | 0.189    | 0.233    | 0.189    | 0.330    |
| stdev    | 0.481    | 0.323    | 0.481    | 0.536    | 0.481    | 0.798    |
| p (t-test) |        | 0.979    |          | 0.530    |          | 0.189    |
| min      | 0.015    | 0.015    | 0.015    | 0.015    | 0.015    | 0.015    |
| max      | 3.990    | 1.060    | 3.990    | 2.870    | 3.990    | 3.180    |
| n (Samp) | 257      | 56       | 257      | 61       | 257      | 26       |
| n (Pat)  | 112      | 56       | 112      | 61       | 112      | 26       | sCr only

|          | 0 hr prior toAKI stage | | 24 hr prior toAKI stage | | 48 hr prior toAKI stage | |
|----------|----------|----------|----------|----------|----------|----------|
|          | Cohort 1 | Cohort 2 | Cohort 1 | Cohort 2 | Cohort 1 | Cohort 2 |
| median   | 0.015    | 0.015    | 0.015    | 0.015    | 0.015    | 0.015    |
| average  | 0.347    | 0.397    | 0.347    | 0.268    | 0.347    | 0.189    |
| stdev    | 3.013    | 0.678    | 3.013    | 0.480    | 3.013    | 0.476    |
| p (t-test) |        | 0.937    |          | 0.894    |          | 0.844    |
| min      | 0.015    | 0.015    | 0.015    | 0.015    | 0.015    | 0.015    |
| max      | 63.800   | 2.390    | 63.800   | 1.840    | 63.800   | 1.680    |
| n (Samp) | 459      | 23       | 459      | 26       | 459      | 14       |
| n (Pat)  | 180      | 23       | 180      | 26       | 180      | 14       |

UO only

|          | 0 hr prior toAKI stage | | 24 hr prior toAKI stage | | 48 hr prior toAKI stage | |
|----------|----------|----------|----------|----------|----------|----------|
|          | Cohort 1 | Cohort 2 | Cohort 1 | Cohort 2 | Cohort 1 | Cohort 2 |
| median   | 0.015    | 0.015    | 0.015    | 0.015    | 0.015    | 0.015    |
| average  | 0.156    | 0.195    | 0.156    | 0.250    | 0.156    | 0.337    |
| stdev    | 0.449    | 0.326    | 0.449    | 0.557    | 0.449    | 0.840    |
| p (t-test) |        | 0.568    |          | 0.196    |          | 0.100    |
| min      | 0.015    | 0.015    | 0.015    | 0.015    | 0.015    | 0.015    |
| max      | 3.990    | 1.060    | 3.990    | 2.870    | 3.990    | 3.180    |
| n (Samp) | 213      | 51       | 213      | 53       | 213      | 23       |
| n (Pat)  | 89       | 51       | 89       | 53       | 89       | 23       | sCr or UO

| Time prior AKI stage | AUC  | SE    | nCohort 1 | nCohort 2 | p     |
|----------------------|------|-------|-----------|-----------|-------|
| 0 hours              | 0.53 | 0.043 | 257       | 56        | 0.504 |
| 24 hours             | 0.51 | 0.041 | 257       | 61        | 0.870 |
| 48 hours             | 0.53 | 0.060 | 257       | 26        | 0.590 |

Fig. 5 Continued sCr only

| Time prior AKI stage | AUC | SE | nCohort 1 | nCohort 2 | p |
|---|---|---|---|---|---|
| 0 hours | 0.56 | 0.063 | 459 | 23 | 0.329 |
| 24 hours | 0.54 | 0.059 | 459 | 26 | 0.548 |
| 48 hours | 0.48 | 0.077 | 459 | 14 | 0.753 |

UO only

| Time prior AKI stage | AUC | SE | nCohort 1 | nCohort 2 | p |
|---|---|---|---|---|---|
| 0 hours | 0.55 | 0.046 | 213 | 51 | 0.285 |
| 24 hours | 0.53 | 0.045 | 213 | 53 | 0.510 |
| 48 hours | 0.55 | 0.065 | 213 | 23 | 0.485 | sCr or UO

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 3.4 | 2.5 | 4.6 |
| | 0 | 100% | 0% | 3 | 0.0 | 0.0 | na |
| | 0.0146 | 25% | 81% | 4 | 1.2 | 0.8 | 1.7 |
| | 0.0146 | 25% | 81% | | | | |
| | 0.639 | 16% | 90% | | | | |
| 24 hours | 0 | 100% | 0% | 1 | | | |
| | 0 | 100% | 0% | 2 | 5.6 | 4.1 | 7.6 |
| | 0 | 100% | 0% | 3 | 0.0 | 0.0 | na |
| | 0.0146 | 20% | 81% | 4 | 1.1 | 0.7 | 1.6 |
| | 0.0146 | 20% | 81% | | | | |
| | 0.639 | 13% | 90% | | | | |
| 48 hours | 0 | 100% | 0% | 1 | | | |
| | 0 | 100% | 0% | 2 | 4.4 | 2.2 | 8.8 |
| | 0 | 100% | 0% | 3 | 0.0 | 0.0 | na |
| | 0.0146 | 27% | 81% | 4 | 1.8 | 0.8 | 4.1 |
| | 0.0146 | 27% | 81% | | | | |
| | 0.639 | 12% | 90% | | | | | sCr only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 16.8 | 2.0 | 141.1 |
| | 0 | 100% | 0% | 3 | 0.0 | 0.0 | na |
| | 0.0146 | 30% | 79% | 4 | 7.3 | 0.8 | 71.0 |
| | 0.359 | 30% | 80% | | | | |
| | 0.773 | 17% | 92% | | | | |
| 24 hours | 0 | 100% | 0% | 1 | | | |
| | 0 | 100% | 0% | 2 | na | na | na |
| | 0 | 100% | 0% | 3 | na | na | na |
| | 0.0146 | 27% | 79% | 4 | na | na | na |
| | 0.359 | 27% | 80% | | | | |
| | 0.773 | 12% | 92% | | | | |
| 48 hours | 0 | 100% | 0% | 1 | | | |
| | 0 | 100% | 0% | 2 | 0.0 | 0.0 | na |
| | 0 | 100% | 0% | 3 | 6.6 | 2.0 | 21.5 |
| | 0.0146 | 14% | 79% | 4 | 0.0 | 0.0 | na |
| | 0.359 | 14% | 80% | | | | |
| | 0.773 | 14% | 92% | | | | |

Fig. 5 Continued

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 6.0 | 4.1 | 9.0 |
| | 0 | 100% | 0% | 3 | 0.0 | 0.0 | na |
| | 0.0146 | 25% | 84% | 4 | 1.8 | 1.1 | 2.8 |
| | 0.0146 | 25% | 84% | | | | |
| | 0.511 | 20% | 91% | | | | |
| 24 hours | 0 | 100% | 0% | 1 | | | |
| | 0 | 100% | 0% | 2 | 5.1 | 3.5 | 7.4 |
| | 0 | 100% | 0% | 3 | 0.3 | 0.1 | 0.8 |
| | 0.0146 | 21% | 84% | 4 | 1.2 | 0.8 | 2.0 |
| | 0.0146 | 21% | 84% | | | | |
| | 0.511 | 17% | 91% | | | | |
| 48 hours | 0 | 100% | 0% | 1 | | | |
| | 0 | 100% | 0% | 2 | 3.9 | 1.9 | 8.0 |
| | 0 | 100% | 0% | 3 | 0.0 | 0.0 | na |
| | 0.0146 | 26% | 84% | 4 | 1.6 | 0.6 | 3.8 |
| | 0.0146 | 26% | 84% | | | | |
| | 0.511 | 9% | 91% | | | | |

Interleukin-10 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 15.000 | 15.650 | 15.000 | 22.300 | 15.000 | 16.500 |
| average | 27.532 | 21.583 | 27.532 | 86.116 | 27.532 | 52.355 |
| stdev | 50.406 | 30.323 | 50.406 | 314.858 | 50.406 | 97.741 |
| p (t-test) | | 0.396 | | 0.005 | | 0.033 |
| min | 0.154 | 0.154 | 0.154 | 0.154 | 0.154 | 4.400 |
| max | 480.000 | 222.000 | 480.000 | 2440.000 | 480.000 | 398.000 |
| n (Samp) | 257 | 56 | 257 | 61 | 257 | 26 |
| n (Pat) | 112 | 56 | 112 | 61 | 112 | 26 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 16.200 | 15.600 | 16.200 | 18.500 | 16.200 | 11.100 |
| average | 63.128 | 30.559 | 63.128 | 43.293 | 63.128 | 35.702 |
| stdev | 635.846 | 46.653 | 635.846 | 52.944 | 635.846 | 81.935 |
| p (t-test) | | 0.806 | | 0.874 | | 0.872 |
| min | 0.154 | 0.154 | 0.154 | 0.154 | 0.154 | 4.400 |
| max | 13400.000 | 222.000 | 13400.000 | 189.000 | 13400.000 | 318.000 |
| n (Samp) | 459 | 23 | 459 | 26 | 459 | 14 |
| n (Pat) | 180 | 23 | 180 | 26 | 180 | 14 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 14.500 | 17.600 | 14.500 | 23.400 | 14.500 | 16.800 |
| average | 24.564 | 21.048 | 24.564 | 92.217 | 24.564 | 46.689 |
| stdev | 35.553 | 16.057 | 35.553 | 336.808 | 35.553 | 85.826 |
| p (t-test) | | 0.492 | | 0.004 | | 0.020 |
| min | 0.154 | 0.154 | 0.154 | 0.154 | 0.154 | 5.050 |
| max | 318.000 | 65.700 | 318.000 | 2440.000 | 318.000 | 398.000 |
| n (Samp) | 213 | 51 | 213 | 53 | 213 | 23 |
| n (Pat) | 89 | 51 | 89 | 53 | 89 | 23 |

Fig. 5 Continued sCr or UO

| Time prior AKI stage | AUC | SE | nCohort 1 | nCohort 2 | p |
|---|---|---|---|---|---|
| 0 hours | 0.49 | 0.042 | 257 | 56 | 0.784 |
| 24 hours | 0.60 | 0.042 | 257 | 61 | 0.015 |
| 48 hours | 0.52 | 0.060 | 257 | 26 | 0.758 | sCr only

| Time prior AKI stage | AUC | SE | nCohort 1 | nCohort 2 | p |
|---|---|---|---|---|---|
| 0 hours | 0.49 | 0.061 | 459 | 23 | 0.862 |
| 24 hours | 0.55 | 0.060 | 459 | 26 | 0.370 |
| 48 hours | 0.39 | 0.071 | 459 | 14 | 0.134 |

UO only

| Time prior AKI stage | AUC | SE | nCohort 1 | nCohort 2 | p |
|---|---|---|---|---|---|
| 0 hours | 0.53 | 0.046 | 213 | 51 | 0.499 |
| 24 hours | 0.63 | 0.045 | 213 | 53 | 0.004 |
| 48 hours | 0.56 | 0.065 | 213 | 23 | 0.363 | sCr or UO

| Time prior AKI stage | Cutoff value | sens | spec | Quartile | OR | 95% CI of OR | |
|---|---|---|---|---|---|---|---|
| 0 hours | 10.2 | 73% | 32% | 1 | | | |
| | 7.57 | 80% | 18% | 2 | 1.7 | 1.2 | 2.3 |
| | 4.88 | 91% | 7% | 3 | 1.1 | 0.8 | 1.6 |
| | 22.8 | 29% | 70% | 4 | 1.1 | 0.8 | 1.6 |
| | 30.4 | 18% | 80% | | | | |
| | 47 | 5% | 90% | | | | |
| 24 hours | 12.5 | 70% | 43% | 1 | | | |
| | 10.5 | 80% | 34% | 2 | 1.2 | 0.8 | 1.8 |
| | 5.01 | 90% | 8% | 3 | 1.4 | 1.0 | 2.1 |
| | 22.8 | 49% | 70% | 4 | 2.3 | 1.7 | 3.3 |
| | 30.4 | 34% | 80% | | | | |
| | 47 | 21% | 90% | | | | |
| 48 hours | 8.18 | 73% | 21% | 1 | | | |
| | 6.65 | 81% | 14% | 2 | 0.2 | 0.1 | 0.7 |
| | 5.01 | 92% | 8% | 3 | 0.7 | 0.4 | 1.3 |
| | 22.8 | 35% | 70% | 4 | 0.9 | 0.5 | 1.5 |
| | 30.4 | 23% | 80% | | | | |
| | 47 | 19% | 90% | | | | | sCr only

| Time prior AKI stage | Cutoff value | sens | spec | Quartile | OR | 95% CI of OR | |
|---|---|---|---|---|---|---|---|
| 0 hours | 9.81 | 74% | 27% | 1 | | | |
| | 7.57 | 83% | 16% | 2 | 0.7 | 0.3 | 1.5 |
| | 4.84 | 91% | 6% | 3 | 1.2 | 0.6 | 2.2 |
| | 24.4 | 26% | 70% | 4 | 1.0 | 0.5 | 2.0 |
| | 32 | 26% | 80% | | | | |
| | 52.3 | 17% | 90% | | | | |
| 24 hours | 9.35 | 73% | 25% | 1 | | | |
| | 8.1 | 81% | 18% | 2 | 0.7 | 0.3 | 1.4 |
| | 6.31 | 92% | 10% | 3 | 0.6 | 0.2 | 1.2 |
| | 24.4 | 42% | 70% | 4 | 1.5 | 0.9 | 2.4 |
| | 32 | 38% | 80% | | | | |
| | 52.3 | 31% | 90% | | | | |

Fig. 5 Continued

| | | | | | | | |
|---|---|---|---|---|---|---|---|
| 48 hours | 8.18 | 71% | 19% | 1 | | | |
| | 5.97 | 86% | 10% | 2 | 0.3 | 0.0 | 4.7 |
| | 5 | 93% | 7% | 3 | 1.7 | 0.6 | 5.0 |
| | 24.4 | 21% | 70% | 4 | 1.7 | 0.6 | 5.0 |
| | 32 | 14% | 80% | | | | |
| | 52.3 | 7% | 90% | | | | |

UO only

| Time prior AKI stage | Cutoff value | sens | spec | Quartile | OR | 95% CI of OR | |
|---|---|---|---|---|---|---|---|
| 0 hours | 11.7 | 71% | 41% | 1 | | | |
| | 8.43 | 80% | 23% | 2 | 0.8 | 0.5 | 1.3 |
| | 6.31 | 90% | 9% | 3 | 1.9 | 1.3 | 2.7 |
| | 22.8 | 31% | 71% | 4 | 1.2 | 0.8 | 1.8 |
| | 28.9 | 24% | 80% | | | | |
| | 45.4 | 8% | 90% | | | | |
| 24 hours | 13.2 | 72% | 46% | 1 | | | |
| | 11 | 81% | 36% | 2 | 1.7 | 1.0 | 2.8 |
| | 6.38 | 91% | 10% | 3 | 2.5 | 1.5 | 4.0 |
| | 22.8 | 53% | 71% | 4 | 3.6 | 2.3 | 5.6 |
| | 28.9 | 32% | 80% | | | | |
| | 45.4 | 21% | 90% | | | | |
| 48 hours | 10.3 | 74% | 33% | 1 | | | |
| | 8.1 | 83% | 19% | 2 | 0.5 | 0.2 | 1.4 |
| | 6.65 | 91% | 12% | 3 | 1.2 | 0.6 | 2.4 |
| | 22.8 | 35% | 71% | 4 | 1.2 | 0.6 | 2.4 |
| | 28.9 | 26% | 80% | | | | |
| | 45.4 | 22% | 90% | | | | |

Interleukin-15 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.172 | 0.013 | 0.172 | 0.013 | 0.172 | 0.069 |
| average | 0.209 | 0.115 | 0.209 | 0.112 | 0.209 | 0.106 |
| stdev | 0.228 | 0.150 | 0.228 | 0.135 | 0.228 | 0.112 |
| p (t-test) | | 0.003 | | 0.002 | | 0.023 |
| min | 0.013 | 0.013 | 0.013 | 0.013 | 0.013 | 0.013 |
| max | 1.760 | 0.628 | 1.760 | 0.471 | 1.760 | 0.359 |
| n (Samp) | 257 | 56 | 257 | 61 | 257 | 26 |
| n (Pat) | 112 | 56 | 112 | 61 | 112 | 26 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.123 | 0.095 | 0.123 | 0.013 | 0.123 | 0.042 |
| average | 0.198 | 0.219 | 0.198 | 0.140 | 0.198 | 0.123 |
| stdev | 0.367 | 0.365 | 0.367 | 0.190 | 0.367 | 0.151 |
| p (t-test) | | 0.787 | | 0.425 | | 0.445 |
| min | 0.013 | 0.013 | 0.013 | 0.013 | 0.013 | 0.013 |
| max | 6.590 | 1.700 | 6.590 | 0.618 | 6.590 | 0.497 |
| n (Samp) | 459 | 23 | 459 | 26 | 459 | 14 |
| n (Pat) | 180 | 23 | 180 | 26 | 180 | 14 |

Fig. 5 Continued

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.154 | 0.013 | 0.154 | 0.068 | 0.154 | 0.110 |
| average | 0.202 | 0.107 | 0.202 | 0.115 | 0.202 | 0.109 |
| stdev | 0.241 | 0.129 | 0.241 | 0.127 | 0.241 | 0.103 |
| p (t-test) |  | 0.007 |  | 0.012 |  | 0.068 |
| min | 0.013 | 0.013 | 0.013 | 0.013 | 0.013 | 0.013 |
| max | 1.760 | 0.565 | 1.760 | 0.471 | 1.760 | 0.359 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
| --- | --- | --- | --- | --- | --- |
| 0 hours | 0.36 | 0.038 | 257 | 56 | 0.000 |
| 24 hours | 0.36 | 0.037 | 257 | 61 | 0.000 |
| 48 hours | 0.36 | 0.052 | 257 | 26 | 0.007 | sCr only

| Time prior AKI stage | AUC | SE | nCohort 1 | nCohort 2 | p |
| --- | --- | --- | --- | --- | --- |
| 0 hours | 0.48 | 0.061 | 459 | 23 | 0.733 |
| 24 hours | 0.41 | 0.054 | 459 | 26 | 0.109 |
| 48 hours | 0.42 | 0.073 | 459 | 14 | 0.249 |

UO only

| Time prior AKI stage | AUC | SE | nCohort 1 | nCohort 2 | p |
| --- | --- | --- | --- | --- | --- |
| 0 hours | 0.38 | 0.041 | 213 | 51 | 0.004 |
| 24 hours | 0.40 | 0.042 | 213 | 53 | 0.016 |
| 48 hours | 0.40 | 0.059 | 213 | 23 | 0.092 | sCr or UO

| Time prior AKI stage | Cutoff value | sens | spec | Quartile | OR | 95% CI of OR | |
| --- | --- | --- | --- | --- | --- | --- | --- |
| 0 hours | 0 | 100% | 0% | 1 |  |  |  |
|  | 0 | 100% | 0% | 2 | 1.3 | 0.8 | 2.1 |
|  | 0 | 100% | 0% | 3 | 3.1 | 2.0 | 4.6 |
|  | 0.271 | 14% | 71% | 4 | 2.7 | 1.8 | 4.0 |
|  | 0.334 | 11% | 80% |  |  |  |  |
|  | 0.431 | 4% | 91% |  |  |  |  |
| 24 hours | 0 | 100% | 0% | 1 |  |  |  |
|  | 0 | 100% | 0% | 2 | 2.1 | 1.3 | 3.3 |
|  | 0 | 100% | 0% | 3 | 3.5 | 2.2 | 5.4 |
|  | 0.271 | 11% | 71% | 4 | 3.8 | 2.4 | 5.8 |
|  | 0.334 | 10% | 80% |  |  |  |  |
|  | 0.431 | 5% | 91% |  |  |  |  |
| 48 hours | 0 | 100% | 0% | 1 |  |  |  |
|  | 0 | 100% | 0% | 2 | 2.1 | 0.7 | 5.9 |
|  | 0 | 100% | 0% | 3 | 1.7 | 0.6 | 5.2 |
|  | 0.271 | 12% | 71% | 4 | 4.7 | 1.9 | 11.3 |
|  | 0.334 | 12% | 80% |  |  |  |  |
|  | 0.431 | 0% | 91% |  |  |  |  |

Fig. 5 Continued sCr only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.7 | 0.3 | 1.5 |
| | 0 | 100% | 0% | 3 | 2.3 | 1.4 | 3.9 |
| | 0.246 | 30% | 72% | 4 | 0.0 | 0.0 | na |
| | 0.323 | 26% | 80% | | | | |
| | 0.425 | 9% | 90% | | | | |
| 24 hours | 0 | 100% | 0% | 1 | | | |
| | 0 | 100% | 0% | 2 | 1.2 | 0.6 | 2.6 |
| | 0 | 100% | 0% | 3 | 1.7 | 0.8 | 3.2 |
| | 0.246 | 19% | 72% | 4 | 1.4 | 0.7 | 2.9 |
| | 0.323 | 19% | 80% | | | | |
| | 0.425 | 12% | 90% | | | | |
| 48 hours | 0 | 100% | 0% | 1 | | | |
| | 0 | 100% | 0% | 2 | 2.1 | 0.5 | 9.2 |
| | 0 | 100% | 0% | 3 | 4.3 | 1.2 | 15.0 |
| | 0.246 | 21% | 72% | 4 | 0.0 | 0.0 | na |
| | 0.323 | 14% | 80% | | | | |
| | 0.425 | 7% | 90% | | | | |

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 1.9 | 1.1 | 3.1 |
| | 0 | 100% | 0% | 3 | 5.8 | 3.8 | 9.0 |
| | 0.246 | 18% | 71% | 4 | 0.7 | 0.3 | 1.4 |
| | 0.33 | 10% | 80% | | | | |
| | 0.431 | 2% | 90% | | | | |
| 24 hours | 0 | 100% | 0% | 1 | | | |
| | 0 | 100% | 0% | 2 | 3.0 | 1.8 | 5.1 |
| | 0 | 100% | 0% | 3 | 1.8 | 1.0 | 3.2 |
| | 0.246 | 15% | 71% | 4 | 5.1 | 3.1 | 8.3 |
| | 0.33 | 6% | 80% | | | | |
| | 0.431 | 4% | 90% | | | | |
| 48 hours | 0 | 100% | 0% | 1 | | | |
| | 0 | 100% | 0% | 2 | 3.2 | 0.8 | 12.8 |
| | 0 | 100% | 0% | 3 | 5.8 | 1.7 | 20.3 |
| | 0.246 | 9% | 71% | 4 | 2.6 | 0.6 | 11.2 |
| | 0.33 | 9% | 80% | | | | |
| | 0.431 | 0% | 90% | | | | |

Fig. 5 Continued

Interleukin-3 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.070 | 0.034 | 0.070 | 0.035 | 0.070 | 0.031 |
| average | 0.100 | 0.064 | 0.100 | 0.046 | 0.100 | 0.043 |
| stdev | 0.102 | 0.082 | 0.102 | 0.055 | 0.102 | 0.053 |
| p (t-test) |  | 0.012 |  | 0.000 |  | 0.005 |
| min | 0.002 | 0.002 | 0.002 | 0.002 | 0.002 | 0.002 |
| max | 0.537 | 0.304 | 0.537 | 0.304 | 0.537 | 0.223 |
| n (Samp) | 257 | 56 | 257 | 61 | 257 | 26 |
| n (Pat) | 112 | 56 | 112 | 61 | 112 | 26 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.058 | 0.045 | 0.058 | 0.044 | 0.058 | 0.039 |
| average | 0.090 | 0.112 | 0.090 | 0.068 | 0.090 | 0.063 |
| stdev | 0.102 | 0.160 | 0.102 | 0.076 | 0.102 | 0.086 |
| p (t-test) |  | 0.315 |  | 0.287 |  | 0.325 |
| min | 0.002 | 0.002 | 0.002 | 0.002 | 0.002 | 0.002 |
| max | 0.566 | 0.550 | 0.566 | 0.304 | 0.566 | 0.271 |
| n (Samp) | 459 | 23 | 459 | 26 | 459 | 14 |
| n (Pat) | 180 | 23 | 180 | 26 | 180 | 14 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.060 | 0.034 | 0.060 | 0.029 | 0.060 | 0.028 |
| average | 0.088 | 0.057 | 0.088 | 0.040 | 0.088 | 0.039 |
| stdev | 0.099 | 0.072 | 0.099 | 0.042 | 0.099 | 0.042 |
| p (t-test) |  | 0.037 |  | 0.001 |  | 0.019 |
| min | 0.002 | 0.002 | 0.002 | 0.002 | 0.002 | 0.002 |
| max | 0.537 | 0.304 | 0.537 | 0.207 | 0.537 | 0.144 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
|---|---|---|---|---|---|
| 0 hours | 0.35 | 0.038 | 257 | 56 | 0.000 |
| 24 hours | 0.30 | 0.034 | 257 | 61 | 0.000 |
| 48 hours | 0.28 | 0.045 | 257 | 26 | 0.000 | sCr only

| Time prior AKI stage | AUC | SE | nCohort 1 | nCohort 2 | p |
|---|---|---|---|---|---|
| 0 hours | 0.47 | 0.061 | 459 | 23 | 0.631 |
| 24 hours | 0.43 | 0.055 | 459 | 26 | 0.234 |
| 48 hours | 0.38 | 0.069 | 459 | 14 | 0.071 |

UO only

| Time prior AKI stage | AUC | SE | nCohort 1 | nCohort 2 | p |
|---|---|---|---|---|---|
| 0 hours | 0.38 | 0.041 | 213 | 51 | 0.004 |
| 24 hours | 0.33 | 0.038 | 213 | 53 | 0.000 |
| 48 hours | 0.33 | 0.053 | 213 | 23 | 0.001 |

Fig. 5 Continued sCr or UO

| Time prior AKI stage | Cutoff value | sens | spec | Quartile | OR | 95% CI of OR | |
|---|---|---|---|---|---|---|---|
| 0 hours | 0.00277 | 71% | 10% | 1 | | | |
| | 0 | 100% | 0% | 2 | 1.9 | 1.1 | 3.1 |
| | 0 | 100% | 0% | 3 | 1.9 | 1.1 | 3.1 |
| | 0.109 | 20% | 70% | 4 | 4.9 | 3.2 | 7.4 |
| | 0.152 | 11% | 80% | | | | |
| | 0.23 | 9% | 90% | | | | |
| 24 hours | 0.0108 | 72% | 10% | 1 | | | |
| | 0 | 100% | 0% | 2 | 2.4 | 1.3 | 4.5 |
| | 0 | 100% | 0% | 3 | 4.4 | 2.5 | 7.6 |
| | 0.109 | 8% | 70% | 4 | 7.8 | 4.6 | 13.2 |
| | 0.152 | 5% | 80% | | | | |
| | 0.23 | 2% | 90% | | | | |
| 48 hours | 0 | 100% | 0% | 1 | | | |
| | 0 | 100% | 0% | 2 | 2.1 | 0.4 | 9.5 |
| | 0 | 100% | 0% | 3 | 4.4 | 1.2 | 15.8 |
| | 0.109 | 12% | 70% | 4 | 7.1 | 2.1 | 23.8 |
| | 0.152 | 4% | 80% | | | | |
| | 0.23 | 0% | 90% | | | | | sCr only

| Time prior AKI stage | Cutoff value | sens | spec | Quartile | OR | 95% CI of OR | |
|---|---|---|---|---|---|---|---|
| 0 hours | 0.0216 | 74% | 23% | 1 | | | |
| | 0 | 100% | 0% | 2 | 0.7 | 0.3 | 1.5 |
| | 0 | 100% | 0% | 3 | 0.8 | 0.4 | 1.8 |
| | 0.0992 | 26% | 70% | 4 | 1.4 | 0.7 | 2.5 |
| | 0.139 | 22% | 80% | | | | |
| | 0.222 | 17% | 90% | | | | |
| 24 hours | 0.0245 | 73% | 26% | 1 | | | |
| | 0 | 100% | 0% | 2 | 0.5 | 0.2 | 1.4 |
| | 0 | 100% | 0% | 3 | 1.7 | 1.0 | 3.0 |
| | 0.0992 | 27% | 70% | 4 | 1.2 | 0.6 | 2.3 |
| | 0.139 | 15% | 80% | | | | |
| | 0.222 | 4% | 90% | | | | |
| 48 hours | 0 | 100% | 0% | 1 | | | |
| | 0 | 100% | 0% | 2 | 0.7 | 0.1 | 3.5 |
| | 0 | 100% | 0% | 3 | 1.0 | 0.3 | 3.9 |
| | 0.0992 | 21% | 70% | 4 | 2.1 | 0.8 | 5.7 |
| | 0.139 | 14% | 80% | | | | |
| | 0.222 | 14% | 90% | | | | |

UO only

| Time prior AKI stage | Cutoff value | sens | spec | Quartile | OR | 95% CI of OR | |
|---|---|---|---|---|---|---|---|
| 0 hours | 0.0108 | 71% | 15% | 1 | | | |
| | 0 | 100% | 0% | 2 | 0.6 | 0.3 | 1.0 |
| | 0 | 100% | 0% | 3 | 1.9 | 1.3 | 2.9 |
| | 0.0972 | 22% | 70% | 4 | 2.1 | 1.4 | 3.1 |
| | 0.133 | 10% | 80% | | | | |
| | 0.205 | 6% | 90% | | | | |
| 24 hours | 0.0108 | 72% | 15% | 1 | | | |
| | 0 | 100% | 0% | 2 | 2.5 | 1.3 | 4.7 |
| | 0 | 100% | 0% | 3 | 4.2 | 2.4 | 7.5 |
| | 0.0972 | 9% | 70% | 4 | 5.4 | 3.1 | 9.5 |
| | 0.133 | 4% | 80% | | | | |
| | 0.205 | 2% | 90% | | | | |

Fig. 5 Continued

| 48 hours | | 0 | 100% | 0% | 1 | | | |
| --- | --- | --- | --- | --- | --- | --- | --- | --- |
| | | 0 | 100% | 0% | 2 | 2.6 | 0.6 | 11.2 |
| | | 0 | 100% | 0% | 3 | 2.6 | 0.6 | 11.2 |
| | | 0.0972 | 13% | 70% | 4 | 6.5 | 1.9 | 22.4 |
| | | 0.133 | 4% | 80% | | | | |
| | | 0.205 | 0% | 90% | | | | |

Myeloperoxidase sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 130.796 | 135.584 | 130.796 | 258.157 | 130.796 | 294.035 |
| average | 182.390 | 227.502 | 182.390 | 281.099 | 182.390 | 318.249 |
| stdev | 201.711 | 282.646 | 201.711 | 241.670 | 201.711 | 390.321 |
| p (t-test) | | 0.262 | | 0.007 | | 0.015 |
| min | 0.000 | 0.000 | 0.000 | 0.000 | 0.000 | 0.000 |
| max | 992.966 | 1177.984 | 992.966 | 1188.715 | 992.966 | 1808.488 |
| n (Samp) | 105 | 48 | 105 | 55 | 105 | 25 |
| n (Pat) | 99 | 48 | 99 | 55 | 99 | 25 | sCr only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 175.159 | 278.376 | 175.159 | 312.041 | 175.159 | 193.386 |
| average | 199.793 | 448.429 | 199.793 | 400.755 | 199.793 | 355.270 |
| stdev | 205.453 | 557.098 | 205.453 | 396.823 | 205.453 | 532.199 |
| p (t-test) | | 0.000 | | 0.000 | | 0.023 |
| min | 0.000 | 0.000 | 0.000 | 0.000 | 0.000 | 0.000 |
| max | 992.966 | 2065.234 | 992.966 | 1580.100 | 992.966 | 1808.488 |
| n (Samp) | 242 | 16 | 242 | 20 | 242 | 12 |
| n (Pat) | 161 | 16 | 161 | 20 | 161 | 12 |

UO only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 179.799 | 112.072 | 179.799 | 237.019 | 179.799 | 239.391 |
| average | 264.384 | 220.640 | 264.384 | 243.321 | 264.384 | 246.966 |
| stdev | 346.972 | 361.876 | 346.972 | 211.887 | 346.972 | 205.555 |
| p (t-test) | | 0.509 | | 0.711 | | 0.825 |
| min | 0.000 | 0.000 | 0.000 | 0.000 | 0.000 | 0.000 |
| max | 1808.488 | 2048.626 | 1808.488 | 862.883 | 1808.488 | 580.899 |
| n (Samp) | 96 | 40 | 96 | 44 | 96 | 21 |
| n (Pat) | 84 | 40 | 84 | 44 | 84 | 21 | sCr or UO

| Time prior AKI stage | AUC | SE | nCohort 1 | nCohort 2 | p |
| --- | --- | --- | --- | --- | --- |
| 0 hours | 0.53 | 0.051 | 105 | 48 | 0.618 |
| 24 hours | 0.64 | 0.047 | 105 | 55 | 0.003 |
| 48 hours | 0.62 | 0.065 | 105 | 25 | 0.075 | sCr only

| Time prior AKI stage | AUC | SE | nCohort 1 | nCohort 2 | p |
| --- | --- | --- | --- | --- | --- |
| 0 hours | 0.62 | 0.077 | 242 | 16 | 0.110 |
| 24 hours | 0.68 | 0.068 | 242 | 20 | 0.010 |
| 48 hours | 0.54 | 0.087 | 242 | 12 | 0.687 |

Fig. 5 Continued

UO only

| Time prior AKI stage | AUC | SE | nCohort 1 | nCohort 2 | p |
|---|---|---|---|---|---|
| 0 hours | 0.45 | 0.053 | 96 | 40 | 0.365 |
| 24 hours | 0.54 | 0.053 | 96 | 44 | 0.405 |
| 48 hours | 0.55 | 0.071 | 96 | 21 | 0.460 | sCr or UO

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 1.0 | 0.6 | 1.6 |
| | 0 | 100% | 0% | 3 | 0.7 | 0.4 | 1.1 |
| | 264.682 | 33% | 70% | 4 | 1.4 | 0.9 | 2.1 |
| | 324.107 | 29% | 80% | | | | |
| | 423.861 | 19% | 90% | | | | |
| 24 hours | 120.089 | 71% | 47% | 1 | | | |
| | 39.0012 | 80% | 39% | 2 | 3.1 | 1.7 | 5.6 |
| | 0 | 100% | 0% | 3 | 3.4 | 1.9 | 6.2 |
| | 264.682 | 49% | 70% | 4 | 5.7 | 3.2 | 10.1 |
| | 324.107 | 36% | 80% | | | | |
| | 423.861 | 22% | 90% | | | | |
| 48 hours | 1E-09 | 72% | 37% | 1 | | | |
| | 0 | 100% | 0% | 2 | 0.4 | 0.1 | 1.0 |
| | 0 | 100% | 0% | 3 | 0.4 | 0.1 | 1.1 |
| | 264.682 | 52% | 70% | 4 | 2.0 | 1.1 | 3.8 |
| | 324.107 | 48% | 80% | | | | |
| | 423.861 | 28% | 90% | | | | | sCr only

| Time prior AKI stage | Cutoff value | sens | spec | Quartile | OR | 95% CI of OR | |
|---|---|---|---|---|---|---|---|
| 0 hours | 130.796 | 75% | 47% | 1 | | | |
| | 0 | 100% | 0% | 2 | 0.5 | 0.1 | 2.2 |
| | 0 | 100% | 0% | 3 | 1.0 | 0.4 | 2.8 |
| | 296.761 | 50% | 71% | 4 | 1.5 | 0.6 | 3.7 |
| | 352.554 | 38% | 80% | | | | |
| | 489.579 | 31% | 90% | | | | |
| 24 hours | 190.649 | 70% | 53% | 1 | | | |
| | 98.2708 | 80% | 41% | 2 | 2.0 | 0.4 | 9.4 |
| | 5.44998 | 90% | 33% | 3 | 2.1 | 0.4 | 9.6 |
| | 296.761 | 50% | 71% | 4 | 5.6 | 1.6 | 19.5 |
| | 352.554 | 40% | 80% | | | | |
| | 489.579 | 25% | 90% | | | | |
| 48 hours | 0 | 100% | 0% | 1 | | | |
| | 0 | 100% | 0% | 2 | 0.2 | 0.0 | 2.1 |
| | 0 | 100% | 0% | 3 | 0.2 | 0.0 | 2.1 |
| | 296.761 | 50% | 71% | 4 | 1.0 | 0.4 | 2.3 |
| | 352.554 | 33% | 80% | | | | |
| | 489.579 | 17% | 90% | | | | |

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 1.0 | 0.6 | 1.8 |
| | 0 | 100% | 0% | 3 | 1.7 | 1.0 | 3.0 |
| | 303.076 | 25% | 71% | 4 | 1.0 | 0.6 | 1.8 |
| | 389.074 | 15% | 80% | | | | |
| | 591.249 | 10% | 91% | | | | |

Fig. 5 Continued

| 24 hours | 109.477 | 70% | 41% | 1 | | | |
| | 0 | 100% | 0% | 2 | 3.2 | 1.7 | 6.0 |
| | 0 | 100% | 0% | 3 | 2.5 | 1.3 | 4.8 |
| | 303.076 | 36% | 71% | 4 | 2.5 | 1.3 | 4.8 |
| | 389.074 | 18% | 80% | | | | |
| | 591.249 | 5% | 91% | | | | |
| 48 hours | 39.0012 | 71% | 33% | 1 | | | |
| | 0 | 100% | 0% | 2 | 0.6 | 0.2 | 1.8 |
| | 0 | 100% | 0% | 3 | 1.3 | 0.5 | 3.0 |
| | 303.076 | 43% | 71% | 4 | 1.5 | 0.6 | 3.4 |
| | 389.074 | 33% | 80% | | | | |
| | 591.249 | 0% | 91% | | | | |

Nidogen-1 sCr or UO

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 243003.731 | 450495.050 | 243003.731 | 522245.116 | 243003.731 | na |
| average | 427963.099 | 439320.859 | 427963.099 | 550302.760 | 427963.099 | na |
| stdev | 520281.599 | 296384.896 | 520281.599 | 388197.207 | 520281.599 | na |
| p (t-test) | | 0.931 | | 0.353 | | na |
| min | 140.129 | 12348.790 | 140.129 | 140.129 | 140.129 | na |
| max | 3173333.333 | 908119.658 | 3173333.333 | 1355072.464 | 3173333.333 | na |
| n (Samp) | 73 | 17 | 73 | 18 | 73 | 0 |
| n (Pat) | 41 | 17 | 41 | 18 | 41 | 0 | sCr only

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 288149.351 | 238969.134 | 288149.351 | 814102.564 | 288149.351 | 73418.675 |
| average | 438323.663 | 244697.453 | 438323.663 | 690692.160 | 438323.663 | 205969.984 |
| stdev | 487226.769 | 177620.813 | 487226.769 | 415362.903 | 487226.769 | 232853.850 |
| p (t-test) | | 0.335 | | 0.075 | | 0.413 |
| min | 140.129 | 57083.333 | 140.129 | 140.129 | 140.129 | 69653.614 |
| max | 3173333.333 | 450495.050 | 3173333.333 | 1245341.615 | 3173333.333 | 474837.662 |
| n (Samp) | 119 | 6 | 119 | 13 | 119 | 3 |
| n (Pat) | 70 | 6 | 70 | 13 | 70 | 3 |

UO only

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 349071.068 | 441558.442 | 349071.068 | 476461.039 | 349071.068 | 44354.839 |
| average | 496863.550 | 444363.574 | 496863.550 | 459481.142 | 496863.550 | 306006.494 |
| stdev | 543037.711 | 292126.250 | 543037.711 | 361869.996 | 543037.711 | na |
| p (t-test) | | 0.696 | | 0.821 | | na |
| min | 44354.839 | 12348.790 | 44354.839 | 34143.519 | 44354.839 | 306006.494 |
| max | 3173333.333 | 908119.658 | 3173333.333 | 1355072.464 | 3173333.333 | 306006.494 |
| n (Samp) | 58 | 18 | 58 | 12 | 58 | 1 |
| n (Pat) | 31 | 18 | 31 | 12 | 31 | 1 | sCr or UO

| Time prior AKI stage | AUC | SE | nCohort 1 | nCohort 2 | p |
|---|---|---|---|---|---|
| 0 hours | 0.57 | 0.079 | 73 | 17 | 0.397 |
| 24 hours | 0.63 | 0.077 | 73 | 18 | 0.088 |
| 48 hours | nd | nd | 73 | 0 | nd |

Fig. 5 Continued sCr only

| Time prior AKI stage | AUC | SE | nCohort 1 | nCohort 2 | p |
|---|---|---|---|---|---|
| 0 hours | 0.39 | 0.109 | 119 | 6 | 0.305 |
| 24 hours | 0.69 | 0.085 | 119 | 13 | 0.028 |
| 48 hours | 0.30 | 0.131 | 119 | 3 | 0.133 |

UO only

| Time prior AKI stage | AUC | SE | nCohort 1 | nCohort 2 | p |
|---|---|---|---|---|---|
| 0 hours | 0.51 | 0.079 | 58 | 18 | 0.855 |
| 24 hours | 0.52 | 0.093 | 58 | 12 | 0.799 |
| 48 hours | 0.47 | 0.286 | 58 | 1 | 0.904 | sCr or UO

| Time prior AKI stage | Cutoff value | sens | spec | Quartile | OR | 95% CI of OR | |
|---|---|---|---|---|---|---|---|
| 0 hours | 259596 | 71% | 55% | 1 | | | |
| | 118873 | 82% | 30% | 2 | 0.6 | 0.1 | 3.8 |
| | 56250 | 94% | 14% | 3 | 2.4 | 0.7 | 7.9 |
| | 495942 | 35% | 71% | 4 | 2.2 | 0.7 | 7.4 |
| | 664530 | 29% | 81% | | | | |
| | 965625 | 0% | 90% | | | | |
| 24 hours | 291919 | 72% | 56% | 1 | | | |
| | 173041 | 83% | 42% | 2 | 1.5 | 0.2 | 9.3 |
| | 6223.52 | 94% | 5% | 3 | 3.5 | 0.8 | 16.1 |
| | 495942 | 50% | 71% | 4 | 4.4 | 1.0 | 19.2 |
| | 664530 | 39% | 81% | | | | |
| | 965625 | 11% | 90% | | | | |
| 48 hours | na | na | na | 1 | | | |
| | na | na | na | 2 | na | na | na |
| | na | na | na | 3 | na | na | na |
| | na | na | na | 4 | na | na | na |
| | na | na | na | | | | |
| | na | na | na | | | | | sCr only

| Time prior AKI stage | Cutoff value | sens | spec | Quartile | OR | 95% CI of OR | |
|---|---|---|---|---|---|---|---|
| 0 hours | 80195.8 | 83% | 14% | 1 | | | |
| | 80195.8 | 83% | 14% | 2 | na | na | na |
| | 56250 | 100% | 13% | 3 | na | na | na |
| | 499188 | 0% | 71% | 4 | na | na | na |
| | 724359 | 0% | 81% | | | | |
| | 985938 | 0% | 91% | | | | |
| 24 hours | 332323 | 77% | 54% | 1 | | | |
| | 304455 | 85% | 53% | 2 | 0.5 | 0.0 | 10.4 |
| | 56250 | 92% | 13% | 3 | 1.6 | 0.3 | 9.0 |
| | 499188 | 69% | 71% | 4 | 4.2 | 1.0 | 16.9 |
| | 724359 | 54% | 81% | | | | |
| | 985938 | 23% | 91% | | | | |
| 48 hours | 56250 | 100% | 13% | 1 | | | |
| | 56250 | 100% | 13% | 2 | na | na | na |
| | 56250 | 100% | 13% | 3 | na | na | na |
| | 499188 | 0% | 71% | 4 | na | na | na |
| | 724359 | 0% | 81% | | | | |
| | 985938 | 0% | 91% | | | | |

Fig. 5 Continued

UO only

| Time prior AKI stage | Cutoff value | sens | spec | Quartile | OR | 95% CI of OR | |
|---|---|---|---|---|---|---|---|
| 0 hours | 259596 | 72% | 45% | 1 | | | |
| | 115587 | 83% | 19% | 2 | 0.5 | 0.1 | 1.9 |
| | 56250 | 94% | 7% | 3 | 1.0 | 0.3 | 2.9 |
| | 553419 | 39% | 71% | 4 | 1.0 | 0.3 | 2.9 |
| | 835470 | 6% | 81% | | | | |
| | 985938 | 0% | 91% | | | | |
| 24 hours | 173041 | 75% | 29% | 1 | | | |
| | 139459 | 83% | 28% | 2 | 1.5 | 0.2 | 10.0 |
| | 123117 | 92% | 22% | 3 | 2.3 | 0.4 | 13.3 |
| | 553419 | 25% | 71% | 4 | 1.5 | 0.2 | 10.0 |
| | 835470 | 8% | 81% | | | | |
| | 985938 | 8% | 91% | | | | |
| 48 hours | 291919 | 100% | 47% | 1 | | | |
| | 291919 | 100% | 47% | 2 | na | na | na |
| | 291919 | 100% | 47% | 3 | na | na | na |
| | 553419 | 0% | 71% | 4 | na | na | na |
| | 835470 | 0% | 81% | | | | |
| | 985938 | 0% | 91% | | | | |

Oxidized low-density lipoprotein receptor 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.428 | 0.368 | 0.428 | 0.554 | 0.428 | 0.454 |
| average | 0.492 | 0.462 | 0.492 | 0.729 | 0.492 | 0.697 |
| stdev | 0.321 | 0.265 | 0.321 | 0.614 | 0.321 | 0.615 |
| p (t-test) | | 0.576 | | 0.002 | | 0.021 |
| min | 0.000 | 0.121 | 0.000 | 0.121 | 0.000 | 0.196 |
| max | 1.737 | 1.282 | 1.737 | 3.013 | 1.737 | 2.441 |
| n (Samp) | 105 | 48 | 105 | 55 | 105 | 25 |
| n (Pat) | 99 | 48 | 99 | 55 | 99 | 25 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 0.443 | 0.472 | 0.443 | 0.539 | 0.443 | 0.336 |
| average | 0.563 | 0.684 | 0.563 | 0.691 | 0.563 | 0.595 |
| stdev | 0.452 | 0.784 | 0.452 | 0.632 | 0.452 | 0.584 |
| p (t-test) | | 0.328 | | 0.240 | | 0.811 |
| min | 0.000 | 0.198 | 0.000 | 0.121 | 0.000 | 0.196 |
| max | 3.215 | 3.428 | 3.215 | 3.013 | 3.215 | 1.920 |
| n (Samp) | 242 | 16 | 242 | 20 | 242 | 12 |
| n (Pat) | 161 | 16 | 161 | 20 | 161 | 12 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 0.435 | 0.366 | 0.435 | 0.612 | 0.435 | 0.478 |
| average | 0.520 | 0.489 | 0.520 | 0.746 | 0.520 | 0.664 |
| stdev | 0.357 | 0.333 | 0.357 | 0.565 | 0.357 | 0.546 |
| p (t-test) | | 0.641 | | 0.005 | | 0.136 |
| min | 0.121 | 0.121 | 0.121 | 0.137 | 0.121 | 0.255 |
| max | 1.920 | 1.623 | 1.920 | 2.441 | 1.920 | 2.441 |
| n (Samp) | 96 | 40 | 96 | 44 | 96 | 21 |
| n (Pat) | 84 | 40 | 84 | 44 | 84 | 21 |

Fig. 5 Continued sCr or UO

| Time prior AKI stage | AUC | SE | nCohort 1 | nCohort 2 | p |
|---|---|---|---|---|---|
| 0 hours | 0.48 | 0.050 | 105 | 48 | 0.692 |
| 24 hours | 0.62 | 0.048 | 105 | 55 | 0.009 |
| 48 hours | 0.57 | 0.066 | 105 | 25 | 0.262 | sCr only

| Time prior AKI stage | AUC | SE | nCohort 1 | nCohort 2 | p |
|---|---|---|---|---|---|
| 0 hours | 0.52 | 0.075 | 242 | 16 | 0.816 |
| 24 hours | 0.57 | 0.069 | 242 | 20 | 0.315 |
| 48 hours | 0.45 | 0.082 | 242 | 12 | 0.505 |

UO only

| Time prior AKI stage | AUC | SE | nCohort 1 | nCohort 2 | p |
|---|---|---|---|---|---|
| 0 hours | 0.46 | 0.054 | 96 | 40 | 0.452 |
| 24 hours | 0.64 | 0.052 | 96 | 44 | 0.008 |
| 48 hours | 0.58 | 0.071 | 96 | 21 | 0.272 | sCr or UO

| Time prior AKI stage | Cutoff value | sens | spec | Quartile | OR | 95% CI of OR | |
|---|---|---|---|---|---|---|---|
| 0 hours | 0.29253 | 71% | 29% | 1 | | | |
| | 0.25471 | 81% | 22% | 2 | 0.9 | 0.5 | 1.5 |
| | 0.19289 | 92% | 13% | 3 | 1.9 | 1.2 | 2.9 |
| | 0.55885 | 29% | 70% | 4 | 1.0 | 0.6 | 1.7 |
| | 0.64778 | 21% | 80% | | | | |
| | 0.94808 | 4% | 90% | | | | |
| 24 hours | 0.35589 | 73% | 43% | 1 | | | |
| | 0.28002 | 80% | 26% | 2 | 0.7 | 0.4 | 1.1 |
| | 0.20473 | 91% | 16% | 3 | 1.1 | 0.7 | 1.8 |
| | 0.55885 | 49% | 70% | 4 | 2.6 | 1.7 | 4.0 |
| | 0.64778 | 40% | 80% | | | | |
| | 0.94808 | 22% | 90% | | | | |
| 48 hours | 0.34901 | 72% | 40% | 1 | | | |
| | 0.2716 | 84% | 26% | 2 | 1.5 | 0.6 | 3.3 |
| | 0.25471 | 92% | 22% | 3 | 1.2 | 0.5 | 3.0 |
| | 0.55885 | 32% | 70% | 4 | 1.5 | 0.6 | 3.3 |
| | 0.64778 | 24% | 80% | | | | |
| | 0.94808 | 24% | 90% | | | | | sCr only

| Time prior AKI stage | Cutoff value | sens | spec | Quartile | OR | 95% CI of OR | |
|---|---|---|---|---|---|---|---|
| 0 hours | 0.28002 | 75% | 23% | 1 | | | |
| | 0.27135 | 81% | 19% | 2 | 0.6 | 0.2 | 1.7 |
| | 0.20473 | 94% | 12% | 3 | 0.8 | 0.3 | 2.0 |
| | 0.60057 | 25% | 71% | 4 | 0.8 | 0.3 | 2.0 |
| | 0.75586 | 25% | 80% | | | | |
| | 1.00077 | 13% | 90% | | | | |
| 24 hours | 0.36432 | 75% | 39% | 1 | | | |
| | 0.29253 | 80% | 25% | 2 | 1.3 | 0.5 | 3.2 |
| | 0.24295 | 90% | 16% | 3 | 1.0 | 0.4 | 2.8 |
| | 0.60057 | 45% | 71% | 4 | 1.8 | 0.8 | 4.2 |
| | 0.75586 | 25% | 80% | | | | |
| | 1.00077 | 25% | 90% | | | | |

Fig. 5 Continued

| | | | | | | | |
|---|---|---|---|---|---|---|---|
| 48 hours | 0.27364 | 75% | 21% | 1 | | | |
| | 0.26318 | 83% | 18% | 2 | 1.6 | 0.3 | 8.5 |
| | 0.24295 | 92% | 16% | 3 | 1.5 | 0.3 | 8.3 |
| | 0.60057 | 17% | 71% | 4 | 2.1 | 0.5 | 9.8 |
| | 0.75586 | 17% | 80% | | | | |
| | 1.00077 | 17% | 90% | | | | |

UO only

| Time prior AKI stage | Cutoff value | sens | spec | Quartile | OR | 95% CI of OR | |
|---|---|---|---|---|---|---|---|
| 0 hours | 0.28844 | 70% | 26% | 1 | | | |
| | 0.25471 | 80% | 22% | 2 | 0.4 | 0.2 | 0.7 |
| | 0.19766 | 90% | 15% | 3 | 1.3 | 0.8 | 2.2 |
| | 0.57009 | 30% | 71% | 4 | 1.0 | 0.6 | 1.7 |
| | 0.66119 | 25% | 80% | | | | |
| | 1.00077 | 5% | 91% | | | | |
| 24 hours | 0.45351 | 70% | 53% | 1 | | | |
| | 0.27603 | 82% | 24% | 2 | 0.3 | 0.1 | 0.7 |
| | 0.21797 | 91% | 18% | 3 | 1.7 | 1.0 | 2.8 |
| | 0.57009 | 52% | 71% | 4 | 2.1 | 1.3 | 3.5 |
| | 0.66119 | 45% | 80% | | | | |
| | 1.00077 | 20% | 91% | | | | |
| 48 hours | 0.35215 | 71% | 36% | 1 | | | |
| | 0.31742 | 81% | 30% | 2 | 1.3 | 0.5 | 3.7 |
| | 0.2716 | 90% | 24% | 3 | 1.6 | 0.6 | 4.3 |
| | 0.57009 | 38% | 71% | 4 | 1.6 | 0.6 | 4.1 |
| | 0.66119 | 24% | 80% | | | | |
| | 1.00077 | 19% | 91% | | | | |

Pappalysin-1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.048 | 0.049 | 0.048 | 0.059 | 0.048 | 0.077 |
| average | 0.198 | 0.070 | 0.198 | 0.081 | 0.198 | 0.084 |
| stdev | 0.939 | 0.060 | 0.939 | 0.071 | 0.939 | 0.052 |
| p (t-test) | | 0.306 | | 0.331 | | 0.534 |
| min | 0.000 | 0.010 | 0.000 | 0.016 | 0.000 | 0.021 |
| max | 9.680 | 0.274 | 9.680 | 0.392 | 9.680 | 0.210 |
| n (Samp) | 257 | 56 | 257 | 61 | 257 | 26 |
| n (Pat) | 112 | 56 | 112 | 61 | 112 | 26 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.053 | 0.058 | 0.053 | 0.053 | 0.053 | 0.083 |
| average | 0.149 | 0.062 | 0.149 | 0.074 | 0.149 | 0.076 |
| stdev | 0.706 | 0.040 | 0.706 | 0.060 | 0.706 | 0.045 |
| p (t-test) | | 0.554 | | 0.588 | | 0.701 |
| min | 0.000 | 0.010 | 0.000 | 0.006 | 0.000 | 0.010 |
| max | 9.680 | 0.158 | 9.680 | 0.291 | 9.680 | 0.168 |
| n (Samp) | 459 | 23 | 459 | 26 | 459 | 14 |
| n (Pat) | 180 | 23 | 180 | 26 | 180 | 14 |

Fig. 5 Continued

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 0.046 | 0.053 | 0.046 | 0.065 | 0.046 | 0.077 |
| average | 0.224 | 0.080 | 0.224 | 0.086 | 0.224 | 0.085 |
| stdev | 1.030 | 0.071 | 1.030 | 0.074 | 1.030 | 0.055 |
| p (t-test) |  | 0.322 |  | 0.334 |  | 0.520 |
| min | 0.000 | 0.010 | 0.000 | 0.019 | 0.000 | 0.021 |
| max | 9.680 | 0.293 | 9.680 | 0.392 | 9.680 | 0.210 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
|---|---|---|---|---|---|
| 0 hours | 0.50 | 0.043 | 257 | 56 | 0.957 |
| 24 hours | 0.58 | 0.042 | 257 | 61 | 0.051 |
| 48 hours | 0.64 | 0.061 | 257 | 26 | 0.025 | sCr only

| Time prior AKI stage | AUC | SE | nCohort 1 | nCohort 2 | p |
|---|---|---|---|---|---|
| 0 hours | 0.47 | 0.061 | 459 | 23 | 0.657 |
| 24 hours | 0.52 | 0.059 | 459 | 26 | 0.681 |
| 48 hours | 0.57 | 0.081 | 459 | 14 | 0.376 |

UO only

| Time prior AKI stage | AUC | SE | nCohort 1 | nCohort 2 | p |
|---|---|---|---|---|---|
| 0 hours | 0.55 | 0.046 | 213 | 51 | 0.255 |
| 24 hours | 0.62 | 0.045 | 213 | 53 | 0.006 |
| 48 hours | 0.64 | 0.065 | 213 | 23 | 0.025 | sCr or UO

| Time prior AKI stage | Cutoff value | sens | spec | Quartile | OR | 95% CI of OR | |
|---|---|---|---|---|---|---|---|
| 0 hours | 0.0298 | 71% | 22% | 1 |  |  |  |
|  | 0.027 | 82% | 19% | 2 | 0.5 | 0.4 | 0.8 |
|  | 0.0105 | 95% | 2% | 3 | 0.7 | 0.5 | 0.9 |
|  | 0.072 | 32% | 70% | 4 | 1.0 | 0.7 | 1.3 |
|  | 0.0896 | 27% | 80% |  |  |  |  |
|  | 0.125 | 14% | 90% |  |  |  |  |
| 24 hours | 0.0433 | 70% | 45% | 1 |  |  |  |
|  | 0.0359 | 80% | 31% | 2 | 1.1 | 0.7 | 1.6 |
|  | 0.0249 | 90% | 16% | 3 | 1.5 | 1.1 | 2.1 |
|  | 0.072 | 39% | 70% | 4 | 1.7 | 1.3 | 2.4 |
|  | 0.0896 | 26% | 80% |  |  |  |  |
|  | 0.125 | 15% | 90% |  |  |  |  |
| 48 hours | 0.0439 | 73% | 45% | 1 |  |  |  |
|  | 0.0396 | 81% | 38% | 2 | 1.3 | 0.5 | 3.2 |
|  | 0.027 | 92% | 19% | 3 | 1.5 | 0.6 | 3.7 |
|  | 0.072 | 58% | 70% | 4 | 3.0 | 1.5 | 6.3 |
|  | 0.0896 | 38% | 80% |  |  |  |  |
|  | 0.125 | 15% | 90% |  |  |  |  |

Fig. 5 Continued sCr only

| Time prior AKI stage | Cutoff value | sens | spec | Quartile | OR | 95% CI of OR | |
|---|---|---|---|---|---|---|---|
| 0 hours | 0.0288 | 74% | 19% | 1 | | | |
| | 0.0273 | 83% | 18% | 2 | 1.4 | 0.7 | 2.9 |
| | 0.0162 | 91% | 5% | 3 | 0.8 | 0.3 | 2.0 |
| | 0.0799 | 30% | 70% | 4 | 1.4 | 0.7 | 2.9 |
| | 0.102 | 13% | 80% | | | | |
| | 0.151 | 4% | 90% | | | | |
| 24 hours | 0.0399 | 73% | 35% | 1 | | | |
| | 0.037 | 81% | 30% | 2 | 2.4 | 1.1 | 4.9 |
| | 0.0214 | 92% | 11% | 3 | 1.5 | 0.7 | 3.6 |
| | 0.0799 | 35% | 70% | 4 | 1.8 | 0.8 | 4.0 |
| | 0.102 | 27% | 80% | | | | |
| | 0.151 | 8% | 90% | | | | |
| 48 hours | 0.0404 | 71% | 36% | 1 | | | |
| | 0.0361 | 86% | 29% | 2 | 5.2 | 0.5 | 56.3 |
| | 0.0348 | 93% | 27% | 3 | 3.1 | 0.2 | 43.1 |
| | 0.0799 | 57% | 70% | 4 | 5.1 | 0.5 | 55.8 |
| | 0.102 | 29% | 80% | | | | |
| | 0.151 | 7% | 90% | | | | |

UO only

| Time prior AKI stage | Cutoff value | sens | spec | Quartile | OR | 95% CI of OR | |
|---|---|---|---|---|---|---|---|
| 0 hours | 0.0341 | 71% | 31% | 1 | | | |
| | 0.029 | 82% | 22% | 2 | 0.7 | 0.5 | 1.1 |
| | 0.0164 | 90% | 6% | 3 | 0.7 | 0.5 | 1.1 |
| | 0.072 | 37% | 70% | 4 | 1.5 | 1.1 | 2.1 |
| | 0.0885 | 33% | 81% | | | | |
| | 0.11 | 25% | 90% | | | | |
| 24 hours | 0.0439 | 72% | 48% | 1 | | | |
| | 0.037 | 81% | 36% | 2 | 1.3 | 0.8 | 2.1 |
| | 0.0236 | 92% | 17% | 3 | 2.5 | 1.6 | 3.9 |
| | 0.072 | 42% | 70% | 4 | 2.7 | 1.7 | 4.1 |
| | 0.0885 | 32% | 81% | | | | |
| | 0.11 | 19% | 90% | | | | |
| 48 hours | 0.0439 | 74% | 48% | 1 | | | |
| | 0.0359 | 83% | 34% | 2 | 1.0 | 0.3 | 2.9 |
| | 0.027 | 91% | 20% | 3 | 1.6 | 0.6 | 3.8 |
| | 0.072 | 57% | 70% | 4 | 2.5 | 1.1 | 5.4 |
| | 0.0885 | 39% | 81% | | | | |
| | 0.11 | 22% | 90% | | | | |

Fig. 5 Continued

P-selectin glycoprotein ligand 1 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 263.784 | 284.769 | 263.784 | 279.848 | 263.784 | 297.424 |
| average | 273.025 | 295.833 | 273.025 | 288.707 | 273.025 | 276.534 |
| stdev | 96.023 | 131.332 | 96.023 | 147.070 | 96.023 | 75.520 |
| p (t-test) |  | 0.176 |  | 0.369 |  | 0.862 |
| min | 85.271 | 70.652 | 85.271 | 11.853 | 85.271 | 84.448 |
| max | 795.623 | 853.893 | 795.623 | 1092.518 | 795.623 | 435.303 |
| n (Samp) | 155 | 54 | 155 | 56 | 155 | 25 |
| n (Pat) | 105 | 54 | 105 | 56 | 105 | 25 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 266.390 | 268.360 | 266.390 | 278.954 | 266.390 | 244.115 |
| average | 272.191 | 307.396 | 272.191 | 314.043 | 272.191 | 265.795 |
| stdev | 94.993 | 154.357 | 94.993 | 185.588 | 94.993 | 75.744 |
| p (t-test) |  | 0.125 |  | 0.058 |  | 0.811 |
| min | 11.853 | 70.652 | 11.853 | 64.815 | 11.853 | 154.011 |
| max | 795.623 | 853.893 | 795.623 | 1092.518 | 795.623 | 435.303 |
| n (Samp) | 314 | 20 | 314 | 24 | 314 | 13 |
| n (Pat) | 170 | 20 | 170 | 24 | 170 | 13 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 248.010 | 274.526 | 248.010 | 295.952 | 248.010 | 302.521 |
| average | 259.290 | 280.101 | 259.290 | 285.814 | 259.290 | 306.725 |
| stdev | 80.359 | 105.760 | 80.359 | 113.957 | 80.359 | 148.451 |
| p (t-test) |  | 0.161 |  | 0.091 |  | 0.031 |
| min | 85.271 | 86.047 | 85.271 | 11.853 | 85.271 | 84.448 |
| max | 531.755 | 654.702 | 531.755 | 653.994 | 531.755 | 853.893 |
| n (Samp) | 129 | 49 | 129 | 45 | 129 | 21 |
| n (Pat) | 84 | 49 | 84 | 45 | 84 | 21 | sCr or UO

| Time prior AKI stage | AUC | SE | nCohort 1 | nCohort 2 | p |
|---|---|---|---|---|---|
| 0 hours | 0.56 | 0.046 | 155 | 54 | 0.179 |
| 24 hours | 0.55 | 0.046 | 155 | 56 | 0.319 |
| 48 hours | 0.55 | 0.063 | 155 | 25 | 0.439 | sCr only

| Time prior AKI stage | AUC | SE | nCohort 1 | nCohort 2 | p |
|---|---|---|---|---|---|
| 0 hours | 0.56 | 0.068 | 314 | 20 | 0.389 |
| 24 hours | 0.56 | 0.063 | 314 | 24 | 0.331 |
| 48 hours | 0.48 | 0.081 | 314 | 13 | 0.827 |

UO only

| Time prior AKI stage | AUC | SE | nCohort 1 | nCohort 2 | p |
|---|---|---|---|---|---|
| 0 hours | 0.56 | 0.049 | 129 | 49 | 0.205 |
| 24 hours | 0.59 | 0.051 | 129 | 45 | 0.070 |
| 48 hours | 0.61 | 0.070 | 129 | 21 | 0.113 |

Fig. 5 Continued sCr or UO

| Time prior AKI stage | Cutoff value | sens | spec | Quartile | OR | 95% CI of OR | |
|---|---|---|---|---|---|---|---|
| 0 hours | 239.878 | 70% | 43% | 1 | | | |
| | 209.719 | 81% | 25% | 2 | 0.9 | 0.6 | 1.4 |
| | 159.304 | 91% | 8% | 3 | 1.5 | 1.0 | 2.2 |
| | 306.856 | 46% | 70% | 4 | 1.3 | 0.9 | 2.0 |
| | 347.212 | 24% | 80% | | | | |
| | 393.363 | 15% | 90% | | | | |
| 24 hours | 228.578 | 71% | 37% | 1 | | | |
| | 196.726 | 80% | 23% | 2 | 0.6 | 0.4 | 1.0 |
| | 127.079 | 91% | 1% | 3 | 1.2 | 0.8 | 1.7 |
| | 306.856 | 39% | 70% | 4 | 1.2 | 0.8 | 1.7 |
| | 347.212 | 27% | 80% | | | | |
| | 393.363 | 11% | 90% | | | | |
| 48 hours | 237.694 | 72% | 42% | 1 | | | |
| | 215.026 | 80% | 27% | 2 | 1.2 | 0.5 | 2.8 |
| | 196.726 | 92% | 23% | 3 | 1.7 | 0.8 | 3.6 |
| | 306.856 | 36% | 70% | 4 | 1.2 | 0.5 | 2.8 |
| | 347.212 | 8% | 80% | | | | |
| | 393.363 | 8% | 90% | | | | | sCr only

| Time prior AKI stage | Cutoff value | sens | spec | Quartile | OR | 95% CI of OR | |
|---|---|---|---|---|---|---|---|
| 0 hours | 238.306 | 70% | 39% | 1 | | | |
| | 229.559 | 80% | 35% | 2 | 2.1 | 0.7 | 5.7 |
| | 195.596 | 90% | 22% | 3 | 1.7 | 0.6 | 5.1 |
| | 313.457 | 30% | 70% | 4 | 2.1 | 0.7 | 5.7 |
| | 339.168 | 30% | 80% | | | | |
| | 388.464 | 15% | 90% | | | | |
| 24 hours | 253.759 | 71% | 45% | 1 | | | |
| | 207.851 | 83% | 24% | 2 | 1.2 | 0.6 | 2.6 |
| | 197.838 | 92% | 23% | 3 | 1.2 | 0.6 | 2.6 |
| | 313.457 | 33% | 70% | 4 | 1.4 | 0.7 | 2.9 |
| | 339.168 | 29% | 80% | | | | |
| | 388.464 | 17% | 90% | | | | |
| 48 hours | 229.92 | 77% | 35% | 1 | | | |
| | 229.559 | 85% | 35% | 2 | 0.7 | 0.1 | 3.5 |
| | 161.252 | 92% | 10% | 3 | 2.1 | 0.7 | 5.8 |
| | 313.457 | 23% | 70% | 4 | 0.7 | 0.1 | 3.6 |
| | 339.168 | 15% | 80% | | | | |
| | 388.464 | 8% | 90% | | | | |

UO only

| Time prior AKI stage | Cutoff value | sens | spec | Quartile | OR | 95% CI of OR | |
|---|---|---|---|---|---|---|---|
| 0 hours | 231.549 | 71% | 40% | 1 | | | |
| | 196.726 | 82% | 26% | 2 | 1.4 | 0.9 | 2.2 |
| | 150.259 | 92% | 9% | 3 | 1.0 | 0.6 | 1.7 |
| | 299.734 | 43% | 71% | 4 | 1.9 | 1.2 | 2.9 |
| | 331.51 | 20% | 81% | | | | |
| | 361.727 | 18% | 91% | | | | |
| 24 hours | 228.578 | 71% | 37% | 1 | | | |
| | 194.127 | 80% | 24% | 2 | 0.6 | 0.3 | 1.1 |
| | 127.079 | 91% | 2% | 3 | 1.1 | 0.7 | 1.9 |
| | 299.734 | 47% | 71% | 4 | 2.1 | 1.3 | 3.2 |
| | 331.51 | 33% | 81% | | | | |
| | 361.727 | 24% | 91% | | | | |

Fig. 5 Continued

| | | | | | | | | |
|---|---|---|---|---|---|---|---|---|
| 48 hours | 257.519 | 71% | 53% | 1 | | | | |
| | 207.851 | 81% | 28% | 2 | 0.7 | 0.2 | 2.5 | |
| | 196.726 | 90% | 26% | 3 | 1.6 | 0.6 | 4.1 | |
| | 299.734 | 52% | 71% | 4 | 2.2 | 0.9 | 5.2 | |
| | 331.51 | 24% | 81% | | | | | |
| | 361.727 | 14% | 91% | | | | | |

Secretory leukocyte peptidase inhibitor sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 61256.092 | 64786.054 | 61256.092 | 66877.971 | 61256.092 | 70709.677 |
| average | 69105.397 | 73236.504 | 69105.397 | 76019.092 | 69105.397 | 77172.027 |
| stdev | 34677.932 | 28059.207 | 34677.932 | 36668.025 | 34677.932 | 32502.455 |
| p (t-test) | | 0.436 | | 0.212 | | 0.279 |
| min | 13520.408 | 30739.726 | 13520.408 | 26653.144 | 13520.408 | 33138.686 |
| max | 199917.831 | 160690.846 | 199917.831 | 218323.747 | 199917.831 | 152842.105 |
| n (Samp) | 148 | 53 | 148 | 56 | 148 | 25 |
| n (Pat) | 104 | 53 | 104 | 56 | 104 | 25 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 63900.192 | 74241.843 | 63900.192 | 66877.971 | 63900.192 | 65060.241 |
| average | 69820.359 | 86120.614 | 69820.359 | 87707.819 | 69820.359 | 76503.059 |
| stdev | 29958.613 | 41784.508 | 29958.613 | 48096.520 | 29958.613 | 33389.876 |
| p (t-test) | | 0.026 | | 0.008 | | 0.434 |
| min | 13520.408 | 30739.726 | 13520.408 | 26653.144 | 13520.408 | 44299.424 |
| max | 199917.831 | 160690.846 | 199917.831 | 218323.747 | 199917.831 | 152842.105 |
| n (Samp) | 306 | 19 | 306 | 24 | 306 | 13 |
| n (Pat) | 169 | 19 | 169 | 24 | 169 | 13 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 61343.570 | 67170.997 | 61343.570 | 69301.205 | 61343.570 | 71614.458 |
| average | 67545.808 | 76340.370 | 67545.808 | 74061.947 | 67545.808 | 74389.033 |
| stdev | 29386.432 | 29685.598 | 29386.432 | 30909.061 | 29386.432 | 29536.749 |
| p (t-test) | | 0.081 | | 0.211 | | 0.326 |
| min | 21505.376 | 38136.201 | 21505.376 | 33630.832 | 21505.376 | 33138.686 |
| max | 183903.282 | 160690.846 | 183903.282 | 170531.178 | 183903.282 | 136649.396 |
| n (Samp) | 123 | 48 | 123 | 45 | 123 | 21 |
| n (Pat) | 83 | 48 | 83 | 45 | 83 | 21 | sCr or UO

| Time prior AKI stage | AUC | SE | nCohort 1 | nCohort 2 | p |
|---|---|---|---|---|---|
| 0 hours | 0.57 | 0.047 | 148 | 53 | 0.151 |
| 24 hours | 0.57 | 0.046 | 148 | 56 | 0.120 |
| 48 hours | 0.59 | 0.064 | 148 | 25 | 0.163 |

Fig. 5 Continued sCr only

| Time prior AKI stage | AUC | SE | nCohort 1 | nCohort 2 | p |
|---|---|---|---|---|---|
| 0 hours | 0.61 | 0.071 | 306 | 19 | 0.116 |
| 24 hours | 0.60 | 0.063 | 306 | 24 | 0.126 |
| 48 hours | 0.55 | 0.084 | 306 | 13 | 0.586 |

UO only

| Time prior AKI stage | AUC | SE | nCohort 1 | nCohort 2 | p |
|---|---|---|---|---|---|
| 0 hours | 0.59 | 0.050 | 123 | 48 | 0.068 |
| 24 hours | 0.57 | 0.051 | 123 | 45 | 0.155 |
| 48 hours | 0.58 | 0.070 | 123 | 21 | 0.250 | sCr or UO

| Time prior AKI stage | Cutoff value | sens | spec | Quartile | OR | 95% CI of OR | |
|---|---|---|---|---|---|---|---|
| 0 hours | 55299.1 | 72% | 40% | 1 | | | |
| | 51538.5 | 81% | 33% | 2 | 2.9 | 1.7 | 4.8 |
| | 44627.6 | 91% | 20% | 3 | 2.6 | 1.6 | 4.4 |
| | 74120.5 | 36% | 70% | 4 | 2.6 | 1.5 | 4.3 |
| | 87078.5 | 23% | 80% | | | | |
| | 108187 | 13% | 91% | | | | |
| 24 hours | 58631.1 | 71% | 45% | 1 | | | |
| | 50083.5 | 80% | 30% | 2 | 0.9 | 0.6 | 1.4 |
| | 39856.6 | 91% | 17% | 3 | 2.8 | 1.9 | 4.0 |
| | 74120.5 | 38% | 70% | 4 | 1.2 | 0.8 | 1.9 |
| | 87078.5 | 21% | 80% | | | | |
| | 108187 | 16% | 91% | | | | |
| 48 hours | 56276.4 | 72% | 41% | 1 | | | |
| | 51196.6 | 80% | 32% | 2 | 1.3 | 0.5 | 3.4 |
| | 43679.2 | 92% | 19% | 3 | 2.2 | 1.0 | 5.2 |
| | 74120.5 | 40% | 70% | 4 | 2.2 | 0.9 | 5.0 |
| | 87078.5 | 32% | 80% | | | | |
| | 108187 | 20% | 91% | | | | | sCr only

| Time prior AKI stage | Cutoff value | sens | spec | Quartile | OR | 95% CI of OR | |
|---|---|---|---|---|---|---|---|
| 0 hours | 62504.2 | 74% | 48% | 1 | | | |
| | 43207.5 | 84% | 13% | 2 | 1.0 | 0.4 | 2.8 |
| | 30739.7 | 95% | 3% | 3 | 0.5 | 0.1 | 2.2 |
| | 75812 | 47% | 70% | 4 | 2.4 | 1.1 | 5.1 |
| | 85475.8 | 37% | 80% | | | | |
| | 105385 | 37% | 90% | | | | |
| 24 hours | 63800.4 | 71% | 50% | 1 | | | |
| | 42472.3 | 83% | 12% | 2 | 0.8 | 0.3 | 2.0 |
| | 39856.6 | 92% | 11% | 3 | 1.0 | 0.4 | 2.3 |
| | 75812 | 46% | 70% | 4 | 2.1 | 1.1 | 4.0 |
| | 85475.8 | 42% | 80% | | | | |
| | 105385 | 29% | 90% | | | | |
| 48 hours | 61168.6 | 77% | 45% | 1 | | | |
| | 51362.8 | 85% | 26% | 2 | 2.0 | 0.4 | 9.3 |
| | 45220.7 | 92% | 17% | 3 | 2.0 | 0.4 | 9.3 |
| | 75812 | 23% | 70% | 4 | 1.5 | 0.3 | 8.1 |
| | 85475.8 | 23% | 80% | | | | |
| | 105385 | 23% | 90% | | | | |

Fig. 5 Continued

UO only

| Time prior AKI stage | Cutoff value | sens | spec | Quartile | OR | 95% CI of OR | |
|---|---|---|---|---|---|---|---|
| 0 hours | 56494.2 | 71% | 41% | 1 | | | |
| | 52488.1 | 81% | 33% | 2 | 2.9 | 1.6 | 5.2 |
| | 45555.6 | 92% | 23% | 3 | 2.6 | 1.4 | 4.7 |
| | 74120.5 | 40% | 71% | 4 | 3.2 | 1.8 | 5.8 |
| | 83630.7 | 29% | 80% | | | | |
| | 104930 | 17% | 90% | | | | |
| 24 hours | 58631.1 | 71% | 46% | 1 | | | |
| | 53122 | 80% | 35% | 2 | 1.3 | 0.8 | 2.3 |
| | 43679.2 | 91% | 16% | 3 | 2.4 | 1.4 | 3.9 |
| | 74120.5 | 38% | 71% | 4 | 1.7 | 1.0 | 2.9 |
| | 83630.7 | 20% | 80% | | | | |
| | 104930 | 13% | 90% | | | | |
| 48 hours | 56276.4 | 71% | 40% | 1 | | | |
| | 49366.6 | 81% | 28% | 2 | 1.0 | 0.3 | 3.0 |
| | 42891.6 | 90% | 15% | 3 | 1.6 | 0.6 | 4.1 |
| | 74120.5 | 43% | 71% | 4 | 1.9 | 0.8 | 4.7 |
| | 83630.7 | 33% | 80% | | | | |
| | 104930 | 14% | 90% | | | | |

Stem cell factor sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 339.000 | 328.000 | 339.000 | 317.000 | 339.000 | 308.500 |
| average | 368.427 | 356.250 | 368.427 | 359.410 | 368.427 | 348.385 |
| stdev | 173.797 | 158.149 | 173.797 | 181.460 | 173.797 | 174.470 |
| p (t-test) | | 0.630 | | 0.718 | | 0.576 |
| min | 89.700 | 127.000 | 89.700 | 110.000 | 89.700 | 113.000 |
| max | 1340.000 | 819.000 | 1340.000 | 1100.000 | 1340.000 | 927.000 |
| n (Samp) | 257 | 56 | 257 | 61 | 257 | 26 |
| n (Pat) | 112 | 56 | 112 | 61 | 112 | 26 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 335.000 | 372.000 | 335.000 | 348.500 | 335.000 | 392.500 |
| average | 380.034 | 408.217 | 380.034 | 383.808 | 380.034 | 410.857 |
| stdev | 308.863 | 190.019 | 308.863 | 190.317 | 308.863 | 190.338 |
| p (t-test) | | 0.665 | | 0.951 | | 0.711 |
| min | 89.700 | 170.000 | 89.700 | 110.000 | 89.700 | 142.000 |
| max | 5840.000 | 769.000 | 5840.000 | 867.000 | 5840.000 | 895.000 |
| n (Samp) | 459 | 23 | 459 | 26 | 459 | 14 |
| n (Pat) | 180 | 23 | 180 | 26 | 180 | 14 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 326.000 | 335.000 | 326.000 | 316.000 | 326.000 | 286.000 |
| average | 354.135 | 362.961 | 354.135 | 362.151 | 354.135 | 345.304 |
| stdev | 156.698 | 159.119 | 156.698 | 188.972 | 156.698 | 174.358 |
| p (t-test) | | 0.719 | | 0.750 | | 0.800 |
| min | 89.700 | 127.000 | 89.700 | 142.000 | 89.700 | 113.000 |
| max | 1260.000 | 819.000 | 1260.000 | 1100.000 | 1260.000 | 927.000 |
| n (Samp) | 213 | 51 | 213 | 53 | 213 | 23 |
| n (Pat) | 89 | 51 | 89 | 53 | 89 | 23 |

Fig. 5 Continued sCr or UO

| Time prior AKI stage | AUC | SE | nCohort 1 | nCohort 2 | p |
|---|---|---|---|---|---|
| 0 hours | 0.48 | 0.042 | 257 | 56 | 0.697 |
| 24 hours | 0.47 | 0.041 | 257 | 61 | 0.468 |
| 48 hours | 0.46 | 0.058 | 257 | 26 | 0.468 | sCr only

| Time prior AKI stage | AUC | SE | nCohort 1 | nCohort 2 | p |
|---|---|---|---|---|---|
| 0 hours | 0.55 | 0.063 | 459 | 23 | 0.428 |
| 24 hours | 0.53 | 0.059 | 459 | 26 | 0.656 |
| 48 hours | 0.59 | 0.081 | 459 | 14 | 0.290 |

UO only

| Time prior AKI stage | AUC | SE | nCohort 1 | nCohort 2 | p |
|---|---|---|---|---|---|
| 0 hours | 0.52 | 0.045 | 213 | 51 | 0.704 |
| 24 hours | 0.48 | 0.044 | 213 | 53 | 0.677 |
| 48 hours | 0.46 | 0.062 | 213 | 23 | 0.475 | sCr or UO

| Time prior AKI stage | Cutoff value | sens | spec | Quartile | OR | 95% CI of OR | |
|---|---|---|---|---|---|---|---|
| 0 hours | 254 | 71% | 25% | 1 | | | |
| | 224 | 80% | 16% | 2 | 0.7 | 0.5 | 1.0 |
| | 171 | 91% | 4% | 3 | 0.9 | 0.7 | 1.3 |
| | 404 | 29% | 70% | 4 | 1.1 | 0.8 | 1.5 |
| | 461 | 23% | 81% | | | | |
| | 564 | 11% | 90% | | | | |
| 24 hours | 266 | 70% | 28% | 1 | | | |
| | 224 | 80% | 16% | 2 | 0.8 | 0.6 | 1.2 |
| | 187 | 90% | 6% | 3 | 1.4 | 1.0 | 1.9 |
| | 404 | 26% | 70% | 4 | 1.3 | 0.9 | 1.8 |
| | 461 | 20% | 81% | | | | |
| | 564 | 8% | 90% | | | | |
| 48 hours | 264 | 73% | 27% | 1 | | | |
| | 254 | 81% | 25% | 2 | 0.6 | 0.3 | 1.6 |
| | 135 | 92% | 1% | 3 | 1.8 | 1.0 | 3.2 |
| | 404 | 31% | 70% | 4 | 1.0 | 0.5 | 2.1 |
| | 461 | 12% | 81% | | | | |
| | 564 | 12% | 90% | | | | | sCr only

| Time prior AKI stage | Cutoff value | sens | spec | Quartile | OR | 95% CI of OR | |
|---|---|---|---|---|---|---|---|
| 0 hours | 255 | 78% | 26% | 1 | | | |
| | 216 | 83% | 15% | 2 | 1.2 | 0.6 | 2.5 |
| | 208 | 91% | 12% | 3 | 0.8 | 0.3 | 2.0 |
| | 406 | 35% | 70% | 4 | 1.6 | 0.8 | 3.2 |
| | 479 | 35% | 80% | | | | |
| | 571 | 26% | 90% | | | | |
| 24 hours | 281 | 73% | 33% | 1 | | | |
| | 231 | 81% | 21% | 2 | 1.0 | 0.5 | 2.0 |
| | 164 | 92% | 5% | 3 | 0.8 | 0.4 | 1.8 |
| | 406 | 38% | 70% | 4 | 1.5 | 0.9 | 2.7 |
| | 479 | 23% | 80% | | | | |
| | 571 | 15% | 90% | | | | |

Fig. 5 Continued

| | | | | | | | |
|---|---|---|---|---|---|---|---|
| 48 hours | 326 | 71% | 48% | 1 | | | |
| | 255 | 86% | 26% | 2 | 1.5 | 0.3 | 8.0 |
| | 187 | 93% | 8% | 3 | 1.5 | 0.3 | 8.0 |
| | 406 | 50% | 70% | 4 | 3.1 | 0.8 | 11.8 |
| | 479 | 21% | 80% | | | | |
| | 571 | 14% | 90% | | | | |

UO only

| Time prior AKI stage | Cutoff value | sens | spec | Quartile | OR | 95% CI of OR | |
|---|---|---|---|---|---|---|---|
| 0 hours | 298 | 71% | 39% | 1 | | | |
| | 224 | 82% | 17% | 2 | 0.7 | 0.4 | 1.0 |
| | 171 | 90% | 7% | 3 | 0.9 | 0.6 | 1.3 |
| | 402 | 31% | 71% | 4 | 1.0 | 0.7 | 1.4 |
| | 445 | 24% | 80% | | | | |
| | 549 | 12% | 91% | | | | |
| 24 hours | 248 | 72% | 23% | 1 | | | |
| | 214 | 81% | 15% | 2 | 0.6 | 0.4 | 0.9 |
| | 177 | 92% | 8% | 3 | 1.1 | 0.8 | 1.5 |
| | 402 | 28% | 71% | 4 | 1.1 | 0.8 | 1.6 |
| | 445 | 25% | 80% | | | | |
| | 549 | 9% | 91% | | | | |
| 48 hours | 264 | 74% | 28% | 1 | | | |
| | 251 | 83% | 24% | 2 | 0.8 | 0.3 | 2.0 |
| | 214 | 91% | 15% | 3 | 1.9 | 1.0 | 3.9 |
| | 402 | 30% | 71% | 4 | 1.0 | 0.4 | 2.4 |
| | 445 | 17% | 80% | | | | |
| | 549 | 9% | 91% | | | | |

Tissue inhibitor of metalloproteinase 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 209.000 | 254.000 | 209.000 | 246.000 | 209.000 | 235.500 |
| average | 260.043 | 276.320 | 260.043 | 348.377 | 260.043 | 317.538 |
| stdev | 176.758 | 138.902 | 176.758 | 236.569 | 176.758 | 232.808 |
| p (t-test) | | 0.518 | | 0.001 | | 0.127 |
| min | 75.400 | 85.800 | 75.400 | 104.000 | 75.400 | 118.000 |
| max | 1207.000 | 664.000 | 1207.000 | 1220.000 | 1207.000 | 1090.000 |
| n (Samp) | 257 | 56 | 257 | 61 | 257 | 26 |
| n (Pat) | 112 | 56 | 112 | 61 | 112 | 26 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 226.000 | 292.000 | 226.000 | 261.500 | 226.000 | 237.000 |
| average | 276.221 | 301.561 | 276.221 | 336.808 | 276.221 | 309.929 |
| stdev | 194.364 | 127.638 | 194.364 | 209.955 | 194.364 | 252.781 |
| p (t-test) | | 0.537 | | 0.124 | | 0.527 |
| min | 56.400 | 85.800 | 56.400 | 104.000 | 56.400 | 118.000 |
| max | 1250.000 | 492.000 | 1250.000 | 829.000 | 1250.000 | 1090.000 |
| n (Samp) | 459 | 23 | 459 | 26 | 459 | 14 |
| n (Pat) | 180 | 23 | 180 | 26 | 180 | 14 |

Fig. 5 Continued

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 225.000 | 263.000 | 225.000 | 246.000 | 225.000 | 236.000 |
| average | 269.024 | 311.941 | 269.024 | 363.655 | 269.024 | 321.757 |
| stdev | 179.268 | 181.310 | 179.268 | 263.366 | 179.268 | 256.705 |
| p (t-test) | | 0.127 | | 0.002 | | 0.202 |
| min | 75.400 | 100.000 | 75.400 | 96.700 | 75.400 | 87.400 |
| max | 1207.000 | 966.000 | 1207.000 | 1220.000 | 1207.000 | 1207.000 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
|---|---|---|---|---|---|
| 0 hours | 0.57 | 0.043 | 257 | 56 | 0.117 |
| 24 hours | 0.63 | 0.042 | 257 | 61 | 0.002 |
| 48 hours | 0.57 | 0.061 | 257 | 26 | 0.272 | sCr only

| Time prior AKI stage | AUC | SE | nCohort 1 | nCohort 2 | p |
|---|---|---|---|---|---|
| 0 hours | 0.62 | 0.064 | 459 | 23 | 0.070 |
| 24 hours | 0.59 | 0.060 | 459 | 26 | 0.120 |
| 48 hours | 0.54 | 0.080 | 459 | 14 | 0.654 |

UO only

| Time prior AKI stage | AUC | SE | nCohort 1 | nCohort 2 | p |
|---|---|---|---|---|---|
| 0 hours | 0.59 | 0.046 | 213 | 51 | 0.060 |
| 24 hours | 0.62 | 0.045 | 213 | 53 | 0.007 |
| 48 hours | 0.55 | 0.065 | 213 | 23 | 0.470 | sCr or UO

| Time prior AKI stage | Cutoff value | sens | spec | Quartile | OR | 95% CI of OR | |
|---|---|---|---|---|---|---|---|
| 0 hours | 183 | 71% | 41% | 1 | | | |
| | 165 | 80% | 30% | 2 | 1.2 | 0.8 | 1.8 |
| | 119 | 91% | 12% | 3 | 1.2 | 0.8 | 1.8 |
| | 285 | 36% | 70% | 4 | 1.9 | 1.4 | 2.7 |
| | 338 | 29% | 80% | | | | |
| | 447 | 16% | 90% | | | | |
| 24 hours | 209 | 70% | 50% | 1 | | | |
| | 190 | 80% | 44% | 2 | 2.0 | 1.3 | 3.2 |
| | 153 | 90% | 27% | 3 | 2.6 | 1.7 | 4.0 |
| | 285 | 38% | 70% | 4 | 3.0 | 2.0 | 4.4 |
| | 338 | 31% | 80% | | | | |
| | 447 | 26% | 90% | | | | |
| 48 hours | 171 | 73% | 34% | 1 | | | |
| | 143 | 85% | 23% | 2 | 0.8 | 0.4 | 1.8 |
| | 134 | 92% | 18% | 3 | 1.0 | 0.5 | 2.0 |
| | 285 | 35% | 70% | 4 | 1.5 | 0.8 | 2.8 |
| | 338 | 27% | 80% | | | | |
| | 447 | 19% | 90% | | | | |

Fig. 5 Continued sCr only

| Time prior AKI stage | Cutoff value | sens | spec | Quartile | OR | 95% CI of OR | |
|---|---|---|---|---|---|---|---|
| 0 hours | 225 | 74% | 50% | 1 | | | |
| | 183 | 83% | 36% | 2 | 1.3 | 0.4 | 4.3 |
| | 107 | 91% | 7% | 3 | 2.4 | 0.9 | 6.4 |
| | 294 | 48% | 70% | 4 | 3.1 | 1.3 | 7.7 |
| | 363 | 35% | 80% | | | | |
| | 502 | 0% | 90% | | | | |
| 24 hours | 214 | 73% | 48% | 1 | | | |
| | 149 | 81% | 23% | 2 | 0.5 | 0.2 | 1.3 |
| | 124 | 92% | 13% | 3 | 1.4 | 0.7 | 2.5 |
| | 294 | 38% | 70% | 4 | 1.5 | 0.9 | 2.7 |
| | 363 | 35% | 80% | | | | |
| | 502 | 23% | 90% | | | | |
| 48 hours | 179 | 71% | 34% | 1 | | | |
| | 143 | 86% | 21% | 2 | 0.7 | 0.1 | 3.5 |
| | 128 | 93% | 14% | 3 | 1.7 | 0.6 | 5.0 |
| | 294 | 29% | 70% | 4 | 1.3 | 0.4 | 4.3 |
| | 363 | 14% | 80% | | | | |
| | 502 | 14% | 90% | | | | |

UO only

| Time prior AKI stage | Cutoff value | sens | spec | Quartile | OR | 95% CI of OR | |
|---|---|---|---|---|---|---|---|
| 0 hours | 191 | 71% | 42% | 1 | | | |
| | 171 | 80% | 31% | 2 | 1.2 | 0.8 | 1.9 |
| | 142 | 90% | 17% | 3 | 1.1 | 0.7 | 1.7 |
| | 297 | 39% | 70% | 4 | 2.1 | 1.4 | 3.1 |
| | 339 | 35% | 81% | | | | |
| | 437 | 22% | 90% | | | | |
| 24 hours | 209 | 72% | 48% | 1 | | | |
| | 195 | 81% | 43% | 2 | 2.0 | 1.2 | 3.3 |
| | 153 | 92% | 22% | 3 | 2.5 | 1.5 | 4.0 |
| | 297 | 38% | 70% | 4 | 3.1 | 2.0 | 4.9 |
| | 339 | 32% | 81% | | | | |
| | 437 | 25% | 90% | | | | |
| 48 hours | 178 | 74% | 34% | 1 | | | |
| | 143 | 83% | 18% | 2 | 0.8 | 0.3 | 2.0 |
| | 134 | 91% | 13% | 3 | 1.5 | 0.7 | 3.1 |
| | 297 | 30% | 70% | 4 | 1.5 | 0.7 | 3.1 |
| | 339 | 26% | 81% | | | | |
| | 437 | 17% | 90% | | | | |

Fig. 5 Continued

Tissue inhibitor of metalloproteinase 2 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 113236.674 | 106839.335 | 113236.674 | 114916.133 | 113236.674 | 109408.332 |
| average | 113305.296 | 109748.951 | 113305.296 | 113547.086 | 113305.296 | 116195.810 |
| stdev | 24378.727 | 24185.906 | 24378.727 | 34192.577 | 24378.727 | 26878.118 |
| p (t-test) |  | 0.403 |  | 0.959 |  | 0.602 |
| min | 58493.008 | 60870.071 | 58493.008 | 1936.748 | 58493.008 | 69010.743 |
| max | 177248.877 | 173634.554 | 177248.877 | 207083.195 | 177248.877 | 162201.416 |
| n (Samp) | 105 | 48 | 105 | 55 | 105 | 25 |
| n (Pat) | 99 | 48 | 99 | 55 | 99 | 25 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 109495.570 | 107485.056 | 109495.570 | 107700.293 | 109495.570 | 109763.809 |
| average | 111989.692 | 115412.123 | 111989.692 | 109184.954 | 111989.692 | 117303.500 |
| stdev | 27125.219 | 36434.754 | 27125.219 | 40754.231 | 27125.219 | 34913.151 |
| p (t-test) |  | 0.633 |  | 0.671 |  | 0.514 |
| min | 1936.748 | 58966.197 | 1936.748 | 1892.018 | 1936.748 | 69010.743 |
| max | 197537.458 | 188983.579 | 197537.458 | 207083.195 | 197537.458 | 179322.577 |
| n (Samp) | 242 | 16 | 242 | 20 | 242 | 12 |
| n (Pat) | 161 | 16 | 161 | 20 | 161 | 12 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 109561.495 | 106839.335 | 109561.495 | 117835.445 | 109561.495 | 127059.834 |
| average | 112682.018 | 111667.497 | 112682.018 | 113894.419 | 112682.018 | 122481.938 |
| stdev | 24939.915 | 25100.763 | 24939.915 | 33355.275 | 24939.915 | 26058.019 |
| p (t-test) |  | 0.830 |  | 0.811 |  | 0.108 |
| min | 58493.008 | 79013.476 | 58493.008 | 1936.748 | 58493.008 | 81511.422 |
| max | 177248.877 | 189045.463 | 177248.877 | 174620.924 | 177248.877 | 162201.416 |
| n (Samp) | 96 | 40 | 96 | 44 | 96 | 21 |
| n (Pat) | 84 | 40 | 84 | 44 | 84 | 21 | sCr or UO

| Time prior AKI stage | AUC | SE | nCohort 1 | nCohort 2 | p |
|---|---|---|---|---|---|
| 0 hours | 0.45 | 0.050 | 105 | 48 | 0.334 |
| 24 hours | 0.50 | 0.048 | 105 | 55 | 0.944 |
| 48 hours | 0.52 | 0.065 | 105 | 25 | 0.701 | sCr only

| Time prior AKI stage | AUC | SE | nCohort 1 | nCohort 2 | p |
|---|---|---|---|---|---|
| 0 hours | 0.52 | 0.075 | 242 | 16 | 0.784 |
| 24 hours | 0.47 | 0.066 | 242 | 20 | 0.651 |
| 48 hours | 0.53 | 0.087 | 242 | 12 | 0.760 |

UO only

| Time prior AKI stage | AUC | SE | nCohort 1 | nCohort 2 | p |
|---|---|---|---|---|---|
| 0 hours | 0.47 | 0.054 | 96 | 40 | 0.614 |
| 24 hours | 0.53 | 0.053 | 96 | 44 | 0.577 |
| 48 hours | 0.60 | 0.071 | 96 | 21 | 0.139 |

Fig. 5 Continued sCr or UO

| Time prior AKI stage | Cutoff value | sens | spec | Quartile | OR | 95% CI of OR | |
|---|---|---|---|---|---|---|---|
| 0 hours | 93773.4 | 71% | 26% | 1 | | | |
| | 86661.6 | 81% | 16% | 2 | 0.4 | 0.2 | 0.8 |
| | 83092.3 | 92% | 9% | 3 | 1.8 | 1.2 | 2.8 |
| | 125255 | 27% | 70% | 4 | 1.2 | 0.7 | 1.9 |
| | 132931 | 19% | 80% | | | | |
| | 142591 | 13% | 90% | | | | |
| 24 hours | 91716.7 | 71% | 24% | 1 | | | |
| | 87479.3 | 80% | 17% | 2 | 1.1 | 0.7 | 1.7 |
| | 76021.5 | 91% | 5% | 3 | 0.6 | 0.4 | 1.0 |
| | 125255 | 33% | 70% | 4 | 1.2 | 0.8 | 1.9 |
| | 132931 | 24% | 80% | | | | |
| | 142591 | 16% | 90% | | | | |
| 48 hours | 94966.8 | 72% | 28% | 1 | | | |
| | 90288.4 | 80% | 22% | 2 | 1.2 | 0.5 | 2.5 |
| | 87479.3 | 92% | 17% | 3 | 0.6 | 0.2 | 1.6 |
| | 125255 | 40% | 70% | 4 | 1.4 | 0.7 | 2.9 |
| | 132931 | 24% | 80% | | | | |
| | 142591 | 20% | 90% | | | | | sCr only

| Time prior AKI stage | Cutoff value | sens | spec | Quartile | OR | 95% CI of OR | |
|---|---|---|---|---|---|---|---|
| 0 hours | 91716.7 | 75% | 26% | 1 | | | |
| | 87876.9 | 81% | 21% | 2 | 1.3 | 0.5 | 3.2 |
| | 58966.2 | 94% | 1% | 3 | 0.5 | 0.1 | 2.2 |
| | 125012 | 38% | 70% | 4 | 1.3 | 0.5 | 3.2 |
| | 133781 | 25% | 80% | | | | |
| | 148411 | 19% | 90% | | | | |
| 24 hours | 90955 | 70% | 25% | 1 | | | |
| | 87876.9 | 80% | 21% | 2 | 1.6 | 0.7 | 3.8 |
| | 82006.3 | 90% | 11% | 3 | 1.0 | 0.4 | 2.8 |
| | 125012 | 25% | 70% | 4 | 1.6 | 0.7 | 3.8 |
| | 133781 | 20% | 80% | | | | |
| | 148411 | 10% | 90% | | | | |
| 48 hours | 90955 | 75% | 25% | 1 | | | |
| | 85864.4 | 83% | 16% | 2 | 1.0 | 0.2 | 3.9 |
| | 83123.8 | 92% | 13% | 3 | 0.3 | 0.0 | 4.7 |
| | 125012 | 42% | 70% | 4 | 1.7 | 0.6 | 5.1 |
| | 133781 | 33% | 80% | | | | |
| | 148411 | 25% | 90% | | | | |

UO only

| Time prior AKI stage | Cutoff value | sens | spec | Quartile | OR | 95% CI of OR | |
|---|---|---|---|---|---|---|---|
| 0 hours | 94129.4 | 70% | 26% | 1 | | | |
| | 88807.1 | 80% | 20% | 2 | 0.2 | 0.1 | 0.5 |
| | 83601.2 | 90% | 10% | 3 | 1.3 | 0.8 | 2.1 |
| | 123879 | 33% | 71% | 4 | 0.8 | 0.4 | 1.3 |
| | 133812 | 20% | 80% | | | | |
| | 148411 | 8% | 91% | | | | |
| 24 hours | 98682.4 | 70% | 30% | 1 | | | |
| | 83092.3 | 82% | 9% | 2 | 0.5 | 0.3 | 0.9 |
| | 74896.6 | 91% | 4% | 3 | 1.1 | 0.7 | 1.8 |
| | 123879 | 36% | 71% | 4 | 1.0 | 0.6 | 1.6 |
| | 133812 | 25% | 80% | | | | |
| | 148411 | 16% | 91% | | | | |

Fig. 5 Continued

| 48 hours | 106923 | 71% | 43% | 1 | | | |
| | 94966.8 | 81% | 27% | 2 | 1.3 | 0.5 | 3.7 |
| | 88807.1 | 90% | 20% | 3 | 1.0 | 0.3 | 3.1 |
| | 123879 | 52% | 71% | 4 | 2.3 | 0.9 | 5.6 |
| | 133812 | 33% | 80% | | | | |
| | 148411 | 24% | 91% | | | | |

Tumor necrosis factor-alpha sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 7.480 | 7.480 | 7.480 | 9.130 | 7.480 | 7.165 |
| average | 12.426 | 9.952 | 12.426 | 15.427 | 12.426 | 13.706 |
| stdev | 28.223 | 9.014 | 28.223 | 27.627 | 28.223 | 20.503 |
| p (t-test) | | 0.517 | | 0.454 | | 0.822 |
| min | 0.040 | 0.040 | 0.040 | 0.040 | 0.040 | 0.040 |
| max | 307.000 | 50.100 | 307.000 | 196.000 | 307.000 | 96.600 |
| n (Samp) | 257 | 56 | 257 | 61 | 257 | 26 |
| n (Pat) | 112 | 56 | 112 | 61 | 112 | 26 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 7.480 | 10.400 | 7.480 | 8.455 | 7.480 | 11.400 |
| average | 13.004 | 11.477 | 13.004 | 14.105 | 13.004 | 18.242 |
| stdev | 38.845 | 8.761 | 38.845 | 16.115 | 38.845 | 25.045 |
| p (t-test) | | 0.851 | | 0.886 | | 0.617 |
| min | 0.040 | 0.040 | 0.040 | 0.829 | 0.040 | 2.160 |
| max | 669.000 | 35.500 | 669.000 | 75.800 | 669.000 | 96.600 |
| n (Samp) | 459 | 23 | 459 | 26 | 459 | 14 |
| n (Pat) | 180 | 23 | 180 | 26 | 180 | 14 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 7.480 | 7.980 | 7.480 | 9.360 | 7.480 | 5.750 |
| average | 11.809 | 9.949 | 11.809 | 14.414 | 11.809 | 10.010 |
| stdev | 24.151 | 8.504 | 24.151 | 27.792 | 24.151 | 10.649 |
| p (t-test) | | 0.589 | | 0.496 | | 0.724 |
| min | 0.040 | 0.040 | 0.040 | 0.040 | 0.040 | 0.040 |
| max | 307.000 | 50.100 | 307.000 | 196.000 | 307.000 | 43.600 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
|---|---|---|---|---|---|
| 0 hours | 0.51 | 0.043 | 257 | 56 | 0.858 |
| 24 hours | 0.55 | 0.042 | 257 | 61 | 0.194 |
| 48 hours | 0.50 | 0.059 | 257 | 26 | 0.966 | sCr only

| Time prior AKI stage | AUC | SE | nCohort 1 | nCohort 2 | p |
|---|---|---|---|---|---|
| 0 hours | 0.59 | 0.064 | 459 | 23 | 0.181 |
| 24 hours | 0.58 | 0.060 | 459 | 26 | 0.200 |
| 48 hours | 0.62 | 0.081 | 459 | 14 | 0.153 |

Fig. 5 Continued

UO only

| Time prior AKI stage | AUC | SE | nCohort 1 | nCohort 2 | p |
|---|---|---|---|---|---|
| 0 hours | 0.52 | 0.045 | 213 | 51 | 0.588 |
| 24 hours | 0.56 | 0.045 | 213 | 53 | 0.168 |
| 48 hours | 0.47 | 0.062 | 213 | 23 | 0.636 | sCr or UO

| Time prior AKI stage | Cutoff value | sens | spec | Quartile | OR | 95% CI of OR | |
|---|---|---|---|---|---|---|---|
| 0 hours | 3.81 | 79% | 25% | 1 | | | |
| | 3.26 | 82% | 20% | 2 | 1.2 | 0.8 | 1.7 |
| | 1.95 | 91% | 13% | 3 | 0.8 | 0.6 | 1.2 |
| | 11.1 | 34% | 70% | 4 | 1.4 | 1.0 | 1.9 |
| | 13.5 | 25% | 81% | | | | |
| | 22 | 7% | 91% | | | | |
| 24 hours | 5.08 | 70% | 36% | 1 | | | |
| | 3.81 | 80% | 25% | 2 | 0.9 | 0.6 | 1.3 |
| | 1.68 | 93% | 12% | 3 | 1.4 | 1.0 | 1.9 |
| | 11.1 | 36% | 70% | 4 | 1.6 | 1.2 | 2.2 |
| | 13.5 | 26% | 81% | | | | |
| | 22 | 13% | 91% | | | | |
| 48 hours | 3.81 | 73% | 25% | 1 | | | |
| | 3.17 | 81% | 20% | 2 | 1.7 | 0.8 | 3.4 |
| | 2.2 | 92% | 14% | 3 | 1.2 | 0.6 | 2.7 |
| | 11.1 | 35% | 70% | 4 | 1.5 | 0.7 | 3.1 |
| | 13.5 | 19% | 81% | | | | |
| | 22 | 15% | 91% | | | | | sCr only

| Time prior AKI stage | Cutoff value | sens | spec | Quartile | OR | 95% CI of OR | |
|---|---|---|---|---|---|---|---|
| 0 hours | 5.28 | 74% | 39% | 1 | | | |
| | 3.81 | 87% | 25% | 2 | 2.0 | 0.7 | 5.6 |
| | 3.26 | 91% | 21% | 3 | 1.7 | 0.6 | 5.0 |
| | 10.9 | 43% | 70% | 4 | 3.1 | 1.3 | 7.7 |
| | 14.1 | 35% | 81% | | | | |
| | 21.4 | 9% | 90% | | | | |
| 24 hours | 6.27 | 73% | 45% | 1 | | | |
| | 4.23 | 81% | 28% | 2 | 0.8 | 0.3 | 2.0 |
| | 0.0399 | 100% | 6% | 3 | 1.6 | 0.8 | 3.2 |
| | 10.9 | 38% | 70% | 4 | 1.8 | 1.0 | 3.5 |
| | 14.1 | 31% | 81% | | | | |
| | 21.4 | 19% | 90% | | | | |
| 48 hours | 6.27 | 71% | 45% | 1 | | | |
| | 4.23 | 86% | 28% | 2 | 1.5 | 0.3 | 8.0 |
| | 3.81 | 93% | 25% | 3 | 2.6 | 0.6 | 10.5 |
| | 10.9 | 57% | 70% | 4 | 2.0 | 0.4 | 9.1 |
| | 14.1 | 29% | 81% | | | | |
| | 21.4 | 14% | 90% | | | | |

UO only

| Time prior AKI stage | Cutoff value | sens | spec | Quartile | OR | 95% CI of OR | |
|---|---|---|---|---|---|---|---|
| 0 hours | 5.08 | 71% | 36% | 1 | | | |
| | 3.81 | 82% | 23% | 2 | 1.1 | 0.7 | 1.7 |
| | 2.49 | 90% | 15% | 3 | 1.3 | 0.9 | 2.0 |
| | 11.4 | 31% | 71% | 4 | 1.3 | 0.9 | 2.0 |
| | 13.5 | 24% | 81% | | | | |
| | 21.4 | 8% | 90% | | | | |

Fig. 5 Continued

| | | | | | | | |
|---|---|---|---|---|---|---|---|
| 24 hours | 5.28 | 72% | 38% | 1 | | | |
| | 3.81 | 81% | 23% | 2 | 1.0 | 0.6 | 1.5 |
| | 1.95 | 91% | 12% | 3 | 1.1 | 0.7 | 1.7 |
| | 11.4 | 40% | 71% | 4 | 2.0 | 1.4 | 2.8 |
| | 13.5 | 25% | 81% | | | | |
| | 21.4 | 8% | 90% | | | | |
| 48 hours | 3.17 | 74% | 18% | 1 | | | |
| | 3.08 | 83% | 17% | 2 | 1.2 | 0.6 | 2.7 |
| | 1.04 | 91% | 9% | 3 | 0.8 | 0.3 | 2.0 |
| | 11.4 | 26% | 71% | 4 | 1.7 | 0.8 | 3.5 |
| | 13.5 | 22% | 81% | | | | |
| | 21.4 | 13% | 90% | | | | |

Vascular cell adhesion molecule 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 664.588 | 631.644 | 664.588 | 752.902 | 664.588 | 694.192 |
| average | 735.893 | 727.942 | 735.893 | 889.248 | 735.893 | 760.608 |
| stdev | 284.567 | 298.511 | 284.567 | 494.917 | 284.567 | 381.004 |
| p (t-test) | | 0.875 | | 0.014 | | 0.716 |
| min | 294.325 | 341.055 | 294.325 | 417.689 | 294.325 | 312.022 |
| max | 1703.672 | 1753.212 | 1703.672 | 2809.360 | 1703.672 | 1737.712 |
| n (Samp) | 105 | 48 | 105 | 55 | 105 | 25 |
| n (Pat) | 99 | 48 | 99 | 55 | 99 | 25 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 655.326 | 748.630 | 655.326 | 860.493 | 655.326 | 858.327 |
| average | 746.904 | 806.176 | 746.904 | 862.564 | 746.904 | 890.534 |
| stdev | 381.956 | 289.999 | 381.956 | 290.267 | 381.956 | 381.906 |
| p (t-test) | | 0.543 | | 0.187 | | 0.205 |
| min | 203.738 | 341.055 | 203.738 | 438.983 | 203.738 | 466.114 |
| max | 2809.360 | 1510.868 | 2809.360 | 1437.352 | 2809.360 | 1737.712 |
| n (Samp) | 241 | 16 | 241 | 20 | 241 | 12 |
| n (Pat) | 160 | 16 | 160 | 20 | 160 | 12 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 695.555 | 647.259 | 695.555 | 756.653 | 695.555 | 694.192 |
| average | 777.562 | 709.203 | 777.562 | 901.494 | 777.562 | 730.977 |
| stdev | 316.077 | 282.174 | 316.077 | 526.727 | 316.077 | 340.084 |
| p (t-test) | | 0.238 | | 0.086 | | 0.547 |
| min | 315.327 | 363.063 | 315.327 | 417.689 | 315.327 | 312.022 |
| max | 1737.712 | 1753.212 | 1737.712 | 2809.360 | 1737.712 | 1611.394 |
| n (Samp) | 96 | 40 | 96 | 44 | 96 | 21 |
| n (Pat) | 84 | 40 | 84 | 44 | 84 | 21 | sCr or UO

| Time prior AKI stage | AUC | SE | nCohort 1 | nCohort 2 | p |
|---|---|---|---|---|---|
| 0 hours | 0.48 | 0.050 | 105 | 48 | 0.643 |
| 24 hours | 0.58 | 0.048 | 105 | 55 | 0.091 |
| 48 hours | 0.49 | 0.064 | 105 | 25 | 0.880 |

Fig. 5 Continued sCr only

| Time prior AKI stage | AUC | SE | nCohort 1 | nCohort 2 | p |
|---|---|---|---|---|---|
| 0 hours | 0.60 | 0.077 | 241 | 16 | 0.197 |
| 24 hours | 0.64 | 0.069 | 241 | 20 | 0.038 |
| 48 hours | 0.64 | 0.088 | 241 | 12 | 0.125 |

UO only

| Time prior AKI stage | AUC | SE | nCohort 1 | nCohort 2 | p |
|---|---|---|---|---|---|
| 0 hours | 0.43 | 0.053 | 96 | 40 | 0.197 |
| 24 hours | 0.56 | 0.053 | 96 | 44 | 0.294 |
| 48 hours | 0.45 | 0.068 | 96 | 21 | 0.456 | sCr or UO

| Time prior AKI stage | Cutoff value | sens | spec | Quartile | OR | 95% CI of OR | |
|---|---|---|---|---|---|---|---|
| 0 hours | 554.542 | 71% | 28% | 1 | | | |
| | 478.156 | 81% | 14% | 2 | 0.7 | 0.4 | 1.2 |
| | 437.503 | 92% | 11% | 3 | 0.9 | 0.6 | 1.5 |
| | 790.308 | 33% | 70% | 4 | 1.0 | 0.7 | 1.6 |
| | 918.539 | 23% | 80% | | | | |
| | 1120.39 | 8% | 90% | | | | |
| 24 hours | 625.519 | 71% | 39% | 1 | | | |
| | 539.828 | 80% | 26% | 2 | 0.7 | 0.4 | 1.1 |
| | 463.048 | 91% | 13% | 3 | 1.4 | 0.9 | 2.1 |
| | 790.308 | 42% | 70% | 4 | 1.4 | 0.9 | 2.1 |
| | 918.539 | 29% | 80% | | | | |
| | 1120.39 | 20% | 90% | | | | |
| 48 hours | 531.18 | 72% | 24% | 1 | | | |
| | 463.048 | 80% | 13% | 2 | 0.6 | 0.3 | 1.3 |
| | 333.403 | 92% | 4% | 3 | 0.6 | 0.3 | 1.2 |
| | 790.308 | 32% | 70% | 4 | 0.9 | 0.4 | 1.7 |
| | 918.539 | 28% | 80% | | | | |
| | 1120.39 | 12% | 90% | | | | | sCr only

| Time prior AKI stage | Cutoff value | sens | spec | Quartile | OR | 95% CI of OR | |
|---|---|---|---|---|---|---|---|
| 0 hours | 618.442 | 75% | 43% | 1 | | | |
| | 588.786 | 81% | 37% | 2 | 6.5 | 0.6 | 68.4 |
| | 549.347 | 94% | 31% | 3 | 3.1 | 0.2 | 45.0 |
| | 769.405 | 44% | 70% | 4 | 6.4 | 0.6 | 67.2 |
| | 938.328 | 31% | 80% | | | | |
| | 1196.9 | 6% | 90% | | | | |
| 24 hours | 664.588 | 70% | 54% | 1 | | | |
| | 556.964 | 80% | 32% | 2 | 5.3 | 0.5 | 59.7 |
| | 542.277 | 90% | 30% | 3 | 4.2 | 0.3 | 51.8 |
| | 769.405 | 55% | 70% | 4 | 11.4 | 1.2 | 105.4 |
| | 938.328 | 40% | 80% | | | | |
| | 1196.9 | 10% | 90% | | | | |
| 48 hours | 549.347 | 75% | 31% | 1 | | | |
| | 542.277 | 83% | 30% | 2 | 1.0 | 0.1 | 7.6 |
| | 503.981 | 92% | 25% | 3 | 1.0 | 0.1 | 7.6 |
| | 769.405 | 58% | 70% | 4 | 3.2 | 0.8 | 12.4 |
| | 938.328 | 33% | 80% | | | | |
| | 1196.9 | 17% | 90% | | | | |

Fig. 5 Continued

UO only

| Time prior AKI stage | Cutoff value | sens | spec | Quartile | OR | 95% CI of OR | |
|---|---|---|---|---|---|---|---|
| 0 hours | 549.347 | 70% | 26% | 1 | | | |
| | 478.156 | 80% | 13% | 2 | 1.2 | 0.6 | 2.2 |
| | 443.626 | 90% | 9% | 3 | 1.6 | 0.9 | 2.8 |
| | 882.489 | 23% | 71% | 4 | 1.8 | 1.0 | 3.1 |
| | 1041.63 | 10% | 80% | | | | |
| | 1200.23 | 5% | 91% | | | | |
| 24 hours | 630.621 | 70% | 36% | 1 | | | |
| | 521.454 | 82% | 20% | 2 | 0.6 | 0.3 | 1.2 |
| | 463.048 | 91% | 11% | 3 | 2.1 | 1.3 | 3.5 |
| | 882.489 | 27% | 71% | 4 | 1.1 | 0.7 | 2.0 |
| | 1041.63 | 25% | 80% | | | | |
| | 1200.23 | 14% | 91% | | | | |
| 48 hours | 531.602 | 71% | 22% | 1 | | | |
| | 419.767 | 81% | 8% | 2 | 2.1 | 0.8 | 5.3 |
| | 333.403 | 90% | 3% | 3 | 0.8 | 0.2 | 2.7 |
| | 882.489 | 29% | 71% | 4 | 2.1 | 0.8 | 5.3 |
| | 1041.63 | 14% | 80% | | | | |
| | 1200.23 | 10% | 91% | | | | |

Vascular endothelial growth factor sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 952.000 | 1095.000 | 952.000 | 939.000 | 952.000 | 836.500 |
| average | 1198.206 | 1318.607 | 1198.206 | 1433.820 | 1198.206 | 1113.115 |
| stdev | 1043.990 | 1136.196 | 1043.990 | 1474.053 | 1043.990 | 782.499 |
| p (t-test) | | 0.442 | | 0.147 | | 0.687 |
| min | 353.000 | 424.000 | 353.000 | 414.000 | 353.000 | 392.000 |
| max | 11500.000 | 8250.000 | 11500.000 | 9620.000 | 11500.000 | 3580.000 |
| n (Samp) | 257 | 56 | 257 | 61 | 257 | 26 |
| n (Pat) | 112 | 56 | 112 | 61 | 112 | 26 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 953.000 | 1380.000 | 953.000 | 1145.000 | 953.000 | 1100.000 |
| average | 1254.007 | 1847.261 | 1254.007 | 1804.346 | 1254.007 | 1721.571 |
| stdev | 1427.206 | 1461.084 | 1427.206 | 1758.063 | 1427.206 | 1408.810 |
| p (t-test) | | 0.053 | | 0.060 | | 0.228 |
| min | 338.000 | 473.000 | 338.000 | 520.000 | 338.000 | 724.000 |
| max | 16200.000 | 7240.000 | 16200.000 | 8830.000 | 16200.000 | 5870.000 |
| n (Samp) | 459 | 23 | 459 | 26 | 459 | 14 |
| n (Pat) | 180 | 23 | 180 | 26 | 180 | 14 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 969.000 | 1100.000 | 969.000 | 922.000 | 969.000 | 850.000 |
| average | 1233.559 | 1404.059 | 1233.559 | 1534.019 | 1233.559 | 1216.739 |
| stdev | 1096.453 | 1208.080 | 1096.453 | 1644.714 | 1096.453 | 892.862 |
| p (t-test) | | 0.329 | | 0.111 | | 0.943 |
| min | 436.000 | 424.000 | 436.000 | 414.000 | 436.000 | 392.000 |
| max | 11500.000 | 8250.000 | 11500.000 | 9620.000 | 11500.000 | 3580.000 |
| n (Samp) | 213 | 51 | 213 | 53 | 213 | 23 |
| n (Pat) | 89 | 51 | 89 | 53 | 89 | 23 |

Fig. 5 Continued sCr or UO

| Time prior AKI stage | AUC | SE | nCohort 1 | nCohort 2 | p |
|---|---|---|---|---|---|
| 0 hours | 0.54 | 0.043 | 257 | 56 | 0.348 |
| 24 hours | 0.52 | 0.041 | 257 | 61 | 0.716 |
| 48 hours | 0.44 | 0.057 | 257 | 26 | 0.289 | sCr only

| Time prior AKI stage | AUC | SE | nCohort 1 | nCohort 2 | p |
|---|---|---|---|---|---|
| 0 hours | 0.70 | 0.062 | 459 | 23 | 0.002 |
| 24 hours | 0.62 | 0.060 | 459 | 26 | 0.044 |
| 48 hours | 0.64 | 0.081 | 459 | 14 | 0.075 |

UO only

| Time prior AKI stage | AUC | SE | nCohort 1 | nCohort 2 | p |
|---|---|---|---|---|---|
| 0 hours | 0.55 | 0.046 | 213 | 51 | 0.290 |
| 24 hours | 0.50 | 0.044 | 213 | 53 | 0.986 |
| 48 hours | 0.44 | 0.061 | 213 | 23 | 0.335 | sCr or UO

| Time prior AKI stage | Cutoff value | sens | spec | Quartile | OR | 95% CI of OR | |
|---|---|---|---|---|---|---|---|
| 0 hours | 765 | 71% | 30% | 1 | | | |
| | 678 | 80% | 21% | 2 | 0.7 | 0.5 | 1.1 |
| | 506 | 91% | 6% | 3 | 1.2 | 0.8 | 1.7 |
| | 1220 | 38% | 70% | 4 | 1.5 | 1.1 | 2.0 |
| | 1450 | 29% | 80% | | | | |
| | 1810 | 14% | 90% | | | | |
| 24 hours | 786 | 70% | 32% | 1 | | | |
| | 667 | 80% | 20% | 2 | 0.8 | 0.6 | 1.1 |
| | 585 | 90% | 13% | 3 | 0.7 | 0.5 | 1.0 |
| | 1220 | 33% | 70% | 4 | 0.9 | 0.7 | 1.2 |
| | 1450 | 25% | 80% | | | | |
| | 1810 | 18% | 90% | | | | |
| 48 hours | 666 | 73% | 20% | 1 | | | |
| | 588 | 81% | 13% | 2 | 0.6 | 0.3 | 1.6 |
| | 449 | 92% | 3% | 3 | 1.4 | 0.7 | 2.6 |
| | 1220 | 27% | 70% | 4 | 1.4 | 0.7 | 2.6 |
| | 1450 | 23% | 80% | | | | |
| | 1810 | 15% | 90% | | | | | sCr only

| Time prior AKI stage | Cutoff value | sens | spec | Quartile | OR | 95% CI of OR | |
|---|---|---|---|---|---|---|---|
| 0 hours | 1060 | 74% | 59% | 1 | | | |
| | 825 | 83% | 37% | 2 | 1.5 | 0.3 | 7.9 |
| | 765 | 91% | 32% | 3 | 3.1 | 0.8 | 11.9 |
| | 1220 | 61% | 70% | 4 | 6.5 | 2.0 | 21.1 |
| | 1460 | 39% | 80% | | | | |
| | 1810 | 30% | 90% | | | | |
| 24 hours | 791 | 73% | 34% | 1 | | | |
| | 786 | 81% | 34% | 2 | 1.7 | 0.6 | 5.0 |
| | 593 | 92% | 14% | 3 | 2.8 | 1.1 | 7.1 |
| | 1220 | 46% | 70% | 4 | 3.5 | 1.5 | 8.5 |
| | 1460 | 31% | 80% | | | | |
| | 1810 | 27% | 90% | | | | |

Fig. 5 Continued

| 48 hours | 943 | 71% | 49% | 1 | | | |
| | 811 | 86% | 35% | 2 | na | na | na |
| | 730 | 93% | 28% | 3 | na | na | na |
| | 1220 | 43% | 70% | 4 | na | na | na |
| | 1460 | 43% | 80% | | | | |
| | 1810 | 29% | 90% | | | | |

UO only

| Time prior AKI stage | Cutoff value | sens | spec | Quartile | OR | 95% CI of OR | |
| --- | --- | --- | --- | --- | --- | --- | --- |
| 0 hours | 778 | 71% | 28% | 1 | | | |
| | 693 | 80% | 19% | 2 | 0.4 | 0.2 | 0.6 |
| | 522 | 90% | 5% | 3 | 0.9 | 0.6 | 1.3 |
| | 1250 | 37% | 71% | 4 | 1.4 | 1.0 | 1.9 |
| | 1490 | 33% | 81% | | | | |
| | 1810 | 18% | 90% | | | | |
| 24 hours | 724 | 72% | 23% | 1 | | | |
| | 667 | 81% | 16% | 2 | 0.5 | 0.3 | 0.7 |
| | 585 | 91% | 9% | 3 | 0.9 | 0.6 | 1.3 |
| | 1250 | 32% | 71% | 4 | 1.1 | 0.8 | 1.5 |
| | 1490 | 23% | 81% | | | | |
| | 1810 | 21% | 90% | | | | |
| 48 hours | 588 | 74% | 9% | 1 | | | |
| | 556 | 83% | 7% | 2 | 0.3 | 0.1 | 1.0 |
| | 442 | 91% | 1% | 3 | 0.7 | 0.3 | 1.5 |
| | 1250 | 30% | 71% | 4 | 1.3 | 0.8 | 2.4 |
| | 1490 | 30% | 81% | | | | |
| | 1810 | 22% | 90% | | | | |

Fig. 5 Continued

Aspartate aminotransferase, cytoplasmic sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 16.600 | 18.600 | 16.600 | 19.650 | 16.600 | 20.650 |
| average | 17.351 | 18.257 | 17.351 | 16.371 | 17.351 | 18.011 |
| stdev | 16.496 | 9.174 | 16.496 | 10.272 | 16.496 | 10.428 |
| p (t-test) |  | 0.774 |  | 0.726 |  | 0.866 |
| min | 0.943 | 1.900 | 0.943 | 2.210 | 0.943 | 2.020 |
| max | 251.000 | 41.100 | 251.000 | 29.700 | 251.000 | 32.100 |
| n (Samp) | 434 | 28 | 434 | 36 | 434 | 18 |
| n (Pat) | 173 | 28 | 173 | 36 | 173 | 18 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 16.600 | 20.800 | 16.600 | 20.450 | 16.600 | 19.200 |
| average | 17.130 | 21.067 | 17.130 | 17.653 | 17.130 | 16.791 |
| stdev | 15.269 | 3.166 | 15.269 | 10.501 | 15.269 | 10.446 |
| p (t-test) |  | 0.528 |  | 0.914 |  | 0.953 |
| min | 0.943 | 16.100 | 0.943 | 2.430 | 0.943 | 2.020 |
| max | 251.000 | 25.700 | 251.000 | 28.400 | 251.000 | 29.100 |
| n (Samp) | 542 | 6 | 542 | 10 | 542 | 7 |
| n (Pat) | 208 | 6 | 208 | 10 | 208 | 7 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 17.450 | 17.800 | 17.450 | 20.500 | 17.450 | 22.350 |
| average | 18.020 | 17.744 | 18.020 | 17.354 | 18.020 | 20.423 |
| stdev | 17.751 | 9.284 | 17.751 | 10.014 | 17.751 | 9.330 |
| p (t-test) |  | 0.936 |  | 0.835 |  | 0.591 |
| min | 1.810 | 1.900 | 1.810 | 2.210 | 1.810 | 2.530 |
| max | 251.000 | 41.100 | 251.000 | 29.700 | 251.000 | 32.100 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
| --- | --- | --- | --- | --- | --- |
| 0 hours | 0.58 | 0.058 | 434 | 28 | 0.172 |
| 24 hours | 0.54 | 0.051 | 434 | 36 | 0.443 |
| 48 hours | 0.60 | 0.072 | 434 | 18 | 0.185 | sCr only

| Time prior AKI stage | AUC | SE | nCohort 1 | nCohort 2 | p |
| --- | --- | --- | --- | --- | --- |
| 0 hours | 0.70 | 0.120 | 542 | 6 | 0.094 |
| 24 hours | 0.59 | 0.095 | 542 | 10 | 0.369 |
| 48 hours | 0.55 | 0.113 | 542 | 7 | 0.664 |

UO only

| Time prior AKI stage | AUC | SE | nCohort 1 | nCohort 2 | p |
| --- | --- | --- | --- | --- | --- |
| 0 hours | 0.54 | 0.059 | 356 | 27 | 0.516 |
| 24 hours | 0.56 | 0.055 | 356 | 32 | 0.294 |
| 48 hours | 0.67 | 0.075 | 356 | 16 | 0.022 |

Fig. 6 sCr or UO

| Time prior AKI stage | Cutoff value | sens | spec | Quartile | OR | 95% CI of OR | |
|---|---|---|---|---|---|---|---|
| 0 hours | 16.9 | 71% | 51% | 1 | | | |
| | 13.7 | 82% | 34% | 2 | 0.6 | 0.2 | 1.7 |
| | 2.59 | 93% | 7% | 3 | 2.6 | 1.4 | 4.6 |
| | 20.4 | 43% | 70% | 4 | 1.6 | 0.8 | 3.2 |
| | 23 | 25% | 80% | | | | |
| | 27.1 | 11% | 90% | | | | |
| 24 hours | 4.51 | 72% | 19% | 1 | | | |
| | 3 | 81% | 11% | 2 | 0.2 | 0.1 | 0.5 |
| | 2.42 | 92% | 5% | 3 | 0.5 | 0.3 | 0.8 |
| | 20.4 | 44% | 70% | 4 | 1.3 | 0.9 | 1.8 |
| | 23 | 39% | 80% | | | | |
| | 27.1 | 14% | 90% | | | | |
| 48 hours | 18 | 72% | 57% | 1 | | | |
| | 3.06 | 83% | 11% | 2 | 0.0 | 0.0 | na |
| | 2.51 | 94% | 6% | 3 | 1.2 | 0.6 | 2.6 |
| | 20.4 | 50% | 70% | 4 | 1.4 | 0.7 | 2.9 |
| | 23 | 39% | 80% | | | | |
| | 27.1 | 22% | 90% | | | | | sCr only

| Time prior AKI stage | Cutoff value | sens | spec | Quartile | OR | 95% CI of OR | |
|---|---|---|---|---|---|---|---|
| 0 hours | 20 | 83% | 68% | 1 | | | |
| | 20 | 83% | 68% | 2 | na | na | na |
| | 16 | 100% | 47% | 3 | na | na | na |
| | 20.6 | 50% | 70% | 4 | na | na | na |
| | 23.4 | 17% | 80% | | | | |
| | 27.4 | 0% | 90% | | | | |
| 24 hours | 16.3 | 70% | 48% | 1 | | | |
| | 4.76 | 80% | 20% | 2 | 0.3 | 0.0 | 4.6 |
| | 3.12 | 90% | 12% | 3 | 0.3 | 0.0 | 4.6 |
| | 20.6 | 50% | 70% | 4 | 1.7 | 0.6 | 5.0 |
| | 23.4 | 40% | 80% | | | | |
| | 27.4 | 20% | 90% | | | | |
| 48 hours | 18 | 71% | 57% | 1 | | | |
| | 2.81 | 86% | 9% | 2 | 0.0 | 0.0 | na |
| | 1.97 | 100% | 1% | 3 | 1.0 | 0.1 | 7.3 |
| | 20.6 | 43% | 70% | 4 | 1.5 | 0.3 | 7.9 |
| | 23.4 | 29% | 80% | | | | |
| | 27.4 | 14% | 90% | | | | |

UO only

| Time prior AKI stage | Cutoff value | sens | spec | Quartile | OR | 95% CI of OR | |
|---|---|---|---|---|---|---|---|
| 0 hours | 16.4 | 70% | 46% | 1 | | | |
| | 12.9 | 81% | 28% | 2 | 1.2 | 0.6 | 2.6 |
| | 2.59 | 93% | 6% | 3 | 1.9 | 1.0 | 3.6 |
| | 21 | 33% | 70% | 4 | 1.4 | 0.7 | 2.9 |
| | 23.4 | 26% | 80% | | | | |
| | 27.7 | 11% | 90% | | | | |
| 24 hours | 14.4 | 72% | 35% | 1 | | | |
| | 3 | 81% | 9% | 2 | 0.5 | 0.3 | 1.0 |
| | 2.46 | 91% | 4% | 3 | 0.4 | 0.2 | 0.9 |
| | 21 | 47% | 70% | 4 | 1.6 | 1.1 | 2.5 |
| | 23.4 | 44% | 80% | | | | |
| | 27.7 | 9% | 90% | | | | |

Fig. 6 Continued

| 48 hours | 19.9 | 75% | 65% | 1 | | | |
| | 18.8 | 81% | 60% | 2 | 0.0 | 0.0 | na |
| | 3.06 | 94% | 10% | 3 | 1.7 | 0.6 | 5.1 |
| | 21 | 69% | 70% | 4 | 2.8 | 1.1 | 7.3 |
| | 23.4 | 38% | 80% | | | | |
| | 27.7 | 19% | 90% | | | | |

CD40 sCr or UO

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 1.610 | 1.990 | 1.610 | 1.815 | 1.610 | 1.780 |
| average | 2.029 | 2.666 | 2.029 | 3.052 | 2.029 | 2.181 |
| stdev | 1.791 | 2.168 | 1.791 | 4.549 | 1.791 | 1.385 |
| p (t-test) | | 0.073 | | 0.006 | | 0.724 |
| min | 0.446 | 0.720 | 0.446 | 0.627 | 0.446 | 0.702 |
| max | 28.000 | 11.100 | 28.000 | 28.100 | 28.000 | 6.600 |
| n (Samp) | 434 | 28 | 434 | 36 | 434 | 18 |
| n (Pat) | 173 | 28 | 173 | 36 | 173 | 18 | sCr only

| | 0 hr prior toAKI stage | | 24 hr prior toAKI stage | | 48 hr prior toAKI stage | |
| | Cohort 1 | Cohort 2 | Cohort 1 | Cohort 2 | Cohort 1 | Cohort 2 |
|---|---|---|---|---|---|---|
| median | 1.695 | 3.525 | 1.695 | 2.615 | 1.695 | 2.380 |
| average | 2.115 | 3.770 | 2.115 | 5.197 | 2.115 | 2.876 |
| stdev | 1.804 | 1.874 | 1.804 | 8.167 | 1.804 | 1.596 |
| p (t-test) | | 0.026 | | 0.000 | | 0.267 |
| min | 0.446 | 1.720 | 0.446 | 1.060 | 0.446 | 1.320 |
| max | 28.000 | 6.650 | 28.000 | 28.100 | 28.000 | 5.280 |
| n (Samp) | 542 | 6 | 542 | 10 | 542 | 7 |
| n (Pat) | 208 | 6 | 208 | 10 | 208 | 7 |

UO only

| | 0 hr prior toAKI stage | | 24 hr prior toAKI stage | | 48 hr prior toAKI stage | |
| | Cohort 1 | Cohort 2 | Cohort 1 | Cohort 2 | Cohort 1 | Cohort 2 |
|---|---|---|---|---|---|---|
| median | 1.610 | 1.990 | 1.610 | 1.815 | 1.610 | 1.760 |
| average | 1.990 | 2.663 | 1.990 | 2.455 | 1.990 | 2.231 |
| stdev | 1.211 | 2.181 | 1.211 | 1.628 | 1.211 | 1.467 |
| p (t-test) | | 0.010 | | 0.044 | | 0.440 |
| min | 0.541 | 0.720 | 0.541 | 0.627 | 0.541 | 0.702 |
| max | 6.970 | 11.100 | 6.970 | 6.510 | 6.970 | 6.600 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
|---|---|---|---|---|---|
| 0 hours | 0.60 | 0.058 | 434 | 28 | 0.076 |
| 24 hours | 0.58 | 0.052 | 434 | 36 | 0.125 |
| 48 hours | 0.56 | 0.071 | 434 | 18 | 0.396 | sCr only

| Time prior AKI stage | AUC | SE | nCohort 1 | nCohort 2 | p |
|---|---|---|---|---|---|
| 0 hours | 0.81 | 0.107 | 542 | 6 | 0.004 |
| 24 hours | 0.70 | 0.093 | 542 | 10 | 0.029 |
| 48 hours | 0.69 | 0.112 | 542 | 7 | 0.091 |

Fig. 6 Continued

UO only

| Time prior AKI stage | AUC | SE | nCohort 1 | nCohort 2 | p |
|---|---|---|---|---|---|
| 0 hours | 0.60 | 0.059 | 356 | 27 | 0.087 |
| 24 hours | 0.58 | 0.055 | 356 | 32 | 0.164 |
| 48 hours | 0.56 | 0.076 | 356 | 16 | 0.424 | sCr or UO

| Time prior AKI stage | Cutoff value | sens | spec | Quartile | OR | 95% CI of OR | |
|---|---|---|---|---|---|---|---|
| 0 hours | 1.59 | 71% | 49% | 1 | | | |
| | 1.23 | 86% | 30% | 2 | 1.5 | 0.6 | 3.5 |
| | 0.87 | 93% | 10% | 3 | 2.4 | 1.1 | 5.0 |
| | 2.17 | 39% | 70% | 4 | 2.3 | 1.1 | 4.9 |
| | 2.59 | 29% | 80% | | | | |
| | 3.39 | 21% | 90% | | | | |
| 24 hours | 1.45 | 72% | 43% | 1 | | | |
| | 1.28 | 81% | 33% | 2 | 1.0 | 0.5 | 1.8 |
| | 0.95 | 92% | 14% | 3 | 1.5 | 0.9 | 2.5 |
| | 2.17 | 39% | 70% | 4 | 1.8 | 1.1 | 2.9 |
| | 2.59 | 31% | 80% | | | | |
| | 3.39 | 19% | 90% | | | | |
| 48 hours | 1.68 | 72% | 51% | 1 | | | |
| | 1.31 | 83% | 35% | 2 | 0.7 | 0.1 | 3.5 |
| | 0.745 | 94% | 4% | 3 | 2.4 | 0.9 | 6.4 |
| | 2.17 | 33% | 70% | 4 | 2.1 | 0.7 | 5.7 |
| | 2.59 | 22% | 80% | | | | |
| | 3.39 | 11% | 90% | | | | | sCr only

| Time prior AKI stage | Cutoff value | sens | spec | Quartile | OR | 95% CI of OR | |
|---|---|---|---|---|---|---|---|
| 0 hours | 2.13 | 83% | 68% | 1 | | | |
| | 2.13 | 83% | 68% | 2 | na | na | na |
| | 1.71 | 100% | 51% | 3 | na | na | na |
| | 2.22 | 67% | 70% | 4 | na | na | na |
| | 2.76 | 67% | 80% | | | | |
| | 3.89 | 50% | 90% | | | | |
| 24 hours | 2.2 | 70% | 70% | 1 | | | |
| | 1.63 | 80% | 48% | 2 | 2.0 | 0.1 | 39.2 |
| | 1.55 | 90% | 44% | 3 | 2.0 | 0.1 | 39.2 |
| | 2.22 | 60% | 70% | 4 | 5.2 | 0.5 | 55.7 |
| | 2.76 | 50% | 80% | | | | |
| | 3.89 | 20% | 90% | | | | |
| 48 hours | 1.77 | 71% | 53% | 1 | | | |
| | 1.73 | 86% | 52% | 2 | na | na | na |
| | 1.31 | 100% | 33% | 3 | na | na | na |
| | 2.22 | 57% | 70% | 4 | na | na | na |
| | 2.76 | 29% | 80% | | | | |
| | 3.89 | 29% | 90% | | | | |

UO only

| Time prior AKI stage | Cutoff value | sens | spec | Quartile | OR | 95% CI of OR | |
|---|---|---|---|---|---|---|---|
| 0 hours | 1.59 | 70% | 49% | 1 | | | |
| | 1.23 | 85% | 30% | 2 | 1.5 | 0.6 | 3.6 |
| | 0.869 | 93% | 9% | 3 | 1.8 | 0.8 | 4.0 |
| | 2.2 | 44% | 71% | 4 | 2.6 | 1.3 | 5.5 |
| | 2.69 | 30% | 80% | | | | |
| | 3.78 | 19% | 90% | | | | |

Fig. 6 Continued

| | | | | | | | |
|---|---|---|---|---|---|---|---|
| 24 hours | 1.45 | 72% | 42% | 1 | | | |
| | 1.27 | 81% | 32% | 2 | 0.8 | 0.4 | 1.8 |
| | 0.95 | 91% | 13% | 3 | 1.9 | 1.1 | 3.4 |
| | 2.2 | 38% | 71% | 4 | 1.7 | 1.0 | 3.1 |
| | 2.69 | 28% | 80% | | | | |
| | 3.78 | 22% | 90% | | | | |
| 48 hours | 1.63 | 75% | 51% | 1 | | | |
| | 1.44 | 81% | 42% | 2 | 0.3 | 0.0 | 4.6 |
| | 0.745 | 94% | 4% | 3 | 2.8 | 1.1 | 7.3 |
| | 2.2 | 31% | 71% | 4 | 1.3 | 0.4 | 4.4 |
| | 2.69 | 25% | 80% | | | | |
| | 3.78 | 13% | 90% | | | | |

CD40 Ligand sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.303 | 0.233 | 0.303 | 0.251 | 0.303 | 0.242 |
| average | 0.473 | 0.428 | 0.473 | 0.322 | 0.473 | 0.291 |
| stdev | 0.476 | 0.475 | 0.476 | 0.264 | 0.476 | 0.248 |
| p (t-test) | | 0.628 | | 0.061 | | 0.108 |
| min | 0.000 | 0.039 | 0.000 | 0.051 | 0.000 | 0.067 |
| max | 4.030 | 1.810 | 4.030 | 1.180 | 4.030 | 0.923 |
| n (Samp) | 434 | 28 | 434 | 36 | 434 | 18 |
| n (Pat) | 173 | 28 | 173 | 36 | 173 | 18 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 0.293 | 0.264 | 0.293 | 0.381 | 0.293 | 0.225 |
| average | 0.446 | 0.578 | 0.446 | 0.381 | 0.446 | 0.333 |
| stdev | 0.450 | 0.693 | 0.450 | 0.298 | 0.450 | 0.263 |
| p (t-test) | | 0.478 | | 0.647 | | 0.509 |
| min | 0.000 | 0.069 | 0.000 | 0.052 | 0.000 | 0.105 |
| max | 4.030 | 1.810 | 4.030 | 1.110 | 4.030 | 0.775 |
| n (Samp) | 542 | 6 | 542 | 10 | 542 | 7 |
| n (Pat) | 208 | 6 | 208 | 10 | 208 | 7 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 0.300 | 0.209 | 0.300 | 0.242 | 0.300 | 0.260 |
| average | 0.471 | 0.347 | 0.471 | 0.314 | 0.471 | 0.363 |
| stdev | 0.492 | 0.380 | 0.492 | 0.260 | 0.492 | 0.442 |
| p (t-test) | | 0.203 | | 0.077 | | 0.389 |
| min | 0.000 | 0.039 | 0.000 | 0.051 | 0.000 | 0.067 |
| max | 4.030 | 1.690 | 4.030 | 1.180 | 4.030 | 1.810 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
|---|---|---|---|---|---|
| 0 hours | 0.43 | 0.054 | 434 | 28 | 0.223 |
| 24 hours | 0.41 | 0.047 | 434 | 36 | 0.066 |
| 48 hours | 0.38 | 0.061 | 434 | 18 | 0.043 |

Fig. 6 Continued sCr only

| Time prior AKI stage | AUC | SE | nCohort 1 | nCohort 2 | p |
|---|---|---|---|---|---|
| 0 hours | 0.49 | 0.118 | 542 | 6 | 0.926 |
| 24 hours | 0.49 | 0.092 | 542 | 10 | 0.941 |
| 48 hours | 0.44 | 0.105 | 542 | 7 | 0.575 |

UO only

| Time prior AKI stage | AUC | SE | nCohort 1 | nCohort 2 | p |
|---|---|---|---|---|---|
| 0 hours | 0.39 | 0.052 | 356 | 27 | 0.041 |
| 24 hours | 0.41 | 0.049 | 356 | 32 | 0.056 |
| 48 hours | 0.40 | 0.067 | 356 | 16 | 0.129 | sCr or UO

| Time prior AKI stage | Cutoff value | sens | spec | Quartile | OR | 95% CI of OR | |
|---|---|---|---|---|---|---|---|
| 0 hours | 0.124 | 71% | 18% | 1 | | | |
| | 0.103 | 82% | 14% | 2 | 1.0 | 0.5 | 2.0 |
| | 0.0599 | 93% | 5% | 3 | 0.8 | 0.4 | 1.8 |
| | 0.547 | 21% | 70% | 4 | 1.9 | 1.1 | 3.3 |
| | 0.746 | 21% | 80% | | | | |
| | 1.03 | 11% | 90% | | | | |
| 24 hours | 0.162 | 72% | 24% | 1 | | | |
| | 0.111 | 83% | 16% | 2 | 2.7 | 1.3 | 5.5 |
| | 0.0871 | 92% | 10% | 3 | 2.9 | 1.4 | 5.9 |
| | 0.547 | 11% | 70% | 4 | 3.0 | 1.5 | 6.0 |
| | 0.746 | 6% | 80% | | | | |
| | 1.03 | 6% | 90% | | | | |
| 48 hours | 0.104 | 72% | 14% | 1 | | | |
| | 0.0798 | 83% | 8% | 2 | 3.1 | 0.8 | 11.9 |
| | 0.0674 | 94% | 6% | 3 | 1.0 | 0.1 | 7.4 |
| | 0.547 | 11% | 70% | 4 | 4.2 | 1.2 | 14.9 |
| | 0.746 | 11% | 80% | | | | |
| | 1.03 | 0% | 90% | | | | | sCr only

| Time prior AKI stage | Cutoff value | sens | spec | Quartile | OR | 95% CI of OR | |
|---|---|---|---|---|---|---|---|
| 0 hours | 0.0738 | 83% | 8% | 1 | | | |
| | 0.0738 | 83% | 8% | 2 | 0.5 | 0.0 | 9.7 |
| | 0.0676 | 100% | 6% | 3 | 0.5 | 0.0 | 9.7 |
| | 0.52 | 33% | 70% | 4 | 1.0 | 0.1 | 7.3 |
| | 0.691 | 33% | 80% | | | | |
| | 0.995 | 17% | 90% | | | | |
| 24 hours | 0.237 | 70% | 42% | 1 | | | |
| | 0.174 | 80% | 28% | 2 | 5.2 | 0.5 | 55.7 |
| | 0.0999 | 90% | 14% | 3 | 2.0 | 0.1 | 39.2 |
| | 0.52 | 10% | 70% | 4 | 2.0 | 0.1 | 39.2 |
| | 0.691 | 10% | 80% | | | | |
| | 0.995 | 10% | 90% | | | | |
| 48 hours | 0.114 | 71% | 17% | 1 | | | |
| | 0.107 | 86% | 16% | 2 | 2.0 | 0.1 | 39.5 |
| | 0.104 | 100% | 15% | 3 | 1.0 | 0.0 | 52.3 |
| | 0.52 | 14% | 70% | 4 | 3.1 | 0.2 | 43.1 |
| | 0.691 | 14% | 80% | | | | |
| | 0.995 | 0% | 90% | | | | |

Fig. 6 Continued

UO only

| Time prior AKI stage | Cutoff value | sens | spec | Quartile | OR | 95% CI of OR | |
|---|---|---|---|---|---|---|---|
| 0 hours | 0.124 | 70% | 17% | 1 | | | |
| | 0.103 | 81% | 13% | 2 | 1.5 | 0.6 | 3.6 |
| | 0.0599 | 93% | 4% | 3 | 1.5 | 0.6 | 3.6 |
| | 0.536 | 15% | 70% | 4 | 3.0 | 1.5 | 6.1 |
| | 0.691 | 15% | 80% | | | | |
| | 1 | 7% | 90% | | | | |
| 24 hours | 0.124 | 72% | 17% | 1 | | | |
| | 0.111 | 81% | 15% | 2 | 2.1 | 1.0 | 4.6 |
| | 0.0738 | 91% | 6% | 3 | 2.7 | 1.3 | 5.5 |
| | 0.536 | 13% | 70% | 4 | 2.7 | 1.3 | 5.5 |
| | 0.691 | 9% | 80% | | | | |
| | 1 | 3% | 90% | | | | |
| 48 hours | 0.088 | 75% | 9% | 1 | | | |
| | 0.0798 | 81% | 7% | 2 | 2.6 | 0.6 | 10.7 |
| | 0.0674 | 94% | 4% | 3 | 1.5 | 0.3 | 8.1 |
| | 0.536 | 13% | 70% | 4 | 3.1 | 0.8 | 12.1 |
| | 0.691 | 13% | 80% | | | | |
| | 1 | 6% | 90% | | | | |

CXCL16 (C-X-C Motif chemokine 16)

sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 4.000 | 5.360 | 4.000 | 4.803 | 4.000 | 4.573 |
| average | 4.881 | 5.726 | 4.881 | 6.294 | 4.881 | 5.776 |
| stdev | 4.251 | 2.277 | 4.251 | 5.000 | 4.251 | 2.726 |
| p (t-test) | | 0.318 | | 0.080 | | 0.379 |
| min | 1.242 | 2.563 | 1.242 | 1.969 | 1.242 | 2.614 |
| max | 45.787 | 11.002 | 45.787 | 29.157 | 45.787 | 11.674 |
| n (Samp) | 301 | 26 | 301 | 32 | 301 | 18 |
| n (Pat) | 167 | 26 | 167 | 32 | 167 | 18 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 4.094 | 9.071 | 4.094 | 7.458 | 4.094 | 6.893 |
| average | 4.976 | 8.709 | 4.976 | 9.710 | 4.976 | 7.096 |
| stdev | 3.948 | 1.418 | 3.948 | 7.783 | 3.948 | 2.495 |
| p (t-test) | | 0.060 | | 0.001 | | 0.158 |
| min | 1.187 | 6.700 | 1.187 | 4.797 | 1.187 | 4.073 |
| max | 45.787 | 9.992 | 45.787 | 29.157 | 45.787 | 11.545 |
| n (Samp) | 383 | 4 | 383 | 9 | 383 | 7 |
| n (Pat) | 199 | 4 | 199 | 9 | 199 | 7 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 4.044 | 5.360 | 4.044 | 4.744 | 4.044 | 4.356 |
| average | 4.586 | 5.552 | 4.586 | 5.588 | 4.586 | 5.342 |
| stdev | 2.265 | 2.067 | 2.265 | 2.840 | 2.265 | 2.542 |
| p (t-test) | | 0.038 | | 0.032 | | 0.213 |
| min | 1.425 | 2.563 | 1.425 | 1.969 | 1.425 | 2.614 |
| max | 18.483 | 11.002 | 18.483 | 14.552 | 18.483 | 11.674 |
| n (Samp) | 252 | 26 | 252 | 28 | 252 | 15 |
| n (Pat) | 135 | 26 | 135 | 28 | 135 | 15 |

Fig. 6 Continued sCr or UO

| Time prior AKI stage | AUC | SE | nCohort 1 | nCohort 2 | p |
|---|---|---|---|---|---|
| 0 hours | 0.67 | 0.060 | 301 | 26 | 0.004 |
| 24 hours | 0.64 | 0.055 | 301 | 32 | 0.010 |
| 48 hours | 0.65 | 0.072 | 301 | 18 | 0.031 | sCr only

| Time prior AKI stage | AUC | SE | nCohort 1 | nCohort 2 | p |
|---|---|---|---|---|---|
| 0 hours | 0.91 | 0.099 | 383 | 4 | 0.000 |
| 24 hours | 0.83 | 0.085 | 383 | 9 | 0.000 |
| 48 hours | 0.79 | 0.102 | 383 | 7 | 0.004 |

UO only

| Time prior AKI stage | AUC | SE | nCohort 1 | nCohort 2 | p |
|---|---|---|---|---|---|
| 0 hours | 0.67 | 0.060 | 252 | 26 | 0.006 |
| 24 hours | 0.62 | 0.059 | 252 | 28 | 0.044 |
| 48 hours | 0.61 | 0.079 | 252 | 15 | 0.174 | sCr or UO

| Time prior AKI stage | Cutoff value | sens | spec | Quartile | OR | 95% CI of OR | |
|---|---|---|---|---|---|---|---|
| 0 hours | 4.24107 | 73% | 59% | 1 | | | |
| | 3.97329 | 81% | 49% | 2 | 1.0 | 0.3 | 3.8 |
| | 2.9312 | 92% | 21% | 3 | 2.4 | 0.9 | 6.5 |
| | 4.86607 | 54% | 70% | 4 | 4.9 | 2.1 | 11.5 |
| | 6.00924 | 38% | 80% | | | | |
| | 7.64595 | 23% | 90% | | | | |
| 24 hours | 4 | 72% | 50% | 1 | | | |
| | 3.73148 | 81% | 42% | 2 | 2.8 | 1.1 | 7.3 |
| | 3.24708 | 91% | 31% | 3 | 2.8 | 1.1 | 7.3 |
| | 4.86607 | 44% | 70% | 4 | 4.9 | 2.1 | 11.5 |
| | 6.00924 | 31% | 80% | | | | |
| | 7.64595 | 22% | 90% | | | | |
| 48 hours | 4.12791 | 72% | 54% | 1 | | | |
| | 3.76453 | 83% | 43% | 2 | 4.1 | 0.3 | 50.1 |
| | 3.54758 | 94% | 40% | 3 | 6.3 | 0.6 | 65.5 |
| | 4.86607 | 39% | 70% | 4 | 7.5 | 0.8 | 74.0 |
| | 6.00924 | 33% | 80% | | | | |
| | 7.64595 | 22% | 90% | | | | |

UO only

| Time prior AKI stage | Cutoff value | sens | spec | Quartile | OR | 95% CI of OR | |
|---|---|---|---|---|---|---|---|
| 0 hours | 4.24107 | 73% | 59% | 1 | | | |
| | 3.97329 | 81% | 47% | 2 | 1.0 | 0.3 | 3.9 |
| | 2.9312 | 92% | 18% | 3 | 2.5 | 0.9 | 6.7 |
| | 4.84012 | 54% | 70% | 4 | 5.0 | 2.1 | 12.0 |
| | 5.8046 | 42% | 80% | | | | |
| | 7.49042 | 19% | 90% | | | | |
| 24 hours | 3.90708 | 71% | 44% | 1 | | | |
| | 3.38663 | 82% | 34% | 2 | 2.9 | 1.1 | 7.5 |
| | 2.75532 | 93% | 12% | 3 | 2.1 | 0.7 | 5.9 |
| | 4.84012 | 43% | 70% | 4 | 4.2 | 1.7 | 10.2 |
| | 5.8046 | 36% | 80% | | | | |
| | 7.49042 | 25% | 90% | | | | |

Fig. 6 Continued

| 48 hours | 3.87963 | 73% | 44% | 1 | | | |
|---|---|---|---|---|---|---|---|
| | 3.76453 | 80% | 41% | 2 | 4.1 | 0.3 | 50.8 |
| | 3.54758 | 93% | 38% | 3 | 6.4 | 0.6 | 67.0 |
| | 4.84012 | 27% | 70% | 4 | 4.1 | 0.3 | 50.8 |
| | 5.8046 | 27% | 80% | | | | |
| | 7.49042 | 20% | 90% | | | | |

EN-RAGE sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 29.596 | 47.452 | 29.596 | 56.090 | 29.596 | 36.174 |
| average | 51.055 | 141.534 | 51.055 | 89.962 | 51.055 | 102.575 |
| stdev | 68.389 | 268.697 | 68.389 | 124.591 | 68.389 | 182.246 |
| p (t-test) | | 0.000 | | 0.013 | | 0.014 |
| min | 0.000 | 9.025 | 0.000 | 3.818 | 0.000 | 2.110 |
| max | 582.406 | 1187.203 | 582.406 | 559.225 | 582.406 | 736.132 |
| n (Samp) | 229 | 19 | 229 | 27 | 229 | 16 |
| n (Pat) | 157 | 19 | 157 | 27 | 157 | 16 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 30.771 | 646.991 | 30.771 | 79.526 | 30.771 | 43.960 |
| average | 58.092 | 646.991 | 58.092 | 273.588 | 58.092 | 180.238 |
| stdev | 75.886 | 763.975 | 75.886 | 396.233 | 75.886 | 311.600 |
| p (t-test) | | 0.000 | | 0.000 | | 0.001 |
| min | 0.000 | 106.780 | 0.000 | 7.818 | 0.000 | 10.808 |
| max | 582.406 | 1187.203 | 582.406 | 1063.972 | 582.406 | 736.132 |
| n (Samp) | 295 | 2 | 295 | 7 | 295 | 5 |
| n (Pat) | 186 | 2 | 186 | 7 | 186 | 5 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 30.404 | 45.999 | 30.404 | 47.304 | 30.404 | 37.003 |
| average | 60.970 | 88.829 | 60.970 | 73.405 | 60.970 | 146.151 |
| stdev | 96.844 | 100.602 | 96.844 | 85.150 | 96.844 | 308.059 |
| p (t-test) | | 0.234 | | 0.541 | | 0.012 |
| min | 0.000 | 9.025 | 0.000 | 3.818 | 0.000 | 2.110 |
| max | 736.132 | 360.114 | 736.132 | 324.143 | 736.132 | 1187.203 |
| n (Samp) | 196 | 19 | 196 | 25 | 196 | 14 |
| n (Pat) | 130 | 19 | 130 | 25 | 130 | 14 | sCr or UO

| Time prior AKI stage | AUC | SE | nCohort 1 | nCohort 2 | p |
|---|---|---|---|---|---|
| 0 hours | 0.66 | 0.071 | 229 | 19 | 0.028 |
| 24 hours | 0.62 | 0.060 | 229 | 27 | 0.053 |
| 48 hours | 0.58 | 0.077 | 229 | 16 | 0.321 | sCr only

| Time prior AKI stage | AUC | SE | nCohort 1 | nCohort 2 | p |
|---|---|---|---|---|---|
| 0 hours | 0.94 | 0.121 | 295 | 2 | 0.000 |
| 24 hours | 0.73 | 0.109 | 295 | 7 | 0.032 |
| 48 hours | 0.62 | 0.135 | 295 | 5 | 0.374 |

Fig. 6 Continued

UO only

| Time prior AKI stage | AUC | SE | nCohort 1 | nCohort 2 | p |
|---|---|---|---|---|---|
| 0 hours | 0.61 | 0.071 | 196 | 19 | 0.118 |
| 24 hours | 0.59 | 0.063 | 196 | 25 | 0.141 |
| 48 hours | 0.59 | 0.082 | 196 | 14 | 0.253 | sCr or UO

| Time prior AKI stage | Cutoff value | sens | spec | Quartile | OR | 95% CI of OR | |
|---|---|---|---|---|---|---|---|
| 0 hours | 29.6272 | 74% | 51% | 1 | | | |
| | 18.7129 | 84% | 31% | 2 | 2.1 | 0.4 | 9.6 |
| | 11.8675 | 95% | 12% | 3 | 2.1 | 0.4 | 9.6 |
| | 46.1644 | 53% | 70% | 4 | 5.1 | 1.4 | 18.1 |
| | 67.6223 | 42% | 80% | | | | |
| | 110.686 | 26% | 90% | | | | |
| 24 hours | 28.2185 | 70% | 50% | 1 | | | |
| | 20.3794 | 81% | 34% | 2 | 1.3 | 0.5 | 3.3 |
| | 7.64999 | 93% | 4% | 3 | 1.8 | 0.8 | 4.3 |
| | 46.1644 | 56% | 70% | 4 | 3.1 | 1.5 | 6.5 |
| | 67.6223 | 33% | 80% | | | | |
| | 110.686 | 15% | 90% | | | | |
| 48 hours | 19.1976 | 75% | 32% | 1 | | | |
| | 18.7129 | 81% | 31% | 2 | 2.1 | 0.4 | 9.6 |
| | 9.71827 | 94% | 7% | 3 | 2.1 | 0.4 | 9.6 |
| | 46.1644 | 38% | 70% | 4 | 3.2 | 0.8 | 12.5 |
| | 67.6223 | 31% | 80% | | | | |
| | 110.686 | 19% | 90% | | | | | sCr only

| Time prior AKI stage | Cutoff value | sens | spec | Quartile | OR | 95% CI of OR | |
|---|---|---|---|---|---|---|---|
| 0 hours | 105.662 | 100% | 87% | 1 | | | |
| | 105.662 | 100% | 87% | 2 | na | na | na |
| | 105.662 | 100% | 87% | 3 | na | na | na |
| | 56.0902 | 100% | 71% | 4 | na | na | na |
| | 77.4131 | 100% | 80% | | | | |
| | 134.68 | 50% | 90% | | | | |
| 24 hours | 68.2725 | 71% | 78% | 1 | | | |
| | 47.3037 | 86% | 67% | 2 | 0.0 | 0.0 | na |
| | 7.64999 | 100% | 4% | 3 | 1.0 | 0.0 | 53.1 |
| | 56.0902 | 71% | 71% | 4 | 5.2 | 0.5 | 57.8 |
| | 77.4131 | 57% | 80% | | | | |
| | 134.68 | 29% | 90% | | | | |
| 48 hours | 34.6857 | 80% | 57% | 1 | | | |
| | 34.6857 | 80% | 57% | 2 | 0.0 | 0.0 | na |
| | 9.71827 | 100% | 8% | 3 | 2.0 | 0.1 | 40.5 |
| | 56.0902 | 40% | 71% | 4 | 2.0 | 0.1 | 40.5 |
| | 77.4131 | 20% | 80% | | | | |
| | 134.68 | 20% | 90% | | | | |

UO only

| Time prior AKI stage | Cutoff value | sens | spec | Quartile | OR | 95% CI of OR | |
|---|---|---|---|---|---|---|---|
| 0 hours | 25.3309 | 74% | 39% | 1 | | | |
| | 18.7129 | 84% | 29% | 2 | 1.3 | 0.4 | 4.5 |
| | 11.8675 | 95% | 12% | 3 | 1.3 | 0.4 | 4.5 |
| | 50.1062 | 42% | 71% | 4 | 2.9 | 1.1 | 7.7 |
| | 68.2725 | 37% | 80% | | | | |
| | 130.902 | 21% | 90% | | | | |
| 24 hours | 25.34 | 72% | 40% | 1 | | | |
| | 22.9584 | 80% | 37% | 2 | 2.1 | 0.7 | 6.1 |
| | 8.70763 | 92% | 6% | 3 | 2.5 | 0.9 | 7.0 |
| | 50.1062 | 48% | 71% | 4 | 3.3 | 1.3 | 8.6 |
| | 68.2725 | 28% | 80% | | | | |

Fig. 6 Continued

|  | 130.902 | 12% | 90% |  |  |  |  |
|---|---|---|---|---|---|---|---|
| 48 hours | 25.3309 | 71% | 39% | 1 |  |  |  |
|  | 18.7129 | 86% | 29% | 2 | 5.3 | 0.5 | 60.4 |
|  | 17.5353 | 93% | 28% | 3 | 3.1 | 0.2 | 46.1 |
|  | 50.1062 | 43% | 71% | 4 | 5.3 | 0.5 | 60.4 |
|  | 68.2725 | 36% | 80% |  |  |  |  |
|  | 130.902 | 21% | 90% |  |  |  |  |

Eotaxin sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 55.400 | 66.850 | 55.400 | 58.850 | 55.400 | 71.950 |
| average | 77.082 | 79.358 | 77.082 | 71.381 | 77.082 | 93.061 |
| stdev | 87.119 | 59.413 | 87.119 | 54.350 | 87.119 | 68.028 |
| p (t-test) |  | 0.892 |  | 0.700 |  | 0.443 |
| min | 0.410 | 0.410 | 0.410 | 0.410 | 0.410 | 16.900 |
| max | 1240.000 | 272.000 | 1240.000 | 200.000 | 1240.000 | 239.000 |
| n (Samp) | 434 | 28 | 434 | 36 | 434 | 18 |
| n (Pat) | 173 | 28 | 173 | 36 | 173 | 18 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 56.800 | 95.650 | 56.800 | 81.750 | 56.800 | 112.000 |
| average | 74.805 | 88.283 | 74.805 | 95.370 | 74.805 | 155.829 |
| stdev | 81.166 | 30.109 | 81.166 | 70.534 | 81.166 | 123.195 |
| p (t-test) |  | 0.685 |  | 0.427 |  | 0.009 |
| min | 0.410 | 47.500 | 0.410 | 15.400 | 0.410 | 44.000 |
| max | 1240.000 | 119.000 | 1240.000 | 200.000 | 1240.000 | 391.000 |
| n (Samp) | 542 | 6 | 542 | 10 | 542 | 7 |
| n (Pat) | 208 | 6 | 208 | 10 | 208 | 7 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 59.950 | 64.900 | 59.950 | 58.850 | 59.950 | 62.950 |
| average | 80.735 | 75.394 | 80.735 | 66.035 | 80.735 | 92.194 |
| stdev | 92.878 | 60.078 | 92.878 | 48.122 | 92.878 | 70.493 |
| p (t-test) |  | 0.769 |  | 0.377 |  | 0.627 |
| min | 0.410 | 0.410 | 0.410 | 0.410 | 0.410 | 16.900 |
| max | 1240.000 | 272.000 | 1240.000 | 200.000 | 1240.000 | 239.000 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
|---|---|---|---|---|---|
| 0 hours | 0.56 | 0.058 | 434 | 28 | 0.268 |
| 24 hours | 0.50 | 0.050 | 434 | 36 | 0.990 |
| 48 hours | 0.60 | 0.072 | 434 | 18 | 0.163 | sCr only

| Time prior AKI stage | AUC | SE | nCohort 1 | nCohort 2 | p |
|---|---|---|---|---|---|
| 0 hours | 0.68 | 0.121 | 542 | 6 | 0.128 |
| 24 hours | 0.59 | 0.095 | 542 | 10 | 0.365 |
| 48 hours | 0.74 | 0.108 | 542 | 7 | 0.023 |

Fig. 6 Continued

UO only

| Time prior AKI stage | AUC | SE | nCohort 1 | nCohort 2 | p |
|---|---|---|---|---|---|
| 0 hours | 0.52 | 0.058 | 356 | 27 | 0.714 |
| 24 hours | 0.47 | 0.052 | 356 | 32 | 0.603 |
| 48 hours | 0.57 | 0.076 | 356 | 16 | 0.353 | sCr or UO

| Time prior AKI stage | Cutoff value | sens | spec | Quartile | OR | 95% CI of OR | |
|---|---|---|---|---|---|---|---|
| 0 hours | 57.7 | 71% | 52% | 1 | | | |
| | 33.3 | 82% | 26% | 2 | 0.6 | 0.2 | 1.7 |
| | 0 | 100% | 0% | 3 | 2.6 | 1.4 | 4.6 |
| | 81.9 | 36% | 71% | 4 | 1.6 | 0.8 | 3.2 |
| | 105 | 25% | 80% | | | | |
| | 149 | 11% | 90% | | | | |
| 24 hours | 38.4 | 72% | 29% | 1 | | | |
| | 27.3 | 83% | 16% | 2 | 0.7 | 0.4 | 1.1 |
| | 8.2 | 94% | 8% | 3 | 0.9 | 0.6 | 1.4 |
| | 81.9 | 33% | 71% | 4 | 1.0 | 0.6 | 1.5 |
| | 105 | 22% | 80% | | | | |
| | 149 | 14% | 90% | | | | |
| 48 hours | 51.2 | 72% | 45% | 1 | | | |
| | 41 | 83% | 35% | 2 | 1.0 | 0.3 | 3.8 |
| | 25.7 | 94% | 15% | 3 | 2.1 | 0.7 | 5.7 |
| | 81.9 | 44% | 71% | 4 | 2.1 | 0.7 | 5.7 |
| | 105 | 28% | 80% | | | | |
| | 149 | 17% | 90% | | | | | sCr only

| Time prior AKI stage | Cutoff value | sens | spec | Quartile | OR | 95% CI of OR | |
|---|---|---|---|---|---|---|---|
| 0 hours | 54.9 | 83% | 49% | 1 | | | |
| | 54.9 | 83% | 49% | 2 | na | na | na |
| | 46.9 | 100% | 39% | 3 | na | na | na |
| | 81.5 | 67% | 70% | 4 | na | na | na |
| | 102 | 33% | 80% | | | | |
| | 147 | 0% | 90% | | | | |
| 24 hours | 43.5 | 70% | 35% | 1 | | | |
| | 27.3 | 90% | 17% | 2 | 0.3 | 0.0 | 4.6 |
| | 27.3 | 90% | 17% | 3 | 0.7 | 0.1 | 3.5 |
| | 81.5 | 50% | 70% | 4 | 1.3 | 0.4 | 4.3 |
| | 102 | 40% | 80% | | | | |
| | 147 | 30% | 90% | | | | |
| 48 hours | 87.8 | 71% | 74% | 1 | | | |
| | 46.5 | 86% | 39% | 2 | na | na | na |
| | 43.5 | 100% | 35% | 3 | na | na | na |
| | 81.5 | 71% | 70% | 4 | na | na | na |
| | 102 | 57% | 80% | | | | |
| | 147 | 43% | 90% | | | | |

Fig. 6 Continued

UO only

| Time prior AKI stage | Cutoff value | sens | spec | Quartile | OR | 95% CI of OR | |
|---|---|---|---|---|---|---|---|
| 0 hours | 52.8 | 70% | 44% | 1 | | | |
| | 33.3 | 81% | 25% | 2 | 0.6 | 0.3 | 1.5 |
| | 0 | 100% | 0% | 3 | 1.9 | 1.1 | 3.3 |
| | 86.2 | 26% | 70% | 4 | 1.0 | 0.5 | 2.0 |
| | 116 | 15% | 81% | | | | |
| | 154 | 11% | 91% | | | | |
| 24 hours | 38.4 | 72% | 27% | 1 | | | |
| | 27.3 | 84% | 16% | 2 | 1.7 | 1.0 | 3.1 |
| | 8.2 | 94% | 9% | 3 | 1.2 | 0.6 | 2.3 |
| | 86.2 | 25% | 70% | 4 | 1.6 | 0.9 | 2.8 |
| | 116 | 13% | 81% | | | | |
| | 154 | 9% | 91% | | | | |
| 48 hours | 50.3 | 75% | 43% | 1 | | | |
| | 41 | 81% | 33% | 2 | 1.7 | 0.6 | 5.1 |
| | 25.7 | 94% | 15% | 3 | 1.0 | 0.3 | 3.9 |
| | 86.2 | 31% | 70% | 4 | 1.7 | 0.6 | 5.1 |
| | 116 | 25% | 81% | | | | |
| | 154 | 19% | 91% | | | | |

E-selectin sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 8.781 | na | 8.781 | 12.197 | 8.781 | 2.991 |
| average | 9.808 | na | 9.808 | 13.647 | 9.808 | 19.984 |
| stdev | 6.407 | na | 6.407 | 10.766 | 6.407 | na |
| p (t-test) | | na | | 0.110 | | na |
| min | 2.991 | na | 2.991 | 3.333 | 2.991 | 19.984 |
| max | 42.140 | na | 42.140 | 46.625 | 42.140 | 19.984 |
| n (Samp) | 46 | 0 | 46 | 13 | 46 | 1 |
| n (Pat) | 43 | 0 | 43 | 13 | 43 | 1 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 8.873 | na | 8.873 | 19.365 | 8.873 | na |
| average | 10.865 | na | 10.865 | 16.061 | 10.865 | na |
| stdev | 8.434 | na | 8.434 | 9.082 | 8.434 | na |
| p (t-test) | | na | | 0.303 | | na |
| min | 1.155 | na | 1.155 | 5.790 | 1.155 | na |
| max | 46.625 | na | 46.625 | 23.028 | 46.625 | na |
| n (Samp) | 59 | 0 | 59 | 3 | 59 | 0 |
| n (Pat) | 54 | 0 | 54 | 3 | 54 | 0 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 7.890 | na | 7.890 | 11.583 | 7.890 | 2.991 |
| average | 9.467 | na | 9.467 | 12.622 | 9.467 | 19.984 |
| stdev | 6.569 | na | 6.569 | 10.811 | 6.569 | na |
| p (t-test) | | na | | 0.210 | | na |
| min | 2.991 | na | 2.991 | 3.333 | 2.991 | 19.984 |
| max | 42.140 | na | 42.140 | 46.625 | 42.140 | 19.984 |
| n (Samp) | 40 | 0 | 40 | 13 | 40 | 1 |
| n (Pat) | 37 | 0 | 37 | 13 | 37 | 1 |

Fig. 6 Continued sCr or UO

| Time prior AKI stage | AUC | SE | nCohort 1 | nCohort 2 | p |
|---|---|---|---|---|---|
| 0 hours | nd | nd | 46 | 0 | nd |
| 24 hours | 0.64 | 0.091 | 46 | 13 | 0.116 |
| 48 hours | 0.98 | 0.104 | 46 | 1 | 0.000 | sCr only

| Time prior AKI stage | AUC | SE | nCohort 1 | nCohort 2 | p |
|---|---|---|---|---|---|
| 0 hours | nd | nd | 59 | 0 | nd |
| 24 hours | 0.72 | 0.171 | 59 | 3 | 0.205 |
| 48 hours | nd | nd | 59 | 0 | nd |

UO only

| Time prior AKI stage | AUC | SE | nCohort 1 | nCohort 2 | p |
|---|---|---|---|---|---|
| 0 hours | nd | nd | 40 | 0 | nd |
| 24 hours | 0.62 | 0.093 | 40 | 13 | 0.209 |
| 48 hours | 0.98 | 0.111 | 40 | 1 | 0.000 | sCr or UO

| Time prior AKI stage | Cutoff value | sens | spec | Quartile | OR | 95% CI of OR | |
|---|---|---|---|---|---|---|---|
| 0 hours | na | na | na | 1 | | | |
| | na | na | na | 2 | na | na | na |
| | na | na | na | 3 | na | na | na |
| | na | na | na | 4 | na | na | na |
| | na | na | na | | | | |
| | na | na | na | | | | |
| 24 hours | 6.92209 | 77% | 39% | 1 | | | |
| | 6.23347 | 85% | 35% | 2 | 3.3 | 0.2 | 60.7 |
| | 5.70931 | 92% | 28% | 3 | 4.7 | 0.3 | 76.1 |
| | 10.9592 | 69% | 72% | 4 | 6.5 | 0.4 | 96.6 |
| | 13.0751 | 31% | 80% | | | | |
| | 17.0471 | 15% | 91% | | | | |
| 48 hours | 18.4916 | 100% | 98% | 1 | | | |
| | 18.4916 | 100% | 98% | 2 | na | na | na |
| | 18.4916 | 100% | 98% | 3 | na | na | na |
| | 10.9592 | 100% | 72% | 4 | na | na | na |
| | 13.0751 | 100% | 80% | | | | |
| | 17.0471 | 100% | 91% | | | | |

UO only

| Time prior AKI stage | Cutoff value | sens | spec | Quartile | OR | 95% CI of OR | |
|---|---|---|---|---|---|---|---|
| 0 hours | na | na | na | 1 | | | |
| | na | na | na | 2 | na | na | na |
| | na | na | na | 3 | na | na | na |
| | na | na | na | 4 | na | na | na |
| | na | na | na | | | | |
| | na | na | na | | | | |
| 24 hours | 6.23347 | 77% | 38% | 1 | | | |
| | 5.94088 | 85% | 35% | 2 | 5.3 | 0.3 | 90.5 |
| | 5.70931 | 92% | 30% | 3 | 3.6 | 0.2 | 70.4 |
| | 10.5341 | 62% | 70% | 4 | 6.7 | 0.4 | 102.5 |
| | 12.427 | 38% | 80% | | | | |
| | 14.6809 | 8% | 90% | | | | |

Fig. 6 Continued

| 48 hours | | 18.1406 | 100% | 98% | 1 | | | |
| --- | --- | --- | --- | --- | --- | --- | --- | --- |
| | | 18.1406 | 100% | 98% | 2 | na | na | na |
| | | 18.1406 | 100% | 98% | 3 | na | na | na |
| | | 10.5341 | 100% | 70% | 4 | na | na | na |
| | | 12.427 | 100% | 80% | | | | |
| | | 14.6809 | 100% | 90% | | | | |

Granulocyte colony-stimulating factor sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 18.800 | 31.950 | 18.800 | 41.650 | 18.800 | 21.600 |
| average | 164.596 | 55.254 | 164.596 | 361.138 | 164.596 | 223.321 |
| stdev | 979.228 | 64.397 | 979.228 | 1116.598 | 979.228 | 456.843 |
| p (t-test) | | 0.555 | | 0.253 | | 0.800 |
| min | 0.050 | 8.110 | 0.050 | 7.730 | 0.050 | 8.480 |
| max | 11103.000 | 320.000 | 11103.000 | 6280.000 | 11103.000 | 1650.000 |
| n (Samp) | 434 | 28 | 434 | 36 | 434 | 18 |
| n (Pat) | 173 | 28 | 173 | 36 | 173 | 18 | sCr only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 21.150 | 54.600 | 21.150 | 37.400 | 21.150 | 20.700 |
| average | 154.888 | 63.667 | 154.888 | 673.260 | 154.888 | 283.843 |
| stdev | 885.759 | 44.824 | 885.759 | 1970.537 | 885.759 | 699.507 |
| p (t-test) | | 0.801 | | 0.076 | | 0.701 |
| min | 0.050 | 19.600 | 0.050 | 11.600 | 0.050 | 9.400 |
| max | 11103.000 | 136.000 | 11103.000 | 6280.000 | 11103.000 | 1870.000 |
| n (Samp) | 542 | 6 | 542 | 10 | 542 | 7 |
| n (Pat) | 208 | 6 | 208 | 10 | 208 | 7 |

UO only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 20.200 | 32.500 | 20.200 | 45.300 | 20.200 | 45.050 |
| average | 188.226 | 52.923 | 188.226 | 208.352 | 188.226 | 640.893 |
| stdev | 1077.984 | 63.329 | 1077.984 | 491.922 | 1077.984 | 1577.158 |
| p (t-test) | | 0.515 | | 0.917 | | 0.109 |
| min | 0.050 | 8.110 | 0.050 | 7.730 | 0.050 | 8.480 |
| max | 11103.000 | 320.000 | 11103.000 | 2160.000 | 11103.000 | 6280.000 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
| --- | --- | --- | --- | --- | --- |
| 0 hours | 0.64 | 0.058 | 434 | 28 | 0.016 |
| 24 hours | 0.68 | 0.051 | 434 | 36 | 0.000 |
| 48 hours | 0.61 | 0.072 | 434 | 18 | 0.137 | sCr only

| Time prior AKI stage | AUC | SE | nCohort 1 | nCohort 2 | p |
| --- | --- | --- | --- | --- | --- |
| 0 hours | 0.72 | 0.119 | 542 | 6 | 0.067 |
| 24 hours | 0.62 | 0.096 | 542 | 10 | 0.196 |
| 48 hours | 0.48 | 0.109 | 542 | 7 | 0.879 |

Fig. 6 Continued

UO only

| Time prior AKI stage | AUC | SE | nCohort 1 | nCohort 2 | p |
|---|---|---|---|---|---|
| 0 hours | 0.63 | 0.059 | 356 | 27 | 0.031 |
| 24 hours | 0.69 | 0.054 | 356 | 32 | 0.000 |
| 48 hours | 0.66 | 0.076 | 356 | 16 | 0.029 | sCr or UO

| Time prior AKI stage | Cutoff value | sens | spec | Quartile | OR | 95% CI of OR | |
|---|---|---|---|---|---|---|---|
| 0 hours | 21.7 | 71% | 55% | 1 | | | |
| | 13.7 | 82% | 36% | 2 | 1.7 | 0.6 | 5.0 |
| | 10.3 | 96% | 24% | 3 | 3.2 | 1.3 | 7.9 |
| | 34.9 | 46% | 70% | 4 | 3.9 | 1.6 | 9.3 |
| | 53.2 | 25% | 80% | | | | |
| | 106 | 14% | 91% | | | | |
| 24 hours | 19.1 | 75% | 50% | 1 | | | |
| | 15.2 | 81% | 41% | 2 | 5.3 | 1.6 | 17.9 |
| | 12.4 | 92% | 31% | 3 | 3.7 | 1.0 | 13.4 |
| | 34.9 | 58% | 70% | 4 | 9.7 | 3.1 | 30.0 |
| | 53.2 | 44% | 80% | | | | |
| | 106 | 25% | 91% | | | | |
| 48 hours | 16.5 | 72% | 44% | 1 | | | |
| | 12.4 | 83% | 31% | 2 | 2.6 | 0.6 | 10.5 |
| | 9.38 | 94% | 20% | 3 | 2.0 | 0.5 | 9.2 |
| | 34.9 | 39% | 70% | 4 | 3.7 | 1.0 | 13.4 |
| | 53.2 | 39% | 80% | | | | |
| | 106 | 28% | 91% | | | | | sCr only

| Time prior AKI stage | Cutoff value | sens | spec | Quartile | OR | 95% CI of OR | |
|---|---|---|---|---|---|---|---|
| 0 hours | 21.9 | 83% | 52% | 1 | | | |
| | 21.9 | 83% | 52% | 2 | na | na | na |
| | 19.4 | 100% | 46% | 3 | na | na | na |
| | 38.4 | 67% | 70% | 4 | na | na | na |
| | 59 | 33% | 80% | | | | |
| | 121 | 17% | 90% | | | | |
| 24 hours | 17.8 | 70% | 43% | 1 | | | |
| | 15.2 | 80% | 36% | 2 | 3.0 | 0.2 | 42.8 |
| | 13.2 | 90% | 29% | 3 | 1.0 | 0.0 | 51.9 |
| | 38.4 | 50% | 70% | 4 | 5.2 | 0.5 | 55.7 |
| | 59 | 40% | 80% | | | | |
| | 121 | 20% | 90% | | | | |
| 48 hours | 12.4 | 71% | 27% | 1 | | | |
| | 11.6 | 86% | 24% | 2 | 2.0 | 0.1 | 39.5 |
| | 9.38 | 100% | 17% | 3 | 2.0 | 0.1 | 39.5 |
| | 38.4 | 29% | 70% | 4 | 2.0 | 0.1 | 39.5 |
| | 59 | 14% | 80% | | | | |
| | 121 | 14% | 90% | | | | |

UO only

| Time prior AKI stage | Cutoff value | sens | spec | Quartile | OR | 95% CI of OR | |
|---|---|---|---|---|---|---|---|
| 0 hours | 25 | 70% | 59% | 1 | | | |
| | 13.7 | 81% | 34% | 2 | 0.7 | 0.2 | 2.4 |
| | 10.3 | 96% | 21% | 3 | 2.6 | 1.3 | 5.5 |
| | 35.6 | 44% | 71% | 4 | 2.6 | 1.3 | 5.5 |
| | 52.8 | 22% | 80% | | | | |
| | 105 | 11% | 90% | | | | |
| 24 hours | 19.4 | 72% | 48% | 1 | | | |
| | 18.6 | 81% | 47% | 2 | 4.9 | 1.4 | 16.8 |
| | 13 | 91% | 29% | 3 | 2.6 | 0.6 | 10.6 |
| | 35.6 | 63% | 71% | 4 | 9.4 | 3.0 | 29.6 |
| | 52.8 | 47% | 80% | | | | |

Fig. 6 Continued

|  | 105 | 25% | 90% |  |  |  |  |
|---|---|---|---|---|---|---|---|
| 48 hours | 18.1 | 75% | 46% | 1 |  |  |  |
|  | 16.5 | 81% | 42% | 2 | 2.0 | 0.5 | 9.3 |
|  | 11.1 | 94% | 24% | 3 | 1.0 | 0.1 | 7.4 |
|  | 35.6 | 50% | 71% | 4 | 4.3 | 1.2 | 15.2 |
|  | 52.8 | 50% | 80% |  |  |  |  |
|  | 105 | 38% | 90% |  |  |  |  |

Heparin-binding growth factor 2 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 89.100 | 151.000 | 89.100 | 176.000 | 89.100 | 92.100 |
| average | 124.856 | 529.694 | 124.856 | 455.832 | 124.856 | 107.181 |
| stdev | 160.959 | 1613.524 | 160.959 | 1462.570 | 160.959 | 107.904 |
| p (t-test) |  | 0.000 |  | 0.000 |  | 0.645 |
| min | 0.980 | 0.980 | 0.980 | 0.980 | 0.980 | 0.980 |
| max | 1280.000 | 8410.000 | 1280.000 | 8750.000 | 1280.000 | 338.000 |
| n (Samp) | 434 | 28 | 434 | 36 | 434 | 18 |
| n (Pat) | 173 | 28 | 173 | 36 | 173 | 18 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 105.000 | 274.500 | 105.000 | 143.000 | 105.000 | 150.000 |
| average | 139.293 | 782.660 | 139.293 | 1057.336 | 139.293 | 714.277 |
| stdev | 211.875 | 1449.361 | 211.875 | 2953.982 | 211.875 | 1531.543 |
| p (t-test) |  | 0.000 |  | 0.000 |  | 0.000 |
| min | 0.980 | 0.980 | 0.980 | 0.980 | 0.980 | 0.980 |
| max | 2520.000 | 3720.000 | 2520.000 | 9460.000 | 2520.000 | 4170.000 |
| n (Samp) | 542 | 6 | 542 | 10 | 542 | 7 |
| n (Pat) | 208 | 6 | 208 | 10 | 208 | 7 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 106.000 | 144.000 | 106.000 | 211.500 | 106.000 | 134.500 |
| average | 131.273 | 555.683 | 131.273 | 522.156 | 131.273 | 132.520 |
| stdev | 163.515 | 1641.518 | 163.515 | 1545.071 | 163.515 | 104.240 |
| p (t-test) |  | 0.000 |  | 0.000 |  | 0.976 |
| min | 0.980 | 0.980 | 0.980 | 0.980 | 0.980 | 0.980 |
| max | 1280.000 | 8410.000 | 1280.000 | 8750.000 | 1280.000 | 338.000 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
|---|---|---|---|---|---|
| 0 hours | 0.60 | 0.058 | 434 | 28 | 0.087 |
| 24 hours | 0.66 | 0.051 | 434 | 36 | 0.002 |
| 48 hours | 0.50 | 0.069 | 434 | 18 | 0.989 | sCr only

| Time prior AKI stage | AUC | SE | nCohort 1 | nCohort 2 | p |
|---|---|---|---|---|---|
| 0 hours | 0.67 | 0.122 | 542 | 6 | 0.168 |
| 24 hours | 0.58 | 0.095 | 542 | 10 | 0.404 |
| 48 hours | 0.57 | 0.114 | 542 | 7 | 0.521 |

Fig. 6 Continued

UO only

| Time prior AKI stage | AUC | SE | nCohort 1 | nCohort 2 | p |
|---|---|---|---|---|---|
| 0 hours | 0.60 | 0.059 | 356 | 27 | 0.102 |
| 24 hours | 0.69 | 0.054 | 356 | 32 | 0.001 |
| 48 hours | 0.56 | 0.076 | 356 | 16 | 0.446 | sCr or UO

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | na | na | na |
| | 0 | 100% | 0% | 3 | na | na | na |
| | 158 | 46% | 70% | 4 | na | na | na |
| | 208 | 39% | 80% | | | | |
| | 300 | 21% | 90% | | | | |
| 24 hours | 131 | 72% | 62% | 1 | | | |
| | 58.2 | 81% | 41% | 2 | 1.5 | 0.6 | 3.5 |
| | 0 | 100% | 0% | 3 | 2.4 | 1.1 | 5.0 |
| | 158 | 64% | 70% | 4 | 4.8 | 2.5 | 9.0 |
| | 208 | 44% | 80% | | | | |
| | 300 | 8% | 90% | | | | |
| 48 hours | 0 | 100% | 0% | 1 | | | |
| | 0 | 100% | 0% | 2 | 0.8 | 0.3 | 2.0 |
| | 0 | 100% | 0% | 3 | 1.9 | 1.0 | 3.6 |
| | 158 | 28% | 70% | 4 | 0.0 | 0.0 | na |
| | 208 | 17% | 80% | | | | |
| | 300 | 6% | 90% | | | | | sCr only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.0 | 0.0 | na |
| | 0 | 100% | 0% | 3 | 0.0 | 0.0 | na |
| | 162 | 67% | 71% | 4 | 2.0 | 0.5 | 9.1 |
| | 218 | 50% | 81% | | | | |
| | 306 | 50% | 90% | | | | |
| 24 hours | 58.2 | 80% | 39% | 1 | | | |
| | 58.2 | 80% | 39% | 2 | 3.0 | 0.2 | 42.8 |
| | 0 | 100% | 0% | 3 | 3.0 | 0.2 | 42.8 |
| | 162 | 30% | 71% | 4 | 3.0 | 0.2 | 42.8 |
| | 218 | 30% | 81% | | | | |
| | 306 | 10% | 90% | | | | |
| 48 hours | 0 | 100% | 0% | 1 | | | |
| | 0 | 100% | 0% | 2 | na | na | na |
| | 0 | 100% | 0% | 3 | na | na | na |
| | 162 | 43% | 71% | 4 | na | na | na |
| | 218 | 43% | 81% | | | | |
| | 306 | 29% | 90% | | | | |

UO only

| Time prior AKI stage | Cutoff value | sens | spec | Quartile | OR | 95% CI of OR | |
|---|---|---|---|---|---|---|---|
| 0 hours | 78.2 | 70% | 47% | 1 | | | |
| | 0 | 100% | 0% | 2 | 1.2 | 0.6 | 2.6 |
| | 0 | 100% | 0% | 3 | 0.8 | 0.3 | 2.0 |
| | 162 | 44% | 72% | 4 | 2.6 | 1.4 | 4.7 |
| | 217 | 41% | 80% | | | | |
| | 319 | 22% | 90% | | | | |

Fig. 6 Continued

| 24 hours | 158 | 72% | 69% | 1 | | | |
| | 58.2 | 84% | 40% | 2 | na | na | na |
| | 0 | 100% | 0% | 3 | na | na | na |
| | 162 | 59% | 72% | 4 | na | na | na |
| | 217 | 47% | 80% | | | | |
| | 319 | 16% | 90% | | | | |
| 48 hours | 76.3 | 75% | 45% | 1 | | | |
| | 0 | 100% | 0% | 2 | 6.3 | 0.6 | 65.2 |
| | 0 | 100% | 0% | 3 | 4.1 | 0.3 | 50.0 |
| | 162 | 38% | 72% | 4 | 5.2 | 0.5 | 57.4 |
| | 217 | 19% | 80% | | | | |
| | 319 | 6% | 90% | | | | |

Hepatocyte growth factor receptor sCr or UO

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| --- | --- | --- | --- | --- | --- | --- |
| median | 257438.017 | 249735.450 | 257438.017 | 253752.897 | 257438.017 | 260743.802 |
| average | 285227.824 | 284992.077 | 285227.824 | 269378.740 | 285227.824 | 282064.897 |
| stdev | 112082.908 | 111190.396 | 112082.908 | 104330.097 | 112082.908 | 59422.507 |
| p (t-test) | | 0.995 | | 0.593 | | 0.961 |
| min | 94852.941 | 192279.412 | 94852.941 | 128361.345 | 94852.941 | 236244.541 |
| max | 680652.681 | 487159.533 | 680652.681 | 501631.702 | 680652.681 | 349206.349 |
| n (Samp) | 123 | 9 | 123 | 16 | 123 | 3 |
| n (Pat) | 72 | 9 | 72 | 16 | 72 | 3 | sCr only

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| --- | --- | --- | --- | --- | --- | --- |
| median | 257758.310 | 324867.725 | 257758.310 | 307851.240 | 257758.310 | 298941.799 |
| average | 285421.915 | 324867.725 | 285421.915 | 361075.287 | 285421.915 | 298941.799 |
| stdev | 114312.681 | 103260.038 | 114312.681 | 108838.532 | 114312.681 | 71084.809 |
| p (t-test) | | 0.628 | | 0.147 | | 0.868 |
| min | 94852.941 | 251851.852 | 94852.941 | 259090.909 | 94852.941 | 248677.249 |
| max | 680652.681 | 397883.598 | 680652.681 | 501631.702 | 680652.681 | 349206.349 |
| n (Samp) | 154 | 2 | 154 | 5 | 154 | 2 |
| n (Pat) | 90 | 2 | 90 | 5 | 90 | 2 |

UO only

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| --- | --- | --- | --- | --- | --- | --- |
| median | 257438.017 | 249735.450 | 257438.017 | 215702.479 | 257438.017 | 248494.172 |
| average | 287875.805 | 284992.077 | 287875.805 | 236196.394 | 287875.805 | 248494.172 |
| stdev | 118979.963 | 111190.396 | 118979.963 | 69950.107 | 118979.963 | 17323.593 |
| p (t-test) | | 0.944 | | 0.116 | | 0.642 |
| min | 94852.941 | 192279.412 | 94852.941 | 128361.345 | 94852.941 | 236244.541 |
| max | 680652.681 | 487159.533 | 680652.681 | 380578.512 | 680652.681 | 260743.802 |
| n (Samp) | 99 | 9 | 99 | 14 | 99 | 2 |
| n (Pat) | 56 | 9 | 56 | 14 | 56 | 2 | sCr or UO

| Time prior AKI stage | AUC | SE | nCohort 1 | nCohort 2 | p |
| --- | --- | --- | --- | --- | --- |
| 0 hours | 0.50 | 0.100 | 123 | 9 | 0.960 |
| 24 hours | 0.46 | 0.075 | 123 | 16 | 0.598 |
| 48 hours | 0.57 | 0.174 | 123 | 3 | 0.698 |

Fig. 6 Continued sCr only

| Time prior AKI stage | AUC | SE | nCohort 1 | nCohort 2 | p |
|---|---|---|---|---|---|
| 0 hours | 0.66 | 0.213 | 154 | 2 | 0.445 |
| 24 hours | 0.72 | 0.131 | 154 | 5 | 0.086 |
| 48 hours | 0.61 | 0.214 | 154 | 2 | 0.606 |

UO only

| Time prior AKI stage | AUC | SE | nCohort 1 | nCohort 2 | p |
|---|---|---|---|---|---|
| 0 hours | 0.49 | 0.100 | 99 | 9 | 0.906 |
| 24 hours | 0.38 | 0.075 | 99 | 14 | 0.103 |
| 48 hours | 0.46 | 0.201 | 99 | 2 | 0.841 | sCr or UO

| Time prior AKI stage | Cutoff value | sens | spec | Quartile | OR | 95% CI of OR | |
|---|---|---|---|---|---|---|---|
| 0 hours | 201058 | 78% | 26% | 1 | | | |
| | 192279 | 89% | 20% | 2 | 1.0 | 0.1 | 8.1 |
| | 191807 | 100% | 20% | 3 | 1.6 | 0.3 | 9.0 |
| | 311111 | 33% | 71% | 4 | 1.0 | 0.1 | 8.1 |
| | 355556 | 22% | 80% | | | | |
| | 423346 | 22% | 90% | | | | |
| 24 hours | 195168 | 75% | 20% | 1 | | | |
| | 191807 | 81% | 20% | 2 | 1.4 | 0.4 | 4.9 |
| | 158193 | 94% | 6% | 3 | 1.4 | 0.4 | 4.9 |
| | 311111 | 31% | 71% | 4 | 1.8 | 0.6 | 6.0 |
| | 355556 | 19% | 80% | | | | |
| | 423346 | 13% | 90% | | | | |
| 48 hours | 231004 | 100% | 40% | 1 | | | |
| | 231004 | 100% | 40% | 2 | na | na | na |
| | 231004 | 100% | 40% | 3 | na | na | na |
| | 311111 | 33% | 71% | 4 | na | na | na |
| | 355556 | 0% | 80% | | | | |
| | 423346 | 0% | 90% | | | | |

UO only

| Time prior AKI stage | Cutoff value | sens | spec | Quartile | OR | 95% CI of OR | |
|---|---|---|---|---|---|---|---|
| 0 hours | 201058 | 78% | 24% | 1 | | | |
| | 192279 | 89% | 19% | 2 | 1.0 | 0.1 | 8.3 |
| | 187605 | 100% | 19% | 3 | 1.0 | 0.1 | 8.3 |
| | 309504 | 33% | 71% | 4 | 1.6 | 0.3 | 9.4 |
| | 364876 | 22% | 81% | | | | |
| | 473152 | 11% | 91% | | | | |
| 24 hours | 195168 | 71% | 20% | 1 | | | |
| | 178782 | 86% | 12% | 2 | 1.6 | 0.3 | 9.6 |
| | 158193 | 93% | 7% | 3 | 2.3 | 0.4 | 11.4 |
| | 309504 | 21% | 71% | 4 | 2.9 | 0.6 | 13.6 |
| | 364876 | 7% | 81% | | | | |
| | 473152 | 0% | 91% | | | | |
| 48 hours | 231004 | 100% | 40% | 1 | | | |
| | 231004 | 100% | 40% | 2 | na | na | na |
| | 231004 | 100% | 40% | 3 | na | na | na |
| | 309504 | 0% | 71% | 4 | na | na | na |
| | 364876 | 0% | 81% | | | | |
| | 473152 | 0% | 91% | | | | |

Fig. 6 Continued

Interleukin-1 receptor antagonist sCr or UO

|          | 0 hr prior to AKI stage | | 24 hr prior to AKI stage | | 48 hr prior to AKI stage | |
|----------|--------:|--------:|--------:|--------:|--------:|--------:|
|          | Cohort 1 | Cohort 2 | Cohort 1 | Cohort 2 | Cohort 1 | Cohort 2 |
| median   | 234.500 | 294.500 | 234.500 | 335.500 | 234.500 | 306.000 |
| average  | 903.000 | 963.946 | 903.000 | 2045.144 | 903.000 | 786.000 |
| stdev    | 4128.635 | 1799.306 | 4128.635 | 7029.515 | 4128.635 | 815.359 |
| p (t-test) |  | 0.938 |  | 0.136 |  | 0.905 |
| min      | 0.150 | 59.300 | 0.150 | 15.200 | 0.150 | 74.000 |
| max      | 58400.000 | 8150.000 | 58400.000 | 42500.000 | 58400.000 | 2170.000 |
| n (Samp) | 434 | 28 | 434 | 36 | 434 | 18 |
| n (Pat)  | 173 | 28 | 173 | 36 | 173 | 18 | sCr only

|          | 0 hr prior toAKI stage | | 24 hr prior toAKI stage | | 48 hr prior toAKI stage | |
|----------|--------:|--------:|--------:|--------:|--------:|--------:|
|          | Cohort 1 | Cohort 2 | Cohort 1 | Cohort 2 | Cohort 1 | Cohort 2 |
| median   | 241.000 | 1980.000 | 241.000 | 1585.000 | 241.000 | 281.000 |
| average  | 823.513 | 3041.667 | 823.513 | 5782.400 | 823.513 | 1200.000 |
| stdev    | 3710.664 | 3173.072 | 3710.664 | 13073.661 | 3710.664 | 1265.570 |
| p (t-test) |  | 0.145 |  | 0.000 |  | 0.789 |
| min      | 0.150 | 174.000 | 0.150 | 127.000 | 0.150 | 261.000 |
| max      | 58400.000 | 8150.000 | 58400.000 | 42500.000 | 58400.000 | 3420.000 |
| n (Samp) | 542 | 6 | 542 | 10 | 542 | 7 |
| n (Pat)  | 208 | 6 | 208 | 10 | 208 | 7 |

UO only

|          | 0 hr prior toAKI stage | | 24 hr prior toAKI stage | | 48 hr prior toAKI stage | |
|----------|--------:|--------:|--------:|--------:|--------:|--------:|
|          | Cohort 1 | Cohort 2 | Cohort 1 | Cohort 2 | Cohort 1 | Cohort 2 |
| median   | 239.000 | 254.000 | 239.000 | 291.000 | 239.000 | 336.500 |
| average  | 916.785 | 427.463 | 916.785 | 985.100 | 916.785 | 3771.875 |
| stdev    | 4337.769 | 448.032 | 4337.769 | 1440.524 | 4337.769 | 10518.586 |
| p (t-test) |  | 0.559 |  | 0.929 |  | 0.019 |
| min      | 0.150 | 59.300 | 0.150 | 15.200 | 0.150 | 74.000 |
| max      | 58400.000 | 1740.000 | 58400.000 | 5550.000 | 58400.000 | 42500.000 |
| n (Samp) | 356 | 27 | 356 | 32 | 356 | 16 |
| n (Pat)  | 138 | 27 | 138 | 32 | 138 | 16 | sCr or UO

| Time prior AKI stage | AUC | SE | nCohort 1 | nCohort 2 | p |
|---|---:|---:|---:|---:|---:|
| 0 hours | 0.58 | 0.058 | 434 | 28 | 0.173 |
| 24 hours | 0.65 | 0.051 | 434 | 36 | 0.004 |
| 48 hours | 0.59 | 0.072 | 434 | 18 | 0.217 | sCr only

| Time prior AKI stage | AUC | SE | nCohort 1 | nCohort 2 | p |
|---|---:|---:|---:|---:|---:|
| 0 hours | 0.82 | 0.106 | 542 | 6 | 0.003 |
| 24 hours | 0.77 | 0.089 | 542 | 10 | 0.003 |
| 48 hours | 0.72 | 0.110 | 542 | 7 | 0.042 |

UO only

| Time prior AKI stage | AUC | SE | nCohort 1 | nCohort 2 | p |
|---|---:|---:|---:|---:|---:|
| 0 hours | 0.54 | 0.059 | 356 | 27 | 0.502 |
| 24 hours | 0.63 | 0.055 | 356 | 32 | 0.019 |
| 48 hours | 0.59 | 0.076 | 356 | 16 | 0.229 |

Fig. 6 Continued sCr or UO

| Time prior AKI stage | Cutoff value | sens | spec | Quartile | OR | 95% CI of OR | |
|---|---|---|---|---|---|---|---|
| 0 hours | 175 | 71% | 35% | 1 | | | |
| | 158 | 82% | 28% | 2 | 2.1 | 1.0 | 4.4 |
| | 126 | 93% | 18% | 3 | 1.3 | 0.5 | 3.2 |
| | 356 | 43% | 70% | 4 | 2.9 | 1.4 | 5.9 |
| | 513 | 29% | 80% | | | | |
| | 980 | 21% | 90% | | | | |
| 24 hours | 199 | 72% | 42% | 1 | | | |
| | 190 | 81% | 39% | 2 | 3.5 | 1.5 | 8.5 |
| | 168 | 92% | 33% | 3 | 2.4 | 0.9 | 6.4 |
| | 356 | 50% | 70% | 4 | 6.0 | 2.6 | 13.4 |
| | 513 | 42% | 80% | | | | |
| | 980 | 33% | 90% | | | | |
| 48 hours | 191 | 72% | 40% | 1 | | | |
| | 134 | 83% | 20% | 2 | 0.4 | 0.1 | 1.6 |
| | 114 | 94% | 15% | 3 | 0.8 | 0.3 | 2.0 |
| | 356 | 39% | 70% | 4 | 1.4 | 0.7 | 2.9 |
| | 513 | 39% | 80% | | | | |
| | 980 | 33% | 90% | | | | | sCr only

| Time prior AKI stage | Cutoff value | sens | spec | Quartile | OR | 95% CI of OR | |
|---|---|---|---|---|---|---|---|
| 0 hours | 414 | 83% | 74% | 1 | | | |
| | 414 | 83% | 74% | 2 | na | na | na |
| | 173 | 100% | 33% | 3 | na | na | na |
| | 364 | 83% | 70% | 4 | na | na | na |
| | 540 | 67% | 80% | | | | |
| | 1020 | 67% | 90% | | | | |
| 24 hours | 414 | 70% | 74% | 1 | | | |
| | 338 | 80% | 67% | 2 | 1.0 | 0.0 | 51.9 |
| | 180 | 90% | 35% | 3 | 2.0 | 0.1 | 39.2 |
| | 364 | 70% | 70% | 4 | 6.2 | 0.6 | 63.1 |
| | 540 | 60% | 80% | | | | |
| | 1020 | 60% | 90% | | | | |
| 48 hours | 270 | 71% | 56% | 1 | | | |
| | 264 | 86% | 54% | 2 | na | na | na |
| | 260 | 100% | 53% | 3 | na | na | na |
| | 364 | 43% | 70% | 4 | na | na | na |
| | 540 | 43% | 80% | | | | |
| | 1020 | 43% | 90% | | | | |

UO only

| Time prior AKI stage | Cutoff value | sens | spec | Quartile | OR | 95% CI of OR | |
|---|---|---|---|---|---|---|---|
| 0 hours | 190 | 70% | 37% | 1 | | | |
| | 156 | 81% | 26% | 2 | 2.1 | 0.9 | 4.5 |
| | 126 | 93% | 16% | 3 | 1.5 | 0.6 | 3.6 |
| | 356 | 37% | 70% | 4 | 2.4 | 1.1 | 5.0 |
| | 505 | 19% | 80% | | | | |
| | 980 | 11% | 90% | | | | |
| 24 hours | 199 | 72% | 40% | 1 | | | |
| | 190 | 81% | 37% | 2 | 5.5 | 1.6 | 18.5 |
| | 168 | 91% | 31% | 3 | 3.1 | 0.8 | 12.1 |
| | 356 | 47% | 70% | 4 | 8.0 | 2.5 | 25.7 |
| | 505 | 41% | 80% | | | | |
| | 980 | 28% | 90% | | | | |

Fig. 6 Continued

|  |  | 142 | 75% | 20% | 1 |  |  |  |
|---|---|---|---|---|---|---|---|---|
| 48 hours |  | 132 | 81% | 18% | 2 | 0.4 | 0.1 | 1.6 |
|  |  | 114 | 94% | 14% | 3 | 0.4 | 0.1 | 1.6 |
|  |  | 356 | 44% | 70% | 4 | 1.4 | 0.7 | 2.9 |
|  |  | 505 | 44% | 80% |  |  |  |  |
|  |  | 980 | 38% | 90% |  |  |  |  |

Interleukin-1 beta sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.015 | 0.015 | 0.015 | 0.015 | 0.015 | 0.015 |
| average | 0.318 | 0.421 | 0.318 | 0.315 | 0.318 | 0.634 |
| stdev | 3.084 | 0.827 | 3.084 | 0.627 | 3.084 | 0.962 |
| p (t-test) |  | 0.861 |  | 0.996 |  | 0.665 |
| min | 0.015 | 0.015 | 0.015 | 0.015 | 0.015 | 0.015 |
| max | 63.800 | 3.740 | 63.800 | 2.870 | 63.800 | 3.180 |
| n (Samp) | 434 | 28 | 434 | 36 | 434 | 18 |
| n (Pat) | 173 | 28 | 173 | 36 | 173 | 18 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 0.015 | 0.015 | 0.015 | 0.015 | 0.015 | 0.015 |
| average | 0.317 | 0.681 | 0.317 | 0.424 | 0.317 | 0.389 |
| stdev | 2.776 | 1.060 | 2.776 | 0.580 | 2.776 | 0.531 |
| p (t-test) |  | 0.748 |  | 0.903 |  | 0.945 |
| min | 0.015 | 0.015 | 0.015 | 0.015 | 0.015 | 0.015 |
| max | 63.800 | 2.390 | 63.800 | 1.420 | 63.800 | 1.290 |
| n (Samp) | 542 | 6 | 542 | 10 | 542 | 7 |
| n (Pat) | 208 | 6 | 208 | 10 | 208 | 7 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 0.015 | 0.015 | 0.015 | 0.015 | 0.015 | 0.175 |
| average | 0.339 | 0.348 | 0.339 | 0.292 | 0.339 | 0.805 |
| stdev | 3.398 | 0.745 | 3.398 | 0.637 | 3.398 | 1.082 |
| p (t-test) |  | 0.989 |  | 0.937 |  | 0.585 |
| min | 0.015 | 0.015 | 0.015 | 0.015 | 0.015 | 0.015 |
| max | 63.800 | 3.740 | 63.800 | 2.870 | 63.800 | 3.180 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
|---|---|---|---|---|---|
| 0 hours | 0.59 | 0.058 | 434 | 28 | 0.118 |
| 24 hours | 0.54 | 0.051 | 434 | 36 | 0.431 |
| 48 hours | 0.64 | 0.072 | 434 | 18 | 0.046 | sCr only

| Time prior AKI stage | AUC | SE | nCohort 1 | nCohort 2 | p |
|---|---|---|---|---|---|
| 0 hours | 0.59 | 0.123 | 542 | 6 | 0.444 |
| 24 hours | 0.61 | 0.096 | 542 | 10 | 0.234 |
| 48 hours | 0.62 | 0.114 | 542 | 7 | 0.304 |

Fig. 6 Continued

UO only

| Time prior AKI stage | AUC | SE | nCohort 1 | nCohort 2 | p |
|---|---|---|---|---|---|
| 0 hours | 0.58 | 0.059 | 356 | 27 | 0.178 |
| 24 hours | 0.53 | 0.054 | 356 | 32 | 0.610 |
| 48 hours | 0.68 | 0.075 | 356 | 16 | 0.017 | sCr or UO

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 1.0 | 0.4 | 2.2 |
| | 0 | 100% | 0% | 3 | 1.6 | 0.8 | 3.2 |
| | 0.0146 | 36% | 81% | 4 | 2.1 | 1.1 | 3.9 |
| | 0.0146 | 36% | 81% | | | | |
| | 0.639 | 21% | 90% | | | | |
| 24 hours | 0 | 100% | 0% | 1 | | | |
| | 0 | 100% | 0% | 2 | 3.5 | 1.8 | 6.9 |
| | 0 | 100% | 0% | 3 | 2.4 | 1.1 | 5.0 |
| | 0.0146 | 25% | 81% | 4 | 2.6 | 1.3 | 5.4 |
| | 0.0146 | 25% | 81% | | | | |
| | 0.639 | 19% | 90% | | | | |
| 48 hours | 0 | 100% | 0% | 1 | | | |
| | 0 | 100% | 0% | 2 | na | na | na |
| | 0 | 100% | 0% | 3 | na | na | na |
| | 0.0146 | 44% | 81% | 4 | na | na | na |
| | 0.0146 | 44% | 81% | | | | |
| | 0.639 | 39% | 90% | | | | |

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | na | na | na |
| | 0 | 100% | 0% | 3 | na | na | na |
| | 0.0146 | 33% | 82% | 4 | na | na | na |
| | 0.0146 | 33% | 82% | | | | |
| | 0.598 | 19% | 90% | | | | |
| 24 hours | 0 | 100% | 0% | 1 | | | |
| | 0 | 100% | 0% | 2 | 1.2 | 0.6 | 2.3 |
| | 0 | 100% | 0% | 3 | 1.7 | 1.0 | 3.1 |
| | 0.0146 | 22% | 82% | 4 | 1.6 | 0.9 | 2.8 |
| | 0.0146 | 22% | 82% | | | | |
| | 0.598 | 19% | 90% | | | | |
| 48 hours | 0 | 100% | 0% | 1 | | | |
| | 0 | 100% | 0% | 2 | na | na | na |
| | 0 | 100% | 0% | 3 | na | na | na |
| | 0.0146 | 50% | 82% | 4 | na | na | na |
| | 0.0146 | 50% | 82% | | | | |
| | 0.598 | 44% | 90% | | | | |

Fig. 6 Continued

Interleukin-10 sCr or UO

|          | 0 hr prior to AKI stage | | 24 hr prior to AKI stage | | 48 hr prior to AKI stage | |
|----------|---------|----------|---------|----------|---------|----------|
|          | Cohort 1 | Cohort 2 | Cohort 1 | Cohort 2 | Cohort 1 | Cohort 2 |
| median   | 15.300 | 18.450 | 15.300 | 23.400 | 15.300 | 13.000 |
| average  | 64.089 | 25.955 | 64.089 | 46.532 | 64.089 | 33.085 |
| stdev    | 653.984 | 29.144 | 653.984 | 54.661 | 653.984 | 43.210 |
| p (t-test) |  | 0.758 |  | 0.872 |  | 0.841 |
| min      | 0.154 | 0.154 | 0.154 | 0.154 | 0.154 | 4.400 |
| max      | 13400.000 | 151.000 | 13400.000 | 217.000 | 13400.000 | 176.000 |
| n (Samp) | 434 | 28 | 434 | 36 | 434 | 18 |
| n (Pat)  | 173 | 28 | 173 | 36 | 173 | 18 | sCr only

|          | 0 hr prior to AKI stage | | 24 hr prior to AKI stage | | 48 hr prior to AKI stage | |
|----------|---------|----------|---------|----------|---------|----------|
|          | Cohort 1 | Cohort 2 | Cohort 1 | Cohort 2 | Cohort 1 | Cohort 2 |
| median   | 16.000 | 59.550 | 16.000 | 18.950 | 16.000 | 13.500 |
| average  | 57.596 | 53.233 | 57.596 | 48.522 | 57.596 | 29.314 |
| stdev    | 585.455 | 22.628 | 585.455 | 57.960 | 585.455 | 32.504 |
| p (t-test) |  | 0.985 |  | 0.961 |  | 0.898 |
| min      | 0.154 | 18.100 | 0.154 | 0.154 | 0.154 | 4.400 |
| max      | 13400.000 | 81.500 | 13400.000 | 159.000 | 13400.000 | 88.400 |
| n (Samp) | 542 | 6 | 542 | 10 | 542 | 7 |
| n (Pat)  | 208 | 6 | 208 | 10 | 208 | 7 |

UO only

|          | 0 hr prior to AKI stage | | 24 hr prior to AKI stage | | 48 hr prior to AKI stage | |
|----------|---------|----------|---------|----------|---------|----------|
|          | Cohort 1 | Cohort 2 | Cohort 1 | Cohort 2 | Cohort 1 | Cohort 2 |
| median   | 15.100 | 18.800 | 15.100 | 23.400 | 15.100 | 19.700 |
| average  | 70.419 | 25.691 | 70.419 | 47.084 | 70.419 | 43.846 |
| stdev    | 721.168 | 29.178 | 721.168 | 52.829 | 721.168 | 53.601 |
| p (t-test) |  | 0.748 |  | 0.855 |  | 0.883 |
| min      | 0.154 | 0.154 | 0.154 | 0.154 | 0.154 | 6.370 |
| max      | 13400.000 | 151.000 | 13400.000 | 217.000 | 13400.000 | 176.000 |
| n (Samp) | 356 | 27 | 356 | 32 | 356 | 16 |
| n (Pat)  | 138 | 27 | 138 | 32 | 138 | 16 | sCr or UO

| Time prior AKI stage | AUC | SE | nCohort 1 | nCohort 2 | p |
|---|---|---|---|---|---|
| 0 hours | 0.55 | 0.058 | 434 | 28 | 0.384 |
| 24 hours | 0.62 | 0.052 | 434 | 36 | 0.025 |
| 48 hours | 0.50 | 0.070 | 434 | 18 | 0.974 | sCr only

| Time prior AKI stage | AUC | SE | nCohort 1 | nCohort 2 | p |
|---|---|---|---|---|---|
| 0 hours | 0.85 | 0.100 | 542 | 6 | 0.000 |
| 24 hours | 0.53 | 0.094 | 542 | 10 | 0.732 |
| 48 hours | 0.49 | 0.109 | 542 | 7 | 0.923 |

UO only

| Time prior AKI stage | AUC | SE | nCohort 1 | nCohort 2 | p |
|---|---|---|---|---|---|
| 0 hours | 0.55 | 0.059 | 356 | 27 | 0.415 |
| 24 hours | 0.66 | 0.054 | 356 | 32 | 0.004 |
| 48 hours | 0.57 | 0.076 | 356 | 16 | 0.334 |

Fig. 6 Continued sCr or UO

| Time prior AKI stage | Cutoff value | sens | spec | Quartile | OR | 95% CI of OR | |
|---|---|---|---|---|---|---|---|
| 0 hours | 12 | 71% | 39% | 1 | | | |
| | 10.2 | 82% | 30% | 2 | 3.1 | 1.3 | 7.8 |
| | 8.43 | 93% | 23% | 3 | 3.6 | 1.5 | 8.6 |
| | 23.1 | 25% | 70% | 4 | 2.0 | 0.7 | 5.6 |
| | 30.4 | 18% | 80% | | | | |
| | 45.4 | 14% | 90% | | | | |
| 24 hours | 11.5 | 72% | 35% | 1 | | | |
| | 9.7 | 81% | 29% | 2 | 0.8 | 0.4 | 1.6 |
| | 4.88 | 94% | 7% | 3 | 1.0 | 0.6 | 1.8 |
| | 23.1 | 53% | 70% | 4 | 2.5 | 1.6 | 3.8 |
| | 30.4 | 42% | 80% | | | | |
| | 45.4 | 31% | 90% | | | | |
| 48 hours | 8.54 | 72% | 23% | 1 | | | |
| | 6.64 | 83% | 13% | 2 | 0.7 | 0.3 | 1.5 |
| | 6.31 | 94% | 11% | 3 | 0.3 | 0.1 | 1.2 |
| | 23.1 | 33% | 70% | 4 | 1.0 | 0.5 | 2.0 |
| | 30.4 | 28% | 80% | | | | |
| | 45.4 | 28% | 90% | | | | | sCr only

| Time prior AKI stage | Cutoff value | sens | spec | Quartile | OR | 95% CI of OR | |
|---|---|---|---|---|---|---|---|
| 0 hours | 35.3 | 83% | 82% | 1 | | | |
| | 35.3 | 83% | 82% | 2 | na | na | na |
| | 18 | 100% | 55% | 3 | na | na | na |
| | 24 | 83% | 71% | 4 | na | na | na |
| | 31.9 | 83% | 80% | | | | |
| | 50.7 | 67% | 90% | | | | |
| 24 hours | 9.26 | 70% | 24% | 1 | | | |
| | 5 | 90% | 6% | 2 | 0.2 | 0.0 | 2.9 |
| | 5 | 90% | 6% | 3 | 0.2 | 0.0 | 2.9 |
| | 24 | 40% | 71% | 4 | 1.0 | 0.4 | 2.7 |
| | 31.9 | 40% | 80% | | | | |
| | 50.7 | 40% | 90% | | | | |
| 48 hours | 13.2 | 71% | 42% | 1 | | | |
| | 8.54 | 86% | 21% | 2 | 0.0 | 0.0 | na |
| | 4.13 | 100% | 5% | 3 | 1.5 | 0.3 | 8.0 |
| | 24 | 29% | 71% | 4 | 1.0 | 0.1 | 7.4 |
| | 31.9 | 29% | 80% | | | | |
| | 50.7 | 29% | 90% | | | | |

UO only

| Time prior AKI stage | Cutoff value | sens | spec | Quartile | OR | 95% CI of OR | |
|---|---|---|---|---|---|---|---|
| 0 hours | 12 | 70% | 39% | 1 | | | |
| | 10.2 | 81% | 30% | 2 | 2.8 | 1.1 | 7.2 |
| | 8.43 | 93% | 22% | 3 | 3.6 | 1.5 | 8.7 |
| | 23.1 | 26% | 70% | 4 | 2.0 | 0.7 | 5.7 |
| | 29.7 | 19% | 80% | | | | |
| | 45.1 | 11% | 90% | | | | |
| 24 hours | 15.6 | 72% | 52% | 1 | | | |
| | 11.1 | 81% | 33% | 2 | 1.5 | 0.6 | 3.6 |
| | 8.83 | 91% | 23% | 3 | 1.8 | 0.8 | 4.1 |
| | 23.1 | 56% | 70% | 4 | 4.3 | 2.2 | 8.3 |
| | 29.7 | 44% | 80% | | | | |
| | 45.1 | 31% | 90% | | | | |

Fig. 6 Continued

| 48 hours | 10.5 | 75% | 31% | 1 | | | |
| | 8.43 | 81% | 22% | 2 | 0.7 | 0.2 | 2.4 |
| | 6.31 | 100% | 10% | 3 | 0.5 | 0.1 | 2.2 |
| | 23.1 | 44% | 70% | 4 | 1.8 | 0.8 | 4.1 |
| | 29.7 | 38% | 80% | | | | |
| | 45.1 | 31% | 90% | | | | |

Interleukin-15 sCr or UO

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 0.151 | 0.013 | 0.151 | 0.013 | 0.151 | 0.040 |
| average | 0.204 | 0.097 | 0.204 | 0.120 | 0.204 | 0.133 |
| stdev | 0.382 | 0.135 | 0.382 | 0.151 | 0.382 | 0.159 |
| p (t-test) | | 0.139 | | 0.190 | | 0.430 |
| min | 0.013 | 0.013 | 0.013 | 0.013 | 0.013 | 0.013 |
| max | 6.590 | 0.551 | 6.590 | 0.628 | 6.590 | 0.492 |
| n (Samp) | 434 | 28 | 434 | 36 | 434 | 18 |
| n (Pat) | 173 | 28 | 173 | 36 | 173 | 18 | sCr only

| | 0 hr prior toAKI stage | | 24 hr prior toAKI stage | | 48 hr prior toAKI stage | |
| | Cohort 1 | Cohort 2 | Cohort 1 | Cohort 2 | Cohort 1 | Cohort 2 |
|---|---|---|---|---|---|---|
| median | 0.119 | 0.041 | 0.119 | 0.013 | 0.119 | 0.013 |
| average | 0.189 | 0.141 | 0.189 | 0.063 | 0.189 | 0.104 |
| stdev | 0.351 | 0.180 | 0.351 | 0.125 | 0.351 | 0.127 |
| p (t-test) | | 0.738 | | 0.256 | | 0.523 |
| min | 0.013 | 0.013 | 0.013 | 0.013 | 0.013 | 0.013 |
| max | 6.590 | 0.405 | 6.590 | 0.405 | 6.590 | 0.338 |
| n (Samp) | 542 | 6 | 542 | 10 | 542 | 7 |
| n (Pat) | 208 | 6 | 208 | 10 | 208 | 7 |

UO only

| | 0 hr prior toAKI stage | | 24 hr prior toAKI stage | | 48 hr prior toAKI stage | |
| | Cohort 1 | Cohort 2 | Cohort 1 | Cohort 2 | Cohort 1 | Cohort 2 |
|---|---|---|---|---|---|---|
| median | 0.129 | 0.013 | 0.129 | 0.062 | 0.129 | 0.111 |
| average | 0.207 | 0.090 | 0.207 | 0.127 | 0.207 | 0.157 |
| stdev | 0.414 | 0.129 | 0.414 | 0.149 | 0.414 | 0.169 |
| p (t-test) | | 0.146 | | 0.279 | | 0.631 |
| min | 0.013 | 0.013 | 0.013 | 0.013 | 0.013 | 0.013 |
| max | 6.590 | 0.551 | 6.590 | 0.628 | 6.590 | 0.492 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
|---|---|---|---|---|---|
| 0 hours | 0.37 | 0.050 | 434 | 28 | 0.008 |
| 24 hours | 0.40 | 0.046 | 434 | 36 | 0.031 |
| 48 hours | 0.42 | 0.065 | 434 | 18 | 0.228 | sCr only

| Time prior AKI stage | AUC | SE | nCohort 1 | nCohort 2 | p |
|---|---|---|---|---|---|
| 0 hours | 0.45 | 0.114 | 542 | 6 | 0.693 |
| 24 hours | 0.30 | 0.070 | 542 | 10 | 0.004 |
| 48 hours | 0.40 | 0.100 | 542 | 7 | 0.318 |

Fig. 6 Continued

UO only

| Time prior AKI stage | AUC | SE | nCohort 1 | nCohort 2 | p |
|---|---|---|---|---|---|
| 0 hours | 0.36 | 0.051 | 356 | 27 | 0.007 |
| 24 hours | 0.43 | 0.051 | 356 | 32 | 0.160 |
| 48 hours | 0.47 | 0.073 | 356 | 16 | 0.708 | sCr or UO

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 1.7 | 0.6 | 5.0 |
| | 0 | 100% | 0% | 3 | 7.4 | 3.3 | 16.3 |
| | 0.246 | 14% | 71% | 4 | 0.3 | 0.0 | 4.7 |
| | 0.328 | 11% | 81% | | | | |
| | 0.422 | 4% | 90% | | | | |
| 24 hours | 0 | 100% | 0% | 1 | | | |
| | 0 | 100% | 0% | 2 | 1.7 | 0.8 | 3.2 |
| | 0 | 100% | 0% | 3 | 5.2 | 3.1 | 8.7 |
| | 0.246 | 17% | 71% | 4 | 0.2 | 0.0 | 2.1 |
| | 0.328 | 14% | 81% | | | | |
| | 0.422 | 3% | 90% | | | | |
| 48 hours | 0 | 100% | 0% | 1 | | | |
| | 0 | 100% | 0% | 2 | 1.7 | 0.6 | 5.0 |
| | 0 | 100% | 0% | 3 | 2.8 | 1.1 | 7.1 |
| | 0.246 | 17% | 71% | 4 | 0.7 | 0.1 | 3.5 |
| | 0.328 | 17% | 81% | | | | |
| | 0.422 | 11% | 90% | | | | | sCr only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.0 | 0.0 | na |
| | 0 | 100% | 0% | 3 | 2.0 | 0.5 | 9.1 |
| | 0.242 | 33% | 70% | 4 | 0.0 | 0.0 | na |
| | 0.313 | 33% | 80% | | | | |
| | 0.418 | 0% | 90% | | | | |
| 24 hours | 0 | 100% | 0% | 1 | | | |
| | 0 | 100% | 0% | 2 | 1.0 | 0.0 | 51.9 |
| | 0 | 100% | 0% | 3 | 8.4 | 0.9 | 78.7 |
| | 0.242 | 10% | 70% | 4 | 0.0 | 0.0 | na |
| | 0.313 | 10% | 80% | | | | |
| | 0.418 | 0% | 90% | | | | |
| 48 hours | 0 | 100% | 0% | 1 | | | |
| | 0 | 100% | 0% | 2 | 2.0 | 0.1 | 39.5 |
| | 0 | 100% | 0% | 3 | 4.1 | 0.3 | 49.2 |
| | 0.242 | 14% | 70% | 4 | 0.0 | 0.0 | na |
| | 0.313 | 14% | 80% | | | | |
| | 0.418 | 0% | 90% | | | | |

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 1.7 | 0.6 | 5.1 |
| | 0 | 100% | 0% | 3 | 7.6 | 3.4 | 17.1 |
| | 0.245 | 11% | 70% | 4 | 0.0 | 0.0 | na |
| | 0.323 | 7% | 80% | | | | |
| | 0.431 | 4% | 91% | | | | |
| 24 hours | 0 | 100% | 0% | 1 | | | |
| | 0 | 100% | 0% | 2 | 2.4 | 1.1 | 5.0 |
| | 0 | 100% | 0% | 3 | 3.6 | 1.8 | 7.1 |
| | 0.245 | 25% | 70% | 4 | 1.5 | 0.6 | 3.6 |
| | 0.323 | 13% | 80% | | | | |

Fig. 6 Continued

|         | 0.431 | 3%   | 91% |   |     |     |     |
|---------|-------|------|-----|---|-----|-----|-----|
| 48 hours | 0    | 100% | 0%  | 1 |     |     |     |
|         | 0     | 100% | 0%  | 2 | 1.0 | 0.4 | 2.8 |
|         | 0     | 100% | 0%  | 3 | 1.5 | 0.6 | 3.6 |
|         | 0.245 | 25%  | 70% | 4 | 0.5 | 0.1 | 2.2 |
|         | 0.323 | 25%  | 80% |   |     |     |     |
|         | 0.431 | 13%  | 91% |   |     |     |     |

Interleukin-3 sCr or UO

|          | 0 hr prior to AKI stage | | 24 hr prior to AKI stage | | 48 hr prior to AKI stage | |
|----------|-------|-------|-------|-------|-------|-------|
|          | Cohort 1 | Cohort 2 | Cohort 1 | Cohort 2 | Cohort 1 | Cohort 2 |
| median   | 0.060 | 0.033 | 0.060 | 0.038 | 0.060 | 0.035 |
| average  | 0.093 | 0.059 | 0.093 | 0.063 | 0.093 | 0.050 |
| stdev    | 0.105 | 0.103 | 0.105 | 0.082 | 0.105 | 0.048 |
| p (t-test) |     | 0.097 |       | 0.095 |       | 0.084 |
| min      | 0.002 | 0.002 | 0.002 | 0.002 | 0.002 | 0.002 |
| max      | 0.566 | 0.550 | 0.566 | 0.404 | 0.566 | 0.164 |
| n (Samp) | 434   | 28    | 434   | 36    | 434   | 18    |
| n (Pat)  | 173   | 28    | 173   | 36    | 173   | 18    | sCr only

|          | 0 hr prior to AKI stage | | 24 hr prior to AKI stage | | 48 hr prior to AKI stage | |
|----------|-------|-------|-------|-------|-------|-------|
|          | Cohort 1 | Cohort 2 | Cohort 1 | Cohort 2 | Cohort 1 | Cohort 2 |
| median   | 0.057 | 0.068 | 0.057 | 0.037 | 0.057 | 0.053 |
| average  | 0.088 | 0.157 | 0.088 | 0.057 | 0.088 | 0.056 |
| stdev    | 0.101 | 0.206 | 0.101 | 0.064 | 0.101 | 0.038 |
| p (t-test) |     | 0.097 |       | 0.335 |       | 0.409 |
| min      | 0.002 | 0.002 | 0.002 | 0.002 | 0.002 | 0.002 |
| max      | 0.566 | 0.550 | 0.566 | 0.211 | 0.566 | 0.123 |
| n (Samp) | 542   | 6     | 542   | 10    | 542   | 7     |
| n (Pat)  | 208   | 6     | 208   | 10    | 208   | 7     |

UO only

|          | 0 hr prior to AKI stage | | 24 hr prior to AKI stage | | 48 hr prior to AKI stage | |
|----------|-------|-------|-------|-------|-------|-------|
|          | Cohort 1 | Cohort 2 | Cohort 1 | Cohort 2 | Cohort 1 | Cohort 2 |
| median   | 0.053 | 0.031 | 0.053 | 0.037 | 0.053 | 0.035 |
| average  | 0.085 | 0.041 | 0.085 | 0.058 | 0.085 | 0.082 |
| stdev    | 0.104 | 0.037 | 0.104 | 0.082 | 0.104 | 0.135 |
| p (t-test) |     | 0.028 |       | 0.151 |       | 0.898 |
| min      | 0.002 | 0.002 | 0.002 | 0.002 | 0.002 | 0.002 |
| max      | 0.566 | 0.121 | 0.566 | 0.404 | 0.566 | 0.550 |
| n (Samp) | 356   | 27    | 356   | 32    | 356   | 16    |
| n (Pat)  | 138   | 27    | 138   | 32    | 138   | 16    | sCr or UO

| Time prior AKI stage | AUC | SE | nCohort 1 | nCohort 2 | p |
|-----|-----|-----|-----|-----|-----|
| 0 hours  | 0.37 | 0.049 | 434 | 28 | 0.007 |
| 24 hours | 0.40 | 0.046 | 434 | 36 | 0.027 |
| 48 hours | 0.38 | 0.062 | 434 | 18 | 0.060 | sCr only

| Time prior AKI stage | AUC | SE | nCohort 1 | nCohort 2 | p |
|-----|-----|-----|-----|-----|-----|
| 0 hours  | 0.58 | 0.123 | 542 | 6  | 0.512 |
| 24 hours | 0.41 | 0.085 | 542 | 10 | 0.291 |
| 48 hours | 0.47 | 0.107 | 542 | 7  | 0.748 |

Fig. 6 Continued

UO only

| Time prior AKI stage | AUC | SE | nCohort 1 | nCohort 2 | p |
|---|---|---|---|---|---|
| 0 hours | 0.38 | 0.051 | 356 | 27 | 0.016 |
| 24 hours | 0.40 | 0.049 | 356 | 32 | 0.042 |
| 48 hours | 0.44 | 0.070 | 356 | 16 | 0.393 | sCr or UO

| Time prior AKI stage | Cutoff value | sens | spec | Quartile | OR | 95% CI of OR | |
|---|---|---|---|---|---|---|---|
| 0 hours | 0.0216 | 71% | 23% | 1 | | | |
| | 0 | 100% | 0% | 2 | 1.7 | 0.6 | 5.0 |
| | 0 | 100% | 0% | 3 | 3.9 | 1.7 | 9.4 |
| | 0.102 | 14% | 70% | 4 | 3.2 | 1.3 | 7.9 |
| | 0.146 | 4% | 80% | | | | |
| | 0.23 | 4% | 90% | | | | |
| 24 hours | 0.00277 | 72% | 15% | 1 | | | |
| | 0 | 100% | 0% | 2 | 2.1 | 1.1 | 3.9 |
| | 0 | 100% | 0% | 3 | 1.4 | 0.7 | 2.9 |
| | 0.102 | 19% | 70% | 4 | 3.1 | 1.7 | 5.4 |
| | 0.146 | 11% | 80% | | | | |
| | 0.23 | 6% | 90% | | | | |
| 48 hours | 0.0218 | 72% | 24% | 1 | | | |
| | 0 | 100% | 0% | 2 | 2.0 | 0.5 | 9.2 |
| | 0 | 100% | 0% | 3 | 2.6 | 0.6 | 10.5 |
| | 0.102 | 11% | 70% | 4 | 3.7 | 1.0 | 13.4 |
| | 0.146 | 6% | 80% | | | | |
| | 0.23 | 0% | 90% | | | | | sCr only

| Time prior AKI stage | Cutoff value | sens | spec | Quartile | OR | 95% CI of OR | |
|---|---|---|---|---|---|---|---|
| 0 hours | 0.0402 | 83% | 41% | 1 | | | |
| | 0.0402 | 83% | 41% | 2 | 2.0 | 0.1 | 39.2 |
| | 0 | 100% | 0% | 3 | 1.0 | 0.0 | 51.9 |
| | 0.0972 | 33% | 70% | 4 | 2.0 | 0.1 | 39.2 |
| | 0.136 | 33% | 80% | | | | |
| | 0.218 | 17% | 90% | | | | |
| 24 hours | 0.0309 | 70% | 33% | 1 | | | |
| | 0 | 100% | 0% | 2 | 3.0 | 0.2 | 42.8 |
| | 0 | 100% | 0% | 3 | 3.0 | 0.2 | 42.8 |
| | 0.0972 | 20% | 70% | 4 | 3.0 | 0.2 | 42.8 |
| | 0.136 | 10% | 80% | | | | |
| | 0.218 | 0% | 90% | | | | |
| 48 hours | 0.0471 | 71% | 45% | 1 | | | |
| | 0.0277 | 86% | 31% | 2 | 2.0 | 0.1 | 39.5 |
| | 0 | 100% | 0% | 3 | 3.1 | 0.2 | 43.1 |
| | 0.0972 | 14% | 70% | 4 | 1.0 | 0.0 | 52.3 |
| | 0.136 | 0% | 80% | | | | |
| | 0.218 | 0% | 90% | | | | |

UO only

| Time prior AKI stage | Cutoff value | sens | spec | Quartile | OR | 95% CI of OR | |
|---|---|---|---|---|---|---|---|
| 0 hours | 0.0218 | 70% | 26% | 1 | | | |
| | 0.00277 | 81% | 17% | 2 | 1.7 | 0.6 | 5.1 |
| | 0 | 100% | 0% | 3 | 4.4 | 1.9 | 10.5 |
| | 0.0944 | 15% | 71% | 4 | 2.5 | 0.9 | 6.5 |
| | 0.121 | 0% | 80% | | | | |
| | 0.207 | 0% | 90% | | | | |

Fig. 6 Continued

| 24 hours | | 0.00277 | 72% | 17% | 1 | | | |
|---|---|---|---|---|---|---|---|---|
| | | 0 | 100% | 0% | 2 | 1.2 | 0.6 | 2.6 |
| | | 0 | 100% | 0% | 3 | 1.9 | 1.0 | 3.6 |
| | | 0.0944 | 16% | 71% | 4 | 2.6 | 1.4 | 4.7 |
| | | 0.121 | 9% | 80% | | | | |
| | | 0.207 | 6% | 90% | | | | |
| 48 hours | | 0.0115 | 75% | 18% | 1 | | | |
| | | 0 | 100% | 0% | 2 | 1.3 | 0.4 | 4.4 |
| | | 0 | 100% | 0% | 3 | 1.3 | 0.4 | 4.4 |
| | | 0.0944 | 25% | 71% | 4 | 1.7 | 0.6 | 5.1 |
| | | 0.121 | 19% | 80% | | | | |
| | | 0.207 | 6% | 90% | | | | |

Myeloperoxidase sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 170.297 | 86.725 | 170.297 | 236.638 | 170.297 | 278.774 |
| average | 218.021 | 352.301 | 218.021 | 250.024 | 218.021 | 267.746 |
| stdev | 268.779 | 625.782 | 268.779 | 231.222 | 268.779 | 191.490 |
| p (t-test) | | 0.070 | | 0.547 | | 0.468 |
| min | 0.000 | 0.000 | 0.000 | 0.000 | 0.000 | 0.000 |
| max | 1808.488 | 2065.234 | 1808.488 | 862.883 | 1808.488 | 585.270 |
| n (Samp) | 230 | 19 | 230 | 28 | 230 | 16 |
| n (Pat) | 158 | 19 | 158 | 28 | 158 | 16 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 165.435 | 2056.930 | 165.435 | 277.618 | 165.435 | 234.462 |
| average | 219.215 | 2056.930 | 219.215 | 416.483 | 219.215 | 258.294 |
| stdev | 257.553 | 11.744 | 257.553 | 561.866 | 257.553 | 178.310 |
| p (t-test) | | 0.000 | | 0.054 | | 0.736 |
| min | 0.000 | 2048.626 | 0.000 | 0.000 | 0.000 | 0.000 |
| max | 1808.488 | 2065.234 | 1808.488 | 1580.100 | 1808.488 | 477.383 |
| n (Samp) | 295 | 2 | 295 | 7 | 295 | 5 |
| n (Pat) | 187 | 2 | 187 | 7 | 187 | 5 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 177.462 | 86.725 | 177.462 | 266.108 | 177.462 | 329.876 |
| average | 230.048 | 175.711 | 230.048 | 342.348 | 230.048 | 411.037 |
| stdev | 283.897 | 211.789 | 283.897 | 415.184 | 283.897 | 512.325 |
| p (t-test) | | 0.418 | | 0.076 | | 0.032 |
| min | 0.000 | 0.000 | 0.000 | 0.000 | 0.000 | 0.000 |
| max | 1808.488 | 663.247 | 1808.488 | 2048.626 | 1808.488 | 2065.234 |
| n (Samp) | 198 | 19 | 198 | 26 | 198 | 14 |
| n (Pat) | 132 | 19 | 132 | 26 | 132 | 14 | sCr or UO

| Time prior AKI stage | AUC | SE | nCohort 1 | nCohort 2 | p |
|---|---|---|---|---|---|
| 0 hours | 0.51 | 0.070 | 230 | 19 | 0.847 |
| 24 hours | 0.57 | 0.059 | 230 | 28 | 0.216 |
| 48 hours | 0.61 | 0.077 | 230 | 16 | 0.151 |

Fig. 6 Continued sCr only

| Time prior AKI stage | AUC | SE | nCohort 1 | nCohort 2 | p |
|---|---|---|---|---|---|
| 0 hours | 1.00 | 0.000 | 295 | 2 | nd |
| 24 hours | 0.60 | 0.115 | 295 | 7 | 0.400 |
| 48 hours | 0.60 | 0.135 | 295 | 5 | 0.473 |

UO only

| Time prior AKI stage | AUC | SE | nCohort 1 | nCohort 2 | p |
|---|---|---|---|---|---|
| 0 hours | 0.47 | 0.068 | 198 | 19 | 0.637 |
| 24 hours | 0.61 | 0.062 | 198 | 26 | 0.084 |
| 48 hours | 0.65 | 0.082 | 198 | 14 | 0.075 | sCr or UO

| Time prior AKI stage | Cutoff value | sens | spec | Quartile | OR | 95% CI of OR | |
|---|---|---|---|---|---|---|---|
| 0 hours | 20.1558 | 74% | 35% | 1 | | | |
| | 0 | 100% | 0% | 2 | na | na | na |
| | 0 | 100% | 0% | 3 | na | na | na |
| | 294.035 | 32% | 70% | 4 | na | na | na |
| | 349.512 | 26% | 80% | | | | |
| | 513.42 | 16% | 90% | | | | |
| 24 hours | 101.348 | 71% | 41% | 1 | | | |
| | 5.44998 | 82% | 34% | 2 | 2.1 | 0.9 | 4.7 |
| | 0 | 100% | 0% | 3 | 1.8 | 0.8 | 4.3 |
| | 294.035 | 36% | 70% | 4 | 2.4 | 1.1 | 5.2 |
| | 349.512 | 32% | 80% | | | | |
| | 513.42 | 11% | 90% | | | | |
| 48 hours | 109.477 | 75% | 42% | 1 | | | |
| | 78.1194 | 81% | 39% | 2 | 0.6 | 0.1 | 3.5 |
| | 0 | 100% | 0% | 3 | 1.4 | 0.4 | 4.6 |
| | 294.035 | 50% | 70% | 4 | 2.5 | 0.9 | 6.7 |
| | 349.512 | 31% | 80% | | | | |
| | 513.42 | 13% | 90% | | | | | sCr only

| Time prior AKI stage | Cutoff value | sens | spec | Quartile | OR | 95% CI of OR | |
|---|---|---|---|---|---|---|---|
| 0 hours | 1808.49 | 100% | 100% | 1 | | | |
| | 1808.49 | 100% | 100% | 2 | na | na | na |
| | 1808.49 | 100% | 100% | 3 | na | na | na |
| | 296.761 | 100% | 70% | 4 | na | na | na |
| | 364.661 | 100% | 80% | | | | |
| | 514.759 | 100% | 90% | | | | |
| 24 hours | 84.1607 | 71% | 38% | 1 | | | |
| | 5.44998 | 86% | 32% | 2 | 2.0 | 0.1 | 39.9 |
| | 0 | 100% | 0% | 3 | 2.0 | 0.1 | 40.5 |
| | 296.761 | 43% | 70% | 4 | 2.0 | 0.1 | 39.9 |
| | 364.661 | 29% | 80% | | | | |
| | 514.759 | 29% | 90% | | | | |
| 48 hours | 218.559 | 80% | 56% | 1 | | | |
| | 218.559 | 80% | 56% | 2 | 0.0 | 0.0 | na |
| | 0 | 100% | 0% | 3 | 2.0 | 0.1 | 40.5 |
| | 296.761 | 40% | 70% | 4 | 2.0 | 0.1 | 40.5 |
| | 364.661 | 20% | 80% | | | | |
| | 514.759 | 0% | 90% | | | | |

Fig. 6 Continued

UO only

| Time prior AKI stage | Cutoff value | sens | spec | Quartile | OR | 95% CI of OR | |
|---|---|---|---|---|---|---|---|
| 0 hours | 20.1558 | 74% | 33% | 1 | | | |
| | 0 | 100% | 0% | 2 | 0.8 | 0.2 | 2.5 |
| | 0 | 100% | 0% | 3 | 2.9 | 1.3 | 6.3 |
| | 294.035 | 26% | 70% | 4 | 0.5 | 0.1 | 2.3 |
| | 364.661 | 21% | 80% | | | | |
| | 550.772 | 11% | 90% | | | | |
| 24 hours | 128.008 | 73% | 45% | 1 | | | |
| | 101.348 | 81% | 41% | 2 | 2.5 | 0.9 | 6.9 |
| | 0 | 100% | 0% | 3 | 2.1 | 0.7 | 6.1 |
| | 294.035 | 42% | 70% | 4 | 3.8 | 1.5 | 9.7 |
| | 364.661 | 27% | 80% | | | | |
| | 550.772 | 12% | 90% | | | | |
| 48 hours | 211.291 | 71% | 55% | 1 | | | |
| | 78.1194 | 86% | 37% | 2 | na | na | na |
| | 0 | 100% | 0% | 3 | na | na | na |
| | 294.035 | 57% | 70% | 4 | na | na | na |
| | 364.661 | 36% | 80% | | | | |
| | 550.772 | 14% | 90% | | | | |

Nidogen-1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 274684.343 | 365099.010 | 274684.343 | 481331.169 | 274684.343 | 306006.494 |
| average | 441895.551 | 439086.795 | 441895.551 | 519762.067 | 441895.551 | 421048.325 |
| stdev | 498707.894 | 325456.181 | 498707.894 | 297315.567 | 498707.894 | 425448.037 |
| p (t-test) | | 0.987 | | 0.545 | | 0.943 |
| min | 140.129 | 4788.306 | 140.129 | 140.129 | 140.129 | 64950.980 |
| max | 3173333.333 | 996875.000 | 3173333.333 | 1355072.464 | 3173333.333 | 892187.500 |
| n (Samp) | 106 | 9 | 106 | 16 | 106 | 3 |
| n (Pat) | 65 | 9 | 65 | 16 | 65 | 3 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 322411.616 | 88217.871 | 322411.616 | 626068.376 | 322411.616 | 482803.087 |
| average | 443314.574 | 88217.871 | 443314.574 | 669422.641 | 443314.574 | 482803.087 |
| stdev | 465755.847 | 44030.886 | 465755.847 | 517323.852 | 465755.847 | 578956.989 |
| p (t-test) | | 0.285 | | 0.290 | | 0.906 |
| min | 140.129 | 57083.333 | 140.129 | 140.129 | 140.129 | 73418.675 |
| max | 3173333.333 | 119352.410 | 3173333.333 | 1193581.781 | 3173333.333 | 892187.500 |
| n (Samp) | 138 | 2 | 138 | 5 | 138 | 2 |
| n (Pat) | 83 | 2 | 83 | 5 | 83 | 2 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 332323.232 | 365099.010 | 332323.232 | 498144.217 | 332323.232 | 185478.737 |
| average | 474489.190 | 439086.795 | 474489.190 | 578158.516 | 474489.190 | 185478.737 |
| stdev | 517120.899 | 325456.181 | 517120.899 | 281479.308 | 517120.899 | 170451.988 |
| p (t-test) | | 0.841 | | 0.467 | | 0.434 |
| min | 34143.519 | 4788.306 | 34143.519 | 222938.144 | 34143.519 | 64950.980 |
| max | 3173333.333 | 996875.000 | 3173333.333 | 1355072.464 | 3173333.333 | 306006.494 |
| n (Samp) | 85 | 9 | 85 | 14 | 85 | 2 |
| n (Pat) | 50 | 9 | 50 | 14 | 50 | 2 |

Fig. 6 Continued sCr or UO

| Time prior AKI stage | AUC | SE | nCohort 1 | nCohort 2 | p |
|---|---|---|---|---|---|
| 0 hours | 0.54 | 0.103 | 106 | 9 | 0.675 |
| 24 hours | 0.64 | 0.079 | 106 | 16 | 0.074 |
| 48 hours | 0.49 | 0.169 | 106 | 3 | 0.955 | sCr only

| Time prior AKI stage | AUC | SE | nCohort 1 | nCohort 2 | p |
|---|---|---|---|---|---|
| 0 hours | 0.18 | 0.112 | 138 | 2 | 0.005 |
| 24 hours | 0.64 | 0.136 | 138 | 5 | 0.302 |
| 48 hours | 0.49 | 0.205 | 138 | 2 | 0.972 |

UO only

| Time prior AKI stage | AUC | SE | nCohort 1 | nCohort 2 | p |
|---|---|---|---|---|---|
| 0 hours | 0.52 | 0.103 | 85 | 9 | 0.854 |
| 24 hours | 0.67 | 0.084 | 85 | 14 | 0.042 |
| 48 hours | 0.28 | 0.152 | 85 | 2 | 0.141 | sCr or UO

| Time prior AKI stage | Cutoff value | sens | spec | Quartile | OR | 95% CI of OR | |
|---|---|---|---|---|---|---|---|
| 0 hours | 291919 | 78% | 52% | 1 | | | |
| | 56250 | 89% | 11% | 2 | 0.0 | 0.0 | na |
| | 1456.57 | 100% | 3% | 3 | 2.1 | 0.4 | 10.6 |
| | 499188 | 33% | 71% | 4 | 1.5 | 0.3 | 8.9 |
| | 741453 | 22% | 80% | | | | |
| | 965625 | 11% | 91% | | | | |
| 24 hours | 356436 | 75% | 58% | 1 | | | |
| | 338474 | 81% | 55% | 2 | 2.0 | 0.1 | 43.3 |
| | 193299 | 94% | 44% | 3 | 10.5 | 1.0 | 111.9 |
| | 499188 | 44% | 71% | 4 | 5.6 | 0.5 | 67.6 |
| | 741453 | 13% | 80% | | | | |
| | 965625 | 6% | 91% | | | | |
| 48 hours | 56250 | 100% | 11% | 1 | | | |
| | 56250 | 100% | 11% | 2 | 1.0 | 0.0 | 60.7 |
| | 56250 | 100% | 11% | 3 | 0.0 | 0.0 | na |
| | 499188 | 33% | 71% | 4 | 1.0 | 0.0 | 60.7 |
| | 741453 | 33% | 80% | | | | |
| | 965625 | 0% | 91% | | | | | sCr only

| Time prior AKI stage | Cutoff value | sens | spec | Quartile | OR | 95% CI of OR | |
|---|---|---|---|---|---|---|---|
| 0 hours | 56250 | 100% | 12% | 1 | | | |
| | 56250 | 100% | 12% | 2 | na | na | na |
| | 56250 | 100% | 12% | 3 | na | na | na |
| | 510684 | 0% | 70% | 4 | na | na | na |
| | 724359 | 0% | 80% | | | | |
| | 965625 | 0% | 91% | | | | |
| 24 hours | 356436 | 80% | 55% | 1 | | | |
| | 356436 | 80% | 55% | 2 | 0.0 | 0.0 | na |
| | 0 | 100% | 0% | 3 | 2.0 | 0.1 | 42.5 |
| | 510684 | 60% | 70% | 4 | 2.0 | 0.1 | 42.5 |
| | 724359 | 40% | 80% | | | | |
| | 965625 | 40% | 91% | | | | |

Fig. 6 Continued

| | | | | | | | |
|---|---|---|---|---|---|---|---|
| 48 hours | 71159.6 | 100% | 13% | 1 | | | |
| | 71159.6 | 100% | 13% | 2 | 0.0 | 0.0 | na |
| | 71159.6 | 100% | 13% | 3 | 0.0 | 0.0 | na |
| | 510684 | 50% | 70% | 4 | 1.0 | 0.0 | 56.6 |
| | 724359 | 50% | 80% | | | | |
| | 965625 | 0% | 91% | | | | |

UO only

| Time prior AKI stage | Cutoff value | sens | spec | Quartile | OR | 95% CI of OR | |
|---|---|---|---|---|---|---|---|
| 0 hours | 291919 | 78% | 48% | 1 | | | |
| | 56250 | 89% | 7% | 2 | 0.5 | 0.0 | 10.3 |
| | 0 | 100% | 0% | 3 | 2.2 | 0.4 | 11.7 |
| | 553419 | 33% | 72% | 4 | 1.0 | 0.1 | 8.1 |
| | 741453 | 22% | 80% | | | | |
| | 965625 | 11% | 91% | | | | |
| 24 hours | 461851 | 71% | 62% | 1 | | | |
| | 332323 | 86% | 51% | 2 | na | na | na |
| | 259596 | 93% | 46% | 3 | na | na | na |
| | 553419 | 43% | 72% | 4 | na | na | na |
| | 741453 | 21% | 80% | | | | |
| | 965625 | 7% | 91% | | | | |
| 48 hours | 56250 | 100% | 7% | 1 | | | |
| | 56250 | 100% | 7% | 2 | na | na | na |
| | 56250 | 100% | 7% | 3 | na | na | na |
| | 553419 | 0% | 72% | 4 | na | na | na |
| | 741453 | 0% | 80% | | | | |
| | 965625 | 0% | 91% | | | | |

Oxidized low-density lipoprotein receptor 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.405 | 0.491 | 0.405 | 0.557 | 0.405 | 0.620 |
| average | 0.499 | 0.723 | 0.499 | 0.832 | 0.499 | 0.785 |
| stdev | 0.336 | 0.747 | 0.336 | 0.729 | 0.336 | 0.658 |
| p (t-test) | | 0.015 | | 0.000 | | 0.003 |
| min | 0.000 | 0.153 | 0.000 | 0.121 | 0.000 | 0.121 |
| max | 2.264 | 3.428 | 2.264 | 3.215 | 2.264 | 2.441 |
| n (Samp) | 230 | 19 | 230 | 28 | 230 | 16 |
| n (Pat) | 158 | 19 | 158 | 28 | 158 | 16 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.440 | 2.526 | 0.440 | 0.659 | 0.440 | 0.573 |
| average | 0.553 | 2.526 | 0.553 | 0.647 | 0.553 | 0.675 |
| stdev | 0.433 | 1.277 | 0.433 | 0.301 | 0.433 | 0.469 |
| p (t-test) | | 0.000 | | 0.565 | | 0.532 |
| min | 0.000 | 1.623 | 0.000 | 0.121 | 0.000 | 0.196 |
| max | 3.215 | 3.428 | 3.215 | 1.020 | 3.215 | 1.179 |
| n (Samp) | 295 | 2 | 295 | 7 | 295 | 5 |
| n (Pat) | 187 | 2 | 187 | 7 | 187 | 5 |

Fig. 6 Continued

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.426 | 0.478 | 0.426 | 0.557 | 0.426 | 0.646 |
| average | 0.543 | 0.581 | 0.543 | 0.882 | 0.543 | 1.068 |
| stdev | 0.416 | 0.433 | 0.416 | 0.763 | 0.416 | 0.949 |
| p (t-test) | | 0.708 | | 0.001 | | 0.000 |
| min | 0.121 | 0.153 | 0.121 | 0.162 | 0.121 | 0.121 |
| max | 3.013 | 2.023 | 3.013 | 3.215 | 3.013 | 3.428 |
| n (Samp) | 198 | 19 | 198 | 26 | 198 | 14 |
| n (Pat) | 132 | 19 | 132 | 26 | 132 | 14 | sCr or UO

| Time prior AKI stage | AUC | SE | nCohort 1 | nCohort 2 | p |
|---|---|---|---|---|---|
| 0 hours | 0.59 | 0.071 | 230 | 19 | 0.225 |
| 24 hours | 0.67 | 0.058 | 230 | 28 | 0.004 |
| 48 hours | 0.65 | 0.077 | 230 | 16 | 0.057 | sCr only

| Time prior AKI stage | AUC | SE | nCohort 1 | nCohort 2 | p |
|---|---|---|---|---|---|
| 0 hours | 0.98 | 0.070 | 295 | 2 | 0.000 |
| 24 hours | 0.66 | 0.114 | 295 | 7 | 0.162 |
| 48 hours | 0.57 | 0.135 | 295 | 5 | 0.581 |

UO only

| Time prior AKI stage | AUC | SE | nCohort 1 | nCohort 2 | p |
|---|---|---|---|---|---|
| 0 hours | 0.53 | 0.070 | 198 | 19 | 0.666 |
| 24 hours | 0.65 | 0.061 | 198 | 26 | 0.011 |
| 48 hours | 0.71 | 0.080 | 198 | 14 | 0.007 | sCr or UO

| Time prior AKI stage | Cutoff value | sens | spec | Quartile | OR | 95% CI of OR | |
|---|---|---|---|---|---|---|---|
| 0 hours | 0.31139 | 74% | 32% | 1 | | | |
| | 0.26785 | 84% | 22% | 2 | 0.2 | 0.0 | 2.1 |
| | 0.15936 | 95% | 4% | 3 | 1.0 | 0.4 | 2.3 |
| | 0.52711 | 42% | 70% | 4 | 1.7 | 0.8 | 3.4 |
| | 0.66119 | 37% | 80% | | | | |
| | 0.94808 | 16% | 90% | | | | |
| 24 hours | 0.47418 | 71% | 60% | 1 | | | |
| | 0.33901 | 82% | 36% | 2 | 1.3 | 0.4 | 4.5 |
| | 0.26318 | 93% | 21% | 3 | 3.3 | 1.3 | 8.5 |
| | 0.52711 | 57% | 70% | 4 | 4.6 | 1.9 | 11.2 |
| | 0.66119 | 43% | 80% | | | | |
| | 0.94808 | 29% | 90% | | | | |
| 48 hours | 0.37277 | 75% | 46% | 1 | | | |
| | 0.34901 | 81% | 37% | 2 | 0.6 | 0.1 | 3.5 |
| | 0.19557 | 94% | 10% | 3 | 0.7 | 0.1 | 3.6 |
| | 0.52711 | 63% | 70% | 4 | 3.3 | 1.3 | 8.4 |
| | 0.66119 | 31% | 80% | | | | |
| | 0.94808 | 19% | 90% | | | | |

Fig. 6 Continued sCr only

| Time prior AKI stage | Cutoff value | sens | spec | Quartile | OR | 95% CI of OR | |
|---|---|---|---|---|---|---|---|
| 0 hours | 1.45111 | 100% | 96% | 1 | | | |
| | 1.45111 | 100% | 96% | 2 | na | na | na |
| | 1.45111 | 100% | 96% | 3 | na | na | na |
| | 0.5758 | 100% | 70% | 4 | na | na | na |
| | 0.72141 | 100% | 80% | | | | |
| | 1.01552 | 100% | 90% | | | | |
| 24 hours | 0.60057 | 71% | 72% | 1 | | | |
| | 0.47817 | 86% | 57% | 2 | 0.0 | 0.0 | na |
| | 1E-09 | 100% | 0% | 3 | 2.0 | 0.1 | 40.5 |
| | 0.5758 | 71% | 70% | 4 | 4.1 | 0.3 | 50.3 |
| | 0.72141 | 29% | 80% | | | | |
| | 1.01552 | 14% | 90% | | | | |
| 48 hours | 0.27364 | 80% | 21% | 1 | | | |
| | 0.27364 | 80% | 21% | 2 | 0.0 | 0.0 | na |
| | 0.19557 | 100% | 9% | 3 | 0.5 | 0.0 | 9.8 |
| | 0.5758 | 40% | 70% | 4 | 1.0 | 0.1 | 7.5 |
| | 0.72141 | 40% | 80% | | | | |
| | 1.01552 | 40% | 90% | | | | |

UO only

| Time prior AKI stage | Cutoff value | sens | spec | Quartile | OR | 95% CI of OR | |
|---|---|---|---|---|---|---|---|
| 0 hours | 0.31139 | 74% | 28% | 1 | | | |
| | 0.26785 | 84% | 20% | 2 | 0.4 | 0.1 | 1.6 |
| | 0.15936 | 95% | 4% | 3 | 1.0 | 0.4 | 2.4 |
| | 0.57009 | 37% | 70% | 4 | 1.4 | 0.7 | 3.0 |
| | 0.75586 | 21% | 80% | | | | |
| | 1.02433 | 5% | 90% | | | | |
| 24 hours | 0.45351 | 73% | 55% | 1 | | | |
| | 0.33901 | 81% | 33% | 2 | 0.7 | 0.2 | 2.5 |
| | 0.26318 | 92% | 19% | 3 | 1.9 | 0.8 | 4.3 |
| | 0.57009 | 46% | 70% | 4 | 3.5 | 1.7 | 7.4 |
| | 0.75586 | 42% | 80% | | | | |
| | 1.02433 | 31% | 90% | | | | |
| 48 hours | 0.61084 | 71% | 75% | 1 | | | |
| | 0.37277 | 86% | 42% | 2 | 2.0 | 0.1 | 41.6 |
| | 0.34901 | 93% | 35% | 3 | 4.2 | 0.3 | 53.2 |
| | 0.57009 | 71% | 70% | 4 | 7.9 | 0.8 | 80.5 |
| | 0.75586 | 36% | 80% | | | | |
| | 1.02433 | 29% | 90% | | | | |

P-selectin glycoprotein ligand 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 277.352 | 231.778 | 277.352 | 259.476 | 277.352 | 257.793 |
| average | 286.966 | 224.435 | 286.966 | 276.426 | 286.966 | 241.709 |
| stdev | 111.502 | 80.123 | 111.502 | 98.036 | 111.502 | 77.743 |
| p (t-test) | | 0.006 | | 0.613 | | 0.091 |
| min | 11.853 | 78.931 | 11.853 | 96.193 | 11.853 | 70.946 |
| max | 1092.518 | 387.856 | 1092.518 | 524.267 | 1092.518 | 388.464 |
| n (Samp) | 293 | 26 | 293 | 31 | 293 | 18 |
| n (Pat) | 165 | 26 | 165 | 31 | 165 | 18 |

Fig. 6 Continued sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 265.873 | 239.642 | 265.873 | 296.740 | 265.873 | 278.939 |
| average | 276.603 | 236.259 | 276.603 | 305.246 | 276.603 | 285.116 |
| stdev | 108.347 | 31.206 | 108.347 | 74.321 | 108.347 | 65.736 |
| p (t-test) |  | 0.458 |  | 0.431 |  | 0.836 |
| min | 11.853 | 196.206 | 11.853 | 194.647 | 11.853 | 198.285 |
| max | 1092.518 | 269.545 | 1092.518 | 437.970 | 1092.518 | 379.297 |
| n (Samp) | 375 | 4 | 375 | 9 | 375 | 7 |
| n (Pat) | 197 | 4 | 197 | 9 | 197 | 7 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 276.939 | 231.672 | 276.939 | 249.294 | 276.939 | 268.053 |
| average | 282.261 | 226.605 | 282.261 | 269.909 | 282.261 | 241.715 |
| stdev | 111.001 | 82.852 | 111.001 | 95.966 | 111.001 | 84.009 |
| p (t-test) |  | 0.014 |  | 0.579 |  | 0.166 |
| min | 11.853 | 78.931 | 11.853 | 96.193 | 11.853 | 70.946 |
| max | 1092.518 | 387.856 | 1092.518 | 524.267 | 1092.518 | 388.464 |
| n (Samp) | 244 | 26 | 244 | 27 | 244 | 15 |
| n (Pat) | 133 | 26 | 133 | 27 | 133 | 15 | sCr or UO

| Time prior AKI stage | AUC | SE | nCohort 1 | nCohort 2 | p |
|---|---|---|---|---|---|
| 0 hours | 0.32 | 0.048 | 293 | 26 | 0.000 |
| 24 hours | 0.48 | 0.054 | 293 | 31 | 0.678 |
| 48 hours | 0.38 | 0.063 | 293 | 18 | 0.067 | sCr only

| Time prior AKI stage | AUC | SE | nCohort 1 | nCohort 2 | p |
|---|---|---|---|---|---|
| 0 hours | 0.37 | 0.127 | 375 | 4 | 0.320 |
| 24 hours | 0.62 | 0.101 | 375 | 9 | 0.252 |
| 48 hours | 0.55 | 0.113 | 375 | 7 | 0.628 |

UO only

| Time prior AKI stage | AUC | SE | nCohort 1 | nCohort 2 | p |
|---|---|---|---|---|---|
| 0 hours | 0.34 | 0.051 | 244 | 26 | 0.002 |
| 24 hours | 0.47 | 0.058 | 244 | 27 | 0.648 |
| 48 hours | 0.40 | 0.070 | 244 | 15 | 0.157 | sCr or UO

| Time prior AKI stage | Cutoff value | sens | spec | Quartile | OR | 95% CI of OR | |
|---|---|---|---|---|---|---|---|
| 0 hours | 179.628 | 73% | 12% | 1 |  |  |  |
|  | 165.473 | 81% | 9% | 2 | 1.0 | 0.3 | 3.9 |
|  | 86.0465 | 92% | 2% | 3 | 3.3 | 1.3 | 8.2 |
|  | 321.846 | 12% | 70% | 4 | 4.2 | 1.7 | 10.1 |
|  | 349.777 | 8% | 80% |  |  |  |  |
|  | 398.829 | 0% | 90% |  |  |  |  |
| 24 hours | 224.212 | 71% | 27% | 1 |  |  |  |
|  | 190.123 | 81% | 15% | 2 | 0.4 | 0.2 | 0.9 |
|  | 175.501 | 90% | 11% | 3 | 1.0 | 0.6 | 1.6 |
|  | 321.846 | 35% | 70% | 4 | 1.0 | 0.6 | 1.6 |
|  | 349.777 | 26% | 80% |  |  |  |  |
|  | 398.829 | 10% | 90% |  |  |  |  |

Fig. 6 Continued

| 48 hours | 197.838 | 72% | 18% | 1 | | | |
| | 191.148 | 83% | 15% | 2 | 6.4 | 0.6 | 66.6 |
| | 85.2713 | 94% | 2% | 3 | 4.2 | 0.3 | 50.8 |
| | 321.846 | 11% | 70% | 4 | 7.7 | 0.8 | 76.3 |
| | 349.777 | 6% | 80% | | | | |
| | 398.829 | 0% | 90% | | | | | sCr only

| Time prior AKI stage | Cutoff value | sens | spec | Quartile | OR | 95% CI of OR | |
|---|---|---|---|---|---|---|---|
| 0 hours | 229.559 | 75% | 34% | 1 | | | |
| | 195.596 | 100% | 21% | 2 | na | na | na |
| | 195.596 | 100% | 21% | 3 | na | na | na |
| | 313.492 | 0% | 70% | 4 | na | na | na |
| | 341.364 | 0% | 80% | | | | |
| | 389.61 | 0% | 90% | | | | |
| 24 hours | 263.209 | 78% | 49% | 1 | | | |
| | 258.919 | 89% | 47% | 2 | 2.0 | 0.1 | 39.9 |
| | 194.423 | 100% | 20% | 3 | 4.1 | 0.3 | 49.9 |
| | 313.492 | 22% | 70% | 4 | 2.0 | 0.1 | 39.9 |
| | 341.364 | 22% | 80% | | | | |
| | 389.61 | 22% | 90% | | | | |
| 48 hours | 256.154 | 71% | 46% | 1 | | | |
| | 237.694 | 86% | 37% | 2 | 2.0 | 0.1 | 39.4 |
| | 197.838 | 100% | 22% | 3 | 2.0 | 0.1 | 39.9 |
| | 313.492 | 29% | 70% | 4 | 2.0 | 0.1 | 39.4 |
| | 341.364 | 29% | 80% | | | | |
| | 389.61 | 0% | 90% | | | | |

UO only

| Time prior AKI stage | Cutoff value | sens | spec | Quartile | OR | 95% CI of OR | |
|---|---|---|---|---|---|---|---|
| 0 hours | 177.65 | 73% | 13% | 1 | | | |
| | 165.473 | 81% | 10% | 2 | 0.5 | 0.1 | 2.3 |
| | 86.0465 | 92% | 2% | 3 | 2.4 | 1.1 | 5.3 |
| | 319.242 | 15% | 70% | 4 | 3.1 | 1.5 | 6.5 |
| | 342.314 | 8% | 80% | | | | |
| | 391.52 | 0% | 90% | | | | |
| 24 hours | 224.212 | 70% | 28% | 1 | | | |
| | 189.689 | 81% | 16% | 2 | 0.3 | 0.1 | 0.9 |
| | 144.347 | 93% | 5% | 3 | 1.0 | 0.6 | 1.7 |
| | 319.242 | 33% | 70% | 4 | 1.0 | 0.6 | 1.8 |
| | 342.314 | 26% | 80% | | | | |
| | 391.52 | 4% | 90% | | | | |
| 48 hours | 197.765 | 73% | 20% | 1 | | | |
| | 191.148 | 80% | 17% | 2 | 4.2 | 0.3 | 51.8 |
| | 85.2713 | 93% | 2% | 3 | 5.3 | 0.5 | 59.7 |
| | 319.242 | 13% | 70% | 4 | 5.4 | 0.5 | 60.7 |
| | 342.314 | 7% | 80% | | | | |
| | 391.52 | 0% | 90% | | | | |

Fig. 6 Continued

Secretory leukocyte peptidase inhibitor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 62595.973 | 78063.439 | 62595.973 | 65709.516 | 62595.973 | 70712.067 |
| average | 69456.204 | 85962.439 | 69456.204 | 79126.168 | 69456.204 | 77609.002 |
| stdev | 31260.478 | 33779.341 | 31260.478 | 41376.549 | 31260.478 | 31939.002 |
| p (t-test) |  | 0.011 |  | 0.115 |  | 0.285 |
| min | 13520.408 | 30802.920 | 13520.408 | 40614.203 | 13520.408 | 43486.529 |
| max | 199917.831 | 160690.846 | 199917.831 | 218323.747 | 199917.831 | 168974.359 |
| n (Samp) | 282 | 26 | 282 | 31 | 282 | 18 |
| n (Pat) | 163 | 26 | 163 | 31 | 163 | 18 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 64830.647 | 97681.047 | 64830.647 | 64659.271 | 64830.647 | 69879.518 |
| average | 70473.504 | 93207.920 | 70473.504 | 99372.792 | 70473.504 | 105227.374 |
| stdev | 29816.401 | 55133.199 | 29816.401 | 60719.800 | 29816.401 | 56107.821 |
| p (t-test) |  | 0.134 |  | 0.006 |  | 0.003 |
| min | 13520.408 | 30802.920 | 13520.408 | 40614.203 | 13520.408 | 51516.315 |
| max | 199917.831 | 146666.667 | 199917.831 | 218323.747 | 199917.831 | 169533.679 |
| n (Samp) | 364 | 4 | 364 | 9 | 364 | 7 |
| n (Pat) | 195 | 4 | 195 | 9 | 195 | 7 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 62461.300 | 78063.439 | 62461.300 | 68406.910 | 62461.300 | 71053.763 |
| average | 68318.825 | 86491.384 | 68318.825 | 76803.702 | 68318.825 | 71866.204 |
| stdev | 28255.445 | 31508.533 | 28255.445 | 34581.318 | 28255.445 | 26210.826 |
| p (t-test) |  | 0.002 |  | 0.150 |  | 0.636 |
| min | 10867.347 | 38136.201 | 10867.347 | 44299.424 | 10867.347 | 30802.920 |
| max | 183903.282 | 160690.846 | 183903.282 | 170531.178 | 183903.282 | 136649.396 |
| n (Samp) | 236 | 26 | 236 | 27 | 236 | 15 |
| n (Pat) | 132 | 26 | 132 | 27 | 132 | 15 | sCr or UO

| Time prior AKI stage | AUC | SE | nCohort 1 | nCohort 2 | p |
|---|---|---|---|---|---|
| 0 hours | 0.66 | 0.060 | 282 | 26 | 0.008 |
| 24 hours | 0.56 | 0.056 | 282 | 31 | 0.255 |
| 48 hours | 0.59 | 0.072 | 282 | 18 | 0.199 | sCr only

| Time prior AKI stage | AUC | SE | nCohort 1 | nCohort 2 | p |
|---|---|---|---|---|---|
| 0 hours | 0.61 | 0.151 | 364 | 4 | 0.472 |
| 24 hours | 0.61 | 0.101 | 364 | 9 | 0.291 |
| 48 hours | 0.66 | 0.114 | 364 | 7 | 0.157 |

UO only

| Time prior AKI stage | AUC | SE | nCohort 1 | nCohort 2 | p |
|---|---|---|---|---|---|
| 0 hours | 0.68 | 0.060 | 236 | 26 | 0.003 |
| 24 hours | 0.57 | 0.060 | 236 | 27 | 0.261 |
| 48 hours | 0.56 | 0.079 | 236 | 15 | 0.435 |

Fig. 6 Continued sCr or UO

| Time prior AKI stage | Cutoff value | sens | spec | Quartile | OR | 95% CI of OR | |
|---|---|---|---|---|---|---|---|
| 0 hours | 67828.8 | 73% | 59% | 1 | | | |
| | 59182.8 | 81% | 44% | 2 | 0.5 | 0.1 | 2.2 |
| | 42891.6 | 92% | 15% | 3 | 2.4 | 1.1 | 5.2 |
| | 75855.4 | 54% | 70% | 4 | 3.0 | 1.5 | 6.3 |
| | 87078.5 | 42% | 80% | | | | |
| | 108187 | 27% | 90% | | | | |
| 24 hours | 59182.8 | 71% | 44% | 1 | | | |
| | 51538.5 | 81% | 29% | 2 | 2.1 | 1.0 | 4.7 |
| | 45220.7 | 90% | 20% | 3 | 3.4 | 1.7 | 6.8 |
| | 75855.4 | 26% | 70% | 4 | 1.8 | 0.8 | 4.1 |
| | 87078.5 | 23% | 80% | | | | |
| | 108187 | 16% | 90% | | | | |
| 48 hours | 59855.4 | 72% | 44% | 1 | | | |
| | 59182.8 | 83% | 44% | 2 | 2.1 | 0.4 | 9.4 |
| | 43992.3 | 94% | 16% | 3 | 4.4 | 1.2 | 15.7 |
| | 75855.4 | 22% | 70% | 4 | 2.1 | 0.4 | 9.4 |
| | 87078.5 | 22% | 80% | | | | |
| | 108187 | 17% | 90% | | | | | sCr only

| Time prior AKI stage | Cutoff value | sens | spec | Quartile | OR | 95% CI of OR | |
|---|---|---|---|---|---|---|---|
| 0 hours | 63518.1 | 75% | 48% | 1 | | | |
| | 30739.7 | 100% | 3% | 2 | 1.0 | 0.0 | 52.6 |
| | 30739.7 | 100% | 3% | 3 | 0.0 | 0.0 | na |
| | 75855.4 | 50% | 70% | 4 | 2.0 | 0.1 | 39.9 |
| | 87887.3 | 50% | 80% | | | | |
| | 108205 | 50% | 90% | | | | |
| 24 hours | 60731.2 | 78% | 43% | 1 | | | |
| | 41965.1 | 89% | 12% | 2 | 1.5 | 0.3 | 8.1 |
| | 39856.6 | 100% | 11% | 3 | 0.0 | 0.0 | na |
| | 75855.4 | 44% | 70% | 4 | 2.0 | 0.4 | 9.2 |
| | 87887.3 | 44% | 80% | | | | |
| | 108205 | 44% | 90% | | | | |
| 48 hours | 61497.1 | 71% | 44% | 1 | | | |
| | 59354.8 | 86% | 39% | 2 | na | na | na |
| | 51362.8 | 100% | 26% | 3 | na | na | na |
| | 75855.4 | 43% | 70% | 4 | na | na | na |
| | 87887.3 | 43% | 80% | | | | |
| | 108205 | 43% | 90% | | | | |

UO only

| Time prior AKI stage | Cutoff value | sens | spec | Quartile | OR | 95% CI of OR | |
|---|---|---|---|---|---|---|---|
| 0 hours | 67828.8 | 73% | 60% | 1 | | | |
| | 61343.6 | 81% | 49% | 2 | 1.0 | 0.3 | 3.9 |
| | 48614.4 | 92% | 22% | 3 | 2.9 | 1.1 | 7.6 |
| | 75698.9 | 54% | 70% | 4 | 4.6 | 1.9 | 11.1 |
| | 84615.4 | 42% | 80% | | | | |
| | 105385 | 27% | 90% | | | | |
| 24 hours | 57927.7 | 70% | 44% | 1 | | | |
| | 51362.8 | 81% | 28% | 2 | 2.9 | 1.1 | 7.5 |
| | 45220.7 | 93% | 18% | 3 | 3.3 | 1.3 | 8.3 |
| | 75698.9 | 26% | 70% | 4 | 2.5 | 0.9 | 6.7 |
| | 84615.4 | 22% | 80% | | | | |
| | 105385 | 15% | 90% | | | | |

Fig. 6 Continued

| 48 hours | 59855.4 | 73% | 45% | 1 | | | |
| | 59401.7 | 80% | 45% | 2 | 0.6 | 0.1 | 3.5 |
| | 43354.8 | 93% | 14% | 3 | 2.5 | 0.9 | 6.7 |
| | 75698.9 | 27% | 70% | 4 | 1.0 | 0.2 | 3.9 |
| | 84615.4 | 20% | 80% | | | | |
| | 105385 | 13% | 90% | | | | |

Stem cell factor sCr or UO

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 332.000 | 350.500 | 332.000 | 353.000 | 332.000 | 318.500 |
| average | 375.711 | 410.250 | 375.711 | 378.056 | 375.711 | 371.500 |
| stdev | 311.554 | 204.270 | 311.554 | 199.648 | 311.554 | 204.434 |
| p (t-test) | | 0.563 | | 0.965 | | 0.955 |
| min | 89.700 | 169.000 | 89.700 | 150.000 | 89.700 | 161.000 |
| max | 5840.000 | 860.000 | 5840.000 | 1100.000 | 5840.000 | 927.000 |
| n (Samp) | 434 | 28 | 434 | 36 | 434 | 18 |
| n (Pat) | 173 | 28 | 173 | 36 | 173 | 18 | sCr only

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 335.000 | 542.500 | 335.000 | 453.500 | 335.000 | 543.000 |
| average | 374.708 | 529.333 | 374.708 | 418.700 | 374.708 | 547.143 |
| stdev | 290.180 | 267.211 | 290.180 | 186.823 | 290.180 | 144.158 |
| p (t-test) | | 0.195 | | 0.633 | | 0.117 |
| min | 89.700 | 188.000 | 89.700 | 174.000 | 89.700 | 316.000 |
| max | 5840.000 | 860.000 | 5840.000 | 660.000 | 5840.000 | 769.000 |
| n (Samp) | 542 | 6 | 542 | 10 | 542 | 7 |
| n (Pat) | 208 | 6 | 208 | 10 | 208 | 7 |

UO only

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 330.500 | 356.000 | 330.500 | 340.500 | 330.500 | 293.000 |
| average | 373.648 | 390.259 | 373.648 | 368.969 | 373.648 | 343.938 |
| stdev | 330.156 | 172.112 | 330.156 | 201.614 | 330.156 | 217.431 |
| p (t-test) | | 0.796 | | 0.937 | | 0.722 |
| min | 89.700 | 169.000 | 89.700 | 150.000 | 89.700 | 161.000 |
| max | 5840.000 | 819.000 | 5840.000 | 1100.000 | 5840.000 | 927.000 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
|---|---|---|---|---|---|
| 0 hours | 0.55 | 0.058 | 434 | 28 | 0.381 |
| 24 hours | 0.50 | 0.050 | 434 | 36 | 0.922 |
| 48 hours | 0.48 | 0.069 | 434 | 18 | 0.778 | sCr only

| Time prior AKI stage | AUC | SE | nCohort 1 | nCohort 2 | p |
|---|---|---|---|---|---|
| 0 hours | 0.68 | 0.121 | 542 | 6 | 0.130 |
| 24 hours | 0.60 | 0.096 | 542 | 10 | 0.308 |
| 48 hours | 0.83 | 0.097 | 542 | 7 | 0.001 |

Fig. 6 Continued

UO only

| Time prior AKI stage | AUC | SE | nCohort 1 | nCohort 2 | p |
|---|---|---|---|---|---|
| 0 hours | 0.55 | 0.059 | 356 | 27 | 0.393 |
| 24 hours | 0.49 | 0.053 | 356 | 32 | 0.784 |
| 48 hours | 0.41 | 0.068 | 356 | 16 | 0.173 | sCr or UO

| Time prior AKI stage | Cutoff value | sens | spec | Quartile | OR | 95% CI of OR | |
|---|---|---|---|---|---|---|---|
| 0 hours | 284 | 71% | 33% | 1 | | | |
|  | 224 | 86% | 17% | 2 | 0.6 | 0.3 | 1.2 |
|  | 187 | 93% | 8% | 3 | 0.7 | 0.4 | 1.4 |
|  | 404 | 39% | 71% | 4 | 1.1 | 0.7 | 1.9 |
|  | 463 | 32% | 80% | | | | |
|  | 563 | 21% | 90% | | | | |
| 24 hours | 229 | 72% | 20% | 1 | | | |
|  | 198 | 81% | 10% | 2 | 0.3 | 0.2 | 0.6 |
|  | 177 | 92% | 7% | 3 | 0.7 | 0.5 | 1.1 |
|  | 404 | 33% | 71% | 4 | 0.9 | 0.6 | 1.3 |
|  | 463 | 25% | 80% | | | | |
|  | 563 | 11% | 90% | | | | |
| 48 hours | 219 | 72% | 16% | 1 | | | |
|  | 214 | 83% | 14% | 2 | 0.4 | 0.1 | 1.6 |
|  | 161 | 94% | 4% | 3 | 1.0 | 0.4 | 2.3 |
|  | 404 | 33% | 71% | 4 | 1.2 | 0.6 | 2.6 |
|  | 463 | 28% | 80% | | | | |
|  | 563 | 17% | 90% | | | | | sCr only

| Time prior AKI stage | Cutoff value | sens | spec | Quartile | OR | 95% CI of OR | |
|---|---|---|---|---|---|---|---|
| 0 hours | 323 | 83% | 48% | 1 | | | |
|  | 323 | 83% | 48% | 2 | 1.0 | 0.0 | 51.9 |
|  | 187 | 100% | 9% | 3 | 1.0 | 0.0 | 51.9 |
|  | 407 | 50% | 70% | 4 | 3.0 | 0.2 | 42.8 |
|  | 482 | 50% | 80% | | | | |
|  | 561 | 50% | 90% | | | | |
| 24 hours | 320 | 70% | 47% | 1 | | | |
|  | 231 | 80% | 22% | 2 | 0.3 | 0.0 | 4.6 |
|  | 173 | 100% | 7% | 3 | 0.0 | 0.0 | na |
|  | 407 | 60% | 70% | 4 | 2.0 | 0.7 | 5.6 |
|  | 482 | 30% | 80% | | | | |
|  | 561 | 30% | 90% | | | | |
| 48 hours | 525 | 71% | 87% | 1 | | | |
|  | 439 | 86% | 75% | 2 | na | na | na |
|  | 315 | 100% | 45% | 3 | na | na | na |
|  | 407 | 86% | 70% | 4 | na | na | na |
|  | 482 | 71% | 80% | | | | |
|  | 561 | 43% | 90% | | | | |

UO only

| Time prior AKI stage | Cutoff value | sens | spec | Quartile | OR | 95% CI of OR | |
|---|---|---|---|---|---|---|---|
| 0 hours | 299 | 70% | 38% | 1 | | | |
|  | 229 | 81% | 20% | 2 | 0.7 | 0.3 | 1.4 |
|  | 198 | 93% | 10% | 3 | 1.0 | 0.5 | 1.8 |
|  | 404 | 37% | 71% | 4 | 1.1 | 0.6 | 2.0 |
|  | 463 | 26% | 81% | | | | |
|  | 551 | 15% | 90% | | | | |

Fig. 6 Continued

| 24 hours | 222 | 72% | 16% | 1 | | | |
| | 198 | 81% | 10% | 2 | 0.9 | 0.5 | 1.5 |
| | 177 | 94% | 7% | 3 | 0.4 | 0.2 | 0.9 |
| | 404 | 28% | 71% | 4 | 1.3 | 0.8 | 1.9 |
| | 463 | 25% | 81% | | | | |
| | 551 | 9% | 90% | | | | |
| 48 hours | 214 | 75% | 14% | 1 | | | |
| | 173 | 81% | 7% | 2 | 0.7 | 0.1 | 3.5 |
| | 161 | 94% | 5% | 3 | 1.3 | 0.4 | 4.4 |
| | 404 | 25% | 71% | 4 | 2.4 | 0.9 | 6.5 |
| | 463 | 19% | 81% | | | | |
| | 551 | 19% | 90% | | | | |

Tissue inhibitor of metalloproteinase 1 sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 217.000 | 272.500 | 217.000 | 271.000 | 217.000 | 264.500 |
| average | 265.817 | 348.268 | 265.817 | 412.575 | 265.817 | 366.194 |
| stdev | 178.612 | 213.601 | 178.612 | 311.598 | 178.612 | 284.211 |
| p (t-test) | | 0.020 | | 0.000 | | 0.024 |
| min | 75.400 | 83.100 | 75.400 | 83.700 | 75.400 | 60.500 |
| max | 1250.000 | 966.000 | 1250.000 | 1220.000 | 1250.000 | 1207.000 |
| n (Samp) | 434 | 28 | 434 | 36 | 434 | 18 |
| n (Pat) | 173 | 28 | 173 | 36 | 173 | 18 | sCr only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 229.000 | 457.500 | 229.000 | 287.000 | 229.000 | 285.000 |
| average | 280.938 | 500.500 | 280.938 | 379.000 | 280.938 | 353.714 |
| stdev | 197.982 | 251.936 | 197.982 | 250.315 | 197.982 | 229.709 |
| p (t-test) | | 0.007 | | 0.123 | | 0.335 |
| min | 56.400 | 237.000 | 56.400 | 104.000 | 56.400 | 131.000 |
| max | 1250.000 | 966.000 | 1250.000 | 829.000 | 1250.000 | 776.000 |
| n (Samp) | 542 | 6 | 542 | 10 | 542 | 7 |
| n (Pat) | 208 | 6 | 208 | 10 | 208 | 7 |

UO only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 221.500 | 277.000 | 221.500 | 281.500 | 221.500 | 287.500 |
| average | 269.575 | 340.796 | 269.575 | 426.084 | 269.575 | 418.531 |
| stdev | 179.160 | 201.793 | 179.160 | 322.719 | 179.160 | 306.921 |
| p (t-test) | | 0.049 | | 0.000 | | 0.002 |
| min | 75.400 | 83.100 | 75.400 | 83.700 | 75.400 | 60.500 |
| max | 1250.000 | 860.000 | 1250.000 | 1220.000 | 1250.000 | 1207.000 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
| --- | --- | --- | --- | --- | --- |
| 0 hours | 0.65 | 0.058 | 434 | 28 | 0.012 |
| 24 hours | 0.66 | 0.051 | 434 | 36 | 0.002 |
| 48 hours | 0.62 | 0.072 | 434 | 18 | 0.087 |

Fig. 6 Continued sCr only

| Time prior AKI stage | AUC | SE | nCohort 1 | nCohort 2 | p |
|---|---|---|---|---|---|
| 0 hours | 0.83 | 0.104 | 542 | 6 | 0.002 |
| 24 hours | 0.63 | 0.096 | 542 | 10 | 0.181 |
| 48 hours | 0.60 | 0.114 | 542 | 7 | 0.367 |

UO only

| Time prior AKI stage | AUC | SE | nCohort 1 | nCohort 2 | p |
|---|---|---|---|---|---|
| 0 hours | 0.64 | 0.059 | 356 | 27 | 0.018 |
| 24 hours | 0.68 | 0.054 | 356 | 32 | 0.001 |
| 48 hours | 0.67 | 0.076 | 356 | 16 | 0.024 | sCr or UO

| Time prior AKI stage | Cutoff value | sens | spec | Quartile | OR | 95% CI of OR | |
|---|---|---|---|---|---|---|---|
| 0 hours | 221 | 71% | 51% | 1 | | | |
| | 201 | 82% | 48% | 2 | 2.0 | 0.7 | 5.6 |
| | 142 | 93% | 21% | 3 | 2.1 | 0.7 | 5.7 |
| | 284 | 46% | 70% | 4 | 4.7 | 2.0 | 10.9 |
| | 344 | 39% | 80% | | | | |
| | 464 | 21% | 90% | | | | |
| 24 hours | 225 | 72% | 52% | 1 | | | |
| | 205 | 81% | 48% | 2 | 2.4 | 0.9 | 6.3 |
| | 163 | 92% | 29% | 3 | 4.3 | 1.9 | 10.2 |
| | 284 | 44% | 70% | 4 | 5.1 | 2.2 | 11.7 |
| | 344 | 39% | 80% | | | | |
| | 464 | 28% | 90% | | | | |
| 48 hours | 221 | 72% | 51% | 1 | | | |
| | 190 | 83% | 42% | 2 | 1.0 | 0.3 | 3.8 |
| | 142 | 94% | 21% | 3 | 2.4 | 0.9 | 6.4 |
| | 284 | 44% | 70% | 4 | 1.7 | 0.6 | 5.0 |
| | 344 | 28% | 80% | | | | |
| | 464 | 22% | 90% | | | | | sCr only

| Time prior AKI stage | Cutoff value | sens | spec | Quartile | OR | 95% CI of OR | |
|---|---|---|---|---|---|---|---|
| 0 hours | 343 | 83% | 78% | 1 | | | |
| | 343 | 83% | 78% | 2 | na | na | na |
| | 236 | 100% | 54% | 3 | na | na | na |
| | 304 | 83% | 70% | 4 | na | na | na |
| | 368 | 67% | 80% | | | | |
| | 502 | 33% | 90% | | | | |
| 24 hours | 237 | 70% | 54% | 1 | | | |
| | 223 | 80% | 48% | 2 | 0.5 | 0.0 | 9.7 |
| | 134 | 90% | 15% | 3 | 1.5 | 0.3 | 8.0 |
| | 304 | 40% | 70% | 4 | 2.0 | 0.5 | 9.1 |
| | 368 | 40% | 80% | | | | |
| | 502 | 20% | 90% | | | | |
| 48 hours | 221 | 71% | 47% | 1 | | | |
| | 143 | 86% | 20% | 2 | 0.5 | 0.0 | 9.7 |
| | 128 | 100% | 14% | 3 | 0.5 | 0.0 | 9.7 |
| | 304 | 43% | 70% | 4 | 1.5 | 0.3 | 7.9 |
| | 368 | 43% | 80% | | | | |
| | 502 | 14% | 90% | | | | |

Fig. 6 Continued

UO only

| Time prior AKI stage | Cutoff value | sens | spec | Quartile | OR | 95% CI of OR | |
|---|---|---|---|---|---|---|---|
| 0 hours | 221 | 70% | 50% | 1 | | | |
| | 201 | 81% | 47% | 2 | 2.0 | 0.7 | 5.7 |
| | 142 | 93% | 17% | 3 | 1.7 | 0.6 | 5.0 |
| | 284 | 48% | 71% | 4 | 4.8 | 2.1 | 11.2 |
| | 341 | 48% | 80% | | | | |
| | 480 | 15% | 90% | | | | |
| 24 hours | 226 | 72% | 52% | 1 | | | |
| | 205 | 81% | 48% | 2 | 3.7 | 1.0 | 13.6 |
| | 184 | 91% | 37% | 3 | 4.9 | 1.4 | 16.8 |
| | 284 | 47% | 71% | 4 | 8.0 | 2.5 | 25.7 |
| | 341 | 41% | 80% | | | | |
| | 480 | 28% | 90% | | | | |
| 48 hours | 226 | 75% | 52% | 1 | | | |
| | 209 | 81% | 48% | 2 | 1.0 | 0.1 | 7.4 |
| | 142 | 94% | 17% | 3 | 3.1 | 0.8 | 12.1 |
| | 284 | 50% | 71% | 4 | 3.1 | 0.8 | 12.1 |
| | 341 | 38% | 80% | | | | |
| | 480 | 31% | 90% | | | | |

Tissue inhibitor of metalloproteinase 2 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 108182.165 | 109652.749 | 108182.165 | 104305.961 | 108182.165 | 104617.577 |
| average | 111994.414 | 112988.720 | 111994.414 | 110005.697 | 111994.414 | 115162.625 |
| stdev | 26296.681 | 26740.378 | 26296.681 | 34143.345 | 26296.681 | 33743.986 |
| p (t-test) | | 0.874 | | 0.716 | | 0.648 |
| min | 1936.748 | 72282.274 | 1936.748 | 35539.194 | 1936.748 | 67378.553 |
| max | 179965.030 | 189045.463 | 179965.030 | 207083.195 | 179965.030 | 172165.058 |
| n (Samp) | 230 | 19 | 230 | 28 | 230 | 16 |
| n (Pat) | 158 | 19 | 158 | 28 | 158 | 16 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 108182.165 | 164727.734 | 108182.165 | 98973.852 | 108182.165 | 125925.775 |
| average | 111625.100 | 164727.734 | 111625.100 | 102238.831 | 111625.100 | 130535.847 |
| stdev | 27189.052 | 34390.462 | 27189.052 | 61125.224 | 27189.052 | 41670.097 |
| p (t-test) | | 0.006 | | 0.386 | | 0.127 |
| min | 1936.748 | 140410.005 | 1936.748 | 1892.018 | 1936.748 | 91182.534 |
| max | 197537.458 | 189045.463 | 197537.458 | 207083.195 | 197537.458 | 188983.579 |
| n (Samp) | 295 | 2 | 295 | 7 | 295 | 5 |
| n (Pat) | 187 | 2 | 187 | 7 | 187 | 5 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 109195.271 | 109652.749 | 109195.271 | 109625.622 | 109195.271 | 110348.228 |
| average | 112534.167 | 116132.526 | 112534.167 | 110635.560 | 112534.167 | 117517.294 |
| stdev | 26081.524 | 35112.079 | 26081.524 | 33294.675 | 26081.524 | 34056.252 |
| p (t-test) | | 0.579 | | 0.736 | | 0.500 |
| min | 1936.748 | 72282.274 | 1936.748 | 35539.194 | 1936.748 | 67378.553 |
| max | 179965.030 | 231513.529 | 179965.030 | 189045.463 | 179965.030 | 172165.058 |
| n (Samp) | 198 | 19 | 198 | 26 | 198 | 14 |
| n (Pat) | 132 | 19 | 132 | 26 | 132 | 14 |

Fig. 6 Continued sCr or UO

| Time prior AKI stage | AUC | SE | nCohort 1 | nCohort 2 | p |
|---|---|---|---|---|---|
| 0 hours | 0.50 | 0.069 | 230 | 19 | 0.989 |
| 24 hours | 0.46 | 0.057 | 230 | 28 | 0.525 |
| 48 hours | 0.50 | 0.075 | 230 | 16 | 0.960 | sCr only

| Time prior AKI stage | AUC | SE | nCohort 1 | nCohort 2 | p |
|---|---|---|---|---|---|
| 0 hours | 0.93 | 0.129 | 295 | 2 | 0.001 |
| 24 hours | 0.41 | 0.102 | 295 | 7 | 0.390 |
| 48 hours | 0.63 | 0.135 | 295 | 5 | 0.329 |

UO only

| Time prior AKI stage | AUC | SE | nCohort 1 | nCohort 2 | p |
|---|---|---|---|---|---|
| 0 hours | 0.49 | 0.069 | 198 | 19 | 0.927 |
| 24 hours | 0.47 | 0.059 | 198 | 26 | 0.657 |
| 48 hours | 0.53 | 0.081 | 198 | 14 | 0.701 | sCr or UO

| Time prior AKI stage | Cutoff value | sens | spec | Quartile | OR | 95% CI of OR | |
|---|---|---|---|---|---|---|---|
| 0 hours | 99908.3 | 74% | 34% | 1 | | | |
| | 93484.9 | 84% | 26% | 2 | 1.0 | 0.4 | 2.4 |
| | 81511.4 | 95% | 9% | 3 | 1.2 | 0.6 | 2.7 |
| | 124324 | 26% | 70% | 4 | 0.6 | 0.2 | 1.8 |
| | 132991 | 16% | 80% | | | | |
| | 145286 | 11% | 90% | | | | |
| 24 hours | 89398.2 | 71% | 21% | 1 | | | |
| | 79303.9 | 82% | 7% | 2 | 0.6 | 0.3 | 1.2 |
| | 74702.4 | 93% | 4% | 3 | 0.7 | 0.4 | 1.4 |
| | 124324 | 32% | 70% | 4 | 1.2 | 0.7 | 2.0 |
| | 132991 | 25% | 80% | | | | |
| | 145286 | 14% | 90% | | | | |
| 48 hours | 89398.2 | 75% | 21% | 1 | | | |
| | 87479.3 | 81% | 17% | 2 | 0.3 | 0.1 | 1.2 |
| | 79303.9 | 94% | 7% | 3 | 0.3 | 0.1 | 1.2 |
| | 124324 | 38% | 70% | 4 | 1.0 | 0.5 | 2.0 |
| | 132991 | 38% | 80% | | | | |
| | 145286 | 31% | 90% | | | | | sCr only

| Time prior AKI stage | Cutoff value | sens | spec | Quartile | OR | 95% CI of OR | |
|---|---|---|---|---|---|---|---|
| 0 hours | 139922 | 100% | 85% | 1 | | | |
| | 139922 | 100% | 85% | 2 | na | na | na |
| | 139922 | 100% | 85% | 3 | na | na | na |
| | 124938 | 100% | 70% | 4 | na | na | na |
| | 134700 | 100% | 80% | | | | |
| | 148411 | 50% | 90% | | | | |
| 24 hours | 89533.2 | 71% | 23% | 1 | | | |
| | 84630.8 | 86% | 15% | 2 | 0.0 | 0.0 | na |
| | 0 | 100% | 0% | 3 | 1.0 | 0.1 | 7.5 |
| | 124938 | 29% | 70% | 4 | 1.5 | 0.3 | 8.3 |
| | 134700 | 14% | 80% | | | | |
| | 148411 | 14% | 90% | | | | |

Fig. 6 Continued

| | | | | | | | |
|---|---|---|---|---|---|---|---|
| 48 hours | 92760.6 | 80% | 27% | 1 | | | |
| | 92760.6 | 80% | 27% | 2 | 1.0 | 0.0 | 53.1 |
| | 90955 | 100% | 25% | 3 | 1.0 | 0.0 | 53.1 |
| | 124938 | 60% | 70% | 4 | 2.0 | 0.1 | 40.5 |
| | 134700 | 40% | 80% | | | | |
| | 148411 | 40% | 90% | | | | |

UO only

| Time prior AKI stage | Cutoff value | sens | spec | Quartile | OR | 95% CI of OR | |
|---|---|---|---|---|---|---|---|
| 0 hours | 99908.3 | 74% | 32% | 1 | | | |
| | 93484.9 | 84% | 24% | 2 | 1.0 | 0.4 | 2.4 |
| | 81511.4 | 95% | 8% | 3 | 1.0 | 0.4 | 2.4 |
| | 124324 | 26% | 70% | 4 | 0.8 | 0.3 | 2.1 |
| | 134700 | 16% | 80% | | | | |
| | 148411 | 11% | 90% | | | | |
| 24 hours | 87479.3 | 73% | 17% | 1 | | | |
| | 79303.9 | 81% | 7% | 2 | 0.6 | 0.3 | 1.2 |
| | 74702.4 | 92% | 4% | 3 | 0.6 | 0.3 | 1.2 |
| | 124324 | 35% | 70% | 4 | 1.0 | 0.6 | 1.8 |
| | 134700 | 27% | 80% | | | | |
| | 148411 | 12% | 90% | | | | |
| 48 hours | 89398.2 | 71% | 20% | 1 | | | |
| | 85864.4 | 86% | 14% | 2 | 0.2 | 0.0 | 2.1 |
| | 79303.9 | 93% | 7% | 3 | 0.4 | 0.1 | 1.6 |
| | 124324 | 43% | 70% | 4 | 1.2 | 0.6 | 2.7 |
| | 134700 | 43% | 80% | | | | |
| | 148411 | 21% | 90% | | | | |

Tumor necrosis factor-alpha sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 7.480 | 8.075 | 7.480 | 9.915 | 7.480 | 9.805 |
| average | 13.194 | 10.634 | 13.194 | 13.273 | 13.194 | 17.533 |
| stdev | 39.858 | 8.132 | 39.858 | 14.058 | 39.858 | 18.876 |
| p (t-test) | | 0.735 | | 0.991 | | 0.646 |
| min | 0.040 | 0.040 | 0.040 | 0.040 | 0.040 | 2.160 |
| max | 669.000 | 35.000 | 669.000 | 75.800 | 669.000 | 78.900 |
| n (Samp) | 434 | 28 | 434 | 36 | 434 | 18 |
| n (Pat) | 173 | 28 | 173 | 36 | 173 | 18 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 7.530 | 12.010 | 7.530 | 12.500 | 7.530 | 8.930 |
| average | 12.856 | 14.500 | 12.856 | 16.733 | 12.856 | 12.849 |
| stdev | 36.059 | 11.658 | 36.059 | 21.229 | 36.059 | 8.935 |
| p (t-test) | | 0.911 | | 0.735 | | 1.000 |
| min | 0.040 | 3.330 | 0.040 | 0.829 | 0.040 | 2.160 |
| max | 669.000 | 35.500 | 669.000 | 75.800 | 669.000 | 23.700 |
| n (Samp) | 542 | 6 | 542 | 10 | 542 | 7 |
| n (Pat) | 208 | 6 | 208 | 10 | 208 | 7 |

Fig. 6 Continued

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 7.480 | 7.550 | 7.480 | 9.765 | 7.480 | 10.210 |
| average | 13.354 | 10.435 | 13.354 | 11.838 | 13.354 | 17.905 |
| stdev | 41.358 | 8.049 | 41.358 | 9.463 | 41.358 | 19.785 |
| p (t-test) | | 0.715 | | 0.836 | | 0.662 |
| min | 0.040 | 0.040 | 0.040 | 0.040 | 0.040 | 2.160 |
| max | 669.000 | 35.000 | 669.000 | 49.300 | 669.000 | 78.900 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
|---|---|---|---|---|---|
| 0 hours | 0.55 | 0.058 | 434 | 28 | 0.388 |
| 24 hours | 0.60 | 0.052 | 434 | 36 | 0.057 |
| 48 hours | 0.64 | 0.072 | 434 | 18 | 0.048 | sCr only

| Time prior AKI stage | AUC | SE | nCohort 1 | nCohort 2 | p |
|---|---|---|---|---|---|
| 0 hours | 0.64 | 0.123 | 542 | 6 | 0.254 |
| 24 hours | 0.64 | 0.095 | 542 | 10 | 0.130 |
| 48 hours | 0.61 | 0.114 | 542 | 7 | 0.330 |

UO only

| Time prior AKI stage | AUC | SE | nCohort 1 | nCohort 2 | p |
|---|---|---|---|---|---|
| 0 hours | 0.55 | 0.059 | 356 | 27 | 0.426 |
| 24 hours | 0.60 | 0.055 | 356 | 32 | 0.079 |
| 48 hours | 0.64 | 0.076 | 356 | 16 | 0.065 | sCr or UO

| Time prior AKI stage | Cutoff value | sens | spec | Quartile | OR | 95% CI of OR | |
|---|---|---|---|---|---|---|---|
| 0 hours | 5.08 | 71% | 36% | 1 | | | |
| | 3.81 | 82% | 24% | 2 | 1.6 | 0.8 | 3.2 |
| | 2.97 | 93% | 17% | 3 | 1.2 | 0.6 | 2.6 |
| | 11.4 | 36% | 71% | 4 | 1.9 | 1.0 | 3.5 |
| | 13.5 | 32% | 80% | | | | |
| | 21.4 | 7% | 90% | | | | |
| 24 hours | 6.61 | 75% | 47% | 1 | | | |
| | 4.23 | 86% | 28% | 2 | 1.2 | 0.6 | 2.5 |
| | 3.1 | 92% | 19% | 3 | 2.6 | 1.4 | 4.6 |
| | 11.4 | 39% | 71% | 4 | 2.8 | 1.6 | 4.9 |
| | 13.5 | 36% | 80% | | | | |
| | 21.4 | 11% | 90% | | | | |
| 48 hours | 7.91 | 72% | 54% | 1 | | | |
| | 4.87 | 83% | 34% | 2 | 0.7 | 0.1 | 3.5 |
| | 3.17 | 94% | 19% | 3 | 1.7 | 0.6 | 5.0 |
| | 11.4 | 44% | 71% | 4 | 2.8 | 1.1 | 7.1 |
| | 13.5 | 44% | 80% | | | | |
| | 21.4 | 28% | 90% | | | | |

Fig. 6 Continued sCr only

| Time prior AKI stage | Cutoff value | sens | spec | Quartile | OR | 95% CI of OR | |
|---|---|---|---|---|---|---|---|
| 0 hours | 5.73 | 83% | 40% | 1 | | | |
| | 5.73 | 83% | 40% | 2 | 1.0 | 0.0 | 51.9 |
| | 3.26 | 100% | 19% | 3 | 1.0 | 0.0 | 51.9 |
| | 11.4 | 50% | 70% | 4 | 3.0 | 0.2 | 42.8 |
| | 14.1 | 50% | 80% | | | | |
| | 21.3 | 17% | 90% | | | | |
| 24 hours | 7.95 | 70% | 52% | 1 | | | |
| | 7.67 | 80% | 51% | 2 | 1.0 | 0.0 | 51.9 |
| | 6.61 | 90% | 45% | 3 | 3.0 | 0.2 | 42.8 |
| | 11.4 | 50% | 70% | 4 | 5.2 | 0.5 | 55.7 |
| | 14.1 | 40% | 80% | | | | |
| | 21.3 | 10% | 90% | | | | |
| 48 hours | 7.95 | 71% | 52% | 1 | | | |
| | 4.87 | 86% | 33% | 2 | 1.0 | 0.0 | 51.9 |
| | 2.07 | 100% | 12% | 3 | 2.0 | 0.1 | 39.2 |
| | 11.4 | 43% | 70% | 4 | 3.0 | 0.2 | 42.4 |
| | 14.1 | 43% | 80% | | | | |
| | 21.3 | 29% | 90% | | | | |

UO only

| Time prior AKI stage | Cutoff value | sens | spec | Quartile | OR | 95% CI of OR | |
|---|---|---|---|---|---|---|---|
| 0 hours | 5.52 | 70% | 40% | 1 | | | |
| | 4.23 | 81% | 28% | 2 | 2.4 | 1.1 | 5.0 |
| | 2.64 | 93% | 17% | 3 | 1.3 | 0.5 | 3.2 |
| | 11.4 | 33% | 71% | 4 | 2.4 | 1.1 | 5.0 |
| | 13.5 | 30% | 81% | | | | |
| | 21.3 | 7% | 90% | | | | |
| 24 hours | 6.61 | 72% | 47% | 1 | | | |
| | 4.23 | 88% | 28% | 2 | 1.5 | 0.6 | 3.6 |
| | 3.26 | 91% | 20% | 3 | 3.0 | 1.5 | 6.1 |
| | 11.4 | 38% | 71% | 4 | 3.0 | 1.5 | 6.1 |
| | 13.5 | 34% | 81% | | | | |
| | 21.3 | 9% | 90% | | | | |
| 48 hours | 6.61 | 75% | 47% | 1 | | | |
| | 4.87 | 81% | 35% | 2 | 0.7 | 0.1 | 3.5 |
| | 3.17 | 94% | 19% | 3 | 1.3 | 0.4 | 4.4 |
| | 11.4 | 44% | 71% | 4 | 2.4 | 0.9 | 6.5 |
| | 13.5 | 44% | 81% | | | | |
| | 21.3 | 25% | 90% | | | | |

Fig. 6 Continued

Vascular endothelial growth factor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 957.000 | 1125.000 | 957.000 | 1060.000 | 957.000 | 1004.500 |
| average | 1148.935 | 1764.286 | 1148.935 | 1830.639 | 1148.935 | 1362.222 |
| stdev | 885.128 | 1765.240 | 885.128 | 1796.119 | 885.128 | 850.515 |
| p (t-test) |  | 0.001 |  | 0.000 |  | 0.316 |
| min | 353.000 | 369.000 | 353.000 | 387.000 | 353.000 | 338.000 |
| max | 11500.000 | 8250.000 | 11500.000 | 9620.000 | 11500.000 | 3580.000 |
| n (Samp) | 434 | 28 | 434 | 36 | 434 | 18 |
| n (Pat) | 173 | 28 | 173 | 36 | 173 | 18 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 974.000 | 1715.000 | 974.000 | 1212.000 | 974.000 | 2530.000 |
| average | 1261.585 | 2872.667 | 1261.585 | 2429.600 | 1261.585 | 2501.286 |
| stdev | 1340.352 | 2461.806 | 1340.352 | 2586.759 | 1340.352 | 1768.124 |
| p (t-test) |  | 0.004 |  | 0.008 |  | 0.016 |
| min | 338.000 | 806.000 | 338.000 | 599.000 | 338.000 | 734.000 |
| max | 16200.000 | 7240.000 | 16200.000 | 8830.000 | 16200.000 | 5870.000 |
| n (Samp) | 542 | 6 | 542 | 10 | 542 | 7 |
| n (Pat) | 208 | 6 | 208 | 10 | 208 | 7 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 963.500 | 1110.000 | 963.500 | 1075.000 | 963.500 | 1004.500 |
| average | 1169.059 | 1725.333 | 1169.059 | 1939.469 | 1169.059 | 1318.500 |
| stdev | 933.550 | 1742.580 | 933.550 | 1939.431 | 933.550 | 801.135 |
| p (t-test) |  | 0.006 |  | 0.000 |  | 0.529 |
| min | 392.000 | 369.000 | 392.000 | 387.000 | 392.000 | 338.000 |
| max | 11500.000 | 8250.000 | 11500.000 | 9620.000 | 11500.000 | 3580.000 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
| --- | --- | --- | --- | --- | --- |
| 0 hours | 0.62 | 0.058 | 434 | 28 | 0.032 |
| 24 hours | 0.63 | 0.052 | 434 | 36 | 0.014 |
| 48 hours | 0.58 | 0.072 | 434 | 18 | 0.243 | sCr only

| Time prior AKI stage | AUC | SE | nCohort 1 | nCohort 2 | p |
| --- | --- | --- | --- | --- | --- |
| 0 hours | 0.79 | 0.110 | 542 | 6 | 0.007 |
| 24 hours | 0.59 | 0.096 | 542 | 10 | 0.341 |
| 48 hours | 0.75 | 0.107 | 542 | 7 | 0.019 |

UO only

| Time prior AKI stage | AUC | SE | nCohort 1 | nCohort 2 | p |
| --- | --- | --- | --- | --- | --- |
| 0 hours | 0.62 | 0.059 | 356 | 27 | 0.047 |
| 24 hours | 0.65 | 0.055 | 356 | 32 | 0.006 |
| 48 hours | 0.57 | 0.076 | 356 | 16 | 0.349 |

Fig. 6 Continued sCr or UO

| Time prior AKI stage | Cutoff value | sens | spec | Quartile | OR | 95% CI of OR | |
|---|---|---|---|---|---|---|---|
| 0 hours | 939 | 71% | 48% | 1 | | | |
| | 803 | 82% | 35% | 2 | 2.0 | 0.7 | 5.6 |
| | 609 | 93% | 15% | 3 | 2.8 | 1.1 | 7.1 |
| | 1210 | 39% | 70% | 4 | 3.9 | 1.6 | 9.3 |
| | 1440 | 36% | 80% | | | | |
| | 1780 | 25% | 90% | | | | |
| 24 hours | 910 | 72% | 45% | 1 | | | |
| | 828 | 81% | 37% | 2 | 1.6 | 0.8 | 3.2 |
| | 703 | 92% | 24% | 3 | 2.1 | 1.1 | 3.9 |
| | 1210 | 42% | 70% | 4 | 2.8 | 1.6 | 4.9 |
| | 1440 | 36% | 80% | | | | |
| | 1780 | 25% | 90% | | | | |
| 48 hours | 822 | 72% | 36% | 1 | | | |
| | 730 | 89% | 28% | 2 | 3.7 | 1.0 | 13.4 |
| | 657 | 94% | 19% | 3 | 1.0 | 0.1 | 7.4 |
| | 1210 | 44% | 70% | 4 | 3.7 | 1.0 | 13.4 |
| | 1440 | 39% | 80% | | | | |
| | 1780 | 22% | 90% | | | | | sCr only

| Time prior AKI stage | Cutoff value | sens | spec | Quartile | OR | 95% CI of OR | |
|---|---|---|---|---|---|---|---|
| 0 hours | 1430 | 83% | 77% | 1 | | | |
| | 1430 | 83% | 77% | 2 | na | na | na |
| | 803 | 100% | 32% | 3 | na | na | na |
| | 1250 | 83% | 70% | 4 | na | na | na |
| | 1490 | 50% | 80% | | | | |
| | 1820 | 50% | 90% | | | | |
| 24 hours | 749 | 70% | 28% | 1 | | | |
| | 712 | 80% | 23% | 2 | 0.7 | 0.1 | 3.5 |
| | 703 | 90% | 22% | 3 | 0.0 | 0.0 | na |
| | 1250 | 50% | 70% | 4 | 1.7 | 0.6 | 5.0 |
| | 1490 | 50% | 80% | | | | |
| | 1820 | 40% | 90% | | | | |
| 48 hours | 1530 | 71% | 81% | 1 | | | |
| | 814 | 86% | 33% | 2 | na | na | na |
| | 730 | 100% | 26% | 3 | na | na | na |
| | 1250 | 71% | 70% | 4 | na | na | na |
| | 1490 | 71% | 80% | | | | |
| | 1820 | 57% | 90% | | | | |

UO only

| Time prior AKI stage | Cutoff value | sens | spec | Quartile | OR | 95% CI of OR | |
|---|---|---|---|---|---|---|---|
| 0 hours | 978 | 70% | 52% | 1 | | | |
| | 847 | 81% | 37% | 2 | 1.0 | 0.4 | 2.8 |
| | 607 | 93% | 14% | 3 | 2.4 | 1.1 | 5.0 |
| | 1220 | 37% | 71% | 4 | 2.6 | 1.3 | 5.5 |
| | 1450 | 37% | 80% | | | | |
| | 1800 | 22% | 91% | | | | |
| 24 hours | 958 | 72% | 50% | 1 | | | |
| | 910 | 81% | 44% | 2 | 2.4 | 0.9 | 6.5 |
| | 825 | 91% | 36% | 3 | 3.6 | 1.5 | 8.8 |
| | 1220 | 44% | 71% | 4 | 4.4 | 1.9 | 10.5 |
| | 1450 | 34% | 80% | | | | |
| | 1800 | 25% | 91% | | | | |

Fig. 6 Continued

| 48 hours | 822 | 75% | 36% | 1 | | | |
| --- | --- | --- | --- | --- | --- | --- | --- |
| | 730 | 81% | 28% | 2 | 1.7 | 0.6 | 5.1 |
| | 657 | 94% | 18% | 3 | 0.7 | 0.1 | 3.5 |
| | 1220 | 44% | 71% | 4 | 2.1 | 0.7 | 5.8 |
| | 1450 | 38% | 80% | | | | |
| | 1800 | 25% | 91% | | | | |

Fig. 6 Continued

EN-RAGE sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 27.697 | 32.831 | 27.697 | 32.831 | 27.697 | 32.831 |
| average | 44.947 | 52.066 | 44.947 | 52.066 | 44.947 | 52.066 |
| stdev | 56.067 | 71.549 | 56.067 | 71.549 | 56.067 | 71.549 |
| p (t-test) |  | 0.687 |  | 0.687 |  | 0.687 |
| min | 1.616 | 2.110 | 1.616 | 2.110 | 1.616 | 2.110 |
| max | 382.303 | 295.699 | 382.303 | 295.699 | 382.303 | 295.699 |
| n (Samp) | 51 | 15 | 51 | 15 | 51 | 15 |
| n (Pat) | 51 | 15 | 51 | 15 | 51 | 15 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 26.387 | 45.706 | 26.387 | 45.706 | 26.387 | 45.706 |
| average | 44.601 | 45.706 | 44.601 | 45.706 | 44.601 | 45.706 |
| stdev | 56.804 | 2.469 | 56.804 | 2.469 | 56.804 | 2.469 |
| p (t-test) |  | 0.979 |  | 0.979 |  | 0.979 |
| min | 2.110 | 43.960 | 2.110 | 43.960 | 2.110 | 43.960 |
| max | 257.339 | 47.452 | 257.339 | 47.452 | 257.339 | 47.452 |
| n (Samp) | 19 | 2 | 19 | 2 | 19 | 2 |
| n (Pat) | 19 | 2 | 19 | 2 | 19 | 2 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 25.340 | 59.492 | 25.340 | 59.492 | 25.340 | 59.492 |
| average | 45.880 | 65.878 | 45.880 | 65.878 | 45.880 | 65.878 |
| stdev | 62.833 | 74.618 | 62.833 | 74.618 | 62.833 | 74.618 |
| p (t-test) |  | 0.348 |  | 0.348 |  | 0.348 |
| min | 1.616 | 3.818 | 1.616 | 3.818 | 1.616 | 3.818 |
| max | 382.303 | 295.699 | 382.303 | 295.699 | 382.303 | 295.699 |
| n (Samp) | 39 | 13 | 39 | 13 | 39 | 13 |
| n (Pat) | 39 | 13 | 39 | 13 | 39 | 13 | sCr or UO

| Time prior AKI stage | AUC | SE | nCohort 1 | nCohort 2 | p |
| --- | --- | --- | --- | --- | --- |
| 0 hours | 0.49 | 0.085 | 51 | 15 | 0.933 |
| 24 hours | 0.49 | 0.085 | 51 | 15 | 0.933 |
| 48 hours | 0.49 | 0.085 | 51 | 15 | 0.933 | sCr only

| Time prior AKI stage | AUC | SE | nCohort 1 | nCohort 2 | p |
| --- | --- | --- | --- | --- | --- |
| 0 hours | 0.74 | 0.212 | 19 | 2 | 0.265 |
| 24 hours | 0.74 | 0.212 | 19 | 2 | 0.265 |
| 48 hours | 0.74 | 0.212 | 19 | 2 | 0.265 |

UO only

| Time prior AKI stage | AUC | SE | nCohort 1 | nCohort 2 | p |
| --- | --- | --- | --- | --- | --- |
| 0 hours | 0.62 | 0.094 | 39 | 13 | 0.191 |
| 24 hours | 0.62 | 0.094 | 39 | 13 | 0.191 |
| 48 hours | 0.62 | 0.094 | 39 | 13 | 0.191 |

Fig. 7 sCr or UO

| Time prior AKI stage | Cutoff value | sens | spec | Quartile | OR | 95% CI of OR | |
|---|---|---|---|---|---|---|---|
| 0 hours | 19.1976 | 73% | 29% | 1 | | | |
| | 14.1057 | 80% | 16% | 2 | 0.6 | 0.1 | 2.2 |
| | 2.11037 | 93% | 2% | 3 | 0.5 | 0.1 | 2.0 |
| | 50.1062 | 40% | 71% | 4 | 0.8 | 0.2 | 2.7 |
| | 61.8752 | 20% | 80% | | | | |
| | 82.5914 | 7% | 90% | | | | |
| 24 hours | 19.1976 | 73% | 29% | 1 | | | |
| | 14.1057 | 80% | 16% | 2 | 0.6 | 0.1 | 2.2 |
| | 2.11037 | 93% | 2% | 3 | 0.5 | 0.1 | 2.0 |
| | 50.1062 | 40% | 71% | 4 | 0.8 | 0.2 | 2.7 |
| | 61.8752 | 20% | 80% | | | | |
| | 82.5914 | 7% | 90% | | | | |
| 48 hours | 19.1976 | 73% | 29% | 1 | | | |
| | 14.1057 | 80% | 16% | 2 | 0.6 | 0.1 | 2.2 |
| | 2.11037 | 93% | 2% | 3 | 0.5 | 0.1 | 2.0 |
| | 50.1062 | 40% | 71% | 4 | 0.8 | 0.2 | 2.7 |
| | 61.8752 | 20% | 80% | | | | |
| | 82.5914 | 7% | 90% | | | | |

UO only

| Time prior AKI stage | Cutoff value | sens | spec | Quartile | OR | 95% CI of OR | |
|---|---|---|---|---|---|---|---|
| 0 hours | 19.6509 | 77% | 38% | 1 | | | |
| | 19.1976 | 85% | 36% | 2 | 1.0 | 0.1 | 10.1 |
| | 13.849 | 92% | 18% | 3 | 3.4 | 0.6 | 20.7 |
| | 56.0902 | 54% | 74% | 4 | 2.4 | 0.4 | 15.8 |
| | 61.8752 | 31% | 82% | | | | |
| | 85.7632 | 15% | 92% | | | | |
| 24 hours | 19.6509 | 77% | 38% | 1 | | | |
| | 19.1976 | 85% | 36% | 2 | 1.0 | 0.1 | 10.1 |
| | 13.849 | 92% | 18% | 3 | 3.4 | 0.6 | 20.7 |
| | 56.0902 | 54% | 74% | 4 | 2.4 | 0.4 | 15.8 |
| | 61.8752 | 31% | 82% | | | | |
| | 85.7632 | 15% | 92% | | | | |
| 48 hours | 19.6509 | 77% | 38% | 1 | | | |
| | 19.1976 | 85% | 36% | 2 | 1.0 | 0.1 | 10.1 |
| | 13.849 | 92% | 18% | 3 | 3.4 | 0.6 | 20.7 |
| | 56.0902 | 54% | 74% | 4 | 2.4 | 0.4 | 15.8 |
| | 61.8752 | 31% | 82% | | | | |
| | 85.7632 | 15% | 92% | | | | |

Fig. 7 Continued

Eotaxin sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 64.800 | 46.500 | 64.800 | 46.500 | 64.800 | 46.500 |
| average | 94.277 | 59.130 | 94.277 | 59.130 | 94.277 | 59.130 |
| stdev | 167.602 | 51.227 | 167.602 | 51.227 | 167.602 | 51.227 |
| p (t-test) |  | 0.350 |  | 0.350 |  | 0.350 |
| min | 0.410 | 0.410 | 0.410 | 0.410 | 0.410 | 0.410 |
| max | 1240.000 | 200.000 | 1240.000 | 200.000 | 1240.000 | 200.000 |
| n (Samp) | 56 | 21 | 56 | 21 | 56 | 21 |
| n (Pat) | 56 | 21 | 56 | 21 | 56 | 21 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 60.900 | 161.000 | 60.900 | 161.000 | 60.900 | 161.000 |
| average | 69.543 | 142.000 | 69.543 | 142.000 | 69.543 | 142.000 |
| stdev | 33.990 | 62.183 | 33.990 | 62.183 | 33.990 | 62.183 |
| p (t-test) |  | 0.001 |  | 0.001 |  | 0.001 |
| min | 25.100 | 74.400 | 25.100 | 74.400 | 25.100 | 74.400 |
| max | 147.000 | 200.000 | 147.000 | 200.000 | 147.000 | 200.000 |
| n (Samp) | 21 | 5 | 21 | 5 | 21 | 5 |
| n (Pat) | 21 | 5 | 21 | 5 | 21 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 66.000 | 45.600 | 66.000 | 45.600 | 66.000 | 45.600 |
| average | 103.018 | 45.685 | 103.018 | 45.685 | 103.018 | 45.685 |
| stdev | 183.972 | 34.312 | 183.972 | 34.312 | 183.972 | 34.312 |
| p (t-test) |  | 0.209 |  | 0.209 |  | 0.209 |
| min | 0.410 | 0.410 | 0.410 | 0.410 | 0.410 | 0.410 |
| max | 1240.000 | 109.000 | 1240.000 | 109.000 | 1240.000 | 109.000 |
| n (Samp) | 46 | 17 | 46 | 17 | 46 | 17 |
| n (Pat) | 46 | 17 | 46 | 17 | 46 | 17 | sCr or UO

| Time prior AKI stage | AUC | SE | nCohort 1 | nCohort 2 | p |
|---|---|---|---|---|---|
| 0 hours | 0.41 | 0.071 | 56 | 21 | 0.210 |
| 24 hours | 0.41 | 0.071 | 56 | 21 | 0.210 |
| 48 hours | 0.41 | 0.071 | 56 | 21 | 0.210 | sCr only

| Time prior AKI stage | AUC | SE | nCohort 1 | nCohort 2 | p |
|---|---|---|---|---|---|
| 0 hours | 0.86 | 0.112 | 21 | 5 | 0.001 |
| 24 hours | 0.86 | 0.112 | 21 | 5 | 0.001 |
| 48 hours | 0.86 | 0.112 | 21 | 5 | 0.001 |

UO only

| Time prior AKI stage | AUC | SE | nCohort 1 | nCohort 2 | p |
|---|---|---|---|---|---|
| 0 hours | 0.34 | 0.073 | 46 | 17 | 0.027 |
| 24 hours | 0.34 | 0.073 | 46 | 17 | 0.027 |
| 48 hours | 0.34 | 0.073 | 46 | 17 | 0.027 |

Fig. 7 Continued sCr or UO

| Time prior AKI stage | Cutoff value | sens | spec | Quartile | OR | 95% CI of OR | |
|---|---|---|---|---|---|---|---|
| 0 hours | 30.2 | 71% | 20% | 1 | | | |
| | 15.6 | 81% | 9% | 2 | 1.4 | 0.5 | 4.5 |
| | 0 | 100% | 0% | 3 | 1.8 | 0.6 | 5.5 |
| | 81.9 | 24% | 71% | 4 | 1.8 | 0.6 | 5.5 |
| | 101 | 19% | 80% | | | | |
| | 129 | 10% | 91% | | | | |
| 24 hours | 30.2 | 71% | 20% | 1 | | | |
| | 15.6 | 81% | 9% | 2 | 1.4 | 0.5 | 4.5 |
| | 0 | 100% | 0% | 3 | 1.8 | 0.6 | 5.5 |
| | 81.9 | 24% | 71% | 4 | 1.8 | 0.6 | 5.5 |
| | 101 | 19% | 80% | | | | |
| | 129 | 10% | 91% | | | | |
| 48 hours | 30.2 | 71% | 20% | 1 | | | |
| | 15.6 | 81% | 9% | 2 | 1.4 | 0.5 | 4.5 |
| | 0 | 100% | 0% | 3 | 1.8 | 0.6 | 5.5 |
| | 81.9 | 24% | 71% | 4 | 1.8 | 0.6 | 5.5 |
| | 101 | 19% | 80% | | | | |
| | 129 | 10% | 91% | | | | |

UO only

| Time prior AKI stage | Cutoff value | sens | spec | Quartile | OR | 95% CI of OR | |
|---|---|---|---|---|---|---|---|
| 0 hours | 25.1 | 71% | 17% | 1 | | | |
| | 0 | 100% | 0% | 2 | 1.6 | 0.2 | 11.1 |
| | 0 | 100% | 0% | 3 | 4.2 | 0.8 | 21.7 |
| | 94.1 | 12% | 72% | 4 | 4.7 | 0.9 | 24.7 |
| | 104 | 6% | 83% | | | | |
| | 154 | 0% | 91% | | | | |
| 24 hours | 25.1 | 71% | 17% | 1 | | | |
| | 0 | 100% | 0% | 2 | 1.6 | 0.2 | 11.1 |
| | 0 | 100% | 0% | 3 | 4.2 | 0.8 | 21.7 |
| | 94.1 | 12% | 72% | 4 | 4.7 | 0.9 | 24.7 |
| | 104 | 6% | 83% | | | | |
| | 154 | 0% | 91% | | | | |
| 48 hours | 25.1 | 71% | 17% | 1 | | | |
| | 0 | 100% | 0% | 2 | 1.6 | 0.2 | 11.1 |
| | 0 | 100% | 0% | 3 | 4.2 | 0.8 | 21.7 |
| | 94.1 | 12% | 72% | 4 | 4.7 | 0.9 | 24.7 |
| | 104 | 6% | 83% | | | | |
| | 154 | 0% | 91% | | | | |

Fig. 7 Continued

Hepatocyte growth factor receptor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 255026.455 | 221074.380 | 255026.455 | 221074.380 | 255026.455 | 221074.380 |
| average | 277098.766 | 216283.545 | 277098.766 | 216283.545 | 277098.766 | 216283.545 |
| stdev | 95004.283 | 59884.354 | 95004.283 | 59884.354 | 95004.283 | 59884.354 |
| p (t-test) |  | 0.100 |  | 0.100 |  | 0.100 |
| min | 136397.059 | 106092.437 | 136397.059 | 106092.437 | 136397.059 | 106092.437 |
| max | 490272.374 | 302892.562 | 490272.374 | 302892.562 | 490272.374 | 302892.562 |
| n (Samp) | 15 | 9 | 15 | 9 | 15 | 9 |
| n (Pat) | 15 | 9 | 15 | 9 | 15 | 9 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 256354.434 | 356371.808 | 256354.434 | 356371.808 | 256354.434 | 356371.808 |
| average | 266320.510 | 356371.808 | 266320.510 | 356371.808 | 266320.510 | 356371.808 |
| stdev | 24029.573 | 136537.342 | 24029.573 | 136537.342 | 24029.573 | 136537.342 |
| p (t-test) |  | 0.219 |  | 0.219 |  | 0.219 |
| min | 250826.446 | 259825.328 | 250826.446 | 259825.328 | 250826.446 | 259825.328 |
| max | 301746.725 | 452918.288 | 301746.725 | 452918.288 | 301746.725 | 452918.288 |
| n (Samp) | 4 | 2 | 4 | 2 | 4 | 2 |
| n (Pat) | 4 | 2 | 4 | 2 | 4 | 2 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 256232.236 | 212809.917 | 256232.236 | 212809.917 | 256232.236 | 212809.917 |
| average | 281826.033 | 210726.013 | 281826.033 | 210726.013 | 281826.033 | 210726.013 |
| stdev | 99662.999 | 61487.842 | 99662.999 | 61487.842 | 99662.999 | 61487.842 |
| p (t-test) |  | 0.084 |  | 0.084 |  | 0.084 |
| min | 136397.059 | 106092.437 | 136397.059 | 106092.437 | 136397.059 | 106092.437 |
| max | 490272.374 | 302892.562 | 490272.374 | 302892.562 | 490272.374 | 302892.562 |
| n (Samp) | 14 | 8 | 14 | 8 | 14 | 8 |
| n (Pat) | 14 | 8 | 14 | 8 | 14 | 8 | sCr or UO

| Time prior AKI stage | AUC | SE | nCohort 1 | nCohort 2 | p |
|---|---|---|---|---|---|
| 0 hours | 0.33 | 0.112 | 15 | 9 | 0.119 |
| 24 hours | 0.33 | 0.112 | 15 | 9 | 0.119 |
| 48 hours | 0.33 | 0.112 | 15 | 9 | 0.119 | sCr only

| Time prior AKI stage | AUC | SE | nCohort 1 | nCohort 2 | p |
|---|---|---|---|---|---|
| 0 hours | 0.75 | 0.241 | 4 | 2 | 0.300 |
| 24 hours | 0.75 | 0.241 | 4 | 2 | 0.300 |
| 48 hours | 0.75 | 0.241 | 4 | 2 | 0.300 |

UO only

| Time prior AKI stage | AUC | SE | nCohort 1 | nCohort 2 | p |
|---|---|---|---|---|---|
| 0 hours | 0.28 | 0.110 | 14 | 8 | 0.042 |
| 24 hours | 0.28 | 0.110 | 14 | 8 | 0.042 |
| 48 hours | 0.28 | 0.110 | 14 | 8 | 0.042 |

Fig. 7 Continued sCr or UO

| Time prior AKI stage | Cutoff value | sens | spec | Quartile | OR | 95% CI of OR | |
|---|---|---|---|---|---|---|---|
| 0 hours | 163235 | 78% | 7% | 1 | | | |
| | 136397 | 89% | 7% | 2 | 2.5 | 0.1 | 114.2 |
| | 0 | 100% | 0% | 3 | 5.0 | 0.1 | 194.0 |
| | 284656 | 11% | 73% | 4 | 5.0 | 0.1 | 194.0 |
| | 301747 | 11% | 80% | | | | |
| | 440083 | 0% | 93% | | | | |
| 24 hours | 163235 | 78% | 7% | 1 | | | |
| | 136397 | 89% | 7% | 2 | 2.5 | 0.1 | 114.2 |
| | 0 | 100% | 0% | 3 | 5.0 | 0.1 | 194.0 |
| | 284656 | 11% | 73% | 4 | 5.0 | 0.1 | 194.0 |
| | 301747 | 11% | 80% | | | | |
| | 440083 | 0% | 93% | | | | |
| 48 hours | 163235 | 78% | 7% | 1 | | | |
| | 136397 | 89% | 7% | 2 | 2.5 | 0.1 | 114.2 |
| | 0 | 100% | 0% | 3 | 5.0 | 0.1 | 194.0 |
| | 284656 | 11% | 73% | 4 | 5.0 | 0.1 | 194.0 |
| | 301747 | 11% | 80% | | | | |
| | 440083 | 0% | 93% | | | | |

UO only

| Time prior AKI stage | Cutoff value | sens | spec | Quartile | OR | 95% CI of OR | |
|---|---|---|---|---|---|---|---|
| 0 hours | 163235 | 75% | 7% | 1 | | | |
| | 136397 | 88% | 7% | 2 | 1.3 | 0.0 | 152.2 |
| | 0 | 100% | 0% | 3 | 5.0 | 0.1 | 194.0 |
| | 284656 | 13% | 71% | 4 | 7.5 | 0.1 | 403.5 |
| | 379894 | 0% | 86% | | | | |
| | 440083 | 0% | 93% | | | | |
| 24 hours | 163235 | 75% | 7% | 1 | | | |
| | 136397 | 88% | 7% | 2 | 1.3 | 0.0 | 152.2 |
| | 0 | 100% | 0% | 3 | 5.0 | 0.1 | 194.0 |
| | 284656 | 13% | 71% | 4 | 7.5 | 0.1 | 403.5 |
| | 379894 | 0% | 86% | | | | |
| | 440083 | 0% | 93% | | | | |
| 48 hours | 163235 | 75% | 7% | 1 | | | |
| | 136397 | 88% | 7% | 2 | 1.3 | 0.0 | 152.2 |
| | 0 | 100% | 0% | 3 | 5.0 | 0.1 | 194.0 |
| | 284656 | 13% | 71% | 4 | 7.5 | 0.1 | 403.5 |
| | 379894 | 0% | 86% | | | | |
| | 440083 | 0% | 93% | | | | |

Fig. 7 Continued

Interleukin-1 beta sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.015 | 0.015 | 0.015 | 0.015 | 0.015 | 0.015 |
| average | 1.355 | 0.220 | 1.355 | 0.220 | 1.355 | 0.220 |
| stdev | 8.504 | 0.444 | 8.504 | 0.444 | 8.504 | 0.444 |
| p (t-test) |  | 0.544 |  | 0.544 |  | 0.544 |
| min | 0.015 | 0.015 | 0.015 | 0.015 | 0.015 | 0.015 |
| max | 63.800 | 1.360 | 63.800 | 1.360 | 63.800 | 1.360 |
| n (Samp) | 56 | 21 | 56 | 21 | 56 | 21 |
| n (Pat) | 56 | 21 | 56 | 21 | 56 | 21 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.015 | 0.598 | 0.015 | 0.598 | 0.015 | 0.598 |
| average | 0.148 | 0.681 | 0.148 | 0.681 | 0.148 | 0.681 |
| stdev | 0.353 | 0.690 | 0.353 | 0.690 | 0.353 | 0.690 |
| p (t-test) |  | 0.019 |  | 0.019 |  | 0.019 |
| min | 0.015 | 0.015 | 0.015 | 0.015 | 0.015 | 0.015 |
| max | 1.360 | 1.420 | 1.360 | 1.420 | 1.360 | 1.420 |
| n (Samp) | 21 | 5 | 21 | 5 | 21 | 5 |
| n (Pat) | 21 | 5 | 21 | 5 | 21 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.015 | 0.015 | 0.015 | 0.015 | 0.015 | 0.015 |
| average | 1.615 | 0.189 | 1.615 | 0.189 | 1.615 | 0.189 |
| stdev | 9.380 | 0.396 | 9.380 | 0.396 | 9.380 | 0.396 |
| p (t-test) |  | 0.535 |  | 0.535 |  | 0.535 |
| min | 0.015 | 0.015 | 0.015 | 0.015 | 0.015 | 0.015 |
| max | 63.800 | 1.180 | 63.800 | 1.180 | 63.800 | 1.180 |
| n (Samp) | 46 | 17 | 46 | 17 | 46 | 17 |
| n (Pat) | 46 | 17 | 46 | 17 | 46 | 17 | sCr or UO

| Time prior AKI stage | AUC | SE | nCohort 1 | nCohort 2 | p |
|---|---|---|---|---|---|
| 0 hours | 0.47 | 0.073 | 56 | 21 | 0.668 |
| 24 hours | 0.47 | 0.073 | 56 | 21 | 0.668 |
| 48 hours | 0.47 | 0.073 | 56 | 21 | 0.668 | sCr only

| Time prior AKI stage | AUC | SE | nCohort 1 | nCohort 2 | p |
|---|---|---|---|---|---|
| 0 hours | 0.74 | 0.138 | 21 | 5 | 0.084 |
| 24 hours | 0.74 | 0.138 | 21 | 5 | 0.084 |
| 48 hours | 0.74 | 0.138 | 21 | 5 | 0.084 |

UO only

| Time prior AKI stage | AUC | SE | nCohort 1 | nCohort 2 | p |
|---|---|---|---|---|---|
| 0 hours | 0.45 | 0.081 | 46 | 17 | 0.521 |
| 24 hours | 0.45 | 0.081 | 46 | 17 | 0.521 |
| 48 hours | 0.45 | 0.081 | 46 | 17 | 0.521 |

Fig. 7 Continued sCr or UO

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.0 | 0.0 | na |
| | 0 | 100% | 0% | 3 | 8.7 | 2.9 | 25.8 |
| | 0.0146 | 19% | 71% | 4 | 1.1 | 0.3 | 3.7 |
| | 0.711 | 19% | 80% | | | | |
| | 0.866 | 14% | 91% | | | | |
| 24 hours | 0 | 100% | 0% | 1 | | | |
| | 0 | 100% | 0% | 2 | 0.0 | 0.0 | na |
| | 0 | 100% | 0% | 3 | 8.7 | 2.9 | 25.8 |
| | 0.0146 | 19% | 71% | 4 | 1.1 | 0.3 | 3.7 |
| | 0.711 | 19% | 80% | | | | |
| | 0.866 | 14% | 91% | | | | |
| 48 hours | 0 | 100% | 0% | 1 | | | |
| | 0 | 100% | 0% | 2 | 0.0 | 0.0 | na |
| | 0 | 100% | 0% | 3 | 8.7 | 2.9 | 25.8 |
| | 0.0146 | 19% | 71% | 4 | 1.1 | 0.3 | 3.7 |
| | 0.711 | 19% | 80% | | | | |
| | 0.866 | 14% | 91% | | | | | sCr only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.8 | 0.0 | 86.2 |
| | 0 | 100% | 0% | 3 | 0.0 | 0.0 | na |
| | 0.0146 | 60% | 86% | 4 | 3.8 | 0.1 | 123.6 |
| | 0.0146 | 60% | 86% | | | | |
| | 0.711 | 40% | 90% | | | | |
| 24 hours | 0 | 100% | 0% | 1 | | | |
| | 0 | 100% | 0% | 2 | 0.8 | 0.0 | 86.2 |
| | 0 | 100% | 0% | 3 | 0.0 | 0.0 | na |
| | 0.0146 | 60% | 86% | 4 | 3.8 | 0.1 | 123.6 |
| | 0.0146 | 60% | 86% | | | | |
| | 0.711 | 40% | 90% | | | | |
| 48 hours | 0 | 100% | 0% | 1 | | | |
| | 0 | 100% | 0% | 2 | 0.8 | 0.0 | 86.2 |
| | 0 | 100% | 0% | 3 | 0.0 | 0.0 | na |
| | 0.0146 | 60% | 86% | 4 | 3.8 | 0.1 | 123.6 |
| | 0.0146 | 60% | 86% | | | | |
| | 0.711 | 40% | 90% | | | | |

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.0 | 0.0 | na |
| | 0 | 100% | 0% | 3 | 9.5 | 2.4 | 37.7 |
| | 0.391 | 18% | 72% | 4 | 1.1 | 0.2 | 5.5 |
| | 0.773 | 12% | 87% | | | | |
| | 1.03 | 12% | 91% | | | | |
| 24 hours | 0 | 100% | 0% | 1 | | | |
| | 0 | 100% | 0% | 2 | 0.0 | 0.0 | na |
| | 0 | 100% | 0% | 3 | 9.5 | 2.4 | 37.7 |
| | 0.391 | 18% | 72% | 4 | 1.1 | 0.2 | 5.5 |
| | 0.773 | 12% | 87% | | | | |
| | 1.03 | 12% | 91% | | | | |

Fig. 7 Continued

|  | 0 | 100% | 0% | 1 |  |  |  |
|---|---|---|---|---|---|---|---|
| 48 hours | 0 | 100% | 0% | 2 | 0.0 | 0.0 | na |
|  | 0 | 100% | 0% | 3 | 9.5 | 2.4 | 37.7 |
|  | 0.391 | 18% | 72% | 4 | 1.1 | 0.2 | 5.5 |
|  | 0.773 | 12% | 87% |  |  |  |  |
|  | 1.03 | 12% | 91% |  |  |  |  |

Interleukin-10 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 15.700 | 23.400 | 15.700 | 23.400 | 15.700 | 23.400 |
| average | 260.477 | 43.302 | 260.477 | 43.302 | 260.477 | 43.302 |
| stdev | 1788.020 | 48.908 | 1788.020 | 48.908 | 1788.020 | 48.908 |
| p (t-test) |  | 0.581 |  | 0.581 |  | 0.581 |
| min | 0.154 | 6.370 | 0.154 | 6.370 | 0.154 | 6.370 |
| max | 13400.000 | 182.000 | 13400.000 | 182.000 | 13400.000 | 182.000 |
| n (Samp) | 56 | 21 | 56 | 21 | 56 | 21 |
| n (Pat) | 56 | 21 | 56 | 21 | 56 | 21 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 15.700 | 15.600 | 15.700 | 15.600 | 15.700 | 15.600 |
| average | 28.166 | 51.256 | 28.166 | 51.256 | 28.166 | 51.256 |
| stdev | 46.628 | 64.215 | 46.628 | 64.215 | 46.628 | 64.215 |
| p (t-test) |  | 0.363 |  | 0.363 |  | 0.363 |
| min | 0.154 | 4.880 | 0.154 | 4.880 | 0.154 | 4.880 |
| max | 222.000 | 159.000 | 222.000 | 159.000 | 222.000 | 159.000 |
| n (Samp) | 21 | 5 | 21 | 5 | 21 | 5 |
| n (Pat) | 21 | 5 | 21 | 5 | 21 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 16.050 | 23.400 | 16.050 | 23.400 | 16.050 | 23.400 |
| average | 309.114 | 41.697 | 309.114 | 41.697 | 309.114 | 41.697 |
| stdev | 1973.081 | 44.703 | 1973.081 | 44.703 | 1973.081 | 44.703 |
| p (t-test) |  | 0.580 |  | 0.580 |  | 0.580 |
| min | 0.154 | 6.370 | 0.154 | 6.370 | 0.154 | 6.370 |
| max | 13400.000 | 182.000 | 13400.000 | 182.000 | 13400.000 | 182.000 |
| n (Samp) | 46 | 17 | 46 | 17 | 46 | 17 |
| n (Pat) | 46 | 17 | 46 | 17 | 46 | 17 | sCr or UO

| Time prior AKI stage | AUC | SE | nCohort 1 | nCohort 2 | p |
|---|---|---|---|---|---|
| 0 hours | 0.63 | 0.074 | 56 | 21 | 0.072 |
| 24 hours | 0.63 | 0.074 | 56 | 21 | 0.072 |
| 48 hours | 0.63 | 0.074 | 56 | 21 | 0.072 | sCr only

| Time prior AKI stage | AUC | SE | nCohort 1 | nCohort 2 | p |
|---|---|---|---|---|---|
| 0 hours | 0.58 | 0.149 | 21 | 5 | 0.586 |
| 24 hours | 0.58 | 0.149 | 21 | 5 | 0.586 |
| 48 hours | 0.58 | 0.149 | 21 | 5 | 0.586 |

Fig. 7 Continued

UO only

| Time prior AKI stage | AUC | SE | nCohort 1 | nCohort 2 | p |
|---|---|---|---|---|---|
| 0 hours | 0.66 | 0.081 | 46 | 17 | 0.051 |
| 24 hours | 0.66 | 0.081 | 46 | 17 | 0.051 |
| 48 hours | 0.66 | 0.081 | 46 | 17 | 0.051 | sCr or UO

| Time prior AKI stage | Cutoff value | sens | spec | Quartile | OR | 95% CI of OR | |
|---|---|---|---|---|---|---|---|
| 0 hours | 13.6 | 71% | 45% | 1 | | | |
| | 9.84 | 81% | 29% | 2 | 0.7 | 0.2 | 2.8 |
| | 6.37 | 90% | 18% | 3 | 1.7 | 0.6 | 5.2 |
| | 24 | 43% | 71% | 4 | 2.5 | 0.9 | 7.0 |
| | 31.3 | 38% | 80% | | | | |
| | 36.1 | 38% | 91% | | | | |
| 24 hours | 13.6 | 71% | 45% | 1 | | | |
| | 9.84 | 81% | 29% | 2 | 0.7 | 0.2 | 2.8 |
| | 6.37 | 90% | 18% | 3 | 1.7 | 0.6 | 5.2 |
| | 24 | 43% | 71% | 4 | 2.5 | 0.9 | 7.0 |
| | 31.3 | 38% | 80% | | | | |
| | 36.1 | 38% | 91% | | | | |
| 48 hours | 13.6 | 71% | 45% | 1 | | | |
| | 9.84 | 81% | 29% | 2 | 0.7 | 0.2 | 2.8 |
| | 6.37 | 90% | 18% | 3 | 1.7 | 0.6 | 5.2 |
| | 24 | 43% | 71% | 4 | 2.5 | 0.9 | 7.0 |
| | 31.3 | 38% | 80% | | | | |
| | 36.1 | 38% | 91% | | | | | sCr only

| Time prior AKI stage | Cutoff value | sens | spec | Quartile | OR | 95% CI of OR | |
|---|---|---|---|---|---|---|---|
| 0 hours | 13.7 | 80% | 48% | 1 | | | |
| | 13.7 | 80% | 48% | 2 | 2.0 | 0.0 | 82.9 |
| | 0.154 | 100% | 10% | 3 | 0.0 | 0.0 | na |
| | 24 | 40% | 76% | 4 | 2.0 | 0.0 | 82.9 |
| | 30.8 | 40% | 81% | | | | |
| | 37.8 | 40% | 90% | | | | |
| 24 hours | 13.7 | 80% | 48% | 1 | | | |
| | 13.7 | 80% | 48% | 2 | 2.0 | 0.0 | 82.9 |
| | 0.154 | 100% | 10% | 3 | 0.0 | 0.0 | na |
| | 24 | 40% | 76% | 4 | 2.0 | 0.0 | 82.9 |
| | 30.8 | 40% | 81% | | | | |
| | 37.8 | 40% | 90% | | | | |
| 48 hours | 13.7 | 80% | 48% | 1 | | | |
| | 13.7 | 80% | 48% | 2 | 2.0 | 0.0 | 82.9 |
| | 0.154 | 100% | 10% | 3 | 0.0 | 0.0 | na |
| | 24 | 40% | 76% | 4 | 2.0 | 0.0 | 82.9 |
| | 30.8 | 40% | 81% | | | | |
| | 37.8 | 40% | 90% | | | | |

UO only

| Time prior AKI stage | Cutoff value | sens | spec | Quartile | OR | 95% CI of OR | |
|---|---|---|---|---|---|---|---|
| 0 hours | 18 | 71% | 59% | 1 | | | |
| | 7.37 | 82% | 22% | 2 | 0.2 | 0.0 | 2.9 |
| | 6.18 | 100% | 17% | 3 | 1.3 | 0.4 | 4.3 |
| | 23.1 | 59% | 72% | 4 | 2.1 | 0.7 | 6.9 |
| | 31.9 | 41% | 80% | | | | |
| | 36.1 | 41% | 91% | | | | |

Fig. 7 Continued

| 24 hours | 18   | 71%  | 59% | 1 |     |     |     |
|          | 7.37 | 82%  | 22% | 2 | 0.2 | 0.0 | 2.9 |
|          | 6.18 | 100% | 17% | 3 | 1.3 | 0.4 | 4.3 |
|          | 23.1 | 59%  | 72% | 4 | 2.1 | 0.7 | 6.9 |
|          | 31.9 | 41%  | 80% |   |     |     |     |
|          | 36.1 | 41%  | 91% |   |     |     |     |
| 48 hours | 18   | 71%  | 59% | 1 |     |     |     |
|          | 7.37 | 82%  | 22% | 2 | 0.2 | 0.0 | 2.9 |
|          | 6.18 | 100% | 17% | 3 | 1.3 | 0.4 | 4.3 |
|          | 23.1 | 59%  | 72% | 4 | 2.1 | 0.7 | 6.9 |
|          | 31.9 | 41%  | 80% |   |     |     |     |
|          | 36.1 | 41%  | 91% |   |     |     |     |

Nidogen-1 sCr or UO

|          | 0 hr prior to AKI stage | | 24 hr prior to AKI stage | | 48 hr prior to AKI stage | |
|          | Cohort 1 | Cohort 2 | Cohort 1 | Cohort 2 | Cohort 1 | Cohort 2 |
|----------|----------|----------|----------|----------|----------|----------|
| median   | 345779.221 | 481331.169 | 345779.221 | 481331.169 | 345779.221 | 481331.169 |
| average  | 428166.624 | 488104.520 | 428166.624 | 488104.520 | 428166.624 | 488104.520 |
| stdev    | 345939.448 | 279488.075 | 345939.448 | 279488.075 | 345939.448 | 279488.075 |
| p (t-test) |        | 0.664    |          | 0.664    |          | 0.664    |
| min      | 69653.614 | 12348.790 | 69653.614 | 12348.790 | 69653.614 | 12348.790 |
| max      | 1050724.638 | 959401.709 | 1050724.638 | 959401.709 | 1050724.638 | 959401.709 |
| n (Samp) | 12       | 10       | 12       | 10       | 12       | 10       |
| n (Pat)  | 12       | 10       | 12       | 10       | 12       | 10       | sCr only

|          | 0 hr prior to AKI stage | | 24 hr prior to AKI stage | | 48 hr prior to AKI stage | |
|          | Cohort 1 | Cohort 2 | Cohort 1 | Cohort 2 | Cohort 1 | Cohort 2 |
|----------|----------|----------|----------|----------|----------|----------|
| median   | 401785.714 | 219734.106 | 401785.714 | 219734.106 | 401785.714 | 219734.106 |
| average  | 386095.752 | 219734.106 | 386095.752 | 219734.106 | 386095.752 | 219734.106 |
| stdev    | 73510.998 | 196366.032 | 73510.998 | 196366.032 | 73510.998 | 196366.032 |
| p (t-test) |        | 0.251    |          | 0.251    |          | 0.251    |
| min      | 306006.494 | 80882.353 | 306006.494 | 80882.353 | 306006.494 | 80882.353 |
| max      | 450495.050 | 358585.859 | 450495.050 | 358585.859 | 450495.050 | 358585.859 |
| n (Samp) | 3        | 2        | 3        | 2        | 3        | 2        |
| n (Pat)  | 3        | 2        | 3        | 2        | 3        | 2        |

UO only

|          | 0 hr prior to AKI stage | | 24 hr prior to AKI stage | | 48 hr prior to AKI stage | |
|          | Cohort 1 | Cohort 2 | Cohort 1 | Cohort 2 | Cohort 1 | Cohort 2 |
|----------|----------|----------|----------|----------|----------|----------|
| median   | 289772.727 | 481331.169 | 289772.727 | 481331.169 | 289772.727 | 481331.169 |
| average  | 426136.767 | 508337.634 | 426136.767 | 508337.634 | 426136.767 | 508337.634 |
| stdev    | 362749.396 | 288569.349 | 362749.396 | 288569.349 | 362749.396 | 288569.349 |
| p (t-test) |        | 0.588    |          | 0.588    |          | 0.588    |
| min      | 69653.614 | 12348.790 | 69653.614 | 12348.790 | 69653.614 | 12348.790 |
| max      | 1050724.638 | 959401.709 | 1050724.638 | 959401.709 | 1050724.638 | 959401.709 |
| n (Samp) | 11       | 9        | 11       | 9        | 11       | 9        |
| n (Pat)  | 11       | 9        | 11       | 9        | 11       | 9        | sCr or UO

| Time prior AKI stage | AUC | SE | nCohort 1 | nCohort 2 | p |
|---|---|---|---|---|---|
| 0 hours  | 0.58 | 0.125 | 12 | 10 | 0.505 |
| 24 hours | 0.58 | 0.125 | 12 | 10 | 0.505 |
| 48 hours | 0.58 | 0.125 | 12 | 10 | 0.505 |

Fig. 7 Continued sCr only

| Time prior AKI stage | AUC | SE | nCohort 1 | nCohort 2 | p |
|---|---|---|---|---|---|
| 0 hours | 0.17 | 0.201 | 3 | 2 | 0.097 |
| 24 hours | 0.17 | 0.201 | 3 | 2 | 0.097 |
| 48 hours | 0.17 | 0.201 | 3 | 2 | 0.097 |

UO only

| Time prior AKI stage | AUC | SE | nCohort 1 | nCohort 2 | p |
|---|---|---|---|---|---|
| 0 hours | 0.59 | 0.131 | 11 | 9 | 0.513 |
| 24 hours | 0.59 | 0.131 | 11 | 9 | 0.513 |
| 48 hours | 0.59 | 0.131 | 11 | 9 | 0.513 | sCr or UO

| Time prior AKI stage | Cutoff value | sens | spec | Quartile | OR | 95% CI of OR | |
|---|---|---|---|---|---|---|---|
| 0 hours | 306006 | 70% | 50% | 1 | | | |
| | 289773 | 80% | 50% | 2 | 4.0 | 0.1 | 171.2 |
| | 176772 | 90% | 42% | 3 | 16.0 | 0.1 | 2148.6 |
| | 698718 | 20% | 75% | 4 | 2.0 | 0.0 | 100.8 |
| | 759375 | 20% | 83% | | | | |
| | 908120 | 10% | 92% | | | | |
| 24 hours | 306006 | 70% | 50% | 1 | | | |
| | 289773 | 80% | 50% | 2 | 4.0 | 0.1 | 171.2 |
| | 176772 | 90% | 42% | 3 | 16.0 | 0.1 | 2148.6 |
| | 698718 | 20% | 75% | 4 | 2.0 | 0.0 | 100.8 |
| | 759375 | 20% | 83% | | | | |
| | 908120 | 10% | 92% | | | | |
| 48 hours | 306006 | 70% | 50% | 1 | | | |
| | 289773 | 80% | 50% | 2 | 4.0 | 0.1 | 171.2 |
| | 176772 | 90% | 42% | 3 | 16.0 | 0.1 | 2148.6 |
| | 698718 | 20% | 75% | 4 | 2.0 | 0.0 | 100.8 |
| | 759375 | 20% | 83% | | | | |
| | 908120 | 10% | 92% | | | | |

UO only

| Time prior AKI stage | Cutoff value | sens | spec | Quartile | OR | 95% CI of OR | |
|---|---|---|---|---|---|---|---|
| 0 hours | 289773 | 78% | 55% | 1 | | | |
| | 176772 | 89% | 45% | 2 | 2.7 | 0.0 | 158.2 |
| | 0 | 100% | 0% | 3 | 16.0 | 0.1 | 2148.6 |
| | 698718 | 22% | 73% | 4 | 2.7 | 0.0 | 158.2 |
| | 759375 | 22% | 82% | | | | |
| | 908120 | 11% | 91% | | | | |
| 24 hours | 289773 | 78% | 55% | 1 | | | |
| | 176772 | 89% | 45% | 2 | 2.7 | 0.0 | 158.2 |
| | 0 | 100% | 0% | 3 | 16.0 | 0.1 | 2148.6 |
| | 698718 | 22% | 73% | 4 | 2.7 | 0.0 | 158.2 |
| | 759375 | 22% | 82% | | | | |
| | 908120 | 11% | 91% | | | | |
| 48 hours | 289773 | 78% | 55% | 1 | | | |
| | 176772 | 89% | 45% | 2 | 2.7 | 0.0 | 158.2 |
| | 0 | 100% | 0% | 3 | 16.0 | 0.1 | 2148.6 |
| | 698718 | 22% | 73% | 4 | 2.7 | 0.0 | 158.2 |
| | 759375 | 22% | 82% | | | | |
| | 908120 | 11% | 91% | | | | |

Fig. 7 Continued

Oxidized low-density lipoprotein receptor 1 sCr or UO

|          | 0 hr prior to AKI stage | | 24 hr prior to AKI stage | | 48 hr prior to AKI stage | |
|----------|---------|---------|---------|---------|---------|---------|
|          | Cohort 1 | Cohort 2 | Cohort 1 | Cohort 2 | Cohort 1 | Cohort 2 |
| median   | 0.368 | 0.514 | 0.368 | 0.514 | 0.368 | 0.514 |
| average  | 0.465 | 0.706 | 0.465 | 0.706 | 0.465 | 0.706 |
| stdev    | 0.271 | 0.692 | 0.271 | 0.692 | 0.271 | 0.692 |
| p (t-test) |     | 0.040 |       | 0.040 |       | 0.040 |
| min      | 0.121 | 0.121 | 0.121 | 0.121 | 0.121 | 0.121 |
| max      | 1.282 | 3.215 | 1.282 | 3.215 | 1.282 | 3.215 |
| n (Samp) | 52    | 17    | 52    | 17    | 52    | 17    |
| n (Pat)  | 52    | 17    | 52    | 17    | 52    | 17    | sCr only

|          | 0 hr prior to AKI stage | | 24 hr prior to AKI stage | | 48 hr prior to AKI stage | |
|----------|---------|---------|---------|---------|---------|---------|
|          | Cohort 1 | Cohort 2 | Cohort 1 | Cohort 2 | Cohort 1 | Cohort 2 |
| median   | 0.440 | 1.069 | 0.440 | 1.069 | 0.440 | 1.069 |
| average  | 0.511 | 1.069 | 0.511 | 1.069 | 0.511 | 1.069 |
| stdev    | 0.288 | 0.156 | 0.288 | 0.156 | 0.288 | 0.156 |
| p (t-test) |     | 0.016 |       | 0.016 |       | 0.016 |
| min      | 0.198 | 0.959 | 0.198 | 0.959 | 0.198 | 0.959 |
| max      | 1.194 | 1.179 | 1.194 | 1.179 | 1.194 | 1.179 |
| n (Samp) | 19    | 2     | 19    | 2     | 19    | 2     |
| n (Pat)  | 19    | 2     | 19    | 2     | 19    | 2     |

UO only

|          | 0 hr prior to AKI stage | | 24 hr prior to AKI stage | | 48 hr prior to AKI stage | |
|----------|---------|---------|---------|---------|---------|---------|
|          | Cohort 1 | Cohort 2 | Cohort 1 | Cohort 2 | Cohort 1 | Cohort 2 |
| median   | 0.356 | 0.502 | 0.356 | 0.502 | 0.356 | 0.502 |
| average  | 0.454 | 0.758 | 0.454 | 0.758 | 0.454 | 0.758 |
| stdev    | 0.279 | 0.787 | 0.279 | 0.787 | 0.279 | 0.787 |
| p (t-test) |     | 0.037 |       | 0.037 |       | 0.037 |
| min      | 0.121 | 0.121 | 0.121 | 0.121 | 0.121 | 0.121 |
| max      | 1.282 | 3.215 | 1.282 | 3.215 | 1.282 | 3.215 |
| n (Samp) | 41    | 14    | 41    | 14    | 41    | 14    |
| n (Pat)  | 41    | 14    | 41    | 14    | 41    | 14    | sCr or UO

| Time prior AKI stage | AUC | SE | nCohort 1 | nCohort 2 | p |
|---|---|---|---|---|---|
| 0 hours | 0.66 | 0.080 | 52 | 17 | 0.040 |
| 24 hours | 0.66 | 0.080 | 52 | 17 | 0.040 |
| 48 hours | 0.66 | 0.080 | 52 | 17 | 0.040 | sCr only

| Time prior AKI stage | AUC | SE | nCohort 1 | nCohort 2 | p |
|---|---|---|---|---|---|
| 0 hours | 0.92 | 0.136 | 19 | 2 | 0.002 |
| 24 hours | 0.92 | 0.136 | 19 | 2 | 0.002 |
| 48 hours | 0.92 | 0.136 | 19 | 2 | 0.002 |

UO only

| Time prior AKI stage | AUC | SE | nCohort 1 | nCohort 2 | p |
|---|---|---|---|---|---|
| 0 hours | 0.69 | 0.087 | 41 | 14 | 0.033 |
| 24 hours | 0.69 | 0.087 | 41 | 14 | 0.033 |
| 48 hours | 0.69 | 0.087 | 41 | 14 | 0.033 |

Fig. 7 Continued sCr or UO

| Time prior AKI stage | Cutoff value | sens | spec | Quartile | OR | 95% CI of OR | |
|---|---|---|---|---|---|---|---|
| 0 hours | 0.44038 | 71% | 67% | 1 | | | |
| | 0.34212 | 82% | 40% | 2 | 3.4 | 0.2 | 60.8 |
| | 0.33021 | 94% | 40% | 3 | 11.2 | 0.9 | 144.7 |
| | 0.50872 | 53% | 71% | 4 | 8.0 | 0.6 | 104.8 |
| | 0.64703 | 29% | 81% | | | | |
| | 0.8854 | 12% | 90% | | | | |
| 24 hours | 0.44038 | 71% | 67% | 1 | | | |
| | 0.34212 | 82% | 40% | 2 | 3.4 | 0.2 | 60.8 |
| | 0.33021 | 94% | 40% | 3 | 11.2 | 0.9 | 144.7 |
| | 0.50872 | 53% | 71% | 4 | 8.0 | 0.6 | 104.8 |
| | 0.64703 | 29% | 81% | | | | |
| | 0.8854 | 12% | 90% | | | | |
| 48 hours | 0.44038 | 71% | 67% | 1 | | | |
| | 0.34212 | 82% | 40% | 2 | 3.4 | 0.2 | 60.8 |
| | 0.33021 | 94% | 40% | 3 | 11.2 | 0.9 | 144.7 |
| | 0.50872 | 53% | 71% | 4 | 8.0 | 0.6 | 104.8 |
| | 0.64703 | 29% | 81% | | | | |
| | 0.8854 | 12% | 90% | | | | |

UO only

| Time prior AKI stage | Cutoff value | sens | spec | Quartile | OR | 95% CI of OR | |
|---|---|---|---|---|---|---|---|
| 0 hours | 0.44038 | 71% | 73% | 1 | | | |
| | 0.33021 | 93% | 41% | 2 | 2.0 | 0.1 | 52.4 |
| | 0.33021 | 93% | 41% | 3 | 12.0 | 0.8 | 175.6 |
| | 0.42395 | 71% | 71% | 4 | 4.8 | 0.3 | 79.7 |
| | 0.64703 | 29% | 80% | | | | |
| | 0.8854 | 14% | 90% | | | | |
| 24 hours | 0.44038 | 71% | 73% | 1 | | | |
| | 0.33021 | 93% | 41% | 2 | 2.0 | 0.1 | 52.4 |
| | 0.33021 | 93% | 41% | 3 | 12.0 | 0.8 | 175.6 |
| | 0.42395 | 71% | 71% | 4 | 4.8 | 0.3 | 79.7 |
| | 0.64703 | 29% | 80% | | | | |
| | 0.8854 | 14% | 90% | | | | |
| 48 hours | 0.44038 | 71% | 73% | 1 | | | |
| | 0.33021 | 93% | 41% | 2 | 2.0 | 0.1 | 52.4 |
| | 0.33021 | 93% | 41% | 3 | 12.0 | 0.8 | 175.6 |
| | 0.42395 | 71% | 71% | 4 | 4.8 | 0.3 | 79.7 |
| | 0.64703 | 29% | 80% | | | | |
| | 0.8854 | 14% | 90% | | | | |

P-selectin glycoprotein ligand 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 311.269 | 239.327 | 311.269 | 239.327 | 311.269 | 239.327 |
| average | 318.895 | 252.903 | 318.895 | 252.903 | 318.895 | 252.903 |
| stdev | 123.002 | 97.315 | 123.002 | 97.315 | 123.002 | 97.315 |
| p (t-test) | | 0.038 | | 0.038 | | 0.038 |
| min | 70.652 | 96.193 | 70.652 | 96.193 | 70.652 | 96.193 |
| max | 853.893 | 524.267 | 853.893 | 524.267 | 853.893 | 524.267 |
| n (Samp) | 53 | 19 | 53 | 19 | 53 | 19 |
| n (Pat) | 53 | 19 | 53 | 19 | 53 | 19 |

Fig. 7 Continued sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 269.837 | 261.702 | 269.837 | 261.702 | 269.837 | 261.702 |
| average | 316.369 | 274.337 | 316.369 | 274.337 | 316.369 | 274.337 |
| stdev | 161.856 | 86.093 | 161.856 | 86.093 | 161.856 | 86.093 |
| p (t-test) |  | 0.624 |  | 0.624 |  | 0.624 |
| min | 70.652 | 194.647 | 70.652 | 194.647 | 70.652 | 194.647 |
| max | 853.893 | 379.297 | 853.893 | 379.297 | 853.893 | 379.297 |
| n (Samp) | 18 | 4 | 18 | 4 | 18 | 4 |
| n (Pat) | 18 | 4 | 18 | 4 | 18 | 4 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 311.586 | 241.675 | 311.586 | 241.675 | 311.586 | 241.675 |
| average | 312.904 | 248.031 | 312.904 | 248.031 | 312.904 | 248.031 |
| stdev | 95.178 | 101.417 | 95.178 | 101.417 | 95.178 | 101.417 |
| p (t-test) |  | 0.025 |  | 0.025 |  | 0.025 |
| min | 162.557 | 96.193 | 162.557 | 96.193 | 162.557 | 96.193 |
| max | 654.702 | 524.267 | 654.702 | 524.267 | 654.702 | 524.267 |
| n (Samp) | 44 | 16 | 44 | 16 | 44 | 16 |
| n (Pat) | 44 | 16 | 44 | 16 | 44 | 16 | sCr or UO

| Time prior AKI stage | AUC | SE | nCohort 1 | nCohort 2 | p |
|---|---|---|---|---|---|
| 0 hours | 0.31 | 0.066 | 53 | 19 | 0.003 |
| 24 hours | 0.31 | 0.066 | 53 | 19 | 0.003 |
| 48 hours | 0.31 | 0.066 | 53 | 19 | 0.003 | sCr only

| Time prior AKI stage | AUC | SE | nCohort 1 | nCohort 2 | p |
|---|---|---|---|---|---|
| 0 hours | 0.40 | 0.153 | 18 | 4 | 0.525 |
| 24 hours | 0.40 | 0.153 | 18 | 4 | 0.525 |
| 48 hours | 0.40 | 0.153 | 18 | 4 | 0.525 |

UO only

| Time prior AKI stage | AUC | SE | nCohort 1 | nCohort 2 | p |
|---|---|---|---|---|---|
| 0 hours | 0.29 | 0.070 | 44 | 16 | 0.003 |
| 24 hours | 0.29 | 0.070 | 44 | 16 | 0.003 |
| 48 hours | 0.29 | 0.070 | 44 | 16 | 0.003 | sCr or UO

| Time prior AKI stage | Cutoff value | sens | spec | Quartile | OR | 95% CI of OR | |
|---|---|---|---|---|---|---|---|
| 0 hours | 212.916 | 74% | 17% | 1 |  |  |  |
|  | 188.395 | 84% | 11% | 2 | 0.3 | 0.0 | 5.1 |
|  | 96.1934 | 95% | 2% | 3 | 2.5 | 0.7 | 8.9 |
|  | 346.99 | 16% | 72% | 4 | 5.0 | 1.5 | 16.9 |
|  | 386.761 | 5% | 81% |  |  |  |  |
|  | 430.758 | 5% | 91% |  |  |  |  |
| 24 hours | 212.916 | 74% | 17% | 1 |  |  |  |
|  | 188.395 | 84% | 11% | 2 | 0.3 | 0.0 | 5.1 |
|  | 96.1934 | 95% | 2% | 3 | 2.5 | 0.7 | 8.9 |
|  | 346.99 | 16% | 72% | 4 | 5.0 | 1.5 | 16.9 |
|  | 386.761 | 5% | 81% |  |  |  |  |
|  | 430.758 | 5% | 91% |  |  |  |  |

Fig. 7 Continued

| 48 hours | 212.916 | 74% | 17% | 1 | | | |
| | 188.395 | 84% | 11% | 2 | 0.3 | 0.0 | 5.1 |
| | 96.1934 | 95% | 2% | 3 | 2.5 | 0.7 | 8.9 |
| | 346.99 | 16% | 72% | 4 | 5.0 | 1.5 | 16.9 |
| | 386.761 | 5% | 81% | | | | |
| | 430.758 | 5% | 91% | | | | | sCr only

| Time prior AKI stage | Cutoff value | sens | spec | Quartile | OR | 95% CI of OR | |
| --- | --- | --- | --- | --- | --- | --- | --- |
| 0 hours | 194.647 | 75% | 11% | 1 | | | |
| | 139.124 | 100% | 11% | 2 | 1.3 | 0.0 | 152.2 |
| | 139.124 | 100% | 11% | 3 | 0.0 | 0.0 | na |
| | 358.862 | 25% | 72% | 4 | 3.3 | 0.1 | 179.3 |
| | 371.516 | 25% | 83% | | | | |
| | 430.758 | 0% | 94% | | | | |
| 24 hours | 194.647 | 75% | 11% | 1 | | | |
| | 139.124 | 100% | 11% | 2 | 1.3 | 0.0 | 152.2 |
| | 139.124 | 100% | 11% | 3 | 0.0 | 0.0 | na |
| | 358.862 | 25% | 72% | 4 | 3.3 | 0.1 | 179.3 |
| | 371.516 | 25% | 83% | | | | |
| | 430.758 | 0% | 94% | | | | |
| 48 hours | 194.647 | 75% | 11% | 1 | | | |
| | 139.124 | 100% | 11% | 2 | 1.3 | 0.0 | 152.2 |
| | 139.124 | 100% | 11% | 3 | 0.0 | 0.0 | na |
| | 358.862 | 25% | 72% | 4 | 3.3 | 0.1 | 179.3 |
| | 371.516 | 25% | 83% | | | | |
| | 430.758 | 0% | 94% | | | | |

UO only

| Time prior AKI stage | Cutoff value | sens | spec | Quartile | OR | 95% CI of OR | |
| --- | --- | --- | --- | --- | --- | --- | --- |
| 0 hours | 191.148 | 75% | 11% | 1 | | | |
| | 188.395 | 81% | 9% | 2 | 0.5 | 0.0 | 11.7 |
| | 96.1934 | 94% | 0% | 3 | 4.3 | 0.8 | 23.1 |
| | 334.792 | 13% | 70% | 4 | 5.7 | 1.1 | 29.8 |
| | 386.761 | 6% | 82% | | | | |
| | 420.825 | 6% | 91% | | | | |
| 24 hours | 191.148 | 75% | 11% | 1 | | | |
| | 188.395 | 81% | 9% | 2 | 0.5 | 0.0 | 11.7 |
| | 96.1934 | 94% | 0% | 3 | 4.3 | 0.8 | 23.1 |
| | 334.792 | 13% | 70% | 4 | 5.7 | 1.1 | 29.8 |
| | 386.761 | 6% | 82% | | | | |
| | 420.825 | 6% | 91% | | | | |
| 48 hours | 191.148 | 75% | 11% | 1 | | | |
| | 188.395 | 81% | 9% | 2 | 0.5 | 0.0 | 11.7 |
| | 96.1934 | 94% | 0% | 3 | 4.3 | 0.8 | 23.1 |
| | 334.792 | 13% | 70% | 4 | 5.7 | 1.1 | 29.8 |
| | 386.761 | 6% | 82% | | | | |
| | 420.825 | 6% | 91% | | | | |

Fig. 7 Continued

Stem cell factor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 343.500 | 266.000 | 343.500 | 266.000 | 343.500 | 266.000 |
| average | 469.107 | 308.143 | 469.107 | 308.143 | 469.107 | 308.143 |
| stdev | 749.057 | 127.739 | 749.057 | 127.739 | 749.057 | 127.739 |
| p (t-test) |  | 0.332 |  | 0.332 |  | 0.332 |
| min | 127.000 | 150.000 | 127.000 | 150.000 | 127.000 | 150.000 |
| max | 5840.000 | 553.000 | 5840.000 | 553.000 | 5840.000 | 553.000 |
| n (Samp) | 56 | 21 | 56 | 21 | 56 | 21 |
| n (Pat) | 56 | 21 | 56 | 21 | 56 | 21 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 307.000 | 613.000 | 307.000 | 613.000 | 307.000 | 613.000 |
| average | 344.143 | 486.600 | 344.143 | 486.600 | 344.143 | 486.600 |
| stdev | 127.539 | 272.120 | 127.539 | 272.120 | 127.539 | 272.120 |
| p (t-test) |  | 0.088 |  | 0.088 |  | 0.088 |
| min | 170.000 | 174.000 | 170.000 | 174.000 | 170.000 | 174.000 |
| max | 575.000 | 769.000 | 575.000 | 769.000 | 575.000 | 769.000 |
| n (Samp) | 21 | 5 | 21 | 5 | 21 | 5 |
| n (Pat) | 21 | 5 | 21 | 5 | 21 | 5 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 363.500 | 305.000 | 363.500 | 305.000 | 363.500 | 305.000 |
| average | 505.435 | 301.824 | 505.435 | 301.824 | 505.435 | 301.824 |
| stdev | 822.057 | 115.063 | 822.057 | 115.063 | 822.057 | 115.063 |
| p (t-test) |  | 0.315 |  | 0.315 |  | 0.315 |
| min | 127.000 | 150.000 | 127.000 | 150.000 | 127.000 | 150.000 |
| max | 5840.000 | 553.000 | 5840.000 | 553.000 | 5840.000 | 553.000 |
| n (Samp) | 46 | 17 | 46 | 17 | 46 | 17 |
| n (Pat) | 46 | 17 | 46 | 17 | 46 | 17 | sCr or UO

| Time prior AKI stage | AUC | SE | nCohort 1 | nCohort 2 | p |
|---|---|---|---|---|---|
| 0 hours | 0.38 | 0.069 | 56 | 21 | 0.080 |
| 24 hours | 0.38 | 0.069 | 56 | 21 | 0.080 |
| 48 hours | 0.38 | 0.069 | 56 | 21 | 0.080 | sCr only

| Time prior AKI stage | AUC | SE | nCohort 1 | nCohort 2 | p |
|---|---|---|---|---|---|
| 0 hours | 0.65 | 0.147 | 21 | 5 | 0.314 |
| 24 hours | 0.65 | 0.147 | 21 | 5 | 0.314 |
| 48 hours | 0.65 | 0.147 | 21 | 5 | 0.314 |

UO only

| Time prior AKI stage | AUC | SE | nCohort 1 | nCohort 2 | p |
|---|---|---|---|---|---|
| 0 hours | 0.34 | 0.074 | 46 | 17 | 0.035 |
| 24 hours | 0.34 | 0.074 | 46 | 17 | 0.035 |
| 48 hours | 0.34 | 0.074 | 46 | 17 | 0.035 |

Fig. 7 Continued sCr or UO

| Time prior AKI stage | Cutoff value | sens | spec | Quartile | OR | 95% CI of OR | |
|---|---|---|---|---|---|---|---|
| 0 hours | 214 | 76% | 18% | 1 | | | |
| | 198 | 81% | 13% | 2 | 1.4 | 0.5 | 4.5 |
| | 173 | 90% | 9% | 3 | 1.1 | 0.3 | 3.7 |
| | 442 | 19% | 71% | 4 | 2.9 | 1.0 | 8.2 |
| | 517 | 10% | 80% | | | | |
| | 608 | 0% | 91% | | | | |
| 24 hours | 214 | 76% | 18% | 1 | | | |
| | 198 | 81% | 13% | 2 | 1.4 | 0.5 | 4.5 |
| | 173 | 90% | 9% | 3 | 1.1 | 0.3 | 3.7 |
| | 442 | 19% | 71% | 4 | 2.9 | 1.0 | 8.2 |
| | 517 | 10% | 80% | | | | |
| | 608 | 0% | 91% | | | | |
| 48 hours | 214 | 76% | 18% | 1 | | | |
| | 198 | 81% | 13% | 2 | 1.4 | 0.5 | 4.5 |
| | 173 | 90% | 9% | 3 | 1.1 | 0.3 | 3.7 |
| | 442 | 19% | 71% | 4 | 2.9 | 1.0 | 8.2 |
| | 517 | 10% | 80% | | | | |
| | 608 | 0% | 91% | | | | | sCr only

| Time prior AKI stage | Cutoff value | sens | spec | Quartile | OR | 95% CI of OR | |
|---|---|---|---|---|---|---|---|
| 0 hours | 216 | 80% | 19% | 1 | | | |
| | 216 | 80% | 19% | 2 | 0.0 | 0.0 | na |
| | 170 | 100% | 5% | 3 | 0.0 | 0.0 | na |
| | 377 | 60% | 71% | 4 | 1.5 | 0.1 | 20.5 |
| | 523 | 60% | 81% | | | | |
| | 534 | 60% | 90% | | | | |
| 24 hours | 216 | 80% | 19% | 1 | | | |
| | 216 | 80% | 19% | 2 | 0.0 | 0.0 | na |
| | 170 | 100% | 5% | 3 | 0.0 | 0.0 | na |
| | 377 | 60% | 71% | 4 | 1.5 | 0.1 | 20.5 |
| | 523 | 60% | 81% | | | | |
| | 534 | 60% | 90% | | | | |
| 48 hours | 216 | 80% | 19% | 1 | | | |
| | 216 | 80% | 19% | 2 | 0.0 | 0.0 | na |
| | 170 | 100% | 5% | 3 | 0.0 | 0.0 | na |
| | 377 | 60% | 71% | 4 | 1.5 | 0.1 | 20.5 |
| | 523 | 60% | 81% | | | | |
| | 534 | 60% | 90% | | | | |

UO only

| Time prior AKI stage | Cutoff value | sens | spec | Quartile | OR | 95% CI of OR | |
|---|---|---|---|---|---|---|---|
| 0 hours | 216 | 71% | 17% | 1 | | | |
| | 198 | 82% | 13% | 2 | 1.6 | 0.2 | 11.1 |
| | 159 | 94% | 7% | 3 | 4.2 | 0.8 | 21.7 |
| | 489 | 12% | 72% | 4 | 4.7 | 0.9 | 24.7 |
| | 517 | 6% | 80% | | | | |
| | 644 | 0% | 91% | | | | |
| 24 hours | 216 | 71% | 17% | 1 | | | |
| | 198 | 82% | 13% | 2 | 1.6 | 0.2 | 11.1 |
| | 159 | 94% | 7% | 3 | 4.2 | 0.8 | 21.7 |
| | 489 | 12% | 72% | 4 | 4.7 | 0.9 | 24.7 |
| | 517 | 6% | 80% | | | | |
| | 644 | 0% | 91% | | | | |

Fig. 7 Continued

| 48 hours | 216 | 71% | 17% | 1 | | | |
| | 198 | 82% | 13% | 2 | 1.6 | 0.2 | 11.1 |
| | 159 | 94% | 7% | 3 | 4.2 | 0.8 | 21.7 |
| | 489 | 12% | 72% | 4 | 4.7 | 0.9 | 24.7 |
| | 517 | 6% | 80% | | | | |
| | 644 | 0% | 91% | | | | |

Fig. 7 Continued

Aspartate aminotransferase, cytoplasmic sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 19.450 | 24.300 | 19.450 | 24.000 | 19.450 | 25.250 |
| average | 21.115 | 23.444 | 21.115 | 21.786 | 21.115 | 24.216 |
| stdev | 28.506 | 7.721 | 28.506 | 9.104 | 28.506 | 9.516 |
| p (t-test) |  | 0.739 |  | 0.924 |  | 0.734 |
| min | 2.080 | 3.650 | 2.080 | 3.650 | 2.080 | 3.560 |
| max | 251.000 | 41.100 | 251.000 | 41.100 | 251.000 | 41.100 |
| n (Samp) | 112 | 17 | 112 | 17 | 112 | 10 |
| n (Pat) | 112 | 17 | 112 | 17 | 112 | 10 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 19.950 | 24.400 | 19.950 | 24.400 | 19.950 | 24.000 |
| average | 19.983 | 25.513 | 19.983 | 25.475 | 19.983 | 26.320 |
| stdev | 23.449 | 7.455 | 23.449 | 7.486 | 23.449 | 9.022 |
| p (t-test) |  | 0.508 |  | 0.510 |  | 0.548 |
| min | 2.040 | 18.700 | 2.040 | 18.700 | 2.040 | 18.700 |
| max | 251.000 | 41.100 | 251.000 | 41.100 | 251.000 | 41.100 |
| n (Samp) | 180 | 8 | 180 | 8 | 180 | 5 |
| n (Pat) | 180 | 8 | 180 | 8 | 180 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 20.400 | 25.000 | 20.400 | 24.300 | 20.400 | 25.500 |
| average | 22.702 | 23.859 | 22.702 | 21.325 | 22.702 | 25.094 |
| stdev | 31.428 | 9.232 | 31.428 | 11.053 | 31.428 | 11.158 |
| p (t-test) |  | 0.904 |  | 0.886 |  | 0.842 |
| min | 1.890 | 3.650 | 1.890 | 3.650 | 1.890 | 3.560 |
| max | 251.000 | 41.100 | 251.000 | 41.100 | 251.000 | 41.100 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
|---|---|---|---|---|---|
| 0 hours | 0.66 | 0.076 | 112 | 17 | 0.034 |
| 24 hours | 0.62 | 0.077 | 112 | 17 | 0.126 |
| 48 hours | 0.69 | 0.096 | 112 | 10 | 0.051 | sCr only

| Time prior AKI stage | AUC | SE | nCohort 1 | nCohort 2 | p |
|---|---|---|---|---|---|
| 0 hours | 0.68 | 0.107 | 180 | 8 | 0.090 |
| 24 hours | 0.68 | 0.107 | 180 | 8 | 0.092 |
| 48 hours | 0.68 | 0.134 | 180 | 5 | 0.175 |

UO only

| Time prior AKI stage | AUC | SE | nCohort 1 | nCohort 2 | p |
|---|---|---|---|---|---|
| 0 hours | 0.66 | 0.094 | 89 | 11 | 0.091 |
| 24 hours | 0.59 | 0.095 | 89 | 11 | 0.325 |
| 48 hours | 0.71 | 0.113 | 89 | 7 | 0.066 |

Fig. 8 sCr or UO

| Time prior AKI stage | Cutoff value | sens | spec | Quartile | OR | 95% CI of OR | |
|---|---|---|---|---|---|---|---|
| 0 hours | 20.7 | 71% | 57% | 1 | | | |
| | 18.9 | 82% | 49% | 2 | 3.2 | 0.2 | 49.9 |
| | 14.6 | 94% | 33% | 3 | 8.7 | 0.8 | 93.9 |
| | 24.3 | 47% | 71% | 4 | 6.9 | 0.6 | 77.7 |
| | 27.1 | 29% | 80% | | | | |
| | 29.2 | 12% | 90% | | | | |
| 24 hours | 18.9 | 71% | 49% | 1 | | | |
| | 14.7 | 82% | 33% | 2 | 5.7 | 0.5 | 69.1 |
| | 4.51 | 94% | 28% | 3 | 7.2 | 0.6 | 80.9 |
| | 24.3 | 41% | 71% | 4 | 5.5 | 0.5 | 66.4 |
| | 27.1 | 29% | 80% | | | | |
| | 29.2 | 12% | 90% | | | | |
| 48 hours | 23.5 | 70% | 66% | 1 | | | |
| | 19.6 | 80% | 54% | 2 | 1.0 | 0.0 | 55.6 |
| | 18.6 | 90% | 47% | 3 | 4.5 | 0.3 | 59.6 |
| | 24.3 | 60% | 71% | 4 | 4.3 | 0.3 | 57.3 |
| | 27.1 | 40% | 80% | | | | |
| | 29.2 | 20% | 90% | | | | |

UO only

| Time prior AKI stage | Cutoff value | sens | spec | Quartile | OR | 95% CI of OR | |
|---|---|---|---|---|---|---|---|
| 0 hours | 22.8 | 73% | 65% | 1 | | | |
| | 20.7 | 82% | 53% | 2 | 2.1 | 0.1 | 46.6 |
| | 14.4 | 91% | 30% | 3 | 4.6 | 0.3 | 63.1 |
| | 24.7 | 55% | 72% | 4 | 4.6 | 0.3 | 63.1 |
| | 27.8 | 18% | 82% | | | | |
| | 30.2 | 9% | 92% | | | | |
| 24 hours | 14.7 | 73% | 30% | 1 | | | |
| | 14.4 | 82% | 30% | 2 | 1.0 | 0.1 | 8.4 |
| | 4.51 | 91% | 26% | 3 | 2.2 | 0.4 | 11.4 |
| | 24.7 | 45% | 72% | 4 | 1.6 | 0.3 | 9.6 |
| | 27.8 | 18% | 82% | | | | |
| | 30.2 | 9% | 92% | | | | |
| 48 hours | 24.7 | 71% | 72% | 1 | | | |
| | 23.5 | 86% | 66% | 2 | 0.0 | 0.0 | na |
| | 3.47 | 100% | 19% | 3 | 3.3 | 0.2 | 53.6 |
| | 24.7 | 71% | 72% | 4 | 3.3 | 0.2 | 53.6 |
| | 27.8 | 29% | 82% | | | | |
| | 30.2 | 14% | 92% | | | | |

Fig. 8 Continued

CD40 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 1.750 | 5.060 | 1.750 | 3.190 | 1.750 | 2.380 |
| average | 2.390 | 5.809 | 2.390 | 5.000 | 2.390 | 2.823 |
| stdev | 2.988 | 6.010 | 2.988 | 6.158 | 2.988 | 1.317 |
| p (t-test) |  | 0.000 |  | 0.005 |  | 0.651 |
| min | 0.547 | 1.680 | 0.547 | 1.640 | 0.547 | 1.560 |
| max | 28.000 | 28.100 | 28.000 | 28.100 | 28.000 | 5.280 |
| n (Samp) | 112 | 17 | 112 | 17 | 112 | 10 |
| n (Pat) | 112 | 17 | 112 | 17 | 112 | 10 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 1.775 | 4.745 | 1.775 | 2.995 | 1.775 | 2.380 |
| average | 2.360 | 7.061 | 2.360 | 6.371 | 2.360 | 3.170 |
| stdev | 2.579 | 8.652 | 2.579 | 8.933 | 2.579 | 1.807 |
| p (t-test) |  | 0.000 |  | 0.000 |  | 0.487 |
| min | 0.547 | 1.680 | 0.547 | 1.640 | 0.547 | 1.560 |
| max | 28.000 | 28.100 | 28.000 | 28.100 | 28.000 | 5.280 |
| n (Samp) | 180 | 8 | 180 | 8 | 180 | 5 |
| n (Pat) | 180 | 8 | 180 | 8 | 180 | 5 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 1.710 | 5.430 | 1.710 | 4.910 | 1.710 | 2.910 |
| average | 2.003 | 4.881 | 2.003 | 4.132 | 2.003 | 3.230 |
| stdev | 1.218 | 1.799 | 1.218 | 1.622 | 1.218 | 1.376 |
| p (t-test) |  | 0.000 |  | 0.000 |  | 0.013 |
| min | 0.547 | 1.900 | 0.547 | 1.690 | 0.547 | 1.690 |
| max | 6.610 | 6.720 | 6.610 | 6.050 | 6.610 | 5.280 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
|---|---|---|---|---|---|
| 0 hours | 0.85 | 0.061 | 112 | 17 | 0.000 |
| 24 hours | 0.78 | 0.068 | 112 | 17 | 0.000 |
| 48 hours | 0.68 | 0.096 | 112 | 10 | 0.055 | sCr only

| Time prior AKI stage | AUC | SE | nCohort 1 | nCohort 2 | p |
|---|---|---|---|---|---|
| 0 hours | 0.83 | 0.091 | 180 | 8 | 0.000 |
| 24 hours | 0.76 | 0.100 | 180 | 8 | 0.008 |
| 48 hours | 0.69 | 0.133 | 180 | 5 | 0.147 |

UO only

| Time prior AKI stage | AUC | SE | nCohort 1 | nCohort 2 | p |
|---|---|---|---|---|---|
| 0 hours | 0.90 | 0.062 | 89 | 11 | 0.000 |
| 24 hours | 0.85 | 0.074 | 89 | 11 | 0.000 |
| 48 hours | 0.77 | 0.107 | 89 | 7 | 0.011 |

Fig. 8 Continued

CD40 Ligand sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.413 | 0.470 | 0.413 | 0.470 | 0.413 | 0.396 |
| average | 0.599 | 0.515 | 0.599 | 0.467 | 0.599 | 0.491 |
| stdev | 0.612 | 0.319 | 0.612 | 0.275 | 0.612 | 0.275 |
| p (t-test) |  | 0.583 |  | 0.385 |  | 0.581 |
| min | 0.019 | 0.069 | 0.019 | 0.051 | 0.019 | 0.191 |
| max | 4.030 | 1.070 | 4.030 | 1.070 | 4.030 | 1.070 |
| n (Samp) | 112 | 17 | 112 | 17 | 112 | 10 |
| n (Pat) | 112 | 17 | 112 | 17 | 112 | 10 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.415 | 0.488 | 0.415 | 0.488 | 0.415 | 0.505 |
| average | 0.599 | 0.595 | 0.599 | 0.571 | 0.599 | 0.649 |
| stdev | 0.582 | 0.395 | 0.582 | 0.378 | 0.582 | 0.289 |
| p (t-test) |  | 0.985 |  | 0.893 |  | 0.851 |
| min | 0.019 | 0.069 | 0.019 | 0.052 | 0.019 | 0.351 |
| max | 4.030 | 1.070 | 4.030 | 1.070 | 4.030 | 1.070 |
| n (Samp) | 180 | 8 | 180 | 8 | 180 | 5 |
| n (Pat) | 180 | 8 | 180 | 8 | 180 | 5 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.413 | 0.480 | 0.413 | 0.480 | 0.413 | 0.364 |
| average | 0.613 | 0.507 | 0.613 | 0.450 | 0.613 | 0.382 |
| stdev | 0.654 | 0.281 | 0.654 | 0.220 | 0.654 | 0.151 |
| p (t-test) |  | 0.595 |  | 0.414 |  | 0.354 |
| min | 0.019 | 0.105 | 0.019 | 0.051 | 0.019 | 0.191 |
| max | 4.030 | 1.070 | 4.030 | 0.895 | 4.030 | 0.624 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
| --- | --- | --- | --- | --- | --- |
| 0 hours | 0.52 | 0.076 | 112 | 17 | 0.838 |
| 24 hours | 0.49 | 0.075 | 112 | 17 | 0.841 |
| 48 hours | 0.52 | 0.096 | 112 | 10 | 0.860 | sCr only

| Time prior AKI stage | AUC | SE | nCohort 1 | nCohort 2 | p |
| --- | --- | --- | --- | --- | --- |
| 0 hours | 0.55 | 0.107 | 180 | 8 | 0.647 |
| 24 hours | 0.54 | 0.107 | 180 | 8 | 0.703 |
| 48 hours | 0.64 | 0.136 | 180 | 5 | 0.300 |

UO only

| Time prior AKI stage | AUC | SE | nCohort 1 | nCohort 2 | p |
| --- | --- | --- | --- | --- | --- |
| 0 hours | 0.53 | 0.094 | 89 | 11 | 0.773 |
| 24 hours | 0.49 | 0.092 | 89 | 11 | 0.872 |
| 48 hours | 0.43 | 0.108 | 89 | 7 | 0.544 |

Fig. 8 Continued sCr or UO

| Time prior AKI stage | Cutoff value | sens | spec | Quartile | OR | 95% CI of OR | |
|---|---|---|---|---|---|---|---|
| 0 hours | 0.338 | 71% | 46% | 1 | | | |
| | 0.237 | 82% | 25% | 2 | 1.0 | 0.2 | 4.2 |
| | 0.0976 | 94% | 12% | 3 | 2.7 | 0.9 | 8.0 |
| | 0.75 | 24% | 71% | 4 | 1.3 | 0.4 | 4.8 |
| | 0.83 | 24% | 80% | | | | |
| | 1.1 | 0% | 90% | | | | |
| 24 hours | 0.338 | 71% | 46% | 1 | | | |
| | 0.237 | 82% | 25% | 2 | 2.8 | 1.0 | 8.2 |
| | 0.0511 | 94% | 1% | 3 | 1.4 | 0.4 | 5.1 |
| | 0.75 | 18% | 71% | 4 | 1.0 | 0.2 | 4.4 |
| | 0.83 | 12% | 80% | | | | |
| | 1.1 | 0% | 90% | | | | |
| 48 hours | 0.338 | 70% | 46% | 1 | | | |
| | 0.324 | 80% | 43% | 2 | 1.5 | 0.3 | 8.8 |
| | 0.226 | 90% | 24% | 3 | 1.6 | 0.3 | 9.2 |
| | 0.75 | 20% | 71% | 4 | 1.0 | 0.1 | 7.9 |
| | 0.83 | 10% | 80% | | | | |
| | 1.1 | 0% | 90% | | | | | sCr only

| Time prior AKI stage | Cutoff value | sens | spec | Quartile | OR | 95% CI of OR | |
|---|---|---|---|---|---|---|---|
| 0 hours | 0.338 | 75% | 46% | 1 | | | |
| | 0.237 | 88% | 28% | 2 | 2.0 | 0.1 | 42.2 |
| | 0.0652 | 100% | 3% | 3 | 2.0 | 0.1 | 42.2 |
| | 0.75 | 38% | 70% | 4 | 3.1 | 0.2 | 46.7 |
| | 0.905 | 38% | 80% | | | | |
| | 1.16 | 0% | 90% | | | | |
| 24 hours | 0.338 | 75% | 46% | 1 | | | |
| | 0.237 | 88% | 28% | 2 | 2.0 | 0.1 | 42.2 |
| | 0.0246 | 100% | 1% | 3 | 2.0 | 0.1 | 42.2 |
| | 0.75 | 38% | 70% | 4 | 3.1 | 0.2 | 46.7 |
| | 0.905 | 25% | 80% | | | | |
| | 1.16 | 0% | 90% | | | | |
| 48 hours | 0.489 | 80% | 56% | 1 | | | |
| | 0.489 | 80% | 56% | 2 | na | na | na |
| | 0.338 | 100% | 46% | 3 | na | na | na |
| | 0.75 | 40% | 70% | 4 | na | na | na |
| | 0.905 | 20% | 80% | | | | |
| | 1.16 | 0% | 90% | | | | |

UO only

| Time prior AKI stage | Cutoff value | sens | spec | Quartile | OR | 95% CI of OR | |
|---|---|---|---|---|---|---|---|
| 0 hours | 0.416 | 73% | 52% | 1 | | | |
| | 0.324 | 82% | 43% | 2 | 1.0 | 0.1 | 8.4 |
| | 0.185 | 91% | 19% | 3 | 2.9 | 0.6 | 13.6 |
| | 0.745 | 18% | 71% | 4 | 1.0 | 0.1 | 8.4 |
| | 0.83 | 18% | 81% | | | | |
| | 1.16 | 0% | 91% | | | | |
| 24 hours | 0.365 | 73% | 48% | 1 | | | |
| | 0.324 | 82% | 43% | 2 | 7.6 | 0.6 | 89.7 |
| | 0.185 | 91% | 19% | 3 | 2.1 | 0.1 | 46.6 |
| | 0.745 | 9% | 71% | 4 | 2.1 | 0.1 | 46.6 |
| | 0.83 | 9% | 81% | | | | |
| | 1.16 | 0% | 91% | | | | |

Fig. 8 Continued

| 48 hours | 0.324 | 71% | 43% | 1 | | | |
| | 0.226 | 86% | 22% | 2 | na | na | na |
| | 0.185 | 100% | 19% | 3 | na | na | na |
| | 0.745 | 0% | 71% | 4 | na | na | na |
| | 0.83 | 0% | 81% | | | | |
| | 1.16 | 0% | 91% | | | | |

CXCL16 (C-X-C Motif chemokine 16)

sCr or UO

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 4.204 | 9.386 | 4.204 | 7.655 | 4.204 | 6.930 |
| average | 6.123 | 10.502 | 6.123 | 9.300 | 6.123 | 6.998 |
| stdev | 6.518 | 5.685 | 6.518 | 6.512 | 6.518 | 2.863 |
| p (t-test) | | 0.012 | | 0.089 | | 0.676 |
| min | 1.960 | 4.866 | 1.960 | 3.894 | 1.960 | 3.894 |
| max | 45.787 | 29.157 | 45.787 | 29.157 | 45.787 | 11.674 |
| n (Samp) | 107 | 16 | 107 | 14 | 107 | 10 |
| n (Pat) | 107 | 16 | 107 | 14 | 107 | 10 | sCr only

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 4.447 | 9.635 | 4.447 | 7.701 | 4.447 | 7.701 |
| average | 5.871 | 11.760 | 5.871 | 11.752 | 5.871 | 7.885 |
| stdev | 5.374 | 7.519 | 5.374 | 8.215 | 5.374 | 2.380 |
| p (t-test) | | 0.003 | | 0.006 | | 0.405 |
| min | 1.960 | 4.866 | 1.960 | 4.866 | 1.960 | 4.866 |
| max | 45.787 | 29.157 | 45.787 | 29.157 | 45.787 | 11.545 |
| n (Samp) | 172 | 8 | 172 | 7 | 172 | 5 |
| n (Pat) | 172 | 8 | 172 | 7 | 172 | 5 |

UO only

| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
|---|---|---|---|---|---|---|
| median | 4.271 | 8.693 | 4.271 | 7.701 | 4.271 | 6.252 |
| average | 5.179 | 9.495 | 5.179 | 7.658 | 5.179 | 6.566 |
| stdev | 2.843 | 3.016 | 2.843 | 3.508 | 2.843 | 2.796 |
| p (t-test) | | 0.000 | | 0.017 | | 0.218 |
| min | 1.960 | 5.778 | 1.960 | 3.894 | 1.960 | 3.894 |
| max | 18.483 | 14.552 | 18.483 | 14.552 | 18.483 | 11.674 |
| n (Samp) | 86 | 10 | 86 | 9 | 86 | 7 |
| n (Pat) | 86 | 10 | 86 | 9 | 86 | 7 | sCr or UO

| Time prior AKI stage | AUC | SE | nCohort 1 | nCohort 2 | p |
|---|---|---|---|---|---|
| 0 hours | 0.85 | 0.062 | 107 | 16 | 0.000 |
| 24 hours | 0.77 | 0.077 | 107 | 14 | 0.000 |
| 48 hours | 0.71 | 0.095 | 107 | 10 | 0.029 | sCr only

| Time prior AKI stage | AUC | SE | nCohort 1 | nCohort 2 | p |
|---|---|---|---|---|---|
| 0 hours | 0.87 | 0.082 | 172 | 8 | 0.000 |
| 24 hours | 0.85 | 0.093 | 172 | 7 | 0.000 |
| 48 hours | 0.80 | 0.121 | 172 | 5 | 0.014 |

Fig. 8 Continued

UO only

| Time prior AKI stage | AUC | SE | nCohort 1 | nCohort 2 | p |
|---|---|---|---|---|---|
| 0 hours | 0.88 | 0.072 | 86 | 10 | 0.000 |
| 24 hours | 0.75 | 0.097 | 86 | 9 | 0.010 |
| 48 hours | 0.68 | 0.115 | 86 | 7 | 0.113 |

EN-RAGE sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 30.036 | 79.526 | 30.036 | 77.235 | 30.036 | 66.341 |
| average | 60.145 | 167.525 | 60.145 | 172.587 | 60.145 | 85.477 |
| stdev | 82.268 | 276.376 | 82.268 | 288.035 | 82.268 | 74.741 |
| p (t-test) |  | 0.003 |  | 0.003 |  | 0.401 |
| min | 0.000 | 18.073 | 0.000 | 18.073 | 0.000 | 18.073 |
| max | 582.406 | 1063.972 | 582.406 | 1063.972 | 582.406 | 260.355 |
| n (Samp) | 99 | 13 | 99 | 12 | 99 | 8 |
| n (Pat) | 99 | 13 | 99 | 12 | 99 | 8 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 33.225 | 88.783 | 33.225 | 81.864 | 33.225 | 74.945 |
| average | 61.700 | 275.688 | 61.700 | 317.915 | 61.700 | 69.229 |
| stdev | 79.092 | 441.263 | 79.092 | 497.724 | 79.092 | 22.952 |
| p (t-test) |  | 0.000 |  | 0.000 |  | 0.870 |
| min | 0.000 | 43.960 | 0.000 | 43.960 | 0.000 | 43.960 |
| max | 582.406 | 1063.972 | 582.406 | 1063.972 | 582.406 | 88.783 |
| n (Samp) | 160 | 5 | 160 | 4 | 160 | 3 |
| n (Pat) | 160 | 5 | 160 | 4 | 160 | 3 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 31.753 | 71.210 | 31.753 | 71.210 | 31.753 | 65.208 |
| average | 52.602 | 91.829 | 52.602 | 91.829 | 52.602 | 85.004 |
| stdev | 56.882 | 71.336 | 56.882 | 71.336 | 56.882 | 80.717 |
| p (t-test) |  | 0.048 |  | 0.048 |  | 0.165 |
| min | 0.000 | 18.073 | 0.000 | 18.073 | 0.000 | 18.073 |
| max | 328.866 | 260.355 | 328.866 | 260.355 | 328.866 | 260.355 |
| n (Samp) | 84 | 10 | 84 | 10 | 84 | 7 |
| n (Pat) | 84 | 10 | 84 | 10 | 84 | 7 | sCr or UO

| Time prior AKI stage | AUC | SE | nCohort 1 | nCohort 2 | p |
|---|---|---|---|---|---|
| 0 hours | 0.77 | 0.080 | 99 | 13 | 0.001 |
| 24 hours | 0.76 | 0.083 | 99 | 12 | 0.002 |
| 48 hours | 0.71 | 0.106 | 99 | 8 | 0.051 | sCr only

| Time prior AKI stage | AUC | SE | nCohort 1 | nCohort 2 | p |
|---|---|---|---|---|---|
| 0 hours | 0.81 | 0.119 | 160 | 5 | 0.011 |
| 24 hours | 0.80 | 0.135 | 160 | 4 | 0.028 |
| 48 hours | 0.73 | 0.168 | 160 | 3 | 0.172 |

Fig. 8 Continued

UO only

| Time prior AKI stage | AUC | SE | nCohort 1 | nCohort 2 | p |
|---|---|---|---|---|---|
| 0 hours | 0.75 | 0.093 | 84 | 10 | 0.008 |
| 24 hours | 0.75 | 0.093 | 84 | 10 | 0.008 |
| 48 hours | 0.70 | 0.114 | 84 | 7 | 0.075 |

Eotaxin sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 69.800 | 92.000 | 69.800 | 92.000 | 69.800 | 104.400 |
| average | 90.773 | 142.906 | 90.773 | 133.976 | 90.773 | 148.700 |
| stdev | 76.700 | 95.471 | 76.700 | 101.333 | 76.700 | 122.092 |
| p (t-test) |  | 0.013 |  | 0.041 |  | 0.032 |
| min | 0.410 | 47.500 | 0.410 | 27.400 | 0.410 | 27.400 |
| max | 441.000 | 424.000 | 441.000 | 424.000 | 441.000 | 424.000 |
| n (Samp) | 112 | 17 | 112 | 17 | 112 | 10 |
| n (Pat) | 112 | 17 | 112 | 17 | 112 | 10 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 74.250 | 140.500 | 74.250 | 123.500 | 74.250 | 131.000 |
| average | 98.645 | 138.763 | 98.645 | 132.000 | 98.645 | 122.860 |
| stdev | 112.726 | 61.558 | 112.726 | 66.143 | 112.726 | 84.249 |
| p (t-test) |  | 0.319 |  | 0.408 |  | 0.635 |
| min | 0.410 | 47.500 | 0.410 | 27.400 | 0.410 | 27.400 |
| max | 1240.000 | 212.000 | 1240.000 | 212.000 | 1240.000 | 212.000 |
| n (Samp) | 180 | 8 | 180 | 8 | 180 | 5 |
| n (Pat) | 180 | 8 | 180 | 8 | 180 | 5 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 67.700 | 88.400 | 67.700 | 77.800 | 67.700 | 77.800 |
| average | 91.580 | 145.727 | 91.580 | 136.845 | 91.580 | 159.514 |
| stdev | 79.355 | 111.879 | 79.355 | 118.218 | 79.355 | 138.025 |
| p (t-test) |  | 0.045 |  | 0.096 |  | 0.043 |
| min | 0.410 | 58.000 | 0.410 | 44.000 | 0.410 | 58.000 |
| max | 441.000 | 424.000 | 441.000 | 424.000 | 441.000 | 424.000 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
|---|---|---|---|---|---|
| 0 hours | 0.71 | 0.074 | 112 | 17 | 0.004 |
| 24 hours | 0.65 | 0.076 | 112 | 17 | 0.054 |
| 48 hours | 0.65 | 0.098 | 112 | 10 | 0.117 | sCr only

| Time prior AKI stage | AUC | SE | nCohort 1 | nCohort 2 | p |
|---|---|---|---|---|---|
| 0 hours | 0.73 | 0.103 | 180 | 8 | 0.027 |
| 24 hours | 0.70 | 0.106 | 180 | 8 | 0.062 |
| 48 hours | 0.60 | 0.136 | 180 | 5 | 0.474 |

Fig. 8 Continued

UO only

| Time prior AKI stage | AUC | SE | nCohort 1 | nCohort 2 | p |
|---|---|---|---|---|---|
| 0 hours | 0.69 | 0.092 | 89 | 11 | 0.037 |
| 24 hours | 0.63 | 0.095 | 89 | 11 | 0.180 |
| 48 hours | 0.67 | 0.116 | 89 | 7 | 0.132 | sCr or UO

| Time prior AKI stage | Cutoff value | sens | spec | Quartile | OR | 95% CI of OR | |
|---|---|---|---|---|---|---|---|
| 0 hours | 81.9 | 71% | 63% | 1 | | | |
| | 73.7 | 82% | 54% | 2 | na | na | na |
| | 57.7 | 94% | 43% | 3 | na | na | na |
| | 99.9 | 47% | 71% | 4 | na | na | na |
| | 129 | 47% | 80% | | | | |
| | 189 | 35% | 90% | | | | |
| 24 hours | 64.9 | 71% | 46% | 1 | | | |
| | 57.7 | 82% | 43% | 2 | 5.7 | 0.5 | 69.1 |
| | 42.9 | 94% | 25% | 3 | 4.4 | 0.3 | 58.6 |
| | 99.9 | 47% | 71% | 4 | 8.3 | 0.8 | 90.1 |
| | 129 | 41% | 80% | | | | |
| | 189 | 35% | 90% | | | | |
| 48 hours | 60 | 70% | 44% | 1 | | | |
| | 58 | 80% | 43% | 2 | 3.1 | 0.2 | 48.6 |
| | 57.7 | 90% | 43% | 3 | 1.0 | 0.0 | 57.7 |
| | 99.9 | 50% | 71% | 4 | 5.6 | 0.5 | 67.6 |
| | 129 | 50% | 80% | | | | |
| | 189 | 40% | 90% | | | | | sCr only

| Time prior AKI stage | Cutoff value | sens | spec | Quartile | OR | 95% CI of OR | |
|---|---|---|---|---|---|---|---|
| 0 hours | 86.2 | 75% | 61% | 1 | | | |
| | 84.7 | 88% | 60% | 2 | na | na | na |
| | 46.5 | 100% | 27% | 3 | na | na | na |
| | 104 | 63% | 70% | 4 | na | na | na |
| | 135 | 50% | 80% | | | | |
| | 200 | 13% | 91% | | | | |
| 24 hours | 86.2 | 75% | 61% | 1 | | | |
| | 84.7 | 88% | 60% | 2 | 0.0 | 0.0 | na |
| | 25.1 | 100% | 10% | 3 | 3.1 | 0.2 | 46.7 |
| | 104 | 63% | 70% | 4 | 4.3 | 0.3 | 54.2 |
| | 135 | 38% | 80% | | | | |
| | 200 | 13% | 91% | | | | |
| 48 hours | 46.5 | 80% | 27% | 1 | | | |
| | 46.5 | 80% | 27% | 2 | 1.0 | 0.0 | 55.0 |
| | 25.1 | 100% | 10% | 3 | 0.0 | 0.0 | na |
| | 104 | 60% | 70% | 4 | 3.1 | 0.2 | 45.7 |
| | 135 | 40% | 80% | | | | |
| | 200 | 20% | 91% | | | | |

UO only

| Time prior AKI stage | Cutoff value | sens | spec | Quartile | OR | 95% CI of OR | |
|---|---|---|---|---|---|---|---|
| 0 hours | 77.6 | 73% | 56% | 1 | | | |
| | 73.7 | 82% | 54% | 2 | na | na | na |
| | 64.9 | 91% | 49% | 3 | na | na | na |
| | 105 | 36% | 71% | 4 | na | na | na |
| | 135 | 36% | 81% | | | | |
| | 189 | 36% | 91% | | | | |

Fig. 8 Continued

| 24 hours | 60   | 73%  | 45% | 1 |     |     |      |
|----------|------|------|-----|---|-----|-----|------|
|          | 57.1 | 82%  | 44% | 2 | 4.6 | 0.3 | 63.1 |
|          | 46.5 | 91%  | 31% | 3 | 2.1 | 0.1 | 46.6 |
|          | 105  | 36%  | 71% | 4 | 4.6 | 0.3 | 63.1 |
|          | 135  | 36%  | 81% |   |     |     |      |
|          | 189  | 36%  | 91% |   |     |     |      |
| 48 hours | 60   | 71%  | 45% | 1 |     |     |      |
|          | 58   | 86%  | 44% | 2 | na  | na  | na   |
|          | 57.1 | 100% | 44% | 3 | na  | na  | na   |
|          | 105  | 43%  | 71% | 4 | na  | na  | na   |
|          | 135  | 43%  | 81% |   |     |     |      |
|          | 189  | 43%  | 91% |   |     |     |      |

E-selectin sCr or UO

|            | 0 hr prior to AKI stage |          | 24 hr prior to AKI stage |          | 48 hr prior to AKI stage |          |
|------------|---------|---------|---------|---------|---------|---------|
|            | Cohort 1 | Cohort 2 | Cohort 1 | Cohort 2 | Cohort 1 | Cohort 2 |
| median     | 8.873   | 12.704  | 8.873   | 12.704  | 8.873   | 12.704  |
| average    | 9.498   | 14.159  | 9.498   | 14.159  | 9.498   | 14.035  |
| stdev      | 4.517   | 6.138   | 4.517   | 6.138   | 4.517   | 3.633   |
| p (t-test) |         | 0.043   |         | 0.043   |         | 0.068   |
| min        | 3.422   | 5.790   | 3.422   | 5.790   | 3.422   | 11.364  |
| max        | 18.492  | 23.028  | 18.492  | 23.028  | 18.492  | 19.365  |
| n (Samp)   | 25      | 6       | 25      | 6       | 25      | 4       |
| n (Pat)    | 25      | 6       | 25      | 6       | 25      | 4       | sCr only

|            | 0 hr prior to AKI stage |          | 24 hr prior to AKI stage |          | 48 hr prior to AKI stage |          |
|------------|---------|---------|---------|---------|---------|---------|
|            | Cohort 1 | Cohort 2 | Cohort 1 | Cohort 2 | Cohort 1 | Cohort 2 |
| median     | 8.883   | 19.365  | 8.883   | 19.365  | 8.883   | 16.288  |
| average    | 11.438  | 18.535  | 11.438  | 18.535  | 11.438  | 16.288  |
| stdev      | 9.229   | 4.961   | 9.229   | 4.961   | 9.229   | 4.352   |
| p (t-test) |         | 0.197   |         | 0.197   |         | 0.467   |
| min        | 3.333   | 13.211  | 3.333   | 13.211  | 3.333   | 13.211  |
| max        | 46.625  | 23.028  | 46.625  | 23.028  | 46.625  | 19.365  |
| n (Samp)   | 44      | 3       | 44      | 3       | 44      | 2       |
| n (Pat)    | 44      | 3       | 44      | 3       | 44      | 2       |

UO only

|            | 0 hr prior to AKI stage |          | 24 hr prior to AKI stage |          | 48 hr prior to AKI stage |          |
|------------|---------|---------|---------|---------|---------|---------|
|            | Cohort 1 | Cohort 2 | Cohort 1 | Cohort 2 | Cohort 1 | Cohort 2 |
| median     | 7.624   | 11.781  | 7.624   | 11.781  | 7.624   | 12.197  |
| average    | 8.954   | 10.641  | 8.954   | 10.641  | 8.954   | 12.258  |
| stdev      | 4.077   | 3.321   | 4.077   | 3.321   | 4.077   | 0.925   |
| p (t-test) |         | 0.440   |         | 0.440   |         | 0.180   |
| min        | 3.422   | 5.790   | 3.422   | 5.790   | 3.422   | 11.364  |
| max        | 18.141  | 13.211  | 18.141  | 13.211  | 18.141  | 13.211  |
| n (Samp)   | 25      | 4       | 25      | 4       | 25      | 3       |
| n (Pat)    | 25      | 4       | 25      | 4       | 25      | 3       | sCr or UO

| Time prior AKI stage | AUC  | SE    | nCohort 1 | nCohort 2 | p     |
|----------------------|------|-------|-----------|-----------|-------|
| 0 hours              | 0.75 | 0.124 | 25        | 6         | 0.047 |
| 24 hours             | 0.75 | 0.124 | 25        | 6         | 0.047 |
| 48 hours             | 0.80 | 0.140 | 25        | 4         | 0.032 |

Fig. 8 Continued sCr only

| Time prior AKI stage | AUC | SE | nCohort 1 | nCohort 2 | p |
|---|---|---|---|---|---|
| 0 hours | 0.89 | 0.128 | 44 | 3 | 0.003 |
| 24 hours | 0.89 | 0.128 | 44 | 3 | 0.003 |
| 48 hours | 0.86 | 0.168 | 44 | 2 | 0.030 |

UO only

| Time prior AKI stage | AUC | SE | nCohort 1 | nCohort 2 | p |
|---|---|---|---|---|---|
| 0 hours | 0.67 | 0.159 | 25 | 4 | 0.284 |
| 24 hours | 0.67 | 0.159 | 25 | 4 | 0.284 |
| 48 hours | 0.80 | 0.160 | 25 | 3 | 0.061 |

Fibronectin sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 259659.017 | 228489.505 | 259659.017 | 228489.505 | 259659.017 | 228489.505 |
| average | 274233.986 | 245585.834 | 274233.986 | 245585.834 | 274233.986 | 244070.377 |
| stdev | 98685.929 | 106449.149 | 98685.929 | 106449.149 | 98685.929 | 96225.453 |
| p (t-test) |  | 0.534 |  | 0.534 |  | 0.574 |
| min | 56713.581 | 128509.435 | 56713.581 | 128509.435 | 56713.581 | 143884.103 |
| max | 467390.708 | 375418.393 | 467390.708 | 375418.393 | 467390.708 | 375418.393 |
| n (Samp) | 25 | 6 | 25 | 6 | 25 | 4 |
| n (Pat) | 25 | 6 | 25 | 6 | 25 | 4 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 238632.730 | 227286.327 | 238632.730 | 227286.327 | 238632.730 | 228489.505 |
| average | 258426.244 | 195162.815 | 258426.244 | 195162.815 | 258426.244 | 228489.505 |
| stdev | 118927.680 | 57736.059 | 118927.680 | 57736.059 | 118927.680 | 1701.552 |
| p (t-test) |  | 0.369 |  | 0.369 |  | 0.726 |
| min | 56713.581 | 128509.435 | 56713.581 | 128509.435 | 56713.581 | 227286.327 |
| max | 620512.175 | 229692.684 | 620512.175 | 229692.684 | 620512.175 | 229692.684 |
| n (Samp) | 44 | 3 | 44 | 3 | 44 | 2 |
| n (Pat) | 44 | 3 | 44 | 3 | 44 | 2 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 259659.017 | 299208.374 | 259659.017 | 299208.374 | 259659.017 | 229692.684 |
| average | 268317.413 | 279429.811 | 268317.413 | 279429.811 | 268317.413 | 249665.060 |
| stdev | 91213.373 | 112596.170 | 91213.373 | 112596.170 | 91213.373 | 117052.141 |
| p (t-test) |  | 0.828 |  | 0.828 |  | 0.747 |
| min | 56713.581 | 143884.103 | 56713.581 | 143884.103 | 56713.581 | 143884.103 |
| max | 413982.406 | 375418.393 | 413982.406 | 375418.393 | 413982.406 | 375418.393 |
| n (Samp) | 25 | 4 | 25 | 4 | 25 | 3 |
| n (Pat) | 25 | 4 | 25 | 4 | 25 | 3 | sCr or UO

| Time prior AKI stage | AUC | SE | nCohort 1 | nCohort 2 | p |
|---|---|---|---|---|---|
| 0 hours | 0.41 | 0.126 | 25 | 6 | 0.493 |
| 24 hours | 0.41 | 0.126 | 25 | 6 | 0.493 |
| 48 hours | 0.39 | 0.145 | 25 | 4 | 0.449 |

Fig. 8 Continued sCr only

| Time prior AKI stage | AUC | SE | nCohort 1 | nCohort 2 | p |
|---|---|---|---|---|---|
| 0 hours | 0.34 | 0.147 | 44 | 3 | 0.280 |
| 24 hours | 0.34 | 0.147 | 44 | 3 | 0.280 |
| 48 hours | 0.44 | 0.202 | 44 | 2 | 0.779 |

UO only

| Time prior AKI stage | AUC | SE | nCohort 1 | nCohort 2 | p |
|---|---|---|---|---|---|
| 0 hours | 0.55 | 0.161 | 25 | 4 | 0.779 |
| 24 hours | 0.55 | 0.161 | 25 | 4 | 0.779 |
| 48 hours | 0.43 | 0.171 | 25 | 3 | 0.697 | sCr or UO

| Time prior AKI stage | Cutoff value | sens | spec | Quartile | OR | 95% CI of OR | |
|---|---|---|---|---|---|---|---|
| 0 hours | 128509 | 83% | 8% | 1 | | | |
| | 128509 | 83% | 8% | 2 | 0.0 | 0.0 | na |
| | 126889 | 100% | 8% | 3 | 1.0 | 0.1 | 13.6 |
| | 326303 | 33% | 72% | 4 | 1.2 | 0.1 | 17.5 |
| | 355014 | 33% | 80% | | | | |
| | 406971 | 0% | 92% | | | | |
| 24 hours | 128509 | 83% | 8% | 1 | | | |
| | 128509 | 83% | 8% | 2 | 0.0 | 0.0 | na |
| | 126889 | 100% | 8% | 3 | 1.0 | 0.1 | 13.6 |
| | 326303 | 33% | 72% | 4 | 1.2 | 0.1 | 17.5 |
| | 355014 | 33% | 80% | | | | |
| | 406971 | 0% | 92% | | | | |
| 48 hours | 222232 | 75% | 32% | 1 | | | |
| | 126889 | 100% | 8% | 2 | 0.0 | 0.0 | na |
| | 126889 | 100% | 8% | 3 | 2.8 | 0.1 | 103.7 |
| | 326303 | 25% | 72% | 4 | 1.2 | 0.0 | 107.9 |
| | 355014 | 25% | 80% | | | | |
| | 406971 | 0% | 92% | | | | |

UO only

| Time prior AKI stage | Cutoff value | sens | spec | Quartile | OR | 95% CI of OR | |
|---|---|---|---|---|---|---|---|
| 0 hours | 222232 | 75% | 32% | 1 | | | |
| | 126889 | 100% | 8% | 2 | 1.0 | 0.0 | 96.9 |
| | 126889 | 100% | 8% | 3 | 0.0 | 0.0 | na |
| | 311697 | 50% | 72% | 4 | 2.0 | 0.1 | 72.7 |
| | 351984 | 50% | 80% | | | | |
| | 398685 | 0% | 92% | | | | |
| 24 hours | 222232 | 75% | 32% | 1 | | | |
| | 126889 | 100% | 8% | 2 | 1.0 | 0.0 | 96.9 |
| | 126889 | 100% | 8% | 3 | 0.0 | 0.0 | na |
| | 311697 | 50% | 72% | 4 | 2.0 | 0.1 | 72.7 |
| | 351984 | 50% | 80% | | | | |
| | 398685 | 0% | 92% | | | | |
| 48 hours | 126889 | 100% | 8% | 1 | | | |
| | 126889 | 100% | 8% | 2 | 0.0 | 0.0 | na |
| | 126889 | 100% | 8% | 3 | 1.0 | 0.0 | 96.9 |
| | 311697 | 33% | 72% | 4 | 1.0 | 0.0 | 96.9 |
| | 351984 | 33% | 80% | | | | |
| | 398685 | 0% | 92% | | | | |

Fig. 8 Continued

Granulocyte colony-stimulating factor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 30.700 | 68.100 | 30.700 | 68.100 | 30.700 | 71.100 |
| average | 102.874 | 596.553 | 102.874 | 595.424 | 102.874 | 166.950 |
| stdev | 392.646 | 1533.660 | 392.646 | 1534.090 | 392.646 | 222.456 |
| p (t-test) |  | 0.005 |  | 0.005 |  | 0.613 |
| min | 0.050 | 16.000 | 0.050 | 16.000 | 0.050 | 16.000 |
| max | 3280.000 | 6280.000 | 3280.000 | 6280.000 | 3280.000 | 640.000 |
| n (Samp) | 112 | 17 | 112 | 17 | 112 | 10 |
| n (Pat) | 112 | 17 | 112 | 17 | 112 | 10 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 32.850 | 95.100 | 32.850 | 95.100 | 32.850 | 83.200 |
| average | 261.537 | 1077.963 | 261.537 | 1077.963 | 261.537 | 434.480 |
| stdev | 1198.176 | 2193.701 | 1198.176 | 2193.701 | 1198.176 | 803.809 |
| p (t-test) |  | 0.072 |  | 0.072 |  | 0.749 |
| min | 0.050 | 31.100 | 0.050 | 31.100 | 0.050 | 31.100 |
| max | 11103.000 | 6280.000 | 11103.000 | 6280.000 | 11103.000 | 1870.000 |
| n (Samp) | 180 | 8 | 180 | 8 | 180 | 5 |
| n (Pat) | 180 | 8 | 180 | 8 | 180 | 5 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 30.900 | 59.000 | 30.900 | 59.000 | 30.900 | 59.000 |
| average | 166.522 | 311.618 | 166.522 | 309.873 | 166.522 | 201.029 |
| stdev | 675.173 | 559.618 | 675.173 | 560.525 | 675.173 | 261.860 |
| p (t-test) |  | 0.496 |  | 0.501 |  | 0.894 |
| min | 0.050 | 16.000 | 0.050 | 16.000 | 0.050 | 16.000 |
| max | 4970.000 | 1870.000 | 4970.000 | 1870.000 | 4970.000 | 640.000 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
| --- | --- | --- | --- | --- | --- |
| 0 hours | 0.75 | 0.071 | 112 | 17 | 0.000 |
| 24 hours | 0.74 | 0.072 | 112 | 17 | 0.001 |
| 48 hours | 0.73 | 0.094 | 112 | 10 | 0.017 | sCr only

| Time prior AKI stage | AUC | SE | nCohort 1 | nCohort 2 | p |
| --- | --- | --- | --- | --- | --- |
| 0 hours | 0.76 | 0.100 | 180 | 8 | 0.008 |
| 24 hours | 0.76 | 0.100 | 180 | 8 | 0.008 |
| 48 hours | 0.72 | 0.131 | 180 | 5 | 0.087 |

UO only

| Time prior AKI stage | AUC | SE | nCohort 1 | nCohort 2 | p |
| --- | --- | --- | --- | --- | --- |
| 0 hours | 0.71 | 0.091 | 89 | 11 | 0.021 |
| 24 hours | 0.69 | 0.092 | 89 | 11 | 0.035 |
| 48 hours | 0.71 | 0.113 | 89 | 7 | 0.065 |

Fig. 8 Continued sCr or UO

| Time prior AKI stage | Cutoff value | sens | spec | Quartile | OR | 95% CI of OR | |
|---|---|---|---|---|---|---|---|
| 0 hours | 58 | 71% | 73% | 1 | | | |
| | 39.2 | 82% | 64% | 2 | 2.1 | 0.1 | 44.5 |
| | 22.5 | 94% | 38% | 3 | 7.2 | 0.6 | 80.9 |
| | 55.9 | 71% | 71% | 4 | 9.9 | 0.9 | 103.7 |
| | 91 | 35% | 80% | | | | |
| | 122 | 29% | 90% | | | | |
| 24 hours | 42.7 | 71% | 65% | 1 | | | |
| | 39.2 | 82% | 64% | 2 | 2.1 | 0.1 | 44.5 |
| | 20 | 94% | 30% | 3 | 7.2 | 0.6 | 80.9 |
| | 55.9 | 65% | 71% | 4 | 9.9 | 0.9 | 103.7 |
| | 91 | 35% | 80% | | | | |
| | 122 | 29% | 90% | | | | |
| 48 hours | 40.1 | 70% | 64% | 1 | | | |
| | 39.2 | 80% | 64% | 2 | 1.0 | 0.0 | 55.6 |
| | 30.9 | 90% | 52% | 3 | 3.2 | 0.2 | 50.6 |
| | 55.9 | 60% | 71% | 4 | 5.6 | 0.5 | 67.6 |
| | 91 | 30% | 80% | | | | |
| | 122 | 30% | 90% | | | | |

UO only

| Time prior AKI stage | Cutoff value | sens | spec | Quartile | OR | 95% CI of OR | |
|---|---|---|---|---|---|---|---|
| 0 hours | 42.7 | 73% | 66% | 1 | | | |
| | 39.2 | 82% | 65% | 2 | 1.0 | 0.0 | 59.3 |
| | 22.5 | 91% | 34% | 3 | 4.6 | 0.3 | 63.1 |
| | 51.1 | 64% | 71% | 4 | 6.0 | 0.5 | 75.4 |
| | 98 | 27% | 81% | | | | |
| | 113 | 27% | 91% | | | | |
| 24 hours | 40.1 | 73% | 65% | 1 | | | |
| | 39.2 | 82% | 65% | 2 | 0.0 | 0.0 | na |
| | 18.2 | 91% | 25% | 3 | 2.2 | 0.4 | 11.4 |
| | 51.1 | 55% | 71% | 4 | 2.9 | 0.6 | 13.6 |
| | 98 | 27% | 81% | | | | |
| | 113 | 27% | 91% | | | | |
| 48 hours | 40.1 | 71% | 65% | 1 | | | |
| | 39.2 | 86% | 65% | 2 | 0.0 | 0.0 | na |
| | 15.1 | 100% | 19% | 3 | 3.3 | 0.2 | 53.6 |
| | 51.1 | 57% | 71% | 4 | 3.3 | 0.2 | 53.6 |
| | 98 | 29% | 81% | | | | |
| | 113 | 29% | 91% | | | | |

Fig. 8 Continued

Granulocyte-macrophage colony-stimulating factor sCr or UO

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 0.574    | 12.100   | 0.574    | 12.100   | 0.574    | 8.195    |
| average  | 7.905    | 15.605   | 7.905    | 13.934   | 7.905    | 12.688   |
| stdev    | 26.882   | 15.694   | 26.882   | 13.509   | 26.882   | 16.912   |
| p (t-test) |        | 0.253    |          | 0.367    |          | 0.582    |
| min      | 0.574    | 0.574    | 0.574    | 0.574    | 0.574    | 0.574    |
| max      | 277.000  | 58.600   | 277.000  | 58.600   | 277.000  | 58.600   |
| n (Samp) | 112      | 17       | 112      | 17       | 112      | 10       |
| n (Pat)  | 112      | 17       | 112      | 17       | 112      | 10       | sCr only

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 0.574    | 13.005   | 0.574    | 11.355   | 0.574    | 6.770    |
| average  | 8.154    | 11.229   | 8.154    | 10.816   | 8.154    | 6.946    |
| stdev    | 23.367   | 8.099    | 23.367   | 7.855    | 23.367   | 7.069    |
| p (t-test) |        | 0.712    |          | 0.749    |          | 0.908    |
| min      | 0.574    | 0.574    | 0.574    | 0.574    | 0.574    | 0.574    |
| max      | 277.000  | 21.500   | 277.000  | 21.500   | 277.000  | 17.600   |
| n (Samp) | 180      | 8        | 180      | 8        | 180      | 5        |
| n (Pat)  | 180      | 8        | 180      | 8        | 180      | 5        |

UO only

|          | 0 hr prior to AKI stage | | 24 hr prior to AKI stage | | 48 hr prior to AKI stage | |
|----------|----------|----------|----------|----------|----------|----------|
|          | Cohort 1 | Cohort 2 | Cohort 1 | Cohort 2 | Cohort 1 | Cohort 2 |
| median   | 0.574    | 12.100   | 0.574    | 12.100   | 0.574    | 9.270    |
| average  | 8.585    | 17.603   | 8.585    | 15.321   | 8.585    | 15.761   |
| stdev    | 29.898   | 18.746   | 29.898   | 16.066   | 29.898   | 19.639   |
| p (t-test) |        | 0.332    |          | 0.466    |          | 0.535    |
| min      | 0.574    | 0.574    | 0.574    | 0.574    | 0.574    | 0.574    |
| max      | 277.000  | 58.600   | 277.000  | 58.600   | 277.000  | 58.600   |
| n (Samp) | 89       | 11       | 89       | 11       | 89       | 7        |
| n (Pat)  | 89       | 11       | 89       | 11       | 89       | 7        | sCr or UO

| Time prior AKI stage | AUC | SE | nCohort 1 | nCohort 2 | p |
|---|---|---|---|---|---|
| 0 hours  | 0.76 | 0.071 | 112 | 17 | 0.000 |
| 24 hours | 0.75 | 0.071 | 112 | 17 | 0.000 |
| 48 hours | 0.69 | 0.096 | 112 | 10 | 0.053 | sCr only

| Time prior AKI stage | AUC | SE | nCohort 1 | nCohort 2 | p |
|---|---|---|---|---|---|
| 0 hours  | 0.69 | 0.106 | 180 | 8 | 0.069 |
| 24 hours | 0.69 | 0.106 | 180 | 8 | 0.074 |
| 48 hours | 0.56 | 0.135 | 180 | 5 | 0.648 |

UO only

| Time prior AKI stage | AUC | SE | nCohort 1 | nCohort 2 | p |
|---|---|---|---|---|---|
| 0 hours  | 0.75 | 0.088 | 89 | 11 | 0.004 |
| 24 hours | 0.75 | 0.088 | 89 | 11 | 0.005 |
| 48 hours | 0.73 | 0.111 | 89 | 7  | 0.037 |

Fig. 8 Continued sCr or UO

| Time prior AKI stage | Cutoff value | sens | spec | Quartile | OR | 95% CI of OR | |
|---|---|---|---|---|---|---|---|
| 0 hours | 7.94 | 71% | 80% | 1 | | | |
| | 4.69 | 82% | 59% | 2 | 2.1 | 0.1 | 44.5 |
| | 0 | 100% | 0% | 3 | 3.2 | 0.2 | 49.9 |
| | 7.23 | 71% | 71% | 4 | 15.5 | 1.6 | 153.1 |
| | 7.94 | 71% | 80% | | | | |
| | 16 | 41% | 90% | | | | |
| 24 hours | 7.94 | 71% | 80% | 1 | | | |
| | 4.69 | 82% | 59% | 2 | 2.1 | 0.1 | 44.5 |
| | 0 | 100% | 0% | 3 | 3.2 | 0.2 | 49.9 |
| | 7.23 | 71% | 71% | 4 | 15.5 | 1.6 | 153.1 |
| | 7.94 | 71% | 80% | | | | |
| | 16 | 35% | 90% | | | | |
| 48 hours | 5.75 | 70% | 64% | 1 | | | |
| | 4.69 | 80% | 59% | 2 | 1.0 | 0.0 | 55.6 |
| | 0 | 100% | 0% | 3 | 3.2 | 0.2 | 50.6 |
| | 7.23 | 50% | 71% | 4 | 5.6 | 0.5 | 67.6 |
| | 7.94 | 50% | 80% | | | | |
| | 16 | 20% | 90% | | | | |

UO only

| Time prior AKI stage | Cutoff value | sens | spec | Quartile | OR | 95% CI of OR | |
|---|---|---|---|---|---|---|---|
| 0 hours | 7.94 | 73% | 79% | 1 | | | |
| | 4.69 | 82% | 60% | 2 | 1.0 | 0.0 | 59.3 |
| | 0 | 100% | 0% | 3 | 2.1 | 0.1 | 46.6 |
| | 7.18 | 73% | 71% | 4 | 9.3 | 0.8 | 106.1 |
| | 11.1 | 55% | 81% | | | | |
| | 17.1 | 36% | 91% | | | | |
| 24 hours | 7.94 | 73% | 79% | 1 | | | |
| | 4.69 | 82% | 60% | 2 | 1.0 | 0.0 | 59.3 |
| | 0 | 100% | 0% | 3 | 2.1 | 0.1 | 46.6 |
| | 7.18 | 73% | 71% | 4 | 9.3 | 0.8 | 106.1 |
| | 11.1 | 55% | 81% | | | | |
| | 17.1 | 36% | 91% | | | | |
| 48 hours | 6.77 | 71% | 69% | 1 | | | |
| | 4.69 | 86% | 60% | 2 | na | na | na |
| | 0 | 100% | 0% | 3 | na | na | na |
| | 7.18 | 57% | 71% | 4 | na | na | na |
| | 11.1 | 43% | 81% | | | | |
| | 17.1 | 29% | 91% | | | | |

Fig. 8 Continued

Heparin-binding growth factor 2 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 133.000 | 338.000 | 133.000 | 276.000 | 133.000 | 238.500 |
| average | 170.456 | 851.494 | 170.456 | 799.965 | 170.456 | 1082.420 |
| stdev | 215.350 | 2223.789 | 215.350 | 2235.439 | 215.350 | 2696.238 |
| p (t-test) |  | 0.002 |  | 0.004 |  | 0.000 |
| min | 0.980 | 61.200 | 0.980 | 61.200 | 0.980 | 61.200 |
| max | 1280.000 | 9460.000 | 1280.000 | 9460.000 | 1280.000 | 8750.000 |
| n (Samp) | 112 | 17 | 112 | 17 | 112 | 10 |
| n (Pat) | 112 | 17 | 112 | 17 | 112 | 10 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 141.000 | 271.000 | 141.000 | 223.000 | 141.000 | 276.000 |
| average | 201.326 | 251.425 | 201.326 | 207.175 | 201.326 | 241.840 |
| stdev | 281.124 | 138.039 | 281.124 | 115.569 | 281.124 | 121.646 |
| p (t-test) |  | 0.617 |  | 0.953 |  | 0.749 |
| min | 0.980 | 61.200 | 0.980 | 61.200 | 0.980 | 61.200 |
| max | 2520.000 | 425.000 | 2520.000 | 386.000 | 2520.000 | 386.000 |
| n (Samp) | 180 | 8 | 180 | 8 | 180 | 5 |
| n (Pat) | 180 | 8 | 180 | 8 | 180 | 5 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 133.000 | 386.000 | 133.000 | 291.000 | 133.000 | 276.000 |
| average | 183.333 | 1194.636 | 183.333 | 1147.182 | 183.333 | 1470.286 |
| stdev | 225.030 | 2744.912 | 225.030 | 2759.612 | 225.030 | 3211.789 |
| p (t-test) |  | 0.001 |  | 0.001 |  | 0.000 |
| min | 0.980 | 122.000 | 0.980 | 122.000 | 0.980 | 122.000 |
| max | 1280.000 | 9460.000 | 1280.000 | 9460.000 | 1280.000 | 8750.000 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
|---|---|---|---|---|---|
| 0 hours | 0.79 | 0.068 | 112 | 17 | 0.000 |
| 24 hours | 0.73 | 0.073 | 112 | 17 | 0.001 |
| 48 hours | 0.71 | 0.095 | 112 | 10 | 0.028 | sCr only

| Time prior AKI stage | AUC | SE | nCohort 1 | nCohort 2 | p |
|---|---|---|---|---|---|
| 0 hours | 0.67 | 0.107 | 180 | 8 | 0.104 |
| 24 hours | 0.60 | 0.108 | 180 | 8 | 0.337 |
| 48 hours | 0.67 | 0.135 | 180 | 5 | 0.213 |

UO only

| Time prior AKI stage | AUC | SE | nCohort 1 | nCohort 2 | p |
|---|---|---|---|---|---|
| 0 hours | 0.85 | 0.075 | 89 | 11 | 0.000 |
| 24 hours | 0.80 | 0.082 | 89 | 11 | 0.000 |
| 48 hours | 0.74 | 0.111 | 89 | 7 | 0.030 |

Fig. 8 Continued

Interleukin-1 receptor antagonist sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 336.500 | 890.000 | 336.500 | 890.000 | 336.500 | 575.000 |
| average | 1430.265 | 4470.118 | 1430.265 | 4252.706 | 1430.265 | 1154.600 |
| stdev | 4910.670 | 10092.217 | 4910.670 | 10073.901 | 4910.670 | 1521.549 |
| p (t-test) |  | 0.047 |  | 0.065 |  | 0.860 |
| min | 0.150 | 175.000 | 0.150 | 175.000 | 0.150 | 175.000 |
| max | 43939.000 | 42500.000 | 43939.000 | 42500.000 | 43939.000 | 5080.000 |
| n (Samp) | 112 | 17 | 112 | 17 | 112 | 10 |
| n (Pat) | 112 | 17 | 112 | 17 | 112 | 10 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 333.500 | 2150.000 | 333.500 | 1870.000 | 333.500 | 358.000 |
| average | 1712.439 | 7290.500 | 1712.439 | 7215.500 | 1712.439 | 1190.800 |
| stdev | 6255.629 | 14424.603 | 6255.629 | 14455.167 | 6255.629 | 1423.932 |
| p (t-test) |  | 0.023 |  | 0.025 |  | 0.853 |
| min | 0.150 | 175.000 | 0.150 | 175.000 | 0.150 | 175.000 |
| max | 58400.000 | 42500.000 | 58400.000 | 42500.000 | 58400.000 | 3420.000 |
| n (Samp) | 180 | 8 | 180 | 8 | 180 | 5 |
| n (Pat) | 180 | 8 | 180 | 8 | 180 | 5 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 320.000 | 792.000 | 320.000 | 792.000 | 320.000 | 792.000 |
| average | 1327.284 | 1949.636 | 1327.284 | 1668.182 | 1327.284 | 1338.571 |
| stdev | 4920.488 | 2401.170 | 4920.488 | 1822.974 | 4920.488 | 1743.981 |
| p (t-test) |  | 0.681 |  | 0.821 |  | 0.995 |
| min | 0.150 | 200.000 | 0.150 | 191.000 | 0.150 | 200.000 |
| max | 43939.000 | 7500.000 | 43939.000 | 5080.000 | 43939.000 | 5080.000 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
|---|---|---|---|---|---|
| 0 hours | 0.71 | 0.074 | 112 | 17 | 0.005 |
| 24 hours | 0.69 | 0.075 | 112 | 17 | 0.011 |
| 48 hours | 0.59 | 0.098 | 112 | 10 | 0.355 | sCr only

| Time prior AKI stage | AUC | SE | nCohort 1 | nCohort 2 | p |
|---|---|---|---|---|---|
| 0 hours | 0.71 | 0.105 | 180 | 8 | 0.042 |
| 24 hours | 0.70 | 0.105 | 180 | 8 | 0.055 |
| 48 hours | 0.56 | 0.135 | 180 | 5 | 0.671 |

UO only

| Time prior AKI stage | AUC | SE | nCohort 1 | nCohort 2 | p |
|---|---|---|---|---|---|
| 0 hours | 0.72 | 0.091 | 89 | 11 | 0.015 |
| 24 hours | 0.70 | 0.092 | 89 | 11 | 0.033 |
| 48 hours | 0.66 | 0.116 | 89 | 7 | 0.169 |

Fig. 8 Continued sCr or UO

| Time prior AKI stage | Cutoff value | sens | spec | Quartile | OR | 95% CI of OR | |
|---|---|---|---|---|---|---|---|
| 0 hours | 356 | 71% | 53% | 1 | | | |
| | 267 | 82% | 38% | 2 | 4.4 | 0.3 | 58.6 |
| | 185 | 94% | 29% | 3 | 3.2 | 0.2 | 49.9 |
| | 687 | 65% | 71% | 4 | 11.6 | 1.1 | 118.6 |
| | 845 | 53% | 80% | | | | |
| | 2350 | 35% | 90% | | | | |
| 24 hours | 356 | 71% | 53% | 1 | | | |
| | 191 | 82% | 29% | 2 | 1.6 | 0.3 | 9.1 |
| | 177 | 94% | 26% | 3 | 1.6 | 0.3 | 9.1 |
| | 687 | 65% | 71% | 4 | 5.6 | 1.5 | 21.6 |
| | 845 | 53% | 80% | | | | |
| | 2350 | 29% | 90% | | | | |
| 48 hours | 210 | 70% | 29% | 1 | | | |
| | 185 | 80% | 29% | 2 | 3.1 | 0.2 | 48.6 |
| | 177 | 90% | 26% | 3 | 1.0 | 0.0 | 57.7 |
| | 687 | 50% | 71% | 4 | 5.6 | 0.5 | 67.6 |
| | 845 | 40% | 80% | | | | |
| | 2350 | 10% | 90% | | | | | sCr only

| Time prior AKI stage | Cutoff value | sens | spec | Quartile | OR | 95% CI of OR | |
|---|---|---|---|---|---|---|---|
| 0 hours | 356 | 75% | 54% | 1 | | | |
| | 211 | 88% | 31% | 2 | 1.0 | 0.0 | 54.9 |
| | 172 | 100% | 22% | 3 | 1.0 | 0.0 | 54.9 |
| | 643 | 63% | 70% | 4 | 5.5 | 0.5 | 62.9 |
| | 905 | 63% | 80% | | | | |
| | 2350 | 50% | 90% | | | | |
| 24 hours | 356 | 75% | 54% | 1 | | | |
| | 177 | 88% | 23% | 2 | 0.0 | 0.0 | na |
| | 172 | 100% | 22% | 3 | 0.5 | 0.0 | 10.1 |
| | 643 | 63% | 70% | 4 | 2.7 | 0.6 | 11.6 |
| | 905 | 63% | 80% | | | | |
| | 2350 | 38% | 90% | | | | |
| 48 hours | 177 | 80% | 23% | 1 | | | |
| | 177 | 80% | 23% | 2 | 0.0 | 0.0 | na |
| | 172 | 100% | 22% | 3 | 0.5 | 0.0 | 10.1 |
| | 643 | 40% | 70% | 4 | 1.0 | 0.1 | 7.6 |
| | 905 | 40% | 80% | | | | |
| | 2350 | 20% | 90% | | | | |

Fig. 8 Continued

Interleukin-1 beta sCr or UO

|            | 0 hr prior to AKI stage |          | 24 hr prior to AKI stage |          | 48 hr prior to AKI stage |          |
|------------|------------|----------|------------|----------|------------|----------|
|            | Cohort 1   | Cohort 2 | Cohort 1   | Cohort 2 | Cohort 1   | Cohort 2 |
| median     | 0.015      | 0.759    | 0.015      | 0.598    | 0.015      | 0.653    |
| average    | 0.341      | 0.891    | 0.341      | 0.698    | 0.341      | 0.709    |
| stdev      | 0.657      | 0.965    | 0.657      | 0.840    | 0.657      | 0.950    |
| p (t-test) |            | 0.003    |            | 0.046    |            | 0.105    |
| min        | 0.015      | 0.015    | 0.015      | 0.015    | 0.015      | 0.015    |
| max        | 3.990      | 3.180    | 3.990      | 3.180    | 3.990      | 3.180    |
| n (Samp)   | 112        | 17       | 112        | 17       | 112        | 10       |
| n (Pat)    | 112        | 17       | 112        | 17       | 112        | 10       | sCr only

|            | 0 hr prior to AKI stage |          | 24 hr prior to AKI stage |          | 48 hr prior to AKI stage |          |
|------------|------------|----------|------------|----------|------------|----------|
|            | Cohort 1   | Cohort 2 | Cohort 1   | Cohort 2 | Cohort 1   | Cohort 2 |
| median     | 0.015      | 0.424    | 0.015      | 0.424    | 0.015      | 0.421    |
| average    | 0.749      | 0.591    | 0.749      | 0.591    | 0.749      | 0.447    |
| stdev      | 4.777      | 0.642    | 4.777      | 0.642    | 4.777      | 0.441    |
| p (t-test) |            | 0.926    |            | 0.926    |            | 0.888    |
| min        | 0.015      | 0.015    | 0.015      | 0.015    | 0.015      | 0.015    |
| max        | 63.800     | 1.420    | 63.800     | 1.420    | 63.800     | 0.953    |
| n (Samp)   | 180        | 8        | 180        | 8        | 180        | 5        |
| n (Pat)    | 180        | 8        | 180        | 8        | 180        | 5        |

UO only

|            | 0 hr prior to AKI stage |          | 24 hr prior to AKI stage |          | 48 hr prior to AKI stage |          |
|------------|------------|----------|------------|----------|------------|----------|
|            | Cohort 1   | Cohort 2 | Cohort 1   | Cohort 2 | Cohort 1   | Cohort 2 |
| median     | 0.015      | 0.759    | 0.015      | 0.598    | 0.015      | 0.598    |
| average    | 0.287      | 1.045    | 0.287      | 0.747    | 0.287      | 0.756    |
| stdev      | 0.643      | 1.087    | 0.643      | 0.943    | 0.643      | 1.122    |
| p (t-test) |            | 0.001    |            | 0.037    |            | 0.084    |
| min        | 0.015      | 0.015    | 0.015      | 0.015    | 0.015      | 0.015    |
| max        | 3.990      | 3.180    | 3.990      | 3.180    | 3.990      | 3.180    |
| n (Samp)   | 89         | 11       | 89         | 11       | 89         | 7        |
| n (Pat)    | 89         | 11       | 89         | 11       | 89         | 7        | sCr or UO

| Time prior AKI stage | AUC  | SE    | nCohort 1 | nCohort 2 | p     |
|----------------------|------|-------|-----------|-----------|-------|
| 0 hours              | 0.68 | 0.075 | 112       | 17        | 0.017 |
| 24 hours             | 0.65 | 0.076 | 112       | 17        | 0.045 |
| 48 hours             | 0.66 | 0.098 | 112       | 10        | 0.110 | sCr only

| Time prior AKI stage | AUC  | SE    | nCohort 1 | nCohort 2 | p     |
|----------------------|------|-------|-----------|-----------|-------|
| 0 hours              | 0.61 | 0.108 | 180       | 8         | 0.331 |
| 24 hours             | 0.61 | 0.108 | 180       | 8         | 0.331 |
| 48 hours             | 0.59 | 0.136 | 180       | 5         | 0.492 |

UO only

| Time prior AKI stage | AUC  | SE    | nCohort 1 | nCohort 2 | p     |
|----------------------|------|-------|-----------|-----------|-------|
| 0 hours              | 0.73 | 0.090 | 89        | 11        | 0.012 |
| 24 hours             | 0.69 | 0.093 | 89        | 11        | 0.037 |
| 48 hours             | 0.66 | 0.116 | 89        | 7         | 0.167 |

Fig. 8 Continued sCr or UO

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.4 | 0.1 | 1.6 |
| | 0 | 100% | 0% | 3 | 0.0 | 0.0 | na |
| | 0.444 | 59% | 71% | 4 | 2.3 | 1.1 | 4.9 |
| | 0.598 | 59% | 80% | | | | |
| | 1.06 | 35% | 90% | | | | |
| 24 hours | 0 | 100% | 0% | 1 | | | |
| | 0 | 100% | 0% | 2 | 0.4 | 0.1 | 1.6 |
| | 0 | 100% | 0% | 3 | 0.2 | 0.0 | 2.1 |
| | 0.444 | 53% | 71% | 4 | 2.0 | 0.9 | 4.3 |
| | 0.598 | 47% | 80% | | | | |
| | 1.06 | 24% | 90% | | | | |
| 48 hours | 0 | 100% | 0% | 1 | | | |
| | 0 | 100% | 0% | 2 | 3.1 | 0.2 | 48.6 |
| | 0 | 100% | 0% | 3 | 0.0 | 0.0 | na |
| | 0.444 | 60% | 71% | 4 | 7.0 | 0.6 | 79.3 |
| | 0.598 | 50% | 80% | | | | |
| | 1.06 | 10% | 90% | | | | | sCr only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | na | na | na |
| | 0 | 100% | 0% | 3 | na | na | na |
| | 0.511 | 50% | 73% | 4 | na | na | na |
| | 0.773 | 50% | 84% | | | | |
| | 1.17 | 25% | 90% | | | | |
| 24 hours | 0 | 100% | 0% | 1 | | | |
| | 0 | 100% | 0% | 2 | na | na | na |
| | 0 | 100% | 0% | 3 | na | na | na |
| | 0.511 | 50% | 73% | 4 | na | na | na |
| | 0.773 | 50% | 84% | | | | |
| | 1.17 | 25% | 90% | | | | |
| 48 hours | 0 | 100% | 0% | 1 | | | |
| | 0 | 100% | 0% | 2 | 0.0 | 0.0 | na |
| | 0 | 100% | 0% | 3 | 0.5 | 0.0 | 10.1 |
| | 0.511 | 40% | 73% | 4 | 1.0 | 0.1 | 7.6 |
| | 0.773 | 40% | 84% | | | | |
| | 1.17 | 0% | 90% | | | | |

Fig. 8 Continued

Interleukin-10 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 20.700 | 86.600 | 20.700 | 86.600 | 20.700 | 34.000 |
| average | 40.290 | 152.265 | 40.290 | 99.365 | 40.290 | 77.260 |
| stdev | 69.922 | 219.982 | 69.922 | 85.415 | 69.922 | 101.514 |
| p (t-test) |  | 0.000 |  | 0.002 |  | 0.126 |
| min | 0.154 | 22.300 | 0.154 | 22.300 | 0.154 | 12.500 |
| max | 480.000 | 942.000 | 480.000 | 348.000 | 480.000 | 348.000 |
| n (Samp) | 112 | 17 | 112 | 17 | 112 | 10 |
| n (Pat) | 112 | 17 | 112 | 17 | 112 | 10 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 22.800 | 84.950 | 22.800 | 78.500 | 22.800 | 35.200 |
| average | 129.997 | 113.150 | 129.997 | 111.538 | 129.997 | 105.340 |
| stdev | 1012.756 | 107.088 | 1012.756 | 107.728 | 1012.756 | 138.065 |
| p (t-test) |  | 0.963 |  | 0.959 |  | 0.957 |
| min | 0.154 | 22.300 | 0.154 | 22.300 | 0.154 | 22.300 |
| max | 13400.000 | 348.000 | 13400.000 | 348.000 | 13400.000 | 348.000 |
| n (Samp) | 180 | 8 | 180 | 8 | 180 | 5 |
| n (Pat) | 180 | 8 | 180 | 8 | 180 | 5 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 20.200 | 86.600 | 20.200 | 86.600 | 20.200 | 35.200 |
| average | 33.583 | 164.264 | 33.583 | 83.682 | 33.583 | 52.786 |
| stdev | 44.847 | 264.189 | 44.847 | 59.866 | 44.847 | 41.343 |
| p (t-test) |  | 0.000 |  | 0.001 |  | 0.276 |
| min | 0.154 | 23.400 | 0.154 | 23.400 | 0.154 | 12.500 |
| max | 318.000 | 942.000 | 318.000 | 217.000 | 318.000 | 126.000 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
| --- | --- | --- | --- | --- | --- |
| 0 hours | 0.84 | 0.061 | 112 | 17 | 0.000 |
| 24 hours | 0.82 | 0.065 | 112 | 17 | 0.000 |
| 48 hours | 0.70 | 0.095 | 112 | 10 | 0.033 | sCr only

| Time prior AKI stage | AUC | SE | nCohort 1 | nCohort 2 | p |
| --- | --- | --- | --- | --- | --- |
| 0 hours | 0.80 | 0.095 | 180 | 8 | 0.001 |
| 24 hours | 0.80 | 0.095 | 180 | 8 | 0.002 |
| 48 hours | 0.73 | 0.130 | 180 | 5 | 0.071 |

UO only

| Time prior AKI stage | AUC | SE | nCohort 1 | nCohort 2 | p |
| --- | --- | --- | --- | --- | --- |
| 0 hours | 0.87 | 0.071 | 89 | 11 | 0.000 |
| 24 hours | 0.83 | 0.078 | 89 | 11 | 0.000 |
| 48 hours | 0.70 | 0.114 | 89 | 7 | 0.075 |

Fig. 8 Continued

Interleukin-3 sCr or UO

|          | 0 hr prior to AKI stage |          | 24 hr prior to AKI stage |          | 48 hr prior to AKI stage |          |
|----------|----------|----------|----------|----------|----------|----------|
|          | Cohort 1 | Cohort 2 | Cohort 1 | Cohort 2 | Cohort 1 | Cohort 2 |
| median   | 0.079 | 0.091 | 0.079 | 0.074 | 0.079 | 0.085 |
| average  | 0.119 | 0.113 | 0.119 | 0.100 | 0.119 | 0.105 |
| stdev    | 0.112 | 0.081 | 0.112 | 0.088 | 0.112 | 0.073 |
| p (t-test) |     | 0.836 |       | 0.508 |       | 0.694 |
| min      | 0.002 | 0.030 | 0.002 | 0.002 | 0.002 | 0.030 |
| max      | 0.537 | 0.271 | 0.537 | 0.271 | 0.537 | 0.271 |
| n (Samp) | 112   | 17    | 112   | 17    | 112   | 10    |
| n (Pat)  | 112   | 17    | 112   | 17    | 112   | 10    | sCr only

|          | 0 hr prior toAKI stage |          | 24 hr prior toAKI stage |          | 48 hr prior toAKI stage |          |
|----------|----------|----------|----------|----------|----------|----------|
|          | Cohort 1 | Cohort 2 | Cohort 1 | Cohort 2 | Cohort 1 | Cohort 2 |
| median   | 0.082 | 0.052 | 0.082 | 0.052 | 0.082 | 0.057 |
| average  | 0.121 | 0.101 | 0.121 | 0.090 | 0.121 | 0.101 |
| stdev    | 0.113 | 0.090 | 0.113 | 0.099 | 0.113 | 0.098 |
| p (t-test) |     | 0.622 |       | 0.457 |       | 0.709 |
| min      | 0.002 | 0.035 | 0.002 | 0.002 | 0.002 | 0.035 |
| max      | 0.566 | 0.271 | 0.566 | 0.271 | 0.566 | 0.271 |
| n (Samp) | 180   | 8     | 180   | 8     | 180   | 5     |
| n (Pat)  | 180   | 8     | 180   | 8     | 180   | 5     |

UO only

|          | 0 hr prior toAKI stage |          | 24 hr prior toAKI stage |          | 48 hr prior toAKI stage |          |
|----------|----------|----------|----------|----------|----------|----------|
|          | Cohort 1 | Cohort 2 | Cohort 1 | Cohort 2 | Cohort 1 | Cohort 2 |
| median   | 0.078 | 0.115 | 0.078 | 0.115 | 0.078 | 0.101 |
| average  | 0.106 | 0.131 | 0.106 | 0.118 | 0.106 | 0.123 |
| stdev    | 0.104 | 0.086 | 0.104 | 0.090 | 0.104 | 0.080 |
| p (t-test) |     | 0.463 |       | 0.726 |       | 0.691 |
| min      | 0.002 | 0.030 | 0.002 | 0.002 | 0.002 | 0.030 |
| max      | 0.537 | 0.271 | 0.537 | 0.271 | 0.537 | 0.271 |
| n (Samp) | 89    | 11    | 89    | 11    | 89    | 7     |
| n (Pat)  | 89    | 11    | 89    | 11    | 89    | 7     | sCr or UO

| Time prior AKI stage | AUC | SE | nCohort 1 | nCohort 2 | p |
|---|---|---|---|---|---|
| 0 hours  | 0.53 | 0.076 | 112 | 17 | 0.733 |
| 24 hours | 0.46 | 0.074 | 112 | 17 | 0.611 |
| 48 hours | 0.52 | 0.096 | 112 | 10 | 0.864 | sCr only

| Time prior AKI stage | AUC | SE | nCohort 1 | nCohort 2 | p |
|---|---|---|---|---|---|
| 0 hours  | 0.45 | 0.101 | 180 | 8 | 0.635 |
| 24 hours | 0.40 | 0.096 | 180 | 8 | 0.297 |
| 48 hours | 0.46 | 0.128 | 180 | 5 | 0.764 |

UO only

| Time prior AKI stage | AUC | SE | nCohort 1 | nCohort 2 | p |
|---|---|---|---|---|---|
| 0 hours  | 0.62 | 0.095 | 89 | 11 | 0.194 |
| 24 hours | 0.57 | 0.095 | 89 | 11 | 0.487 |
| 48 hours | 0.61 | 0.117 | 89 | 7  | 0.356 |

Fig. 8 Continued sCr or UO

| Time prior AKI stage | Cutoff value | sens | spec | Quartile | OR | 95% CI of OR | |
|---|---|---|---|---|---|---|---|
| 0 hours | 0.0467 | 71% | 30% | 1 | | | |
| | 0.0432 | 82% | 28% | 2 | 1.8 | 0.5 | 5.9 |
| | 0.0338 | 94% | 23% | 3 | 1.8 | 0.5 | 5.9 |
| | 0.146 | 29% | 71% | 4 | 1.3 | 0.4 | 4.8 |
| | 0.2 | 24% | 80% | | | | |
| | 0.274 | 0% | 90% | | | | |
| 24 hours | 0.0456 | 71% | 29% | 1 | | | |
| | 0.0284 | 82% | 21% | 2 | 1.9 | 0.6 | 6.0 |
| | 0 | 100% | 0% | 3 | 1.4 | 0.4 | 5.1 |
| | 0.146 | 29% | 71% | 4 | 1.9 | 0.6 | 6.0 |
| | 0.2 | 18% | 80% | | | | |
| | 0.274 | 0% | 90% | | | | |
| 48 hours | 0.0713 | 70% | 44% | 1 | | | |
| | 0.0537 | 80% | 35% | 2 | 1.5 | 0.3 | 8.8 |
| | 0.0338 | 90% | 23% | 3 | 2.2 | 0.4 | 10.8 |
| | 0.146 | 20% | 71% | 4 | 0.5 | 0.0 | 10.1 |
| | 0.2 | 10% | 80% | | | | |
| | 0.274 | 0% | 90% | | | | | sCr only

| Time prior AKI stage | Cutoff value | sens | spec | Quartile | OR | 95% CI of OR | |
|---|---|---|---|---|---|---|---|
| 0 hours | 0.0432 | 75% | 26% | 1 | | | |
| | 0.0361 | 88% | 23% | 2 | 0.5 | 0.0 | 10.1 |
| | 0.0346 | 100% | 22% | 3 | 1.5 | 0.3 | 8.6 |
| | 0.136 | 25% | 70% | 4 | 1.0 | 0.1 | 7.7 |
| | 0.2 | 25% | 80% | | | | |
| | 0.27 | 13% | 90% | | | | |
| 24 hours | 0.0346 | 75% | 22% | 1 | | | |
| | 0 | 100% | 0% | 2 | 0.5 | 0.0 | 10.1 |
| | 0 | 100% | 0% | 3 | 1.0 | 0.1 | 7.7 |
| | 0.136 | 25% | 70% | 4 | 1.5 | 0.3 | 8.6 |
| | 0.2 | 25% | 80% | | | | |
| | 0.27 | 13% | 90% | | | | |
| 48 hours | 0.0467 | 80% | 29% | 1 | | | |
| | 0.0467 | 80% | 29% | 2 | 1.0 | 0.0 | 56.2 |
| | 0.0346 | 100% | 22% | 3 | 2.1 | 0.1 | 43.2 |
| | 0.136 | 20% | 70% | 4 | 1.0 | 0.0 | 56.2 |
| | 0.2 | 20% | 80% | | | | |
| | 0.27 | 20% | 90% | | | | |

UO only

| Time prior AKI stage | Cutoff value | sens | spec | Quartile | OR | 95% CI of OR | |
|---|---|---|---|---|---|---|---|
| 0 hours | 0.0713 | 73% | 46% | 1 | | | |
| | 0.0467 | 82% | 36% | 2 | 3.3 | 0.2 | 53.0 |
| | 0.0456 | 91% | 35% | 3 | 3.3 | 0.2 | 53.0 |
| | 0.132 | 36% | 72% | 4 | 4.6 | 0.3 | 63.1 |
| | 0.196 | 27% | 81% | | | | |
| | 0.25 | 18% | 91% | | | | |
| 24 hours | 0.0467 | 73% | 36% | 1 | | | |
| | 0.0456 | 82% | 35% | 2 | 1.6 | 0.3 | 9.6 |
| | 0.0284 | 91% | 25% | 3 | 1.0 | 0.1 | 8.4 |
| | 0.132 | 36% | 72% | 4 | 2.2 | 0.4 | 11.4 |
| | 0.196 | 18% | 81% | | | | |
| | 0.25 | 18% | 91% | | | | |

Fig. 8 Continued

| 48 hours | 0.0735 | 71% | 46% | 1 | | | |
| | 0.0713 | 86% | 46% | 2 | 2.1 | 0.1 | 47.1 |
| | 0.0284 | 100% | 25% | 3 | 2.1 | 0.1 | 47.1 |
| | 0.132 | 43% | 72% | 4 | 2.1 | 0.1 | 47.1 |
| | 0.196 | 14% | 81% | | | | |
| | 0.25 | 14% | 91% | | | | |

Myeloperoxidase sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 128.008 | 469.412 | 128.008 | 410.983 | 128.008 | 352.554 |
| average | 184.155 | 691.230 | 184.155 | 555.491 | 184.155 | 429.229 |
| stdev | 205.515 | 593.936 | 205.515 | 408.360 | 205.515 | 208.507 |
| p (t-test) | | 0.000 | | 0.000 | | 0.003 |
| min | 0.000 | 244.989 | 0.000 | 244.989 | 0.000 | 244.989 |
| max | 992.966 | 2048.626 | 992.966 | 1580.100 | 992.966 | 862.883 |
| n (Samp) | 99 | 11 | 99 | 10 | 99 | 7 |
| n (Pat) | 99 | 11 | 99 | 10 | 99 | 7 | sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 204.402 | 477.383 | 204.402 | 377.501 | 204.402 | 277.618 |
| average | 218.288 | 925.743 | 218.288 | 645.022 | 218.288 | 333.330 |
| stdev | 215.478 | 832.701 | 215.478 | 631.793 | 215.478 | 125.816 |
| p (t-test) | | 0.000 | | 0.000 | | 0.359 |
| min | 0.000 | 244.989 | 0.000 | 244.989 | 0.000 | 244.989 |
| max | 992.966 | 2048.626 | 992.966 | 1580.100 | 992.966 | 477.383 |
| n (Samp) | 161 | 5 | 161 | 4 | 161 | 3 |
| n (Pat) | 161 | 5 | 161 | 4 | 161 | 3 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 154.673 | 410.983 | 154.673 | 410.983 | 154.673 | 404.053 |
| average | 222.959 | 462.148 | 222.959 | 462.148 | 222.959 | 454.498 |
| stdev | 286.781 | 208.424 | 286.781 | 208.424 | 286.781 | 216.349 |
| p (t-test) | | 0.024 | | 0.024 | | 0.056 |
| min | 0.000 | 244.989 | 0.000 | 244.989 | 0.000 | 244.989 |
| max | 1808.488 | 862.883 | 1808.488 | 862.883 | 1808.488 | 862.883 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
|---|---|---|---|---|---|
| 0 hours | 0.87 | 0.071 | 99 | 11 | 0.000 |
| 24 hours | 0.86 | 0.077 | 99 | 10 | 0.000 |
| 48 hours | 0.83 | 0.096 | 99 | 7 | 0.000 | sCr only

| Time prior AKI stage | AUC | SE | nCohort 1 | nCohort 2 | p |
|---|---|---|---|---|---|
| 0 hours | 0.83 | 0.114 | 161 | 5 | 0.004 |
| 24 hours | 0.78 | 0.137 | 161 | 4 | 0.038 |
| 48 hours | 0.71 | 0.170 | 161 | 3 | 0.209 |

Fig. 8 Continued

UO only

| Time prior AKI stage | AUC | SE | nCohort 1 | nCohort 2 | p |
|---|---|---|---|---|---|
| 0 hours | 0.83 | 0.092 | 84 | 8 | 0.000 |
| 24 hours | 0.83 | 0.092 | 84 | 8 | 0.000 |
| 48 hours | 0.82 | 0.107 | 84 | 6 | 0.003 |

Oxidized low-density lipoprotein receptor 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 0.440 | 1.068 | 0.440 | 1.044 | 0.440 | 1.020 |
| average | 0.505 | 1.212 | 0.505 | 1.130 | 0.505 | 0.983 |
| stdev | 0.324 | 0.759 | 0.324 | 0.746 | 0.324 | 0.735 |
| p (t-test) | | 0.000 | | 0.000 | | 0.001 |
| min | 0.121 | 0.342 | 0.121 | 0.342 | 0.121 | 0.342 |
| max | 1.737 | 2.441 | 1.737 | 2.441 | 1.737 | 2.441 |
| n (Samp) | 99 | 11 | 99 | 10 | 99 | 7 |
| n (Pat) | 99 | 11 | 99 | 10 | 99 | 7 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 0.478 | 1.150 | 0.478 | 1.085 | 0.478 | 1.150 |
| average | 0.592 | 1.213 | 0.592 | 1.008 | 0.592 | 1.117 |
| stdev | 0.471 | 0.499 | 0.471 | 0.227 | 0.471 | 0.085 |
| p (t-test) | | 0.004 | | 0.080 | | 0.056 |
| min | 0.121 | 0.683 | 0.121 | 0.683 | 0.121 | 1.020 |
| max | 3.215 | 2.034 | 3.215 | 1.179 | 3.215 | 1.179 |
| n (Samp) | 161 | 5 | 161 | 4 | 161 | 3 |
| n (Pat) | 161 | 5 | 161 | 4 | 161 | 3 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 0.435 | 1.109 | 0.435 | 1.109 | 0.435 | 0.773 |
| average | 0.527 | 1.200 | 0.527 | 1.200 | 0.527 | 0.977 |
| stdev | 0.367 | 0.825 | 0.367 | 0.825 | 0.367 | 0.805 |
| p (t-test) | | 0.000 | | 0.000 | | 0.010 |
| min | 0.121 | 0.342 | 0.121 | 0.342 | 0.121 | 0.342 |
| max | 1.920 | 2.441 | 1.920 | 2.441 | 1.920 | 2.441 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
|---|---|---|---|---|---|
| 0 hours | 0.83 | 0.078 | 99 | 11 | 0.000 |
| 24 hours | 0.81 | 0.085 | 99 | 10 | 0.000 |
| 48 hours | 0.74 | 0.111 | 99 | 7 | 0.033 | sCr only

| Time prior AKI stage | AUC | SE | nCohort 1 | nCohort 2 | p |
|---|---|---|---|---|---|
| 0 hours | 0.89 | 0.097 | 161 | 5 | 0.000 |
| 24 hours | 0.87 | 0.116 | 161 | 4 | 0.002 |
| 48 hours | 0.90 | 0.117 | 161 | 3 | 0.001 |

Fig. 8 Continued

UO only

| Time prior AKI stage | AUC | SE | nCohort 1 | nCohort 2 | p |
|---|---|---|---|---|---|
| 0 hours | 0.78 | 0.099 | 84 | 8 | 0.004 |
| 24 hours | 0.78 | 0.099 | 84 | 8 | 0.004 |
| 48 hours | 0.69 | 0.124 | 84 | 6 | 0.132 |

Pappalysin-1 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.053 | 0.107 | 0.053 | 0.099 | 0.053 | 0.091 |
| average | 0.153 | 0.165 | 0.153 | 0.138 | 0.153 | 0.112 |
| stdev | 0.910 | 0.120 | 0.910 | 0.111 | 0.910 | 0.083 |
| p (t-test) |  | 0.956 |  | 0.945 |  | 0.886 |
| min | 0.000 | 0.029 | 0.000 | 0.029 | 0.000 | 0.027 |
| max | 9.680 | 0.412 | 9.680 | 0.392 | 9.680 | 0.258 |
| n (Samp) | 112 | 17 | 112 | 17 | 112 | 10 |
| n (Pat) | 112 | 17 | 112 | 17 | 112 | 10 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.057 | 0.096 | 0.057 | 0.071 | 0.057 | 0.056 |
| average | 0.132 | 0.100 | 0.132 | 0.081 | 0.132 | 0.058 |
| stdev | 0.719 | 0.053 | 0.719 | 0.051 | 0.719 | 0.031 |
| p (t-test) |  | 0.900 |  | 0.844 |  | 0.820 |
| min | 0.000 | 0.029 | 0.000 | 0.029 | 0.000 | 0.029 |
| max | 9.680 | 0.187 | 9.680 | 0.187 | 9.680 | 0.107 |
| n (Samp) | 180 | 8 | 180 | 8 | 180 | 5 |
| n (Pat) | 180 | 8 | 180 | 8 | 180 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.043 | 0.158 | 0.043 | 0.115 | 0.043 | 0.141 |
| average | 0.169 | 0.201 | 0.169 | 0.171 | 0.169 | 0.143 |
| stdev | 1.021 | 0.131 | 1.021 | 0.120 | 1.021 | 0.080 |
| p (t-test) |  | 0.919 |  | 0.993 |  | 0.947 |
| min | 0.000 | 0.036 | 0.000 | 0.036 | 0.000 | 0.027 |
| max | 9.680 | 0.412 | 9.680 | 0.392 | 9.680 | 0.258 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
|---|---|---|---|---|---|
| 0 hours | 0.77 | 0.069 | 112 | 17 | 0.000 |
| 24 hours | 0.71 | 0.074 | 112 | 17 | 0.005 |
| 48 hours | 0.64 | 0.098 | 112 | 10 | 0.151 | sCr only

| Time prior AKI stage | AUC | SE | nCohort 1 | nCohort 2 | p |
|---|---|---|---|---|---|
| 0 hours | 0.67 | 0.107 | 180 | 8 | 0.118 |
| 24 hours | 0.57 | 0.108 | 180 | 8 | 0.513 |
| 48 hours | 0.45 | 0.127 | 180 | 5 | 0.709 |

Fig. 8 Continued

UO only

| Time prior AKI stage | AUC | SE | nCohort 1 | nCohort 2 | p |
|---|---|---|---|---|---|
| 0 hours | 0.85 | 0.075 | 89 | 11 | 0.000 |
| 24 hours | 0.83 | 0.079 | 89 | 11 | 0.000 |
| 48 hours | 0.80 | 0.103 | 89 | 7 | 0.003 | sCr or UO

| Time prior AKI stage | Cutoff value | sens | spec | Quartile | OR | 95% CI of OR | |
|---|---|---|---|---|---|---|---|
| 0 hours | 0.0854 | 71% | 71% | 1 | | | |
| | 0.0623 | 82% | 59% | 2 | 0.0 | 0.0 | na |
| | 0.0358 | 94% | 27% | 3 | 2.8 | 0.6 | 12.6 |
| | 0.0854 | 71% | 71% | 4 | 6.5 | 1.7 | 24.6 |
| | 0.095 | 59% | 80% | | | | |
| | 0.135 | 47% | 90% | | | | |
| 24 hours | 0.0645 | 71% | 60% | 1 | | | |
| | 0.0492 | 82% | 47% | 2 | 1.6 | 0.3 | 9.1 |
| | 0.0358 | 94% | 27% | 3 | 1.6 | 0.3 | 9.1 |
| | 0.0854 | 59% | 71% | 4 | 5.6 | 1.5 | 21.6 |
| | 0.095 | 53% | 80% | | | | |
| | 0.135 | 35% | 90% | | | | |
| 48 hours | 0.0533 | 70% | 52% | 1 | | | |
| | 0.0312 | 80% | 21% | 2 | 0.0 | 0.0 | na |
| | 0.0273 | 90% | 19% | 3 | 0.6 | 0.1 | 3.8 |
| | 0.0854 | 50% | 71% | 4 | 1.7 | 0.5 | 5.7 |
| | 0.095 | 50% | 80% | | | | |
| | 0.135 | 40% | 90% | | | | | sCr only

| Time prior AKI stage | Cutoff value | sens | spec | Quartile | OR | 95% CI of OR | |
|---|---|---|---|---|---|---|---|
| 0 hours | 0.0635 | 75% | 57% | 1 | | | |
| | 0.058 | 88% | 52% | 2 | 0.0 | 0.0 | na |
| | 0.0292 | 100% | 19% | 3 | 3.1 | 0.2 | 46.7 |
| | 0.0856 | 50% | 70% | 4 | 4.3 | 0.3 | 54.2 |
| | 0.11 | 25% | 80% | | | | |
| | 0.165 | 13% | 90% | | | | |
| 24 hours | 0.0494 | 75% | 44% | 1 | | | |
| | 0.0362 | 88% | 28% | 2 | 3.1 | 0.2 | 46.7 |
| | 0.0292 | 100% | 19% | 3 | 1.0 | 0.0 | 54.9 |
| | 0.0856 | 38% | 70% | 4 | 3.1 | 0.2 | 46.7 |
| | 0.11 | 13% | 80% | | | | |
| | 0.165 | 13% | 90% | | | | |
| 48 hours | 0.0331 | 80% | 22% | 1 | | | |
| | 0.0331 | 80% | 22% | 2 | 1.0 | 0.0 | 56.2 |
| | 0.0292 | 100% | 19% | 3 | 1.0 | 0.0 | 56.2 |
| | 0.0856 | 20% | 70% | 4 | 2.1 | 0.1 | 43.2 |
| | 0.11 | 0% | 80% | | | | |
| | 0.165 | 0% | 90% | | | | |

UO only

| Time prior AKI stage | Cutoff value | sens | spec | Quartile | OR | 95% CI of OR | |
|---|---|---|---|---|---|---|---|
| 0 hours | 0.0928 | 73% | 83% | 1 | | | |
| | 0.0854 | 82% | 75% | 2 | na | na | na |
| | 0.0725 | 91% | 67% | 3 | na | na | na |
| | 0.0817 | 82% | 71% | 4 | na | na | na |
| | 0.0901 | 73% | 81% | | | | |
| | 0.132 | 55% | 91% | | | | |

Fig. 8 Continued

| | | | | | | | |
|---|---|---|---|---|---|---|---|
| 24 hours | | 0.0928 | 73% | 83% | 1 | | | |
| | | 0.0725 | 82% | 67% | 2 | na | na | na |
| | | 0.0623 | 91% | 64% | 3 | na | na | na |
| | | 0.0817 | 73% | 71% | 4 | na | na | na |
| | | 0.0901 | 73% | 81% | | | | |
| | | 0.132 | 45% | 91% | | | | |
| 48 hours | | 0.095 | 71% | 87% | 1 | | | |
| | | 0.0725 | 86% | 67% | 2 | 0.0 | 0.0 | na |
| | | 0.027 | 100% | 19% | 3 | 1.0 | 0.0 | 59.8 |
| | | 0.0817 | 71% | 71% | 4 | 6.1 | 0.5 | 76.8 |
| | | 0.0901 | 71% | 81% | | | | |
| | | 0.132 | 57% | 91% | | | | |

P-selectin glycoprotein ligand 1 sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 277.352 | 270.312 | 277.352 | 286.946 | 277.352 | 270.312 |
| average | 286.799 | 287.974 | 286.799 | 293.820 | 286.799 | 278.498 |
| stdev | 102.462 | 74.907 | 102.462 | 79.001 | 102.462 | 73.529 |
| p (t-test) | | 0.965 | | 0.806 | | 0.803 |
| min | 85.271 | 192.048 | 85.271 | 192.048 | 85.271 | 192.048 |
| max | 795.623 | 437.970 | 795.623 | 437.970 | 795.623 | 385.562 |
| n (Samp) | 105 | 16 | 105 | 14 | 105 | 10 |
| n (Pat) | 105 | 16 | 105 | 14 | 105 | 10 | sCr only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 288.212 | 280.106 | 288.212 | 296.740 | 288.212 | 263.473 |
| average | 295.318 | 297.784 | 295.318 | 304.711 | 295.318 | 279.653 |
| stdev | 99.419 | 89.000 | 99.419 | 93.772 | 99.419 | 89.160 |
| p (t-test) | | 0.945 | | 0.806 | | 0.728 |
| min | 85.271 | 192.048 | 85.271 | 192.048 | 85.271 | 192.048 |
| max | 795.623 | 437.970 | 795.623 | 437.970 | 795.623 | 379.297 |
| n (Samp) | 170 | 8 | 170 | 7 | 170 | 5 |
| n (Pat) | 170 | 8 | 170 | 7 | 170 | 5 |

UO only

| | 0 hr prior toAKI stage | | 24 hr prior toAKI stage | | 48 hr prior toAKI stage | |
|---|---|---|---|---|---|---|
| | Cohort 1 | Cohort 2 | Cohort 1 | Cohort 2 | Cohort 1 | Cohort 2 |
| median | 269.920 | 294.993 | 269.920 | 312.834 | 269.920 | 312.834 |
| average | 271.304 | 296.977 | 271.304 | 302.774 | 271.304 | 304.454 |
| stdev | 86.237 | 67.854 | 86.237 | 70.017 | 86.237 | 70.486 |
| p (t-test) | | 0.367 | | 0.294 | | 0.326 |
| min | 85.271 | 209.144 | 85.271 | 197.838 | 85.271 | 197.838 |
| max | 531.755 | 385.562 | 531.755 | 385.562 | 531.755 | 385.562 |
| n (Samp) | 84 | 10 | 84 | 9 | 84 | 7 |
| n (Pat) | 84 | 10 | 84 | 9 | 84 | 7 |

Fig. 8 Continued sCr or UO

| Time prior AKI stage | AUC | SE | nCohort 1 | nCohort 2 | p |
|---|---|---|---|---|---|
| 0 hours | 0.52 | 0.078 | 105 | 16 | 0.814 |
| 24 hours | 0.54 | 0.084 | 105 | 14 | 0.615 |
| 48 hours | 0.49 | 0.096 | 105 | 10 | 0.944 | sCr only

| Time prior AKI stage | AUC | SE | nCohort 1 | nCohort 2 | p |
|---|---|---|---|---|---|
| 0 hours | 0.51 | 0.106 | 170 | 8 | 0.900 |
| 24 hours | 0.54 | 0.114 | 170 | 7 | 0.734 |
| 48 hours | 0.46 | 0.128 | 170 | 5 | 0.754 |

UO only

| Time prior AKI stage | AUC | SE | nCohort 1 | nCohort 2 | p |
|---|---|---|---|---|---|
| 0 hours | 0.60 | 0.100 | 84 | 10 | 0.318 |
| 24 hours | 0.63 | 0.104 | 84 | 9 | 0.226 |
| 48 hours | 0.63 | 0.117 | 84 | 7 | 0.258 | sCr or UO

| Time prior AKI stage | Cutoff value | sens | spec | Quartile | OR | 95% CI of OR | |
|---|---|---|---|---|---|---|---|
| 0 hours | 228.945 | 75% | 31% | 1 | | | |
| | 227.979 | 81% | 30% | 2 | 2.3 | 0.7 | 7.0 |
| | 195.596 | 94% | 21% | 3 | 1.0 | 0.2 | 4.3 |
| | 321.667 | 31% | 70% | 4 | 1.3 | 0.4 | 4.8 |
| | 358.289 | 25% | 80% | | | | |
| | 401.74 | 6% | 90% | | | | |
| 24 hours | 237.694 | 71% | 34% | 1 | | | |
| | 197.838 | 86% | 21% | 2 | 1.3 | 0.4 | 4.9 |
| | 195.596 | 93% | 21% | 3 | 1.0 | 0.2 | 4.1 |
| | 321.667 | 36% | 70% | 4 | 1.3 | 0.4 | 4.9 |
| | 358.289 | 29% | 80% | | | | |
| | 401.74 | 7% | 90% | | | | |
| 48 hours | 237.694 | 70% | 34% | 1 | | | |
| | 197.838 | 80% | 21% | 2 | 1.0 | 0.1 | 8.2 |
| | 195.596 | 90% | 21% | 3 | 1.6 | 0.3 | 9.2 |
| | 321.667 | 30% | 70% | 4 | 1.6 | 0.3 | 9.6 |
| | 358.289 | 20% | 80% | | | | |
| | 401.74 | 0% | 90% | | | | | sCr only

| Time prior AKI stage | Cutoff value | sens | spec | Quartile | OR | 95% CI of OR | |
|---|---|---|---|---|---|---|---|
| 0 hours | 247.135 | 75% | 34% | 1 | | | |
| | 197.838 | 88% | 17% | 2 | 1.0 | 0.1 | 7.6 |
| | 190.485 | 100% | 14% | 3 | 0.5 | 0.0 | 10.1 |
| | 335.606 | 38% | 70% | 4 | 1.5 | 0.3 | 8.4 |
| | 361.727 | 38% | 80% | | | | |
| | 401.74 | 13% | 90% | | | | |
| 24 hours | 258.919 | 71% | 36% | 1 | | | |
| | 197.838 | 86% | 17% | 2 | 0.5 | 0.0 | 10.1 |
| | 190.485 | 100% | 14% | 3 | 0.5 | 0.0 | 10.1 |
| | 335.606 | 43% | 70% | 4 | 1.5 | 0.3 | 8.4 |
| | 361.727 | 43% | 80% | | | | |
| | 401.74 | 14% | 90% | | | | |

Fig. 8 Continued

| 48 hours | 197.838 | 80% | 17% | 1 | | | |
| --- | --- | --- | --- | --- | --- | --- | --- |
| | 197.838 | 80% | 17% | 2 | 0.0 | 0.0 | na |
| | 190.485 | 100% | 14% | 3 | 0.5 | 0.0 | 10.1 |
| | 335.606 | 40% | 70% | 4 | 1.0 | 0.1 | 8.0 |
| | 361.727 | 40% | 80% | | | | |
| | 401.74 | 0% | 90% | | | | |

UO only

| Time prior AKI stage | Cutoff value | sens | spec | Quartile | OR | 95% CI of OR | |
| --- | --- | --- | --- | --- | --- | --- | --- |
| 0 hours | 237.694 | 70% | 37% | 1 | | | |
| | 228.627 | 80% | 33% | 2 | 3.1 | 0.2 | 51.5 |
| | 224.212 | 90% | 32% | 3 | 2.1 | 0.1 | 47.6 |
| | 310.047 | 50% | 70% | 4 | 4.4 | 0.3 | 61.5 |
| | 347.212 | 30% | 81% | | | | |
| | 383.222 | 10% | 90% | | | | |
| 24 hours | 237.694 | 78% | 37% | 1 | | | |
| | 224.212 | 89% | 32% | 2 | 2.1 | 0.1 | 47.6 |
| | 195.182 | 100% | 24% | 3 | 2.1 | 0.1 | 47.6 |
| | 310.047 | 56% | 70% | 4 | 4.4 | 0.3 | 61.5 |
| | 347.212 | 33% | 81% | | | | |
| | 383.222 | 11% | 90% | | | | |
| 48 hours | 275.164 | 71% | 54% | 1 | | | |
| | 237.694 | 86% | 37% | 2 | 1.0 | 0.0 | 57.7 |
| | 195.182 | 100% | 24% | 3 | 2.0 | 0.1 | 45.6 |
| | 310.047 | 57% | 70% | 4 | 3.2 | 0.2 | 52.0 |
| | 347.212 | 29% | 81% | | | | |
| | 383.222 | 14% | 90% | | | | |

Secretory leukocyte peptidase inhibitor sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 65642.439 | 110949.914 | 65642.439 | 107269.829 | 65642.439 | 99670.689 |
| average | 75387.460 | 126262.264 | 75387.460 | 122213.065 | 75387.460 | 108930.142 |
| stdev | 36562.166 | 44661.931 | 36562.166 | 46469.954 | 36562.166 | 41678.233 |
| p (t-test) | | 0.000 | | 0.000 | | 0.007 |
| min | 13520.408 | 72946.237 | 13520.408 | 64659.271 | 13520.408 | 64659.271 |
| max | 199917.831 | 218323.747 | 199917.831 | 218323.747 | 199917.831 | 170531.178 |
| n (Samp) | 104 | 15 | 104 | 14 | 104 | 10 |
| n (Pat) | 104 | 15 | 104 | 14 | 104 | 10 | sCr only

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 71251.981 | 151191.710 | 71251.981 | 155716.753 | 71251.981 | 155716.753 |
| average | 76070.778 | 148234.164 | 76070.778 | 144702.729 | 76070.778 | 132494.761 |
| stdev | 33362.429 | 43304.158 | 33362.429 | 51559.754 | 33362.429 | 46580.729 |
| p (t-test) | | 0.000 | | 0.000 | | 0.000 |
| min | 13520.408 | 81282.051 | 13520.408 | 64659.271 | 13520.408 | 64659.271 |
| max | 199917.831 | 218323.747 | 199917.831 | 218323.747 | 199917.831 | 169533.679 |
| n (Samp) | 169 | 8 | 169 | 7 | 169 | 5 |
| n (Pat) | 169 | 8 | 169 | 7 | 169 | 5 |

Fig. 8 Continued

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 66409.639 | 95751.634 | 66409.639 | 95751.634 | 66409.639 | 95751.634 |
| average | 73308.303 | 115923.102 | 73308.303 | 114812.342 | 73308.303 | 107439.722 |
| stdev | 31111.701 | 41351.778 | 31111.701 | 39523.478 | 31111.701 | 40874.582 |
| p (t-test) |  | 0.000 |  | 0.000 |  | 0.008 |
| min | 21505.376 | 72946.237 | 21505.376 | 72946.237 | 21505.376 | 70370.370 |
| max | 183903.282 | 179530.516 | 183903.282 | 170531.178 | 183903.282 | 170531.178 |
| n (Samp) | 83 | 9 | 83 | 9 | 83 | 7 |
| n (Pat) | 83 | 9 | 83 | 9 | 83 | 7 | sCr or UO

| Time prior AKI stage | AUC | SE | nCohort 1 | nCohort 2 | p |
|---|---|---|---|---|---|
| 0 hours | 0.84 | 0.065 | 104 | 15 | 0.000 |
| 24 hours | 0.82 | 0.071 | 104 | 14 | 0.000 |
| 48 hours | 0.76 | 0.091 | 104 | 10 | 0.004 | sCr only

| Time prior AKI stage | AUC | SE | nCohort 1 | nCohort 2 | p |
|---|---|---|---|---|---|
| 0 hours | 0.92 | 0.068 | 169 | 8 | 0.000 |
| 24 hours | 0.87 | 0.088 | 169 | 7 | 0.000 |
| 48 hours | 0.83 | 0.113 | 169 | 5 | 0.003 |

UO only

| Time prior AKI stage | AUC | SE | nCohort 1 | nCohort 2 | p |
|---|---|---|---|---|---|
| 0 hours | 0.83 | 0.085 | 83 | 9 | 0.000 |
| 24 hours | 0.83 | 0.085 | 83 | 9 | 0.000 |
| 48 hours | 0.77 | 0.107 | 83 | 7 | 0.011 |

Stem cell factor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 356.000 | 642.000 | 356.000 | 549.000 | 356.000 | 516.500 |
| average | 415.158 | 609.882 | 415.158 | 551.000 | 415.158 | 520.600 |
| stdev | 220.079 | 257.385 | 220.079 | 277.790 | 220.079 | 259.667 |
| p (t-test) |  | 0.001 |  | 0.024 |  | 0.155 |
| min | 89.700 | 233.000 | 89.700 | 174.000 | 89.700 | 233.000 |
| max | 1340.000 | 1100.000 | 1340.000 | 1100.000 | 1340.000 | 927.000 |
| n (Samp) | 112 | 17 | 112 | 17 | 112 | 10 |
| n (Pat) | 112 | 17 | 112 | 17 | 112 | 10 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 387.000 | 660.500 | 387.000 | 651.000 | 387.000 | 584.000 |
| average | 460.909 | 596.125 | 460.909 | 519.625 | 460.909 | 591.000 |
| stdev | 454.552 | 237.155 | 454.552 | 281.473 | 454.552 | 242.288 |
| p (t-test) |  | 0.405 |  | 0.718 |  | 0.525 |
| min | 89.700 | 289.000 | 89.700 | 174.000 | 89.700 | 233.000 |
| max | 5840.000 | 895.000 | 5840.000 | 895.000 | 5840.000 | 895.000 |
| n (Samp) | 180 | 8 | 180 | 8 | 180 | 5 |
| n (Pat) | 180 | 8 | 180 | 8 | 180 | 5 |

Fig. 8 Continued

UO only

|        | 0 hr prior toAKI stage | | 24 hr prior toAKI stage | | 48 hr prior toAKI stage | |
|---|---|---|---|---|---|---|
|        | Cohort 1 | Cohort 2 | Cohort 1 | Cohort 2 | Cohort 1 | Cohort 2 |
| median   | 356.000  | 679.000  | 356.000  | 549.000  | 356.000  | 484.000 |
| average  | 397.873  | 652.091  | 397.873  | 616.727  | 397.873  | 527.000 |
| stdev    | 195.813  | 270.409  | 195.813  | 275.574  | 195.813  | 285.084 |
| p (t-test) |        | 0.000    |          | 0.001    |          | 0.108   |
| min      | 89.700   | 233.000  | 89.700   | 233.000  | 89.700   | 233.000 |
| max      | 1260.000 | 1100.000 | 1260.000 | 1100.000 | 1260.000 | 927.000 |
| n (Samp) | 89       | 11       | 89       | 11       | 89       | 7       |
| n (Pat)  | 89       | 11       | 89       | 11       | 89       | 7       | sCr or UO

| Time prior AKI stage | AUC | SE | nCohort 1 | nCohort 2 | p |
|---|---|---|---|---|---|
| 0 hours  | 0.73 | 0.073 | 112 | 17 | 0.002 |
| 24 hours | 0.64 | 0.077 | 112 | 17 | 0.065 |
| 48 hours | 0.62 | 0.098 | 112 | 10 | 0.236 | sCr only

| Time prior AKI stage | AUC | SE | nCohort 1 | nCohort 2 | p |
|---|---|---|---|---|---|
| 0 hours  | 0.70 | 0.105 | 180 | 8 | 0.053 |
| 24 hours | 0.59 | 0.108 | 180 | 8 | 0.429 |
| 48 hours | 0.72 | 0.132 | 180 | 5 | 0.100 |

UO only

| Time prior AKI stage | AUC | SE | nCohort 1 | nCohort 2 | p |
|---|---|---|---|---|---|
| 0 hours  | 0.78 | 0.085 | 89 | 11 | 0.001 |
| 24 hours | 0.74 | 0.089 | 89 | 11 | 0.007 |
| 48 hours | 0.61 | 0.117 | 89 | 7  | 0.349 | sCr or UO

| Time prior AKI stage | Cutoff value | sens | spec | Quartile | OR | 95% CI of OR | |
|---|---|---|---|---|---|---|---|
| 0 hours  | 382 | 71%  | 55% | 1 |     |     |      |
|          | 322 | 82%  | 42% | 2 | 1.0 | 0.1 | 8.1  |
|          | 278 | 94%  | 25% | 3 | 1.0 | 0.1 | 8.1  |
|          | 439 | 65%  | 71% | 4 | 7.5 | 2.0 | 27.9 |
|          | 551 | 65%  | 80% |   |     |     |      |
|          | 653 | 47%  | 90% |   |     |     |      |
| 24 hours | 382 | 71%  | 55% | 1 |     |     |      |
|          | 229 | 88%  | 15% | 2 | 0.2 | 0.0 | 3.0  |
|          | 171 | 100% | 4%  | 3 | 0.7 | 0.2 | 2.6  |
|          | 439 | 65%  | 71% | 4 | 2.6 | 1.1 | 6.2  |
|          | 551 | 47%  | 80% |   |     |     |      |
|          | 653 | 35%  | 90% |   |     |     |      |
| 48 hours | 315 | 70%  | 39% | 1 |     |     |      |
|          | 278 | 80%  | 25% | 2 | 1.0 | 0.1 | 7.9  |
|          | 229 | 100% | 15% | 3 | 0.5 | 0.0 | 10.5 |
|          | 439 | 60%  | 71% | 4 | 2.7 | 0.6 | 12.3 |
|          | 551 | 40%  | 80% |   |     |     |      |
|          | 653 | 30%  | 90% |   |     |     |      |

Fig. 8 Continued sCr only

| Time prior AKI stage | Cutoff value | sens | spec | Quartile | OR | 95% CI of OR | |
|---|---|---|---|---|---|---|---|
| 0 hours | 377 | 75% | 47% | 1 | | | |
| | 322 | 88% | 36% | 2 | 2.0 | 0.1 | 42.2 |
| | 288 | 100% | 25% | 3 | 0.0 | 0.0 | na |
| | 494 | 63% | 70% | 4 | 5.5 | 0.5 | 62.9 |
| | 553 | 63% | 80% | | | | |
| | 702 | 25% | 90% | | | | |
| 24 hours | 229 | 75% | 13% | 1 | | | |
| | 171 | 100% | 3% | 2 | 0.0 | 0.0 | na |
| | 171 | 100% | 3% | 3 | 0.0 | 0.0 | na |
| | 494 | 63% | 70% | 4 | 1.7 | 0.6 | 5.4 |
| | 553 | 63% | 80% | | | | |
| | 702 | 13% | 90% | | | | |
| 48 hours | 523 | 80% | 77% | 1 | | | |
| | 523 | 80% | 77% | 2 | 0.0 | 0.0 | na |
| | 229 | 100% | 13% | 3 | 0.0 | 0.0 | na |
| | 494 | 80% | 70% | 4 | 4.2 | 0.3 | 53.0 |
| | 553 | 60% | 80% | | | | |
| | 702 | 20% | 90% | | | | |

UO only

| Time prior AKI stage | Cutoff value | sens | spec | Quartile | OR | 95% CI of OR | |
|---|---|---|---|---|---|---|---|
| 0 hours | 571 | 73% | 91% | 1 | | | |
| | 382 | 82% | 60% | 2 | 0.0 | 0.0 | na |
| | 278 | 91% | 25% | 3 | 0.5 | 0.0 | 10.7 |
| | 428 | 73% | 71% | 4 | 5.4 | 1.3 | 22.5 |
| | 549 | 73% | 82% | | | | |
| | 571 | 73% | 91% | | | | |
| 24 hours | 443 | 73% | 73% | 1 | | | |
| | 382 | 82% | 60% | 2 | 0.0 | 0.0 | na |
| | 278 | 91% | 25% | 3 | 1.0 | 0.1 | 8.4 |
| | 428 | 73% | 71% | 4 | 4.5 | 1.0 | 19.1 |
| | 549 | 45% | 82% | | | | |
| | 571 | 45% | 91% | | | | |
| 48 hours | 315 | 71% | 38% | 1 | | | |
| | 278 | 86% | 25% | 2 | 2.1 | 0.1 | 47.1 |
| | 229 | 100% | 16% | 3 | 1.0 | 0.0 | 59.8 |
| | 428 | 57% | 71% | 4 | 3.3 | 0.2 | 53.6 |
| | 549 | 29% | 82% | | | | |
| | 571 | 29% | 91% | | | | |

Fig. 8 Continued

Tissue inhibitor of metalloproteinase 1 sCr or UO

|          | 0 hr prior to AKI stage | | 24 hr prior to AKI stage | | 48 hr prior to AKI stage | |
|----------|--------:|--------:|--------:|--------:|--------:|--------:|
|          | Cohort 1 | Cohort 2 | Cohort 1 | Cohort 2 | Cohort 1 | Cohort 2 |
| median   | 259.500 | 484.000 | 259.500 | 444.000 | 259.500 | 362.500 |
| average  | 308.191 | 597.176 | 308.191 | 539.765 | 308.191 | 404.000 |
| stdev    | 201.488 | 319.091 | 201.488 | 293.413 | 201.488 | 189.259 |
| p (t-test) |       | 0.000   |         | 0.000   |         | 0.150   |
| min      | 75.400  | 227.000 | 75.400  | 226.000 | 75.400  | 226.000 |
| max      | 1207.000 | 1220.000 | 1207.000 | 1220.000 | 1207.000 | 739.000 |
| n (Samp) | 112     | 17      | 112     | 17      | 112     | 10      |
| n (Pat)  | 112     | 17      | 112     | 17      | 112     | 10      | sCr only

|          | 0 hr prior to AKI stage | | 24 hr prior to AKI stage | | 48 hr prior to AKI stage | |
|----------|--------:|--------:|--------:|--------:|--------:|--------:|
|          | Cohort 1 | Cohort 2 | Cohort 1 | Cohort 2 | Cohort 1 | Cohort 2 |
| median   | 263.000 | 512.500 | 263.000 | 459.000 | 263.000 | 444.000 |
| average  | 337.145 | 576.125 | 337.145 | 514.000 | 337.145 | 446.600 |
| stdev    | 236.891 | 257.790 | 236.891 | 243.295 | 236.891 | 208.024 |
| p (t-test) |       | 0.006   |         | 0.040   |         | 0.308   |
| min      | 75.400  | 246.000 | 75.400  | 246.000 | 75.400  | 246.000 |
| max      | 1250.000 | 966.000 | 1250.000 | 829.000 | 1250.000 | 776.000 |
| n (Samp) | 180     | 8       | 180     | 8       | 180     | 5       |
| n (Pat)  | 180     | 8       | 180     | 8       | 180     | 5       |

UO only

|          | 0 hr prior to AKI stage | | 24 hr prior to AKI stage | | 48 hr prior to AKI stage | |
|----------|--------:|--------:|--------:|--------:|--------:|--------:|
|          | Cohort 1 | Cohort 2 | Cohort 1 | Cohort 2 | Cohort 1 | Cohort 2 |
| median   | 262.000 | 474.000 | 262.000 | 474.000 | 262.000 | 432.000 |
| average  | 320.321 | 617.545 | 320.321 | 574.000 | 320.321 | 436.714 |
| stdev    | 215.000 | 346.836 | 215.000 | 317.024 | 215.000 | 214.474 |
| p (t-test) |       | 0.000   |         | 0.001   |         | 0.171   |
| min      | 75.400  | 227.000 | 75.400  | 226.000 | 75.400  | 226.000 |
| max      | 1207.000 | 1220.000 | 1207.000 | 1220.000 | 1207.000 | 739.000 |
| n (Samp) | 89      | 11      | 89      | 11      | 89      | 7       |
| n (Pat)  | 89      | 11      | 89      | 11      | 89      | 7       | sCr or UO

| Time prior AKI stage | AUC | SE | nCohort 1 | nCohort 2 | p |
|---|---:|---:|---:|---:|---:|
| 0 hours  | 0.82 | 0.065 | 112 | 17 | 0.000 |
| 24 hours | 0.77 | 0.070 | 112 | 17 | 0.000 |
| 48 hours | 0.69 | 0.096 | 112 | 10 | 0.052 | sCr only

| Time prior AKI stage | AUC | SE | nCohort 1 | nCohort 2 | p |
|---|---:|---:|---:|---:|---:|
| 0 hours  | 0.80 | 0.096 | 180 | 8 | 0.002 |
| 24 hours | 0.75 | 0.101 | 180 | 8 | 0.013 |
| 48 hours | 0.71 | 0.132 | 180 | 5 | 0.102 |

UO only

| Time prior AKI stage | AUC | SE | nCohort 1 | nCohort 2 | p |
|---|---:|---:|---:|---:|---:|
| 0 hours  | 0.82 | 0.080 | 89 | 11 | 0.000 |
| 24 hours | 0.77 | 0.086 | 89 | 11 | 0.001 |
| 48 hours | 0.69 | 0.115 | 89 | 7  | 0.091 |

Fig. 8 Continued

Tissue inhibitor of metalloproteinase 2 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 111542.535 | 142079.866 | 111542.535 | 134002.820 | 111542.535 | 145549.173 |
| average | 113632.608 | 134474.118 | 113632.608 | 128419.349 | 113632.608 | 133076.767 |
| stdev | 24617.965 | 37132.928 | 24617.965 | 34173.363 | 24617.965 | 37080.962 |
| p (t-test) |  | 0.013 |  | 0.084 |  | 0.054 |
| min | 58493.008 | 84650.482 | 58493.008 | 84650.482 | 58493.008 | 89776.943 |
| max | 177248.877 | 189045.463 | 177248.877 | 188983.579 | 177248.877 | 188983.579 |
| n (Samp) | 99 | 11 | 99 | 10 | 99 | 7 |
| n (Pat) | 99 | 11 | 99 | 10 | 99 | 7 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 113284.580 | 131902.122 | 113284.580 | 110839.533 | 113284.580 | 125925.775 |
| average | 115893.688 | 136871.718 | 115893.688 | 123828.282 | 115893.688 | 134895.432 |
| stdev | 25995.299 | 51008.377 | 25995.299 | 48321.125 | 25995.299 | 50207.870 |
| p (t-test) |  | 0.088 |  | 0.556 |  | 0.219 |
| min | 58493.008 | 84650.482 | 58493.008 | 84650.482 | 58493.008 | 89776.943 |
| max | 197537.458 | 189045.463 | 197537.458 | 188983.579 | 197537.458 | 188983.579 |
| n (Samp) | 161 | 5 | 161 | 4 | 161 | 3 |
| n (Pat) | 161 | 5 | 161 | 4 | 161 | 3 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 109561.495 | 143814.520 | 109561.495 | 143814.520 | 109561.495 | 147764.677 |
| average | 112998.806 | 139467.801 | 112998.806 | 138720.758 | 112998.806 | 140293.404 |
| stdev | 25433.473 | 29594.364 | 25433.473 | 29886.612 | 25433.473 | 34821.351 |
| p (t-test) |  | 0.007 |  | 0.008 |  | 0.015 |
| min | 58493.008 | 99652.346 | 58493.008 | 99652.346 | 58493.008 | 99652.346 |
| max | 177248.877 | 188983.579 | 177248.877 | 188983.579 | 177248.877 | 188983.579 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
|---|---|---|---|---|---|
| 0 hours | 0.67 | 0.093 | 99 | 11 | 0.072 |
| 24 hours | 0.63 | 0.099 | 99 | 10 | 0.192 |
| 48 hours | 0.66 | 0.116 | 99 | 7 | 0.175 | sCr only

| Time prior AKI stage | AUC | SE | nCohort 1 | nCohort 2 | p |
|---|---|---|---|---|---|
| 0 hours | 0.60 | 0.136 | 161 | 5 | 0.454 |
| 24 hours | 0.50 | 0.147 | 161 | 4 | 0.979 |
| 48 hours | 0.61 | 0.175 | 161 | 3 | 0.523 |

UO only

| Time prior AKI stage | AUC | SE | nCohort 1 | nCohort 2 | p |
|---|---|---|---|---|---|
| 0 hours | 0.75 | 0.103 | 84 | 8 | 0.014 |
| 24 hours | 0.75 | 0.103 | 84 | 8 | 0.017 |
| 48 hours | 0.73 | 0.121 | 84 | 6 | 0.059 |

Fig. 8 Continued sCr or UO

| Time prior AKI stage | Cutoff value | sens | spec | Quartile | OR | 95% CI of OR | |
|---|---|---|---|---|---|---|---|
| 0 hours | 99703.7 | 73% | 31% | 1 | | | |
| | 98973.9 | 82% | 30% | 2 | 1.0 | 0.1 | 8.0 |
| | 89077.1 | 91% | 18% | 3 | 0.5 | 0.0 | 10.6 |
| | 125509 | 64% | 71% | 4 | 3.4 | 0.8 | 14.9 |
| | 135666 | 55% | 81% | | | | |
| | 145286 | 45% | 91% | | | | |
| 24 hours | 99703.7 | 70% | 31% | 1 | | | |
| | 98973.9 | 80% | 30% | 2 | 1.0 | 0.1 | 8.3 |
| | 89077.1 | 90% | 18% | 3 | 0.5 | 0.0 | 10.6 |
| | 125509 | 60% | 71% | 4 | 2.7 | 0.6 | 12.6 |
| | 135666 | 50% | 81% | | | | |
| | 145286 | 40% | 91% | | | | |
| 48 hours | 99703.7 | 71% | 31% | 1 | | | |
| | 98973.9 | 86% | 30% | 2 | 2.0 | 0.1 | 44.3 |
| | 89077.1 | 100% | 18% | 3 | 0.0 | 0.0 | na |
| | 125509 | 57% | 71% | 4 | 4.3 | 0.3 | 59.3 |
| | 135666 | 57% | 81% | | | | |
| | 145286 | 57% | 91% | | | | | sCr only

| Time prior AKI stage | Cutoff value | sens | spec | Quartile | OR | 95% CI of OR | |
|---|---|---|---|---|---|---|---|
| 0 hours | 89388.9 | 80% | 17% | 1 | | | |
| | 89388.9 | 80% | 17% | 2 | 0.0 | 0.0 | na |
| | 84630.8 | 100% | 10% | 3 | 0.5 | 0.0 | 10.2 |
| | 127129 | 60% | 70% | 4 | 1.0 | 0.1 | 7.6 |
| | 135952 | 40% | 80% | | | | |
| | 149556 | 40% | 90% | | | | |
| 24 hours | 89388.9 | 75% | 17% | 1 | | | |
| | 84630.8 | 100% | 10% | 2 | 0.0 | 0.0 | na |
| | 84630.8 | 100% | 10% | 3 | 0.0 | 0.0 | na |
| | 127129 | 50% | 70% | 4 | 1.0 | 0.1 | 7.6 |
| | 135952 | 25% | 80% | | | | |
| | 149556 | 25% | 90% | | | | |
| 48 hours | 89388.9 | 100% | 17% | 1 | | | |
| | 89388.9 | 100% | 17% | 2 | 0.0 | 0.0 | na |
| | 89388.9 | 100% | 17% | 3 | 1.0 | 0.0 | 55.6 |
| | 127129 | 33% | 70% | 4 | 1.0 | 0.0 | 55.6 |
| | 135952 | 33% | 80% | | | | |
| | 149556 | 33% | 90% | | | | |

Tumor necrosis factor-alpha sCr or UO

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 9.515 | 14.100 | 9.515 | 14.100 | 9.515 | 9.915 |
| average | 17.458 | 20.223 | 17.458 | 18.072 | 17.458 | 14.210 |
| stdev | 40.048 | 18.380 | 40.048 | 18.459 | 40.048 | 14.279 |
| p (t-test) | | 0.780 | | 0.951 | | 0.800 |
| min | 0.040 | 5.680 | 0.040 | 3.330 | 0.040 | 0.829 |
| max | 307.000 | 75.800 | 307.000 | 75.800 | 307.000 | 50.900 |
| n (Samp) | 112 | 17 | 112 | 17 | 112 | 10 |
| n (Pat) | 112 | 17 | 112 | 17 | 112 | 10 |

Fig. 8 Continued sCr only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 9.865 | 20.150 | 9.865 | 14.300 | 9.865 | 13.000 |
| average | 20.544 | 24.643 | 20.544 | 20.955 | 20.544 | 13.418 |
| stdev | 59.969 | 22.923 | 59.969 | 23.252 | 59.969 | 9.447 |
| p (t-test) | | 0.848 | | 0.985 | | 0.791 |
| min | 0.040 | 5.680 | 0.040 | 3.330 | 0.040 | 0.829 |
| max | 669.000 | 75.800 | 669.000 | 75.800 | 669.000 | 23.300 |
| n (Samp) | 180 | 8 | 180 | 8 | 180 | 5 |
| n (Pat) | 180 | 8 | 180 | 8 | 180 | 5 |

UO only

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| median | 8.220 | 14.100 | 8.220 | 14.100 | 8.220 | 10.700 |
| average | 15.575 | 17.441 | 15.575 | 16.798 | 15.575 | 17.173 |
| stdev | 34.035 | 12.238 | 34.035 | 12.748 | 34.035 | 16.100 |
| p (t-test) | | 0.858 | | 0.907 | | 0.903 |
| min | 0.040 | 6.910 | 0.040 | 4.300 | 0.040 | 3.830 |
| max | 307.000 | 50.900 | 307.000 | 50.900 | 307.000 | 50.900 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
|---|---|---|---|---|---|
| 0 hours | 0.67 | 0.076 | 112 | 17 | 0.023 |
| 24 hours | 0.61 | 0.077 | 112 | 17 | 0.149 |
| 48 hours | 0.52 | 0.097 | 112 | 10 | 0.825 | sCr only

| Time prior AKI stage | AUC | SE | nCohort 1 | nCohort 2 | p |
|---|---|---|---|---|---|
| 0 hours | 0.69 | 0.106 | 180 | 8 | 0.066 |
| 24 hours | 0.62 | 0.108 | 180 | 8 | 0.272 |
| 48 hours | 0.56 | 0.135 | 180 | 5 | 0.645 |

UO only

| Time prior AKI stage | AUC | SE | nCohort 1 | nCohort 2 | p |
|---|---|---|---|---|---|
| 0 hours | 0.71 | 0.092 | 89 | 11 | 0.023 |
| 24 hours | 0.67 | 0.094 | 89 | 11 | 0.074 |
| 48 hours | 0.60 | 0.117 | 89 | 7 | 0.374 | sCr or UO

| Time prior AKI stage | Cutoff value | sens | spec | Quartile | OR | 95% CI of OR | |
|---|---|---|---|---|---|---|---|
| 0 hours | 9.01 | 71% | 48% | 1 | | | |
| | 8.34 | 82% | 48% | 2 | 5.7 | 0.5 | 69.1 |
| | 6.61 | 94% | 33% | 3 | 4.4 | 0.3 | 58.6 |
| | 13.5 | 53% | 71% | 4 | 8.3 | 0.8 | 90.1 |
| | 18 | 35% | 80% | | | | |
| | 27.7 | 18% | 90% | | | | |
| 24 hours | 8.34 | 71% | 48% | 1 | | | |
| | 6.61 | 88% | 33% | 2 | 2.1 | 0.4 | 10.7 |
| | 3.85 | 94% | 13% | 3 | 3.5 | 0.8 | 14.7 |
| | 13.5 | 53% | 71% | 4 | 2.7 | 0.6 | 12.1 |
| | 18 | 24% | 80% | | | | |
| | 27.7 | 12% | 90% | | | | |

Fig. 8 Continued

| 48 hours | 7.98 | 70% | 46% | 1 | | | |
| | 6.61 | 80% | 33% | 2 | 1.5 | 0.3 | 8.8 |
| | 3.81 | 90% | 10% | 3 | 1.0 | 0.1 | 8.2 |
| | 13.5 | 30% | 71% | 4 | 1.5 | 0.3 | 8.8 |
| | 18 | 20% | 80% | | | | |
| | 27.7 | 10% | 90% | | | | | sCr only

| Time prior AKI stage | Cutoff value | sens | spec | Quartile | OR | 95% CI of OR | |
|---|---|---|---|---|---|---|---|
| 0 hours | 8.34 | 75% | 46% | 1 | | | |
| | 7.98 | 88% | 43% | 2 | 2.0 | 0.1 | 42.2 |
| | 5.52 | 100% | 23% | 3 | 0.0 | 0.0 | na |
| | 14.1 | 63% | 72% | 4 | 5.5 | 0.5 | 62.9 |
| | 18.4 | 50% | 80% | | | | |
| | 25.4 | 25% | 90% | | | | |
| 24 hours | 7.98 | 75% | 43% | 1 | | | |
| | 6.61 | 88% | 30% | 2 | 2.0 | 0.1 | 42.2 |
| | 3.26 | 100% | 7% | 3 | 2.0 | 0.1 | 42.2 |
| | 14.1 | 63% | 72% | 4 | 3.1 | 0.2 | 46.7 |
| | 18.4 | 38% | 80% | | | | |
| | 25.4 | 13% | 90% | | | | |
| 48 hours | 7.98 | 80% | 43% | 1 | | | |
| | 7.98 | 80% | 43% | 2 | 1.0 | 0.0 | 55.0 |
| | 0.0399 | 100% | 2% | 3 | 1.0 | 0.0 | 55.0 |
| | 14.1 | 40% | 72% | 4 | 2.0 | 0.1 | 41.3 |
| | 18.4 | 40% | 80% | | | | |
| | 25.4 | 0% | 90% | | | | |

UO only

| Time prior AKI stage | Cutoff value | sens | spec | Quartile | OR | 95% CI of OR | |
|---|---|---|---|---|---|---|---|
| 0 hours | 11.4 | 73% | 63% | 1 | | | |
| | 9.01 | 82% | 53% | 2 | na | na | na |
| | 8.34 | 91% | 53% | 3 | na | na | na |
| | 13 | 55% | 71% | 4 | na | na | na |
| | 17.4 | 27% | 81% | | | | |
| | 27.7 | 9% | 91% | | | | |
| 24 hours | 10.4 | 73% | 57% | 1 | | | |
| | 8.34 | 82% | 53% | 2 | 2.1 | 0.1 | 46.6 |
| | 6.61 | 91% | 37% | 3 | 3.3 | 0.2 | 53.0 |
| | 13 | 55% | 71% | 4 | 6.0 | 0.5 | 75.4 |
| | 17.4 | 27% | 81% | | | | |
| | 27.7 | 9% | 91% | | | | |
| 48 hours | 8.34 | 71% | 53% | 1 | | | |
| | 6.61 | 86% | 37% | 2 | 1.0 | 0.0 | 59.8 |
| | 3.81 | 100% | 10% | 3 | 2.1 | 0.1 | 47.1 |
| | 13 | 43% | 71% | 4 | 3.3 | 0.2 | 53.6 |
| | 17.4 | 29% | 81% | | | | |
| | 27.7 | 14% | 91% | | | | |

Fig. 8 Continued

Vascular cell adhesion molecule 1 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 664.588 | 969.442 | 664.588 | 947.936 | 664.588 | 894.409 |
| average | 737.563 | 1068.585 | 737.563 | 1070.037 | 737.563 | 908.300 |
| stdev | 286.542 | 571.648 | 286.542 | 597.604 | 286.542 | 450.080 |
| p (t-test) |  | 0.001 |  | 0.001 |  | 0.125 |
| min | 315.327 | 474.555 | 315.327 | 474.555 | 315.327 | 474.555 |
| max | 1703.672 | 2442.930 | 1703.672 | 2442.930 | 1703.672 | 1836.748 |
| n (Samp) | 99 | 13 | 99 | 12 | 99 | 8 |
| n (Pat) | 99 | 13 | 99 | 12 | 99 | 8 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 669.279 | 909.701 | 669.279 | 918.065 | 669.279 | 733.001 |
| average | 782.551 | 827.184 | 782.551 | 847.716 | 782.551 | 719.443 |
| stdev | 387.161 | 203.336 | 387.161 | 228.729 | 387.161 | 197.386 |
| p (t-test) |  | 0.798 |  | 0.738 |  | 0.779 |
| min | 304.293 | 515.627 | 304.293 | 515.627 | 304.293 | 515.627 |
| max | 2809.360 | 1039.105 | 2809.360 | 1039.105 | 2809.360 | 909.701 |
| n (Samp) | 160 | 5 | 160 | 4 | 160 | 3 |
| n (Pat) | 160 | 5 | 160 | 4 | 160 | 3 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 670.806 | 1042.538 | 670.806 | 1007.706 | 670.806 | 909.701 |
| average | 750.448 | 1170.449 | 750.448 | 1139.839 | 750.448 | 964.396 |
| stdev | 302.673 | 613.458 | 302.673 | 628.200 | 302.673 | 454.933 |
| p (t-test) |  | 0.000 |  | 0.001 |  | 0.088 |
| min | 315.327 | 474.555 | 315.327 | 474.555 | 315.327 | 474.555 |
| max | 1737.712 | 2442.930 | 1737.712 | 2442.930 | 1737.712 | 1836.748 |
| n (Samp) | 84 | 10 | 84 | 10 | 84 | 7 |
| n (Pat) | 84 | 10 | 84 | 10 | 84 | 7 | sCr or UO

| Time prior AKI stage | AUC | SE | nCohort 1 | nCohort 2 | p |
| --- | --- | --- | --- | --- | --- |
| 0 hours | 0.71 | 0.085 | 99 | 13 | 0.015 |
| 24 hours | 0.69 | 0.089 | 99 | 12 | 0.031 |
| 48 hours | 0.60 | 0.110 | 99 | 8 | 0.346 | sCr only

| Time prior AKI stage | AUC | SE | nCohort 1 | nCohort 2 | p |
| --- | --- | --- | --- | --- | --- |
| 0 hours | 0.64 | 0.136 | 160 | 5 | 0.298 |
| 24 hours | 0.65 | 0.151 | 160 | 4 | 0.332 |
| 48 hours | 0.53 | 0.171 | 160 | 3 | 0.884 |

UO only

| Time prior AKI stage | AUC | SE | nCohort 1 | nCohort 2 | p |
| --- | --- | --- | --- | --- | --- |
| 0 hours | 0.73 | 0.094 | 84 | 10 | 0.013 |
| 24 hours | 0.71 | 0.096 | 84 | 10 | 0.026 |
| 48 hours | 0.64 | 0.117 | 84 | 7 | 0.216 |

Fig. 8 Continued sCr or UO

| Time prior AKI stage | Cutoff value | sens | spec | Quartile | OR | 95% CI of OR | |
|---|---|---|---|---|---|---|---|
| 0 hours | 745.011 | 77% | 65% | 1 | | | |
| | 601.367 | 85% | 34% | 2 | 0.5 | 0.0 | 10.6 |
| | 512.57 | 92% | 22% | 3 | 1.0 | 0.1 | 8.3 |
| | 790.308 | 69% | 71% | 4 | 5.2 | 1.3 | 21.1 |
| | 955.241 | 54% | 81% | | | | |
| | 1126.83 | 15% | 91% | | | | |
| 24 hours | 727.836 | 75% | 61% | 1 | | | |
| | 601.367 | 83% | 34% | 2 | 0.5 | 0.0 | 10.2 |
| | 512.57 | 92% | 22% | 3 | 1.0 | 0.1 | 8.0 |
| | 790.308 | 67% | 71% | 4 | 4.2 | 1.0 | 17.4 |
| | 955.241 | 50% | 81% | | | | |
| | 1126.83 | 17% | 91% | | | | |
| 48 hours | 512.57 | 75% | 22% | 1 | | | |
| | 506.491 | 88% | 21% | 2 | 0.0 | 0.0 | na |
| | 466.49 | 100% | 14% | 3 | 0.3 | 0.0 | 4.7 |
| | 790.308 | 63% | 71% | 4 | 1.3 | 0.4 | 5.0 |
| | 955.241 | 38% | 81% | | | | |
| | 1126.83 | 13% | 91% | | | | | sCr only

| Time prior AKI stage | Cutoff value | sens | spec | Quartile | OR | 95% CI of OR | |
|---|---|---|---|---|---|---|---|
| 0 hours | 745.011 | 80% | 62% | 1 | | | |
| | 745.011 | 80% | 62% | 2 | 0.0 | 0.0 | na |
| | 512.57 | 100% | 23% | 3 | 1.0 | 0.0 | 55.6 |
| | 816.421 | 60% | 70% | 4 | 3.1 | 0.2 | 46.4 |
| | 1002.77 | 20% | 80% | | | | |
| | 1303.86 | 0% | 90% | | | | |
| 24 hours | 905.004 | 75% | 76% | 1 | | | |
| | 512.57 | 100% | 23% | 2 | 0.0 | 0.0 | na |
| | 512.57 | 100% | 23% | 3 | 1.0 | 0.0 | 55.6 |
| | 816.421 | 75% | 70% | 4 | 2.1 | 0.1 | 42.9 |
| | 1002.77 | 25% | 80% | | | | |
| | 1303.86 | 0% | 90% | | | | |
| 48 hours | 512.57 | 100% | 23% | 1 | | | |
| | 512.57 | 100% | 23% | 2 | 0.0 | 0.0 | na |
| | 512.57 | 100% | 23% | 3 | 1.0 | 0.0 | 54.3 |
| | 816.421 | 33% | 70% | 4 | 1.0 | 0.0 | 54.3 |
| | 1002.77 | 0% | 80% | | | | |
| | 1303.86 | 0% | 90% | | | | |

UO only

| Time prior AKI stage | Cutoff value | sens | spec | Quartile | OR | 95% CI of OR | |
|---|---|---|---|---|---|---|---|
| 0 hours | 955.241 | 70% | 77% | 1 | | | |
| | 882.489 | 80% | 74% | 2 | 1.0 | 0.0 | 57.4 |
| | 601.367 | 90% | 32% | 3 | 2.1 | 0.1 | 47.6 |
| | 779.457 | 80% | 70% | 4 | 7.3 | 0.6 | 88.0 |
| | 1033.49 | 60% | 81% | | | | |
| | 1126.83 | 20% | 90% | | | | |
| 24 hours | 882.489 | 70% | 74% | 1 | | | |
| | 728.274 | 80% | 61% | 2 | 1.0 | 0.0 | 57.4 |
| | 601.367 | 90% | 32% | 3 | 3.3 | 0.2 | 54.3 |
| | 779.457 | 70% | 70% | 4 | 5.8 | 0.5 | 73.7 |
| | 1033.49 | 50% | 81% | | | | |
| | 1126.83 | 20% | 90% | | | | |

Fig. 8 Continued

| 48 hours | 807.384 | 71% | 73% | 1 | | | |
| --- | --- | --- | --- | --- | --- | --- | --- |
| | 503.794 | 86% | 20% | 2 | 0.0 | 0.0 | na |
| | 466.49 | 100% | 14% | 3 | 1.0 | 0.1 | 8.2 |
| | 779.457 | 71% | 70% | 4 | 1.5 | 0.2 | 9.3 |
| | 1033.49 | 43% | 81% | | | | |
| | 1126.83 | 14% | 90% | | | | |

Vascular endothelial growth factor sCr or UO

| | 0 hr prior to AKI stage | | 24 hr prior to AKI stage | | 48 hr prior to AKI stage | |
| --- | --- | --- | --- | --- | --- | --- |
| | Cohort 1 | Cohort 2 | Cohort 1 | Cohort 2 | Cohort 1 | Cohort 2 |
| median | 1045.000 | 3010.000 | 1045.000 | 2910.000 | 1045.000 | 2240.000 |
| average | 1392.214 | 3403.235 | 1392.214 | 3166.059 | 1392.214 | 2762.800 |
| stdev | 1337.321 | 2248.559 | 1337.321 | 2383.915 | 1337.321 | 2627.380 |
| p (t-test) | | 0.000 | | 0.000 | | 0.006 |
| min | 417.000 | 935.000 | 417.000 | 705.000 | 417.000 | 714.000 |
| max | 11500.000 | 9620.000 | 11500.000 | 9620.000 | 11500.000 | 9620.000 |
| n (Samp) | 112 | 17 | 112 | 17 | 112 | 10 |
| n (Pat) | 112 | 17 | 112 | 17 | 112 | 10 | sCr only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 1080.000 | 2960.000 | 1080.000 | 2960.000 | 1080.000 | 2910.000 |
| average | 1481.711 | 2763.750 | 1481.711 | 2391.875 | 1481.711 | 2434.800 |
| stdev | 1649.766 | 1149.807 | 1649.766 | 1396.769 | 1649.766 | 982.057 |
| p (t-test) | | 0.031 | | 0.126 | | 0.201 |
| min | 417.000 | 1440.000 | 417.000 | 705.000 | 417.000 | 714.000 |
| max | 16200.000 | 4320.000 | 16200.000 | 4010.000 | 16200.000 | 3010.000 |
| n (Samp) | 180 | 8 | 180 | 8 | 180 | 5 |
| n (Pat) | 180 | 8 | 180 | 8 | 180 | 5 |

UO only

| | 0 hr prior toAKI stage | | 24 hr prior toAKI stage | | 48 hr prior toAKI stage | |
| --- | --- | --- | --- | --- | --- | --- |
| | Cohort 1 | Cohort 2 | Cohort 1 | Cohort 2 | Cohort 1 | Cohort 2 |
| median | 1040.000 | 3370.000 | 1040.000 | 3010.000 | 1040.000 | 1570.000 |
| average | 1419.629 | 3829.545 | 1419.629 | 3733.455 | 1419.629 | 2999.143 |
| stdev | 1430.533 | 2579.281 | 1430.533 | 2626.820 | 1430.533 | 3094.531 |
| p (t-test) | | 0.000 | | 0.000 | | 0.013 |
| min | 458.000 | 935.000 | 458.000 | 838.000 | 458.000 | 834.000 |
| max | 11500.000 | 9620.000 | 11500.000 | 9620.000 | 11500.000 | 9620.000 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
| --- | --- | --- | --- | --- | --- |
| 0 hours | 0.85 | 0.060 | 112 | 17 | 0.000 |
| 24 hours | 0.76 | 0.071 | 112 | 17 | 0.000 |
| 48 hours | 0.73 | 0.094 | 112 | 10 | 0.016 | sCr only

| Time prior AKI stage | AUC | SE | nCohort 1 | nCohort 2 | p |
| --- | --- | --- | --- | --- | --- |
| 0 hours | 0.86 | 0.084 | 180 | 8 | 0.000 |
| 24 hours | 0.67 | 0.107 | 180 | 8 | 0.103 |
| 48 hours | 0.78 | 0.123 | 180 | 5 | 0.022 |

Fig. 8 Continued

UO only

| Time prior AKI stage | AUC | SE | nCohort 1 | nCohort 2 | p |
|---|---|---|---|---|---|
| 0 hours | 0.85 | 0.074 | 89 | 11 | 0.000 |
| 24 hours | 0.84 | 0.076 | 89 | 11 | 0.000 |
| 48 hours | 0.74 | 0.111 | 89 | 7 | 0.032 | sCr or UO

| Time prior AKI stage | Cutoff value | sens | spec | Quartile | OR | 95% CI of OR | |
|---|---|---|---|---|---|---|---|
| 0 hours | 1680 | 71% | 79% | 1 | | | |
| | 1450 | 82% | 73% | 2 | na | na | na |
| | 1120 | 94% | 58% | 3 | na | na | na |
| | 1380 | 88% | 71% | 4 | na | na | na |
| | 1700 | 65% | 80% | | | | |
| | 2300 | 59% | 90% | | | | |
| 24 hours | 1540 | 71% | 75% | 1 | | | |
| | 836 | 82% | 32% | 2 | 1.0 | 0.1 | 8.1 |
| | 749 | 94% | 22% | 3 | 1.0 | 0.1 | 8.1 |
| | 1380 | 71% | 71% | 4 | 7.5 | 2.0 | 27.9 |
| | 1700 | 65% | 80% | | | | |
| | 2300 | 59% | 90% | | | | |
| 48 hours | 1240 | 70% | 63% | 1 | | | |
| | 1120 | 80% | 58% | 2 | 1.0 | 0.0 | 55.6 |
| | 825 | 90% | 31% | 3 | 3.2 | 0.2 | 50.6 |
| | 1380 | 60% | 71% | 4 | 5.6 | 0.5 | 67.6 |
| | 1700 | 50% | 80% | | | | |
| | 2300 | 50% | 90% | | | | | sCr only

| Time prior AKI stage | Cutoff value | sens | spec | Quartile | OR | 95% CI of OR | |
|---|---|---|---|---|---|---|---|
| 0 hours | 1580 | 75% | 74% | 1 | | | |
| | 1450 | 88% | 71% | 2 | na | na | na |
| | 1410 | 100% | 70% | 3 | na | na | na |
| | 1410 | 100% | 70% | 4 | na | na | na |
| | 1700 | 63% | 80% | | | | |
| | 2340 | 63% | 90% | | | | |
| 24 hours | 803 | 75% | 27% | 1 | | | |
| | 749 | 88% | 22% | 2 | 0.5 | 0.0 | 10.1 |
| | 701 | 100% | 17% | 3 | 0.0 | 0.0 | na |
| | 1410 | 63% | 70% | 4 | 2.7 | 0.6 | 11.6 |
| | 1700 | 63% | 80% | | | | |
| | 2340 | 63% | 90% | | | | |
| 48 hours | 2520 | 80% | 92% | 1 | | | |
| | 2520 | 80% | 92% | 2 | 0.0 | 0.0 | na |
| | 709 | 100% | 17% | 3 | 0.0 | 0.0 | na |
| | 1410 | 80% | 70% | 4 | 4.2 | 0.3 | 53.0 |
| | 1700 | 80% | 80% | | | | |
| | 2340 | 80% | 90% | | | | |

Fig. 8 Continued

METHODS AND COMPOSITIONS FOR DIAGNOSIS AND PROGNOSIS OF RENAL INJURY AND RENAL FAILURE

CROSS-REFERENCE TO RELATED APPLICATIONS

This application is a divisional of application Ser. No. 13/125,360, now U.S. Pat. No. 8,778,615, issued Jul. 15, 2014, which is the U.S. National Stage of International Application No. PCT/US2009/061561, filed Oct. 21, 2009, which designated the U.S. and claims the benefit of priority to U.S. Provisional Patent Application 61/115,044 filed Nov. 15, 2008; U.S. Provisional Patent Application 61/107,290 filed Oct. 21, 2008; U.S. Provisional Patent Application 61/113,102 filed Nov. 10, 2008; U.S. Provisional Patent Application 61/107,301 filed Oct. 21, 2008; U.S. Provisional Patent Application 61/115,047 filed Nov. 15, 2008; U.S. Provisional Patent Application 61/115,051 filed Nov. 15, 2008; U.S. Provisional Patent Application 61/113,045 filed Nov. 10, 2008; U.S. Provisional Patent Application 61/115,057 filed Nov. 15, 2008; U.S. Provisional Patent Application 61/117,167 filed Nov. 22, 2008; U.S. Provisional Patent Application 61/117,157 filed Nov. 22, 2008; U.S. Provisional Patent Application 61/117,146 filed Nov. 22, 2008; U.S. Provisional Patent Application 61/107,281 filed Oct. 21, 2008; U.S. Provisional Patent Application 61/115,022 filed Nov. 14, 2008; U.S. Provisional Patent Application 61/117,154 filed Nov. 22, 2008; U.S. Provisional Patent Application 61/117,152 filed Nov. 22, 2008; U.S. Provisional Patent Application 61/115,019 filed Nov. 14, 2008; U.S. Provisional Patent Application 61/115,017 filed Nov. 14, 2008; U.S. Provisional Patent Application 61/113,021 filed Nov. 10, 2008; U.S. Provisional Patent Application 61/113,056 filed Nov. 10, 2008; U.S. Provisional Patent Application 61/107,297 filed Oct. 21, 2008; U.S. Provisional Patent Application 61/115,045 filed Nov. 15, 2008; U.S. Provisional Patent Application 61/107,304 filed Oct. 21, 2008; U.S. Provisional Patent Application 61/113,050 filed Nov. 10, 2008; U.S. Provisional Patent Application 61/115,048 filed Nov. 15, 2008; U.S. Provisional Patent Application 61/113,096 filed Nov. 10, 2008; U.S. Provisional Patent Application 61/117,140 filed Nov. 22, 2008; U.S. Provisional Patent Application 61/117,172 filed Nov. 22, 2008; U.S. Provisional Patent Application 61/113,083 filed Nov. 10, 2008; and U.S. Provisional Patent Application 61/117,141 filed Nov. 22, 2008, each of which is hereby incorporated in its entirety including all tables, figures, and claims.

SEQUENCE LISTING

The instant application contains a Sequence Listing which has been submitted via EFS-Web and is hereby incorporated by reference in its entirety. Said ASCII copy, created on Jul. 9, 2014, is named AST18200DV.txt, and is 120 kilobytes in size.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, $17^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, $47^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, $17^{th}$ ed., Chapter 222, and which is hereby incorporated by reference in their entirety:

| Type | Risk Factors |
| --- | --- |
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased | ACE inhibitors or angiotensin II receptor blockers |

| Type | Risk Factors |
|---|---|
| GFR from reduced glomerular transcapillary pressure, especially in patients with bilateral renal artery stenosis) | |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, *Curr Opin Nephrol Hypertens* 14:265-270, 2005 and Chertow et al, *J Am Soc Nephrol* 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, J Am Soc Nephrol 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., *Crit Care*. 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production<0.5 ml/kg/hr for 12 h;

"Failure": serum creatinine increased 3.0 fold from baseline OR creatinine>355 μmol/l (with a rise of >44) or urine output below 0.3 ml/kg/hr for 24 h or anuria for at least 12 hours;

And included two clinical outcomes:

"Loss": persistent need for renal replacement therapy for more than four weeks.

"ESRD": end stage renal disease—the need for dialysis for more than 3 months.

These criteria are called the RIFLE criteria, which provide a useful clinical tool to classify renal status. As discussed in Kellum, *Crit. Care Med.* 36: S141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 μmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine ≥354 μmol/L accompanied by an acute increase of at least 44 μmol/L OR urine output less than 0.3 mL/kg per hour for 24 hours or anuria for 12 hours.

The CIN Consensus Working Panel (McCollough et al, Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (prerenal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a subject. As described herein, measurement of one or more markers selected from the group consisting of Cytoplasmic aspartate aminotransferase, soluble Tumor necrosis factor receptor superfamily member 5, soluble CD40 Ligand, soluble C-X-C Motif chemokine 16, 5100-A12, Eotaxin, soluble E-selectin, Fibronectin, Granulocyte colony-stimulating factor, Granulocyte-macrophage colony-stimulating factor, Heparin-binding growth factor 2, soluble Hepatocyte growth factor receptor, Interleukin-1 receptor antagonist, Interleukin-1 beta, Interleukin-10, Interleukin-15, Interleukin-3, Myeloperoxidase, Nidogen-1, soluble Oxidized low-density lipoprotein receptor 1, Pappalysin-1, soluble P-selectin glycoprotein ligand 1, Antileukoproteinase, soluble Kit ligand, Tissue inhibitor of metalloproteinase 1, Tissue inhibitor of metalloproteinase 2, soluble Tumor necrosis factor, soluble Vascular cell adhesion molecule 1, and Vascular endothelial growth factor A (collectively referred to herein as "kidney injury markers, and individually as a "kidney injury marker") can be used for diagnosis, prognosis, risk stratification, staging, monitoring, categorizing and determination of further diagnosis and treatment regimens in subjects suffering or at risk of suffering from an injury to renal function, reduced renal function, and/or acute renal failure (also called acute kidney injury).

These kidney injury markers may be used, individually or in panels comprising a plurality of kidney injury markers, for risk stratification (that is, to identify subjects at risk for a future injury to renal function, for future progression to reduced renal function, for future progression to ARF, for future improvement in renal function, etc.); for diagnosis of existing disease (that is, to identify subjects who have suffered an injury to renal function, who have progressed to reduced renal function, who have progressed to ARF, etc.); for monitoring for deterioration or improvement of renal function; and for predicting a future medical outcome, such as improved or worsening renal function, a decreased or increased mortality risk, a decreased or increased risk that a subject will require renal replacement therapy (i.e., hemodialysis, peritoneal dialysis, hemofiltration, and/or renal transplantation, a decreased or increased risk that a subject will recover from an injury to renal function, a decreased or increased risk that a subject will recover from ARF, a decreased or increased risk that a subject will progress to end stage renal disease, a decreased or increased risk that a subject will progress to chronic renal failure, a decreased or increased risk that a subject will suffer rejection of a transplanted kidney, etc.

In a first aspect, the present invention relates to methods for evaluating renal status in a subject. These methods comprise performing an assay method that is configured to detect one or more kidney injury markers of the present invention in a body fluid sample obtained from the subject. The assay result(s), for example a measured concentration of one or more markers selected from the group consisting of Cytoplasmic aspartate aminotransferase, soluble Tumor necrosis factor receptor superfamily member 5, soluble CD40 Ligand, soluble C-X-C Motif chemokine 16, S100-A12, Eotaxin, soluble E-selectin, Fibronectin, Granulocyte colony-stimulating factor, Granulocyte-macrophage colony-stimulating factor, Heparin-binding growth factor 2, soluble Hepatocyte growth factor receptor, Interleukin-1 receptor antagonist, Interleukin-1 beta, Interleukin-10, Interleukin-15, Interleukin-3, Myeloperoxidase, Nidogen-1, soluble Oxidized low-density lipoprotein receptor 1, Pappalysin-1, soluble P-selectin glycoprotein ligand 1, Antileukoproteinase, soluble Kit ligand, Tissue inhibitor of metalloproteinase 1, Tissue inhibitor of metalloproteinase 2, soluble Tumor necrosis factor, soluble Vascular cell adhesion molecule 1, and Vascular endothelial growth factor A is/are then correlated to the renal status of the subject. This correlation to renal status may include correlating the assay result(s) to one or more of risk stratification, diagnosis, prognosis, staging, classifying and monitoring of the subject as described herein. Thus, the present invention utilizes one or more kidney injury markers of the present invention for the evaluation of renal injury.

In certain embodiments, the methods for evaluating renal status described herein are methods for risk stratification of the subject; that is, assigning a likelihood of one or more future changes in renal status to the subject. In these embodiments, the assay result(s) is/are correlated to one or more such future changes. The following are preferred risk stratification embodiments.

In preferred risk stratification embodiments, these methods comprise determining a subject's risk for a future injury to renal function, and the assay result(s) is/are correlated to a likelihood of such a future injury to renal function. For example, the measured concentration(s) may each be compared to a threshold value. For a "positive going" kidney injury marker, an increased likelihood of suffering a future injury to renal function is assigned to the subject when the measured concentration is above the threshold, relative to a likelihood assigned when the measured concentration is below the threshold. For a "negative going" kidney injury marker, an increased likelihood of suffering a future injury to renal function is assigned to the subject when the measured concentration is below the threshold, relative to a likelihood assigned when the measured concentration is above the threshold.

In other preferred risk stratification embodiments, these methods comprise determining a subject's risk for future reduced renal function, and the assay result(s) is/are correlated to a likelihood of such reduced renal function. For example, the measured concentrations may each be compared to a threshold value. For a "positive going" kidney injury marker, an increased likelihood of suffering a future reduced renal function is assigned to the subject when the measured concentration is above the threshold, relative to a likelihood assigned when the measured concentration is below the threshold. For a "negative going" kidney injury marker, an increased likelihood of future reduced renal function is assigned to the subject when the measured concentration is below the threshold, relative to a likelihood assigned when the measured concentration is above the threshold.

In still other preferred risk stratification embodiments, these methods comprise determining a subject's likelihood for a future improvement in renal function, and the assay result(s) is/are correlated to a likelihood of such a future improvement in renal function. For example, the measured concentration(s) may each be compared to a threshold value. For a "positive going" kidney injury marker, an increased likelihood of a future improvement in renal function is assigned to the subject when the measured concentration is below the threshold, relative to a likelihood assigned when the measured concentration is above the threshold. For a "negative going" kidney injury marker, an increased likelihood of a future improvement in renal function is assigned to the subject when the measured concentration is above the threshold, relative to a likelihood assigned when the measured concentration is below the threshold.

In yet other preferred risk stratification embodiments, these methods comprise determining a subject's risk for progression to ARF, and the result(s) is/are correlated to a likelihood of such progression to ARF. For example, the measured concentration(s) may each be compared to a threshold value. For a "positive going" kidney injury marker, an increased likelihood of progression to ARF is assigned to the subject when the measured concentration is above the threshold, relative to a likelihood assigned when the measured concentration is below the threshold. For a "negative going" kidney injury marker, an increased likelihood of progression to ARF is assigned to the subject when the measured concentration is below the threshold, relative to a likelihood assigned when the measured concentration is above the threshold.

And in other preferred risk stratification embodiments, these methods comprise determining a subject's outcome risk, and the assay result(s) is/are correlated to a likelihood of the occurrence of a clinical outcome related to a renal injury suffered by the subject. For example, the measured concentration(s) may each be compared to a threshold value. For a "positive going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is above the threshold, relative to a likelihood assigned when the measured concentration is below the threshold. For a "negative going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is below the threshold, relative to a likelihood assigned when the measured concentration is above the threshold.

In such risk stratification embodiments, preferably the likelihood or risk assigned is that an event of interest is more or less likely to occur within 180 days of the time at which the body fluid sample is obtained from the subject. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the subject is equivalent to diagnosis of a current condition.

In preferred risk stratification embodiments, the subject is selected for risk stratification based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin are all preferred subjects for monitoring risks according to the methods described herein. This list is not meant to be limiting. By "pre-existence" in this context is meant that the risk factor exists at the time the body fluid sample is obtained from the subject. In particularly preferred embodiments, a subject is chosen for risk stratification based on an existing diagnosis of injury to renal function, reduced renal function, or ARF.

In other embodiments, the methods for evaluating renal status described herein are methods for diagnosing a renal injury in the subject; that is, assessing whether or not a subject has suffered from an injury to renal function, reduced renal function, or ARF. In these embodiments, the assay result(s), for example a measured concentration of one or more markers selected from the group consisting of Cytoplasmic aspartate aminotransferase, soluble Tumor necrosis factor receptor superfamily member 5, soluble CD40 Ligand, soluble C-X-C Motif chemokine 16, S100-A12, Eotaxin, soluble E-selectin, Fibronectin, Granulocyte colony-stimulating factor, Granulocyte-macrophage colony-stimulating factor, Heparin-binding growth factor 2, soluble Hepatocyte growth factor receptor, Interleukin-1 receptor antagonist, Interleukin-1 beta, Interleukin-10, Interleukin-15, Interleukin-3, Myeloperoxidase, Nidogen-1, soluble Oxidized low-density lipoprotein receptor 1, Pappalysin-1, soluble P-selectin glycoprotein ligand 1, Antileukoprotein- ase, soluble Kit ligand, Tissue inhibitor of metalloproteinase 1, Tissue inhibitor of metalloproteinase 2, soluble Tumor necrosis factor, soluble Vascular cell adhesion molecule 1, and Vascular endothelial growth factor A is/are correlated to the occurrence or nonoccurrence of a change in renal status. The following are preferred diagnostic embodiments.

In preferred diagnostic embodiments, these methods comprise diagnosing the occurrence or nonoccurrence of an injury to renal function, and the assay result(s) is/are correlated to the occurrence or nonoccurrence of such an injury. For example, each of the measured concentration(s) may be compared to a threshold value. For a positive going marker, an increased likelihood of the occurrence of an injury to renal function is assigned to the subject when the measured concentration is above the threshold (relative to the likelihood assigned when the measured concentration is below the threshold); alternatively, when the measured concentration is below the threshold, an increased likelihood of the nonoccurrence of an injury to renal function may be assigned to the subject (relative to the likelihood assigned when the measured concentration is above the threshold). For a negative going marker, an increased likelihood of the occurrence of an injury to renal function is assigned to the subject when the measured concentration is below the threshold (relative to the likelihood assigned when the measured concentration is above the threshold); alternatively, when the measured concentration is above the threshold, an increased likelihood of the nonoccurrence of an injury to renal function may be assigned to the subject (relative to the likelihood assigned when the measured concentration is below the threshold).

In other preferred diagnostic embodiments, these methods comprise diagnosing the occurrence or nonoccurrence of reduced renal function, and the assay result(s) is/are correlated to the occurrence or nonoccurrence of an injury causing reduced renal function. For example, each of the measured concentration(s) may be compared to a threshold value. For a positive going marker, an increased likelihood of the occurrence of an injury causing reduced renal function is assigned to the subject when the measured concentration is above the threshold (relative to the likelihood assigned when the measured concentration is below the threshold); alternatively, when the measured concentration is below the threshold, an increased likelihood of the nonoccurrence of an injury causing reduced renal function may be assigned to the subject (relative to the likelihood assigned when the measured concentration is above the threshold). For a negative going marker, an increased likelihood of the occurrence of an injury causing reduced renal function is assigned to the subject when the measured concentration is below the threshold (relative to the likelihood assigned when the measured concentration is above the threshold); alternatively, when the measured concentration is above the threshold, an increased likelihood of the nonoccurrence of an injury causing reduced renal function may be assigned to the subject (relative to the likelihood assigned when the measured concentration is below the threshold).

In yet other preferred diagnostic embodiments, these methods comprise diagnosing the occurrence or nonoccurrence of ARF, and the assay result(s) is/are correlated to the occurrence or nonoccurrence of an injury causing ARF. For example, each of the measured concentration(s) may be compared to a threshold value. For a positive going marker, an increased likelihood of the occurrence of ARF is assigned to the subject when the measured concentration is above the threshold (relative to the likelihood assigned when the measured concentration is below the threshold); alternatively, when the measured concentration is below the threshold, an increased likelihood of the nonoccurrence of ARF may be assigned to the subject (relative to the likelihood assigned when the measured concentration is above the threshold). For a negative going marker, an increased likelihood of the occurrence of ARF is assigned to the subject when the measured concentration is below the threshold (relative to the likelihood assigned when the measured concentration is above the threshold); alternatively, when the measured concentration is above the threshold, an increased likelihood of the nonoccurrence of ARF may be assigned to the subject (relative to the likelihood assigned when the measured concentration is below the threshold).

In still other preferred diagnostic embodiments, these methods comprise diagnosing a subject as being in need of renal replacement therapy, and the assay result(s) is/are correlated to a need for renal replacement therapy. For example, each of the measured concentration(s) may be compared to a threshold value. For a positive going marker, an increased likelihood of the occurrence of an injury creating a need for renal replacement therapy is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal replacement therapy may be assigned to the subject (relative to the likelihood assigned when the measured concentration is above the threshold). For a negative going marker, an increased likelihood of the occurrence of an injury creating a need for renal replacement therapy is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal replacement therapy may be assigned to the subject (relative to the likelihood assigned when the measured concentration is below the threshold).

In still other preferred diagnostic embodiments, these methods comprise diagnosing a subject as being in need of renal transplantation, and the assay result (s0 is/are correlated to a need for renal transplantation. For example, each of the measured concentration(s) may be compared to a threshold value. For a positive going marker, an increased likelihood of the occurrence of an injury creating a need for renal transplantation is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal transplantation may be assigned to the subject (relative to the likelihood assigned when the measured concentration is above the threshold). For a negative going marker, an increased likelihood of the occurrence of an injury creating a need for renal transplantation is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal transplantation may be assigned to the subject (relative to the likelihood assigned when the measured concentration is below the threshold).

In still other embodiments, the methods for evaluating renal status described herein are methods for monitoring a renal injury in the subject; that is, assessing whether or not renal function is improving or worsening in a subject who has suffered from an injury to renal function, reduced renal function, or ARF. In these embodiments, the assay result(s), for example a measured concentration of one or more markers selected from the group consisting of Cytoplasmic aspartate aminotransferase, soluble Tumor necrosis factor receptor superfamily member 5, soluble CD40 Ligand, soluble C-X-C Motif chemokine 16, S100-A12, Eotaxin, soluble E-selectin, Fibronectin, Granulocyte colony-stimulating factor, Granulocyte-macrophage colony-stimulating factor, Heparin-binding growth factor 2, soluble Hepatocyte growth factor receptor, Interleukin-1 receptor antagonist, Interleukin-1 beta, Interleukin-10, Interleukin-15, Interleukin-3, Myeloperoxidase, Nidogen-1, soluble Oxidized low-density lipoprotein receptor 1, Pappalysin-1, soluble P-selectin glycoprotein ligand 1, Antileukoproteinase, soluble Kit ligand, Tissue inhibitor of metalloproteinase 1, Tissue inhibitor of metalloproteinase 2, soluble Tumor necrosis factor, soluble Vascular cell adhesion molecule 1, and Vascular endothelial growth factor A is/are correlated to the occurrence or nonoccurrence of a change in renal status. The following are preferred monitoring embodiments.

In preferred monitoring embodiments, these methods comprise monitoring renal status in a subject suffering from an injury to renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other preferred monitoring embodiments, these methods comprise monitoring renal status in a subject suffering from reduced renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject suffering from acute renal failure, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other additional preferred monitoring embodiments, these methods comprise monitoring renal status in a subject at risk of an injury to renal function due to the pre-existence of one or more known risk factors for prerenal, intrinsic renal, or postrenal ARF, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In still other embodiments, the methods for evaluating renal status described herein are methods for classifying a renal injury in the subject; that is, determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage. In these embodiments, the assay result(s), for example a measured concentration of one or more markers selected from the group consisting of Cytoplasmic aspartate aminotransferase, soluble Tumor necrosis factor receptor superfamily member 5, soluble CD40 Ligand, soluble C-X-C Motif chemokine 16, S100-A12, Eotaxin, soluble E-selectin, Fibronectin, Granulocyte colony-stimulating factor, Granulocyte-macrophage colony-stimulating factor, Heparin-binding growth factor 2, soluble Hepatocyte growth factor receptor, Interleukin-1 receptor antagonist, Interleukin-1 beta, Interleukin-10, Interleukin-15, Interleukin-3, Myeloperoxidase, Nidogen-1, soluble Oxidized low-density lipoprotein receptor 1, Pappalysin-1, soluble P-selectin glycoprotein ligand 1, Antileukoproteinase, soluble Kit ligand, Tissue inhibitor of metalloproteinase 1, Tissue inhibitor of metalloproteinase 2, soluble Tumor necrosis factor, soluble Vascular cell adhesion molecule 1, and Vascular endothelial growth factor A is/are correlated to a particular class and/or subclass. The following are preferred classification embodiments.

In preferred classification embodiments, these methods comprise determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage, and the assay result(s) is/are correlated to the injury classification for the subject. For example, the measured concentration may be compared to a threshold value, and when the measured concentration is above the threshold, a particular classification is assigned; alternatively, when the measured concentration is below the threshold, a different classification may be assigned to the subject.

A variety of methods may be used by the skilled artisan to arrive at a desired threshold value for use in these methods. For example, the threshold value may be determined from a population of normal subjects by selecting a concentration representing the $75^{th}$, $85^{th}$, $90^{th}$, $95^{th}$, or $99^{th}$ percentile of a kidney injury marker measured in such normal subjects. Alternatively, the threshold value may be determined from a "diseased" population of subjects, e.g., those suffering from an injury or having a predisposition for an injury (e.g., progression to ARF or some other clinical outcome such as death, dialysis, renal transplantation, etc.), by selecting a concentration representing the $75^{th}$, $85^{th}$, $90^{th}$, $95^{th}$, or $99^{th}$ percentile of a kidney injury marker measured in such subjects. In another alternative, the threshold value may be determined from a prior measurement of a kidney injury marker in the same subject; that is, a temporal change in the level of a kidney injury marker in the subject may be used to assign risk to the subject.

The foregoing discussion is not meant to imply, however, that the kidney injury markers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that the kidney injury marker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the subject selected from the group consisting of demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, $17^{th}$ Ed., McGraw Hill, New York, pages 1741-1830, and Current Medical Diagnosis & Treatment 2008, $47^{th}$ Ed, McGraw Hill, New York, pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

BRIEF DESCRIPTION OF THE FIGURES

FIG. 1 provides data tables determined in accordance with Example 6 for the comparison of marker levels in urine samples collected for Cohort 1 (patients that did not progress beyond RIFLE stage 0) and in urine samples collected from subjects at 0, 24 hours, and 48 hours prior to reaching stage R, I or F in Cohort 2. Tables provide descriptive statistics, AUC analysis, and sensitivity, specificity and odds ratio calculations at various threshold (cutoff) levels for the various markers.

FIG. 2 provides data tables determined in accordance with Example 7 for the comparison of marker levels in urine samples collected for Cohort 1 (patients that did not progress beyond RIFLE stage 0 or R) and in urine samples collected from subjects at 0, 24 hours, and 48 hours prior to reaching stage I or F in Cohort 2. Tables provide descriptive statistics, AUC analysis, and sensitivity, specificity and odds ratio calculations at various threshold (cutoff) levels for the various markers.

FIG. 3 provides data tables determined in accordance with Example 8 for the comparison of marker levels in urine samples collected for Cohort 1 (patients that reached, but did not progress beyond, RIFLE stage R) and in urine samples collected from subjects at 0, 24 hours, and 48 hours prior to reaching stage I or F in Cohort 2. Tables provide descriptive statistics, AUC analysis, and sensitivity, specificity and odds ratio calculations at various threshold (cutoff) levels for the various markers.

FIG. 4 provides data tables determined in accordance with Example 9 for the comparison of marker levels in urine samples collected for Cohort 1 (patients that did not progress beyond RIFLE stage 0) and in urine samples collected from subjects at 0, 24 hours, and 48 hours prior to reaching stage F in Cohort 2. Tables provide descriptive statistics, AUC analysis, and sensitivity, specificity and odds ratio calculations at various threshold (cutoff) levels for the various markers.

FIG. 5 provides data tables determined in accordance with Example 6 for the comparison of marker levels in plasma samples collected for Cohort 1 (patients that did not progress beyond RIFLE stage 0) and in plasma samples collected from subjects at 0, 24 hours, and 48 hours prior to reaching stage R, I or F in Cohort 2. Tables provide descriptive statistics, AUC analysis, and sensitivity, specificity and odds ratio calculations at various threshold (cutoff) levels for the various markers.

FIG. 6 provides data tables determined in accordance with Example 7 for the comparison of marker levels in plasma samples collected for Cohort 1 (patients that did not progress beyond RIFLE stage 0 or R) and in plasma samples collected from subjects at 0, 24 hours, and 48 hours prior to reaching stage I or F in Cohort 2. Tables provide descriptive statistics, AUC analysis, and sensitivity, specificity and odds ratio calculations at various threshold (cutoff) levels for the various markers.

FIG. 7 provides data tables determined in accordance with Example 8 for the comparison of marker levels in plasma samples collected for Cohort 1 (patients that reached, but did not progress beyond, RIFLE stage R) and in plasma samples collected from subjects at 0, 24 hours, and 48 hours prior to reaching stage I or F in Cohort 2. Tables provide descriptive statistics, AUC analysis, and sensitivity, specificity and odds ratio calculations at various threshold (cutoff) levels for the various markers.

FIG. 8 provides data tables determined in accordance with Example 9 for the comparison of marker levels in plasma samples collected for Cohort 1 (patients that did not progress beyond RIFLE stage 0) and in plasma samples collected from subjects at 0, 24 hours, and 48 hours prior to reaching stage F in Cohort 2. Tables provide descriptive statistics, AUC analysis, and sensitivity, specificity and odds ratio calculations at various threshold (cutoff) levels for the various markers.

DETAILED DESCRIPTION OF THE INVENTION

The present invention relates to methods and compositions for diagnosis, differential diagnosis, risk stratification, monitoring, classifying and determination of treatment regimens in subjects suffering or at risk of suffering from injury to renal function, reduced renal function and/or acute renal failure through measurement of one or more kidney injury markers. In various embodiments, a measured concentration of one or more markers selected from the group consisting of Cytoplasmic aspartate aminotransferase, soluble Tumor necrosis factor receptor superfamily member 5, soluble CD40 Ligand, soluble C-X-C Motif chemokine 16, S100-A12, Eotaxin, soluble E-selectin, Fibronectin, Granulocyte colony-stimulating factor, Granulocyte-macrophage colony-stimulating factor, Heparin-binding growth factor 2, soluble Hepatocyte growth factor receptor, Interleukin-1 receptor antagonist, Interleukin-1 beta, Interleukin-10, Interleukin-15, Interleukin-3, Myeloperoxidase, Nidogen-1, soluble Oxidized low-density lipoprotein receptor 1, Pappalysin-1, soluble P-selectin glycoprotein ligand 1, Antileukoproteinase, soluble Kit ligand, Tissue inhibitor of metalloproteinase 1, Tissue inhibitor of metalloproteinase 2, soluble Tumor necrosis factor, soluble Vascular cell adhesion molecule 1, and Vascular endothelial growth factor A, or one or more markers related thereto, are correlated to the renal status of the subject.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours)

measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL (≥8.8 µmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl (≥26.4 µmol/l), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quatitation). This list is not meant to be limiting.

As used herein, the term "Cytoplasmic aspartate aminotransferase" refers to one or more polypeptides present in a biological sample that are derived from the Cytoplasmic aspartate aminotransferase precursor (Swiss-Prot P17174 (SEQ ID NO: 1)).

```
            10         20         30         40         50         60
     MAPPSVFAEV PQAQPVLVFK LTADFREDPD PRKVNLGVGA YRTDDCHPWV LPVVKKVEQK 70         80         90        100        110        120
     IANDNSLNHE YLPILGLAEF RSCASRLALG DDSPALKEKR VGGVQSLGGT GALRIGADFL 130        140        150        160        170        180
     ARWYNGTNNK NTPVYVSSPT WENHNAVFSA AGFKDIRSYR YWDAEKRGLD LQGFLNDLEN 190        200        210        220        230        240
     APEFSIVVLH ACAHNPTGID PTPEQWKQIA SVMKHRFLFP FFDSAYQGFA SGNLERDAWA 250        260        270        280        290        300
     IRYFVSEGFE FFCAQSFSKN FGLYNERVGN LTVVGKEPES ILQVLSQMEK IVRITWSNPP 310        320        330        340        350        360
     AQGARIVAST LSNPELFEEW TGNVKTMADR ILTMRSELRA RLEALKTPGT WNHITDQIGM 370        380        390        400        410
     FSFTGLNPKQ VEYLVNEKHI YLLPSGRINV SGLTTKNLDY VATSIHEAVT KIQ
```

The following domains have been identified in Cytoplasmic aspartate aminotransferase:

| Residues | Length | Domain ID |
| --- | --- | --- |
| 1 | 1 | Initiator methionine |
| 2-413 | 412 | Cytoplasmic aspartate aminotransferase |

As used herein, the term "tumor necrosis factor receptor superfamily member 5" refers to one or more polypeptides present in a biological sample that are derived from the tumor necrosis factor receptor superfamily member 5 precursor (Swiss-Prot P25942 (SEQ ID NO: 2)).

```
            10         20         30         40         50         60
     MVRLPLQCVL WGCLLTAVHP EPPTACREKQ YLINSQCCSL CQPGQKLVSD CTEFTETECL 70         80         90        100        110        120
     PCGESEFLDT WNRETHCHQH KYCDPNLGLR VQQKGTSETD TICTCEEGWH CTSEACESCV 130        140        150        160        170        180
     LHRSCSPGFG VKQIATGVSD TICEPCPVGF FSNVSSAFEK CHPWTSCETK DLVVQQAGTN 190        200        210        220        230        240
     KTDVVCGPQD RLRALVVIPI IFGILFAILL VLVFIKKVAK KPTNKAPHPK QEPQEINFPD 250        260        270
     DLPGSNTAAP VQETLHGCQP VTQEDGKESR ISVQERQ
```

Most preferably, the tumor necrosis factor receptor superfamily member 5 assay detects one or more soluble forms of tumor necrosis factor receptor superfamily member 5. Tumor necrosis factor receptor superfamily member 5 is a single-pass type I membrane protein having a large extracellular domain, most or all of which is present in soluble forms of tumor necrosis factor receptor superfamily member 5 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in tumor necrosis factor receptor superfamily member 5:

| Residues | Length | Domain ID |
|---|---|---|
| 1-20 | 20 | signal sequence |
| 21-277 | 257 | tumor necrosis factor receptor superfamily member 5 |
| 21-193 | 173 | extracellular |
| 194-215 | 22 | transmembrane |
| 216-277 | 62 | cytoplasmic |

In addition, 1 alternative splice form of tumor necrosis factor receptor superfamily member 5 is known. This form is considered a tumor necrosis factor receptor superfamily member 5 for purposes of the present invention, and soluble forms of this alternative splice form is considered a soluble tumor necrosis factor receptor superfamily member 5 for purposes of the present invention.

As used herein, the term "CD40 ligand" refers to one or more polypeptides present in a biological sample that are derived from the CD40 ligand precursor (Swiss-Prot P29965 (SEQ ID NO: 3)).

```
            10         20         30         40         50         60
    MIETYNQTSP RSAATGLPIS MKIFMYLLTV FLITQMIGSA LFAVYLHRRL DKIEDERNLH 70         80         90        100        110        120
    EDFVFMKTIQ RCNTGERSLS LLNCEEIKSQ FEGFVKDIML NKEETKKENS FEMQKGDQNP 130        140        150        160        170        180
    QIAAHVISEA SSKTTSVLQW AEKGYYTMSN NLVTLENGKQ LTVKRQGLYY IYAQVTFCSN 190        200        210        220        230        240
    REASSQAPFI ASLCLKSPGR FERILLRAAN THSSAKPCGQ QSIHLGGVFE LQPGASVFVN 250        260
    VTDPSQVSHG TGFTSFGLLK L
```

Most preferably, the CD40 ligand assay detects one or more soluble forms of CD40 ligand. CD40 ligand is a single-pass type II membrane protein having a large extracellular domain, most or all of which is present in soluble forms of CD40 ligand generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in CD40 ligand:

| Residues | Length | Domain ID |
|---|---|---|
| 1-261 | 261 | CD40 ligand, membrane bound form |
| 113-261 | 149 | CD40 ligand, soluble form |
| 47-261 | 215 | extracellular |
| 23-46 | 24 | anchor signal |
| 1-22 | 22 | cytoplasmic |
| 112-113 | 2 | cleavage site |

As used herein, the term "C-X-C motif chemokine 16" refers to one or more polypeptides present in a biological sample that are derived from the C-X-C motif chemokine 16 precursor (Swiss-Prot Q9H2A7 (SEQ ID NO: 4)).

```
                        10         20         30         40         50         60
                MGRDLRPGSR VLLLLLLLLL VYLTQPGNGN EGSVTGSCYC GKRISSDSPP SVQFMNRLRK 70         80         90        100        110        120
                HLRAYHRCLY YTRFQLLSWS VCGGNKDPWV QELMSCLDLK ECGHAYSGIV AHQKHLLPTS
```

-continued

```
         130        140        150        160        170        180
PPISQASEGA SSDIHTPAQM LLSTLQSTQR PTLPVGSLSS DKELTRPNET TIHTAGHSLA 190        200        210        220        230        240
AGPEAGENQK QPEKNAGPTA RTSATVPVLC LLAIIFILTA ALSYVLCKRR RGQSPQSSPD

250
LPVHYIPVAP DSNT
```

Most preferably, the C-X-C motif chemokine 16 assay detects one or more soluble forms of C-X-C motif chemokine 16. C-X-C motif chemokine 16 is a single-pass type I membrane protein having a large extracellular domain, most or all of which is present in soluble forms of C-X-C motif chemokine 16 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in C-X-C motif chemokine 16:

| Residues | Length | Domain ID |
|---|---|---|
| 1-29 | 29 | signal sequence |
| 30-254 | 225 | C-X-C motif chemokine 16 |
| 30-205 | 176 | extracellular |
| 206-226 | 21 | transmembrane |
| 227-254 | 28 | cytoplasmic |

As used herein, the term "Protein S100-A12" refers to one or more polypeptides present in a biological sample that are derived from the Protein S100-A12 precursor (Swiss-Prot P80511 (SEQ ID NO: 5)).

```
         10         20         30         40         50         60
MTKLEEHLEG IVNIFHQYSV RKGHFDTLSK GELKQLLTKE LANTIKNIKD KAVIDEIFQG 70         80         90
LDANQDEQVD FQEFISLVAI ALKAAHYHTH KE
```

The following domains have been identified in Protein S100-A12:

| Residues | Length | Domain ID |
|---|---|---|
| 1 | 1 | Initiator methionine |
| 2-92 | 91 | Protein S100-A12 |

As used herein, the term "Eotaxin" refers to one or more polypeptides present in a biological sample that are derived from the Eotaxin precursor (Swiss-Prot P51671 (SEQ ID NO: 6)).

```
         10         20         30         40         50         60
MKVSAALLWL LLIAAAFSPQ GLAGPASVPT TCCFNLANRK IPLQRLESYR RITSGKCPQK 70         80         90
AVIFKTKLAK DICADPKKKW VQDSMKYLDQ KSPTPKP
```

The following domains have been identified in Eotaxin:

| Residues | Length | Domain ID |
|---|---|---|
| 1-23 | 23 | Signal peptide |
| 24-97 | 74 | Eotaxin |

As used herein, the term "E-selectin" refers to one or more polypeptides present in a biological sample that are derived from the E-selectin precursor (Swiss-Prot P16581 (SEQ ID NO: 7)).

```
         10         20         30         40         50         60
MIASQFLSAL TLVLLIKESG AWSYNTSTEA MTYDEASAYC QQRYTHLVAI QNKEEIEYLN 70         80         90        100        110        120
SILSYSPSYY WIGIRKVNNV WVWVGTQKPL TEEAKNWAPG EPNNRQKDED CVEIYIKREK 130        140        150        160        170        180
DVGMWNDERC SKKKLALCYT AACTNTSCSG HGECVETINN YTCKCDPGFS GLKCEQIVNC 190        200        210        220        230        240
TALESPEHGS LVCSHPLGNF SYNSSCSISC DRGYLPSSME TMQCMSSGEW SAPIPACNVV 250        260        270        280        290        300
ECDAVTNPAN GFVECFQNPG SFPWNTTCTF DCEEGFELMG AQSLQCTSSG NWDNEKPTCK 310        320        330        340        350        360
AVTCRAVRQP QNGSVRCSHS PAGEFTFKSS CNFTCEEGFM LQGPAQVECT TQGQWTQQIP 370        380        390        400        410        420
VCEAFQCTAL SNPERGYMNC LPSASGSFRY GSSCEFSCEQ GFVLKGSKRL QCGPTGEWDN 430        440        450        460        470        480
EKPTCEAVRC DAVHQPPKGL VRCAHSPIGE FTYKSSCAFS CEEGFELHGS TQLECTSQGQ 490        500        510        520        530        540
WTEEVPSCQV VKCSSLAVPG KINMSCSGEP VFGTVCKFAC PEGWTLNGSA ARTCGATGHW 550        560        570        580        590        600
SGLLPTCEAP TESNIPLVAG LSAAGLSLLT LAPFLLWLRK CLRKAKKFVP ASSCQSLESD

610
GSYQKPSYIL
```

Most preferably, the E-selectin assay detects one or more soluble forms of E-selectin. E-selectin is a single-pass type I membrane protein having a large extracellular domain, most or all of which is present in soluble forms of E-selectin generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in E-selectin:

| Residues | Length | Domain ID |
| --- | --- | --- |
| 1-21 | 21 | signal sequence |
| 22-610 | 589 | E-selectin |

-continued

| Residues | Length | Domain ID |
| --- | --- | --- |
| 22-556 | 535 | extracellular |
| 557-578 | 22 | transmembrane |
| 579-610 | 32 | cytoplasmic |

As used herein, the term "Fibronectin" refers to one or more polypeptides present in a biological sample that are derived from the Fibronectin precursor (Swiss-Prot P02751 (SEQ ID NO: 8)).

```
                           10         20         30         40         50         60
                    MLRGPGPGLL LLAVQCLGTA VPSTGASKSK RQAQQMVQPQ SPVAVSQSKP GCYDNGKHYQ 70         80         90        100        110        120
                    INQQWERTYL GNALVCTCYG GSRGFNCESK PEAEETCFDK YTGNTYRVGD TYERPKDSMI 130        140        150        160        170        180
                    WDCTCIGAGR GRISCTIANR CHEGGQSYKI GDTWRRPHET GGYMLECVCL GNGKGEWTCK 190        200        210        220        230        240
                    PIAEKCFDHA AGTSYVVGET WEKPYQGWMM VDCTCLGEGS GRITCTSRNR CNDQDTRTSY 250        260        270        280        290        300
                    RIGDTWSKKD NRGNLLQCIC TGNGRGEWKC ERHTSVQTTS SGSGPFTDVR AAVYQPQPHP 310        320        330        340        350        360
                    QPPPYGHCVT DSGVVYSVGM QWLKTQGNKQ MLCTCLGNGV SCQETAVTQT YGGNSNGEPC 370        380        390        400        410        420
                    VLPFTYNGRT FYSCTTEGRQ DGHLWCSTTS NYEQDQKYSF CTDHTVLVQT QGGNSNGALC 430        440        450        460        470        480
                    HFPFLYNNHN YTDCTSEGRR DNMKWCGTTQ NYDADQKFGF CPMAAHEEIC TTNEGVMYRI
```

-continued

```
       490        500        510        520        530        540
GDQWDKQHDM GHMMRCTCVG NGRGEWTCIA YSQLRDQCIV DDITYNVNDT FHKRHEEGHM 550        560        570        580        590        600
LNCTCFGQGR GRWKCDPVDQ CQDSETGTFY QIGDSWEKYV HGVRYQCYCY GRGIGEWHCQ 610        620        630        640        650        660
PLQTYPSSSG PVEVFITETP SQPNSHPIQW NAPQPSHISK YILRWRPKNS VGRWKEATIP 670        680        690        700        710        720
GHLNSYTIKG LKPGVVYEGQ LISIQQYGHQ EVTRFDFTTT STSTPVTSNT VTGETTPFSP 730        740        750        760        770        780
LVATSESVTE ITASSFVVSW VSASDTVSGF RVEYELSEEG DEPQYLDLPS TATSVNIPDL 790        800        810        820        830        840
LPGRKYIVNV YQISEDGEQS LILSTSQTTA PDAPPDPTVD QVDDTSIVVR WSRPQAPITG 850        860        870        880        890        900
YRIVYSPSVE GSSTELNLPE TANSVTLSDL QPGVQYNITI YAVEENQEST PVVIQQETTG 910        920        930        940        950        960
TPRSDTVPSP RDLQFVEVTD VKVTIMWTPP ESAVTGYRVD VIPVNLPGEH GQRLPISRNT 970        980        990       1000       1010       1020
FAEVTGLSPG VTYYFKVFAV SHGRESKPLT AQQTTKLDAP TNLQFVNETD STVLVRWTPP 1030       1040       1050       1060       1070       1080
RAQITGYRLT VGLTRRGQPR QYNVGPSVSK YPLRNLQPAS EYTVSLVAIK GNQESPKATG 1090       1100       1110       1120       1130       1140
VFTTLQPGSS IPPYNTEVTE TTIVITWTPA PRIGFKLGVR PSQGGEAPRE VTSDSGSIVV 1150       1160       1170       1180       1190       1200
SGLTPGVEYV YTIQVLRDGQ ERDAPIVNKV VTPLSPPTNL HLEANPDTGV LTVSWERSTT 1210       1220       1230       1240       1250       1260
PDITGYRITT TPTNGQQGNS LEEVVHADQS SCTFDNLSPG LEYNVSVYTV KDDKESVPIS 1270       1280       1290       1300       1310       1320
DTIIPAVPPP TDLRFTNIGP DTMRVTWAPP PSIDLTNFLV RYSPVKNEED VAELSISPSD 1330       1340       1350       1360       1370       1380
NAVVLTNLLP GTEYVVSVSS VYEQHESTPL RGRQKTGLDS PTGIDFSDIT ANSFTVHWIA 1390       1400       1410       1420       1430       1440
PRATITGYRI RHHPEHFSGR PREDRVPHSR NSITLTNLTP GTEYVVSIVA LNGREESPLL 1450       1460       1470       1480       1490       1500
IGQQSTVSDV PRDLEVVAAT PTSLLISWDA PAVTVRYYRI TYGETGGNSP VQEFTVPGSK 1510       1520       1530       1540       1550       1560
STATISGLKP GVDYTITVYA VTGRGDSPAS SKPISINYRT EIDKPSQMQV TDVQDNSISV 1570       1580       1590       1600       1610       1620
KWLPSSSPVT GYRVTTTPKN GPGPTKTKTA GPDQTEMTIE GLQPTVEYVV SVYAQNPSGE 1630       1640       1650       1660       1670       1680
SQPLVQTAVT NIDRPKGLAF TDVDVDSIKI AWESPQGQVS RYRVTYSSPE DGIHELFPAP 1690       1700       1710       1720       1730       1740
DGEEDTAELQ GLRPGSEYTV SVVALHDDME SQPLIGTQST AIPAPTDLKF TQVTPTSLSA 1750       1760       1770       1780       1790       1800
QWTPPNVQLT GYRVRVTPKE KTGPMKEINL APDSSSVVVS GLMVATKYEV SVYALKDTLT 1810       1820       1830       1840       1850       1860
SRPAQGVVTT LENVSPPRRA RVTDATETTI TISWRTKTET ITGFQVDAVP ANGQTPIQRT 1870       1880       1890       1900       1910       1920
IKPDVRSYTI TGLQPGTDYK IYLYTLNDNA RSSPVVIDAS TAIDAPSNLR FLATTPNSLL 1930       1940       1950       1960       1970       1980
VSWQPPRARI TGYIIKYEKP GSPPREVVPR PRPGVTEATI TGLEPGTEYT IYVIALKNNQ 1990       2000       2010       2020       2030       2040
KSEPLIGRKK TDELPQLVTL PHPNLHGPEI LDVPSTVQKT PFVTHPGYDT GNGIQLPGTS 2050       2060       2070       2080       2090       2100
```

-continued

```

GQQPSVGQQM  IFEEHGFRRT  TPPTTATPIR  HRPRPYPPNV  GEEIQIGHIP  REDVDYHLYP 2110        2120        2130        2140        2150        2160
HGPGLNPNAS  TGQEALSQTT  ISWAPFQDTS  EYIISCHPVG  TDEEPLQFRV  PGTSTSATLT 2170        2180        2190        2200        2210        2220
GLTRGATYNI  IVEALKDQQR  HKVREEVVTV  GNSVNEGLNQ  PTDDSCFDPY  TVSHYAVGDE 2230        2240        2250        2260        2270        2280
WERMSESGFK  LLCQCLGFGS  GHFRCDSSRW  CHDNGVNYKI  GEKWDRQGEN  GQMMSCTCLG 2290        2300        2310        2320        2330        2340
NGKGEFKCDP  HEATCYDDGK  TYHVGEQWQK  EYLGAICSCT  CFGGQRGWRC  DNCRRPGGEP 2350        2360        2370        2380
SPEGTTGQSY  NQYSQRYHQR  TNTNVNCPIE  CFMPLDVQAD  REDSRE
```

The following domains have been identified in Fibronectin:

| Residues | Length | Domain ID |
|---|---|---|
| 1-31 | 31 | Signal peptide |
| 32-2386 | 2355 | Fibronectin |

At least 14 other isoforms of Fibronectin are known and are considered "fibronectin" for purposes of the present invention.

As used herein, the term "Granulocyte colony-stimulating factor" refers to one or more polypeptides present in a biological sample that are derived from the Granulocyte colony-stimulating factor precursor (Swiss-Prot P09919 (SEQ ID NO: 9)).

```
          10          20          30          40          50          60
MAGPATQSPM  KLMALQLLLW  HSALWTVQEA  TPLGPASSLP  QSFLLKCLEQ  VRKIQGDGAA 70          80          90         100         110         120
LQEKLVSECA  TYKLCHPEEL  VLLGHSLGIP  WAPLSSCPSQ  ALQLAGCLSQ  LHSGLFLYQG 130         140         150         160         170         180
LLQALEGISP  ELGPTLDTLQ  LDVADFATTI  WQQMEELGMA  PALQPTQGAM  PAFASAFQRR 190         200
AGGVLVASHL  QSFLEVSYRV  LRHLAQP
```

The following domains have been identified in Granulocyte colony-stimulating factor:

| Residues | Length | Domain ID |
|---|---|---|
| 1-29 | 29 | Signal peptide |
| 30-207 | 178 | Granulocyte colony-stimulating factor |

As used herein, the term "Granulocyte-macrophage colony-stimulating factor" refers to one or more polypeptides present in a biological sample that are derived from the Granulocyte-macrophage colony-stimulating factor precursor (Swiss-Prot P04141 (SEQ ID NO: 10)).

```
          10          20          30          40          50          60
MWLQSLLLLG  TVACSISAPA  RSPSPSTQPW  EHVNAIQEAR  RLLNLSRDTA  AEMNETVEVI 70          80          90         100         110         120
SEMFDLQEPT  CLQTRLELYK  QGLRGSLTKL  KGPLTMMASH  YKQHCPPTPE  TSCATQIITF 130         140
ESFKENLKDF  LLVIPFDCWE  PVQE
```

The following domains have been identified in Granulocyte-macrophage colony-stimulating factor:

| Residues | Length | Domain ID |
|---|---|---|
| 1-17 | 17 | Signal peptide |
| 18-144 | 127 | Granulocyte-macrophage colony-stimulating factor |

As used herein, the term "Heparin-binding growth factor 2" refers to one or more polypeptides present in a biological sample that are derived from the Heparin-binding growth factor 2 precursor (Swiss-Prot P09038 (SEQ ID NO: 11)).

```
          10         20         30         40         50         60
  MAAGSITTLP ALPEDGGSGA FPPGHFKDPK RLYCKNGGFF LRIHPDGRVD GVREKSDPHI 70         80         90        100        110        120
  KLQLQAEERG VVSIKGVCAN RYLAMKEDGR LLASKCVTDE CFFFERLESN NYNTYRSRKY 130        140        150
  TSWYVALKRT GQYKLGSKTG PGQKAILFLP MSAKS
```

The following domains have been identified in Heparin-binding growth factor 2:

| Residues | Length | Domain ID |
|---|---|---|
| 1-9 | 9 | Propeptide |
| 10-155 | 146 | Heparin-binding growth factor 2 |

As used herein, the term "hepatocyte growth factor receptor" refers to one or more polypeptides present in a biological sample that are derived from the hepatocyte growth factor receptor precursor (Swiss-Prot P08581 (SEQ ID NO: 12)).

```
          10         20         30         40         50         60
  MKAPAVLAPG ILVLLFTLVQ RSNGECKEAL AKSEMNVNMK YQLPNFTAET PIQNVILHEH 70         80         90        100        110        120
  HIFLGATNYI YVLNEEDLQK VAEYKTGPVL EHPDCFPCQD CSSKANLSGG VWKDNINMAL 130        140        150        160        170        180
  VVDTYYDDQL ISCGSVNRGT CQRHVFPHNH TADIQSEVHC IFSPQIEEPS QCPDCVVSAL 190        200        210        220        230        240
  GAKVLSSVKD RFINFFVGNT INSSYFPDHP LHSISVRRLK ETKDGFMFLT DQSYIDVLPE 250        260        270        280        290        300
  FRDSYPIKYV HAFESNNFIY FLTVQRETLD AQTFHTRIIR FCSINSGLHS YMEMPLECIL 310        320        330        340        350        360
  TEKRKKRSTK KEVFNILQAA YVSKPGAQLA RQIGASLNDD ILFGVFAQSK PDSAEPMDRS 370        380        390        400        410        420
  AMCAFPIKYV NDFFNKIVNK NNVRCLQHFY GPNHEHCFNR TLLRNSSGCE ARRDEYRTEF 430        440        450        460        470        480
  TTALQRVDLF MGQFSEVLLT SISTFIKGDL TIANLGTSEG RFMQVVVSRS GPSTPHVNFL 490        500        510        520        530        540
  LDSHPVSPEV IVEHTLNQNG YTLVITGKKI TKIPLNGLGC RHFQSCSQCL SAPPFVQCGW 550        560        570        580        590        600
  CHDKCVRSEE CLSGTWTQQI CLPAIYKVFP NSAPLEGGTR LTICGWDFGF RRNNKFDLKK 610        620        630        640        650        660
  TRVLLGNESC TLTLSESTMN TLKCTVGPAM NKHFNMSIII SNGHGTTQYS TFSYVDPVIT
```

-continued

```
              670        680        690        700        710        720
       SISPKYGPMA GGTLLTLTGN YLNSGNSRHI SIGGKTCTLK SVSNSILECY TPAQTISTEF 730        740        750        760        770        780
       AVKLKIDLAN RETSIFSYRE DPIVYEIHPT KSFISGGSTI TGVGKNLNSV SVPRMVINVH 790        800        810        820        830        840
       EAGRNFTVAC QHRSNSEIIC CTTPSLQQLN LQLPLKTKAF FMLDGILSKY FDLIYVHNPV 850        860        870        880        890        900
       FKPFEKPVMI SMGNENVLEI KGNDIDPEAV KGEVLKVGNK SCENIHLHSE AVLCTVPNDL 910        920        930        940        950        960
       LKLNSELNIE WKQAISSTVL GKVIVQPDQN FTGLIAGVVS ISTALLLLLG FFLWLKKRKQ 970        980        990       1000       1010       1020
       IKDLGSELVR YDARVHTPHL DRLVSARSVS PTTEMVSNES VDYRATFPED QFPNSSQNGS 1030       1040       1050       1060       1070       1080
       CRQVQYPLTD MSPILTSGDS DISSPLLQNT VHIDLSALNP ELVQAVQHVV IGPSSLIVHF 1090       1100       1110       1120       1130       1140
       NEVIGRGHFG CVYHGTLLDN DGKKIHCAVK SLNRITDIGE VSQFLTEGII MKDFSHPNVL 1150       1160       1170       1180       1190       1200
       SLLGICLRSE GSPLVVLPYM KHGDLRNFIR NETHNPTVKD LIGFGLQVAK GMKYLASKKF 1210       1220       1230       1240       1250       1260
       VHRDLAARNC MLDEKFTVKV ADFGLARDMY DKEYYSVHNK TGAKLPVKWM ALESLQTQKF 1270       1280       1290       1300       1310       1320
       TTKSDVWSFG VVLWELMTRG APPYPDVNTF DITVYLLQGR RLLQPEYCPD PLYEVMLKCW 1330       1340       1350       1360       1370       1380
       HPKAEMRPSF SELVSRISAI FSTFIGEHYV HVNATYVNVK CVAPYPSLLS SEDNADDEVD

1390
       TRPASFWETS
```

Most preferably, the hepatocyte growth factor receptor assay detects one or more soluble forms of hepatocyte growth factor receptor. Hepatocyte growth factor receptor is a single-pass type I membrane protein having a large extracellular domain, most or all of which is present in soluble forms of hepatocyte growth factor receptor generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in hepatocyte growth factor receptor:

| Residues | Length | Domain ID |
|---|---|---|
| 1-24 | 24 | signal sequence |
| 25-1390 | 1366 | hepatocyte growth factor receptor |
| 25-932 | 908 | extracellular |
| 933-955 | 23 | transmembrane |
| 956-1390 | 435 | cytoplasmic |

As used herein, the term "Interleukin-1 receptor antagonist protein" refers to one or more polypeptides present in a biological sample that are derived from the Interleukin-1 receptor antagonist protein precursor (Swiss-Prot P18510 (SEQ ID NO: 13)).

```
              10         20         30         40         50         60
       MEICRGLRSH LITLLLFLFH SETICRPSGR KSSKMQAFRI WDVNQKTFYL RNNQLVAGYL 70         80         90        100        110        120
       QGPNVNLEEK IDVVPIEPHA LFLGIHGGKM CLSCVKSGDE TRLQLEAVNI TDLSENRKQD 130        140        150        160        170
       KRFAFIRSDS GPTTSFESAA CPGWFLCTAM EADQPVSLTN MPDEGVMVTK FYFQEDE
```

The following domains have been identified in Interleukin-1 receptor antagonist protein:

| Residues | Length | Domain ID |
|---|---|---|
| 1-25 | 25 | Signal peptide |
| 26-177 | 152 | Interleukin-1 receptor antagonist protein |

In addition, three variant isoforms of Interleukin-1 receptor antagonist protein are known. Isoform 2 replaces residues 1-21 with MAL; isoform 3 replaces residues 1-21 with MALADLYEEGGGGGGEGEDNADSK (SEQ ID NO: 33); and isoform 4 lacks residues 1-34.

As used herein, the term "Interleukin-1 beta" refers to one or more polypeptides present in a biological sample that are derived from the Interleukin-1 beta precursor (Swiss-Prot P01584 (SEQ ID NO: 14)).

```
        10         20         30         40         50         60
MAEVPELASE MMAYYSGNED DLFFEADGPK QMKCSFQDLD LCPLDGGIQL RISDHHYSKG 70         80         90        100        110        120
FRQAASVVVA MDKLRKMLVP CPQTFQENDL STFFPFIFEE EPIFFDTWDN EAYVHDAPVR 130        140        150        160        170        180
SLNCTLRDSQ QKSLVMSGPY ELKALHLQGQ DMEQQVVFSM SFVQGEESND KIPVALGLKE 190        200        210        220        230        240
KNLYLSCVLK DDKPTLQLES VDPKNYPKKK MEKRFVFNKI EINNKLEFES AQFPNWYIST 250        260
SQAENMPVFL GGTKGGQDIT DFTMQFVSS
```

The following domains have been identified in Interleukin-1 beta:

| Residues | Length | Domain ID |
| --- | --- | --- |
| 1-116 | 116 | Propeptide |
| 117-269 | 153 | Interleukin-1 beta |

As used herein, the term "Interleukin-10" refers to one or more polypeptides present in a biological sample that are derived from the Interleukin-10 precursor (Swiss-Prot P22301 (SEQ ID NO: 15)).

```
    10    20    30    40    50    60
MHSSALLCCL VLLTGVRASP GQGTQSENSC THFPGNLPNM LRDLRDAFSR VKTFFQMKDQ 70    80    90   100   110   120
LDNLLLKESL LEDFKGYLGC QALSEMIQFY LEEVMPQAEN QDPDIKAHVN SLGENLKTLR 130   140   150   160   170
LRLRRCHRFL PCENKSKAVE QVKNAFNKLQ EKGIYKAMSE FDIFINYIEA YMTMKIRN
```

The following domains have been identified in Interleukin-10:

| Residues | Length | Domain ID |
| --- | --- | --- |
| 1-18 | 18 | Signal peptide |
| 19-178 | 160 | Interleukin-10 |

As used herein, the term "Interleukin-15" refers to one or more polypeptides present in a biological sample that are derived from the Interleukin-15 precursor (Swiss-Prot P40933 (SEQ ID NO: 16)).

```
    10    20    30    40    50    60
MRISKPHLRS ISIQCYLCLL LNSHFLTEAG IHVFILGCFS AGLPKTEANW VNVISDLKKI 70    80    90   100   110   120
EDLIQSMHID ATLYTESDVH PSCKVTAMKC FLLELQVISL ESGDASIHDT VENLIILANN 130   140   150   160
SLSSNGNVTE SGCKECEELE EKNIKEFLQS FVHIVQMFIN TS
```

The following domains have been identified in Interleukin-15:

| Residues | Length | Domain ID |
|---|---|---|
| 1-29 | 29 | Signal peptide |
| 30-48 | 19 | Propeptide |
| 49-162 | 114 | Interleukin-15 |

In addition, two variant Interleukin-15 isoforms are known. Isoform 2 replaces residues 1-37 with MVLGTIDLCS (SEQ ID NO: 17; and isoform 3 replaces residues 1-47 with MDFQVQIFSFLLISASVIMSR (SEQ ID NO: 18).

As used herein, the term "Interleukin-3" refers to one or more polypeptides present in a biological sample that are derived from the Interleukin-3 precursor (Swiss-Prot P08700 (SEQ ID NO: 19)).

```
         10         20         30         40         50         60
MSRLPVLLLL QLLVRPGLQA PMTQTTPLKT SWVNCSNMID EIITHLKQPP LPLLDFNNLN 70         80         90        100        110        120
GEDQDILMEN NLRRPNLEAF NRAVKSLQNA SAIESILKNL LPCLPLATAA PTRHPIHIKD 130        140        150
GDWNEFRRKL TFYLKTLENA QAQQTTLSLA IF
```

The following domains have been identified in Interleukin-3:

| Residues | Length | Domain ID |
|---|---|---|
| 1-19 | 19 | Signal peptide |
| 20-152 | 133 | Interleukin-3 |

As used herein, the term "Myeloperoxidase" refers to one or more polypeptides present in a biological sample that are derived from the Myeloperoxidase precursor (Swiss-Prot P05164 (SEQ ID NO: 20)).

```
         10         20         30         40         50         60
MGVPFFSSLR CMVDLGPCWA GGLTAEMKLL LALAGLLAIL ATPQPSEGAA PAVLGEVDTS 70         80         90        100        110        120
LVLSSMEEAK QLVDKAYKER RESIKQRLRS GSASPMELLS YFKQPVAATR TAVRAADYLH 130        140        150        160        170        180
VALDLLERKL RSLWRRPFNV TDVLTPAQLN VLSKSSGCAY QDVGVTCPEQ DKYRTITGMC 190        200        210        220        230        240
NNRRSPTLGA SNRAFVRWLP AEYEDGFSLP YGWTPGVKRN GFPVALARAV SNEIVRFPTD 250        260        270        280        290        300
QLTPDQERSL MFMQWGQLLD HDLDFTPEPA ARASFVTGVN CETSCVQQPP CFPLKIPPND 310        320        330        340        350        360
PRIKNQADCI PFFRSCPACP GSNITIRNQI NALTSFVDAS MVYGSEEPLA RNLRNMSNQL 370        380        390        400        410        420
GLLAVNQRFQ DNGRALLPFD NLHDDPCLLT NRSARIPCFL AGDTRSSEMP ELTSMHTLLL 430        440        450        460        470        480
REHNRLATEL KSLNPRWDGE RLYQEARKIV GAMVQIITYR DYLPLVLGPT AMRKYLPTYR 490        500        510        520        530        540
SYNDSVDPRI ANVFTNAFRY GHTLIQPFMF RLDNRYQPME PNPRVPLSRV FFASWRVVLE 550        560        570        580        590        600
```

```
                                                -continued
GGIDPILRGL MATPAKLNRQ NQIAVDEIRE RLFEQVMRIG LDLPALNMQR SRDHGLPGYN 610        620        630        640        650        660
AWRRFCGLPQ PETVGQLGTV LRNLKLARKL MEQYGTPNNI DIWMGGVSEP LKRKGRVGPL 670        680        690        700        710        720
LACIIGTQFR KLRDGDRFWW ENEGVFSMQQ RQALAQISLP RIICDNTGIT TVSKNNIFMS 730        740
NSYPRDFVNC STLPALNLAS WREAS
```

The following domains have been identified in Myeloperoxidase:

| Residues | Length | Domain ID |
|---|---|---|
| 1-48 | 48 | Signal peptide |
| 49-745 | 697 | 89 kDa Myeloperoxidase |
| 49-164 | 116 | propeptide |
| 155-745 | 591 | 84 kDa Myeloperoxidase |
| 165-278 | 114 | Myeloperoxidase light chain |
| 279-745 | 467 | Myeloperoxidase heavy chain |

As used herein, the term "Nidogen-1" refers to one or more polypeptides present in a biological sample that are derived from the Nidogen-1 precursor (Swiss-Prot P14543 (SEQ ID NO: 21)).

```
              10         20         30         40         50         60
      MLASSSRIRA AWTRALLLPL LLAGPVGCLS RQELFPFGPG QGDLELEDGD DFVSPALELS 70         80         90        100        110        120
      GALRFYDRSD IDAVYVTTNG IIATSEPPAK ESHPGLFPPT FGAVAPFLAD LDTTDGLGKV 130        140        150        160        170        180
      YYREDLSPSI TQRAAECVHR GFPEISFQPS SAVVVTWESV APYQGPSRDP DQKGKRNTFQ 190        200        210        220        230        240
      AVLASSDSSS YAIFLYPEDG LQFHTTFSKK ENNQVPAVVA FSQGSVGFLW KSNGAYNIFA 250        260        270        280        290        300
      NDRESIENLA KSSNSGQQGV WVFEIGSPAT TNGVVPADVI LGTEDGAEYD DEDEDYDLAT 310        320        330        340        350        360
      TRLGLEDVGT TPFSYKALRR GGADTYSVPS VLSPRRAATE RPLGPPTERT RSFQLAVETF 370        380        390        400        410        420
      HQQHPQVIDV DEVEETGVVF SYNTDSRQTC ANNRHQCSVH AECRDYATGF CCSCVAGYTG 430        440        450        460        470        480
      NGRQCVAEGS PQRVNGKVKG RIFVGSSQVP IVFENTDLHS YVVMNHGRSY TAISTIPETV 490        500        510        520        530        540
      GYSLLPLAPV GGIIGWMFAV EQDGFKNGFS ITGGEFTRQA EVTFVGHPGN LVIKQRFSGI 550        560        570        580        590        600
      DEHGHLTIDT ELEGRVPQIP FGSSVHIEPY TELYHYSTSV ITSSSTREYT VTEPERDGAS 610        620        630        640        650        660
      PSRIYTYQWR QTITFQECVH DDSRPALPST QQLSVDSVFV LYNQEEKILR YAFSNSIGPV 670        680        690        700        710        720
      REGSPDALQN PCYIGTHGCD TNAACRPGPR TQFTCECSIG FRGDGRTCYD IDECSEQPSV 730        740        750        760        770        780
      CGSHTICNNH PGTFRCECVE GYQFSDEGTC VAVVDQRPIN YCETGLHNCD IPQRAQCIYT 790        800        810        820        830        840
      GGSSYTCSCL PGFSGDGQAC QDVDECQPSR CHPDAFCYNT PGSFTCQCKP GYQGDGFRCV 850        860        870        880        890        900
      PGEVEKTRCQ HEREHILGAA GATDPQRPIP PGLFVPECDA HGHYAPTQCH GSTGYCWCVD 910        920        930        940        950        960
      RDGREVEGTR TRPGMTPPCL STVAPPIHQG PAVPTAVIPL PPGTHLLFAQ TGKIERLPLE 970        980        990       1000       1010       1020
      GNTMRKTEAK AFLHVPAKVI IGLAFDCVDK MVYWTDITEP SIGRASLHGG EPTTIIRQDL 1030       1040       1050       1060       1070       1080
      GSPEGIAVDH LGRNIFWTDS NLDRIEVAKL DGTQRRVLFE TDLVNPRGIV TDSVRGNLYW
```

```
       1090 1100      1110 1120      1130 1140
TDWNRDNPKI ETSYMDGTNR RILVQDDLGL PNGLTFDAFS SQLCWVDAGT NRAECLNPSQ 1150 1160      1170 1180      1190 1200
PSRRKALEGL QYPFAVTSYG KNLYFTDWKM NSVVALDLAI SKETDAFQPH KQTRLYGITT 1210 1220      1230 1240
ALSQCPQGHN YCSVNNGGCT HLCLATPGSR TCRCPDNTLG VDCIERK
```

The following domains have been identified in Nidogen-1:

| Residues | Length | Domain ID |
|---|---|---|
| 1-28 | 28 | signal sequence |
| 29-1247 | 1219 | Nidogen-1 |

As used herein, the term "oxidized low-density lipoprotein receptor 1" refers to one or more polypeptides present in a biological sample that are derived from the oxidized low-density lipoprotein receptor 1 precursor (Swiss-Prot P78380 (SEQ ID NO: 22)).

```
        10     20     30     40     50     60
MTFDDLKIQT VKDQPDEKSN GKKAKGLQFL YSPWWCLAAA TLGVLCLGLV VTIMVLGMQL 70     80     90    100    110    120
SQVSDLLTQE QANLTHQKKK LEGQISARQQ AEEASQESEN ELKEMIETLA RKLNEKSKEQ 130    140    150    160    170    180
MELHHQNLNL QETLKRVANC SAPCPQDWIW HGENCYLFSS GSFNWEKSQE KCLSLDAKLL 190    200    210    220    230    240
KINSTADLDF IQQAISYSSF PFWMGLSRRN PSYPWLWEDG SPLMPHLFRV RGAVSQTYPS 250    260    270
GTCAYIQRGA VYAENCILAA FSICQKKANL RAQ
```

Most preferably, the oxidized low-density lipoprotein receptor 1 assay detects one or more soluble forms of oxidized low-density lipoprotein receptor 1. Oxidized low-density lipoprotein receptor 1 is a single-pass type II membrane protein having a large extracellular domain, most or all of which is present in soluble forms of oxidized low-density lipoprotein receptor 1 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in oxidized low-density lipoprotein receptor 1:

| Residues | Length | Domain ID |
|---|---|---|
| 1-273 | 273 | oxidized low-density lipoprotein receptor 1, membrane bound form |
| 1-36 | 36 | cytoplasmic |
| 37-57 | 21 | membrane anchor signal |
| 58-273 | 216 | extracellular |

As used herein, the term "Pappalysin-1" refers to one or more polypeptides present in a biological sample that are derived from the Pappalysin-1 precursor (Swiss-Prot Q13219 (SEQ ID NO: 23)).

```
        10     20     30     40     50     60
MRLWSWVLHL GLLSAALGCG LAERPRRARR DPRAGRPPRP AAGPATCATR AARGRRASPP 70     80     90    100    110    120
PPPPPGGAWE AVRVPRRRQQ REARGATEEP SPPSRALYFS GRGEQLRVLR ADLELPRDAF 130    140    150    160    170    180
TLQVWLRAEG GQRSPAVITG LYDKCSYISR DRGWVVGIHT ISDQDNKDPR YFFSLKTDRA 190    200    210    220    230    240
RQVTTINAHR SYLPGQWVYL AATYDGQFMK LYVNGAQVAT SGEQVGGIFS PLTQKCKVLM 250    260    270    280    290    300
LGGSALNHNY RGYIEHFSLW KVARTQREIL SDMETHGAHT ALPQLLLQEN WDNVKHAWSP 310    320    330    340    350    360
MKDGSSPKVE FSNAHGFLLD TSLEPPLCGQ TLCDNTEVIA SYNQLSSFRQ PKVVRYRVVN
```

```
            370        380        390        400        410        420
     LYEDDHKNPT VTREQVDFQH HQLAEAFKQY NISWELDVLE VSNSSLRRRL ILANCDISKI 430        440        450        460        470        480
     GDENCDPECN HTLTGHDGGD CRHLRHPAFV KKQHNGVCDM DCNYERFNFD GGECCDPEIT 490        500        510   520        530        540
     NVTQTCFDPD SPHRAYLDVN ELKNILKLDG STHLNIFFAK SSEEELAGVA TWPWDKEALM 550        560        570        580        590        600
     HLGGIVLNPS FYGMPGHTHT MIHEIGHSLG LYHVFRGISE IQSCSDPCME TEPSFETGDL 610        620        630        640        650        660
     CNDTNPAPKH KSCGDPGPGN DTCGFHSFFN TPYNNFMSYA DDDCTDSFTP NQVARMHCYL 670        680        690        700        710        720
     DLVYQGWQPS RKPAPVALAP QVLGHTTDSV TLEWFPPIDG HFFERELGSA CHLCLEGRIL 730        740        750        760        770        780
     VQYASNASSP MPCSPSGHWS PREAEGHPDV EQPCKSSVRT WSPNSAVNPH TVPPACPEPQ 790        800        810        820        830        840
     GCYLELEFLY PLVPESLTIW VTFVSTDWDS SGAVNDIKLL AVSGKNISLG PQNVFCDVPL 850        860        870        880        890        900
     TIRLWDVGEE VYGIQIYTLD EHLEIDAAML TSTADTPLCL QCKPLKYKVV RDPPLQMDVA 910        920        930        940        950        960
     SILHLNRKFV DMDLNLGSVY QYWVITISGT EESEPSPAVT YIHGRGYCGD GIIQKDQGEQ 970        980        990       1000       1010       1020
     CDDMNKINGD GCSLFCRQEV SFNCIDEPSR CYFHDGDGVC EEFEQKTSIK DCGVYTPQGF 1030       1040       1050       1060       1070       1080
     LDQWASNASV SHQDQQCPGW VIIGQPAASQ VCRTKVIDLS EGISQHAWYP CTISYPYSQL 1090       1100       1110       1120       1130       1140
     AQTTFWLRAY FSQPMVAAAV IVHLVTDGTY YGDQKQETIS VQLLDTKDQS HDLGLHVLSC 1150       1160       1170       1180  1190       1200
     RNNPLIIPVV HDLSQPFYHS QAVRVSFSSP LVAISGVALR SFDNFDPVTL SSCQRGETYS 1210       1220       1230       1240       1250       1260
     PAEQSCVHFA CEKTDCPELA VENASLNCSS SDRYHGAQCT VSCRTGYVLQ IRRDDELIKS 1270       1280       1290 1300       1310       1320
     QTGPSVTVTC TEGKWNKQVA CEPVDCSIPD HHQVYAASFS CPEGTTFGSQ CSFQCRHPAQ 1330       1340       1350       1360       1370       1380
     LKGNNSLLTC MEDGLWSFPE ALCELMCLAP PPVPNADLQT ARCRENKHKV GSFCKYKCKP 1390       1400       1410       1420       1430  1440
     GYHVPGSSRK SKKRAFKTQC TQDGSWQEGA CVPVTCDPPP PKFHGLYQCT NGFQFNSECR 1450       1460       1470       1480       1490       1500
     IKCEDSDASQ GLGSNVIHCR KDGTWNGSFH VCQEMQGQCS VPNELNSNLK LQCPDGYAIG 1510       1520       1530       1540       1550       1560
     SECATSCLDH NSESIILPMN VTVRDIPHWL NPTRVERVVC TAGLKWYPHP ALIHCVKGCE 1570       1580       1590       1600       1610       1620
     PFMGDNYCDA INNRAFCNYD GGDCCTSTVK TKKVTPFPMS CDLQGDCACR DPQAQEHSRK

DLRGYSHG
```

The following domains have been identified in Pappalysin-1:

| Residues | Length | Domain ID |
|---|---|---|
| 1-22 | 22 | Signal peptide |
| 23-80 | 58 | Propeptide |
| 81-1628 | 1548 | Pappalysin-1 |

As used herein, the term "P-selectin glycoprotein ligand 1" refers to one or more polypeptides present in a biological sample that are derived from the P-selectin glycoprotein ligand 1 precursor (Swiss-Prot Q14242 (SEQ ID NO: 24)).

```
        10         20         30         40         50         60
MPLQLLLLLI LLGPGNSLQL WDTWADEAEK ALGPLLARDR RQATEYEYLD YDFLPETEPP 70         80         90        100        110        120
EMLRNSTDTT PLTGPGTPES TTVEPAARRS TGLDAGGAVT ELTTELANMG NLSTDSAAME 130        140        150        160        170        180
IQTTQPAATE AQTTQPVPTE AQTTPLAATE AQTTRLTATE AQTTPLAATE AQTTPPAATE 190        200        210        220        230        240
AQTTQPTGLE AQTTAPAAME AQTTAPAAME AQTTPPAAME AQTTQTTAME AQTTAPEATE 250        260        270        280        290        300
AQTTQPTATE AQTTPLAAME ALSTEPSATE ALSMEPTTKR GLFIPFSVSS VTHKGIPMAA 310        320        330        340        350        360
SNLSVNYPVG APDHISVKQC LLAILILALV ATIFFVCTVV LAVRLSRKGH MYPVRNYSPT 370        380        390        400        410
EMVCISSLLP DGGEGPSATA NGGLSKAKSP GLTPEPREDR EGDDLTLHSF LP
```

Most preferably, the P-selectin glycoprotein ligand 1 assay detects one or more soluble forms of P-selectin glycoprotein ligand 1. P-selectin glycoprotein ligand 1 is a single-pass type I membrane protein having a large extracellular domain, most or all of which is present in soluble forms of P-selectin glycoprotein ligand 1 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in P-selectin glycoprotein ligand 1:

| Residues | Length | Domain ID |
|---|---|---|
| 1-17 | 17 | signal sequence |
| 18-41 | 24 | propeptide |
| 42-412 | 371 | P-selectin glycoprotein ligand 1 |
| 18-320 | 303 | extracellular |
| 321-341 | 21 | transmembrane |
| 342-412 | 71 | cytoplasmic |

As used herein, the term "Antileukoproteinase" refers to one or more polypeptides present in a biological sample that are derived from the Antileukoproteinase precursor (Swiss-Prot P03973 (SEQ ID NO: 25)).

```
        10         20         30         40         50         60
MKSSGLFPFL VLLALGTLAP WAVEGSGKSF KAGVCPPKKS AQCLRYKKPE CQSDWQCPGK 70         80         90        100        110        120
KRCCPDTCGI KCLDPVDTPN PTRRKPGKCP VTYGQCLMLN PPNFCEMDGQ CKRDLKCCMG

130
MCGKSCVSPV KA
```

The following domains have been identified in Antileukoproteinase:

| Residues | Length | Domain ID |
|---|---|---|
| 1-25 | 25 | signal sequence |
| 26-132 | 107 | Antileukoproteinase |

As used herein, the term "Kit ligand" refers to one or more polypeptides present in a biological sample that are derived from the Kit ligand precursor (Swiss-Prot P21583 (SEQ ID NO: 26)).

```
         10         20         30         40         50         60
MKKTQTWILT CIYLQLLLFN PLVKTEGICR NRVTNNVKDV TKLVANLPKD YMITLKYVPG 70         80         90        100        110        120
MDVLPSHCWI SEMVVQLSDS LTDLLDKFSN ISEGLSNYSI IDKLVNIVDD LVECVKENSS 130        140        150        160        170        180
KDLKKSFKSP EPRLFTPEEF FRIFNRSIDA FKDFVVASET SDCVVSSTLS PEKDSRVSVT 190        200        210        220        230        240
KPFMLPPVAA SSLRNDSSSS NRKAKNPPGD SSLHWAAMAL PALFSLIIGF AFGALYWKKR 250        260        270
QPSLTRAVEN IQINEEDNEI SMLQEKEREF QEV
```

In addition, a soluble splice variant form of Kit ligand has been described (SEQ ID NO:27):

```
         10         20         30         40         50         60
MKKTQTWILT CIYLQLLLFN PLVKTEGICR NRVTNNVKDV TKLVANLPKD YMITLKYVPG 70         80         90        100        110        120
MDVLPSHCWI SEMVVQLSDS LTDLLDKFSN ISEGLSNYSI IDKLVNIVDD LVECVKENSS 130        140        150        160        170        180
KDLKKSFKSP EPRLFTPEEF FRIFNRSIDA FKDFVVASET SDCVVSSTLS PEKGKAKNPP 190        200        210        220        230        240
GDSSLHWAAM ALPALFSLII GFAFGALYWK KRQPSLTRAV ENIQINEEDN EISMLQEKER
```

Most preferably, the Kit ligand assay detects one or more soluble forms of Kit ligand. Kit ligand is a single-pass type I membrane protein having a large extracellular domain, most or all of which is present in soluble forms of Kit ligand generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Kit ligand:

| Residues | Length | Domain ID |
|---|---|---|
| 1-25 | 25 | signal sequence |
| 26-273 | 248 | Kit ligand |
| 26-214 | 189 | extracellular |
| 215-237 | 23 | transmembrane |
| 238-273 | 36 | cytoplasmic |

As used herein, the term "Metalloproteinase inhibitor 1" refers to one or more polypeptides present in a biological sample that are derived from the Metalloproteinase inhibitor 1 precursor (Swiss-Prot P01033 (SEQ ID NO: 28)).

```
         10         20         30         40         50         60
MAPFEPLASG ILLLLWLIAP SRACTCVPPH PQTAFCNSDL VIRAKFVGTP EVNQTTLYQR 70         80         90        100        110        120
YEIKMTKMYK GFQALGDAAD IRFVYTPAME SVCGYFHRSH NRSEEFLIAG KLQDGLLHIT 130        140        150        160        170        180
TCSFVAPWNS LSLAQRRGFT KTYTVGCEEC TVFPCLSIPC KLQSGTHCLW TDQLLQGSEK 190        200
GFQSRHLACL PREPGLCTWQ SLRSQIA
```

The following domains have been identified in Metalloproteinase inhibitor 1:

| Residues | Length | Domain ID |
|---|---|---|
| 1-18 | 23 | signal sequence |
| 24-207 | 184 | Metalloproteinase inhibitor 1 |

As used herein, the term "Metalloproteinase inhibitor 2" refers to one or more polypeptides present in a biological sample that are derived from the Metalloproteinase inhibitor 2 precursor (Swiss-Prot P16035 (SEQ ID NO: 29)).

```
        10         20         30         40         50         60
MGAAARTLRL ALGLLLLATL LRPADACSCS PVHPQQAFCN ADVVIRAKAV SEKEVDSGND 70         80         90        100        110        120
IYGNPIKRIQ YEIKQIKMFK GPEKDIEFIY TAPSSAVCGV SLDVGGKKEY LIAGKAEGDG 130        140        150        160        170        180
KMHITLCDFI VPWDTLSTTQ KKSLNHRYQM GCECKITRCP MIPCYISSPD ECLWMDWVTE 190 200        210        220
KNINGHQAKF FACIKRSDGS CAWYRGAAPP KQEFLDIEDP
```

The following domains have been identified in Metalloproteinase inhibitor 2:

| Residues | Length | Domain ID |
|---|---|---|
| 1-26 | 26 | Signal peptide |
| 27-220 | 194 | Metalloproteinase inhibitor 2 |

As used herein, the term "Tumor necrosis factor" refers to one or more polypeptides present in a biological sample that are derived from the Tumor necrosis factor precursor (Swiss-Prot P01375 (SEQ ID NO: 30)).

```
        10         20         30         40         50         60
MSTESMIRDV ELAEEALPKK TGGPQGSRRC LFLSLFSFLI VAGATTLFCL LHFGVIGPQR 70         80         90        100        110        120
EEFPRDLSLI SPLAQAVRSS SRTPSDKPVA HVVANPQAEG QLQWLNRRAN ALLANGVELR 130        140        150        160        170        180
DNQLVVPSEG LYLIYSQVLF KGQGCPSTHV LLTHTISRIA VSYQTKVNLL SAIKSPCQRE 190        200        210        220        230
TPEGAEAKPW YEPIYLGGVF QLEKGDRLSA EINRPDYLDF AESGQVYFGI IAL
```

Most preferably, the Tumor necrosis factor assay detects one or more soluble forms of Tumor necrosis factor. Tumor necrosis factor is a single-pass type II membrane protein having a large extracellular domain, some or all of which is present in soluble forms of Tumor necrosis factor generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Tumor necrosis factor:

| Residues | Length | Domain ID |
|---|---|---|
| 1-233 | 233 | Tumor necrosis factor, membrane form |
| 77-233 | 157 | Tumor necrosis factor, soluble form |
| 36-56 | 35 | Anchor signal |
| 57-233 | 177 | extracellular |
| 1-35 | 35 | cytoplasmic |

As used herein, the term "Vascular cell adhesion molecule 1" refers to one or more polypeptides present in a biological sample that are derived from the Vascular cell adhesion molecule 1 precursor (Swiss-Prot P19320 (SEQ ID NO: 31)).

```
  10         20         30         40         50         60
MPGKMVVILG ASNILWIMFA ASQAFKIETT PESRYLAQIG DSVSLTCSTT GCESPFFSWR 70         80         90        100        110        120
TQIDSPLNGK VTNEGTTSTL TMNPVSFGNE HSYLCTATCE SRKLEKGIQV EIYSFPKDPE 130        140        150        160        170        180
IHLSGPLEAG KPITVKCSVA DVYPFDRLEI DLLKGDHLMK SQEFLEDADR KSLETKSLEV 190        200        210        220        230        240
TFTPVIEDIG KVLVCRAKLH IDEMDSVPTV RQAVKELQVY ISPKNTVISV NPSTKLQEGG 250        260        270        280        290        300
SVTMTCSSEG LPAPEIFWSK KLDNGNLQHL SGNATLTLIA MRMEDSGIYV CEGVNLIGKN 310        320        330        340        350        360
RKEVELIVQE KPFTVEISPG PRIAAQIGDS VMLTCSVMGC ESPSFSWRTQ IDSPLSGKVR 370        380        390        400        410        420
SEGTNSTLTL SPVSFENEHS YLCTVTCGHK KLEKGIQVEL YSFPRDPEIE MSGGLVNGSS 430        440        450        460        470        480
VTVSCKVPSV YPLDRLEIEL LKGETILENI EFLEDTDMKS LENKSLEMTF IPTIEDTGKA 490        500        510        520        530        540
LVCQAKLHID DMEFEPKQRQ STQTLYVNVA PRDTTVLVSP SSILEEGSSV NMTCLSQGFP 550        560        570        580        590        600
APKILWSRQL PNGELQPLSE NATLTLISTK MEDSGVYLCE GINQAGRSRK EVELIIQVTP 610        620        630        640        650        660
KDIKLTAFPS ESVKEGDTVI ISCTCGNVPE TWIILKKKAE TGDTVLKSID GAYTIRKAQL 670        680        690        700        710        720
KDAGVYECES KNKVGSQLRS LTLDVQGREN NKDYFSPELL VLYFASSLII PAIGMIIYFA

730
RKANMKGSYS LVEAQKSKV
```

Most preferably, the Vascular cell adhesion molecule 1 assay detects one or more soluble forms of Vascular cell adhesion molecule 1. Vascular cell adhesion molecule 1 is a single-pass type I membrane protein having a large extracellular domain, most or all of which is present in soluble forms of Vascular cell adhesion molecule 1 generated either through alternative splicing event which deletes all or a portion of the transmembrane domain, or by proteolysis of the membrane-bound form. In the case of an immunoassay, one or more antibodies that bind to epitopes within this extracellular domain may be used to detect these soluble form(s). The following domains have been identified in Vascular cell adhesion molecule 1:

| Residues | Length | Domain ID |
|---|---|---|
| 1-24 | 24 | signal sequence |
| 25-739 | 715 | Vascular cell adhesion molecule 1 |

-continued

| Residues | Length | Domain ID |
|---|---|---|
| 25-698 | 674 | extracellular |
| 699-720 | 22 | transmembrane |
| 721-739 | 19 | cytoplasmic |

As used herein, the term "Vascular endothelial growth factor A" refers to one or more polypeptides present in a biological sample that are derived from the Vascular endothelial growth factor A precursor (Swiss-Prot P15692 (SEQ ID NO: 32)).

```
  10         20         30         40         50         60
MNFLLSWVHW SLALLLYLHH AKWSQAAPMA EGGGQNHHEV VKFMDVYQRS YCHPIETLVD 70         80         90        100        110        120
IFQEYPDEIE YIFKPSCVPL MRCGGCCNDE GLECVPTEES NITMQIMRIK PHQGQHIGEM 130        140        150        160        170        180
SFLQHNKCEC RPKKDRARQE KKSVRGKGKG QKRKRKKSRY KSWSVYVGAR CCLMPWSLPG 190        200        210        220        230
PHPCGPCSER RKHLFVQDPQ TCKCSCKNTD SRCKARQLEL NERTCRCDKP RR
```

The following domains have been identified in Vascular endothelial growth factor A:

| Residues | Length | Domain ID |
|---|---|---|
| 1-26 | 26 | Signal peptide |
| 27-232 | 483 | Vascular endothelial growth factor A |

In addition, nine other variant forms of Vascular endothelial growth factor A are known, and are considered Vascular endothelial growth factor A for purposes of the present invention. These are VEGF189, VEGF183, VEGF165, VEGF148, VEGF145, VEGF121, VEGF165B, VEGF121B, and VEGF111.

As used herein, the term "relating a signal to the presence or amount" of an analyte reflects this understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

The term "positive going" marker as that term is used herein refer to a marker that is determined to be elevated in subjects suffering from a disease or condition, relative to subjects not suffering from that disease or condition. The term "negative going" marker as that term is used herein refer to a marker that is determined to be reduced in subjects suffering from a disease or condition, relative to subjects not suffering from that disease or condition.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGel™ resins (Rapp Polymere GmbH), AgroGel™ resins (I.L.S.A. Industria Lavorazione Sottoprodotti Animali S.P.A.), polyethylene glycol and acrylamide (PEGA) gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7 M^{-1}$, and preferably between about $10^8 M^{-1}$ to about $10^9 M^{-1}$, about $10^9 M^{-1}$ to about $10^{10} M^{-1}$, or about $10^{10} M^{-1}$ to about $10^{12} M^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the $97.5^{th}$ percentile of the concentration seen in a normal population. Another method may be to look at serial samples from the same patient, where a prior "baseline" result is used to monitor for temporal changes in a biomarker level.

Population studies may also be used to select a decision threshold. Reciever Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1-specificity, the ROC graph is sometimes called the sensitivity vs (1-specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Additional clinical indicia may be combined with the kidney injury marker assay result(s) of the present invention. These include other biomarkers related to renal status. Examples include the following, which recite the common biomarker name, followed by the Swiss-Prot entry number for that biomarker or its parent: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase (Renin, P00797); Annexin A2 (P07355); Beta-glucuronidase (P08236); B-2-microglobulin (P61679); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase (Q16790); Casein Kinase 2 (P68400); Cathepsin B (P07858); Ceruloplasmin (P00450); Clusterin (P10909); Complement C3 (P01024); Cysteine-rich protein (CYR61, O00622); Cytochrome C (P99999); Epidermal growth factor (EGF, P01133); Endothelin-1 (P05305); Exosomal Fetuin-A (P02765); Fatty acid-binding protein, heart (FABP3, P05413); Fatty acid-binding protein, liver (P07148); Ferritin (light chain, P02793; heavy chain P02794); Fructose-1,6-biphosphatase (P09467); GRO-alpha (CXCL1, (P09341); Growth Hormone (P01241); Hepatocyte growth factor (P14210); Insulin-like growth factor I (P01343); Immunoglobulin G; Immunoglobulin Light Chains (Kappa and Lambda); Interferon gamma (P01308); Lysozyme (P61626); Interleukin-1alpha (P01583); Interleukin-2 (P60568); Interleukin-4 (P60568); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (O95631); Neutral endopeptidase (P08473); Osteopontin (P10451); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform (NHE3, P48764); Spermidine/spermine N1-acetyltransferase (P21673); TGF-Beta1 (P01137); Transferrin (P02787); Trefoil factor 3 (TFF3, Q07654); Toll-Like protein 4 (O00206); Total protein; Tubulointerstitial nephritis antigen (Q9UJW2); Uromodulin (Tamm-Horsfall protein, P07911).

For purposes of risk stratification, Adiponectin (Q15848); Alkaline phosphatase (P05186); Aminopeptidase N (P15144); CalbindinD28k (P05937); Cystatin C (P01034); 8 subunit of F1FO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itm1, P46977); Interleukin-6 (P05231); Interleukin-8 (P10145); Interleukin-18 (Q14116); IP-10 (10 kDa interferon-gamma-induced protein, P02778); IRPR (IFRD1, O00458); Isovaleryl-CoA dehydrogenase (IVD, P26440); I-TAC/CXCL11 (O14625); Keratin 19 (P08727); Kim-1 (Hepatitis A virus cellular receptor 1, O43656); L-arginine:glycine amidinotransferase (P50440); Leptin (P41159); Lipocalin2 (NGAL, P80188); MCP-1 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, O15244); Osteoprotegerin (O14788); P8 protein (O60356); Plasminogen activator inhibitor 1 (PAI-1, P05121); ProANP(1-98) (P01160); Protein phosphatase 1-beta (PPI-beta, P62140); Rab GDI-beta (P50395); Renal kallikrein (Q86U61); RT1.B-1 (alpha) chain of the integral membrane protein (Q5Y7A8); Soluble tumor necrosis factor receptor superfamily member 1A (sTNFR-I, P19438); Soluble tumor necrosis factor receptor superfamily member 1B (sTNFR-II, P20333); Tissue inhibitor of metalloproteinases 3 (TIMP-3, P35625); uPAR (Q03405) may be combined with the kidney injury marker assay result(s) of the present invention.

Other clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined with the kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m$^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr-corrected} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., *Nephrol. Dial. Transplant.* 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N.J., 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1

Contrast-Induced Nephropathy Sample Collection

The objective of this sample collection study is to collect samples of plasma and urine and clinical data from patients before and after receiving intravascular contrast media. Approximately 250 adults undergoing radiographic/angiographic procedures involving intravascular administration of iodinated contrast media are enrolled. To be enrolled in the study, each patient must meet all of the following inclusion criteria and none of the following exclusion criteria:

Inclusion Criteria
males and females 18 years of age or older;
undergoing a radiographic/angiographic procedure (such as a CT scan or coronary intervention) involving the intravascular administration of contrast media;
expected to be hospitalized for at least 48 hours after contrast administration.
able and willing to provide written informed consent for study participation and to comply with all study procedures.

Exclusion Criteria
renal transplant recipients;
acutely worsening renal function prior to the contrast procedure;
already receiving dialysis (either acute or chronic) or in imminent need of dialysis at enrollment;
expected to undergo a major surgical procedure (such as involving cardiopulmonary bypass) or an additional imaging procedure with contrast media with significant risk for further renal insult within the 48 hrs following contrast administration;
participation in an interventional clinical study with an experimental therapy within the previous 30 days;
known infection with human immunodeficiency virus (HIV) or a hepatitis virus.

Immediately prior to the first contrast administration (and after any pre-procedure hydration), an EDTA anti-coagulated blood sample (10 mL) and a urine sample (10 mL) are collected from each patient. Blood and urine samples are then collected at 4 ($\pm$0.5), 8 ($\pm$1), 24 ($\pm$2) 48 ($\pm$2), and 72 ($\pm$2) hrs following the last administration of contrast media during the index contrast procedure. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Serum creatinine is assessed at the site immediately prior to the first contrast administration (after any pre-procedure hydration) and at 4 ($\pm$0.5), 8 ($\pm$1), 24 ($\pm$2) and 48 ($\pm$2)), and 72 ($\pm$2) hours following the last administration of contrast (ideally at the same time as the study samples are obtained). In addition, each patient's status is evaluated through day 30 with regard to additional serum and urine creatinine measurements, a need for dialysis, hospitalization status, and adverse clinical outcomes (including mortality).

Prior to contrast administration, each patient is assigned a risk based on the following assessment: systolic blood pressure<80 mm Hg=5 points; intra-arterial balloon pump=5 points; congestive heart failure (Class III-IV or history of pulmonary edema)=5 points; age>75 yrs=4 points; hematocrit level<39% for men, <35% for women=3 points; diabetes=3 points; contrast media volume=1 point for each 100 mL; serum creatinine level>1.5 g/dL=4 points OR estimated GFR 40-60 mL/min/1.73 $m^2$=2 points, 20-40 mL/min/1.73 $m^2$=4 points, <20 mL/min/1.73 $m^2$=6 points. The risks assigned are as follows: risk for CIN and dialysis: 5 or less total points=risk of CIN—7.5%, risk of dialysis—0.04%; 6-10 total points=risk of CIN—14%, risk of dialysis—0.12%; 11-16 total points=risk of CIN—26.1%, risk of dialysis—1.09%; >16 total points=risk of CIN—57.3%, risk of dialysis—12.8%.

Example 2

Cardiac Surgery Sample Collection

The objective of this sample collection study is to collect samples of plasma and urine and clinical data from patients before and after undergoing cardiovascular surgery, a procedure known to be potentially damaging to kidney function. Approximately 900 adults undergoing such surgery are enrolled. To be enrolled in the study, each patient must meet all of the following inclusion criteria and none of the following exclusion criteria:

Inclusion Criteria
males and females 18 years of age or older;
undergoing cardiovascular surgery;
Toronto/Ottawa Predictive Risk Index for Renal Replacement risk score of at least 2 (Wijeysundera et al., *JAMA* 297: 1801-9, 2007); and
able and willing to provide written informed consent for study participation and to comply with all study procedures.

Exclusion Criteria
known pregnancy;
previous renal transplantation;

acutely worsening renal function prior to enrollment (e.g., any category of RIFLE criteria);
already receiving dialysis (either acute or chronic) or in imminent need of dialysis at enrollment;
currently enrolled in another clinical study or expected to be enrolled in another clinical study within 7 days of cardiac surgery that involves drug infusion or a therapeutic intervention for AKI;
known infection with human immunodeficiency virus (HIV) or a hepatitis virus.

Within 3 hours prior to the first incision (and after any pre-procedure hydration), an EDTA anti-coagulated blood sample (10 mL), whole blood (3 mL), and a urine sample (35 mL) are collected from each patient. Blood and urine samples are then collected at 3 (±0.5), 6 (±0.5), 12 (±1), 24 (±2) and 48 (±2) hrs following the procedure and then daily on days 3 through 7 if the subject remains in the hospital. Blood is collected via direct venipuncture or via other available venous access, such as an existing femoral sheath, central venous line, peripheral intravenous line or hep-lock. These study blood samples are frozen and shipped to Astute Medical, Inc., San Diego, Calif. The study urine samples are frozen and shipped to Astute Medical, Inc.

Example 3

Acutely Ill Subject Sample Collection

The objective of this study is to collect samples from acutely ill patients. Approximately 900 adults expected to be in the ICU for at least 48 hours will be enrolled. To be enrolled in the study, each patient must meet all of the following inclusion criteria and none of the following exclusion criteria:
Inclusion Criteria
males and females 18 years of age or older;
Study population 1: approximately 300 patients that have at least one of:
shock (SBP<90 mmHg and/or need for vasopressor support to maintain MAP>60 mmHg and/or documented drop in SBP of at least 40 mmHg); and
sepsis;
Study population 2: approximately 300 patients that have at least one of:
IV antibiotics ordered in computerized physician order entry (CPOE) within 24 hours of enrollment;
contrast media exposure within 24 hours of enrollment;
increased Intra-Abdominal Pressure with acute decompensated heart failure; and
severe trauma as the primary reason for ICU admission and likely to be hospitalized in the ICU for 48 hours after enrollment;
Study population 3: approximately 300 patients
expected to be hospitalized through acute care setting (ICU or ED) with a known risk factor for acute renal injury (e.g. sepsis, hypotension/shock (Shock=systolic BP<90 mmHg and/or the need for vasopressor support to maintain a MAP>60 mmHg and/or a documented drop in SBP>40 mmHg), major trauma, hemorrhage, or major surgery); and/or expected to be hospitalized to the ICU for at least 24 hours after enrollment.
Exclusion Criteria
known pregnancy;
institutionalized individuals;
previous renal transplantation;
known acutely worsening renal function prior to enrollment (e.g., any category of RIFLE criteria);
received dialysis (either acute or chronic) within 5 days prior to enrollment or in imminent need of dialysis at the time of enrollment;
known infection with human immunodeficiency virus (HIV) or a hepatitis virus;
meets only the SBP<90 mmHg inclusion criterion set forth above, and does not have shock in the attending physician's or principal investigator's opinion.

After providing informed consent, an EDTA anti-coagulated blood sample (10 mL) and a urine sample (25-30 mL) are collected from each patient. Blood and urine samples are then collected at 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Example 4

Immunoassay Format

Analytes are is measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards.

Concentrations are expressed in the following examples as follows: Cytoplasmic aspartate aminotransferase—µg/mL, soluble Tumor necrosis factor receptor superfamily member 5 ("CD40")—ng/mL, soluble CD40 Ligand—ng/mL, soluble C-X-C Motif chemokine 16—ng/mL, S100-A12 ("EN-RAGE")—ng/mL, Eotaxin—pg/mL, soluble E-selectin—ng/mL, Fibronectin—ng/mL, Granulocyte colony-stimulating factor—pg/mL, Granulocyte-macrophage colony-stimulating factor—pg/mL, Heparin-binding growth factor 2—pg/mL, soluble Hepatocyte growth factor receptor—pg/mL, Interleukin-1 receptor antagonist—pg/mL, Interleukin-1 beta—pg/mL, Interleukin-10—pg/mL, Interleukin-15—ng/mL, Interleukin-3—ng/mL, Myeloperoxidase—ng/mL, Nidogen-1—pg/mL, soluble Oxidized low-density lipoprotein receptor 1—ng/mL, Pappalysin-1—mIU/mL, soluble P-selectin glycoprotein ligand 1—U/mL, Antileukoproteinase ("Secretory leukocyte peptidase inhibitor")—pg/mL, soluble Kit ligand ("Stem cell factor")—pg/mL, Tissue inhibitor of metalloproteinase 1—ng/mL, Tissue inhibitor of metalloproteinase 2—pg/mL, soluble Tumor necrosis factor—pg/mL, soluble Vascular cell adhesion molecule 1—ng/mL, and Vascular endothelial growth factor A—pg/mL.

Example 5

Apparently Healthy Donor and Chronic Disease Patient Samples

Human urine samples from donors with no known chronic or acute disease ("Apparently Healthy Donors") were purchased from two vendors (Golden West Biologicals, Inc., 27625 Commerce Center Dr., Temecula, Calif. 92590 and Virginia Medical Research, Inc., 915 First Colonial Rd., Virginia Beach, Va. 23454). The urine samples were shipped and stored frozen at less than −20° C. The vendors supplied demographic information for the individual donors including gender, race (Black/White), smoking status and age.

Human urine samples from donors with various chronic diseases ("Chronic Disease Patients") including congestive heart failure, coronary artery disease, chronic kidney disease, chronic obstructive pulmonary disease, diabetes mellitus and hypertension were purchased from Virginia Medical Research, Inc., 915 First Colonial Rd., Virginia Beach, Va. 23454. The urine samples were shipped and stored frozen at less than −20 degrees centigrade. The vendor provided a case report form for each individual donor with age, gender, race (Black/White), smoking status and alcohol use, height, weight, chronic disease(s) diagnosis, current medications and previous surgeries.

Example 6

Kidney Injury Markers for Evaluating Renal Status in Patients at RIFLE Stage 0

Patients from the intensive care unit (ICU) were classified by kidney status as non-injury (0), risk of injury (R), injury (I), and failure (F) according to the maximum stage reached within 7 days of enrollment as determined by the RIFLE criteria.

Two cohorts were defined as (Cohort 1) patients that did not progress beyond stage 0, and (Cohort 2) patients that reached stage R, I, or F within 10 days. To address normal marker fluctuations that occur within patients at the ICU and thereby assess utility for monitoring AKI status, marker levels were measured in urine samples collected for Cohort 1. Marker concentrations were measured in urine samples collected from a subject at 0, 24 hours, and 48 hours prior to reaching stage R, I or F in Cohort 2. In the following tables, the time "prior max stage" represents the time at which a sample is collected, relative to the time a particular patient reaches the lowest disease stage as defined for that cohort, binned into three groups which are +/−12 hours. For example, 24 hr prior for this example (0 vs R, I, F) would mean 24 hr (+/−12 hours) prior to reaching stage R (or I if no sample at R, or F if no sample at R or I).

Each marker was measured by standard immunoassay methods using commercially available assay reagents. A receiver operating characteristic (ROC) curve was generated for each marker and the area under each ROC curve (AUC) was determined. Patients in Cohort 2 were also separated according to the reason for adjudication to stage R, I, or F as being based on serum creatinine measurements (sCr), being based on urine output (UO), or being based on either serum creatinine measurements or urine output. That is, for those patients adjudicated to stage R, I, or F on the basis of serum creatinine measurements alone, the stage 0 cohort may have included patients adjudicated to stage R, I, or F on the basis of urine output; for those patients adjudicated to stage R, I, or F on the basis of urine output alone, the stage 0 cohort may have included patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, for those patients adjudicated to stage R, I, or F on the basis of serum creatinine measurements or urine output, the adjudication method which yielded the most severe RIFLE stage was used.

The ability to distinguish cohort 1 (subjects remaining in RIFLE 0) from Cohort 2 (subjects progressing to RIFLE R, I or F) was determined using ROC analysis. SE is the standard error of the AUC, n is the number of sample or individual patients ("pts," as indicated). Standard errors were calculated as described in Hanley, J. A., and McNeil, B. J., The meaning and use of the area under a receiver operating characteristic (ROC) curve. Radiology (1982) 143: 29-36; p values were calculated with a two-tailed Z-test. An AUC<0.5 is indicative of a negative going marker for the comparison, and an AUC>0.5 is indicative of a positive going marker for the comparison.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 1.

Example 7

Kidney Injury Markers for Evaluating Renal Status in Patients at RIFLE Stages 0 and R Patients were classified and analyzed as described in Example 6. However, patients that reached stage R but did not progress to stage I or F were grouped with patients from non-injury stage 0 in Cohort 1. Cohort 2 in this example included only patients that progressed to stage I or F. Marker concentrations in urine samples were included for Cohort 1. Marker concentrations in urine samples collected within 0, 24, and 48 hours of reaching stage I or F were included for Cohort 2.

The ability to distinguish cohort 1 (subjects remaining in RIFLE 0 or R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 2.

Example 8

Kidney Injury Markers for Evaluating Renal Status in Patients Progressing from Stage R to Stages I and F Patients were classified and analyzed as described in Example 6, but only those patients that reached Stage R were included in this example. Cohort 1 contained patients that reached stage R but did not progress to stage I or F within 10 days, and Cohort 2 included only patients that progressed to stage I or F. Marker concentrations in urine samples collected within 12 hours of reaching stage R were included in the analysis for both Cohort 1 and 2.

The ability to distinguish cohort 1 (subjects remaining in RIFLE R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 3.

Example 9

Kidney Injury Markers for Evaluating Renal Status in Patients at RIFLE Stage 0

Patients were classified and analyzed as described in Example 6. However, patients that reached stage R or I but did not progress to stage F were eliminated from the analysis. Patients from non-injury stage 0 are included in Cohort 1. Cohort 2 in this example included only patients that progressed to stage F. The maximum marker concentrations in urine samples were included for each patient in Cohort 1. The maximum marker concentrations in urine samples collected within 0, 24, and 48 hours of reaching stage F were included for each patient in Cohort 2.

The ability to distinguish cohort 1 (subjects remaining in RIFLE 0 or R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 4.

Example 10

Kidney Injury Markers for Evaluating Renal Status in Patients at RIFLE Stage 0

Patients from the intensive care unit (ICU) were classified by kidney status as non-injury (0), risk of injury (R), injury (I), and failure (F) according to the maximum stage reached within 7 days of enrollment as determined by the RIFLE criteria.

Two cohorts were defined as (Cohort 1) patients that did not progress beyond stage 0, and (Cohort 2) patients that reached stage R, I, or F within 10 days. To address normal marker fluctuations that occur within patients at the ICU and thereby assess utility for monitoring AKI status, marker levels were measured in the plasma component of blood samples collected for Cohort 1. Marker concentrations were measured in the plasma component of blood samples collected from a subject at 0, 24 hours, and 48 hours prior to reaching stage R, I or F in Cohort 2. In the following tables, the time "prior max stage" represents the time at which a sample is collected, relative to the time a particular patient reaches the lowest disease stage as defined for that cohort, binned into three groups which are +/−12 hours. For example, 24 hr prior for this example (0 vs R, I, F) would mean 24 hr (+/−12 hours) prior to reaching stage R (or I if no sample at R, or F if no sample at R or I).

Each marker was measured by standard immunoassay methods using commercially available assay reagents. A receiver operating characteristic (ROC) curve was generated for each marker and the area under each ROC curve (AUC) was determined. Patients in Cohort 2 were also separated according to the reason for adjudication to stage R, I, or F as being based on serum creatinine measurements (sCr), being based on urine output (UO), or being based on either serum creatinine measurements or urine output. That is, for those patients adjudicated to stage R, I, or F on the basis of serum creatinine measurements alone, the stage 0 cohort may have included patients adjudicated to stage R, I, or F on the basis of urine output; for those patients adjudicated to stage R, I, or F on the basis of urine output alone, the stage 0 cohort may have included patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, for those patients adjudicated to stage R, I, or F on the basis of serum creatinine measurements or urine output, the adjudication method which yielded the most severe RIFLE stage was used.

The ability to distinguish cohort 1 (subjects remaining in RIFLE 0) from Cohort 2 (subjects progressing to RIFLE R, I or F) was determined using ROC analysis. SE is the standard error of the AUC, n is the number of sample or individual patients ("pts," as indicated). Standard errors were calculated as described in Hanley, J. A., and McNeil, B. J., The meaning and use of the area under a receiver operating characteristic (ROC) curve. Radiology (1982) 143: 29-36; p values were calculated with a two-tailed Z-test. An AUC<0.5 is indicative of a negative going marker for the comparison, and an AUC>0.5 is indicative of a positive going marker for the comparison.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 5.

Example 11

Kidney Injury Markers for Evaluating Renal Status in Patients at RIFLE Stages 0 and R Patients were classified and analyzed as described in Example 10. However, patients that reached stage R but did not progress to stage I or F were grouped with patients from non-injury stage 0 in Cohort 1. Cohort 2 in this example included only patients that progressed to stage I or F. Marker concentrations in the plasma component of blood samples were included for Cohort 1. Marker concentrations in the plasma component of blood samples collected within 0, 24, and 48 hours of reaching stage I or F were included for Cohort 2.

The ability to distinguish cohort 1 (subjects remaining in RIFLE 0 or R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 6.

Example 12

Kidney Injury Markers for Evaluating Renal Status in Patients Progressing from Stage R to Stages I and F Patients were classified and analyzed as described in Example 10, but only those patients that reached Stage R were included in this example. Cohort 1 contained patients that reached stage R but did not progress to stage I or F within 10 days, and Cohort 2 included only patients that progressed to stage I or F. Marker concentrations in the plasma component of blood samples collected within 12 hours of reaching stage R were included in the analysis for both Cohort 1 and 2.

The ability to distinguish cohort 1 (subjects remaining in RIFLE R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 7.

Example 13

Kidney Injury Markers for Evaluating Renal Status in Patients at RIFLE Stage 0

Patients were classified and analyzed as described in Example 10. However, patients that reached stage R or I but did not progress to stage F were eliminated from the analysis. Patients from non-injury stage 0 are included in Cohort 1. Cohort 2 in this example included only patients that progressed to stage F. The maximum marker concentrations in the plasma component of blood samples were included from each patient in Cohort 1. The maximum marker concentrations in the plasma component of blood samples collected within 0, 24, and 48 hours of reaching stage F were included from each patient in Cohort 2.

The ability to distinguish cohort 1 (subjects remaining in RIFLE 0 or R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 8.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

The invention claimed is:

1. A method for evaluating renal status in a patient and treating the patient based on the evaluation, comprising: performing an immunoassay configured to detect Antileukoproteinase by introducing a body fluid sample obtained from the patient into an assay instrument which contacts the sample with an antibody which specifically binds for detection of Antileukoproteinase and generates an assay result indicative of binding of Antileukoproteinase to the antibody, wherein the body fluid sample comprises a urine sample, blood sample, serum sample, or plasma sample; correlating the assay result to an increased risk of having acute renal failure within 48 hours of the time at which the sample is obtained from the patient, when the assay result is above a predetermined; and treating the patient having an increased risk of having acute renal failure within 48 hours with a compatible treatment regimen, wherein the compatible treatment regimen comprises one or more of initiating renal replacement therapy, withdrawing delivery of compounds that are known to be damaging to the kidney, delaying procedures that are known to be damaging to the kidney, and modifying diuretic administration.

2. A method according to claim 1, wherein said assay result is a measured concentration of Antileukoproteinase.

3. A method according to claim 1, wherein the patient is selected for evaluation of renal status based on the pre-existence in the patient of one or more known risk factors for prerenal, intrinsic renal, or postrenal ARE.

4. A method according to claim 1, wherein the patient is selected for evaluation of renal status based on an existing diagnosis of sepsis.

5. A method according to claim 1, wherein the risk of having acute renal failure is within 24 hours of the time at which the body fluid sample is obtained from the patient.

6. The method according to claim 1, wherein the risk of having acute renal failure within 48 hours is the risk of developing future acute renal failure.

7. A method of testing a patient at risk of having or developing acute renal failure comprising: obtaining a urine sample from the patient; and performing an assay to detect the level of Antileukoproteinase within the sample.

8. The method of claim 7, wherein the sample is obtained within 7 days after an acute medical event which predisposes the patient for developing acute renal failure, wherein the acute medical event comprises shock, sepsis, hemorrhage, an ischemic surgery, increased intra-abdominal pressure with acute decompensated heart failure, ischemia, pulmonary embolism, pancreatitis, a burn, or excess diuresis.

9. The method of claim 8, wherein the sample is obtained within 72 hours after the acute medical event.

10. The method of claim 9, wherein the sample is obtained within 48 hours after the acute medical event.

11. The method of claim 7, wherein the sample is obtained within 7 days after an acute medical event which predisposes the patient for developing acute renal failure, wherein the acute medical event comprises exposure to NSAIDs, cyclosporines, tacrolimus, aminoglycosides, foscarnet, ethylene glycol, hemoglobin, myoglobin, ifosfamid, heavy metals, methotrexate, radiopaque contrast media, or streptozotocin.

12. The method of claim 11, wherein the sample is obtained within 72 hours after the acute medical event.

13. The method of claim 12, wherein the sample is obtained within 48 hours after the acute medical event.

14. The method of claim 7, further comprising measuring a volume of urine output, urine flow rate, serum creatinine, or urine creatinine within 7 days after the sample is obtained.

15. The method of claim 7, further comprising measuring a volume of urine output, urine flow rate, serum creatinine, or urine creatinine within 72 hours after the sample is obtained.

16. The method of claim 7, further comprising measuring a volume of urine output, urine flow rate, serum creatinine, or urine creatinine within 48 hours after the sample is obtained.

17. The method of claim 14, further comprising calculating a glomerular filtration rate of the patient within 7 days after the sample is obtained.

18. The method of claim 7, wherein the sample is obtained during a period in which the patient is hospitalized in an intensive care unit (ICU).

19. A method of detecting Antileukoproteinase in a patient following an acute medical event, the method comprising:
   obtaining a urine sample from the patient; and
   performing an assay to detect the level of Antileukoproteinase within the urine sample, wherein the urine sample is obtained within 7 days after the acute medical event, wherein the acute medical event comprises shock, sepsis, hemorrhage, an ischemic surgery, increased intra-abdominal pressure with acute decompensated heart failure, ischemia, pulmonary embolism, pancreatitis, a burn, or excessive diuresis, or wherein the acute medical event comprises exposure to NSAIDs, cyclosporines, tacrolimus, aminoglycosides, foscarnet, ethylene glycol, hemoglobin, myoglobin, ifosfamid, heavy metals, methotrexate, radiopaque contrast media, or streptozotocin.

* * * * *

UNITED STATES PATENT AND TRADEMARK OFFICE
CERTIFICATE OF CORRECTION

PATENT NO. : 10,823,733 B2
APPLICATION NO. : 14/327513
DATED : November 3, 2020
INVENTOR(S) : Joseph Anderberg et al.

It is certified that error appears in the above-identified patent and that said Letters Patent is hereby corrected as shown below:

In the Claims

Claim 1, Column 147, Line 26, the text "predetermined; and treating the patient having an increased" should be changed to --predetermined threshold; and treating the patient having an increased--

Claim 3, Column 147, Line 39, the text "prerenal, intrinsic renal, or postrenal ARE" should be changed to --prerenal, intrinsic renal, or postrenal ARF--

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 33

<210> SEQ ID NO 1
<211> LENGTH: 413
<212> TYPE: PRT
<213> ORGANISM: Homo sapiens

<400> SEQUENCE: 1
```

-continued

```
Met Ala Pro Pro Ser Val Phe Ala Glu Val Pro Gln Ala Gln Pro Val
1               5                   10                  15

Leu Val Phe Lys Leu Thr Ala Asp Phe Arg Glu Asp Pro Asp Pro Arg
                20                  25                  30

Lys Val Asn Leu Gly Val Gly Ala Tyr Arg Thr Asp Asp Cys His Pro
            35                  40                  45

Trp Val Leu Pro Val Val Lys Lys Val Glu Gln Lys Ile Ala Asn Asp
        50                  55                  60

Asn Ser Leu Asn His Glu Tyr Leu Pro Ile Leu Gly Leu Ala Glu Phe
65                  70                  75                  80

Arg Ser Cys Ala Ser Arg Leu Ala Leu Gly Asp Asp Ser Pro Ala Leu
                85                  90                  95

Lys Glu Lys Arg Val Gly Gly Val Gln Ser Leu Gly Gly Thr Gly Ala
            100                 105                 110

Leu Arg Ile Gly Ala Asp Phe Leu Ala Arg Trp Tyr Asn Gly Thr Asn
        115                 120                 125

Asn Lys Asn Thr Pro Val Tyr Val Ser Ser Pro Thr Trp Glu Asn His
130                 135                 140

Asn Ala Val Phe Ser Ala Ala Gly Phe Lys Asp Ile Arg Ser Tyr Arg
145                 150                 155                 160

Tyr Trp Asp Ala Glu Lys Arg Gly Leu Asp Leu Gln Gly Phe Leu Asn
                165                 170                 175

Asp Leu Glu Asn Ala Pro Glu Phe Ser Ile Val Leu His Ala Cys
            180                 185                 190

Ala His Asn Pro Thr Gly Ile Asp Pro Thr Pro Glu Gln Trp Lys Gln
            195                 200                 205

Ile Ala Ser Val Met Lys His Arg Phe Leu Phe Pro Phe Phe Asp Ser
210                 215                 220

Ala Tyr Gln Gly Phe Ala Ser Gly Asn Leu Glu Arg Asp Ala Trp Ala
225                 230                 235                 240

Ile Arg Tyr Phe Val Ser Glu Gly Phe Glu Phe Phe Cys Ala Gln Ser
                245                 250                 255

Phe Ser Lys Asn Phe Gly Leu Tyr Asn Glu Arg Val Gly Asn Leu Thr
            260                 265                 270

Val Val Gly Lys Glu Pro Glu Ser Ile Leu Gln Val Leu Ser Gln Met
        275                 280                 285

Glu Lys Ile Val Arg Ile Thr Trp Ser Asn Pro Pro Ala Gln Gly Ala
290                 295                 300

Arg Ile Val Ala Ser Thr Leu Ser Asn Pro Glu Leu Phe Glu Glu Trp
305                 310                 315                 320

Thr Gly Asn Val Lys Thr Met Ala Asp Arg Ile Leu Thr Met Arg Ser
                325                 330                 335

Glu Leu Arg Ala Arg Leu Glu Ala Leu Lys Thr Pro Gly Thr Trp Asn
            340                 345                 350

His Ile Thr Asp Gln Ile Gly Met Phe Ser Phe Thr Gly Leu Asn Pro
        355                 360                 365

Lys Gln Val Glu Tyr Leu Val Asn Glu Lys His Ile Tyr Leu Leu Pro
    370                 375                 380

Ser Gly Arg Ile Asn Val Ser Gly Leu Thr Thr Lys Asn Leu Asp Tyr
385                 390                 395                 400

Val Ala Thr Ser Ile His Glu Ala Val Thr Lys Ile Gln
                405                 410
```

<210> SEQ ID NO 2
<211> LENGTH: 277
<212> TYPE: PRT
<213> ORGANISM: Homo sapiens

<400> SEQUENCE: 2

Met Val Arg Leu Pro Leu Gln Cys Val Leu Trp Gly Cys Leu Leu Thr
1               5                   10                  15

Ala Val His Pro Glu Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 3
<211> LENGTH: 261
<212> TYPE: PRT
<213> ORGANISM: Homo sapiens

<400> SEQUENCE: 3

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

```
Arg Leu Asp Lys Ile Glu Asp Glu Arg Asn Leu His Glu Asp Phe Val
         50                  55                  60

Phe Met Lys Thr Ile Gln Arg Cys Asn Thr Gly Glu Arg Ser Leu Ser
 65                  70                  75                  80

Leu Leu Asn Cys Glu Glu Ile Lys Ser Gln Phe Glu Gly Phe Val Lys
                 85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 4
<211> LENGTH: 254
<212> TYPE: PRT
<213> ORGANISM: Homo sapiens

<400> SEQUENCE: 4

Met Gly Arg Asp Leu Arg Pro Gly Ser Arg Val Leu Leu Leu Leu Leu
 1               5                  10                  15

Leu Leu Leu Leu Val Tyr Leu Thr Gln Pro Gly Asn Gly Asn Glu Gly
                 20                  25                  30

Ser Val Thr Gly Ser Cys Tyr Cys Gly Lys Arg Ile Ser Ser Asp Ser
             35                  40                  45

Pro Pro Ser Val Gln Phe Met Asn Arg Leu Arg Lys His Leu Arg Ala
 50                  55                  60

Tyr His Arg Cys Leu Tyr Tyr Thr Arg Phe Gln Leu Leu Ser Trp Ser
 65                  70                  75                  80

Val Cys Gly Gly Asn Lys Asp Pro Trp Val Gln Glu Leu Met Ser Cys
                 85                  90                  95

Leu Asp Leu Lys Glu Cys Gly His Ala Tyr Ser Gly Ile Val Ala His
            100                 105                 110

Gln Lys His Leu Leu Pro Thr Ser Pro Pro Ile Ser Gln Ala Ser Glu
            115                 120                 125

Gly Ala Ser Ser Asp Ile His Thr Pro Ala Gln Met Leu Leu Ser Thr
130                 135                 140

Leu Gln Ser Thr Gln Arg Pro Thr Leu Pro Val Gly Ser Leu Ser Ser
145                 150                 155                 160
```

-continued

```
Asp Lys Glu Leu Thr Arg Pro Asn Glu Thr Thr Ile His Thr Ala Gly
                165                 170                 175

His Ser Leu Ala Ala Gly Pro Glu Ala Gly Glu Asn Gln Lys Gln Pro
            180                 185                 190

Glu Lys Asn Ala Gly Pro Thr Ala Arg Thr Ser Ala Thr Val Pro Val
        195                 200                 205

Leu Cys Leu Leu Ala Ile Ile Phe Ile Leu Thr Ala Ala Leu Ser Tyr
    210                 215                 220

Val Leu Cys Lys Arg Arg Arg Gly Gln Ser Pro Gln Ser Ser Pro Asp
225                 230                 235                 240

Leu Pro Val His Tyr Ile Pro Val Ala Pro Asp Ser Asn Thr
                245                 250

<210> SEQ ID NO 5
<211> LENGTH: 92
<212> TYPE: PRT
<213> ORGANISM: Homo sapiens

<400> SEQUENCE: 5

Met Thr Lys Leu Glu Glu His Leu Gly Ile Val Asn Ile Phe His
1               5                   10                  15

Gln Tyr Ser Val Arg Lys Gly His Phe Asp Thr Leu Ser Lys Gly Glu
            20                  25                  30

Leu Lys Gln Leu Leu Thr Lys Glu Leu Ala Asn Thr Ile Lys Asn Ile
        35                  40                  45

Lys Asp Lys Ala Val Ile Asp Glu Ile Phe Gln Gly Leu Asp Ala Asn
50                  55                  60

Gln Asp Glu Gln Val Asp Phe Gln Glu Phe Ile Ser Leu Val Ala Ile
65                  70                  75                  80

Ala Leu Lys Ala Ala His Tyr His Thr His Lys Glu
                85                  90

<210> SEQ ID NO 6
<211> LENGTH: 97
<212> TYPE: PRT
<213> ORGANISM: Homo sapiens

<400> SEQUENCE: 6

Met Lys Val Ser Ala Ala Leu Leu Trp Leu Leu Leu Ile Ala Ala Ala
1               5                   10                  15

Phe Ser Pro Gln Gly Leu Ala Gly Pro Ala Ser Val Pro Thr Thr Cys
            20                  25                  30

Cys Phe Asn Leu Ala Asn Arg Lys Ile Pro Leu Gln Arg Leu Glu Ser
        35                  40                  45

Tyr Arg Arg Ile Thr Ser Gly Lys Cys Pro Gln Lys Ala Val Ile Phe
    50                  55                  60

Lys Thr Lys Leu Ala Lys Asp Ile Cys Ala Asp Pro Lys Lys Lys Trp
65                  70                  75                  80

Val Gln Asp Ser Met Lys Tyr Leu Asp Gln Lys Ser Pro Thr Pro Lys
                85                  90                  95

Pro

<210> SEQ ID NO 7
<211> LENGTH: 610
<212> TYPE: PRT
<213> ORGANISM: Homo sapiens
```

<400> SEQUENCE: 7

```
Met Ile Ala Ser Gln Phe Leu Ser Ala Leu Thr Leu Val Leu Leu Ile
1               5                   10                  15

Lys Glu Ser Gly Ala Trp Ser Tyr Asn Thr Ser Thr Glu Ala Met Thr
            20                  25                  30

Tyr Asp Glu Ala Ser Ala Tyr Cys Gln Gln Arg Tyr Thr His Leu Val
        35                  40                  45

Ala Ile Gln Asn Lys Glu Glu Ile Glu Tyr Leu Asn Ser Ile Leu Ser
    50                  55                  60

Tyr Ser Pro Ser Tyr Tyr Trp Ile Gly Ile Arg Lys Val Asn Asn Val
65                  70                  75                  80

Trp Val Trp Val Gly Thr Gln Lys Pro Leu Thr Glu Glu Ala Lys Asn
                85                  90                  95

Trp Ala Pro Gly Glu Pro Asn Asn Arg Gln Lys Asp Glu Asp Cys Val
            100                 105                 110

Glu Ile Tyr Ile Lys Arg Glu Lys Asp Val Gly Met Trp Asn Asp Glu
        115                 120                 125

Arg Cys Ser Lys Lys Leu Ala Leu Cys Tyr Thr Ala Ala Cys Thr
    130                 135                 140

Asn Thr Ser Cys Ser Gly His Gly Glu Cys Val Glu Thr Ile Asn Asn
145                 150                 155                 160

Tyr Thr Cys Lys Cys Asp Pro Gly Phe Ser Gly Leu Lys Cys Glu Gln
                165                 170                 175

Ile Val Asn Cys Thr Ala Leu Glu Ser Pro Glu His Gly Ser Leu Val
            180                 185                 190

Cys Ser His Pro Leu Gly Asn Phe Ser Tyr Asn Ser Ser Cys Ser Ile
        195                 200                 205

Ser Cys Asp Arg Gly Tyr Leu Pro Ser Ser Met Glu Thr Met Gln Cys
    210                 215                 220

Met Ser Ser Gly Glu Trp Ser Ala Pro Ile Pro Ala Cys Asn Val Val
225                 230                 235                 240

Glu Cys Asp Ala Val Thr Asn Pro Ala Asn Gly Phe Val Glu Cys Phe
                245                 250                 255

Gln Asn Pro Gly Ser Phe Pro Trp Asn Thr Thr Cys Thr Phe Asp Cys
            260                 265                 270

Glu Glu Gly Phe Glu Leu Met Gly Ala Gln Ser Leu Gln Cys Thr Ser
        275                 280                 285

Ser Gly Asn Trp Asp Asn Glu Lys Pro Thr Cys Lys Ala Val Thr Cys
    290                 295                 300

Arg Ala Val Arg Gln Pro Gln Asn Gly Ser Val Arg Cys Ser His Ser
305                 310                 315                 320

Pro Ala Gly Glu Phe Thr Phe Lys Ser Ser Cys Asn Phe Thr Cys Glu
                325                 330                 335

Glu Gly Phe Met Leu Gln Gly Pro Ala Gln Val Glu Cys Thr Thr Gln
            340                 345                 350

Gly Gln Trp Thr Gln Gln Ile Pro Val Cys Glu Ala Phe Gln Cys Thr
        355                 360                 365

Ala Leu Ser Asn Pro Glu Arg Gly Tyr Met Asn Cys Leu Pro Ser Ala
    370                 375                 380

Ser Gly Ser Phe Arg Tyr Gly Ser Ser Cys Glu Phe Ser Cys Glu Gln
385                 390                 395                 400

Gly Phe Val Leu Lys Gly Ser Lys Arg Leu Gln Cys Gly Pro Thr Gly
                405                 410                 415
```

```
Glu Trp Asp Asn Glu Lys Pro Thr Cys Glu Ala Val Arg Cys Asp Ala
                420                 425                 430

Val His Gln Pro Pro Lys Gly Leu Val Arg Cys Ala His Ser Pro Ile
            435                 440                 445

Gly Glu Phe Thr Tyr Lys Ser Ser Cys Ala Phe Ser Cys Glu Glu Gly
        450                 455                 460

Phe Glu Leu His Gly Ser Thr Gln Leu Glu Cys Thr Ser Gln Gly Gln
465                 470                 475                 480

Trp Thr Glu Glu Val Pro Ser Cys Gln Val Val Lys Cys Ser Ser Leu
                485                 490                 495

Ala Val Pro Gly Lys Ile Asn Met Ser Cys Ser Gly Glu Pro Val Phe
            500                 505                 510

Gly Thr Val Cys Lys Phe Ala Cys Pro Glu Gly Trp Thr Leu Asn Gly
        515                 520                 525

Ser Ala Ala Arg Thr Cys Gly Ala Thr Gly His Trp Ser Gly Leu Leu
530                 535                 540

Pro Thr Cys Glu Ala Pro Thr Glu Ser Asn Ile Pro Leu Val Ala Gly
545                 550                 555                 560

Leu Ser Ala Ala Gly Leu Ser Leu Leu Thr Leu Ala Pro Phe Leu Leu
                565                 570                 575

Trp Leu Arg Lys Cys Leu Arg Lys Ala Lys Lys Phe Val Pro Ala Ser
            580                 585                 590

Ser Cys Gln Ser Leu Glu Ser Asp Gly Ser Tyr Gln Lys Pro Ser Tyr
        595                 600                 605

Ile Leu
    610

<210> SEQ ID NO 8
<211> LENGTH: 2386
<212> TYPE: PRT
<213> ORGANISM: Homo sapiens

<400> SEQUENCE: 8

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
```

```
                    165                 170                 175
Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Gln Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590
```

```
Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
        610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Ser Thr Ser Thr
            690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
        755                 760                 765

Pro Ser Thr Ala Thr Ser Val Asn Ile Pro Asp Leu Leu Pro Gly Arg
770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
    850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005
```

```
Thr Asp Ser Thr Val Leu Val Arg Trp Thr Pro Arg Ala Gln
1010             1015                 1020

Ile Thr Gly Tyr Arg Leu Thr Val Gly Leu Thr Arg Arg Gly Gln
1025             1030                 1035

Pro Arg Gln Tyr Asn Val Gly Pro Ser Val Ser Lys Tyr Pro Leu
1040             1045                 1050

Arg Asn Leu Gln Pro Ala Ser Glu Tyr Thr Val Ser Leu Val Ala
1055             1060                 1065

Ile Lys Gly Asn Gln Glu Ser Pro Lys Ala Thr Gly Val Phe Thr
1070             1075                 1080

Thr Leu Gln Pro Gly Ser Ser Ile Pro Pro Tyr Asn Thr Glu Val
1085             1090                 1095

Thr Glu Thr Thr Ile Val Ile Thr Trp Thr Pro Ala Pro Arg Ile
1100             1105                 1110

Gly Phe Lys Leu Gly Val Arg Pro Ser Gln Gly Gly Glu Ala Pro
1115             1120                 1125

Arg Glu Val Thr Ser Asp Ser Gly Ser Ile Val Val Ser Gly Leu
1130             1135                 1140

Thr Pro Gly Val Glu Tyr Val Tyr Thr Ile Gln Val Leu Arg Asp
1145             1150                 1155

Gly Gln Glu Arg Asp Ala Pro Ile Val Asn Lys Val Val Thr Pro
1160             1165                 1170

Leu Ser Pro Pro Thr Asn Leu His Leu Glu Ala Asn Pro Asp Thr
1175             1180                 1185

Gly Val Leu Thr Val Ser Trp Glu Arg Ser Thr Thr Pro Asp Ile
1190             1195                 1200

Thr Gly Tyr Arg Ile Thr Thr Thr Pro Thr Asn Gly Gln Gln Gly
1205             1210                 1215

Asn Ser Leu Glu Glu Val Val His Ala Asp Gln Ser Ser Cys Thr
1220             1225                 1230

Phe Asp Asn Leu Ser Pro Gly Leu Glu Tyr Asn Val Ser Val Tyr
1235             1240                 1245

Thr Val Lys Asp Asp Lys Glu Ser Val Pro Ile Ser Asp Thr Ile
1250             1255                 1260

Ile Pro Ala Val Pro Pro Thr Asp Leu Arg Phe Thr Asn Ile
1265             1270                 1275

Gly Pro Asp Thr Met Arg Val Thr Trp Ala Pro Pro Pro Ser Ile
1280             1285                 1290

Asp Leu Thr Asn Phe Leu Val Arg Tyr Ser Pro Val Lys Asn Glu
1295             1300                 1305

Glu Asp Val Ala Glu Leu Ser Ile Ser Pro Ser Asp Asn Ala Val
1310             1315                 1320

Val Leu Thr Asn Leu Leu Pro Gly Thr Glu Tyr Val Val Ser Val
1325             1330                 1335

Ser Ser Val Tyr Glu Gln His Glu Ser Thr Pro Leu Arg Gly Arg
1340             1345                 1350

Gln Lys Thr Gly Leu Asp Ser Pro Thr Gly Ile Asp Phe Ser Asp
1355             1360                 1365

Ile Thr Ala Asn Ser Phe Thr Val His Trp Ile Ala Pro Arg Ala
1370             1375                 1380

Thr Ile Thr Gly Tyr Arg Ile Arg His His Pro Glu His Phe Ser
1385             1390                 1395

Gly Arg Pro Arg Glu Asp Arg Val Pro His Ser Arg Asn Ser Ile
```

-continued

```
                1400                1405                1410

Thr Leu Thr Asn Leu Thr Pro Gly Thr Glu Tyr Val Val Ser Ile
    1415                1420                1425

Val Ala Leu Asn Gly Arg Glu Glu Ser Pro Leu Leu Ile Gly Gln
    1430                1435                1440

Gln Ser Thr Val Ser Asp Val Pro Arg Asp Leu Glu Val Val Ala
    1445                1450                1455

Ala Thr Pro Thr Ser Leu Leu Ile Ser Trp Asp Ala Pro Ala Val
    1460                1465                1470

Thr Val Arg Tyr Tyr Arg Ile Thr Tyr Gly Glu Thr Gly Gly Asn
    1475                1480                1485

Ser Pro Val Gln Glu Phe Thr Val Pro Gly Ser Lys Ser Thr Ala
    1490                1495                1500

Thr Ile Ser Gly Leu Lys Pro Gly Val Asp Tyr Thr Ile Thr Val
    1505                1510                1515

Tyr Ala Val Thr Gly Arg Gly Asp Ser Pro Ala Ser Ser Lys Pro
    1520                1525                1530

Ile Ser Ile Asn Tyr Arg Thr Glu Ile Asp Lys Pro Ser Gln Met
    1535                1540                1545

Gln Val Thr Asp Val Gln Asp Asn Ser Ile Ser Val Lys Trp Leu
    1550                1555                1560

Pro Ser Ser Ser Pro Val Thr Gly Tyr Arg Val Thr Thr Thr Pro
    1565                1570                1575

Lys Asn Gly Pro Gly Pro Thr Lys Thr Lys Thr Ala Gly Pro Asp
    1580                1585                1590

Gln Thr Glu Met Thr Ile Glu Gly Leu Gln Pro Thr Val Glu Tyr
    1595                1600                1605

Val Val Ser Val Tyr Ala Gln Asn Pro Ser Gly Glu Ser Gln Pro
    1610                1615                1620

Leu Val Gln Thr Ala Val Thr Asn Ile Asp Arg Pro Lys Gly Leu
    1625                1630                1635

Ala Phe Thr Asp Val Asp Val Asp Ser Ile Lys Ile Ala Trp Glu
    1640                1645                1650

Ser Pro Gln Gly Gln Val Ser Arg Tyr Arg Val Thr Tyr Ser Ser
    1655                1660                1665

Pro Glu Asp Gly Ile His Glu Leu Phe Pro Ala Pro Asp Gly Glu
    1670                1675                1680

Glu Asp Thr Ala Glu Leu Gln Gly Leu Arg Pro Gly Ser Glu Tyr
    1685                1690                1695

Thr Val Ser Val Val Ala Leu His Asp Asp Met Glu Ser Gln Pro
    1700                1705                1710

Leu Ile Gly Thr Gln Ser Thr Ala Ile Pro Ala Pro Thr Asp Leu
    1715                1720                1725

Lys Phe Thr Gln Val Thr Pro Thr Ser Leu Ser Ala Gln Trp Thr
    1730                1735                1740

Pro Pro Asn Val Gln Leu Thr Gly Tyr Arg Val Arg Val Thr Pro
    1745                1750                1755

Lys Glu Lys Thr Gly Pro Met Lys Glu Ile Asn Leu Ala Pro Asp
    1760                1765                1770

Ser Ser Ser Val Val Val Ser Gly Leu Met Val Ala Thr Lys Tyr
    1775                1780                1785

Glu Val Ser Val Tyr Ala Leu Lys Asp Thr Leu Thr Ser Arg Pro
    1790                1795                1800
```

```
Ala Gln Gly Val Val Thr Thr Leu Glu Asn Val Ser Pro Pro Arg
1805                1810                1815

Arg Ala Arg Val Thr Asp Ala Thr Glu Thr Thr Ile Thr Ile Ser
1820                1825                1830

Trp Arg Thr Lys Thr Glu Thr Ile Thr Gly Phe Gln Val Asp Ala
1835                1840                1845

Val Pro Ala Asn Gly Gln Thr Pro Ile Gln Arg Thr Ile Lys Pro
1850                1855                1860

Asp Val Arg Ser Tyr Thr Ile Thr Gly Leu Gln Pro Gly Thr Asp
1865                1870                1875

Tyr Lys Ile Tyr Leu Tyr Thr Leu Asn Asp Asn Ala Arg Ser Ser
1880                1885                1890

Pro Val Val Ile Asp Ala Ser Thr Ala Ile Asp Ala Pro Ser Asn
1895                1900                1905

Leu Arg Phe Leu Ala Thr Thr Pro Asn Ser Leu Leu Val Ser Trp
1910                1915                1920

Gln Pro Pro Arg Ala Arg Ile Thr Gly Tyr Ile Ile Lys Tyr Glu
1925                1930                1935

Lys Pro Gly Ser Pro Pro Arg Glu Val Val Pro Arg Pro Arg Pro
1940                1945                1950

Gly Val Thr Glu Ala Thr Ile Thr Gly Leu Glu Pro Gly Thr Glu
1955                1960                1965

Tyr Thr Ile Tyr Val Ile Ala Leu Lys Asn Asn Gln Lys Ser Glu
1970                1975                1980

Pro Leu Ile Gly Arg Lys Lys Thr Asp Glu Leu Pro Gln Leu Val
1985                1990                1995

Thr Leu Pro His Pro Asn Leu His Gly Pro Glu Ile Leu Asp Val
2000                2005                2010

Pro Ser Thr Val Gln Lys Thr Pro Phe Val Thr His Pro Gly Tyr
2015                2020                2025

Asp Thr Gly Asn Gly Ile Gln Leu Pro Gly Thr Ser Gly Gln Gln
2030                2035                2040

Pro Ser Val Gly Gln Gln Met Ile Phe Glu Glu His Gly Phe Arg
2045                2050                2055

Arg Thr Thr Pro Pro Thr Thr Ala Thr Pro Ile Arg His Arg Pro
2060                2065                2070

Arg Pro Tyr Pro Pro Asn Val Gly Glu Glu Ile Gln Ile Gly His
2075                2080                2085

Ile Pro Arg Glu Asp Val Asp Tyr His Leu Tyr Pro His Gly Pro
2090                2095                2100

Gly Leu Asn Pro Asn Ala Ser Thr Gly Gln Glu Ala Leu Ser Gln
2105                2110                2115

Thr Thr Ile Ser Trp Ala Pro Phe Gln Asp Thr Ser Glu Tyr Ile
2120                2125                2130

Ile Ser Cys His Pro Val Gly Thr Asp Glu Glu Pro Leu Gln Phe
2135                2140                2145

Arg Val Pro Gly Thr Ser Thr Ser Ala Thr Leu Thr Gly Leu Thr
2150                2155                2160

Arg Gly Ala Thr Tyr Asn Ile Ile Val Glu Ala Leu Lys Asp Gln
2165                2170                2175

Gln Arg His Lys Val Arg Glu Glu Val Val Thr Val Gly Asn Ser
2180                2185                2190
```

Val Asn Glu Gly Leu Asn Gln Pro Thr Asp Asp Ser Cys Phe Asp
2195                2200                2205

Pro Tyr Thr Val Ser His Tyr Ala Val Gly Asp Glu Trp Glu Arg
2210                2215                2220

Met Ser Glu Ser Gly Phe Lys Leu Leu Cys Gln Cys Leu Gly Phe
2225                2230                2235

Gly Ser Gly His Phe Arg Cys Asp Ser Ser Arg Trp Cys His Asp
2240                2245                2250

Asn Gly Val Asn Tyr Lys Ile Gly Glu Lys Trp Asp Arg Gln Gly
2255                2260                2265

Glu Asn Gly Gln Met Met Ser Cys Thr Cys Leu Gly Asn Gly Lys
2270                2275                2280

Gly Glu Phe Lys Cys Asp Pro His Glu Ala Thr Cys Tyr Asp Asp
2285                2290                2295

Gly Lys Thr Tyr His Val Gly Glu Gln Trp Gln Lys Glu Tyr Leu
2300                2305                2310

Gly Ala Ile Cys Ser Cys Thr Cys Phe Gly Gly Gln Arg Gly Trp
2315                2320                2325

Arg Cys Asp Asn Cys Arg Arg Pro Gly Gly Glu Pro Ser Pro Glu
2330                2335                2340

Gly Thr Thr Gly Gln Ser Tyr Asn Gln Tyr Ser Gln Arg Tyr His
2345                2350                2355

Gln Arg Thr Asn Thr Asn Val Asn Cys Pro Ile Glu Cys Phe Met
2360                2365                2370

Pro Leu Asp Val Gln Ala Asp Arg Glu Asp Ser Arg Glu
2375                2380                2385

<210> SEQ ID NO 9
<211> LENGTH: 207
<212> TYPE: PRT
<213> ORGANISM: Homo sapiens

<400> SEQUENCE: 9

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Arg His Leu Ala Gln Pro
            195                 200                 205

<210> SEQ ID NO 10
<211> LENGTH: 144
<212> TYPE: PRT
<213> ORGANISM: Homo sapiens

<400> SEQUENCE: 10

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 11
<211> LENGTH: 155
<212> TYPE: PRT
<213> ORGANISM: Homo sapiens

<400> SEQUENCE: 11

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

```
<210> SEQ ID NO 12
<211> LENGTH: 1390
<212> TYPE: PRT
<213> ORGANISM: Homo sapiens

<400> SEQUENCE: 12

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
```

```
              370                 375                 380
Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                    420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
        450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
        610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
        690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
            755                 760                 765

Ser Val Ser Val Pro Arg Met Val Ile Asn Val His Glu Ala Gly Arg
        770                 775                 780

Asn Phe Thr Val Ala Cys Gln His Arg Ser Asn Ser Glu Ile Ile Cys
785                 790                 795                 800
```

-continued

```
Cys Thr Thr Pro Ser Leu Gln Gln Leu Asn Leu Gln Leu Pro Leu Lys
            805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
            850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
            885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
            915                 920                 925

Gln Asn Phe Thr Gly Leu Ile Ala Gly Val Val Ser Ile Ser Thr Ala
            930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
            965                 970                 975

Thr Pro His Leu Asp Arg Leu Val Ser Ala Arg Ser Val Ser Pro Thr
            980                 985                 990

Thr Glu Met Val Ser Asn Glu Ser Val Asp Tyr Arg Ala Thr Phe Pro
            995                 1000                1005

Glu Asp Gln Phe Pro Asn Ser Ser Gln Asn Gly Ser Cys Arg Gln
            1010                1015                1020

Val Gln Tyr Pro Leu Thr Asp Met Ser Pro Ile Leu Thr Ser Gly
            1025                1030                1035

Asp Ser Asp Ile Ser Ser Pro Leu Leu Gln Asn Thr Val His Ile
            1040                1045                1050

Asp Leu Ser Ala Leu Asn Pro Glu Leu Val Gln Ala Val Gln His
            1055                1060                1065

Val Val Ile Gly Pro Ser Ser Leu Ile Val His Phe Asn Glu Val
            1070                1075                1080

Ile Gly Arg Gly His Phe Gly Cys Val Tyr His Gly Thr Leu Leu
            1085                1090                1095

Asp Asn Asp Gly Lys Lys Ile His Cys Ala Val Lys Ser Leu Asn
            1100                1105                1110

Arg Ile Thr Asp Ile Gly Glu Val Ser Gln Phe Leu Thr Glu Gly
            1115                1120                1125

Ile Ile Met Lys Asp Phe Ser His Pro Asn Val Leu Ser Leu Leu
            1130                1135                1140

Gly Ile Cys Leu Arg Ser Glu Gly Ser Pro Leu Val Val Leu Pro
            1145                1150                1155

Tyr Met Lys His Gly Asp Leu Arg Asn Phe Ile Arg Asn Glu Thr
            1160                1165                1170

His Asn Pro Thr Val Lys Asp Leu Ile Gly Phe Gly Leu Gln Val
            1175                1180                1185

Ala Lys Gly Met Lys Tyr Leu Ala Ser Lys Lys Phe Val His Arg
            1190                1195                1200
```

-continued

Asp Leu Ala Ala Arg Asn Cys Met Leu Asp Glu Lys Phe Thr Val
1205                1210                1215

Lys Val Ala Asp Phe Gly Leu Ala Arg Asp Met Tyr Asp Lys Glu
1220                1225                1230

Tyr Tyr Ser Val His Asn Lys Thr Gly Ala Lys Leu Pro Val Lys
1235                1240                1245

Trp Met Ala Leu Glu Ser Leu Gln Thr Gln Lys Phe Thr Thr Lys
1250                1255                1260

Ser Asp Val Trp Ser Phe Gly Val Val Leu Trp Glu Leu Met Thr
1265                1270                1275

Arg Gly Ala Pro Pro Tyr Pro Asp Val Asn Thr Phe Asp Ile Thr
1280                1285                1290

Val Tyr Leu Leu Gln Gly Arg Arg Leu Leu Gln Pro Glu Tyr Cys
1295                1300                1305

Pro Asp Pro Leu Tyr Glu Val Met Leu Lys Cys Trp His Pro Lys
1310                1315                1320

Ala Glu Met Arg Pro Ser Phe Ser Glu Leu Val Ser Arg Ile Ser
1325                1330                1335

Ala Ile Phe Ser Thr Phe Ile Gly Glu His Tyr Val His Val Asn
1340                1345                1350

Ala Thr Tyr Val Asn Val Lys Cys Val Ala Pro Tyr Pro Ser Leu
1355                1360                1365

Leu Ser Ser Glu Asp Asn Ala Asp Asp Glu Val Asp Thr Arg Pro
1370                1375                1380

Ala Ser Phe Trp Glu Thr Ser
1385                1390

<210> SEQ ID NO 13
<211> LENGTH: 177
<212> TYPE: PRT
<213> ORGANISM: Homo sapiens

<400> SEQUENCE: 13

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
                20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu

<210> SEQ ID NO 14
<211> LENGTH: 269
<212> TYPE: PRT
<213> ORGANISM: Homo sapiens

<400> SEQUENCE: 14

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
    130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
    210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 15
<211> LENGTH: 178
<212> TYPE: PRT
<213> ORGANISM: Homo sapiens

<400> SEQUENCE: 15

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

```
Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
                100                 105                 110

Gly Glu Asn Leu Lys Thr Leu Arg Leu Arg Leu Arg Cys His Arg
                115                 120                 125

Phe Leu Pro Cys Glu Asn Lys Ser Lys Ala Val Glu Gln Val Lys Asn
130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

<210> SEQ ID NO 16
<211> LENGTH: 162
<212> TYPE: PRT
<213> ORGANISM: Homo sapiens

<400> SEQUENCE: 16

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
                35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
                100                 105                 110

Asn Leu Ile Ile Leu Ala Asn Asn Ser Leu Ser Ser Asn Gly Asn Val
                115                 120                 125

Thr Glu Ser Gly Cys Lys Glu Cys Glu Glu Leu Glu Glu Lys Asn Ile
130                 135                 140

Lys Glu Phe Leu Gln Ser Phe Val His Ile Val Gln Met Phe Ile Asn
145                 150                 155                 160

Thr Ser
```

<210> SEQ ID NO 17
<211> LENGTH: 10
<212> TYPE: PRT
<213> ORGANISM: Homo sapiens

<400> SEQUENCE: 17

```
Met Val Leu Gly Thr Ile Asp Leu Cys Ser
1               5                   10
```

<210> SEQ ID NO 18

```
<211> LENGTH: 21
<212> TYPE: PRT
<213> ORGANISM: Homo sapiens

<400> SEQUENCE: 18

Met Asp Phe Gln Val Gln Ile Phe Ser Phe Leu Leu Ile Ser Ala Ser
1               5                   10                  15

Val Ile Met Ser Arg
            20

<210> SEQ ID NO 19
<211> LENGTH: 152
<212> TYPE: PRT
<213> ORGANISM: Homo sapiens

<400> SEQUENCE: 19

Met Ser Arg Leu Pro Val Leu Leu Leu Gln Leu Leu Val Arg Pro
1               5                   10                  15

Gly Leu Gln Ala Pro Met Thr Gln Thr Thr Pro Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150

<210> SEQ ID NO 20
<211> LENGTH: 745
<212> TYPE: PRT
<213> ORGANISM: Homo sapiens

<400> SEQUENCE: 20

Met Gly Val Pro Phe Phe Ser Ser Leu Arg Cys Met Val Asp Leu Gly
1               5                   10                  15

Pro Cys Trp Ala Gly Gly Leu Thr Ala Glu Met Lys Leu Leu Leu Ala
            20                  25                  30

Leu Ala Gly Leu Leu Ala Ile Leu Ala Thr Pro Gln Pro Ser Glu Gly
        35                  40                  45

Ala Ala Pro Ala Val Leu Gly Glu Val Asp Thr Ser Leu Val Leu Ser
    50                  55                  60

Ser Met Glu Glu Ala Lys Gln Leu Val Asp Lys Ala Tyr Lys Glu Arg
65                  70                  75                  80

Arg Glu Ser Ile Lys Gln Arg Leu Arg Ser Gly Ser Ala Ser Pro Met
                85                  90                  95

Glu Leu Leu Ser Tyr Phe Lys Gln Pro Val Ala Ala Thr Arg Thr Ala
            100                 105                 110
```

```
Val Arg Ala Ala Asp Tyr Leu His Val Ala Leu Asp Leu Leu Glu Arg
            115                 120                 125

Lys Leu Arg Ser Leu Trp Arg Arg Pro Phe Asn Val Thr Asp Val Leu
    130                 135                 140

Thr Pro Ala Gln Leu Asn Val Leu Ser Lys Ser Ser Gly Cys Ala Tyr
145                 150                 155                 160

Gln Asp Val Gly Val Thr Cys Pro Glu Gln Asp Lys Tyr Arg Thr Ile
                165                 170                 175

Thr Gly Met Cys Asn Asn Arg Arg Ser Pro Thr Leu Gly Ala Ser Asn
            180                 185                 190

Arg Ala Phe Val Arg Trp Leu Pro Ala Glu Tyr Glu Asp Gly Phe Ser
    195                 200                 205

Leu Pro Tyr Gly Trp Thr Pro Gly Val Lys Arg Asn Gly Phe Pro Val
    210                 215                 220

Ala Leu Ala Arg Ala Val Ser Asn Glu Ile Val Arg Phe Pro Thr Asp
225                 230                 235                 240

Gln Leu Thr Pro Asp Gln Glu Arg Ser Leu Met Phe Met Gln Trp Gly
                245                 250                 255

Gln Leu Leu Asp His Asp Leu Asp Phe Thr Pro Glu Pro Ala Ala Arg
            260                 265                 270

Ala Ser Phe Val Thr Gly Val Asn Cys Glu Thr Ser Cys Val Gln Gln
    275                 280                 285

Pro Pro Cys Phe Pro Leu Lys Ile Pro Pro Asn Asp Pro Arg Ile Lys
    290                 295                 300

Asn Gln Ala Asp Cys Ile Pro Phe Phe Arg Ser Cys Pro Ala Cys Pro
305                 310                 315                 320

Gly Ser Asn Ile Thr Ile Arg Asn Gln Ile Asn Ala Leu Thr Ser Phe
                325                 330                 335

Val Asp Ala Ser Met Val Tyr Gly Ser Glu Glu Pro Leu Ala Arg Asn
            340                 345                 350

Leu Arg Asn Met Ser Asn Gln Leu Gly Leu Leu Ala Val Asn Gln Arg
    355                 360                 365

Phe Gln Asp Asn Gly Arg Ala Leu Leu Pro Phe Asp Asn Leu His Asp
    370                 375                 380

Asp Pro Cys Leu Leu Thr Asn Arg Ser Ala Arg Ile Pro Cys Phe Leu
385                 390                 395                 400

Ala Gly Asp Thr Arg Ser Ser Glu Met Pro Glu Leu Thr Ser Met His
                405                 410                 415

Thr Leu Leu Leu Arg Glu His Asn Arg Leu Ala Thr Glu Leu Lys Ser
            420                 425                 430

Leu Asn Pro Arg Trp Asp Gly Glu Arg Leu Tyr Gln Glu Ala Arg Lys
    435                 440                 445

Ile Val Gly Ala Met Val Gln Ile Ile Thr Tyr Arg Asp Tyr Leu Pro
    450                 455                 460

Leu Val Leu Gly Pro Thr Ala Met Arg Lys Tyr Leu Pro Thr Tyr Arg
465                 470                 475                 480

Ser Tyr Asn Asp Ser Val Asp Pro Arg Ile Ala Asn Val Phe Thr Asn
                485                 490                 495

Ala Phe Arg Tyr Gly His Thr Leu Ile Gln Pro Phe Met Phe Arg Leu
            500                 505                 510

Asp Asn Arg Tyr Gln Pro Met Glu Pro Asn Pro Arg Val Pro Leu Ser
    515                 520                 525

Arg Val Phe Phe Ala Ser Trp Arg Val Val Leu Glu Gly Gly Ile Asp
```

```
                    530                 535                 540
Pro Ile Leu Arg Gly Leu Met Ala Thr Pro Ala Lys Leu Asn Arg Gln
545                 550                 555                 560

Asn Gln Ile Ala Val Asp Glu Ile Arg Glu Arg Leu Phe Glu Gln Val
                565                 570                 575

Met Arg Ile Gly Leu Asp Leu Pro Ala Leu Asn Met Gln Arg Ser Arg
                580                 585                 590

Asp His Gly Leu Pro Gly Tyr Asn Ala Trp Arg Arg Phe Cys Gly Leu
                595                 600                 605

Pro Gln Pro Glu Thr Val Gly Gln Leu Gly Thr Val Leu Arg Asn Leu
                610                 615                 620

Lys Leu Ala Arg Lys Leu Met Glu Gln Tyr Gly Thr Pro Asn Asn Ile
625                 630                 635                 640

Asp Ile Trp Met Gly Gly Val Ser Glu Pro Leu Lys Arg Lys Gly Arg
                645                 650                 655

Val Gly Pro Leu Leu Ala Cys Ile Ile Gly Thr Gln Phe Arg Lys Leu
                660                 665                 670

Arg Asp Gly Asp Arg Phe Trp Trp Glu Asn Glu Gly Val Phe Ser Met
                675                 680                 685

Gln Gln Arg Gln Ala Leu Ala Gln Ile Ser Leu Pro Arg Ile Ile Cys
                690                 695                 700

Asp Asn Thr Gly Ile Thr Thr Val Ser Lys Asn Asn Ile Phe Met Ser
705                 710                 715                 720

Asn Ser Tyr Pro Arg Asp Phe Val Asn Cys Ser Thr Leu Pro Ala Leu
                725                 730                 735

Asn Leu Ala Ser Trp Arg Glu Ala Ser
                740                 745

<210> SEQ ID NO 21
<211> LENGTH: 1247
<212> TYPE: PRT
<213> ORGANISM: Homo sapiens

<400> SEQUENCE: 21

Met Leu Ala Ser Ser Arg Ile Arg Ala Ala Trp Thr Arg Ala Leu
1               5                   10                  15

Leu Leu Pro Leu Leu Leu Ala Gly Pro Val Gly Cys Leu Ser Arg Gln
                20                  25                  30

Glu Leu Phe Pro Phe Gly Pro Gly Gln Gly Asp Leu Glu Leu Glu Asp
                35                  40                  45

Gly Asp Asp Phe Val Ser Pro Ala Leu Glu Leu Ser Gly Ala Leu Arg
50                  55                  60

Phe Tyr Asp Arg Ser Asp Ile Asp Ala Val Tyr Val Thr Thr Asn Gly
65                  70                  75                  80

Ile Ile Ala Thr Ser Glu Pro Pro Ala Lys Glu Ser His Pro Gly Leu
                85                  90                  95

Phe Pro Pro Thr Phe Gly Ala Val Ala Pro Phe Leu Ala Asp Leu Asp
                100                 105                 110

Thr Thr Asp Gly Leu Gly Lys Val Tyr Tyr Arg Glu Asp Leu Ser Pro
                115                 120                 125

Ser Ile Thr Gln Arg Ala Ala Glu Cys Val His Arg Gly Phe Pro Glu
                130                 135                 140

Ile Ser Phe Gln Pro Ser Ser Ala Val Val Val Thr Trp Glu Ser Val
145                 150                 155                 160
```

-continued

Ala Pro Tyr Gln Gly Pro Ser Arg Asp Pro Asp Gln Lys Gly Lys Arg
                165                 170                 175

Asn Thr Phe Gln Ala Val Leu Ala Ser Ser Asp Ser Ser Tyr Ala
        180                 185                 190

Ile Phe Leu Tyr Pro Glu Asp Gly Leu Gln Phe His Thr Thr Phe Ser
        195                 200                 205

Lys Lys Glu Asn Asn Gln Val Pro Ala Val Val Ala Phe Ser Gln Gly
    210                 215                 220

Ser Val Gly Phe Leu Trp Lys Ser Asn Gly Ala Tyr Asn Ile Phe Ala
225                 230                 235                 240

Asn Asp Arg Glu Ser Ile Glu Asn Leu Ala Lys Ser Ser Asn Ser Gly
                245                 250                 255

Gln Gln Gly Val Trp Val Phe Glu Ile Gly Ser Pro Ala Thr Thr Asn
            260                 265                 270

Gly Val Val Pro Ala Asp Val Ile Leu Gly Thr Glu Asp Gly Ala Glu
        275                 280                 285

Tyr Asp Asp Glu Asp Glu Asp Tyr Asp Leu Ala Thr Thr Arg Leu Gly
        290                 295                 300

Leu Glu Asp Val Gly Thr Thr Pro Phe Ser Tyr Lys Ala Leu Arg Arg
305                 310                 315                 320

Gly Gly Ala Asp Thr Tyr Ser Val Pro Ser Val Leu Ser Pro Arg Arg
                325                 330                 335

Ala Ala Thr Glu Arg Pro Leu Gly Pro Pro Thr Glu Arg Thr Arg Ser
            340                 345                 350

Phe Gln Leu Ala Val Glu Thr Phe His Gln His Pro Gln Val Ile
        355                 360                 365

Asp Val Asp Glu Val Glu Glu Thr Gly Val Val Phe Ser Tyr Asn Thr
        370                 375                 380

Asp Ser Arg Gln Thr Cys Ala Asn Asn Arg His Gln Cys Ser Val His
385                 390                 395                 400

Ala Glu Cys Arg Asp Tyr Ala Thr Gly Phe Cys Cys Ser Cys Val Ala
                405                 410                 415

Gly Tyr Thr Gly Asn Gly Arg Gln Cys Val Ala Glu Gly Ser Pro Gln
            420                 425                 430

Arg Val Asn Gly Lys Val Lys Gly Arg Ile Phe Val Gly Ser Ser Gln
        435                 440                 445

Val Pro Ile Val Phe Glu Asn Thr Asp Leu His Ser Tyr Val Val Met
        450                 455                 460

Asn His Gly Arg Ser Tyr Thr Ala Ile Ser Thr Ile Pro Glu Thr Val
465                 470                 475                 480

Gly Tyr Ser Leu Leu Pro Leu Ala Pro Val Gly Gly Ile Ile Gly Trp
                485                 490                 495

Met Phe Ala Val Glu Gln Asp Gly Phe Lys Asn Gly Phe Ser Ile Thr
            500                 505                 510

Gly Gly Glu Phe Thr Arg Gln Ala Glu Val Thr Phe Val Gly His Pro
        515                 520                 525

Gly Asn Leu Val Ile Lys Gln Arg Phe Ser Gly Ile Asp Glu His Gly
        530                 535                 540

His Leu Thr Ile Asp Thr Glu Leu Glu Gly Arg Val Pro Gln Ile Pro
545                 550                 555                 560

Phe Gly Ser Ser Val His Ile Glu Pro Tyr Thr Glu Leu Tyr His Tyr
                565                 570                 575

Ser Thr Ser Val Ile Thr Ser Ser Ser Thr Arg Glu Tyr Thr Val Thr

```
            580                 585                 590
Glu Pro Glu Arg Asp Gly Ala Ser Pro Ser Arg Ile Tyr Thr Tyr Gln
            595                 600                 605

Trp Arg Gln Thr Ile Thr Phe Gln Glu Cys Val His Asp Asp Ser Arg
            610                 615                 620

Pro Ala Leu Pro Ser Thr Gln Gln Leu Ser Val Asp Ser Val Phe Val
            625                 630                 635             640

Leu Tyr Asn Gln Glu Glu Lys Ile Leu Arg Tyr Ala Phe Ser Asn Ser
                    645                 650                 655

Ile Gly Pro Val Arg Glu Gly Ser Pro Asp Ala Leu Gln Asn Pro Cys
                    660                 665                 670

Tyr Ile Gly Thr His Gly Cys Asp Thr Asn Ala Ala Cys Arg Pro Gly
                    675                 680                 685

Pro Arg Thr Gln Phe Thr Cys Glu Cys Ser Ile Gly Phe Arg Gly Asp
            690                 695                 700

Gly Arg Thr Cys Tyr Asp Ile Asp Glu Cys Ser Glu Gln Pro Ser Val
705                 710                 715                 720

Cys Gly Ser His Thr Ile Cys Asn Asn His Pro Gly Thr Phe Arg Cys
                    725                 730                 735

Glu Cys Val Glu Gly Tyr Gln Phe Ser Asp Glu Gly Thr Cys Val Ala
                    740                 745                 750

Val Val Asp Gln Arg Pro Ile Asn Tyr Cys Glu Thr Gly Leu His Asn
                    755                 760                 765

Cys Asp Ile Pro Gln Arg Ala Gln Cys Ile Tyr Thr Gly Gly Ser Ser
            770                 775                 780

Tyr Thr Cys Ser Cys Leu Pro Gly Phe Ser Gly Asp Gly Gln Ala Cys
785                 790                 795                 800

Gln Asp Val Asp Glu Cys Gln Pro Ser Arg Cys His Pro Asp Ala Phe
                    805                 810                 815

Cys Tyr Asn Thr Pro Gly Ser Phe Thr Cys Gln Cys Lys Pro Gly Tyr
                    820                 825                 830

Gln Gly Asp Gly Phe Arg Cys Val Pro Gly Glu Val Glu Lys Thr Arg
                    835                 840                 845

Cys Gln His Glu Arg Glu His Ile Leu Gly Ala Ala Gly Ala Thr Asp
            850                 855                 860

Pro Gln Arg Pro Ile Pro Pro Gly Leu Phe Val Pro Glu Cys Asp Ala
865                 870                 875                 880

His Gly His Tyr Ala Pro Thr Gln Cys His Gly Ser Thr Gly Tyr Cys
                    885                 890                 895

Trp Cys Val Asp Arg Asp Gly Arg Glu Val Glu Gly Thr Arg Thr Arg
                    900                 905                 910

Pro Gly Met Thr Pro Pro Cys Leu Ser Thr Val Ala Pro Pro Ile His
            915                 920                 925

Gln Gly Pro Ala Val Pro Thr Ala Val Ile Pro Leu Pro Pro Gly Thr
            930                 935                 940

His Leu Leu Phe Ala Gln Thr Gly Lys Ile Glu Arg Leu Pro Leu Glu
945                 950                 955                 960

Gly Asn Thr Met Arg Lys Thr Glu Ala Lys Ala Phe Leu His Val Pro
                    965                 970                 975

Ala Lys Val Ile Ile Gly Leu Ala Phe Asp Cys Val Asp Lys Met Val
                    980                 985                 990

Tyr Trp Thr Asp Ile Thr Glu Pro  Ser Ile Gly Arg Ala  Ser Leu His
            995                 1000                1005
```

```
Gly Gly Glu Pro Thr Thr Ile Ile Arg Gln Asp Leu Gly Ser Pro
    1010                1015                1020

Glu Gly Ile Ala Val Asp His Leu Gly Arg Asn Ile Phe Trp Thr
    1025                1030                1035

Asp Ser Asn Leu Asp Arg Ile Glu Val Ala Lys Leu Asp Gly Thr
    1040                1045                1050

Gln Arg Arg Val Leu Phe Glu Thr Asp Leu Val Asn Pro Arg Gly
    1055                1060                1065

Ile Val Thr Asp Ser Val Arg Gly Asn Leu Tyr Trp Thr Asp Trp
    1070                1075                1080

Asn Arg Asp Asn Pro Lys Ile Glu Thr Ser Tyr Met Asp Gly Thr
    1085                1090                1095

Asn Arg Arg Ile Leu Val Gln Asp Asp Leu Gly Leu Pro Asn Gly
    1100                1105                1110

Leu Thr Phe Asp Ala Phe Ser Ser Gln Leu Cys Trp Val Asp Ala
    1115                1120                1125

Gly Thr Asn Arg Ala Glu Cys Leu Asn Pro Ser Gln Pro Ser Arg
    1130                1135                1140

Arg Lys Ala Leu Glu Gly Leu Gln Tyr Pro Phe Ala Val Thr Ser
    1145                1150                1155

Tyr Gly Lys Asn Leu Tyr Phe Thr Asp Trp Lys Met Asn Ser Val
    1160                1165                1170

Val Ala Leu Asp Leu Ala Ile Ser Lys Glu Thr Asp Ala Phe Gln
    1175                1180                1185

Pro His Lys Gln Thr Arg Leu Tyr Gly Ile Thr Thr Ala Leu Ser
    1190                1195                1200

Gln Cys Pro Gln Gly His Asn Tyr Cys Ser Val Asn Asn Gly Gly
    1205                1210                1215

Cys Thr His Leu Cys Leu Ala Thr Pro Gly Ser Arg Thr Cys Arg
    1220                1225                1230

Cys Pro Asp Asn Thr Leu Gly Val Asp Cys Ile Glu Arg Lys
    1235                1240                1245

<210> SEQ ID NO 22
<211> LENGTH: 273
<212> TYPE: PRT
<213> ORGANISM: Homo sapiens

<400> SEQUENCE: 22

Met Thr Phe Asp Asp Leu Lys Ile Gln Thr Val Lys Asp Gln Pro Asp
1               5                   10                  15

Glu Lys Ser Asn Gly Lys Lys Ala Lys Gly Leu Gln Phe Leu Tyr Ser
                20                  25                  30

Pro Trp Trp Cys Leu Ala Ala Ala Thr Leu Gly Val Leu Cys Leu Gly
            35                  40                  45

Leu Val Val Thr Ile Met Val Leu Gly Met Gln Leu Ser Gln Val Ser
        50                  55                  60

Asp Leu Leu Thr Gln Glu Gln Ala Asn Leu Thr His Gln Lys Lys Lys
65                  70                  75                  80

Leu Glu Gly Gln Ile Ser Ala Arg Gln Gln Ala Glu Glu Ala Ser Gln
                85                  90                  95

Glu Ser Glu Asn Glu Leu Lys Glu Met Ile Glu Thr Leu Ala Arg Lys
                100                 105                 110

Leu Asn Glu Lys Ser Lys Glu Gln Met Glu Leu His His Gln Asn Leu
```

```
                115                 120                 125
Asn Leu Gln Glu Thr Leu Lys Arg Val Ala Asn Cys Ser Ala Pro Cys
            130                 135                 140
Pro Gln Asp Trp Ile Trp His Gly Glu Asn Cys Tyr Leu Phe Ser Ser
145                 150                 155                 160
Gly Ser Phe Asn Trp Glu Lys Ser Gln Glu Lys Cys Leu Ser Leu Asp
                165                 170                 175
Ala Lys Leu Leu Lys Ile Asn Ser Thr Ala Asp Leu Asp Phe Ile Gln
            180                 185                 190
Gln Ala Ile Ser Tyr Ser Ser Phe Pro Phe Trp Met Gly Leu Ser Arg
                195                 200                 205
Arg Asn Pro Ser Tyr Pro Trp Leu Trp Glu Asp Gly Ser Pro Leu Met
            210                 215                 220
Pro His Leu Phe Arg Val Arg Gly Ala Val Ser Gln Thr Tyr Pro Ser
225                 230                 235                 240
Gly Thr Cys Ala Tyr Ile Gln Arg Gly Ala Val Tyr Ala Glu Asn Cys
                245                 250                 255
Ile Leu Ala Ala Phe Ser Ile Cys Gln Lys Lys Ala Asn Leu Arg Ala
            260                 265                 270
Gln Gln

<210> SEQ ID NO 23
<211> LENGTH: 1628
<212> TYPE: PRT
<213> ORGANISM: Homo sapiens

<400> SEQUENCE: 23

Met Arg Leu Trp Ser Trp Val Leu His Leu Gly Leu Ser Ala Ala
1               5                   10                  15
Leu Gly Cys Gly Leu Ala Glu Arg Pro Arg Ala Arg Arg Asp Pro
                20                  25                  30
Arg Ala Gly Arg Pro Pro Arg Pro Ala Ala Gly Pro Ala Thr Cys Ala
            35                  40                  45
Thr Arg Ala Ala Arg Gly Arg Arg Ala Ser Pro Pro Pro Pro Pro
    50                  55                  60
Pro Gly Gly Ala Trp Glu Ala Val Arg Val Pro Arg Arg Arg Gln Gln
65                  70                  75                  80
Arg Glu Ala Arg Gly Ala Thr Glu Glu Pro Ser Pro Ser Arg Ala
                85                  90                  95
Leu Tyr Phe Ser Gly Arg Gly Gln Leu Arg Val Leu Arg Ala Asp
            100                 105                 110
Leu Glu Leu Pro Arg Asp Ala Phe Thr Leu Gln Val Trp Leu Arg Ala
        115                 120                 125
Glu Gly Gly Gln Arg Ser Pro Ala Val Ile Thr Gly Leu Tyr Asp Lys
    130                 135                 140
Cys Ser Tyr Ile Ser Arg Asp Arg Gly Trp Val Val Gly Ile His Thr
145                 150                 155                 160
Ile Ser Asp Gln Asp Asn Lys Asp Pro Arg Tyr Phe Phe Ser Leu Lys
                165                 170                 175
Thr Asp Arg Ala Arg Gln Val Thr Thr Ile Asn Ala His Arg Ser Tyr
            180                 185                 190
Leu Pro Gly Gln Trp Val Tyr Leu Ala Ala Thr Tyr Asp Gly Gln Phe
        195                 200                 205
Met Lys Leu Tyr Val Asn Gly Ala Gln Val Ala Thr Ser Gly Glu Gln
```

```
                210                 215                 220
Val Gly Gly Ile Phe Ser Pro Leu Thr Gln Lys Cys Lys Val Leu Met
225                 230                 235                 240

Leu Gly Gly Ser Ala Leu Asn His Asn Tyr Arg Gly Tyr Ile Glu His
                245                 250                 255

Phe Ser Leu Trp Lys Val Ala Arg Thr Gln Arg Glu Ile Leu Ser Asp
                260                 265                 270

Met Glu Thr His Gly Ala His Thr Ala Leu Pro Gln Leu Leu Leu Gln
                275                 280                 285

Glu Asn Trp Asp Asn Val Lys His Ala Trp Ser Pro Met Lys Asp Gly
290                 295                 300

Ser Ser Pro Lys Val Glu Phe Ser Asn Ala His Gly Phe Leu Leu Asp
305                 310                 315                 320

Thr Ser Leu Glu Pro Pro Leu Cys Gly Gln Thr Leu Cys Asp Asn Thr
                325                 330                 335

Glu Val Ile Ala Ser Tyr Asn Gln Leu Ser Ser Phe Arg Gln Pro Lys
                340                 345                 350

Val Val Arg Tyr Arg Val Val Asn Leu Tyr Glu Asp Asp His Lys Asn
                355                 360                 365

Pro Thr Val Thr Arg Glu Gln Val Asp Phe Gln His Gln Leu Ala
370                 375                 380

Glu Ala Phe Lys Gln Tyr Asn Ile Ser Trp Glu Leu Asp Val Leu Glu
385                 390                 395                 400

Val Ser Asn Ser Ser Leu Arg Arg Arg Leu Ile Leu Ala Asn Cys Asp
                405                 410                 415

Ile Ser Lys Ile Gly Asp Glu Asn Cys Asp Pro Glu Cys Asn His Thr
                420                 425                 430

Leu Thr Gly His Asp Gly Gly Asp Cys Arg His Leu Arg His Pro Ala
                435                 440                 445

Phe Val Lys Lys Gln His Asn Gly Val Cys Asp Met Asp Cys Asn Tyr
450                 455                 460

Glu Arg Phe Asn Phe Asp Gly Gly Glu Cys Cys Asp Pro Glu Ile Thr
465                 470                 475                 480

Asn Val Thr Gln Thr Cys Phe Asp Pro Asp Ser Pro His Arg Ala Tyr
                485                 490                 495

Leu Asp Val Asn Glu Leu Lys Asn Ile Leu Lys Leu Asp Gly Ser Thr
                500                 505                 510

His Leu Asn Ile Phe Phe Ala Lys Ser Ser Glu Glu Leu Ala Gly
                515                 520                 525

Val Ala Thr Trp Pro Trp Asp Lys Glu Ala Leu Met His Leu Gly Gly
530                 535                 540

Ile Val Leu Asn Pro Ser Phe Tyr Gly Met Pro Gly His Thr His Thr
545                 550                 555                 560

Met Ile His Glu Ile Gly His Ser Leu Gly Leu Tyr His Val Phe Arg
                565                 570                 575

Gly Ile Ser Glu Ile Gln Ser Cys Ser Asp Pro Cys Met Glu Thr Glu
                580                 585                 590

Pro Ser Phe Glu Thr Gly Asp Leu Cys Asn Asp Thr Asn Pro Ala Pro
                595                 600                 605

Lys His Lys Ser Cys Gly Asp Pro Gly Pro Gly Asn Asp Thr Cys Gly
                610                 615                 620

Phe His Ser Phe Phe Asn Thr Pro Tyr Asn Asn Phe Met Ser Tyr Ala
625                 630                 635                 640
```

-continued

```
Asp Asp Asp Cys Thr Asp Ser Phe Thr Pro Asn Gln Val Ala Arg Met
            645                 650                 655

His Cys Tyr Leu Asp Leu Val Tyr Gln Gly Trp Gln Pro Ser Arg Lys
            660                 665                 670

Pro Ala Pro Val Ala Leu Ala Pro Gln Val Leu Gly His Thr Thr Asp
            675                 680                 685

Ser Val Thr Leu Glu Trp Phe Pro Pro Ile Asp Gly His Phe Phe Glu
            690                 695                 700

Arg Glu Leu Gly Ser Ala Cys His Leu Cys Leu Gly Arg Ile Leu
705             710                 715                 720

Val Gln Tyr Ala Ser Asn Ala Ser Pro Met Pro Cys Ser Pro Ser
            725                 730                 735

Gly His Trp Ser Pro Arg Glu Ala Gly His Pro Asp Val Glu Gln
            740                 745                 750

Pro Cys Lys Ser Ser Val Arg Thr Trp Ser Pro Asn Ser Ala Val Asn
            755                 760                 765

Pro His Thr Val Pro Pro Ala Cys Pro Glu Pro Gln Gly Cys Tyr Leu
            770                 775                 780

Glu Leu Glu Phe Leu Tyr Pro Leu Val Pro Glu Ser Leu Thr Ile Trp
785             790                 795                 800

Val Thr Phe Val Ser Thr Asp Trp Asp Ser Ser Gly Ala Val Asn Asp
            805                 810                 815

Ile Lys Leu Leu Ala Val Ser Gly Lys Asn Ile Ser Leu Gly Pro Gln
            820                 825                 830

Asn Val Phe Cys Asp Val Pro Leu Thr Ile Arg Leu Trp Asp Val Gly
            835                 840                 845

Glu Glu Val Tyr Gly Ile Gln Ile Tyr Thr Leu Asp Glu His Leu Glu
            850                 855                 860

Ile Asp Ala Ala Met Leu Thr Ser Thr Ala Asp Thr Pro Leu Cys Leu
865             870                 875                 880

Gln Cys Lys Pro Leu Lys Tyr Lys Val Val Arg Asp Pro Pro Leu Gln
            885                 890                 895

Met Asp Val Ala Ser Ile Leu His Leu Asn Arg Lys Phe Val Asp Met
            900                 905                 910

Asp Leu Asn Leu Gly Ser Val Tyr Gln Tyr Trp Val Ile Thr Ile Ser
            915                 920                 925

Gly Thr Glu Glu Ser Glu Pro Ser Pro Ala Val Thr Tyr Ile His Gly
            930                 935                 940

Arg Gly Tyr Cys Gly Asp Gly Ile Ile Gln Lys Asp Gln Gly Glu Gln
945             950                 955                 960

Cys Asp Asp Met Asn Lys Ile Asn Gly Asp Gly Cys Ser Leu Phe Cys
            965                 970                 975

Arg Gln Glu Val Ser Phe Asn Cys Ile Asp Glu Pro Ser Arg Cys Tyr
            980                 985                 990

Phe His Asp Gly Asp Gly Val Cys Glu Glu Phe Glu Gln Lys Thr Ser
            995                 1000                1005

Ile Lys Asp Cys Gly Val Tyr Thr Pro Gln Gly Phe Leu Asp Gln
            1010                1015                1020

Trp Ala Ser Asn Ala Ser Val Ser His Gln Asp Gln Gln Cys Pro
            1025                1030                1035

Gly Trp Val Ile Ile Gly Gln Pro Ala Ala Ser Gln Val Cys Arg
            1040                1045                1050
```

```
Thr Lys Val Ile Asp Leu Ser Glu Gly Ile Ser Gln His Ala Trp
    1055                1060                1065
Tyr Pro Cys Thr Ile Ser Tyr Pro Tyr Ser Gln Leu Ala Gln Thr
    1070                1075                1080
Thr Phe Trp Leu Arg Ala Tyr Phe Ser Gln Pro Met Val Ala Ala
    1085                1090                1095
Ala Val Ile Val His Leu Val Thr Asp Gly Thr Tyr Tyr Gly Asp
    1100                1105                1110
Gln Lys Gln Glu Thr Ile Ser Val Gln Leu Leu Asp Thr Lys Asp
    1115                1120                1125
Gln Ser His Asp Leu Gly Leu His Val Leu Ser Cys Arg Asn Asn
    1130                1135                1140
Pro Leu Ile Ile Pro Val Val His Asp Leu Ser Gln Pro Phe Tyr
    1145                1150                1155
His Ser Gln Ala Val Arg Val Ser Phe Ser Ser Pro Leu Val Ala
    1160                1165                1170
Ile Ser Gly Val Ala Leu Arg Ser Phe Asp Asn Phe Asp Pro Val
    1175                1180                1185
Thr Leu Ser Ser Cys Gln Arg Gly Glu Thr Tyr Ser Pro Ala Glu
    1190                1195                1200
Gln Ser Cys Val His Phe Ala Cys Glu Lys Thr Asp Cys Pro Glu
    1205                1210                1215
Leu Ala Val Glu Asn Ala Ser Leu Asn Cys Ser Ser Ser Asp Arg
    1220                1225                1230
Tyr His Gly Ala Gln Cys Thr Val Ser Cys Arg Thr Gly Tyr Val
    1235                1240                1245
Leu Gln Ile Arg Arg Asp Asp Glu Leu Ile Lys Ser Gln Thr Gly
    1250                1255                1260
Pro Ser Val Thr Val Thr Cys Thr Glu Gly Lys Trp Asn Lys Gln
    1265                1270                1275
Val Ala Cys Glu Pro Val Asp Cys Ser Ile Pro Asp His His Gln
    1280                1285                1290
Val Tyr Ala Ala Ser Phe Ser Cys Pro Glu Gly Thr Thr Phe Gly
    1295                1300                1305
Ser Gln Cys Ser Phe Gln Cys Arg His Pro Ala Gln Leu Lys Gly
    1310                1315                1320
Asn Asn Ser Leu Leu Thr Cys Met Glu Asp Gly Leu Trp Ser Phe
    1325                1330                1335
Pro Glu Ala Leu Cys Glu Leu Met Cys Leu Ala Pro Pro Pro Val
    1340                1345                1350
Pro Asn Ala Asp Leu Gln Thr Ala Arg Cys Arg Glu Asn Lys His
    1355                1360                1365
Lys Val Gly Ser Phe Cys Lys Tyr Lys Cys Lys Pro Gly Tyr His
    1370                1375                1380
Val Pro Gly Ser Ser Arg Lys Ser Lys Lys Arg Ala Phe Lys Thr
    1385                1390                1395
Gln Cys Thr Gln Asp Gly Ser Trp Gln Glu Gly Ala Cys Val Pro
    1400                1405                1410
Val Thr Cys Asp Pro Pro Pro Lys Phe His Gly Leu Tyr Gln
    1415                1420                1425
Cys Thr Asn Gly Phe Gln Phe Asn Ser Glu Cys Arg Ile Lys Cys
    1430                1435                1440
Glu Asp Ser Asp Ala Ser Gln Gly Leu Gly Ser Asn Val Ile His
```

```
              1445                1450                1455

Cys Arg Lys Asp Gly Thr Trp Asn Gly Ser Phe His Val Cys Gln
        1460                1465                1470

Glu Met Gln Gly Gln Cys Ser Val Pro Asn Glu Leu Asn Ser Asn
    1475                1480                1485

Leu Lys Leu Gln Cys Pro Asp Gly Tyr Ala Ile Gly Ser Glu Cys
    1490                1495                1500

Ala Thr Ser Cys Leu Asp His Asn Ser Glu Ser Ile Ile Leu Pro
    1505                1510                1515

Met Asn Val Thr Val Arg Asp Ile Pro His Trp Leu Asn Pro Thr
    1520                1525                1530

Arg Val Glu Arg Val Val Cys Thr Ala Gly Leu Lys Trp Tyr Pro
    1535                1540                1545

His Pro Ala Leu Ile His Cys Val Lys Gly Cys Glu Pro Phe Met
    1550                1555                1560

Gly Asp Asn Tyr Cys Asp Ala Ile Asn Asn Arg Ala Phe Cys Asn
    1565                1570                1575

Tyr Asp Gly Gly Asp Cys Cys Thr Ser Thr Val Lys Thr Lys Lys
    1580                1585                1590

Val Thr Pro Phe Pro Met Ser Cys Asp Leu Gln Gly Asp Cys Ala
    1595                1600                1605

Cys Arg Asp Pro Gln Ala Gln Glu His Ser Arg Lys Asp Leu Arg
    1610                1615                1620

Gly Tyr Ser His Gly
    1625

<210> SEQ ID NO 24
<211> LENGTH: 412
<212> TYPE: PRT
<213> ORGANISM: Homo sapiens

<400> SEQUENCE: 24

Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
            20                  25                  30

Gly Pro Leu Leu Ala Arg Asp Arg Arg Gln Ala Thr Glu Tyr Glu Tyr
            35                  40                  45

Leu Asp Tyr Asp Phe Leu Pro Glu Thr Glu Pro Pro Glu Met Leu Arg
50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Arg Ser Thr Gly Leu Asp Ala Gly
            85                  90                  95

Gly Ala Val Thr Glu Leu Thr Thr Glu Leu Ala Asn Met Gly Asn Leu
            100                 105                 110

Ser Thr Asp Ser Ala Ala Met Glu Ile Gln Thr Thr Gln Pro Ala Ala
            115                 120                 125

Thr Glu Ala Gln Thr Thr Gln Pro Val Pro Thr Glu Ala Gln Thr Thr
    130                 135                 140

Pro Leu Ala Ala Thr Glu Ala Gln Thr Thr Arg Leu Thr Ala Thr Glu
145                 150                 155                 160

Ala Gln Thr Thr Pro Leu Ala Thr Glu Ala Gln Thr Thr Pro Pro
            165                 170                 175
```

```
Ala Ala Thr Glu Ala Gln Thr Thr Gln Pro Thr Gly Leu Glu Ala Gln
            180                 185                 190

Thr Thr Ala Pro Ala Ala Met Glu Ala Gln Thr Thr Ala Pro Ala Ala
        195                 200                 205

Met Glu Ala Gln Thr Thr Pro Pro Ala Ala Met Glu Ala Gln Thr Thr
    210                 215                 220

Gln Thr Thr Ala Met Glu Ala Gln Thr Thr Ala Pro Glu Ala Thr Glu
225                 230                 235                 240

Ala Gln Thr Thr Gln Pro Thr Ala Thr Glu Ala Gln Thr Thr Pro Leu
                245                 250                 255

Ala Ala Met Glu Ala Leu Ser Thr Glu Pro Ser Ala Thr Glu Ala Leu
            260                 265                 270

Ser Met Glu Pro Thr Thr Lys Arg Gly Leu Phe Ile Pro Phe Ser Val
        275                 280                 285

Ser Ser Val Thr His Lys Gly Ile Pro Met Ala Ala Ser Asn Leu Ser
    290                 295                 300

Val Asn Tyr Pro Val Gly Ala Pro Asp His Ile Ser Val Lys Gln Cys
305                 310                 315                 320

Leu Leu Ala Ile Leu Ile Leu Ala Leu Val Ala Thr Ile Phe Phe Val
                325                 330                 335

Cys Thr Val Val Leu Ala Val Arg Leu Ser Arg Lys Gly His Met Tyr
            340                 345                 350

Pro Val Arg Asn Tyr Ser Pro Thr Glu Met Val Cys Ile Ser Ser Leu
        355                 360                 365

Leu Pro Asp Gly Gly Glu Gly Pro Ser Ala Thr Ala Asn Gly Gly Leu
    370                 375                 380

Ser Lys Ala Lys Ser Pro Gly Leu Thr Pro Glu Pro Arg Glu Asp Arg
385                 390                 395                 400

Glu Gly Asp Asp Leu Thr Leu His Ser Phe Leu Pro
                405                 410

<210> SEQ ID NO 25
<211> LENGTH: 132
<212> TYPE: PRT
<213> ORGANISM: Homo sapiens

<400> SEQUENCE: 25

Met Lys Ser Ser Gly Leu Phe Pro Phe Leu Val Leu Leu Ala Leu Gly
1               5                   10                  15

Thr Leu Ala Pro Trp Ala Val Glu Gly Ser Gly Lys Ser Phe Lys Ala
            20                  25                  30

Gly Val Cys Pro Pro Lys Lys Ser Ala Gln Cys Leu Arg Tyr Lys Lys
        35                  40                  45

Pro Glu Cys Gln Ser Asp Trp Gln Cys Pro Gly Lys Lys Arg Cys Cys
    50                  55                  60

Pro Asp Thr Cys Gly Ile Lys Cys Leu Asp Pro Val Asp Thr Pro Asn
65                  70                  75                  80

Pro Thr Arg Arg Lys Pro Gly Lys Cys Pro Val Thr Tyr Gly Gln Cys
                85                  90                  95

Leu Met Leu Asn Pro Pro Asn Phe Cys Glu Met Asp Gly Gln Cys Lys
            100                 105                 110

Arg Asp Leu Lys Cys Cys Met Gly Met Cys Gly Lys Ser Cys Val Ser
        115                 120                 125

Pro Val Lys Ala
    130
```

```
<210> SEQ ID NO 26
<211> LENGTH: 273
<212> TYPE: PRT
<213> ORGANISM: Homo sapiens

<400> SEQUENCE: 26

Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
                20                  25                  30

Val Thr Asn Asn Val Lys Asp Val Thr Lys Leu Val Ala Asn Leu Pro
            35                  40                  45

Lys Asp Tyr Met Ile Thr Leu Lys Tyr Val Pro Gly Met Asp Val Leu
    50                  55                  60

Pro Ser His Cys Trp Ile Ser Glu Met Val Val Gln Leu Ser Asp Ser
65                  70                  75                  80

Leu Thr Asp Leu Leu Asp Lys Phe Ser Asn Ile Ser Glu Gly Leu Ser
                85                  90                  95

Asn Tyr Ser Ile Ile Asp Lys Leu Val Asn Ile Val Asp Asp Leu Val
                100                 105                 110

Glu Cys Val Lys Glu Asn Ser Ser Lys Asp Leu Lys Lys Ser Phe Lys
            115                 120                 125

Ser Pro Glu Pro Arg Leu Phe Thr Pro Glu Glu Phe Arg Ile Phe
        130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Asp Ser Arg
                165                 170                 175

Val Ser Val Thr Lys Pro Phe Met Leu Pro Pro Val Ala Ala Ser Ser
                180                 185                 190

Leu Arg Asn Asp Ser Ser Ser Asn Arg Lys Ala Lys Asn Pro Pro
        195                 200                 205

Gly Asp Ser Ser Leu His Trp Ala Ala Met Ala Leu Pro Ala Leu Phe
    210                 215                 220

Ser Leu Ile Ile Gly Phe Ala Phe Gly Ala Leu Tyr Trp Lys Lys Arg
225                 230                 235                 240

Gln Pro Ser Leu Thr Arg Ala Val Glu Asn Ile Gln Ile Asn Glu Glu
                245                 250                 255

Asp Asn Glu Ile Ser Met Leu Gln Glu Lys Glu Arg Glu Phe Gln Glu
            260                 265                 270

Val

<210> SEQ ID NO 27
<211> LENGTH: 245
<212> TYPE: PRT
<213> ORGANISM: Homo sapiens

<400> SEQUENCE: 27

Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
                20                  25                  30

Val Thr Asn Asn Val Lys Asp Val Thr Lys Leu Val Ala Asn Leu Pro
            35                  40                  45
```

```
Lys Asp Tyr Met Ile Thr Leu Lys Tyr Val Pro Gly Met Asp Val Leu
 50                  55                  60

Pro Ser His Cys Trp Ile Ser Glu Met Val Val Gln Leu Ser Asp Ser
 65                  70                  75                  80

Leu Thr Asp Leu Leu Asp Lys Phe Ser Asn Ile Ser Glu Gly Leu Ser
                 85                  90                  95

Asn Tyr Ser Ile Ile Asp Lys Leu Val Asn Ile Val Asp Asp Leu Val
                100                 105                 110

Glu Cys Val Lys Glu Asn Ser Ser Lys Asp Leu Lys Lys Ser Phe Lys
                115                 120                 125

Ser Pro Glu Pro Arg Leu Phe Thr Pro Glu Gly Phe Phe Arg Ile Phe
130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Gly Lys Ala
                165                 170                 175

Lys Asn Pro Pro Gly Asp Ser Ser Leu His Trp Ala Ala Met Ala Leu
                180                 185                 190

Pro Ala Leu Phe Ser Leu Ile Ile Gly Phe Ala Phe Gly Ala Leu Tyr
                195                 200                 205

Trp Lys Lys Arg Gln Pro Ser Leu Thr Arg Ala Val Glu Asn Ile Gln
210                 215                 220

Ile Asn Glu Glu Asp Asn Glu Ile Ser Met Leu Gln Glu Lys Glu Arg
225                 230                 235                 240

Glu Phe Gln Glu Val
                245

<210> SEQ ID NO 28
<211> LENGTH: 207
<212> TYPE: PRT
<213> ORGANISM: Homo sapiens

<400> SEQUENCE: 28

Met Ala Pro Phe Glu Pro Leu Ala Ser Gly Ile Leu Leu Leu Leu Trp
 1               5                  10                  15

Leu Ile Ala Pro Ser Arg Ala Cys Thr Cys Val Pro Pro His Pro Gln
                 20                  25                  30

Thr Ala Phe Cys Asn Ser Asp Leu Val Ile Arg Ala Lys Phe Val Gly
                 35                  40                  45

Thr Pro Glu Val Asn Gln Thr Thr Leu Tyr Gln Arg Tyr Glu Ile Lys
 50                  55                  60

Met Thr Lys Met Tyr Lys Gly Phe Gln Ala Leu Gly Asp Ala Ala Asp
 65                  70                  75                  80

Ile Arg Phe Val Tyr Thr Pro Ala Met Glu Ser Val Cys Gly Tyr Phe
                 85                  90                  95

His Arg Ser His Asn Arg Ser Glu Glu Phe Leu Ile Ala Gly Lys Leu
                100                 105                 110

Gln Asp Gly Leu Leu His Ile Thr Thr Cys Ser Phe Val Ala Pro Trp
                115                 120                 125

Asn Ser Leu Ser Leu Ala Gln Arg Arg Gly Phe Thr Lys Thr Tyr Thr
130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175
```

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
            195                 200                 205

<210> SEQ ID NO 29
<211> LENGTH: 220
<212> TYPE: PRT
<213> ORGANISM: Homo sapiens

<400> SEQUENCE: 29

Met Gly Ala Ala Ala Arg Thr Leu Arg Leu Ala Leu Gly Leu Leu Leu
1               5                   10                  15

Leu Ala Thr Leu Leu Arg Pro Ala Asp Ala Cys Ser Cys Ser Pro Val
            20                  25                  30

His Pro Gln Gln Ala Phe Cys Asn Ala Asp Val Val Ile Arg Ala Lys
        35                  40                  45

Ala Val Ser Glu Lys Glu Val Asp Ser Gly Asn Asp Ile Tyr Gly Asn
    50                  55                  60

Pro Ile Lys Arg Ile Gln Tyr Glu Ile Lys Gln Ile Lys Met Phe Lys
65                  70                  75                  80

Gly Pro Glu Lys Asp Ile Glu Phe Ile Tyr Thr Ala Pro Ser Ser Ala
                85                  90                  95

Val Cys Gly Val Ser Leu Asp Val Gly Lys Lys Glu Tyr Leu Ile
            100                 105                 110

Ala Gly Lys Ala Glu Gly Asp Gly Lys Met His Ile Thr Leu Cys Asp
        115                 120                 125

Phe Ile Val Pro Trp Asp Thr Leu Ser Thr Thr Gln Lys Lys Ser Leu
    130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
            180                 185                 190

Cys Ile Lys Arg Ser Asp Gly Ser Cys Ala Trp Tyr Arg Gly Ala Ala
        195                 200                 205

Pro Pro Lys Gln Glu Phe Leu Asp Ile Glu Asp Pro
    210                 215                 220

<210> SEQ ID NO 30
<211> LENGTH: 233
<212> TYPE: PRT
<213> ORGANISM: Homo sapiens

<400> SEQUENCE: 30

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

```
Ser Arg Thr Pro Ser Asp Lys Pro Val Ala His Val Ala Asn Pro
            85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
            130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
            210                 215                 220

Gln Val Tyr Phe Gly Ile Ile Ala Leu
225                 230
```

<210> SEQ ID NO 31
<211> LENGTH: 739
<212> TYPE: PRT
<213> ORGANISM: Homo sapiens

<400> SEQUENCE: 31

```
Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
                20                  25                  30

Ser Arg Tyr Leu Ala Gln Ile Gly Asp Ser Val Ser Leu Thr Cys Ser
            35                  40                  45

Thr Thr Gly Cys Glu Ser Pro Phe Phe Ser Trp Arg Thr Gln Ile Asp
        50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
            115                 120                 125

Ala Gly Lys Pro Ile Thr Val Lys Cys Ser Val Ala Asp Val Tyr Pro
            130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
            195                 200                 205

Thr Val Arg Gln Ala Val Lys Glu Leu Gln Val Tyr Ile Ser Pro Lys
```

```
            210                 215                 220
Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
                260                 265                 270

Asn Ala Thr Leu Thr Leu Ile Ala Met Arg Met Glu Asp Ser Gly Ile
                275                 280                 285

Tyr Val Cys Glu Gly Val Asn Leu Ile Gly Lys Asn Arg Lys Glu Val
                290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
                340                 345                 350

Ser Pro Leu Ser Gly Lys Val Arg Ser Glu Gly Thr Asn Ser Thr Leu
                355                 360                 365

Thr Leu Ser Pro Val Ser Phe Glu Asn Glu His Ser Tyr Leu Cys Thr
                370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415

Asn Gly Ser Ser Val Thr Val Ser Cys Lys Val Pro Ser Val Tyr Pro
                420                 425                 430

Leu Asp Arg Leu Glu Ile Glu Leu Leu Lys Gly Glu Thr Ile Leu Glu
                435                 440                 445

Asn Ile Glu Phe Leu Glu Asp Thr Asp Met Lys Ser Leu Glu Asn Lys
                450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
                500                 505                 510

Asp Thr Thr Val Leu Val Ser Pro Ser Ser Ile Leu Glu Glu Gly Ser
                515                 520                 525

Ser Val Asn Met Thr Cys Leu Ser Gln Gly Phe Pro Ala Pro Lys Ile
                530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
                580                 585                 590

Glu Leu Ile Ile Gln Val Thr Pro Lys Asp Ile Lys Leu Thr Ala Phe
                595                 600                 605

Pro Ser Glu Ser Val Lys Glu Gly Asp Thr Val Ile Ile Ser Cys Thr
                610                 615                 620

Cys Gly Asn Val Pro Glu Thr Trp Ile Ile Leu Lys Lys Lys Ala Glu
625                 630                 635                 640
```

Thr Gly Asp Thr Val Leu Lys Ser Ile Asp Gly Ala Tyr Thr Ile Arg
            645                 650                 655

Lys Ala Gln Leu Lys Asp Ala Gly Val Tyr Glu Cys Glu Ser Lys Asn
        660                 665                 670

Lys Val Gly Ser Gln Leu Arg Ser Leu Thr Leu Asp Val Gln Gly Arg
    675                 680                 685

Glu Asn Asn Lys Asp Tyr Phe Ser Pro Glu Leu Leu Val Leu Tyr Phe
690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val

<210> SEQ ID NO 32
<211> LENGTH: 232
<212> TYPE: PRT
<213> ORGANISM: Homo sapiens

<400> SEQUENCE: 32

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 33
<211> LENGTH: 24
<212> TYPE: PRT
<213> ORGANISM: Homo sapiens

```
<400> SEQUENCE: 33

Met Ala Leu Ala Asp Leu Tyr Glu Glu Gly Gly Gly Gly Gly Gly Glu
1               5                   10                  15

Gly Glu Asp Asn Ala Asp Ser Lys
                20
```